US012433895B2

(12) United States Patent
Konteatis et al.

(10) Patent No.: US 12,433,895 B2
(45) **Date of Patent: *Oct. 7, 2025**

(54) THERAPEUTICALLY ACTIVE COMPOUNDS AND THEIR METHODS OF USE

(71) Applicant: Servier Pharmaceuticals LLC, Boston, MA (US)

(72) Inventors: Zenon D. Konteatis, Chatham, NJ (US); Janeta Popovici-Muller, Windham, NH (US); Jeremy M. Travins, Southborough, MA (US); Robert Zahler, Pennington, NJ (US); Zhenwei Cai, Princeton, NJ (US); Ding Zhou, Shanghai (CN)

(73) Assignee: Servier Pharmaceuticals LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/376,981

(22) Filed: Oct. 5, 2023

(65) Prior Publication Data

US 2024/0335448 A1 Oct. 10, 2024

Related U.S. Application Data

(63) Continuation of application No. 17/158,867, filed on Jan. 26, 2021, now Pat. No. 11,844,758, which is a continuation of application No. 16/167,725, filed on Oct. 23, 2018, now Pat. No. 10,946,023, which is a continuation of application No. 15/392,681, filed on Dec. 28, 2016, now Pat. No. 10,172,864, which is a continuation of application No. 14/328,885, filed on Jul. 11, 2014, now Pat. No. 9,579,324.

(30) Foreign Application Priority Data

Jul. 11, 2013 (WO) ................ PCT/CN2013/079200
Jul. 10, 2014 (WO) ................ PCT/CN2014/081957

(51) Int. Cl.

| | |
|---|---|
| ***A61K 31/53*** | (2006.01) |
| ***A61K 31/506*** | (2006.01) |
| ***A61K 31/5377*** | (2006.01) |
| ***A61K 45/06*** | (2006.01) |
| ***C07D 251/18*** | (2006.01) |
| ***C07D 251/48*** | (2006.01) |
| ***C07D 401/04*** | (2006.01) |
| ***C07D 401/14*** | (2006.01) |
| ***C07D 403/04*** | (2006.01) |
| ***C07D 403/10*** | (2006.01) |
| ***C07D 405/12*** | (2006.01) |
| ***C07D 405/14*** | (2006.01) |
| ***C07D 413/04*** | (2006.01) |
| ***C07D 413/14*** | (2006.01) |
| ***C07D 417/04*** | (2006.01) |
| ***C07D 417/14*** | (2006.01) |

(52) U.S. Cl.

CPC ............ *A61K 31/53* (2013.01); *A61K 31/506* (2013.01); *A61K 31/5377* (2013.01); *A61K 45/06* (2013.01); *C07D 251/18* (2013.01); *C07D 251/48* (2013.01); *C07D 401/04* (2013.01); *C07D 401/14* (2013.01); *C07D 403/04* (2013.01); *C07D 403/10* (2013.01); *C07D 405/12* (2013.01); *C07D 405/14* (2013.01); *C07D 413/04* (2013.01); *C07D 413/14* (2013.01); *C07D 417/04* (2013.01); *C07D 417/14* (2013.01)

(58) Field of Classification Search

None
See application file for complete search history.

(56) References Cited

U.S. PATENT DOCUMENTS

| | | | |
|---|---|---|---|
| 2,390,529 | A | 12/1945 | Friedheim |
| 3,755,322 | A | 8/1973 | Winter et al. |
| 3,867,383 | A | 2/1975 | Winter |
| 4,084,053 | A | 4/1978 | Desai et al. |
| 4,157,893 | A | 6/1979 | Dehnert et al. |
| 4,180,488 | A | 12/1979 | Stern et al. |
| 5,021,421 | A | 6/1991 | Hino et al. |
| 5,441,563 | A | 8/1995 | Sideman et al. |
| 5,489,591 | A | 2/1996 | Kobayashi et al. |
| 5,807,876 | A | 9/1998 | Armistead et al. |
| 5,834,485 | A | 11/1998 | Dyke et al. |
| 5,965,559 | A | 10/1999 | Faull et al. |
| 5,965,569 | A | 10/1999 | Camps Garcia et al. |
| 5,984,882 | A | 11/1999 | Rosenschein et al. |
| 6,262,113 | B1 | 7/2001 | Widdowson et al. |

(Continued)

FOREIGN PATENT DOCUMENTS

| | | | |
|---|---|---|---|
| CN | 101296909 | A | 10/2008 |
| CN | 101307029 | A | 11/2008 |

(Continued)

OTHER PUBLICATIONS

International Search Report for PCT/US2011044254 dated May 10, 2011.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Ito et al. "A medium-term rat liver bioassay for rapid in vivo detection of carcinogenic potential of chemicals," Cancer Sci., 2003, 94(1):3-8.

(Continued)

*Primary Examiner* — Adam C Milligan
*Assistant Examiner* — Jed A Kucharczk
(74) *Attorney, Agent, or Firm* — GOODWIN PROCTER LLP

(57) ABSTRACT

Provided are compounds useful for treating cancer and methods of treating cancer comprising administering to a subject in need thereof a compound described herein.

20 Claims, No Drawings

(56) References Cited

U.S. PATENT DOCUMENTS

| | | | |
|---|---|---|---|
| 6,274,620 | B1 | 8/2001 | Labrecque et al. |
| 6,313,127 | B1 | 11/2001 | Waterson et al. |
| 6,399,358 | B1 | 6/2002 | Williams et al. |
| 6,576,235 | B1 | 6/2003 | Williams et al. |
| 6,723,730 | B2 | 4/2004 | Bakthavatchalam et al. |
| 6,783,965 | B1 | 8/2004 | Sherman et al. |
| 6,979,675 | B2 | 12/2005 | Tidmarsh |
| 7,173,025 | B1 | 2/2007 | Stocker et al. |
| 7,858,782 | B2 | 12/2010 | Tao et al. |
| 8,133,900 | B2 | 3/2012 | Hood et al. |
| 8,465,673 | B2 | 6/2013 | Yasuda et al. |
| 9,474,779 | B2 | 10/2016 | Lemieux et al. |
| 9,579,324 | B2 | 2/2017 | Konteatis et al. |
| 10,017,495 | B2 | 7/2018 | Travins et al. |
| 10,028,961 | B2 | 7/2018 | Konteatis et al. |
| 10,172,864 | B2 | 1/2019 | Konteatis et al. |
| 10,376,510 | B2 | 8/2019 | Konteatis et al. |
| 2002/0049310 | A1 | 4/2002 | Tateishi et al. |
| 2002/0188027 | A1 | 12/2002 | Robinson et al. |
| 2003/0095958 | A1 | 5/2003 | Bhisetti et al. |
| 2003/0109527 | A1 | 6/2003 | Jin et al. |
| 2003/0207882 | A1 | 11/2003 | Stocker et al. |
| 2003/0213405 | A1 | 11/2003 | Harada et al. |
| 2004/0067234 | A1 | 4/2004 | Einat et al. |
| 2004/0248221 | A1 | 12/2004 | Stockwell |
| 2005/0261268 | A1 | 11/2005 | Arnost et al. |
| 2006/0084645 | A1 | 4/2006 | Pal et al. |
| 2006/0281122 | A1 | 12/2006 | Bryant et al. |
| 2007/0244088 | A1 | 10/2007 | Brickmann et al. |
| 2008/0132490 | A1 | 6/2008 | Bergman et al. |
| 2008/0300208 | A1 | 12/2008 | Einat et al. |
| 2009/0093526 | A1 | 4/2009 | Miller et al. |
| 2009/0163508 | A1 | 6/2009 | Kori et al. |
| 2009/0163545 | A1 | 6/2009 | Goldfarb |
| 2009/0281089 | A1 | 11/2009 | Gunzner et al. |
| 2010/0129350 | A1 | 5/2010 | Zacharie et al. |
| 2010/0144722 | A1 | 6/2010 | Alexander et al. |
| 2010/0273808 | A1 | 10/2010 | Armitage et al. |
| 2010/0331307 | A1 | 12/2010 | Salituro et al. |
| 2011/0073007 | A1 | 3/2011 | Yasuda et al. |
| 2011/0086088 | A1 | 4/2011 | Berry |
| 2011/0183954 | A1 | 7/2011 | Almeida et al. |
| 2011/0288065 | A1 | 11/2011 | Fujihara et al. |
| 2012/0121515 | A1 | 5/2012 | Dang et al. |
| 2012/0129865 | A1 | 5/2012 | Wang et al. |
| 2012/0164143 | A1 | 6/2012 | Teeling et al. |
| 2012/0202818 | A1 | 8/2012 | Tao et al. |
| 2012/0238576 | A1 | 9/2012 | Tao et al. |
| 2012/0277233 | A1* | 11/2012 | Tao ...................... C07D 401/04 544/212 |
| 2013/0035329 | A1 | 2/2013 | Saunders et al. |
| 2013/0109643 | A1 | 5/2013 | Riggins et al. |
| 2013/0183281 | A1 | 7/2013 | Su et al. |
| 2013/0184222 | A1 | 7/2013 | Popovici-Muller et al. |
| 2013/0190249 | A1 | 7/2013 | Lemieux et al. |
| 2013/0190287 | A1 | 7/2013 | Cianchetta et al. |
| 2013/0197106 | A1 | 8/2013 | Fantin et al. |
| 2014/0187435 | A1 | 7/2014 | Dang et al. |
| 2014/0206673 | A1 | 7/2014 | Cao et al. |
| 2014/0213580 | A1 | 7/2014 | Cao et al. |
| 2015/0018328 | A1 | 1/2015 | Konteatis et al. |
| 2015/0031627 | A1 | 1/2015 | Lemieux et al. |
| 2015/0044716 | A1 | 2/2015 | Balss et al. |
| 2015/0087600 | A1 | 3/2015 | Popovici-Muller et al. |
| 2015/0240286 | A1 | 8/2015 | Dang et al. |
| 2015/0299115 | A1 | 10/2015 | Popovici-Muller et al. |
| 2015/0315182 | A1 | 11/2015 | Lee et al. |
| 2016/0158230 | A1 | 6/2016 | Konteatis et al. |
| 2016/0159771 | A1 | 6/2016 | Travins et al. |
| 2016/0220572 | A1 | 8/2016 | Konteatis et al. |
| 2016/0264621 | A1 | 9/2016 | Popovici-Muller et al. |
| 2017/0015703 | A1 | 1/2017 | Popovici-Muller et al. |
| 2017/0107194 | A1 | 4/2017 | Konteatis et al. |
| 2017/0298045 | A1 | 10/2017 | Cianchetta et al. |
| 2019/0117661 | A1 | 4/2019 | Konteatis et al. |
| 2019/0161473 | A1 | 5/2019 | Wang et al. |

FOREIGN PATENT DOCUMENTS

| | | | |
|---|---|---|---|
| CN | 101575408 | A | 11/2009 |
| CN | 102573481 | A | 7/2012 |
| CN | 102573485 | A | 7/2012 |
| CN | 102573487 | A | 7/2012 |
| CN | 102659765 | A | 9/2012 |
| CN | 103097340 | A | 5/2013 |
| DE | 2263878 | A1 | 7/1973 |
| DE | 3103110 | A1 | 8/1982 |
| DE | 3314663 | A1 | 10/1983 |
| DE | 3512630 | A1 | 10/1986 |
| EP | 0022958 | A1 | 1/1981 |
| EP | 0384228 | A1 | 8/1990 |
| EP | 0385237 | A2 | 9/1990 |
| EP | 0834523 | A1 | 4/1998 |
| EP | 0945446 | A1 | 9/1999 |
| EP | 1391487 | A2 | 2/2004 |
| FR | 2735127 | A1 | 12/1996 |
| GB | 1033266 | A | 6/1966 |
| JP | S5170779 | A | 6/1976 |
| JP | H04099768 | A | 3/1992 |
| JP | H05140126 | A | 6/1993 |
| JP | H09291034 | A | 11/1997 |
| JP | H11158073 | A | 6/1999 |
| JP | 2004107220 | A | 4/2004 |
| JP | 2005264016 | A | 9/2005 |
| JP | 2009237115 | A | 10/2009 |
| JP | 2010079130 | A | 4/2010 |
| JP | 2010181540 | A | 8/2010 |
| JP | 4753336 | B2 | 8/2011 |
| JP | 4753363 | B2 | 8/2011 |
| JP | 2013519858 | A | 5/2013 |
| MX | 2013/000614 | A | 6/2013 |
| TW | 201028381 | A | 8/2010 |
| WO | 1996030343 | A1 | 10/1996 |
| WO | 9728128 | A1 | 8/1997 |
| WO | 9728129 | A1 | 8/1997 |
| WO | 1997044322 | A1 | 11/1997 |
| WO | 1999031088 | A1 | 6/1999 |
| WO | 9932463 | A1 | 7/1999 |
| WO | 00002864 | A1 | 1/2000 |
| WO | 2000025780 | A1 | 5/2000 |
| WO | 2001016097 | A1 | 3/2001 |
| WO | 2001019788 | A2 | 3/2001 |
| WO | 2001019798 | A2 | 3/2001 |
| WO | 01/047897 | A1 | 7/2001 |
| WO | 2001064642 | A2 | 9/2001 |
| WO | 2001064643 | A2 | 9/2001 |
| WO | 2002/102313 | A2 | 12/2002 |
| WO | 2002100822 | A1 | 12/2002 |
| WO | 030016289 | A1 | 2/2003 |
| WO | 2003055930 | A1 | 7/2003 |
| WO | 2003078426 | A1 | 9/2003 |
| WO | 2003087057 | A1 | 10/2003 |
| WO | 2004009562 | A1 | 1/2004 |
| WO | 2004046120 | A2 | 6/2004 |
| WO | 2004050033 | A2 | 6/2004 |
| WO | 2004073619 | A2 | 9/2004 |
| WO | 2004074438 | A2 | 9/2004 |
| WO | 2004089470 | A2 | 10/2004 |
| WO | 2004099163 | A1 | 11/2004 |
| WO | 2005003103 | A2 | 1/2005 |
| WO | 2005035507 | A2 | 4/2005 |
| WO | 2005/065691 | A1 | 7/2005 |
| WO | 2005060956 | A1 | 7/2005 |
| WO | 2005103015 | A1 | 11/2005 |
| WO | 2005120474 | A2 | 12/2005 |
| WO | 2006034341 | A2 | 3/2006 |
| WO | 2006038594 | A1 | 4/2006 |
| WO | 2006070198 | A1 | 7/2006 |
| WO | 2006079791 | A1 | 8/2006 |
| WO | 2006/110761 | A2 | 10/2006 |
| WO | 2007003934 | A2 | 1/2007 |
| WO | 2007023186 | A1 | 3/2007 |

(56) References Cited

FOREIGN PATENT DOCUMENTS

| | | | |
|---|---|---|---|
| WO | 2007095812 | A1 | 8/2007 |
| WO | 2008036835 | A2 | 3/2008 |
| WO | 2008050168 | A1 | 5/2008 |
| WO | 2008052190 | A2 | 5/2008 |
| WO | 2008070661 | A1 | 6/2008 |
| WO | 2008073670 | A2 | 6/2008 |
| WO | 2008076883 | A2 | 6/2008 |
| WO | 2008131547 | A1 | 11/2008 |
| WO | 2008154026 | A1 | 12/2008 |
| WO | 2009013126 | A1 | 1/2009 |
| WO | 2009015254 | A1 | 1/2009 |
| WO | 2009016410 | A2 | 2/2009 |
| WO | 2009049157 | A1 | 4/2009 |
| WO | 2009091388 | A2 | 7/2009 |
| WO | 2009/126863 | A2 | 10/2009 |
| WO | 2009118567 | A2 | 10/2009 |
| WO | 2009150248 | A1 | 12/2009 |
| WO | 2009150462 | A1 | 12/2009 |
| WO | 2010007756 | A1 | 1/2010 |
| WO | 2010028099 | A1 | 3/2010 |
| WO | 2010105243 | A1 | 9/2010 |
| WO | 2010129596 | A1 | 11/2010 |
| WO | 2010130638 | A1 | 11/2010 |
| WO | 2010/144359 | A1 | 12/2010 |
| WO | 2010/144394 | A1 | 12/2010 |
| WO | 2010/144522 | A1 | 12/2010 |
| WO | 2010144338 | A1 | 12/2010 |
| WO | 2010144404 | A1 | 12/2010 |
| WO | 201105210 | A1 | 1/2011 |
| WO | 2011002817 | A1 | 1/2011 |
| WO | 2011/027249 | A2 | 3/2011 |
| WO | 2011032169 | A2 | 3/2011 |
| WO | 2011/050210 | A1 | 4/2011 |
| WO | 2011047432 | A1 | 4/2011 |
| WO | 2011072174 | A1 | 6/2011 |
| WO | 2012/009678 | A1 | 1/2012 |
| WO | 2012006506 | A1 | 1/2012 |
| WO | 2012074999 | A1 | 6/2012 |
| WO | 2012092442 | A1 | 7/2012 |
| WO | 2012151452 | A1 | 11/2012 |
| WO | 2012160034 | A1 | 11/2012 |
| WO | 2012171337 | A1 | 12/2012 |
| WO | 2012171506 | A1 | 12/2012 |
| WO | 2012173682 | A2 | 12/2012 |
| WO | 2013/007708 | A1 | 1/2013 |
| WO | 2013004332 | A1 | 1/2013 |
| WO | 2013016206 | A1 | 1/2013 |
| WO | 2013/107291 | A1 | 7/2013 |
| WO | 2013102431 | A1 | 7/2013 |
| WO | 2013107405 | A1 | 7/2013 |
| WO | 2013/133367 | A1 | 9/2013 |
| WO | 2014015422 | A1 | 1/2014 |
| WO | 2015/003360 | A2 | 1/2015 |
| WO | 2015003640 | A1 | 1/2015 |
| WO | 2015006592 | A1 | 1/2015 |
| WO | 2015017821 | A2 | 2/2015 |
| WO | 2015018060 | A1 | 2/2015 |
| WO | 2017066571 | A1 | 4/2017 |
| WO | 2018048847 | A1 | 3/2018 |

OTHER PUBLICATIONS

Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.

Jennings et al., Expression and mutagenesis of mammalian cytosolic NADP+-specific isocitrate dehydrogenase, Biochemistry (1997)vol. 36, pp. 13743-13747.

Jin et al. "Substituted 3-(4-(1,3,5-triazin-2-yl)-phenyl)-2-aminopropanoic acids as novel triptophan hydroxylase inhibitors," Bioorganic & Medicinal Chemistry Letters, 2009, 19:5229-5232.

Kaila et al. "A convenient one-pot synthesis of trisubstituted 1,3,5-triazines through intermediary amidinothioureas" Tetrahedron Letters (2010) vol. 51, pp. 1486-1489.

Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.

Kim et al "Ser95, Asn97, and Thr78 are important for the catalytic function of porcine NADP-dependent isocitrate dehydrogenase" Protein Science (2005) 14: pp. 140-147.

Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.

Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.

Kranendijk et al. "IDH2 Mutations in Patients with D-2-Hydroxyglutaric Aciduria" Science (2010) vol. 330, p. 336.

Krell et al., "IDH mutations in tumorigenesis and their potential role as novel therapeutic targets" Future Oncology (2013) vol. 9, Iss 12, pp. 1923-1935.

Kumar et al., "4-Anilinoquinoline triazines: A novel class of hybrid antimalarial agents" European Journal of Medicinal Chemistry (2011) vol. 46, pp. 676-690.

Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.

Kusakabe et al. Chemical Abstracts vol. 152, No. 191956, Abstract for WO2010007756 (2010).

Lee et al. "Combinatorial Solid-Phase Synthesis of 6-Aryl-1,3,4-triazines via Suzuki Coupling" Aust. J. Chem. (2011) vol. 64, pp. 540-544.

Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.

Lou. "IDH1: function follows form." SciBX, 2009, 1-2.

Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.

Madsen-Duggan et al. "Lead optimization of 5.6-diarylpyridines as CB1 receptor inverse agonists" Bioorganic & Medicinal Chemistry Letters (2007) vol. 17, pp. 2031-2035.

Maison, "Multicomponent synthesis of novel amino acid-nucleobase chimeras: a versatile approach to PNA-monomers," Bioorganic & Medicinal Chemistry (2000) vol. 8, pp. 1343-1360.

May et al, How many species are there on earth, Science (1988) vol. 241, p. 1441.

McRobbie et al. "MRI from Picture to Proton," Cambridge University Press, 2007, pp. 307-308.

Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.

Mikhaylichenko, Svetlana, et al. "Synthesis and structure of new 1, 2, 3-triazolyl substituted 1, 3, 5-triazines." European Journal of Chemistry 3.1 (2012): 1-9.

Moffatt. "Contributions to the chemistry of synthetic antimalarials. Part IX. Some pyrimidine derivatives," Journal of the Chemical Society, 1950, 1603-6.

Moreno et al. "Identification of diamine linkers with differing reactivity and their applicationin the synthesis of melamine dendrimers" Tetrahedron Letters (2008) vol. 49, pp. 1152-1154.

Moreno et al. "Molecular recognition in dendrimers based on melamine" Polymer Preprints (2005) vol. 46, No. 2, pp. 1127.

Paronikyan et al. "Synthesis and biological activity of 3-piperazinylpyrano [3,4-C] pyridines" Armyanskii Khimicheskii Zhurnal (1990) vol. 43, No. 8, pp. 518-523.

Parsons et al. "An Integrated Genomic Analysis of Human Glioblastoma Multiforme" Science vol. 321 (2008) pp. 1807-1812 and Supplemental Data.

Pitts et al., "Rapid Synthesis of Triazine Inhibitors of Inosine Monophosphate Dehydrogenase," Bioorganic & Medicinal Chemistry Letters (2002) vol. 12, pp. 2137-2140.

(56) References Cited

OTHER PUBLICATIONS

Pollard et al, "Cancer. Puzzling patterns of predisposition." Science. Apr. 10, 2009, vol. 324, 1-5, 15-16, 18-22,35-38 No. 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
PubChem Compound—pccompound 1-200 of 487, create date 2008-2012, search date Aug. 29, 2017.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Jul. 3, 2008, CAS Registration No. 1032461-94-1.
Registry (STN) [online], Jul. 3, 2008, CAS Registration No. 1032470-22-6.
Registry (STN) [online], Jul. 4, 2008, CAS Registration No. 1032747-65-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Apr. 16, 2010, CAS Registration No. 1219379-97-1.
Reitman et al. "Article Navigation Isocitrate Dehydrogenase 1 and 2 Mutations in Cancer: Alterations at a Crossroads of Cellular Metabolism," J Natl Cancer Inst, 2010, vol. 102, No. 13, p. 932-941.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Rohle et al. "An Inhibitor of Mutant IDH1 Delays Growth and Promotes Differentiation of Glioma Cells" Science, vol. 340, No. 6132 pp. 626-630 (2013).
Saleh et al. "Synthesis and antimicrobial activity of 2-fluorophenyl-4,6-disubstituted [1,3,5]triazines," Bioorganic & Medicinal Chemistry Letters, 2010, 20(3):945-949.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
Shih et al. "The Role of Mutations in Epigenetic Regulators in Myeloid Malignancies" Nature Reviews Cancer (2012) vol. 12, No. 9, pp. 599-612.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
STN Accession No. 2007:612528.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 228575-14-2, entered STN on Jul. 22, 1999, Chemical Abstracts Index Name "4,6-Pyrminidinediamine, N4-cyclohexyl-N6, 2-diphenyl-".
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN registry database compound 1111735-41-1, entered STN Feb. 25, 2009.
STN registry database compound 228575-15-3 (entered STN Jul. 22, 1999).
STN registry database compound 68935-65-9 (entered STN Nov. 16, 1984).
STN Registry, L23 Answer 2 oF 3 (Cas No. 1032450-21-7), Database: Asinex Ltd.,Entered STN: Jul. 3, 2008 (Jul. 3, 2008).
STN Registry. L23 Answer 1 of 3 (Cas No. 1038821-72-5), Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-1-piperazinyl)carbonyl]phenyl]-- ".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-1-piperazinyl]carbonyl]phenyl]-".

(56) References Cited

OTHER PUBLICATIONS

STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-1-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl]-2, 3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-1-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters 92004 vol. 557, pp. 115-120.
Struys et al. "Mutations in the D-2-hydroxyglutarate dehydrogenase gene cause D-2-hydroxyglutaric aciduria" American Journal of Human Genetics, 2005. 76:358-360.
Struys, EA. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.
Aghili et al. "Hydroxyglutaric aciduria and malignant brain tumor: a case report and literature review", Journal of Neuroncology, 2008. 91:233-236.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Arulmurugan et al. "Synthesis and potential cytotoxic activity of some new benzoxazoles, imidazoles, benzimidazoles and tetrazoles," Acta Pharmaceutica, 2013, 63(2):253-264.
Balss, "Analysis of the IDH1 codon 132 mutation in brain tumors", Acata Neuropathol (2008) vol. 116, pp. 597-602.
Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p.R132 (IDH1 (R132)) occur frequently in high-grade 18-22 gliomas but not in other solid tumors." Hum Mutal., Jan. 2009, vol. 30, No. 1, pp. 7-11.
Bork et al. "Palladium-catalyzed cross-coupling reaction of resin-bound chlorotriazines," Tetrahedron Letters, 2003, 44(32):6141-6144.
Braun et al. "Triazine-based polymers: 4. MALDI-MS of triazine-based polyamines" Polymer (1996) vol. 37, No. 5, pp. 777-783.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cas Reg No. 1242468-06-9, STN Entry Date Sep. 23, 2010; 6-[(3R)-3-(aminomethyl)-1-piperidinyl]-N2-[(1S)-1-(5-fluoro-2-pyrimidinyl)ethyl]-N4-(5-methyl-1H-pyrazol-3-yl)-1,3,5-triazine-2,4-diamine.
Cas Reg No. 1242816-34-7, STN Entry Date Sep. 26, 2010; 6-[(3R)-3-amino-1-piperidinyl]-N2-[(1S)-1-(5-fluoro-2-pyrimidinyl)ethyl]-N4-(5-methyl-1H-pyrazol-3-yl)-1,3,5-triazine-2,4-diamine.
Cas Reg No. 1242816-35-8, STN Entry Date Sep. 26, 2010; 6-[(3S)-3-amino-1-piperidinyl]-N2-[(1S)-1-(5-fluoro-2-pyrimidinyl)ethyl]-N4-(5-methyl-1H-pyrazol-3-yl)-1,3,5-triazine-2,4-diamine.
Cas Reg No. 1242816-38-1, STN Entry Date Sep. 26, 2010; 6-[(3S)-3-(aminomethyl)-1-piperidinyl]-N2-[(1S)-1-(5-fluoro-2-pyrimidinyl)ethyl]-N4-(5-methyl-1H-pyrazol-3-yl)-1,3,5-triazine-2,4-diamine.
Cas RN 21834-29-7 (entered STN Nov. 16, 1984).
Cas RN 50377-40-7 (Entered STN: Nov. 16, 1984).
Cas RN 942045-38-7 (entered into STN Jul. 10, 2007).
Cecil Textbook of Medicine, edited by Bennet, J.C., and Plum F., 20th edition, vol. 1, 1004-1010, 1996.
Chan et al. "Multi-domain hydrogen-bond forming metal chelates: X-ray crystal structuresof dicyclopalladated 2,3-bis [6-(2-amino-4-phenylamino-1 ,3,5-triazinyl)]pyrazine(H2L) [Pd2Br2L] and 2,6-bis[6-(2-amino-4-phenylamino-1,3,5-triazinylium)]-pyridine dichloride" Chemical Communications (1996) No. 1, pp. 81-83.

(56) References Cited

OTHER PUBLICATIONS

Chapman et al. "Substituted aminopyrimidine protein kinase B (PknB) inhibitorsshow activity against *Mycobacterium tuberculosis*" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry, 1995. vol. 32 pp. 543-545.
Courme et al. "Synthesis of aryl phosphates based on pyrimidine and triazine scaffolds," European Journal of Medicinal Chemistry, 2010, 46:244-255.
Dang et al., "Cancer-associated IDH1 mutations produce 2-hydroxyglutarate." Nature, 10 29-32 Dec. 2009, vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Database CA [Online] Chemical Abstracts Service, Columbus, Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 Coden: KZARF3; ISSN: 1561-4190, 2011.
Database CA [Online] Chemical Abstracts Service. Columbus.Ohio. US; Baibulova M. S. et al:Syntheses from pyridylguanamines"_ XP002764691. retrieved from STN Database accession No. 1990:406282 *abstract* & Bai Bulova, M. S. et al: Syntheses from pyridylguanamines", Izvestiya Akademii Nauk Kazakhskoi SSR, Seriya Khimicheskaya, (5), 40-2 Coden: Ikakak; ISSN: 0002-3205, 1989.
Database CA [Online] Chemical Abstracts Service. Columbus.Ohio. US; Krimmer. Hans Peter et al: "Reaction of .beta.-mercapto .alpha.-amino acids with nitriles".XP002764690. retrieved from STN Database accession No. 1988:529623* abstract* & Krimmer. Hans Peter et al: "Reaction of .beta.-mercapto .alpha.-amino acids with nitriles".Chemiker-Zeitung â€¢ 111(12). 357-61 Coden: Cmkzat; ISSN: 0009-2894.1987.
Database Registry [Online] Chemical Abstracts Service, Columbus, Ohio, US; Aug. 6, 2002, accession No. 442648-48-8.
Database Registry [Online] Retrieved from STN, Entered STN: Feb. 25, 2009, Date of search: Apr. 24, 2018, CAS Registry No. 1111680-26-2.
Database Registry [Online] Retrieved from STN, Entered STN: Feb. 25, 2009, Date of search: Apr. 24, 2018, CAS Registry No. 1111713-81-5.
Database Registry [Online] Retrieved from STN, Entered STN: Feb. 25, 2009, Date of search: Apr. 24, 2018, CAS Registry No. 1111714-20-5.
Database Registry [Online] Retrieved from STN, Entered STN: Feb. 25, 2009, Date of search: Apr. 24, 2018, CAS Registry No. 1111734-89-4.
Database Registry [Online] Retrieved from STN, Entered STN: Feb. 25, 2009, Date of search: Apr. 24, 2018, CAS Registry No. 1111744-53-6.
Database Registry [Online] Retrieved from STN, Entered STN: Feb. 25, 2009, Date of search: Apr. 24, 2018, CAS Registry No. 1111752-20-5.
Database Registry [Online] Retrieved from STN, Entered STN: Feb. 25, 2009, Date of search: Apr. 24, 2018, CAS Registry No. 1111766-41-6.
Database Registry [Online] Retrieved from STN, Entered STN: Feb. 25, 2009, Date of search: Apr. 24, 2018, CAS Registry No. 1111766-65-4.
Database Registry [Online] Retrieved from STN, Entered STN: Feb. 25, 2009, Date of search: Apr. 24, 2018, CAS Registry No. 1111766-90-5.
Database Registry [Online] Retrieved from STN, Entered STN: Feb. 25, 2009, Date of search: Apr. 24, 2018, CAS Registry No. 1111855-40-3.
Database Registry [Online] Retrieved from STN, Entered STN: Feb. 25, 2009, Date of search: Apr. 24, 2018, CAS Registry No. 1111862-93-1.
Database Registry [Online] Retrieved from STN, Entered STN: Feb. 25, 2009, Date of search: Apr. 24, 2018, CAS Registry No. 1111885-63-2.
Database Registry [Online] Retrieved from STN, Entered STN: Feb. 25, 2009, Date of search: Apr. 24, 2018, CAS Registry No. 1111894-77-9.
Database Registry [Online] Retrieved from STN, Posted on Feb. 10, 2014, Search date: Apr. 6, 2018, CAS Registry No. 1540600-93-8.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer et al., "Another Anniversary for the War on Cancer", Bio/Technology, 1994, 12:320.
Desai et al. "Synthesis of a novel class of some 1,3,5-triazine derivatives and their anti-HIV activity," International Journal of Drug Design and Discovery, 2011, 2(1):361-368.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Drew, MGB, et al. "Solvent extraction and lanthanide complexation studies with new terdentate ligands containing two 1, 3, 5-triazine moieties." Dalton Transactions 2 (2004): 244-251.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Supplementary European Search Report for EP Application No. 10825707.2 dated Jun. 28, 2013.
Supplementary Search Report for EP10794668 Mailed Oct. 18, 2012.
Supplimentary European Search Report for EP 10751525 Mailed Dec. 14, 2012.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Wang et al. "A novel ligand N,N?-di(2-pyridyl)-2,4-diamino-6-phenyl-1,3,5-triazine (dpdapt) and its complexes: [Cu (dpdapt)Cl2] and [Cu(dpdapt)(NO3)(H2O)] Â· NO3 Â· H2O" Polyhedron, 2006. vol. 25, Issue 1. pp 195-202.
Ward, Patrick S, "The Common Feature of Leukemia-Associated IDH1 and IDH2 Mutations Is a Neomorphic Enzyme Activity Converting [alpha]-Ketoglutarate to 2-Hydroxyglutarate" Cancer cell, vol. 17,Nr:3, pp. 225-234, 2010.
Watanabe et al., "IDH1 Mutations Are Early Events in the Development of Astrocytomas and Oligodendrogliomas". American Journal of Pathology, Apr. 2009 (published online Feb. 26, 2009), vol. 174, No. 4, pp. 1149-1153; Abstract, p. 1150, col. 1.
Written Opinion for PCT/US2010/027253 mailed Aug. 19, 2010.

(56) References Cited

OTHER PUBLICATIONS

Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas" The New England Journal of Medicine, 79 Feb. 18-22, 2009, vol. 360, No. 8, pp. 765-773.
Yrjola et al., "Discovery of novel cannabinoid receptor ligands by a virtual screening approach: Further development of 2,4,6-trisubstituted 1,3,5-triazines as CB2 agonists," European Journal of Pharmaceutical Sciences (2013) vol. 48, pp. 9-20.
Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Padalkar et al. "Synthesis of novel fluorescent 1,3,5-trisubstituted triazine derivatives and photophysical property evaluation of fluorophores and their BSA conjugates," Heterocyclic Communications, 2012, 18(3): 127-134.
International Search Report and Written Opinion for International Application No. PCT/US2022/015994 dated May 3, 2022.
Konteantis et al., Vorasidenib (AG-881): A First-in-Class, Brain-Penetrant Dual Inhibitor of Mutant IDH1 and 2 for Treatment of Glioma, ACS Med. Chem Lett. 2020, 11, 101-107 (Year: 2020).
Enholm, EJ., Jed M. Hastings, and Chris Edwards. "Hydrogen-Bonded Arrays Coupled by Cross-Metathesis." Synlett Feb. 2008 (2008): 203-206.
EP Search Report & Written Opinion for EP 10825706 Dated Mar. 20, 2013.
EP10751525.6—European Search Report, dated Dec. 14, 2012.
European Search Report for European Application No. 12799802.9 dated Sep. 24, 2014.
European Search Report for European Application No. EP 12800001.5 dated Oct. 10, 2014.
Eurpoean Search Report for EP Application No. 11763425.3 dated Sep. 23, 2013.
Extended European Search Report for European application No. 14823630.0 dated Oct. 21, 2016.
Extended European Search Report for European application No. 16152308.9 dated Jul. 18, 2016.
Extended European Search Report for PCT/CN2014081957 dated Dec. 9, 2016.
Freshney et al., Culture of Animal Cells, A Manual of Basic Technique, Alan R. Liss, Inc., 1983, New York, p. 4.
Genetics Home Reference. "L2HGDH." accessed at <http://ghr.nlm.nih.gov/gene/L2HGDH> on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Holmes et al., 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
Intemational Search Report for PCT/CN2013/000068 dated Apr. 25, 2013.
Intemational Search Report for PCT/UUS2010053624 dated Apr. 7, 2011.
International Preliminary Report for related application No. PCT/US2010/059778 dated Jun. 21, 2012.
International Preliminary Report for related application No. PCT/US2011/067752 dated Apr. 11, 2013.
International Preliminary Report on Patentability for Application No. PCT/US2010/053623 dated Apr. 24, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 mailed Sep. 13, 2011.
International Preliminary Report on Patentability for PCT/US2010/040486 dated Jan. 12, 2012.
International Preliminary Report on Patentability for PCT/US2010/053624 dated Apr. 7, 2011.
International Preliminary Report on Patentability for PCT/US2011/030692 dated Oct. 2, 2012.
International Search Report & Written Opinion for PCT/CN2013/070755 dated Apr. 25, 2013.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US15/020349 dated Jun. 15, 2015.
International Search Report and Written Opinion for International Application No. PCT/US2014/046202 dated Sep. 30, 2014.
International Search Report and Written Opinion for International Application No. PCT/US2014/049469 dated Jan. 22, 2015.
International Search Report and Written Opinion for International Application No. PCT/US2015/020346 dated Jun. 18, 2015.
International Search Report dated Mar. 5, 2012 for related international application No. PCT/US2011/067752.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/CN2014/082869 dated Sep. 30, 2014.
International Search Report for International Application No. PCT/US2014/046204 dated Oct. 1, 2014.
International Search Report for PCT/CN2012/000841 dated Sep. 27, 2012.
International Search Report for PCT/CN2012/077096 dated Oct. 4, 2012.
International Search Report for PCT/CN2013/000009 dated Apr. 18, 2013.
International Search Report for PCT/US10/040486 dated Sep. 1, 2010.
International Search Report for PCT/US201/030692 dated Jul. 27, 2011.
International Search Report for PCT/US2010/027253 mailed Aug. 19, 2010.
International Search Report for PCT/US2010/059778 dated Mar. 17, 2011.
International Search Report for PCT/US2010/53623 dated Jan. 18, 2011.
U.S. Appl. No. 14/328,885, filed Jul. 11, 2014, Zenon Konteatis et al.

(56) References Cited

OTHER PUBLICATIONS

U.S. Appl. No. 15/093,345, filed Apr. 7, 2016, Zenon Konteatis et al.
U.S. Appl. No. 15/392,681, filed Dec. 28, 2016, Zenon Konteatis et al.
U.S. Appl. No. 16/167,725, filed Oct. 23, 2018, Zenon Konteatis et al.
U.S. Appl. No. 17/158,867, filed Jan. 26, 2021, Zenon Konteatis et al.
U.S. Appl. No. 14/903,952, filed Jan. 8, 2016, Travins et al.
U.S. Appl. No. 17/668,649, filed Feb. 10, 2022, Prakash.
U.S. Appl. No. 18/479,185, filed Oct. 2, 2023, Prakash.

* cited by examiner

THERAPEUTICALLY ACTIVE COMPOUNDS AND THEIR METHODS OF USE

CLAIM OF PRIORITY

This application is a continuation of U.S. Ser. No. 17/158,867, filed Jan. 26, 2021, which is a continuation of U.S. Ser. No. 16/167,725, filed Oct. 23, 2018, now U.S. Pat. No. 10,946,023, which is a continuation of U.S. application Ser. No. 15/392,681 filed Dec. 28, 2016, now U.S. Pat. No. 10,172,864, which is a continuation of U.S. application Ser. No. 14/328,885 filed Jul. 11, 2014, now U.S. Pat. No. 9,579,324, which claims priority from International Application Serial No. PCT/CN2013/079200 filed Jul. 11, 2013, and International Application Serial No. PCT/CN2014/081957 filed Jul. 10, 2014, each of which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December-2008) to UniProtKB; Kullmann et al., Submitted (June-1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate thereby reducing $NAD^+$ ($NADP^+$) to NADH (NADPH), e.g., in the forward reaction:

$$\text{Isocitrate}+NAD^+(NADP^+)\rightarrow\alpha\text{-KG}+CO_2+NADH(NADPH)+H^+.$$

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al., Nature 2009, 462:739-44).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing $NAD^+$ ($NADP^+$) to NADH (NADPH), e.g., in the forward reaction:

$$\text{Isocitrate}+NAD^+(NADP^+)\rightarrow\alpha\text{-KG}+CO_2+NADH(NADPH)+H^+.$$

It has been discovered that mutations of IDH2 present in certain cancer cells result in a new ability of the enzyme to catalyze the NAPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

The inhibition of mutant IDH1 and/or mutant IDH2 and their neoactivity is therefore a potential therapeutic treatment for cancer. Accordingly, there is an ongoing need for inhibitors of IDH1 and/or IDH2 mutants having alpha hydroxyl neoactivity.

SUMMARY OF INVENTION

Described herein are compounds of Formula I, or a pharmaceutically acceptable salt or hydrate thereof:

(I)

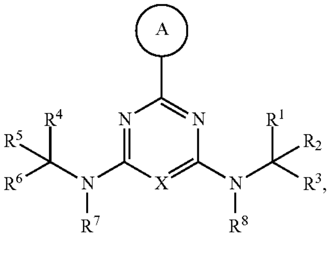

wherein:

- ring A is an optionally substituted 5-6 member monocyclic aryl or monocyclic heteroaryl;
- X is N, CH or C-halo;
- $R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;
- $R^2$ and $R^5$ are each independently selected from: —($C_1$-$C_6$ alkyl), —($C_1$-$C_6$ alkyl)-C(O)—$NH_2$, —($C_1$-$C_6$alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_1$-$C_6$ alkylene)-Q, —($C_1$-$C_6$ alkylene)-N($R^6$)($R^6$), —($C_1$-$C_6$ alkylene)-N($R^6$)—$S(O)_{1-2}$—($C_1$-$C_6$ alkyl), —($C_1$-$C_6$ alkylene)-N($R^6$)—$S(O)_{1-2}$—($C_0$-$C_6$ alkyl)-Q, —($C_1$-$C_6$ alkylene)-$S(O)_{1-2}$—N($R^6$)($R^6$), —($C_1$-$C_4$ alkylene)-$S(O)_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-$S(O)_{0-2}$—($C_1$-$C_6$ alkyl), —($C_0$-$C_6$ alkylene)-$S(O)_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, $C(O)CH_3$, $C(O)CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein:

(i) when X is N and A is optionally substituted phenyl, then (a) neither N($R^7$)C($R^4$)($R^5$)($R^6$) nor N($R^8$)C($R^1$)($R^2$)($R^3$) is $NHCH_2CH_2OCH_2CH_2OCH_2CH_2NH_2$, 4-[[2-[2-(2-aminoethoxy)ethoxy]ethyl]amino] and (b) N($R^7$)C($R^4$)($R^5$)($R^6$) and N($R^8$)C($R^1$)($R^2$)($R^3$) are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is CH or C—Cl and A is phenyl optionally substituted with F, Cl or $SO_2CH_3$, then neither N($R^7$)C($R^4$)($R^5$)($R^6$) nor N($R^8$)C($R^1$)($R^2$)($R^3$) is $N(CH_3)CH_2C(O)$NH-i-propyl, $NHCH(CH_3)(CH_2)_3N(CH_2CH_3)_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2CH(OH)CH_3$, $N(CH_2CH_3)_2$, NH-i-propyl, $NHCH_2CH_2NHC(O)OCH_3$, $NHCH_2CH_2NHC(O)CH_3$, $NHCH_2CH_2NH_2$, or $NHCH_2$-phenyl;

(iii) when X is CH and A is optionally substituted pyridyl, then neither N($R^7$)C($R^4$)($R^5$)($R^6$) nor N($R^8$)C($R^1$)($R^2$)($R^3$) is $NHCH_2$-phenyl, $NHCH_2$-(2,4-difluorophenyl), $N(CH_3)CH_2CH_2C(O)OH$, $NHCH_2CH_2C(O)OH$, $NHCH_2CH_2C(O)OCH_2CH_3$, $NHCH_2CH_2C(O)O$-t-butyl, $NHCH_2CH_2C(O)NH_2$, $NHCH_2CH_2$-phenyl, $NHCH_2CH_2OH$, $NHCH_2CH_2NH_2$, $NHCH_2CH_2N(CH_3)_2$, or $NHCH_2CH_2CH_3$;

(iv) when X is CH and A is optionally substituted 1-imidazolyl, optionally substituted 1-pyrrolyl or optionally substituted 1-pyrazolyl, then neither N($R^7$)C($R^4$)($R^5$)($R^6$) nor N($R^8$)C($R^1$)($R^2$)($R^3$) is $NH(CH_2)_7CH_3$, $NHCH_2$-(o-chloro-phenyl), or $NHCH_2CH_2OH$;

(v) when X is N and A is an optionally substituted pyridyl, then (A) neither N($R^7$)C($R^4$)($R^5$)($R^6$) nor N($R^8$)C($R^1$)($R^2$)($R^3$) is NHC(O)-[2-chloro-4-(methylsulfonyl)], $N(CH_3)_2$, $NHCH_2CH_2CH_2SO_2CH_2CH_2Cl$, $NHCH_2CH_2OCH_2CH_2SO_2CH_2CH_2Cl$, or $NHCH_2CH_2SO_2CH_2CH_2Cl$, (B) N($R^7$)C($R^4$)($R^5$)($R^6$) and N($R^8$)C($R^1$)($R^2$)($R^3$) are not both $NHC(O)C(CH_3)_3$, $NHC(O)CH{=}CH_2$, $NHC(O)C(CH_3){=}CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when N($R^7$)C($R^4$)($R^5$)($R^6$) is $NHC(CH_3)_3$, then N($R^8$)C($R^1$)($R^2$)($R^3$) is not $NHCH_2$-phenyl or NH—$CH_2CH_3$;

(vi) when X is N and A is an optionally substituted heteroaryl, then N($R^7$)C($R^4$)($R^5$)($R^6$) and N($R^8$)C($R^1$)($R^2$)($R^3$) are not both $N(CH_2CH_3)_2$, $NHCH_2CH_2$-i-propyl, $NHCH_2CH(CH_3)_2$, and $NHC(O)CH_3$;

(vii) when X is CH and A is unsubstituted 2-pyridinyl, then the ring formed by $R^4$ and $R^5$ is not 5-methyl-1H-pyrazol-3-yl;

(viii) when A is optionally substituted 1-pyrazolyl, then neither N($R^7$)C($R^4$)($R^5$)($R^6$) nor N($R^8$)C($R^1$)($R^2$)($R^3$) is $N(CH_3)_2$, $NHCH_3$, NHAc, NHisopropyl, $NHCH_2CH_3$, $NHCH_2CH_2SO_3H$ or $N(CH_2CH_3)_2$;

(ix) when X is N and A is optionally substituted phenyl, thienyl, or pyridinyl, then neither N($R^7$)C($R^4$)($R^5$)($R^6$) nor N($R^8$)C($R^1$)($R^2$)($R^3$) is NHcyclohexylC(O)$NHCH_2R$, wherein R is phenyl or pyridinyl which is substituted with one or more of $OCF_3$, $OCH_3$, chloro, or $CF_3$;

(x) when X is N, A is an optionally substituted phenyl and $R^4$ and $R^5$ form an optionally substituted phenyl, then N($R^8$)C($R^1$)($R^2$)($R^3$) is not $NHCH_2$(4-fluorophenyl), $NHCH_2CO_2H$, $NHCH_2C(O)Cl$, $NHCH(CO_2H)(CH_2SCH_2$phenyl), $NHCH_2C(O)NHC(O)NHR$ or $NHCH_2C(O)NHC(S)NHR$, wherein R is optionally substituted phenyl or naphthyl;

(xi) when X is N, A is an oxadiazole substituted with an optionally substituted pyridinyl, then $R^4$ and $R^5$ do not form an optionally substituted phenyl;

(xii) when A is substituted 1-pyrazolyl, then (A) then N($R^7$)C($R^4$)($R^5$)($R^6$) and N($R^8$)C($R^1$)($R^2$)($R^3$) are not both $NHC(CH_3)_3$, and (B) A is not substituted with N═N—R, wherein R is a ring;

(xiii) ring A is not an optionally substituted triazolyl, 3,5-dimethyl-1H-pyrazol-1-yl;

(xix) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl; and (xx) the compound is not selected from the group:

(1) N-(2-aminophenyl)-4-[[[4-[(2,3-dihydro-1H-inden-2-yl)amino]-6-phenyl-1,3,5-triazin-2-yl]amino]methyl]-benzamide;

(2) 2-chloro-N-[4-(cyclopropylamino)-6-(2-pyridinyl)-1,3,5-triazin-2-yl]-4-(methylsulfonyl)-benzamide;

(3) 2-[[1-[4-(cyclopropylamino)-6-(ethylamino)-1,3,5-triazin-2-yl]-1H-1,2,4-triazol-3-yl]thio]-acetamide;

(4) $N^2$-cyclopropyl-$N^4$-ethyl-6-[3-[(phenylmethyl)thio]-1H-1,2,4-triazol-1-yl]-1,3,5-triazine-2,4-diamine;

(5) 2-[[1-[4-(cyclopropylamino)-6-(ethylamino)-1,3,5-triazin-2-yl]-1H-1,2,4-triazol-3-yl]thio]-acetic acid methyl ester;

(6) N-[[4-[[[4-(cyclopropylamino)-6-(2-pyridinyl)-1,3,5-triazin-2-yl]amino]methyl]cyclohexyl] methyl]-4-fluoro-benzenesulfonamide;

(7) $N^2$-cyclopropyl-6-(3,5-dimethyl-1H-pyrazol-1-yl)-$N^4$-phenyl-1,3,5-triazine-2,4-diamine;

(8) $N^2$,$N^4$-dicyclohexyl-6-[3-(4-methoxyphenyl)-5-(methylthio)-1H-pyrazol-1-yl]-1,3,5-triazine-2,4-diamine;

(9) $N^2$,$N^4$-dicyclohexyl-6-[3-(3,4-dimethoxyphenyl)-5-(methylthio)-1H-pyrazol-1-yl]-1,3,5-triazine-2,4-diamine;

(10) $N^2$,$N^4$-dicyclohexyl-6-[5-(methylthio)-3-(3,4,5-trimethoxyphenyl)-1H-pyrazol-1-yl]-1,3,5-triazine-2,4-diamine;

(11) $N^2$,$N^4$-dicyclohexyl-6-phenyl-1,3,5-triazine-2,4-diamine;

(12) 1,1'-[(6-phenyl-s-triazine-2,4-diyl)diimino]bis[dodecahydro-anthraquinone];

(13) 4,4'-[(6-phenyl-1,3,5-triazine-2,4-diyl)bis(iminomethylene)]bis[2,6-bis(1,1-dimethylethyl)-phenol;

(14) N-[4-[(4-aminobutyl)amino]-6-[5-[[[[4-chloro-3-(trifluoromethyl)phenyl]amino]carbonyl] amino]-2-methylphenyl]-1,3,5-triazin-2-yl]-glycine;

(15) 4-[2-[[4-[(5-aminopentyl)amino]-6-(3-fluorophenyl)-1,3,5-triazin-2-yl]amino]ethyl]-phenol;

(16) 4-[2-[[4-[(5-aminopentyl)amino]-6-(4-fluorophenyl)-1,3,5-triazin-2-yl]amino]ethyl]-phenol;

(17) 6-(4-aminopyridin-3-yl)-$N^2$-benzyl-$N^4$-(tert-butyl)-1,3,5-triazine-2,4-diamine;

(18) $N^2$,$N^4$-bis(cyclohexylmethyl)-6-phenyl-1,3,5-triazine-2,4-diamine;

(19) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol;

(20) 4,4'-[(6-phenyl-1,3,5-triazine-2,4-diyl)bis(imino-3,1-propanediyl)]bis[2,6-bis(1,1-dimethylethyl)-phenol;

(21) N-[6-[(2,3-dihydro-1H-inden-2-yl)amino]-2-(2-pyridinyl)-4-pyrimidinyl]-3 alanine;

(22) $N^4$-cyclopentyl-2-phenyl-$N^6$-(phenylmethyl)-4,6-pyrimidinediamine;

(23) 2-[[6-(bicyclo[2.2.1]hept-2-ylamino)-2-phenyl-4-pyrimidinyl]amino]-ethanol;

(24) $N^2$-isopropyl-6-phenyl-N4-(tetrahydro-2H-pyran-4-yl)-1,3,5-triazine-2,4-diamine;

(25) 2-chloro-4-(methylsulfonyl)-N-[4-[(phenylmethyl)amino]-6-(2-pyridinyl)-1,3,5-triazin-2-yl]-benzamide;

(26) N-[[4-[[[4-(cyclopropylamino)-6-(2-pyridinyl)-1,3,5-triazin-2-yl]amino]methyl]cyclohexyl]methyl]-4-fluoro-benzenesulfonamide;

(27) [[4-[[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol;

(28) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino] bis-methanol;

(29) 5-[4,6-bis(diethylamino)-1,3,5-triazin-2-yl]-2H-tetrazole-2-acetic acid ethyl ester;

(30) $N^2$,$N^2$,$N^4$,$N^4$-tetraethyl-6-(2H-tetrazol-5-yl)-1,3,5-triazine-2,4-diamine;

(31) N,N-[6-[4-(acetylamino)-1,2,5-oxadiazol-3-yl]-1,3,5-triazine-2,4-diyl]bis-acetamide;

(32) N-(2-chloro-6-methylphenyl)-5-[[4-(dimethylamino)-6-(2-pyridinyl)-1,3,5-triazin-2-yl]amino]-1,3,4-Oxadiazole-2-carboxamide;

(33) N4-(5-methyl-1H-pyrazol-3-yl)-2-(2-pyridinyl)-N6-(tetrahydro-2H-pyran-4-yl)-4,6-Pyrimidinediamine;

(34) 6-(4-chlorophenyl)-N2-[4-chloro-3-(trifluoromethyl)phenyl]-N4-[3-(diethylamino)propyl]-1,3,5-Triazine-2,4-diamine;

(35) 6-(4-chlorophenyl)-N2-[4-chloro-3-(trifluoromethyl)phenyl]-N4-[3-(dimethylamino)propyl]-1,3,5-Triazine-2,4-diamine;

(36) N2-[3,5-bis(trifluoromethyl)phenyl]-6-(4-chlorophenyl)-N4-[3-(diethylamino)propyl]-1,3,5-Triazine-2,4-diamine;

(37) N2,N4-bis[(4-methoxyphenyl)methyl]-6-[4-(trifluoromethoxy)phenyl]-1,3,5-Triazine-2,4-diamine;

(38) N,N''-(6-phenyl-1,3,5-triazine-2,4-diyl)bis[N'-(2-chloroethyl)-Urea;

(39) N-[4-chloro-3-(trifluoromethyl)phenyl]-N'-[4-methyl-3-[[4-phenyl-6-(propylamino)-1,3,5-triazin-2-yl]amino] phenyl]-urea;

(40) N-[4-[[5-[[[[4-chloro-3-(trifluoromethyl)phenyl]amino]carbonyl]amino]-2-methylphenyl]amino]-6-(4-pyridinyl)-1,3,5-triazin-2-yl]-glycine;

(41) N-[4-[[5-[[[[4-chloro-3-(trifluoromethyl)phenyl]amino]carbonyl]amino]-2-methylphenyl]amino]-6-(5-thiazolyl)-1,3,5-triazin-2-yl]-L-Valine;

(42) s-Triazine, 2-phenyl-4,6-bis[[6-[[4-phenyl-6-[[6-[[4-phenyl-6-(trichloromethyl)-s-triazin-2-yl]amino]hexyl]amino]-s-triazin-2-yl]amino]hexyl]amino]-;

(43) α,α'-[(6-phenyl-1,3,5-triazine-2,4-diyl)bis[imino(1,1,2,2-tetrafluoro-3-oxo-3,1-propanediyl)]]bis[ω-[tetrafluoro(trifluoromethyl)ethoxy]-Poly[oxy[trifluoro(trifluoromethyl)-1,2-ethanediyl]];

(44) α-[[4-[[(3-chlorophenyl)methyl]amino]-6-(1H-imidazol-1-yl)-1,3,5-triazin-2-yl]amino]-N-[[4-(trifluoromethyl)phenyl]methyl]-, (αR)-Cyclohexanepropanamide;

(45) 6-(1H-imidazol-1-yl)-N2,N4-bis(1-methylethyl)-1,3,5-Triazine-2,4-diamine; and

(46) N2,N4-bis(1-methylpropyl)-6-phenyl-1,3,5-Triazine-2,4-diamine.

The compounds of Formula I, Ia, Ib, B, C, Ic, Id, Ie, If, Ig, II, III, IIIa, IIIb, IIIc, and IIId, or as described in any one of the embodiments herein inhibits mutant IDH1 or mutant IDH2. Also described herein are pharmaceutical compositions comprising a compound of Formula I, Ia, Ib, B, C, Ic, Id, Ie, If, Ig, II, III, IIIa, IIIb, IIIc, and IIId, and methods of using such compositions to treat cancers characterized by the presence of a mutant IDH1 or mutant IDH2.

DETAILED DESCRIPTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a fully saturated or unsaturated hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The term "alkyl" includes "alkenyl" and "alkynyl".

The term "alkylene" refers to a divalent alkyl, e.g., $—CH_2—$, $—CH_2CH_2—$, $—CH_2CH_2CH_2—$ and $—CH_2CH(CH_3)CH_2—$.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

Unless otherwise specified, the term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents. The term "monocyclic aryl" means a monocyclic fully romatic hydrocarbon ring system, optionally substituted by one or more substituents which can not form a fused bicyclic or tricyclic ring.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems. Carbocyclyl groups also include spirocyclic moieties. Examples of spirocyclic moieties include, but are not limited to, bicyclo[3.1.0]hexanyl, spiro[2.2]pentanyl, spiro[3.3]heptanyl, spiro[2.5]octanyl, spiro[3.5]nonanyl, spiro[4.5]decanyl, and spiro[3.6]decanyl. Unless otherwise specified, any ring atom in a carbocyclyl can be substituted by one or more substituents.

Bicyclic or tricyclic ring systems where an aryl is fused to a carbocyclyl and the point of attachment from the ring system to the rest of the molecule is through the non-aromatic ring are considered to be carbocyclyl (e.g., cycloalkyl). Examples of such carbocyclyl moieties include, but are not limited to, 2,3-dihydro-1H-indene and 1,2,3,4-tetrahydronaphthalene.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

Unless otherwise specified, the term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+—O^-$, S(O) and $S(O)_2$). The term "monocyclic heteroaryl" means a monocyclic fully romatic ring system having 1-3 heteroatoms, optionally substituted by one or more substituents which can not form a fused bicyclic or tricyclic ring.

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+—O^-$, S(O) and $S(O)_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings are considered to be heterocyclyl or heteroaryl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups, respectively. Bicyclic or tricyclic ring systems where an aryl or a heteroaryl is fused to a carbocyclyl or heterocyclyl and the point of attachment from the ring system to the rest of the molecule is through the non-aromatic ring are considered to be carbocyclyl (e.g., cycloalkyl) or heterocyclyl groups, respectively.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, $—OR^b$, $—OR^{b'}$, $—SR^b$, $—SR^{b'}$, —($C_1$-$C_4$ alkyl)-N($R^b$)($R^b$), —($C_1$-$C_4$ alkyl)-N($R^b$)($R^{b'}$), —N($R^b$)($R^b$), —N($R^b$)($R^{b'}$), —O—($C_1$-$C_4$ alkyl)-N($R^b$)($R^b$), —O—($C_1$-$C_4$ alkyl)-N($R^b$)($R^{b'}$), —($C_1$-$C_4$ alkyl)-

O—($C_1$-$C_4$ alkyl)-N($R^b$)($R^b$), —($C_1$-$C_4$ alkyl)-O—($C_1$-$C_4$ alkyl)-N($R^b$)($R^{b'}$), —C(O)—N($R^b$)($R^b$), —($C_1$-$C_4$ alkyl)-C(O)—N($R^b$)($R^b$), —($C_1$-$C_4$ alkyl)-C(O)—N($R^b$)($R^{b'}$), —$OR^{b'}$, $R^{b'}$, —C(O)($C_1$-$C_4$ alkyl), —C(O)$R^{b'}$, —C(O)N($R^{b'}$)($R^b$), —N($R^b$)C(O)($R^b$), —N($R^b$)C(O)($R^{b'}$), —N($R^b$)$SO_2$($R^b$), —$SO_2$N($R^b$)($R^b$), —N($R^b$)$SO_2$($R^{b'}$), and —$SO_2$N($R^b$)($R^{b'}$), wherein any alkyl substituent is optionally further substituted with one or more of —OH, —O—($C_1$-$C_4$ alkyl), halo, —$NH_2$, —NH($C_1$-$C_4$ alkyl), or —N($C_1$-$C_4$ alkyl)$_2$;

each $R^b$ is independently selected from hydrogen, and —$C_1$-$C_4$ alkyl; or two $R^b$s are taken together with the nitrogen atom to which they are bound to form a 4- to 8-membered heterocyclyl optionally comprising one additional heteroatom selected from N, S, and O; and each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —$NH_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group. The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment. As used herein, the term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound of Formula I, or a pharmaceutically acceptable salt or hydrate thereof:

(I)

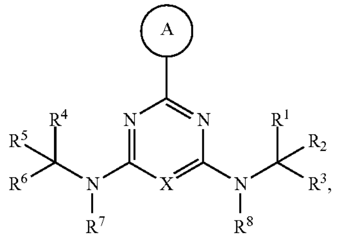

wherein:

ring A is an optionally substituted 5-6 member monocyclic aryl or monocyclic heteroaryl;

X is N, CH or C-halo;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein:

(i) when X is N and A is optionally substituted phenyl, then (a) neither $N(R^7)C(R^4)(R^5)(R^6)$ nor $N(R^8)C(R^1)(R^2)(R^3)$ is $NHCH_2CH_2OCH_2CH_2OCH_2CH_2NH_2$, 4-[[2-[2-(2-aminoethoxy)ethoxy]ethyl]amino] and (b) $N(R^7)C(R^4)(R^5)(R^6)$ and $N(R^8)C(R^1)(R^2)(R^3)$ are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is CH or C—Cl and A is phenyl optionally substituted with F, Cl or $SO_2CH_3$, then neither $N(R^7)C(R^4)(R^5)(R^6)$ nor $N(R^8)C(R^1)(R^2)(R^3)$ is $N(CH_3)CH_2C(O)NH$-i-propyl, $NHCH(CH_3)(CH_2)_3N(CH_2CH_3)_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2CH(OH)CH_3$, $N(CH_2CH_3)_2$, NH-i-propyl, $NHCH_2CH_2NHC(O)OCH_3$, $NHCH_2CH_2NHC(O)CH_3$, $NHCH_2CH_2NH_2$, or $NHCH_2$-phenyl;

(iii) when X is CH and A is optionally substituted pyridyl, then neither $N(R^7)C(R^4)(R^5)(R^6)$ nor $N(R^8)C(R^1)(R^2)(R^3)$ is $NHCH_2$-phenyl, $NHCH_2$-(2,4-difluorophenyl), $N(CH_3)CH_2CH_2C(O)OH$, $NHCH_2CH_2C(O)OH$, $NHCH_2CH_2C(O)OCH_2CH_3$, $NHCH_2CH_2C(O)O$-t-butyl, $NHCH_2CH_2C(O)NH_2$, $NHCH_2CH_2$-phenyl, $NHCH_2CH_2OH$, $NHCH_2CH_2NH_2$, $NHCH_2CH_2N(CH_3)_2$, or $NHCH_2CH_2CH_3$;

(iv) when X is CH and A is optionally substituted 1-imidazolyl, optionally substituted 1-pyrrolyl or optionally substituted 1-pyrazolyl, then neither $N(R^7)C(R^4)(R^5)(R^6)$ nor $N(R^8)C(R^1)(R^2)(R^3)$ is $NH(CH_2)_7CH_3$, $NHCH_2$-(o-chloro-phenyl), or $NHCH_2CH_2OH$;

(v) when X is N and A is an optionally substituted pyridyl, then (A) neither $N(R^7)C(R^4)(R^5)(R^6)$ nor $N(R^8)C(R^1)(R^2)(R^3)$ is NHC(O)-[2-chloro-4-(methylsulfonyl)], $N(CH_3)_2$, $NHCH_2CH_2CH_2SO_2CH_2CH_2Cl$, $NHCH_2CH_2OCH_2CH_2SO_2CH_2CH_2Cl$, or $NHCH_2CH_2SO_2CH_2CH_2Cl$, (B) $N(R^7)C(R^4)(R^5)(R^6)$ and $N(R^8)C(R^1)(R^2)(R^3)$ are not both $NHC(O)C(CH_3)_3$, $NHC(O)CH{=}CH_2$, $NHC(O)C(CH_3){=}CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when $N(R^7)C(R^4)(R^5)(R^6)$ is $NHC(CH_3)_3$, then $N(R^8)C(R^1)(R^2)(R^3)$ is not $NHCH_2$-phenyl or NH—$CH_2CH_3$;

(vi) when X is N and A is an optionally substituted heteroaryl, then $N(R^7)C(R^4)(R^5)(R^6)$ and $N(R^8)C(R^1)(R^2)(R^3)$ are not both $N(CH_2CH_3)_2$, $NHCH_2CH_2$-i-propyl, $NHCH_2CH(CH_3)_2$, and $NHC(O)CH_3$;

(vii) when X is CH and A is unsubstituted 2-pyridinyl, then the ring formed by $R^4$ and $R^5$ is not 5-methyl-1H-pyrazol-3-yl, (viii) when A is optionally substituted 1-pyrazolyl, then neither $N(R^7)C(R^4)(R^5)(R^6)$ nor $N(R^8)C(R^1)(R^2)(R^3)$ is $N(CH_3)_2$, $NHCH_3$, NHAc, NHisopropyl, $NHCH_2CH_3$, $NHCH_2CH_2SO_3H$ or $N(CH_2CH_3)_2$, (ix) when X is N and A is optionally substituted phenyl, thienyl, or pyridinyl, then neither $N(R^7)C(R^4)(R^5)(R^6)$ nor $N(R^8)C(R^1)(R^2)(R^3)$ is NHcyclohexylC(O)$NHCH_2R$, wherein R is phenyl or pyridinyl which is substituted with one or more of $OCF_3$, $OCH_3$, chloro, or $CF_3$, (x) when X is N, A is an optionally substituted phenyl and $R^4$ and $R^5$ form an optionally substituted phenyl, then $N(R^8)C(R^1)(R^2)(R^3)$ is not $NHCH_2$(4-fluorophenyl), $NHCH_2CO_2H$, $NHCH_2C(O)Cl$, $NHCH(CO_2H)(CH_2SCH_2phenyl)$, or $NHCH_2C(O)NHC(O)NHR$ or $NHCH_2C(O)NHC(S)NHR$, wherein R is optionally substituted phenyl or naphthyl, (xi) when X is N, A is an oxadiazole substituted with an optionally substituted pyridinyl, then $R^4$ and $R^5$ do not form an optionally substituted phenyl, (xii) when A is substituted 1-pyrazolyl, then (A) then $N(R^7)C(R^4)(R^5)(R^6)$ and $N(R^8)C(R^1)(R^2)(R^3)$ are not both $NHC(CH_3)_3$, and (B) A is not substituted with N═N—R, wherein R is a ring, (xiii) ring A is not an optionally substituted triazolyl, 3,5-dimethyl-1H-pyrazol-1-yl, (xix) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl; and (xx) the compound is not selected from the group:

(1) N-(2-aminophenyl)-4-[[[4-[(2,3-dihydro-1H-inden-2-yl)amino]-6-phenyl-1,3,5-triazin-2-yl]amino]methyl]-benzamide, (2) 2-chloro-N-[4-(cyclopropylamino)-6-(2-pyridinyl)-1,3,5-triazin-2-yl]-4-(methylsulfonyl)-benzamide, (3) 2-[[1-[4-(cyclopropylamino)-6-(ethylamino)-1,3,5-triazin-2-yl]-1H-1,2,4-triazol-3-yl]thio]-acetamide, (4) $N^2$-cyclopropyl-$N^4$-ethyl-6-[3-[(phenylmethyl)thio]-1H-1,2,4-triazol-1-yl]-1,3,5-triazine-2,4-diamine, (5) 2-[[1-[4-(cyclopropylamino)-6-(ethylamino)-1,3,5-triazin-2-yl]-1H-1,2,4-triazol-3-yl]thio]-acetic acid methyl ester, (6) N-[[4-[[[4-(cyclopropylamino)-6-(2-pyridinyl)-1,3,5-triazin-2-yl]amino]methyl]cyclohexyl]methyl]-4-fluorobenzenesulfonamide, (7) $N^2$-cyclopropyl-6-(3,5-dimethyl-1H-pyrazol-1-yl)-$N^4$-phenyl-1,3,5-triazine-2,4-diamine, (8) $N^2$,$N^4$-dicyclohexyl-6-[3-(4-methoxyphenyl)-5-(methylthio)-1H-pyrazol-1-yl]-1,3,5-triazine-2,4-diamine, (9) $N^2$,$N^4$-dicyclohexyl-6-[3-(3,4-dimethoxyphenyl)-5-(methylthio)-1H-pyrazol-1-yl]-1,3,5-triazine-2,4-diamine,

(10) $N^2$,$N^4$-dicyclohexyl-6-[5-(methylthio)-3-(3,4,5-trimethoxyphenyl)-1H-pyrazol-1-yl]-1,3,5-triazine-2,4-diamine,

(11) $N^2$,$N^4$-dicyclohexyl-6-phenyl-1,3,5-triazine-2,4-diamine,

(12) 1,1'-[(6-phenyl-s-triazine-2,4-diyl)diimino]bis[dodecahydro-anthraquinone],

(13) 4,4'-[(6-phenyl-1,3,5-triazine-2,4-diyl)bis(iminomethylene)]bis[2,6-bis(1,1-dimethylethyl)-phenol,

(14) N-[4-[(4-aminobutyl)amino]-6-[5-[[[[4-chloro-3-(trifluoromethyl)phenyl]amino]carbonyl]amino]-2-methylphenyl]-1,3,5-triazin-2-yl]-glycine,

(15) 4-[2-[[4-[(5-aminopentyl)amino]-6-(3-fluorophenyl)-1,3,5-triazin-2-yl]amino]ethyl]-phenol,

(16) 4-[2-[[4-[(5-aminopentyl)amino]-6-(4-fluorophenyl)-1,3,5-triazin-2-yl]amino]ethyl]-phenol,

(17) 6-(4-aminopyridin-3-yl)-$N^2$-benzyl-$N^4$-(tert-butyl)-1,3,5-triazine-2,4-diamine,

(18) $N^2$,$N^4$-bis(cyclohexylmethyl)-6-phenyl-1,3,5-triazine-2,4-diamine,

(19) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,

(20) 4,4'-[(6-phenyl-1,3,5-triazine-2,4-diyl)bis(imino-3,1-propanediyl)]bis[2,6-bis(1,1-dimethylethyl)-phenol,

(21) N-[6-[(2,3-dihydro-1H-inden-2-yl)amino]-2-(2-pyridinyl)-4-pyrimidinyl]-3 alanine,

(22) $N^4$-cyclopentyl-2-phenyl-$N^6$-(phenylmethyl)-4,6-pyrimidinediamine,

(23) 2-[[6-(bicyclo[2.2.1]hept-2-ylamino)-2-phenyl-4-pyrimidinyl]amino]-ethanol,

(24) $N^2$-isopropyl-6-phenyl-N4-(tetrahydro-2H-pyran-4-yl)-1,3,5-triazine-2,4-diamine,

(25) 2-chloro-4-(methylsulfonyl)-N-[4-[(phenylmethyl)amino]-6-(2-pyridinyl)-1,3,5-triazin-2-yl]-benzamide,

(26) N-[[4-[[[4-(cyclopropylamino)-6-(2-pyridinyl)-1,3,5-triazin-2-yl]amino]methyl]cyclohexyl]methyl]-4-fluoro-benzenesulfonamide,

(27) [[4-[[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol,

(28) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino] bis-methanol,

(29) 5-[4,6-bis(diethylamino)-1,3,5-triazin-2-yl]-2H-tetrazole-2-acetic acid ethyl ester,

(30) $N^2$,$N^2$,$N^4$,$N^4$-tetraethyl-6-(2H-tetrazol-5-yl)-1,3,5-triazine-2,4-diamine,

(31) N,N'-[6-[4-(acetylamino)-1,2,5-oxadiazol-3-yl]-1,3,5-triazine-2,4-diyl]bis-acetamide,

(32) N-(2-chloro-6-methylphenyl)-5-[[4-(dimethylamino)-6-(2-pyridinyl)-1,3,5-triazin-2-yl]amino]-1,3,4-Oxadiazole-2-carboxamide,

(33) N4-(5-methyl-1H-pyrazol-3-yl)-2-(2-pyridinyl)-N6-(tetrahydro-2H-pyran-4-yl)-4,6-Pyrimidinediamine,

(34) 6-(4-chlorophenyl)-N2-[4-chloro-3-(trifluoromethyl)phenyl]-N4-[3-(diethylamino)propyl]-1,3,5-Triazine-2,4-diamine,

(35) 6-(4-chlorophenyl)-N2-[4-chloro-3-(trifluoromethyl)phenyl]-N4-[3-(dimethylamino)propyl]-1,3,5-Triazine-2,4-diamine,

(36) N2-[3,5-bis(trifluoromethyl)phenyl]-6-(4-chlorophenyl)-N4-[3-(diethylamino)propyl]-1,3,5-Triazine-2,4-diamine,

(37) N2,N4-bis[(4-methoxyphenyl)methyl]-6-[4-(trifluoromethoxy)phenyl]-1,3,5-Triazine-2,4-diamine,

(38) N,N''-(6-phenyl-1,3,5-triazine-2,4-diyl)bis[N'-(2-chloroethyl)-Urea,

(39) N-[4-chloro-3-(trifluoromethyl)phenyl]-N'-[4-methyl-3-[[4-phenyl-6-(propylamino)-1,3,5-triazin-2-yl]amino] phenyl]-urea,

(40) N-[4-[[5-[[[[4-chloro-3-(trifluoromethyl)phenyl]amino]carbonyl]amino]-2-methylphenyl]amino]-6-(4-pyridinyl)-1,3,5-triazin-2-yl]-glycine,

(41) N-[4-[[5-[[[[4-chloro-3-(trifluoromethyl)phenyl]amino]carbonyl]amino]-2-methylphenyl]amino]-6-(5-thiazolyl)-1,3,5-triazin-2-yl]-L-Valine,

(42) s-Triazine, 2-phenyl-4,6-bis[[6-[[4-phenyl-6-[[6-[[4-phenyl-6-(trichloromethyl)-s-triazin-2-yl]amino]hexyl]amino]-s-triazin-2-yl]amino]hexyl]amino]-,

(43) α,α'-[(6-phenyl-1,3,5-triazine-2,4-diyl)bis[imino(1,1,2,2-tetrafluoro-3-oxo-3,1-propanediyl)]]bis[ω-[tetrafluoro(trifluoromethyl)ethoxy]-Poly[oxy[trifluoro(trifluoromethyl)-1,2-ethanediyl]],

(44) α-[[4-[[(3-chlorophenyl)methyl]amino]-6-(1H-imidazol-1-yl)-1,3,5-triazin-2-yl]amino]-N-[[4-(trifluoromethyl)phenyl]methyl]-, (αR)-Cyclohexanepropanamide,

(45) 6-(1H-imidazol-1-yl)-N2,N4-bis(1-methylethyl)-1,3,5-Triazine-2,4-diamine, and

(46) N2,N4-bis(1-methylpropyl)-6-phenyl-1,3,5-Triazine-2,4-diamine.

Provided is a compound of Formula I, or a pharmaceutically acceptable salt or hydrate thereof:

(I)

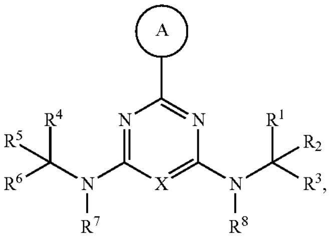

wherein:

ring A is an optionally substituted 5-6 member monocyclic aryl or monocyclic heteroaryl;

X is N, CH or C-halo;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2$H, or halo;

any terminal methyl moiety present in $R^2$ and $R^5$ is optionally replaced with —$CH_2$OH, $CF_3$, —$CH_2$F, —$CH_2$Cl, C(O)$CH_3$, C(O)$CF_3$, CN, or $CO_2$H;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl;

wherein:

(i) when X is N and A is optionally substituted phenyl, then (a) neither N($R^7$)C($R^4$)($R^5$)($R^6$) nor N($R^8$)C($R^1$)($R^2$)($R^3$) is 4-[[2-[2-(2-aminoethoxy)ethoxy]ethyl]amino] and (b) N($R^7$)C($R^4$)($R^5$)($R^6$) and N($R^8$)C($R^1$)($R^2$)($R^3$) are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is CH or C—Cl and A is phenyl optionally substituted with F, Cl or $SO_2CH_3$, then neither N($R^7$)C($R^4$)($R^5$)($R^6$) nor N($R^8$)C(R')($R^2$)($R^3$) is N($CH_3$)$CH_2$C(O)NH-i-propyl, $NHCH(CH_3)(CH_2)_3N(CH_2CH_3)_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2CH(OH)CH_3$, $N(CH_2CH_3)_2$, NH-i-propyl, $NHCH_2CH_2NHC(O)OCH_3$, $NHCH_2CH_2NHC(O)CH_3$, $NHCH_2CH_2NH_2$, or $NHCH_2$-phenyl;

(iii) when X is CH and A is optionally substituted pyridyl, then neither N($R^7$)C($R^4$)($R^5$)($R^6$) nor N($R^8$)C(R')($R^2$)($R^3$) is $NHCH_2$-phenyl, $NHCH_2$-(2,4-difluorophenyl), $N(CH_3)CH_2CH_2C(O)OH$, $NHCH_2CH_2C(O)OH$, $NHCH_2CH_2C(O)OCH_2CH_3$, $NHCH_2CH_2C(O)O$-t-butyl, $NHCH_2CH_2C(O)NH_2$, $NHCH_2CH_2$-phenyl, $NHCH_2CH_2OH$, $NHCH_2CH_2NH_2$, $NHCH_2CH_2N(CH_3)_2$, or $NHCH_2CH_2CH_3$;

(iv) when X is CH and A is optionally substituted 1-imidazolyl, optionally substituted 1-pyrrolyl or optionally substituted 1-pyrazolyl, then neither N($R^7$)C($R^4$)($R^5$)($R^6$) nor N($R^8$)C(R')($R^2$)($R^3$) is $NH(CH_2)_7CH_3$, $NHCH_2$-(o-chloro-phenyl), or $NHCH_2CH_2OH$;

(v) when X is N and A is an optionally substituted pyridyl, then (A) neither N($R^7$)C($R^4$)($R^5$)($R^6$) nor N($R^8$)C(R')($R^2$)($R^3$) is NHC(O)-[2-chloro-4-(methylsulfonyl)], (B) N($R^7$)C($R^4$)($R^5$)($R^6$) and N($R^8$)C(R')($R^2$)($R^3$) are not both $NHC(O)C(CH_3)_3$, NHC(O)CH═$CH_2$, $NHC(O)C(CH_3)$═$CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when N($R^7$)C($R^4$)($R^5$)($R^6$) is $NHC(CH_3)_3$, then N($R^8$)C(R')($R^2$)($R^3$) is not $NHCH_2$-phenyl or NH—$CH_2CH_3$;

(vi) when X is N and A is an optionally substituted heteroaryl, then N($R^7$)C($R^4$)($R^5$)($R^6$) and N($R^8$)C(R')($R^2$)($R^3$) are not both $N(CH_2CH_3)_2$, $NHCH_2CH_2$-i-propyl, $NHCH_2CH(CH_3)_2$, and $NHC(O)CH_3$;

(vii) the compound is not selected from the group:

(1) $N^2$-[2-[2-(2-aminoethoxy)ethoxy]ethyl]-$N^4$-cyclopentyl-6-phenyl-1,3,5-triazine-2,4-diamine,
(2) $N^2$-[2-[2-(2-aminoethoxy)ethoxy]ethyl]-$N^4$-cyclopentyl-6-(4-methoxyphenyl)-1,3,5-triazine-2,4-diamine,
(3) $N^2$-[2-[2-(2-aminoethoxy)ethoxy]ethyl]-$N^4$-cyclopentyl-6-(3-nitrophenyl)-1,3,5-triazine-2,4-diamine,
(4) $N^2$-[2-[2-(2-aminoethoxy)ethoxy]ethyl]-$N^4$-cyclopentyl-6-(4-fluorophenyl)-1,3,5-triazine-2,4-diamine,
(5) $N^2$-[2-[2-(2-aminoethoxy)ethoxy]ethyl]-$N^4$-cyclopentyl-6-(4-trifluoromethoxy-phenyl)-1,3,5-triazine-2,4-diamine,
(6) $N^2$-[2-[2-(2-aminoethoxy)ethoxy]ethyl]-$N^4$-cyclopentyl-6-(4-t-butyl-phenyl)-1,3,5-triazine-2,4-diamine,
(7) $N^2$-[2-[2-(2-aminoethoxy)ethoxy]ethyl]-$N^4$-cyclopentyl-6-(2-thienyl)-1,3,5-triazine-2,4-diamine,
(8) N-(2-aminophenyl)-4-[[[4-[(2,3-dihydro-1H-inden-2-yl)amino]-6-phenyl-1,3,5-triazin-2-yl]amino]methyl]-benzamide,
(9) 2-chloro-N-[4-(cyclopropylamino)-6-(2-pyridinyl)-1,3,5-triazin-2-yl]-4-(methylsulfonyl)-benzamide,
(10) $N^2$-[2-[2-(2-aminoethoxy)ethoxy]ethyl]-$N^4$-cyclopropyl-6-(4-methoxyphenyl)-1,3,5-triazine-2,4-diamine,
(11) 2-[[1-[4-(cyclopropylamino)-6-(ethylamino)-1,3,5-triazin-2-yl]-1H-1,2,4-triazol-3-yl]thio]-acetamide,
(12) $N^2$-cyclopropyl-$N^4$-ethyl-6-[3-[(phenylmethyl)thio]-1H-1,2,4-triazol-1-yl]-1,3,5-triazine-2,4-diamine,
(13) 2-[[1-[4-(cyclopropylamino)-6-(ethylamino)-1,3,5-triazin-2-yl]-1H-1,2,4-triazol-3-yl]thio]-acetic acid methyl ester,
(14) $N^2$-[2-[2-(2-aminoethoxy)ethoxy]ethyl]-$N^4$-cyclopropyl-6-(2,4,6-trimethylphenyl)-1,3,5-triazine-2,4-diamine,
(15) $N^2$-[2-[2-(2-aminoethoxy)ethoxy]ethyl]-$N^4$-cyclopropyl-6-phenyl-1,3,5-triazine-2,4-diamine,
(16) $N^2$-[2-[2-(2-aminoethoxy)ethoxy]ethyl]-$N^4$-cyclopropyl-6-(4-methylphenyl)-1,3,5-triazine-2,4-diamine,
(17) $N^2$-[2-[2-(2-aminoethoxy)ethoxy]ethyl]-$N^4$-cyclopropyl-6-(4-chlorophenyl)-1,3,5-triazine-2,4-diamine,
(18) N-[[4-[[[4-(cyclopropylamino)-6-(2-pyridinyl)-1,3,5-triazin-2-yl]amino]methyl]cyclohexyl] methyl]-4-fluorobenzenesulfonamide,

(19) $N^2$-cyclopropyl-6-(3,5-dimethyl-1H-pyrazol-1-yl)-$N^4$-phenyl-1,3,5-triazine-2,4-diamine,

(20) $N^2$,$N^4$-dicyclohexyl-6-[3-(4-methoxyphenyl)-5-(methylthio)-1H-pyrazol-1-yl]-1,3,5-triazine-2,4-diamine,

(21) $N^2$,$N^4$-dicyclohexyl-6-[3-(3,4-dimethoxyphenyl)-5-(methylthio)-1H-pyrazol-1-yl]-1,3,5-triazine-2,4-diamine,

(22) $N^2$,$N^4$-dicyclohexyl-6-[5-(methylthio)-3-(3,4,5-trimethoxyphenyl)-1H-pyrazol-1-yl]-1,3,5-triazine-2,4-diamine,

(23) $N^2$,$N^4$-dicyclohexyl-6-phenyl-1,3,5-triazine-2,4-diamine,

(24) 1,1'-[(6-phenyl-s-triazine-2,4-diyl)diimino]bis[dodecahydro-anthraquinone],

(25) 4,4'-[(6-phenyl-1,3,5-triazine-2,4-diyl)bis(iminomethylene)]bis[2,6-bis(1,1-dimethylethyl)-phenol,

(26) N-[4-[(4-aminobutyl)amino]-6-[5-[[[[4-chloro-3-(trifluoromethyl)phenyl]amino]carbonyl] amino]-2-methylphenyl]-1,3,5-triazin-2-yl]-glycine,

(27) 4-[2-[[4-[(5-aminopentyl)amino]-6-(3-fluorophenyl)-1,3,5-triazin-2-yl]amino]ethyl]-phenol,

(28) 4-[2-[[4-[(5-aminopentyl)amino]-6-(4-fluorophenyl)-1,3,5-triazin-2-yl]amino]ethyl]-phenol,

(29) 6-(4-aminopyridin-3-yl)-$N^2$-benzyl-$N^4$-(tert-butyl)-1,3,5-triazine-2,4-diamine,

(30) $N^2$,$N^4$-bis(cyclohexylmethyl)-6-phenyl-1,3,5-triazine-2,4-diamine,

(31) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,

(32) 4,4'-[(6-phenyl-1,3,5-triazine-2,4-diyl)bis(imino-3,1-propanediyl)]bis[2,6-bis(1,1-dimethylethyl)-phenol,

(33) N-[6-[(2,3-dihydro-1H-inden-2-yl)amino]-2-(2-pyridinyl)-4-pyrimidinyl]-3 alanine,

(34) $N^4$-cyclopentyl-2-phenyl-$N^6$-(phenylmethyl)-4,6-pyrimidinediamine,

(35) 2-[[6-(bicyclo[2.2.1]hept-2-ylamino)-2-phenyl-4-pyrimidinyl]amino]-ethanol,

(36) $N^2$-isopropyl-6-phenyl-N4-(tetrahydro-2H-pyran-4-yl)-1,3,5-triazine-2,4-diamine,

(37) 2-chloro-4-(methylsulfonyl)-N-[4-[(phenylmethyl) amino]-6-(2-pyridinyl)-1,3,5-triazin-2-yl]-benzamide,

(38) N-[[4-[[[4-(cyclopropylamino)-6-(2-pyridinyl)-1,3,5-triazin-2-yl]amino]methyl]cyclohexyl]methyl]-4-fluoro-benzenesulfonamide,

(39) [[4-[[[[[4-amino-6-(4-pyridinyl)-1,3,5-triazin-2-yl] amino]methoxy]methyl]amino]-6-(4-pyridinyl)-1,3,5-triazin-2-yl]imino]bis-methanol,

(40) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino] bis-methanol,

(41) 5-[4,6-bis(diethylamino)-1,3,5-triazin-2-yl]-2H-tetrazole-2-acetic acid ethyl ester,

(42) $N^2$,$N^2$,$N^4$,$N^4$-tetraethyl-6-(2H-tetrazol-5-yl)-1,3,5-triazine-2,4-diamine, and

(43) N,N'-[6-[4-(acetylamino)-1,2,5-oxadiazol-3-yl]-1,3,5-triazine-2,4-diyl]bis-acetamide.

Provided is a compound of Formula I, or a pharmaceutically acceptable salt or hydrate thereof:

(I)

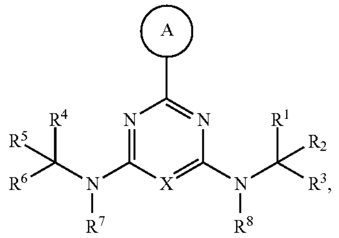

wherein:

ring A is an optionally substituted 5-6 member monocyclic aryl or monocyclic heteroaryl;

X is N or CH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl;

wherein:

(i) when X is N and A is optionally substituted phenyl, then (a) neither $N(R^7)C(R^4)(R^5)(R^6)$ nor $N(R^8)C(R^1)(R^2)(R^3)$ is 4-[[2-[2-(2-aminoethoxy)ethoxy]ethyl]amino] and (b) $N(R^7)C(R^4)(R^5)(R^6)$ and $N(R^8)C(R^1)(R^2)(R^3)$ are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is CH or C—Cl and A is phenyl optionally substituted with F, Cl or $SO_2CH_3$, then neither $N(R^7)C(R^4)(R^5)(R^6)$ nor $N(R^8)C(R^1)(R^2)(R^3)$ is $N(CH_3)CH_2C(O)$NH-i-propyl, $NHCH(CH_3)(CH_2)_3N(CH_2CH_3)_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2CH(OH)CH_3$, $N(CH_2CH_3)_2$, NH-i-propyl, $NHCH_2CH_2NHC(O)OCH_3$, $NHCH_2CH_2NHC(O)CH_3$, $NHCH_2CH_2NH_2$, or $NHCH_2$-phenyl;

(iii) when X is CH and A is optionally substituted pyridyl, then neither $N(R^7)C(R^4)(R^5)(R^6)$ nor $N(R^8)C(R^1)(R^2)(R^3)$ is $NHCH_2$-phenyl, $NHCH_2$-(2,4-difluorophenyl), $N(CH_3)CH_2CH_2C(O)OH$, $NHCH_2CH_2C(O)OH$, $NHCH_2CH_2C(O)OCH_2CH_3$, $NHCH_2CH_2C(O)O$-t-butyl, $NHCH_2CH_2C(O)NH_2$, $NHCH_2CH_2$-phenyl, $NHCH_2CH_2OH$, $NHCH_2CH_2NH_2$, $NHCH_2CH_2N(CH_3)_2$, or $NHCH_2CH_2CH_3$;

(iv) when X is CH and A is optionally substituted 1-imidazolyl, optionally substituted 1-pyrrolyl or optionally substituted 1-pyrazolyl, then neither $N(R^7)C(R^4)(R^5)(R^6)$ nor $N(R^8)C(R^1)(R^2)(R^3)$ is $NH(CH_2)_7CH_3$, $NHCH_2$-(o-chloro-phenyl), or $NHCH_2CH_2OH$;

(v) when X is N and A is an optionally substituted pyridyl, then (A) neither $N(R^7)C(R^4)(R^5)(R^6)$ nor $N(R^8)C(R^1)(R^2)(R^3)$ is NHC(O)-[2-chloro-4-(methylsulfonyl)], (B) $N(R^7)C(R^4)(R^5)(R^6)$ and $N(R^8)C(R^1)(R^2)(R^3)$ are not both $NHC(O)C(CH_3)_3$, $NHC(O)CH{=}CH_2$, $NHC(O)C(CH_3){=}CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when $N(R^7)C(R^4)(R^5)(R^6)$ is $NHC(CH_3)_3$, then $N(R^8)C(R')(R^2)(R^3)$ is not $NHCH_2$-phenyl or NH—$CH_2CH_3$;

(vi) when X is N and A is an optionally substituted heteroaryl, then $N(R^7)C(R^4)(R^5)(R^6)$ and $N(R^8)C(R^1)(R^2)(R^3)$ are not both $N(CH_2CH_3)_2$, $NHCH_2CH_2$-i-propyl, $NHCH_2CH(CH_3)_2$, and $NHC(O)CH_3$;

(vii) the compound is not selected from the group:

(1) $N^2$-[2-[2-(2-aminoethoxy)ethoxy]ethyl]-$N^4$-cyclopentyl-6-phenyl-1,3,5-triazine-2,4-diamine, (2) $N^2$-[2-[2-(2-aminoethoxy)ethoxy]ethyl]-$N^4$-cyclopentyl-6-(4-methoxyphenyl)-1,3,5-triazine-2,4-diamine, (3) $N^2$-[2-[2-(2-aminoethoxy)ethoxy]ethyl]-$N^4$-cyclopentyl-6-(3-nitrophenyl)-1,3,5-triazine-2,4-diamine, (4) $N^2$-[2-[2-(2-aminoethoxy)ethoxy]ethyl]-$N^4$-cyclopentyl-6-(4-fluorophenyl)-1,3,5-triazine-2,4-diamine, (5) $N^2$-[2-[2-(2-aminoethoxy)ethoxy]ethyl]-$N^4$-cyclopentyl-6-(4-trifluoromethoxy-phenyl)-1,3,5-triazine-2,4-diamine, (6) $N^2$-[2-[2-(2-aminoethoxy)ethoxy]ethyl]-$N^4$-cyclopentyl-6-(4-t-butyl-phenyl)-1,3,5-triazine-2,4-diamine, (7) $N^2$-[2-[2-(2-aminoethoxy)ethoxy]ethyl]-$N^4$-cyclopentyl-6-(2-thienyl)-1,3,5-triazine-2,4-diamine, (8) N-(2-aminophenyl)-4-[[[4-[(2,3-dihydro-1H-inden-2-yl)amino]-6-phenyl-1,3,5-triazin-2-yl]amino]methyl]-benzamide, (9) 2-chloro-N-[4-(cyclopropylamino)-6-(2-pyridinyl)-1,3,5-triazin-2-yl]-4-(methylsulfonyl)-benzamide,

(10) $N^2$-[2-[2-(2-aminoethoxy)ethoxy]ethyl]-$N^4$-cyclopropyl-6-(4-methoxyphenyl)-1,3,5-triazine-2,4-diamine,

(11) 2-[[1-[4-(cyclopropylamino)-6-(ethylamino)-1,3,5-triazin-2-yl]-1H-1,2,4-triazol-3-yl]thio]-acetamide,

(12) $N^2$-cyclopropyl-$N^4$-ethyl-6-[3-[(phenylmethyl)thio]-1H-1,2,4-triazol-1-yl]-1,3,5-triazine-2,4-diamine,

(13) 2-[[1-[4-(cyclopropylamino)-6-(ethylamino)-1,3,5-triazin-2-yl]-1H-1,2,4-triazol-3-yl]thio]-acetic acid methyl ester,

(14) $N^2$-[2-[2-(2-aminoethoxy)ethoxy]ethyl]-$N^4$-cyclopropyl-6-(2,4,6-trimethylphenyl)-1,3,5-triazine-2,4-diamine,

(15) $N^2$-[2-[2-(2-aminoethoxy)ethoxy]ethyl]-$N^4$-cyclopropyl-6-phenyl-1,3,5-triazine-2,4-diamine,

(16) $N^2$-[2-[2-(2-aminoethoxy)ethoxy]ethyl]-$N^4$-cyclopropyl-6-(4-methylphenyl)-1,3,5-triazine-2,4-diamine,

(17) $N^2$-[2-[2-(2-aminoethoxy)ethoxy]ethyl]-$N^4$-cyclopropyl-6-(4-chlorophenyl)-1,3,5-triazine-2,4-diamine,

(18) N-[[4-[[[4-(cyclopropylamino)-6-(2-pyridinyl)-1,3,5-triazin-2-yl]amino]methyl]cyclohexyl] methyl]-4-fluorobenzenesulfonamide,

(19) $N^2$-cyclopropyl-6-(3,5-dimethyl-1H-pyrazol-1-yl)-$N^4$-phenyl-1,3,5-triazine-2,4-diamine,

(20) $N^2$,$N^4$-dicyclohexyl-6-[3-(4-methoxyphenyl)-5-(methylthio)-1H-pyrazol-1-yl]-1,3,5-triazine-2,4-diamine,

(21) $N^2$,$N^4$-dicyclohexyl-6-[3-(3,4-dimethoxyphenyl)-5-(methylthio)-1H-pyrazol-1-yl]-1,3,5-triazine-2,4-diamine,

(22) $N^2$,$N^4$-dicyclohexyl-6-[5-(methylthio)-3-(3,4,5-trimethoxyphenyl)-1H-pyrazol-1-yl]-1,3,5-triazine-2,4-diamine,

(23) $N^2$,$N^4$-dicyclohexyl-6-phenyl-1,3,5-triazine-2,4-diamine,

(24) 1,1'-[(6-phenyl-s-triazine-2,4-diyl)diimino]bis[dodecahydro-anthraquinone],

(25) 4,4'-[(6-phenyl-1,3,5-triazine-2,4-diyl)bis(iminomethylene)]bis[2,6-bis(1,1-dimethylethyl)-phenol,

(26) N-[4-[(4-aminobutyl)amino]-6-[5-[[[[4-chloro-3-(trifluoromethyl)phenyl]amino]carbonyl] amino]-2-methylphenyl]-1,3,5-triazin-2-yl]-glycine,

(27) 4-[2-[[4-[(5-aminopentyl)amino]-6-(3-fluorophenyl)-1,3,5-triazin-2-yl]amino]ethyl]-phenol,

(28) 4-[2-[[4-[(5-aminopentyl)amino]-6-(4-fluorophenyl)-1,3,5-triazin-2-yl]amino]ethyl]-phenol,

(29) 6-(4-aminopyridin-3-yl)-$N^2$-benzyl-$N^4$-(tert-butyl)-1,3,5-triazine-2,4-diamine,

(30) $N^2$,$N^4$-bis(cyclohexylmethyl)-6-phenyl-1,3,5-triazine-2,4-diamine,

(31) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,
(32) 4,4'-[(6-phenyl-1,3,5-triazine-2,4-diyl)bis(imino-3,1-propanediyl)]bis[2,6-bis(1,1-dimethylethyl)-phenol,
(33) N-[6-[(2,3-dihydro-1H-inden-2-yl)amino]-2-(2-pyridinyl)-4-pyrimidinyl]-βalanine,
(34) $N^4$-cyclopentyl-2-phenyl-$N^6$-(phenylmethyl)-4,6-pyrimidinediamine,
(35) 2-[[6-(bicyclo[2.2.1]hept-2-ylamino)-2-phenyl-4-pyrimidinyl]amino]-ethanol,
(36) $N^2$-isopropyl-6-phenyl-N4-(tetrahydro-2H-pyran-4-yl)-1,3,5-triazine-2,4-diamine,
(37) 2-chloro-4-(methylsulfonyl)-N-[4-[(phenylmethyl)amino]-6-(2-pyridinyl)-1,3,5-triazin-2-yl]-benzamide,
(38) N-[[4-[[[4-(cyclopropylamino)-6-(2-pyridinyl)-1,3,5-triazin-2-yl]amino]methyl]cyclohexyl]methyl]-4-fluorobenzenesulfonamide,
(39) [[4-[[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol,
(40) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino]bis-methanol,
(41) 5-[4,6-bis(diethylamino)-1,3,5-triazin-2-yl]-2H-tetrazole-2-acetic acid ethyl ester,
(42) $N^2$,$N^2$,$N^4$,$N^4$-tetraethyl-6-(2H-tetrazol-5-yl)-1,3,5-triazine-2,4-diamine, and
(43) N,N'-[6-[4-(acetylamino)-1,2,5-oxadiazol-3-yl]-1,3,5-triazine-2,4-diyl]bis-acetamide.

Also provided is a compound of Formula I, or a pharmaceutically acceptable salt or hydrate thereof:

(I)

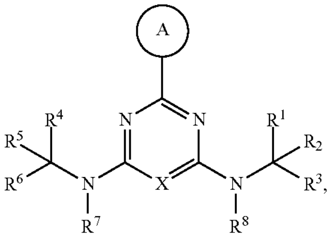

wherein:

ring A is an optionally substituted 5-6 member monocyclic aryl or monocyclic heteroaryl;

X is N or CH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2$H, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2$H, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein:

(i) when X is N and A is optionally substituted phenyl, then (a) neither N($R^7$)C($R^4$)($R^5$)($R^6$) nor N($R^8$)C($R^1$)($R^2$)($R^3$) is $NHCH_2CH_2OCH_2CH_2OCH_2CH_2NH_2$, 4-[[2-[2-(2-aminoethoxy)ethoxy]ethyl]amino] and (b) N($R^7$)C($R^4$)($R^5$)($R^6$) and N($R^8$)C($R^1$)($R^2$)($R^3$) are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is CH or C—Cl and A is phenyl optionally substituted with F, Cl or $SO_2CH_3$, then neither N($R^7$)C($R^4$)($R^5$)($R^6$) nor N($R^8$)C($R^1$)($R^2$)($R^3$) is N($CH_3$)$CH_2C(O)NH$-i-propyl, $NHCH(CH_3)(CH_2)_3N(CH_2CH_3)_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2CH(OH)CH_3$, $N(CH_2CH_3)_2$, NH-i-propyl, $NHCH_2CH_2NHC(O)OCH_3$, $NHCH_2CH_2NHC(O)CH_3$, $NHCH_2CH_2NH_2$, or $NHCH_2$-phenyl;

(iii) when X is CH and A is optionally substituted pyridyl, then neither $N(R^7)C(R^4)(R^5)(R^6)$ nor $N(R^8)C(R^1)(R^2)(R^3)$ is $NHCH_2$-phenyl, $NHCH_2$-(2,4-difluorophenyl), $N(CH_3)CH_2CH_2C(O)OH$, $NHCH_2CH_2C(O)OH$, $NHCH_2CH_2C(O)OCH_2CH_3$, $NHCH_2CH_2C(O)O$-t-butyl, $NHCH_2CH_2C(O)NH_2$, $NHCH_2CH_2$-phenyl, $NHCH_2CH_2OH$, $NHCH_2CH_2NH_2$, $NHCH_2CH_2N(CH_3)_2$, or $NHCH_2CH_2CH_3$;

(iv) when X is CH and A is optionally substituted 1-imidazolyl, optionally substituted 1-pyrrolyl or optionally substituted 1-pyrazolyl, then neither $N(R^7)C(R^4)(R^5)(R^6)$ nor $N(R^8)C(R^1)(R^2)(R^3)$ is $NH(CH_2)_7CH_3$, $NHCH_2$-(o-chloro-phenyl), or $NHCH_2CH_2OH$;

(v) when X is N and A is an optionally substituted pyridyl, then (A) neither $N(R^7)C(R^4)(R^5)(R^6)$ nor $N(R^8)C(R^1)(R^2)(R^3)$ is NHC(O)-[2-chloro-4-(methylsulfonyl)], $N(CH_3)_2$, $NHCH_2CH_2CH_2SO_2CH_2CH_2Cl$, $NHCH_2CH_2OCH_2CH_2SO_2CH_2CH_2Cl$, or $NHCH_2CH_2SO_2CH_2CH_2Cl$, (B) $N(R^7)C(R^4)(R^5)(R^6)$ and $N(R^8)C(R^1)(R^2)(R^3)$ are not both $NHC(O)C(CH_3)_3$, $NHC(O)CH{=}CH_2$, $NHC(O)C(CH_3){=}CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when $N(R^7)C(R^4)(R^5)(R^6)$ is $NHC(CH_3)_3$, then $N(R^8)C(R^1)(R^2)(R^3)$ is not $NHCH_2$-phenyl or $NH{-}CH_2CH_3$;

(vi) when X is N and A is an optionally substituted heteroaryl, then $N(R^7)C(R^4)(R^5)(R^6)$ and $N(R^8)C(R^1)(R^2)(R^3)$ are not both $N(CH_2CH_3)_2$, $NHCH_2CH_2$-i-propyl, $NHCH_2CH(CH_3)_2$, and $NHC(O)CH_3$;

(vii) when X is CH and A is unsubstituted 2-pyridinyl, then the ring formed by $R^4$ and $R^5$ is not 5-methyl-1H-pyrazol-3-yl, (viii) when A is optionally substituted 1-pyrazolyl, then neither $N(R^7)C(R^4)(R^5)(R^6)$ nor $N(R^8)C(R^1)(R^2)(R^3)$ is $N(CH_3)_2$, $NHCH_3$, NHAc, NHisopropyl, $NHCH_2CH_3$, $NHCH_2CH_2SO_3H$ or $N(CH_2CH_3)_2$, (ix) when X is N and A is optionally substituted phenyl, thienyl, or pyridinyl, then neither $N(R^7)C(R^4)(R^5)(R^6)$ nor $N(R^8)C(R^1)(R^2)(R^3)$ is NHcyclohexylC(O)$NHCH_2R$, wherein R is phenyl or pyridinyl which is substituted with one or more of $OCF_3$, $OCH_3$, chloro, or $CF_3$, (x) when X is N, A is an optionally substituted phenyl and $R^4$ and $R^5$ form an optionally substituted phenyl, then $N(R^8)C(R^1)(R^2)(R^3)$ is not $NHCH_2$(4-fluorophenyl), $NHCH_2CO_2H$, $NHCH_2C(O)Cl$, $NHCH(CO_2H)(CH_2SCH_2phenyl)$, or $NHCH_2C(O)NHC(O)NHR$ or $NHCH_2C(O)NHC(S)NHR$, wherein R is optionally substituted phenyl or naphthyl, (xi) when X is N, A is an oxadiazole substituted with an optionally substituted pyridinyl, then $R^4$ and $R^5$ do not form an optionally substituted phenyl, (xii) when A is substituted 1-pyrazolyl, then (A) then $N(R^7)C(R^4)(R^5)(R^6)$ and $N(R^8)C(R^1)(R^2)(R^3)$ are not both $NHC(CH_3)_3$, and (B) A is not substituted with N═N—R, wherein R is a ring, (xiii) ring A is not an optionally substituted triazolyl, 3,5-dimethyl-1H-pyrazol-1-yl, (xix) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl; and (xx) the compound is not selected from the group:

(1) N-(2-aminophenyl)-4-[[[4-[(2,3-dihydro-1H-inden-2-yl)amino]-6-phenyl-1,3,5-triazin-2-yl]amino]methyl]-benzamide, (2) 2-chloro-N-[4-(cyclopropylamino)-6-(2-pyridinyl)-1,3,5-triazin-2-yl]-4-(methylsulfonyl)-benzamide, (3) 2-[[1-[4-(cyclopropylamino)-6-(ethylamino)-1,3,5-triazin-2-yl]-1H-1,2,4-triazol-3-yl]thio]-acetamide, (4) $N^2$-cyclopropyl-$N^4$-ethyl-6-[3-[(phenylmethyl)thio]-1H-1,2,4-triazol-1-yl]-1,3,5-triazine-2,4-diamine, (5) 2-[[1-[4-(cyclopropylamino)-6-(ethylamino)-1,3,5-triazin-2-yl]-1H-1,2,4-triazol-3-yl]thio]-acetic acid methyl ester, (6) N-[[4-[[[4-(cyclopropylamino)-6-(2-pyridinyl)-1,3,5-triazin-2-yl]amino]methyl]cyclohexyl]methyl]-4-fluoro-benzenesulfonamide, (7) $N^2$-cyclopropyl-6-(3,5-dimethyl-1H-pyrazol-1-yl)-$N^4$-phenyl-1,3,5-triazine-2,4-diamine, (8) $N^2$,$N^4$-dicyclohexyl-6-[3-(4-methoxyphenyl)-5-(methylthio)-1H-pyrazol-1-yl]-1,3,5-triazine-2,4-diamine, (9) $N^2$,$N^4$-dicyclohexyl-6-[3-(3,4-dimethoxyphenyl)-5-(methylthio)-1H-pyrazol-1-yl]-1,3,5-triazine-2,4-diamine,

(10) $N^2$,$N^4$-dicyclohexyl-6-[5-(methylthio)-3-(3,4,5-trimethoxyphenyl)-1H-pyrazol-1-yl]-1,3,5-triazine-2,4-diamine,

(11) $N^2$,$N^4$-dicyclohexyl-6-phenyl-1,3,5-triazine-2,4-diamine,

(12) 1,1'-[(6-phenyl-s-triazine-2,4-diyl)diimino]bis[dodecahydro-anthraquinone],

(13) 4,4'-[(6-phenyl-1,3,5-triazine-2,4-diyl)bis(iminomethylene)]bis[2,6-bis(1,1-dimethylethyl)-phenol,

(14) N-[4-[(4-aminobutyl)amino]-6-[5-[[[[4-chloro-3-(trifluoromethyl)phenyl]amino]carbonyl]amino]-2-methylphenyl]-1,3,5-triazin-2-yl]-glycine,

(15) 4-[2-[[4-[(5-aminopentyl)amino]-6-(3-fluorophenyl)-1,3,5-triazin-2-yl]amino]ethyl]-phenol,

(16) 4-[2-[[4-[(5-aminopentyl)amino]-6-(4-fluorophenyl)-1,3,5-triazin-2-yl]amino]ethyl]-phenol,

(17) 6-(4-aminopyridin-3-yl)-$N^2$-benzyl-$N^4$-(tert-butyl)-1,3,5-triazine-2,4-diamine,

(18) $N^2$,$N^4$-bis(cyclohexylmethyl)-6-phenyl-1,3,5-triazine-2,4-diamine,

(19) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,

(20) 4,4'-[(6-phenyl-1,3,5-triazine-2,4-diyl)bis(imino-3,1-propanediyl)]bis[2,6-bis(1,1-dimethylethyl)-phenol,

(21) N-[6-[(2,3-dihydro-1H-inden-2-yl)amino]-2-(2-pyridinyl)-4-pyrimidinyl]-3 alanine,

(22) $N^4$-cyclopentyl-2-phenyl-$N^6$-(phenylmethyl)-4,6-pyrimidinediamine,

(23) 2-[[6-(bicyclo[2.2.1]hept-2-ylamino)-2-phenyl-4-pyrimidinyl]amino]-ethanol,

(24) $N^2$-isopropyl-6-phenyl-N4-(tetrahydro-2H-pyran-4-yl)-1,3,5-triazine-2,4-diamine,

(25) 2-chloro-4-(methylsulfonyl)-N-[4-[(phenylmethyl)amino]-6-(2-pyridinyl)-1,3,5-triazin-2-yl]-benzamide,

(26) N-[[4-[[[4-(cyclopropylamino)-6-(2-pyridinyl)-1,3,5-triazin-2-yl]amino]methyl]cyclohexyl]methyl]-4-fluoro-benzenesulfonamide,

(27) [[4-[[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol,

(28) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino]bis-methanol,

(29) 5-[4,6-bis(diethylamino)-1,3,5-triazin-2-yl]-2H-tetrazole-2-acetic acid ethyl ester,

(30) $N^2$,$N^2$,$N^4$,$N^4$-tetraethyl-6-(2H-tetrazol-5-yl)-1,3,5-triazine-2,4-diamine,

(31) N,N'-[6-[4-(acetylamino)-1,2,5-oxadiazol-3-yl]-1,3,5-triazine-2,4-diyl]bis-acetamide,

(32) N-(2-chloro-6-methylphenyl)-5-[[4-(dimethylamino)-6-(2-pyridinyl)-1,3,5-triazin-2-yl]amino]-1,3,4-Oxadiazole-2-carboxamide,

(33) N4-(5-methyl-1H-pyrazol-3-yl)-2-(2-pyridinyl)-N6-(tetrahydro-2H-pyran-4-yl)-4,6-Pyrimidinediamine,

(34) 6-(4-chlorophenyl)-N2-[4-chloro-3-(trifluoromethyl)phenyl]-N4-[3-(diethylamino)propyl]-1,3,5-Triazine-2,4-diamine,

(35) 6-(4-chlorophenyl)-N2-[4-chloro-3-(trifluoromethyl)phenyl]-N4-[3-(dimethylamino)propyl]-1,3,5-Triazine-2,4-diamine,

(36) N2-[3,5-bis(trifluoromethyl)phenyl]-6-(4-chlorophenyl)-N4-[3-(diethylamino)propyl]-1,3,5-Triazine-2,4-diamine,

(37) N2,N4-bis[(4-methoxyphenyl)methyl]-6-[4-(trifluoromethoxy)phenyl]-1,3,5-Triazine-2,4-diamine,

(38) N,N''-(6-phenyl-1,3,5-triazine-2,4-diyl)bis[N'-(2-chloroethyl)-Urea,

(39) N-[4-chloro-3-(trifluoromethyl)phenyl]-N'-[4-methyl-3-[[4-phenyl-6-(propylamino)-1,3,5-triazin-2-yl]amino]phenyl]-urea,

(40) N-[4-[[5-[[[[4-chloro-3-(trifluoromethyl)phenyl]amino]carbonyl]amino]-2-methylphenyl]amino]-6-(4-pyridinyl)-1,3,5-triazin-2-yl]-glycine,

(41) N-[4-[[5-[[[[4-chloro-3-(trifluoromethyl)phenyl]amino]carbonyl]amino]-2-methylphenyl]amino]-6-(5-thiazolyl)-1,3,5-triazin-2-yl]-L-Valine,

(42) s-Triazine, 2-phenyl-4,6-bis[[6-[[4-phenyl-6-[[6-[[4-phenyl-6-(trichloromethyl)-s-triazin-2-yl]amino]hexyl]amino]-s-triazin-2-yl]amino]hexyl]amino]-,

(43) α,α'-[(6-phenyl-1,3,5-triazine-2,4-diyl)bis[imino(1,1,2,2-tetrafluoro-3-oxo-3,1-propanediyl)]]bis[ω-[tetrafluoro(trifluoromethyl)ethoxy]-Poly[oxy[trifluoro(trifluoromethyl)-1,2-ethanediyl]],

(44) α-[[4-[[(3-chlorophenyl)methyl]amino]-6-(1H-imidazol-1-yl)-1,3,5-triazin-2-yl]amino]-N-[[4-(trifluoromethyl)phenyl]methyl]-, (αR)-Cyclohexanepropanamide,

(45) 6-(1H-imidazol-1-yl)-N2,N4-bis(1-methylethyl)-1,3,5-Triazine-2,4-diamine, and

(46) N2,N4-bis(1-methylpropyl)-6-phenyl-1,3,5-Triazine-2,4-diamine.

Also provided is a compound of Formula Ia, or a pharmaceutically acceptable salt or hydrate thereof:

(Ia)

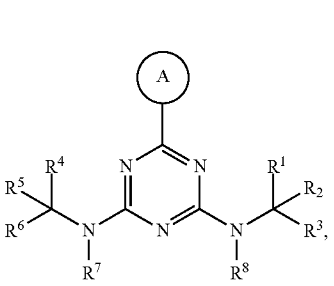

wherein:

ring A is an optionally substituted 5-6 member monocyclic aryl or monocyclic heteroaryl;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl;

wherein:

(i) when A is optionally substituted phenyl, then (a) neither N($R^7$)C($R^4$)($R^5$)($R^6$) nor N($R^8$)C($R^1$)($R^2$)($R^3$) is 4-[[2-[2-(2-aminoethoxy)ethoxy]ethyl]amino] and (b) N($R^7$)C($R^4$)($R^5$)($R^6$) and N($R^8$)C($R^1$)($R^2$)($R^3$) are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when X is N and A is an optionally substituted pyridyl, then (A) neither $N(R^7)C(R^4)(R^5)(R^6)$ nor $N(R^8)C(R^1)(R^2)(R^3)$ is NHC(O)-[2-chloro-4-(methylsulfonyl)], (B) $N(R^7)C(R^4)(R^5)(R^6)$ and $N(R^8)C(R^1)(R^2)(R^3)$ are not both $NHC(O)C(CH_3)_3$, $NHC(O)CH{=}CH_2$, $NHC(O)C(CH_3){=}CH_2$, $NHCH_2CH_2OH$, NH-cyclohexyl, $NHCH_2$-phenyl, NHC(O)phenyl, $NHC(O)(CH_2)_5NH_2$, $NHC(O)OCH_3$, $NHC(O)CH_3$, and NHC(O)NH-optionally substituted phenyl, and (C) when $N(R^7)C(R^4)(R^5)(R^6)$ is $NHC(CH_3)_3$, then $N(R^8)C(R')(R^2)(R^3)$ is not $NHCH_2$-phenyl or $NH—CH_2CH_3$;

(iii) when X is N and A is an optionally substituted heteroaryl, then $N(R^7)C(R^4)(R^5)(R^6)$ and $N(R^8)C(R^1)(R^2)(R^3)$ are not both $N(CH_2CH_3)_2$, $NHCH_2CH_2$-i-propyl, $NHCH_2CH(CH_3)_2$, and $NHC(O)CH_3$; and (iv) the compound is not selected from the group:

(1) $N^2$-[2-[2-(2-aminoethoxy)ethoxy]ethyl]-$N^4$-cyclopentyl-6-phenyl-1,3,5-triazine-2,4-diamine,
(2) $N^2$-[2-[2-(2-aminoethoxy)ethoxy]ethyl]-$N^4$-cyclopentyl-6-(4-methoxyphenyl)-1,3,5-triazine-2,4-diamine,
(3) $N^2$-[2-[2-(2-aminoethoxy)ethoxy]ethyl]-$N^4$-cyclopentyl-6-(3-nitrophenyl)-1,3,5-triazine-2,4-diamine,
(4) $N^2$-[2-[2-(2-aminoethoxy)ethoxy]ethyl]-$N^4$-cyclopentyl-6-(4-fluorophenyl)-1,3,5-triazine-2,4-diamine,
(5) $N^2$-[2-[2-(2-aminoethoxy)ethoxy]ethyl]-$N^4$-cyclopentyl-6-(4-trifluoromethoxy-phenyl)-1,3,5-triazine-2,4-diamine,
(6) $N^2$-[2-[2-(2-aminoethoxy)ethoxy]ethyl]-$N^4$-cyclopentyl-6-(4-t-butyl-phenyl)-1,3,5-triazine-2,4-diamine,
(7) $N^2$-[2-[2-(2-aminoethoxy)ethoxy]ethyl]-$N^4$-cyclopentyl-6-(2-thienyl)-1,3,5-triazine-2,4-diamine,
(8) N-(2-aminophenyl)-4-[[[4-[(2,3-dihydro-1H-inden-2-yl)amino]-6-phenyl-1,3,5-triazin-2-yl]amino]methyl]-benzamide,
(9) 2-chloro-N-[4-(cyclopropylamino)-6-(2-pyridinyl)-1,3,5-triazin-2-yl]-4-(methylsulfonyl)-benzamide,
(10) $N^2$-[2-[2-(2-aminoethoxy)ethoxy]ethyl]-$N^4$-cyclopropyl-6-(4-methoxyphenyl)-1,3,5-triazine-2,4-diamine,
(11) 2-[[1-[4-(cyclopropylamino)-6-(ethylamino)-1,3,5-triazin-2-yl]-1H-1,2,4-triazol-3-yl]thio]-acetamide,
(12) $N^2$-cyclopropyl-$N^4$-ethyl-6-[3-[(phenylmethyl)thio]-1H-1,2,4-triazol-1-yl]-1,3,5-triazine-2,4-diamine,
(13) 2-[[1-[4-(cyclopropylamino)-6-(ethylamino)-1,3,5-triazin-2-yl]-1H-1,2,4-triazol-3-yl]thio]-acetic acid methyl ester,
(14) $N^2$-[2-[2-(2-aminoethoxy)ethoxy]ethyl]-$N^4$-cyclopropyl-6-(2,4,6-trimethylphenyl)-1,3,5-triazine-2,4-diamine,
(15) $N^2$-[2-[2-(2-aminoethoxy)ethoxy]ethyl]-$N^4$-cyclopropyl-6-phenyl-1,3,5-triazine-2,4-diamine,
(16) $N^2$-[2-[2-(2-aminoethoxy)ethoxy]ethyl]-$N^4$-cyclopropyl-6-(4-methylphenyl)-1,3,5-triazine-2,4-diamine,
(17) $N^2$-[2-[2-(2-aminoethoxy)ethoxy]ethyl]-$N^4$-cyclopropyl-6-(4-chlorophenyl)-1,3,5-triazine-2,4-diamine,
(18) N-[[4-[[[4-(cyclopropylamino)-6-(2-pyridinyl)-1,3,5-triazin-2-yl]amino]methyl]cyclohexyl] methyl]-4-fluorobenzenesulfonamide,
(19) $N^2$-cyclopropyl-6-(3,5-dimethyl-1H-pyrazol-1-yl)-$N^4$-phenyl-1,3,5-triazine-2,4-diamine,
(20) $N^2$,$N^4$-dicyclohexyl-6-[3-(4-methoxyphenyl)-5-(methylthio)-1H-pyrazol-1-yl]-1,3,5-triazine-2,4-diamine,
(21) $N^2$,$N^4$-dicyclohexyl-6-[3-(3,4-dimethoxyphenyl)-5-(methylthio)-1H-pyrazol-1-yl]-1,3,5-triazine-2,4-diamine,
(22) $N^2$,$N^4$-dicyclohexyl-6-[5-(methylthio)-3-(3,4,5-trimethoxyphenyl)-1H-pyrazol-1-yl]-1,3,5-triazine-2,4-diamine,
(23) $N^2$,$N^4$-dicyclohexyl-6-phenyl-1,3,5-triazine-2,4-diamine,
(24) 1,1'-[(6-phenyl-s-triazine-2,4-diyl)diimino]bis[dodecahydro-anthraquinone],
(25) 4,4'-[(6-phenyl-1,3,5-triazine-2,4-diyl)bis(iminomethylene)]bis[2,6-bis(1,1-dimethylethyl)-phenol,
(26) N-[4-[(4-aminobutyl)amino]-6-[5-[[[[4-chloro-3-(trifluoromethyl)phenyl]amino]carbonyl] amino]-2-methylphenyl]-1,3,5-triazin-2-yl]-glycine,
(27) 4-[2-[[4-[(5-aminopentyl)amino]-6-(3-fluorophenyl)-1,3,5-triazin-2-yl]amino]ethyl]-phenol,
(28) 4-[2-[[4-[(5-aminopentyl)amino]-6-(4-fluorophenyl)-1,3,5-triazin-2-yl]amino]ethyl]-phenol,
(29) 6-(4-aminopyridin-3-yl)-$N^2$-benzyl-$N^4$-(tert-butyl)-1,3,5-triazine-2,4-diamine,
(30) $N^2$,$N^4$-bis(cyclohexylmethyl)-6-phenyl-1,3,5-triazine-2,4-diamine,
(31) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,
(32) 4,4'-[(6-phenyl-1,3,5-triazine-2,4-diyl)bis(imino-3,1-propanediyl)]bis[2,6-bis(1,1-dimethylethyl)-phenol,
(33) $N^2$-isopropyl-6-phenyl-N4-(tetrahydro-2H-pyran-4-yl)-1,3,5-triazine-2,4-diamine,
(34) 2-chloro-4-(methylsulfonyl)-N-[4-[(phenylmethyl)amino]-6-(2-pyridinyl)-1,3,5-triazin-2-yl]-benzamide,
(35) N-[[4-[[[4-(cyclopropylamino)-6-(2-pyridinyl)-1,3,5-triazin-2-yl]amino]methyl]cyclohexyl]methyl]-4-fluorobenzenesulfonamide,
(36) [[4-[[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol,
(37) [[4-[[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino]bis-methanol,
(38) 5-[4,6-bis(diethylamino)-1,3,5-triazin-2-yl]-2H-tetrazole-2-acetic acid ethyl ester,
(39) $N^2$,$N^2$,$N^4$,$N^4$-tetraethyl-6-(2H-tetrazol-5-yl)-1,3,5-triazine-2,4-diamine, and
(40) N,N-[6-[4-(acetylamino)-1,2,5-oxadiazol-3-yl]-1,3,5-triazine-2,4-diyl]bis-acetamide.

Also provided is a compound of Formula Ia, or a pharmaceutically acceptable salt or hydrate thereof:

(Ia)

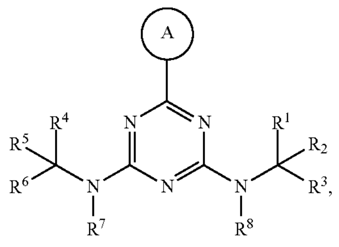

wherein:

ring A is an optionally substituted 5-6 member monocyclic aryl or monocyclic heteroaryl;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein:

(i) when A is optionally substituted phenyl, then (a) neither N($R^7$)C($R^4$)($R^5$)($R^6$) nor N($R^8$)C($R^1$)($R^2$)($R^3$) is $NHCH_2CH_2OCH_2CH_2OCH_2CH_2NH_2$ or 4-[[2-[2-(2-aminoethoxy)ethoxy]ethyl]amino] and (b) N($R^7$)C($R^4$)($R^5$)($R^6$) and N($R^8$)C($R^1$)($R^2$)($R^3$) are not both NHEt, NH(n-propyl), NH(n-butyl), NH(n-docecyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$;

(ii) when A is an optionally substituted pyridyl, then (A) neither N($R^7$)C($R^4$)($R^5$)($R^6$) nor N($R^8$)C($R^1$)($R^2$)($R^3$) is NHC(O)-[2-chloro-4-(methylsulfonyl)], $N(CH_3)_2$, $NHCH_2CH_2CH_2SO_2CH_2CH_2Cl$, $NHCH_2CH_2OCH_2CH_2SO_2CH_2CH_2Cl$, or $NHCH_2CH_2SO_2CH_2CH_2Cl$, (B) N($R^7$)C($R^4$)($R^5$)($R^6$) and N($R^8$)C($R^1$)($R^2$)($R^3$) are not both NHC(O)C$(CH_3)_3$, NHC(O)CH═$CH_2$, NHC(O)C($CH_3$)═$CH_2$, $NHCH_2CH_2OH$, NH-cyclohexyl, $NHCH_2$-phenyl, NHC(O)phenyl, NHC(O)$(CH_2)_5NH_2$, NHC(O)$OCH_3$, NHC(O)$CH_3$, and NHC(O)NH-optionally substituted phenyl, and (C) when N($R^7$)C($R^4$)($R^5$)($R^6$) is NHC$(CH_3)_3$, then N($R^8$)C($R^1$)($R^2$)($R^3$) is not $NHCH_2$-phenyl or NH—$CH_2CH_3$;

(iii) when A is an optionally substituted heteroaryl, then N($R^7$)C($R^4$)($R^5$)($R^6$) and N($R^8$)C($R^1$)($R^2$)($R^3$) are not both $N(CH_2CH_3)_2$, $NHCH_2CH_2$-i-propyl, $NHCH_2CH(CH_3)_2$, and NHC(O)$CH_3$;

(iv) when A is optionally substituted 1-pyrazolyl, then neither N($R^7$)C($R^4$)($R^5$)($R^6$) nor N($R^8$)C($R^1$)($R^2$)($R^3$) is $N(CH_3)_2$, $NHCH_3$, NHAc, NHisopropyl, $NHCH_2CH_3$, $NHCH_2CH_2SO_3H$ or $N(CH_2CH_3)_2$, (v) when A is optionally substituted phenyl, thienyl, or pyridinyl, then neither N($R^7$)C($R^4$)($R^5$)($R^6$) nor N($R^8$)C($R^1$)($R^2$)($R^3$) is NHcyclohexylC(O)$NHCH_2$R, wherein R is phenyl or pyridinyl which is substituted with one or more of $OCF_3$, $OCH_3$, chloro, or $CF_3$, (vi) when A is an optionally substituted phenyl and $R^4$ and $R^5$ form an optionally substituted phenyl, then N($R^8$)C($R^1$)($R^2$)($R^3$) is not $NHCH_2$(4-fluorophenyl), $NHCH_2CO_2H$, $NHCH_2C(O)Cl$, NHCH($CO_2H$)($CH_2SCH_2$phenyl), or $NHCH_2C(O)NHC(O)NHR$ or $NHCH_2C(O)NHC(S)NHR$, wherein R is optionally substituted phenyl or naphthyl, (vii) when A is an oxadiazole substituted with an optionally substituted pyridinyl, then $R^4$ and $R^5$ do not form an optionally substituted phenyl, (viii) when A is substituted 1-pyrazolyl, then (A) then N($R^7$)C($R^4$)($R^5$)($R^6$) and N($R^8$)C($R^1$)($R^2$)($R^3$) are not both NHC$(CH_3)_3$, and (B) A is not substituted with N═N—R, wherein R is a ring, (ix) ring A is not an optionally substituted triazolyl, 3,5-dimethyl-1H-pyrazol-1-yl, (x) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl;

(xi) the compound is not selected from the group:

(1) N-(2-aminophenyl)-4-[[[4-[(2,3-dihydro-1H-inden-2-yl)amino]-6-phenyl-1,3,5-triazin-2-yl]amino]methyl]-benzamide, (2) 2-chloro-N-[4-(cyclopropylamino)-6-(2-pyridinyl)-1,3,5-triazin-2-yl]-4-(methylsulfonyl)-benzamide, (3) 2-[[1-[4-(cyclopropylamino)-6-(ethylamino)-1,3,5-triazin-2-yl]-1H-1,2,4-triazol-3-yl]thio]-acetamide, (4) $N^2$-cyclopropyl-$N^4$-ethyl-6-[3-[(phenylmethyl)thio]-1H-1,2,4-triazol-1-yl]-1,3,5-triazine-2,4-diamine, (5) 2-[[1-[4-(cyclopropylamino)-6-(ethylamino)-1,3,5-triazin-2-yl]-1H-1,2,4-triazol-3-yl]thio]-acetic acid methyl ester, (6) N-[[4-[[[4-(cyclopropylamino)-6-(2-pyridinyl)-1,3,5-triazin-2-yl]amino]methyl]cyclohexyl]methyl]-4-fluoro-benzenesulfonamide, (7) $N^2$-cyclopropyl-6-(3,5-dimethyl-1H-pyrazol-1-yl)-$N^4$-phenyl-1,3,5-triazine-2,4-diamine, (8) $N^2$,$N^4$-dicyclohexyl-6-[3-(4-methoxyphenyl)-5-(methylthio)-1H-pyrazol-1-yl]-1,3,5-triazine-2,4-diamine, (9) $N^2$,$N^4$-dicyclohexyl-6-[3-(3,4-dimethoxyphenyl)-5-(methylthio)-1H-pyrazol-1-yl]-1,3,5-triazine-2,4-diamine,

(10) $N^2$,$N^4$-dicyclohexyl-6-[5-(methylthio)-3-(3,4,5-trimethoxyphenyl)-1H-pyrazol-1-yl]-1,3,5-triazine-2,4-diamine,

(11) $N^2$,$N^4$-dicyclohexyl-6-phenyl-1,3,5-triazine-2,4-diamine,

(12) 1,1'-[(6-phenyl-s-triazine-2,4-diyl)diimino]bis[dodecahydro-anthraquinone],

(13) 4,4'-[(6-phenyl-1,3,5-triazine-2,4-diyl)bis(iminomethylene)]bis[2,6-bis(1,1-dimethylethyl)-phenol,

(14) N-[4-[(4-aminobutyl)amino]-6-[5-[[[[4-chloro-3-(trifluoromethyl)phenyl]amino]carbonyl]amino]-2-methylphenyl]-1,3,5-triazin-2-yl]-glycine,

(15) 4-[2-[[4-[(5-aminopentyl)amino]-6-(3-fluorophenyl)-1,3,5-triazin-2-yl]amino]ethyl]-phenol,

(16) 4-[2-[[4-[(5-aminopentyl)amino]-6-(4-fluorophenyl)-1,3,5-triazin-2-yl]amino]ethyl]-phenol,

(17) 6-(4-aminopyridin-3-yl)-$N^2$-benzyl-$N^4$-(tert-butyl)-1,3,5-triazine-2,4-diamine,

(18) $N^2$,$N^4$-bis(cyclohexylmethyl)-6-phenyl-1,3,5-triazine-2,4-diamine,

(19) 4,4'-[[6-[3,5-bis(1,1-dimethylethyl)-4-hydroxyphenyl]-1,3,5-triazine-2,4-diyl]bis(imino-3,1-propanediyl)]bis[2,6-bis(1,1-dimethylethyl)-phenol,

(20) 4,4'-[(6-phenyl-1,3,5-triazine-2,4-diyl)bis(imino-3,1-propanediyl)]bis[2,6-bis(1,1-dimethylethyl)-phenol,

(21) $N^2$-isopropyl-6-phenyl-N4-(tetrahydro-2H-pyran-4-yl)-1,3,5-triazine-2,4-diamine,

(22) 2-chloro-4-(methylsulfonyl)-N-[4-[(phenylmethyl)amino]-6-(2-pyridinyl)-1,3,5-triazin-2-yl]-benzamide,

(23) N-[[4-[[[4-(cyclopropylamino)-6-(2-pyridinyl)-1,3,5-triazin-2-yl]amino]methyl]cyclohexyl]methyl]-4-fluoro-benzenesulfonamide,

(24) [[4-[[[[4-amino-6-(4-pyridinyl)-1,3,5-triazin-2-yl]amino]methoxy]methyl]amino]-6-(4-pyridinyl)-1,3,5-triazin-2-yl]imino]bis-methanol,

(25) [[4-[[[[4-[bis(hydroxymethyl)amino]-6-(4-pyridinyl)-1,3,5-triazin-2-yl]amino]methoxy]methyl](hydroxymethyl)amino]-6-(4-pyridinyl)-1,3,5-triazin-2-yl]imino]bis-methanol,

(26) 5-[4,6-bis(diethylamino)-1,3,5-triazin-2-yl]-2H-tetrazole-2-acetic acid ethyl ester,

(27) $N^2$,$N^2$,$N^4$,$N^4$-tetraethyl-6-(2H-tetrazol-5-yl)-1,3,5-triazine-2,4-diamine,

(28) N,N'-[6-[4-(acetylamino)-1,2,5-oxadiazol-3-yl]-1,3,5-triazine-2,4-diyl]bis-acetamide,

(29) N-(2-chloro-6-methylphenyl)-5-[[4-(dimethylamino)-6-(2-pyridinyl)-1,3,5-triazin-2-yl]amino]-1,3,4-Oxadiazole-2-carboxamide,

(30) 6-(4-chlorophenyl)-N2-[4-chloro-3-(trifluoromethyl)phenyl]-N4-[3-(diethylamino)propyl]-1,3,5-Triazine-2,4-diamine,

(31) 6-(4-chlorophenyl)-N2-[4-chloro-3-(trifluoromethyl)phenyl]-N4-[3-(dimethylamino)propyl]-1,3,5-Triazine-2,4-diamine,

(32) N2-[3,5-bis(trifluoromethyl)phenyl]-6-(4-chlorophenyl)-N4-[3-(diethylamino)propyl]-1,3,5-Triazine-2,4-diamine,

(33) N2,N4-bis[(4-methoxyphenyl)methyl]-6-[4-(trifluoromethoxy)phenyl]-1,3,5-Triazine-2,4-diamine,

(34) N,N''-(6-phenyl-1,3,5-triazine-2,4-diyl)bis[N'-(2-chloroethyl)-Urea,

(35) N-[4-chloro-3-(trifluoromethyl)phenyl]-N'-[4-methyl-3-[[4-phenyl-6-(propylamino)-1,3,5-triazin-2-yl]amino]phenyl]-urea,

(36) N-[4-[[5-[[[[4-chloro-3-(trifluoromethyl)phenyl]amino]carbonyl]amino]-2-methylphenyl]amino]-6-(4-pyridinyl)-1,3,5-triazin-2-yl]-glycine,

(37) N-[4-[[5-[[[[4-chloro-3-(trifluoromethyl)phenyl]amino]carbonyl]amino]-2-methylphenyl]amino]-6-(5-thiazolyl)-1,3,5-triazin-2-yl]-L-Valine,

(38) s-Triazine, 2-phenyl-4,6-bis[[6-[[4-phenyl-6-[[6-[[4-phenyl-6-(trichloromethyl)-s-triazin-2-yl]amino]hexyl]amino]-s-triazin-2-yl]amino]hexyl]amino]-,

(39) α,α'-[(6-phenyl-1,3,5-triazine-2,4-diyl)bis[imino(1,1,2,2-tetrafluoro-3-oxo-3,1-propanediyl)]]bis[ω-[tetrafluoro(trifluoromethyl)ethoxy]-Poly[oxy[trifluoro(trifluoromethyl)-1,2-ethanediyl]],

(40) α-[[4-[[(3-chlorophenyl)methyl]amino]-6-(1H-imidazol-1-yl)-1,3,5-triazin-2-yl]amino]-N-[[4-(trifluoromethyl)phenyl]methyl]-, (αR)-Cyclohexanepropanamide,

(41) N,N'-[6-[4-(acetylamino)-1,2,5-oxadiazol-3-yl]-1,3,5-triazine-2,4-diyl]bis-acetamide,

(42) 6-(1H-imidazol-1-yl)-N2,N4-bis(1-methylethyl)-1,3,5-Triazine-2,4-diamine, and

(43) N2,N4-bis(1-methylpropyl)-6-phenyl-1,3,5-Triazine-2,4-diamine.

In some embodiments, $R^1$ and $R^4$ are each independently selected from hydrogen, —$CH_3$, —$CH_2CH_3$, —$CH_2OH$, —$CH(CH_3)OH$, —$C(CH_3)_2OH$, $CF_3$, CN, or $R^1$ and $R^3$ are taken together to form ═O; or $R^4$ and $R^6$ are optionally taken together with the carbon atom to which they are attached to form C(═O).

In some embodiments, $R^1$ and $R^2$ are taken together to form carbocyclyl or heterocyclyl, either of which is optionally substituted with up to 3 substituents independently selected from halo, e.g., fluoro, $C_1$-$C_4$ alkyl, $C_1$-$C_4$ haloalkyl, $C_1$-$C_4$ alkoxy, —CN, ═O, —OH, and —$C(O)C_1$-$C_4$ alkyl. In some embodiments, $R^1$ and $R^2$ are taken together to form a carbocyclyl or heterocyclyl, either of which is optionally substituted with up to 3 substituents independently selected from halo, e.g., fluoro, $C_1$-$C_4$ alkyl, $C_1$-$C_4$ haloalkyl, $C_1$-$C_4$ alkoxy, —CN, ═O, —OH, aryl, heteroaryl —$SO_2C_1$-$C_4$ alkyl, —$CO_2C_1$-$C_4$ alkyl, —C(O)aryl, and —$C(O)C_1$-$C_4$ alkyl. In some embodiments $R^1$ and $R^2$ are taken together to form a carbocyclyl or heterocyclyl, either of which is optionally substituted with aryl or heteroaryl, which is optionally substituted with up to 2 substituents independently selected from halo, $C_1$-$C_4$ alkyl, $C_1$-$C_4$ haloalkyl, $C_1$-$C_4$ alkoxy, —CN, and —OH. In some embodiments $R^1$ and $R^2$ are taken together to form a carbocyclyl or heterocyclyl, either of which is optionally substituted with phenyl, pyridinyl or pyrimidinyl, which is optionally substituted with up to 2 substituents independently selected from halo, $C_1$-$C_4$ alkyl, $C_1$-$C_4$ haloalkyl, $C_1$-$C_4$ alkoxy, —CN, and —OH.

In some embodiments, $R^4$ and $R^5$ are taken together to form carbocyclyl or heterocyclyl, either of which is optionally substituted with up to 3 substituents independently selected from halo, e.g., fluoro, $C_1$-$C_4$ alkyl, $C_1$-$C_4$ haloalkyl, $C_1$-$C_4$ alkoxy, —CN, ═O, —OH, and —C(O)$C_1$-$C_4$ alkyl. In some embodiments, $R^4$ and $R^5$ are taken together to form a carbocyclyl or heterocyclyl, either of which is optionally substituted with up to 3 substituents independently selected from halo, e.g., fluoro, $C_1$-$C_4$ alkyl, $C_1$-$C_4$ haloalkyl, $C_1$-$C_4$ alkoxy, —CN, ═O, —OH, aryl, heteroaryl —$SO_2C_1$-$C_4$ alkyl, —$CO_2C_1$-$C_4$ alkyl, —C(O)aryl, and —C(O)$C_1$-$C_4$ alkyl. In some embodiments $R^1$ and $R^2$ are taken together to form a carbocyclyl or heterocyclyl, either of which is optionally substituted with aryl or heteroaryl, which is optionally substituted with up to 2 substituents independently selected from halo, $C_1$-$C_4$ alkyl, $C_1$-$C_4$ haloalkyl, $C_1$-$C_4$ alkoxy, —CN, and —OH. In some embodiments $R^1$ and $R^2$ are taken together to form a carbocyclyl or heterocyclyl, either of which is optionally substituted with phenyl, pyridinyl or pyrimidinyl, which is optionally substituted with up to 2 substituents independently selected from halo, $C_1$-$C_4$ alkyl, $C_1$-$C_4$ haloalkyl, $C_1$-$C_4$ alkoxy, —CN, and —OH.

In some embodiments, $R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), —($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein Q is optionally substituted with up to 3 substituents independently selected from $C_1$-$C_4$ alkyl, $C_1$-$C_4$ haloalkyl, $C_1$-$C_4$ alkoxy, ═O, —C(O)—$C_1$-$C_4$ alkyl, —CN, and halo.

In some embodiments, $R^2$ and $R^5$ are each independently selected from: —($C_1$-$C_4$ alkyl) optionally substituted with halo, e.g., fluoro or —OH; —($C_0$-$C_4$ alkylene)-O—($C_1$-$C_4$ alkyl), —($C_0$-$C_2$ alkylene)-N($R^6$)—($C_1$-$C_6$ alkyl), —($C_1$-$C_6$ alkyl)-C(O)—$NH_2$, —($C_0$-$C_2$ alkylene)-Q, —($C_0$-$C_6$ alkylene)-C(O)—($C_1$-$C_6$ alkyl), and —O—($C_0$-$C_2$ alkylene)-Q, wherein Q is optionally substituted with up to 3 substituents independently selected from $C_1$-$C_4$ alkyl, $C_1$-$C_4$ haloalkyl, $C_1$-$C_4$ alkoxy, ═O, —C(O)—$C_1$-$C_4$ alkyl, —CN, and halo. In one aspect of these embodiments, Q is selected from pyridinyl, tetrahydrofuranyl, cyclobutyl, cyclopropyl, phenyl, pyrazolyl, morpholinyl and oxetanyl, wherein Q is optionally substituted with up to 2 substituents independently selected from $C_1$-$C_4$ alkyl, $C_1$-$C_4$ haloalkyl, ═O, fluoro, chloro, and bromo. In another aspect of these embodiments, Q is selected from pyridinyl, tetrahydrofuranyl, cyclobutyl, cyclopropyl, phenyl, pyrazolyl, morpholinyl and oxetanyl, wherein Q is optionally substituted with up to 2 substituents independently selected from —$CH_3$ and ═O.

In some embodiments, $R^1$ and $R^2$ are taken together to form cyclopropyl, cyclobutyl, cyclopentyl, cyclohexyl, tetrahydrofuranyl, tetrahydropyranyl, oxetanyl, bicyclo[2.2.1]heptanyl, oxobicyclo[3.1.0]hexanyl, azetidinyl, any of which is optionally substituted with up to 2 substituents independently selected from $C_1$-$C_4$ alkyl, $C_1$-$C_4$ alkoxy, $C_3$-$C_6$ cycloalkyl, —OH, —C(O)$CH_3$, fluoro, and chloro.

In some embodiments, $R^4$ and $R^5$ are taken together to form cyclopropyl, cyclobutyl, cyclopentyl, cyclohexyl, tetrahydrofuranyl, tetrahydropyranyl, oxetanyl, bicyclo[2.2.1]heptanyl, oxobicyclo[3.1.0]hexanyl, or azetidinyl, any of which is optionally substituted with up to 2 substituents independently selected from $C_1$-$C_4$ alkyl, $C_1$-$C_4$ alkoxy, $C_3$-$C_6$ cycloalkyl, —OH, —C(O)$CH_3$, fluoro, and chloro. In some embodiments, $R^4$ and $R^5$ are taken together to form phenyl, pyrazolyl, imidazolyl, pyrrolidinyl, oxazolyl, isoxazolyl, pyridinyl, pyrimidinyl, pyrazinyl, triazinyl, thiazolyl, thiadiazolyl or isothiazolyl, any of which is optionally substituted with up to 2 substituents independently selected from halo, CN, $C_1$-$C_4$ alkyl, $C_1$-$C_4$ haloalkyl, $C_1$-$C_4$ alkoxy, $C_3$-$C_6$ cycloalkyl, phenyl, —OH, —C(O)$CH_3$, wherein any alkyl, cycloalkyl, or phenyl moiety is optionally substituted with fluoro, chloro, —OH, —$NH_2$, or —CN. In some embodiments the $C_3$-$C_6$ cycloalkyl is

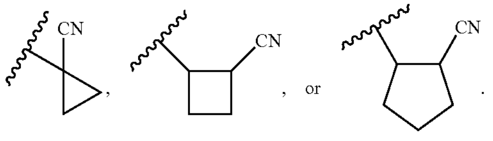 [SMILES: *C1(C#N)CC1 ; *C1CCC1C#N ; *C1CCCC1C#N]

In some embodiments, $R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$; and $R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), and —($C_0$-$C_6$ alkylene)-C(O)—($C_1$-$C_6$ alkyl), wherein: any alkyl or alkylene moiety present in $R^2$ and $R^5$ is optionally substituted with one or more —OH, —O($C_1$-$C_4$ alkyl), —$CO_2H$, or halo; and any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$; or $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl; or $R^4$ and $R^5$ are optionally taken together to form an optionally substituted carbocyclyl, wherein, when A is an optionally substituted phenyl, 2-pyrrolyl, or 1-imidazolyl, then N($R^7$)C($R^4$)($R^5$)($R^6$) is not the same as N($R^8$)C($R^1$)($R^2$)($R^3$), and the compound is not 2-(1,2-dibromoethyl)-4-phenyl-6-(1,1,2,2,3,3,4,4,5,5,6,6,6-tridecafluorohexyl-1,3,5-Triazine.

In some embodiments, ring A is an optionally substituted 6-membered monocyclic aryl. In some embodiments, ring A is an optionally substituted 5-6 membered heteroaryl. In some embodiments, ring A is an optionally substituted 5-membered heteroaryl.

In some embodiments, ring A is a substituted 5-6 member monocyclic aryl or monocyclic heteroaryl, which is substituted with up to two substituents independently selected from halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, —($C_1$-$C_6$ alkylene)-O—($C_1$-$C_6$ alkyl), azetidinyl, phenyl, and cyclopropyl optionally substituted with OH. In some embodiments, ring A is a substituted 5-6 member monocyclic aryl or monocyclic heteroaryl, which is substituted with up to two substituents independently selected from fluoro, chloro, $CF_3$, $CF_2$, —OH, —$OCH_3$, —$OCF_3$, —CN, —$NH_2$. In some embodiments, ring A is a substituted 6-membered monocyclic aryl. In some embodiments, ring A is a substituted 5-6 membered heteroaryl. In some embodiments, ring A is a substituted 5-membered heteroaryl.

In some embodiments, ring A is selected from phenyl, pyrazolyl, oxazolyl, isoxazolyl, pyridinyl, pyrimidinyl, pyrazinyl, and thiazolyl, wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —CN, —$S(O)_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH.

In some embodiments, ring A is selected from phenyl, pyrazolyl, imidazolyl, pyrrolidinyl, oxazolyl, isoxazolyl, pyridinyl, pyrimidinyl, pyrazinyl, triazinyl, thiazolyl, thiadiazolyl and isothiazolyl, wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —CN, —$S(O)_2$—($C_1$-$C_4$ alkyl), $C_1$-$C_4$ alkoxy, —NH($C_1$-$C_4$ alkyl), —OH, —CN, and —$NH_2$.

In some embodiments, ring A is monocyclic heteroaryl optionally substituted with halo, —$C_1$-$C_4$ alkyl, —$C_1$-$C_4$ haloalkyl, —O—$C_1$-$C_4$ haloalkyl, —OH, —CN, and —$NH_2$; $R^1$, $R^3$, $R^4$, and $R^6$ are each independently selected from hydrogen and $C_1$-$C_4$ alkyl; and $R^2$ and $R^5$ are each independently —($C_0$-$C_6$ alkylene)-Q; or $R^1$ and $R^2$ are optionally taken together to form an optionally substituted carbocyclyl, an optionally substituted heterocyclyl or an optionally substituted heteroaryl; or $R^4$ and $R^5$ are optionally taken together to form an optionally substituted carbocyclyl, an optionally substituted heterocyclyl or an optionally substituted heteroaryl.

In some embodiments, ring A is monocyclic heteroaryl optionally substituted with halo, —$C_1$-$C_4$ alkyl, —$C_1$-$C_4$ haloalkyl, —O—$C_1$-$C_4$ haloalkyl, —OH, —CN, and —$NH_2$; $R^1$, $R^3$, $R^4$, and $R^6$ are each independently selected from hydrogen and $C_1$-$C_4$ alkyl; and $R^2$ and $R^5$ are each independently —($C_0$-$C_6$ alkylene)-Q; or $R^1$ and $R^2$ are optionally taken together to form an optionally substituted carbocyclyl or an optionally substituted heterocyclyl; or $R^4$ and $R^5$ are optionally taken together to form an optionally substituted carbocyclyl, an optionally substituted heterocyclyl or an optionally substituted heteroaryl.

In some embodiments, ring A is:

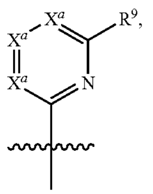

wherein $R^9$ is selected from hydrogen, halo, and —$C_1$-$C_4$ haloalkyl; each $X^a$ is independently N or C—$R^{9a}$, provided that when one $X^a$ is N, then the other two $X^a$ are both C—$R^{9a}$; and $R^{9a}$ is selected from hydrogen, halo, and —$C_1$-$C_4$ haloalkyl.

In some embodiments, ring A is:

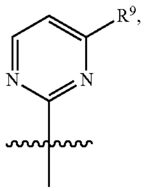

wherein $R^9$ is selected from hydrogen, halo, and —$C_1$-$C_4$ haloalkyl. In some embodiments, ring A is:

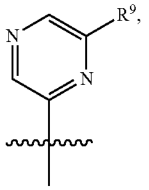

wherein $R^9$ is selected from hydrogen, halo, and —$C_1$-$C_4$ haloalkyl. In some embodiments, ring A is:

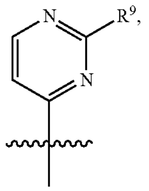

wherein $R^9$ is selected from hydrogen, halo, and —$C_1$-$C_4$ haloalkyl.

In some embodiments, ring A is pyridinyl optionally substituted with halo or —$C_1$-$C_4$ haloalkyl.

In some embodiments, ring A is pyridinyl optionally substituted with halo, e.g., chloro or fluoro.

In some embodiments, ring A is pyridin-2-yl substituted with —$C_1$-$C_4$ haloalkyl, e.g., —$CHF_2$ and $CF_3$. In some embodiments, ring A is:

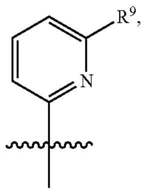

wherein $R^9$ is selected from hydrogen, halo, and —$C_1$-$C_4$ haloalkyl. In some embodiments, ring A is:

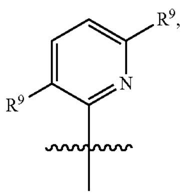

wherein each $R^9$ is independently selected from hydrogen, halo, and —$C_1$-$C_4$ haloalkyl. In some embodiments, $R^9$ is chloro or fluoro. In some embodiments, $R^9$ is —$CHF_2$ or $CF_3$. In some embodiments, $R^9$ is $CF_3$ or chloro. In some embodiments, $R^9$ is $CF_3$.

In some embodiments, ring A is:

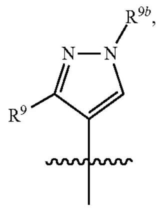

wherein $R^{9b}$ is selected from hydrogen and —$C_1$-$C_4$ alkyl, and wherein $R^9$ is selected from hydrogen, halo, and —$C_1$-$C_4$ haloalkyl.

In some embodiments, ring A is:

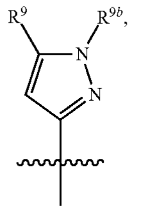

wherein $R^{9b}$ is selected from hydrogen and —$C_1$-$C_4$ alkyl, and wherein $R^9$ is selected from hydrogen, halo, and —$C_1$-$C_4$ haloalkyl.

In some embodiments, ring A is:

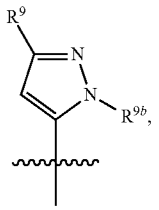

wherein $R^{9b}$ is selected from hydrogen and —$C_1$-$C_4$ alkyl, and wherein $R^9$ is selected from hydrogen, halo, and —$C_1$-$C_4$ haloalkyl.

In some embodiments, ring A is:

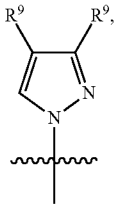

wherein $R^9$ is selected from hydrogen, halo, and —$C_1$-$C_4$ haloalkyl. In some embodiments, ring A is pyrazolyl optionally substituted with halo or —$C_1$-$C_4$ haloalkyl. In some embodiments, ring A is pyrazolyl optionally substituted with halo, e.g., chloro or fluoro. In some embodiments, ring A is 1H-pyrazol-1-yl substituted with —$C_1$-$C_4$ haloalkyl, e.g., —$CHF_2$ and $CF_3$. In some embodiments, ring A is:

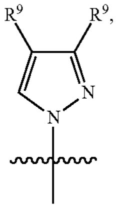

wherein $R^9$ is selected from hydrogen, halo, and —$C_1$-$C_4$ haloalkyl. In some embodiments, $R^9$ is chloro or fluoro. In some embodiments, $R^9$ is —$CHF_2$ or $CF_3$. In some embodiments, $R^9$ is $CF_3$ or chloro. In some embodiments, $R^9$ is $CF_3$.

In some embodiments, ring A is:

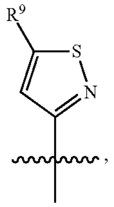

herein $R^9$ is selected from hydrogen, halo, and —$C_1$-$C_4$ haloalkyl.

In some embodiments, ring A is:

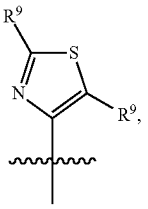

wherein $R^9$ is selected from hydrogen, halo, and —$C_1$-$C_4$ haloalkyl.

In some embodiments, ring A is:

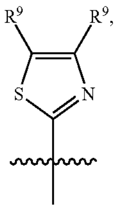

wherein $R^9$ is selected from hydrogen, halo, and —$C_1$-$C_4$ haloalkyl.

In some embodiments, ring A is:

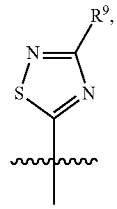

wherein $R^9$ is selected from hydrogen, halo, and —$C_1$-$C_4$ haloalkyl.

In some embodiments, ring A is:

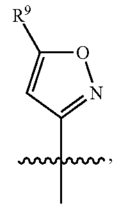

wherein $R^9$ is selected from hydrogen, halo, and —$C_1$-$C_4$ haloalkyl.

In some embodiments, ring A is:

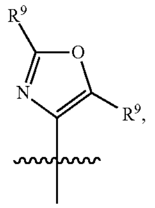

wherein $R^9$ is selected from hydrogen, halo, and —$C_1$-$C_4$ haloalkyl.

In some embodiments, ring A is:

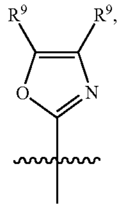

wherein $R^9$ is selected from hydrogen, halo, and —$C_1$-$C_4$ haloalkyl.

In some embodiments, ring A is pyridinyl optionally substituted with halo or —$C_1$-$C_4$ haloalkyl.

In some embodiments, ring A is pyridinyl substituted with halo, e.g., chloro or fluoro. In some embodiments, ring A is pyridinyl substituted with —$C_1$-$C_4$ haloalkyl, e.g., —$CHF_2$ and $CF_3$. In some embodiments, ring A is pyrazinyl optionally substituted with halo or —$C_1$-$C_4$ haloalkyl. In some embodiments, ring A is pyrazinyl substituted with halo, e.g., chloro or fluoro. In some embodiments, ring A is pyrazinyl substituted with —$C_1$-$C_4$ haloalkyl, e.g., —$CHF_2$ and $CF_3$. In some embodiments, ring A is pyrimidinyl optionally substituted with halo or —$C_1$-$C_4$ haloalkyl.

In some embodiments, ring A is pyrimidinyl substituted with halo, e.g., chloro or fluoro. In some embodiments, ring A is pyrimidinyl substituted with —$C_1$-$C_4$ haloalkyl, e.g., —$CHF_2$ and $CF_3$. In some embodiments, ring A is pyrazolyl optionally substituted with halo or —$C_1$-$C_4$ haloalkyl. In some embodiments, ring A is pyrazolyl substituted with halo, e.g., chloro or fluoro. In some embodiments, ring A is pyrazolyl substituted with —$C_1$-$C_4$ haloalkyl, e.g., —$CHF_2$ and $CF_3$.

In some embodiments, $R^1$, $R^3$, $R^4$, and $R^6$ are each independently selected from hydrogen and $C_1$-$C_4$ alkyl; and $R^2$ and $R^5$ are each independently —($C_0$-$C_6$ alkylene)-Q. In some embodiments, $R^1$ and $R^4$ are each hydrogen. In some embodiments, $R^3$ and $R^6$ are each $C_1$-$C_4$ alkyl. In some embodiments, $R^3$ and $R^6$ are each $C_1$-$C_4$ haloalkyl. In some embodiments, Q is selected from aryl, heteroaryl, carbocyclyl and heterocyclyl, any of which is optionally substituted. In some embodiments, Q is optionally substituted carbocyclyl. In some embodiments, Q is optionally substituted cyclopropyl. In some embodiments, Q is unsubstituted cyclopropyl. In some embodiments, $R^2$ and $R^5$ are each independently unsubstituted cyclopropyl. In some embodiments, $R^1$ and $R^4$ are each hydrogen, $R^3$ and $R^6$ are each —$CH_3$, and $R^2$ and $R^5$ are each unsubstituted cyclopropyl. In some embodiments, $R^2$ is —($C_0$-$C_6$ alkylene)-cyclopropyl and $R^5$ is —($C_0$-$C_6$ alkylene)-aryl, e.g., optionally substituted phenyl. In some embodiments, $R^2$ is cyclopropyl and $R^5$ is phenyl substituted with halo, e.g., fluoro.

In some embodiments, ring A is pyridinyl optionally substituted with halo or —$C_1$-$C_4$ haloalkyl. In some embodiments, ring A is pyridinyl substituted with halo, e.g., chloro or fluoro. In some embodiments, ring A is pyridinyl substituted with —$C_1$-$C_4$ haloalkyl, e.g., —$CHF_2$ and $CF_3$. In some embodiments, ring A is pyrazinyl optionally substituted with halo or —$C_1$-$C_4$ haloalkyl. In some embodiments, ring A is pyrazinyl substituted with halo, e.g., chloro or fluoro. In some embodiments, ring A is pyrazinyl substituted with —$C_1$-$C_4$ haloalkyl, e.g., —$CHF_2$ and $CF_3$. In some embodiments, ring A is pyrimidinyl optionally substituted with halo or —$C_1$-$C_4$ haloalkyl. In some embodiments, ring A is pyrimidinyl substituted with halo, e.g., chloro or fluoro. In some embodiments, ring A is pyrimidinyl substituted with —$C_1$-$C_4$ haloalkyl, e.g., —$CHF_2$ and $CF_3$. In some embodiments, ring A is pyrazolyl optionally substituted with halo or —$C_1$-$C_4$ haloalkyl. In some embodiments, ring A is pyrazolyl substituted with halo, e.g., chloro or fluoro. In some embodiments, ring A is pyrazolyl substituted with —$C_1$-$C_4$ haloalkyl, e.g., —$CHF_2$ and $CF_3$.

In some embodiments, $R^3$ and $R^6$ are each independently selected from hydrogen and $C_1$-$C_4$ alkyl; $R^1$ and $R^2$ are taken together to form an optionally substituted carbocyclyl; and $R^4$ and $R^5$ are taken together to form an optionally substituted carbocyclyl. In some embodiments, $R^1$ and $R^2$ are taken together to form a cyclobutyl, cyclopentyl or cyclohexyl, each optionally substituted. In some embodiments, $R^1$ and $R^2$ are taken together to form a cyclopentyl or cyclohexyl, each optionally substituted. In some embodiments, $R^4$ and $R^5$ are taken together to form a cyclobutyl, cyclopentyl or cyclohexyl, each optionally substituted. In some embodiments, $R^4$ and $R^5$ are taken together to form a cyclopentyl or cyclohexyl, each optionally substituted. In some embodiments, $R^1$ and $R^2$ are taken together to form a cyclopentyl or cyclohexyl, each substituted by one or more halo, e.g., fluoro; and $R^4$ and $R^5$ are taken together to form a cyclobutyl, cyclopentyl or cyclohexyl, each substituted by one or more halo, e.g., fluoro. In some embodiments, $R^1$ and $R^2$ are taken together to form a bicyclo[3.1.0]hexanyl; and $R^4$ and $R^5$ are taken together to form a bicyclo[3.1.0]hexanyl. In some embodiments, $R^1$ and $R^2$ taken together, and $R^4$ and $R^5$ taken together form:

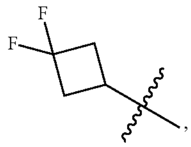,
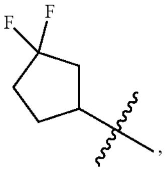, or
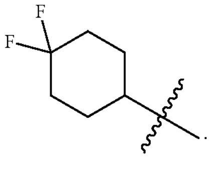.

In some embodiments, $R^1$ and $R^2$ taken together, and $R^4$ and $R^5$ taken together form:

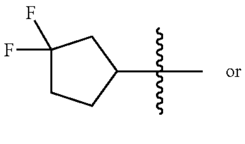 or 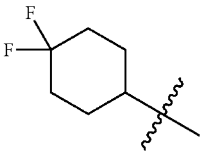.

In some embodiments, $R^1$ and $R^2$ taken together, and $R^4$ and $R^5$ taken together form:

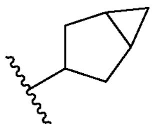.

In some embodiments, $R^1$ and $R^2$ taken together, and $R^4$ and $R^5$ taken together form:

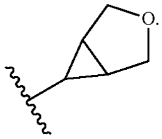 [SMILES: *C1C2COCC12]

In some embodiments, $R^1$ and $R^2$ taken together, and $R^4$ and $R^5$ taken together form:

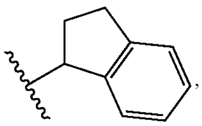 [SMILES: *C1CCc2ccccc21], which is optionally substituted with cyano or halo, e.g. fluoro, chloro, or bromo. In some embodiments, $R^1$ and $R^2$ taken together, and $R^4$ and $R^5$ taken together form:

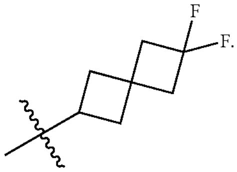 [SMILES: *C1CC2(C1)CC(F)(F)C2]

In some embodiments, $R^1$ and $R^2$ are taken together to form a cyclobutyl, cyclopentyl or cyclohexyl, each substituted by one or more 6-member monocyclic aryl, e.g., phenyl, which is optionally substituted with halo, e.g. fluoro, chloro, or bromo; and $R^4$ and $R^5$ are taken together to form a cyclobutyl, cyclopentyl or cyclohexyl, each substituted by one or more 6-member monocyclic aryl, e.g., phenyl, which is optionally substituted with halo, e.g. fluoro, chloro, or bromo. In some embodiments, $R^1$ and $R^2$ or $R^4$ and $R^5$ are taken together form:

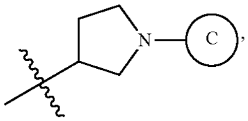, wherein Ring C is phenyl, pyridyl, or pyrimidinyl, which is optionally substituted with cyano or halo, e.g. fluoro, chloro, or bromo. In some embodiments, $R^1$ and $R^2$ or $R^4$ and $R^5$ are taken together form:

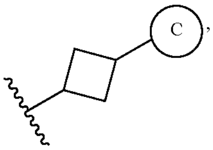, wherein Ring C is phenyl, pyridyl, or pyrimidinyl, which is optionally substituted with cyano or halo, e.g. fluoro, chloro, or bromo. In some embodiments, $R^1$ and $R^2$ or $R^4$ and $R^5$ are taken together form:

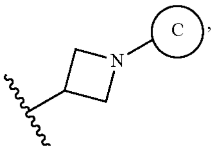, wherein Ring C is phenyl, pyridyl, or pyrimidinyl, which is optionally substituted with cyano or halo, e.g. fluoro, chloro, or bromo. In some embodiments, ring A is pyridinyl optionally substituted with halo or $-C_1$-$C_4$ haloalkyl. In some embodiments, ring A is pyridinyl substituted with halo, e.g., chloro or fluoro. In some embodiments, ring A is pyridinyl substituted with $-C_1$-$C_4$ haloalkyl, e.g., $-CHF_2$ and $CF_3$. In some embodiments, ring A is pyrazinyl optionally substituted with halo or $-C_1$-$C_4$ haloalkyl. In some embodiments, ring A is pyrazinyl substituted with halo, e.g., chloro or fluoro. In some embodiments, ring A is pyrazinyl substituted with $-C_1$-$C_4$ haloalkyl, e.g., $-CHF_2$ and $CF_3$. In some embodiments, ring A is pyrimidinyl optionally substituted with halo or —$C_1$-$C_4$ haloalkyl. In some embodiments, ring A is pyrimidinyl substituted with halo, e.g., chloro or fluoro. In some embodiments, ring A is pyrimidinyl substituted with —$C_1$-$C_4$ haloalkyl, e.g., —$CHF_2$ and $CF_3$. In some embodiments, ring A is pyrazolyl optionally substituted with halo or —$C_1$-$C_4$ haloalkyl. In some embodiments, ring A is pyrazolyl substituted with halo, e.g., chloro or fluoro. In some embodiments, ring A is pyrazolyl substituted with —$C_1$-$C_4$ haloalkyl, e.g., —$CHF_2$ and $CF_3$.

In some embodiments, $R^1$, $R^3$, $R^4$, and $R^6$ are each independently selected from hydrogen, $C_1$-$C_4$ alkyl, and —CN, wherein each said alkyl moiety of $R^1$, $R^3$, $R^4$, and $R^6$ are each independently optionally substituted with —OH, —$NH_2$, —CN, —O—$C_1$-$C_4$ alkyl; and $R^2$ and $R^5$ are each independently selected from —($C_1$-$C_6$ alkyl) and —($C_0$-$C_6$ alkylene)-Q. In some embodiments, $R^1$, $R^3$, $R^4$, and $R^6$ are each independently selected from hydrogen, $C_1$-$C_4$ alkyl, and —CN; and $R^2$ and $R^5$ are each independently —($C_1$-$C_6$ alkyl) and —($C_0$-$C_6$ alkylene)-Q. In some embodiments, $R^1$, $R^3$, $R^4$, and $R^6$ are each independently selected from hydrogen, $C_1$-$C_4$ alkyl, and —CN; $R^2$ is —($C_1$-$C_6$ alkyl); and $R^5$ is —($C_0$-$C_6$ alkylene)-Q, wherein Q is optionally substituted carbocyclyl. In some embodiments, Q is unsubstituted carbocyclyl. In some embodiments, Q is cyclopropyl. In some embodiments, ring A is pyridinyl optionally substituted with halo or —$C_1$-$C_4$ haloalkyl. In some embodiments, ring A is pyridinyl substituted with —$C_1$-$C_4$ haloalkyl, e.g., —$CHF_2$ and $CF_3$. In some embodiments, ring A is pyrazinyl optionally substituted with halo or —$C_1$-$C_4$ haloalkyl. In some embodiments, ring A is pyrazinyl substituted with halo, e.g., chloro or fluoro. In some embodiments, ring A is pyrazinyl substituted with —$C_1$-$C_4$ haloalkyl, e.g., —$CHF_2$ and $CF_3$. In some embodiments, ring A is pyrimidinyl optionally substituted with halo or —$C_1$-$C_4$ haloalkyl. In some embodiments, ring A is pyrimidinyl substituted with halo, e.g., chloro or fluoro. In some embodiments, ring A is pyrimidinyl substituted with —$C_1$-$C_4$ haloalkyl, e.g., —$CHF_2$ and $CF_3$. In some embodiments, ring A is pyrazolyl optionally substituted with halo or —$C_1$-$C_4$ haloalkyl. In some embodiments, ring A is pyrazolyl substituted with halo, e.g., chloro or fluoro. In some embodiments, ring A is pyrazolyl substituted with —$C_1$-$C_4$ haloalkyl, e.g., —$CHF_2$ and $CF_3$.

In some embodiments, $R^1$, $R^3$, and $R^6$ are each independently selected from hydrogen and $C_1$-$C_4$ alkyl, wherein each said alkyl moiety of $R^1$, $R^3$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$; $R^2$ is —($C_0$-$C_6$ alkylene)-Q; and $R^4$ and $R^5$ taken together form an optionally substituted carbocyclyl, optionally substituted heterocyclyl or optionally substituted heteroaryl. In some embodiments, $R^4$ and $R^5$ taken together form an optionally substituted carbocyclyl. In some embodiments, the carbocyclyl is selected from cyclopentyl and cyclohexyl optionally substituted with —OH, —O($C_1$-$C_4$ alkyl), —$CO_2$H, or halo. In some embodiments, $R^4$ and $R^5$ taken together form an optionally substituted heterocyclyl optionally substituted with —OH, —O($C_1$-$C_4$ alkyl), —$CO_2$H, or halo. In some embodiments, $R^4$ and $R^5$ taken together form an optionally substituted tetrahydrofuran. In some embodiments, $R^1$, $R^3$, and $R^6$ are each independently selected from hydrogen and $C_1$-$C_4$ alkyl, wherein each said alkyl moiety of $R^1$, $R^3$, and $R^6$ are each independently optionally substituted with —OH, —$NH_2$, —CN, —O—$C_1$-$C_4$ alkyl; $R^2$ is —($C_0$-$C_6$ alkylene)-Q; and $R^5$ is $C_1$-$C_4$ alkyl. In some embodiments, $R^1$, $R^3$, and $R^6$ are each independently selected from hydrogen, $C_1$-$C_4$ alkyl, or carbocyclyl, wherein any alkyl or carbocyclyl portion of $R^1$, $R^3$, and $R^6$ are each independently optionally substituted with —OH, —$NH_2$, —CN, —O—$C_1$-$C_4$ alkyl, —$SO_2$-$C_1$-$C_4$ alkyl, —C(O)$NH_2$, —O—$R^{12}$, —$CO_2R^{12}$ or —C(O)$R^{12}$, wherein $R^{12}$ is morpholino, piperidinyl, phenyl, pyridyl, or pyrimidinyl. In some embodiments, $R^1$, $R^3$, and $R^6$ are each independently selected from hydrogen and $C_1$-$C_4$ alkyl, wherein each said alkyl moiety of $R^1$, $R^3$, and $R^6$ are each independently optionally substituted with —OH, —$NH_2$, —CN, —O—$C_1$-$C_4$ alkyl, —O—$R^{12}$, wherein $R^{12}$ is phenyl, pyridyl, or pyrimidinyl; $R^2$ is —($C_0$-$C_6$ alkylene)-Q; and $R^5$ is $C_1$-$C_4$ alkyl.

In some embodiments, $R^7$ is H. In some embodiments, $R^8$ is H. In some embodiments, both $R^7$ and $R^8$ are H.

In some embodiments, ring A, $R^1$, $R^2$, $R^3$, $R^4$, $R^5$, $R^6$, $R^7$, $R^8$ are selected from any one of the preceding embodiments.

Also provided is a compound of Formula B, or pharmaceutically acceptable salt or hydrate thereof:

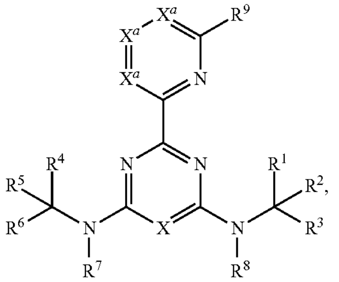

(B)

wherein:

X is N, CH or C-halo;

$X^a$ is N or C—$R^{9a}$, provided that when one $X^a$ is N, then the other two $X^a$ are both C—$R^{9a}$; $R^9$ is halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, —($C_1$-$C_6$ alkylene)-O—($C_1$-$C_6$ alkyl), aryl, and cyclopropyl optionally substituted with OH; each $R^{9a}$ is independently selected from hydrogen, halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, —($C_1$-$C_6$ alkylene)-O—($C_1$-$C_6$ alkyl), aryl, and cyclopropyl optionally substituted with OH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2$H, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), —($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2$H, or halo;

any terminal methyl moiety present in $R^2$ and $R^5$ is optionally replaced with —$CH_2$OH, $CF_3$, —$CH_2$F, —$CH_2$Cl, C(O)$CH_3$, C(O)$CF_3$, CN, or $CO_2$H;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl, an optionally substituted 5-6 member monocyclic aryl, or an optionally substituted 5-6 member monocyclic heteroaryl;

wherein the compound is not selected from the group:

(1) 4,6-Pyrimidinediamine, 2-(6-methyl-2-pyridinyl)-N4, N6-dipropyl-;

(2) 4,6-Pyrimidinediamine, N4-ethyl-2-(6-methyl-2-pyridinyl)-N6-propyl-;

(3) 4,6-Pyrimidinediamine, N4,N4-diethyl-2-(6-methyl-2-pyridinyl)-N6-propyl-;

(4) [2,4'-Bipyrimidine]-2',4,6-triamine, N6-[2-(dimethylamino)ethyl]-N2',N2',N4,N4-tetramethyl-; or (5) [2,4'-Bipyrimidine]-2',4,6-triamine, N6-[2-(dimethylamino)ethyl]-N2',N2',N4,N4-tetramethyl-, phosphate.

In some embodiments, X is N and $R^4$ and $R^5$ are optionally taken together to form an optionally substituted carbocyclyl or optionally substituted heterocyclyl.

Also provided is a compound of Formula Ib, or pharmaceutically acceptable salt or hydrate thereof:

(Ib)

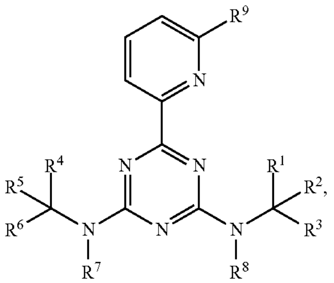

wherein:

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2$H, —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2$H, or halo;

any terminal methyl moiety present in $R^2$ and $R^5$ is optionally replaced with —$CH_2$OH, $CF_3$, —$CH_2$F, —$CH_2$Cl, C(O)$CH_3$, C(O)$CF_3$, CN, or $CO_2$H;

$R^7$ and $R^8$ are each independently selected from hydrogen and $C_1$-$C_6$ alkyl;

$R^9$ is selected from hydrogen, halo, and —$C_1$-$C_4$ haloalkyl; and

Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl, optionally substituted heterocyclyl; or $R^4$ and $R^5$ are optionally taken together to form an optionally substituted carbocyclyl, optionally substituted heterocyclyl;

wherein:

(i) neither $N(R^7)C(R^4)(R^5)(R^6)$ nor $N(R^8)C(R^1)(R^2)(R^3)$ is NHC(O)-[2-chloro-4-(methylsulfonyl)] or $N(CH_3)_2$, (ii) $N(R^7)C(R^4)(R^5)(R^6)$ and $N(R^8)C(R^1)(R^2)(R^3)$ are not both NHC(O)C$(CH_3)_3$, NHC(O)CH═$CH_2$, NHC(O)C($CH_3$)═$CH_2$, NH$CH_2CH_2$OH, NH-cyclohexyl, NH$CH_2$-phenyl, NHC(O)phenyl, NHC(O)$(CH_2)_5NH_2$, NHC(O)O$CH_3$, NHC(O)$CH_3$, and NHC(O)NH-optionally substituted phenyl, and (iii) when $N(R^7)C(R^4)(R^5)(R^6)$ is NHC$(CH_3)_3$, then $N(R^8)C(R^1)(R^2)(R^3)$ is not NH$CH_2$-phenyl or NH—$CH_2CH_3$; and wherein the compound is not:

(1) 2-chloro-N-[4-(cyclopropylamino)-6-(2-pyridinyl)-1,3,5-triazin-2-yl]-4-(methylsulfonyl)-benzamide, (2) N-[[4-[[[4-(cyclopropylamino)-6-(2-pyridinyl)-1,3,5-triazin-2-yl]amino]methyl]cyclohexyl]methyl]-4-fluorobenzenesulfonamide, (3) 2-chloro-4-(methylsulfonyl)-N-[4-[(phenylmethyl)amino]-6-(2-pyridinyl)-1,3,5-triazin-2-yl]-benzamide, or (4) N-[[4-[[[4-(cyclopropylamino)-6-(2-pyridinyl)-1,3,5-triazin-2-yl]amino]methyl]cyclohexyl]methyl]-4-fluorobenzenesulfonamide.

Also provided is a compound of Formula Ia, or a pharmaceutically acceptable salt or hydrate thereof:

(Ig)

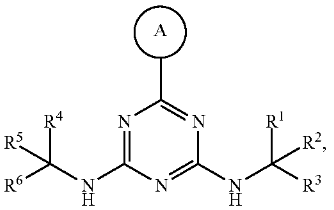

wherein:

ring A is is an optionally substituted 5-6 member monocyclic aryl or monocyclic heteroaryl;

$R^3$ and $R^6$ are both hydrogen;

$R^1$ and $R^4$ are each independently selected from $C_1$-$C_4$ alkyl and $C_1$-$C_4$ haloalkyl; and $R^2$ and $R^5$ are each —($C_1$-$C_6$ alkyl); or $R^1$ and $R^2$ are optionally taken together to form an optionally substituted monocyclic carbocyclyl; or $R^4$ and $R^5$ are optionally taken together to form an optionally substituted monocyclic carbocyclyl;

wherein:

(i) ring A is not an optionally substituted triazolyl, 3,5-dimethyl-1H-pyrazol-1-yl, (ii) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl; and (iii) the compound is not selected from the group:

(1) 6-(1H-imidazol-1-yl)-N2,N4-bis(1-methylethyl)-1,3,5-Triazine-2,4-diamine, or (2) N2,N4-bis(1-methylpropyl)-6-phenyl-1,3,5-Triazine-2,4-diamine.

Also provided is a compound of Formula C, or pharmaceutically acceptable salt or hydrate thereof:

(C)

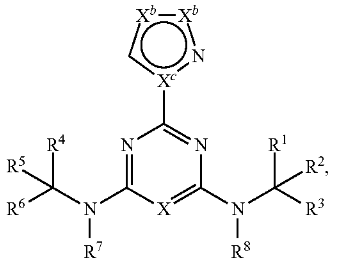

wherein:

X is N, CH or C-halo;

each $X^b$ is independently N—$R^{9b}$, O, S, C—H, or C—$R^{9c}$, provided that at least one $X^b$ is C—$R^{9c}$, and when one $X^b$ is C—H or C—$R^9$ and the other is C—$R^{9c}$ then $X^c$ is N, and when one $X^b$ is N—$R^{9b}$, O, or S, then $X^c$ is C;

$R^{9b}$ is hydrogen or —$C_1$-$C_4$ alkyl;

$R^{9c}$ is halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —CN, —$S(O)_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, —($C_1$-$C_6$ alkylene)-O—($C_1$-$C_6$ alkyl), aryl, and cyclopropyl optionally substituted with OH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl, an optionally substituted 5-6 member monocyclic aryl, or an optionally substituted heteroaryl;

wherein:

(i) when X is CH and A is optionally substituted 1-imidazolyl, optionally substituted 1-pyrrolyl or optionally substituted 1-pyrazolyl, then neither N($R^7$)C($R^4$)($R^5$)($R^6$) nor N($R^8$)C($R^1$)($R^2$)($R^3$) is NH$(CH_2)_7CH_3$, NH$CH_2$-(o-chloro-phenyl), or NH$CH_2CH_2OH$; and (ii) when X and X are both N, then neither N($R^7$)C($R^4$)($R^5$)($R^6$) nor N($R^8$)C(R')($R^2$)($R^3$) is N$(CH_3)_2$, NH$CH_3$, or N$(CH_2CH_3)_2$.

Also provided is a compound having Formula Id, or pharmaceutically acceptable salt or hydrate thereof:

(Id)

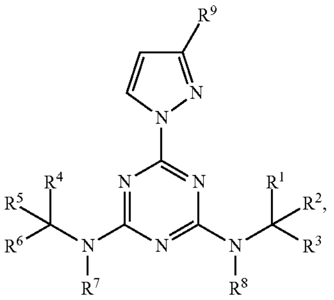

wherein:

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl;

$R^9$ is halo or —$C_1$-$C_4$ haloalkyl; and

Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O);

$R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein the compound is not:

(1) N2,N2,N4-trimethyl-6-[3-(trifluoromethyl)-1H-pyrazol-1-yl]-1,3,5-Triazine-2,4-diamine, or (2) N4-ethyl-N2,N2-dimethyl-6-[3-(trifluoromethyl-1H-pyrazol-1-yl]-1,3,5-Triazine-2,4-diamine.

A compound having Formula Ie, or pharmaceutically acceptable salt or hydrate thereof:

(Ie)

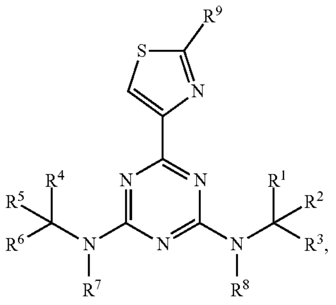

wherein $R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl;

$R^9$ is selected from hydrogen, halo, and —$C_1$-$C_4$ haloalkyl; and

Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O);

$R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl.

A compound having Formula If, or pharmaceutically acceptable salt or hydrate thereof:

(If)

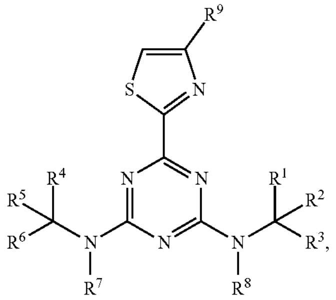

wherein $R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl;

$R^9$ is selected from hydrogen, halo, and —$C_1$-$C_4$ haloalkyl; and

Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O);

$R^1$ and $R^2$ are optionally taken together to form an optionally substituted carbocyclyl or optionally substituted heterocyclyl; or $R^4$ and $R^5$ are optionally taken together to form an optionally substituted carbocyclyl or optionally substituted heterocyclyl.

Also provided is a compound of Formula II, or pharmaceutically acceptable salt or hydrate thereof:

(II)

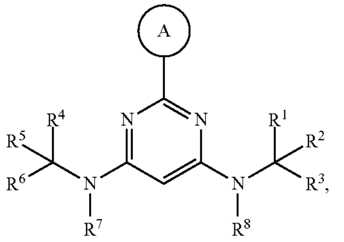

wherein:

ring A is an optionally substituted 5-6 member monocyclic aryl or monocyclic heteroaryl;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-S(O)$_{0-2}$—($C_0$-$C_6$ alkylene)-Q, —($C_1$-$C_6$ alkylene)-N($R^6$)—C(O)—N($R^6$)—($C_1$-$C_6$ alkyl), —($C_0$-$C_6$ alkylene)-Q, —($C_0$-$C_6$ alkylene)-C(O)—($C_1$-$C_6$ alkyl), —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl or optionally substituted heterocyclyl; or $R^4$ and $R^5$ are optionally taken together to form an optionally substituted carbocyclyl, optionally substituted heterocyclyl, an optionally substituted aryl, or an optionally substituted heteroaryl;

wherein:

(i) when A is phenyl optionally substituted with F, Cl or $SO_2CH_3$, then neither N($R^7$)C($R^4$)($R^5$)($R^6$) nor N($R^8$)C($R^1$)($R^2$)($R^3$) is N($CH_3$)$CH_2$C(O)NH-i-propyl, NHCH($CH_3$)($CH_2$)$_3$N($CH_2CH_3$)$_2$, $NHCH_2CH_2OH$, $NHCH_2CH_2OCH_3$, $NHCH_2CH_2OSO_3H$, $NHCH_2CH_2CH_2OCH_2CH_2O$-phenyl, $NHCH_2CH_2CH_2OH$, $NHCH_2CH_2CH_2OCH_3$, $NHCH_2$CH(OH)$CH_3$, N($CH_2CH_3$)$_2$, NH-i-propyl, $NHCH_2CH_2$NHC(O)$OCH_3$, $NHCH_2CH_2$NHC(O)$CH_3$, $NHCH_2CH_2NH_2$, or $NHCH_2$-phenyl;

(ii) when A is optionally substituted pyridyl, then neither N($R^7$)C($R^4$)($R^5$)($R^6$) nor N($R^8$)C($R^1$)($R^2$)($R^3$) is $NHCH_2$-phenyl, $NHCH_2$-(2,4-difluorophenyl), N($CH_3$)$CH_2CH_2$C(O)OH, $NHCH_2CH_2$C(O)OH, $NHCH_2CH_2$C(O)$OCH_2CH_3$, $NHCH_2CH_2$C(O)O-t-butyl, $NHCH_2CH_2$C(O)$NH_2$, $NHCH_2CH_2$-phenyl, $NHCH_2CH_2OH$, $NHCH_2CH_2NH_2$, $NHCH_2CH_2$N($CH_3$)$_2$, or $NHCH_2CH_2CH_3$;

(iii) when A is optionally substituted 1-imidazolyl, optionally substituted 1-pyrrolyl or optionally substituted 1-pyrazolyl, then neither N($R^7$)C($R^4$)($R^5$)($R^6$) nor N($R^8$)C($R^1$)($R^2$)($R^3$) is NH($CH_2$)$_7CH_3$, $NHCH_2$-(o-chloro-phenyl), or $NHCH_2CH_2OH$;

(iv) when A is unsubstituted 2-pyridinyl, then the ring formed by $R^4$ and $R^5$ is not 5-methyl-1H-pyrazol-3-yl; and (v) when A is optionally substituted 1-pyrazolyl, then neither N($R^7$)C($R^4$)($R^5$)($R^6$) nor N($R^8$)C($R^1$)($R^2$)($R^3$) is N($CH_3$)$_2$, $NHCH_3$, NHAc, NHisopropyl, $NHCH_2CH_3$, $NHCH_2CH_2SO_3H$ or N($CH_2CH_3$)$_2$, (vi) ring A is not an optionally substituted triazolyl, 3,5-dimethyl-1H-pyrazol-1-yl, (vii) when $R^1$ and $R^2$ are optionally taken together to form an unsubstituted cyclohexyl, and $R^4$ and $R^5$ are optionally taken together to form an unsubstituted cyclohexyl, then A is not a disubstituted 1-pyrazolyl or an unsubstituted phenyl; and (viii) the compound is not selected from the group:

(1) 6-(1H-imidazol-1-yl)-N2,N4-bis(1-methylethyl)-1,3,5-Triazine-2,4-diamine, or (2) N2,N4-bis(1-methylpropyl)-6-phenyl-1,3,5-Triazine-2,4-diamine.

Also provided is a compound of Formula Ic, or pharmaceutically acceptable salt or hydrate thereof:

(Ic)

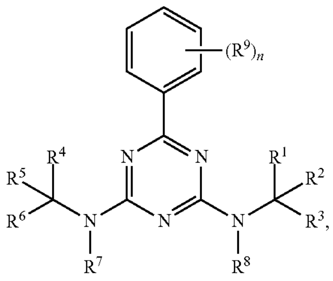

wherein:

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

each $R^9$ is independently selected from halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, —($C_1$-$C_6$ alkylene)-O—($C_1$-$C_6$ alkyl), aryl, and cyclopropyl optionally substituted with OH;

n is 1 to 3;

$R^2$ and $R^5$ are each independently selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), ($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from carbocyclyl and heterocyclyl, any of which is optionally substituted; wherein $R^1$ and $R^3$ are optionally taken together with the carbon atom to which they are attached to form C(═O); or $R^4$ and $R^6$ are optionally taken together with the carbon atom to which they are attached to form C(═O); or $R^1$ and $R^2$ are optionally taken together to form an optionally substituted carbocyclyl; or $R^4$ and $R^5$ are optionally taken together to form an optionally substituted carbocyclyl;

wherein:

(i) neither N($R^7$)C($R^4$)($R^5$)($R^6$) nor N($R^8$)C($R^1$)($R^2$)($R^3$) is $NHCH_2CH_2OCH_2CH_2OCH_2CH_2NH_2$, or 4-[[2-[2-(2-aminoethoxy)ethoxy]ethyl]amino], (ii) N($R^7$)C($R^4$)($R^5$)($R^6$) and N($R^8$)C($R^1$)($R^2$)($R^3$) are not both NHEt, NH(n-propyl), NH(n-butyl), NH(n-decyl), NH-[(4-methoxyphenyl)methyl], $NHCH_2CH_2CHO$, $NHCH_2CH_2OCH_3$, $NHCH_2CH_2OH$, $NHCH_2CH(OH)CH_3$, $NHCH_2CH_2OC(O)$phenyl, $NHCH_2CH_2CH_2OH$, $NHCH_2CH_2CH_2N(CH_3)$phenyl, $NHCH_2C(O)OCH_3$, $NHCH_2C(O)OCH_2CH_3$, $NHCH_2$phenyl, $NHCH(CH_3)CH_2CH_3$, or $NHCH_2CH_2OC(O)CH_3$; and (iii) neither N($R^7$)C($R^4$)($R^5$)($R^6$) nor N($R^8$)C($R^1$)($R^2$)($R^3$) is NHcyclohexylC(O)$NHCH_2$R, wherein R is phenyl or pyridinyl which is substituted with one or more of $OCF_3$, $OCH_3$, chloro, or $CF_3$.

Also provided is a compound of Formula III, or pharmaceutically acceptable salt or hydrate thereof:

(III)

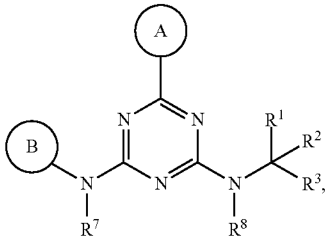

wherein:

ring A is an optionally substituted 5-6 member monocyclic heteroaryl;

ring B is an optionally substituted 5-6 member monocyclic aryl or monocyclic heteroaryl;

$R^1$ and $R^3$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ is selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), —($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein:

any alkyl or alkylene moiety present in $R^2$ is optionally substituted with one or more —OH, —O($C_1$-$C_4$ alkyl), —$CO_2H$, or halo;

any terminal methyl moiety present in $R^2$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^1$ and $R^2$ are optionally taken together to form an optionally substituted carbocyclyl or optionally substituted heterocyclyl;

wherein when A is an oxadiazole substituted with an optionally substituted pyridinyl, then G is not an optionally substituted phenyl.

In some embodiments, G is substituted with 1 or 2 substituents selected from halo, $C_1$-$C_4$ alkyl, $C_1$-$C_4$ haloalkyl, $C_1$-$C_4$ alkoxy, —CN, ═O, —OH, aryl, heteroaryl —$SO_2C_1$-$C_4$ alkyl, —$CO_2C_1$-$C_4$ alkyl, —C(O)aryl, and —C(O)$C_1$-$C_4$ alkyl.

Also provided is a compound of Formula IIIa, or pharmaceutically acceptable salt or hydrate thereof:

(IIIa)

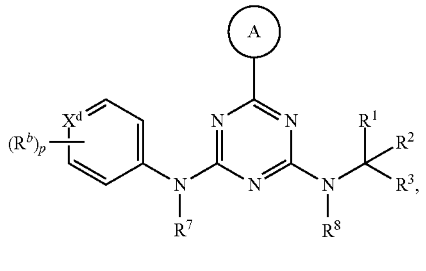

wherein:

ring A is a substituted 5-6 member monocyclic heteroaryl;

$X^d$ is C or N;

each $R^b$ is independently selected from halo, CN, $C_1$-$C_4$ alkyl, $C_1$-$C_4$ haloalkyl, $C_1$-$C_4$ alkoxy, $C_3$-$C_6$ cycloalkyl, phenyl, —OH, —C(O)$CH_3$, wherein any alkyl, cycloalkyl, or phenyl moiety is optionally substituted with fluoro, chloro, —OH, —$NH_2$, or —CN;

p is 1 to 2;

$R^1$ and $R^3$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ is selected from: —($C_1$-$C_6$ alkyl), —($C_1$-$C_6$ alkyl)-C(O)—$NH_2$, —($C_1$-$C_6$ alkyl)-$CO_2$H, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), —($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein:

any alkyl or alkylene moiety present in $R^2$ is optionally substituted with one or more —OH, —O($C_1$-$C_4$ alkyl), —$CO_2$H, or halo;

any terminal methyl moiety present in $R^2$ is optionally replaced with —$CH_2$OH, $CF_3$, —$CH_2$F, —$CH_2$Cl, C(O)$CH_3$, C(O)$CF_3$, CN, or $CO_2$H;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^1$ and $R^2$ are optionally taken together to form an optionally substituted carbocyclyl or optionally substituted heterocyclyl;

wherein when A is an oxadiazole substituted with an optionally substituted pyridinyl, then $X^d$ is not C.

Also provided is a compound of Formula IIIb, or pharmaceutically acceptable salt or hydrate thereof:

(IIIb)

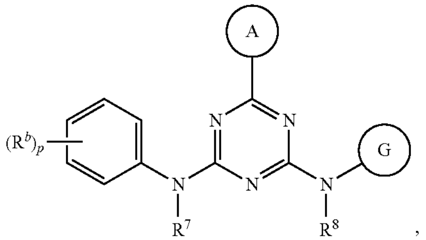

wherein:

ring A is a substituted 5-6 member monocyclic heteroaryl;

$R^7$ and $R^8$ are each independently selected from hydrogen and $C_1$-$C_6$ alkyl;

each $R^b$ is independently selected from halo, CN, $C_1$-$C_4$ alkyl, $C_1$-$C_4$ haloalkyl, $C_1$-$C_4$ alkoxy, $C_3$-$C_6$ cycloalkyl, phenyl, —OH, —C(O)$CH_3$, wherein any alkyl, cycloalkyl, or phenyl moiety is optionally substituted with fluoro, chloro, —OH, —$NH_2$, or —CN;

p is 1 to 2; and

G is an optionally substituted carbocyclyl or heterocyclyl, wherein A is not an oxadiazole substituted with an optionally substituted pyridinyl.

Also provided is a compound of Formula IIIc, or pharmaceutically acceptable salt or hydrate thereof:

(IIIc)

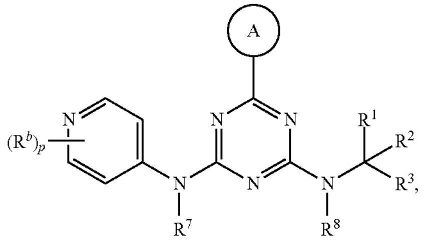

wherein:

ring A is a substituted 5-6 member monocyclic heteroaryl;

$R^1$ and $R^3$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ is selected from: —($C_1$-$C_6$ alkyl), —($C_1$-$C_6$ alkyl)-C(O)—$NH_2$, —($C_1$-$C_6$ alkyl)-$CO_2H$, —($C_2$-$C_6$ alkenyl or alkynyl), —($C_1$-$C_6$ alkylene)-O—($C_1$-$C_6$ alkyl), —($C_0$-$C_6$ alkylene)-C(O)N($R^6$)—($C_1$-$C_6$ alkyl), —($C_0$-$C_6$ alkylene)-Q, —($C_0$-$C_6$ alkylene)-C(O)—($C_1$-$C_6$ alkyl), and —($C_0$-$C_6$ alkylene)-C(O)—($C_0$-$C_6$ alkylene)-Q, wherein:

any alkyl or alkylene moiety present in $R^2$ is optionally substituted with one or more —OH, —O($C_1$-$C_4$ alkyl), —$CO_2H$, or halo;

any terminal methyl moiety present in $R^2$ is optionally replaced with —$CH_2OH$, $CF_3$, —$CH_2F$, —$CH_2Cl$, C(O)$CH_3$, C(O)$CF_3$, CN, or $CO_2H$;

$R^7$ and $R^8$ are each independently selected from hydrogen and $C_1$-$C_6$ alkyl; and Q is selected from aryl, heteroaryl, carbocyclyl and heterocyclyl, any of which is optionally substituted; wherein $R^1$ and $R^3$ are optionally taken together with the carbon atom to which they are attached to form C(═O); or $R^1$ and $R^2$ are optionally taken together to form an optionally substituted carbocyclyl or optionally substituted heterocyclyl;

each $R^b$ is independently selected from halo, CN, $C_1$-$C_4$ alkyl, $C_1$-$C_4$ haloalkyl, $C_1$-$C_4$ alkoxy, $C_3$-$C_6$ cycloalkyl, phenyl, —OH, —C(O)$CH_3$, wherein any alkyl, cycloalkyl, or phenyl moiety is optionally substituted with fluoro, chloro, —OH, —$NH_2$, or —CN; and p is 1 to 2.

Also provided is a compound of Formula IIId, or pharmaceutically acceptable salt or hydrate thereof:

(IIId)

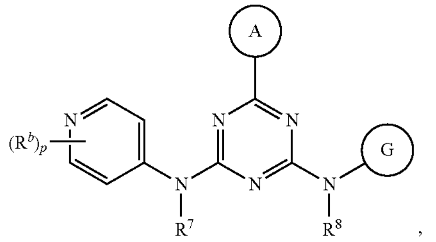

wherein:

ring A is a substituted 5-6 member monocyclic heteroaryl;

$R^7$ and $R^8$ are each independently selected from hydrogen and $C_1$-$C_6$ alkyl;

each $R^b$ is independently selected from halo, CN, $C_1$-$C_4$ alkyl, $C_1$-$C_4$ haloalkyl, $C_1$-$C_4$ alkoxy, $C_3$-$C_6$ cycloalkyl, phenyl, —OH, —C(O)$CH_3$, wherein any alkyl, cycloalkyl, or phenyl moiety is optionally substituted with fluoro, chloro, —OH, —$NH_2$, or —CN;

p is 1 to 2; and

G is an optionally substituted carbocyclyl or heterocyclyl.

Further embodiments provided herein include combinations of one or more of the particular embodiments set forth above.

In another embodiment, the compound is selected from any one of the compounds set forth in Table 1, below.

TABLE 1

| Representative Compounds | |
|---|---|
| Compound Number | Structure |
| 1 | 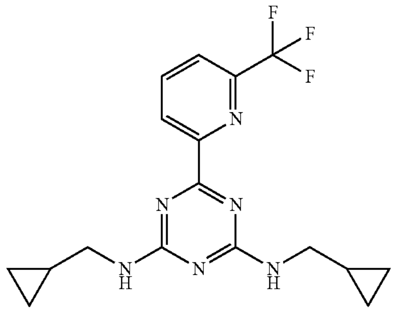 [SMILES: FC(F)(F)c1cccc(-c2nc(NCC3CC3)nc(NCC3CC3)n2)n1] |
| 2 | 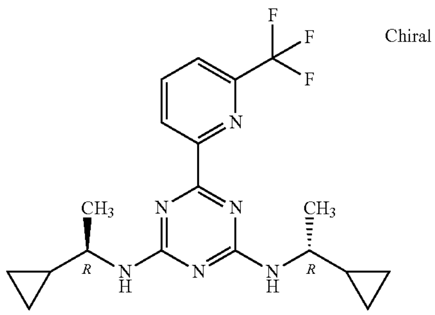 Chiral |

TABLE 1-continued
Representative Compounds
| Compound Number | Structure |
| --- | --- |
| 3 | 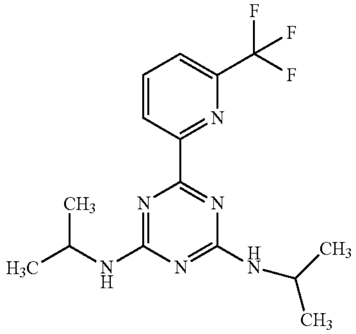 [SMILES: CC(C)Nc1nc(NC(C)C)nc(-c2cccc(C(F)(F)F)n2)n1] |
| 4 | 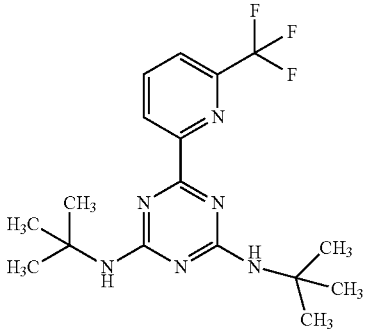 [SMILES: CC(C)(C)Nc1nc(NC(C)(C)C)nc(-c2cccc(C(F)(F)F)n2)n1] |
| 5 | 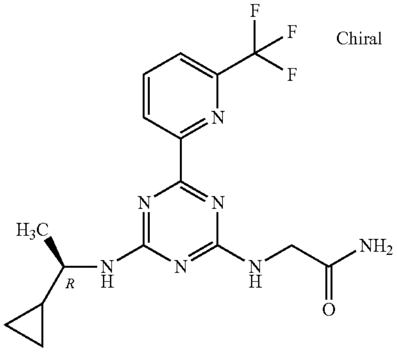 Chiral |
| 6 | 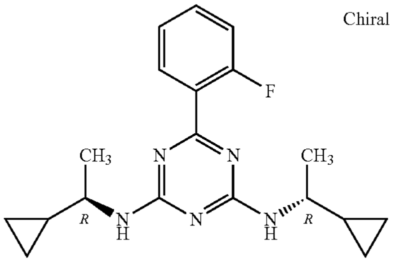 Chiral |

TABLE 1-continued
| Representative Compounds | |
|---|---|
| Compound Number | Structure |
| 7 | 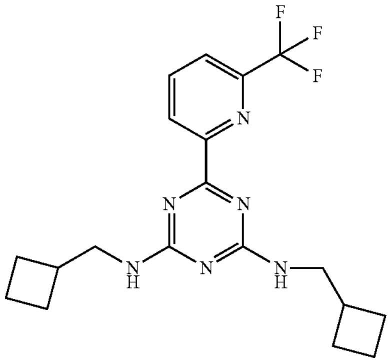 [SMILES: FC(F)(F)c1cccc(-c2nc(NCC3CCC3)nc(NCC3CCC3)n2)n1] |
| 8 | 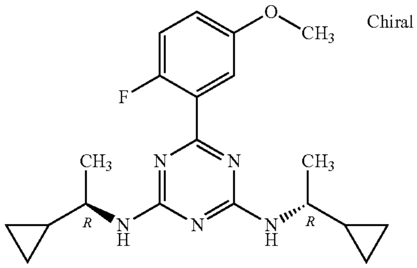 Chiral |
| 9 | 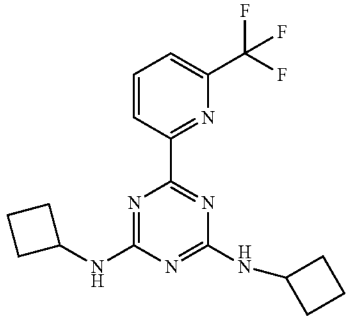 [SMILES: FC(F)(F)c1cccc(-c2nc(NC3CCC3)nc(NC3CCC3)n2)n1] |
| 10 | 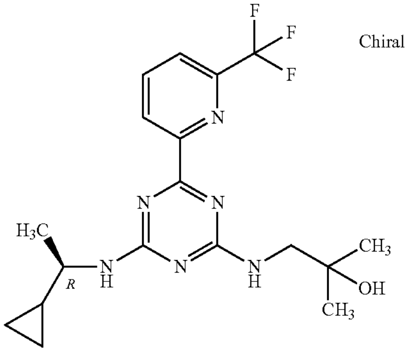 Chiral |

TABLE 1-continued
| Representative Compounds | |
|---|---|
| Compound Number | Structure |
| 11 | 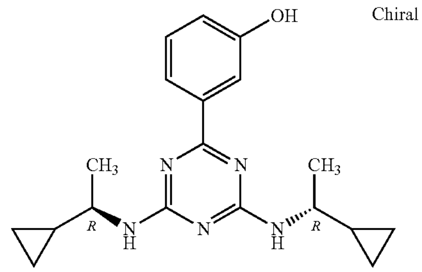 Chiral |
| 12 | 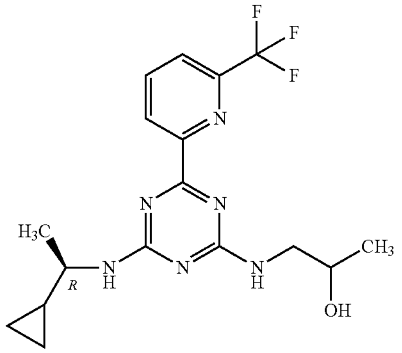 |
| 13 | 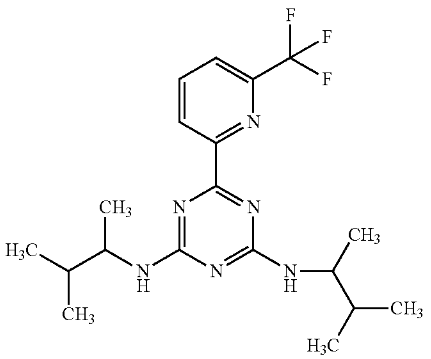 |
| 14 | 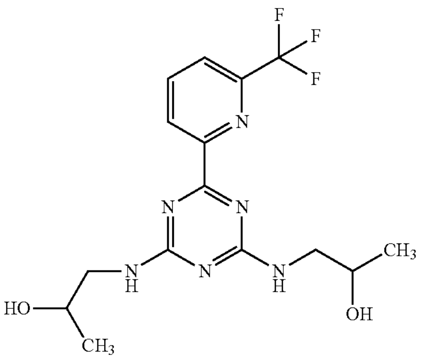 [SMILES: CC(O)CNc1nc(NCC(C)O)nc(-c2cccc(C(F)(F)F)n2)n1] |

TABLE 1-continued
| Representative Compounds | |
|---|---|
| Compound Number | Structure |
| 15 | 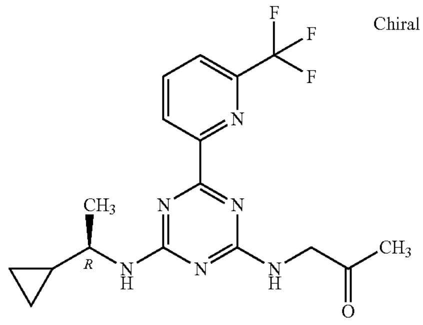 Chiral |
| 16 | 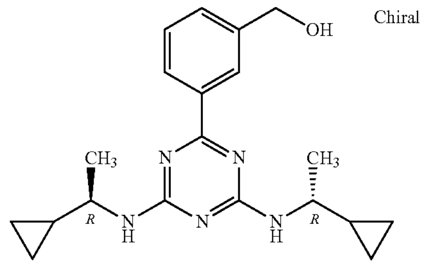 Chiral |
| 17 | 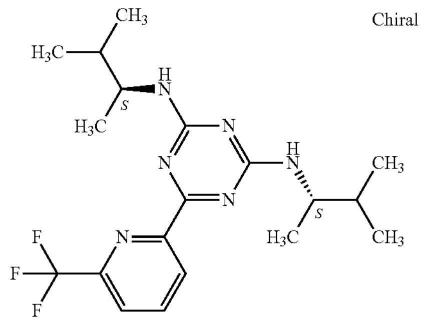 Chiral |
| 18 | 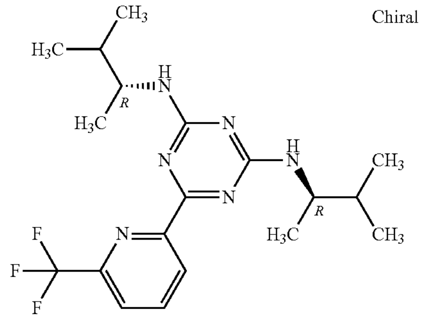 Chiral |

TABLE 1-continued
| Representative Compounds | |
|---|---|
| Compound Number | Structure |
| 19 | 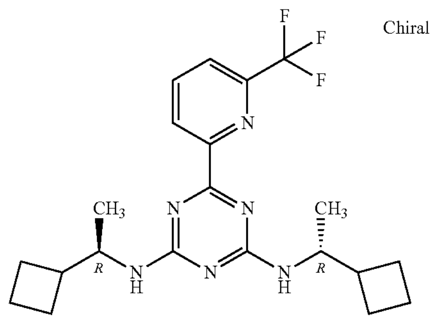 Chiral |
| 20 | 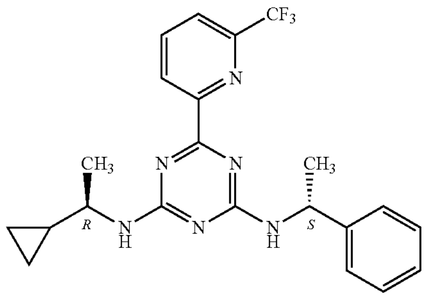 Chiral |
| 21 | 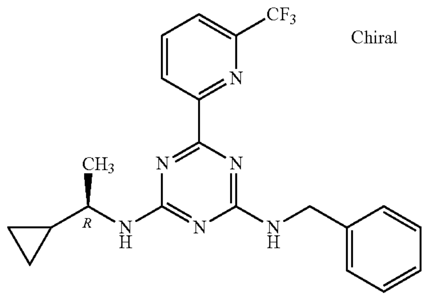 Chiral |
| 22 | 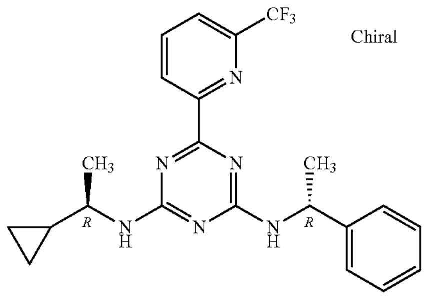 Chiral |

TABLE 1-continued
| Representative Compounds | |
|---|---|
| Compound Number | Structure |
| 23 | 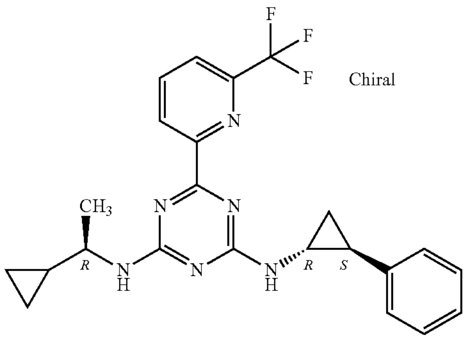 |
| 24 | 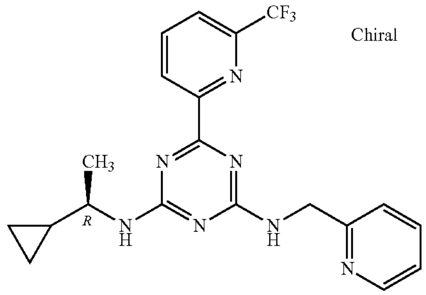 |
| 25 | 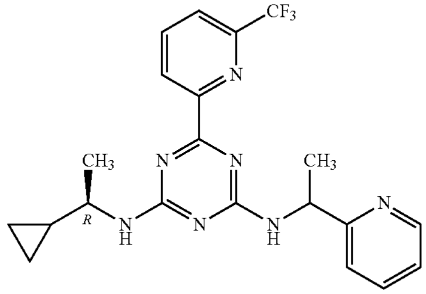 |
| 26 | 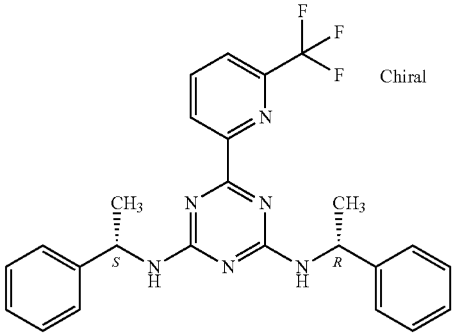 |

TABLE 1-continued
| Compound Number | Structure |
| --- | --- |
| 27 | 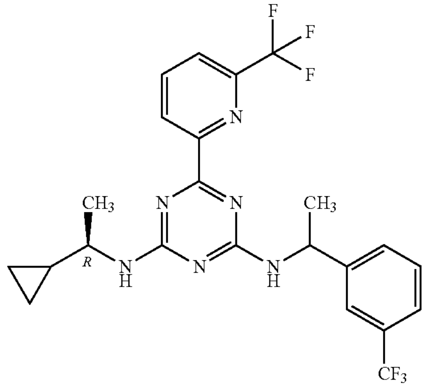 |
| 28 | 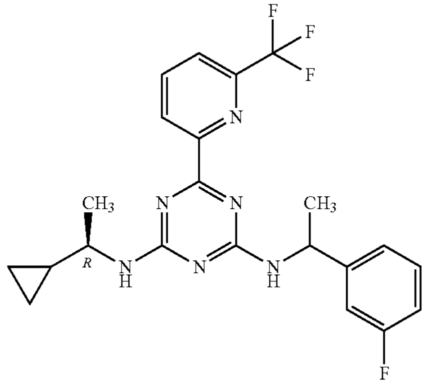 |
| 29 | 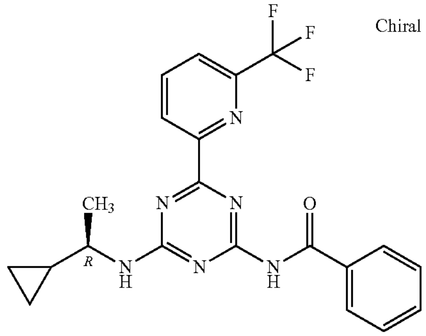 Chiral |
| 30 | 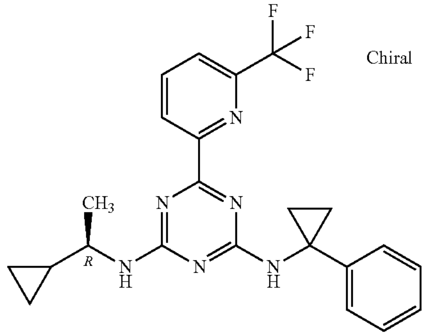 Chiral |
Representative Compounds TABLE 1-continued
| Representative Compounds | |
|---|---|
| Compound Number | Structure |
| 31 | 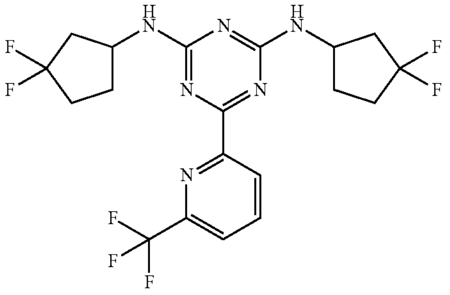 [SMILES: FC1(F)CCC(Nc2nc(NC3CCC(F)(F)C3)nc(-c3cccc(C(F)(F)F)n3)n2)C1] |
| 32 | 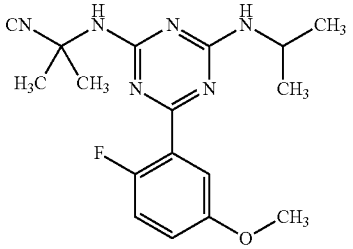 |
| 33 | 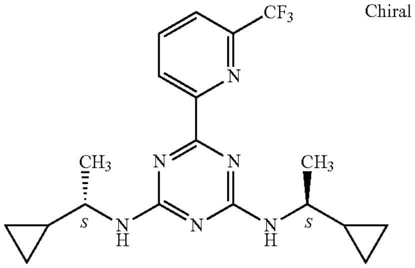 Chiral |
| 34 | 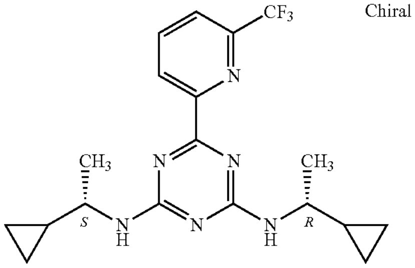 Chiral |
| 35 | 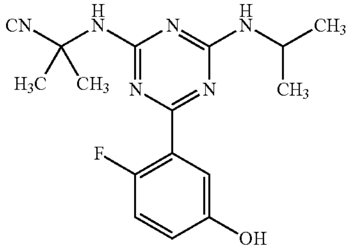 |

TABLE 1-continued
| Representative Compounds | |
|---|---|
| Compound Number | Structure |
| 36 | 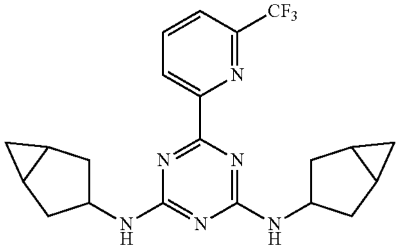 [SMILES: FC(F)(F)c1cccc(-c2nc(NC3CC4CC4C3)nc(NC3CC4CC4C3)n2)n1] |
| 37 | 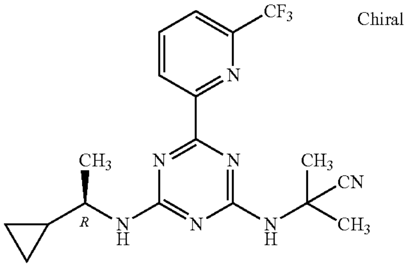 |
| 38 | 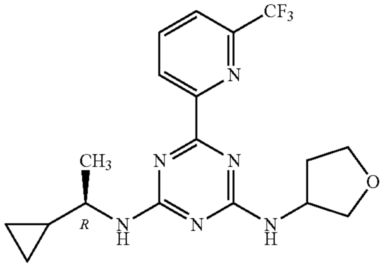 |
| 39 | 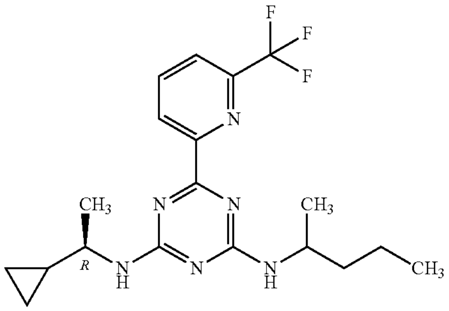 |
| 40 | 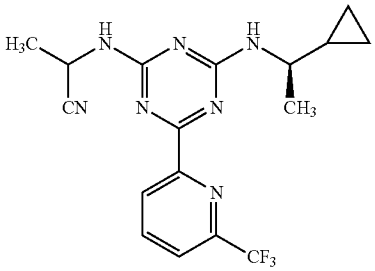 [SMILES: CC(C#N)Nc1nc(N[C@H](C)C2CC2)nc(-c2cccc(C(F)(F)F)n2)n1] |

TABLE 1-continued
| Representative Compounds | |
|---|---|
| Compound Number | Structure |
| 41 | 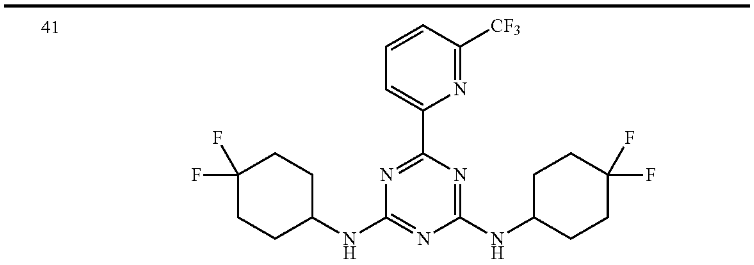 |
| 42 | 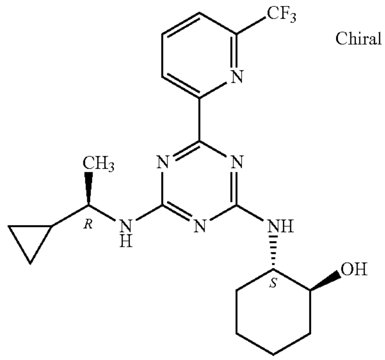 Chiral |
| 43 | 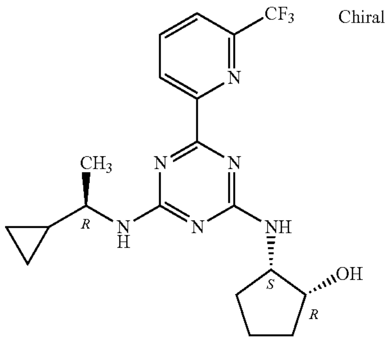 Chiral |
| 44 | 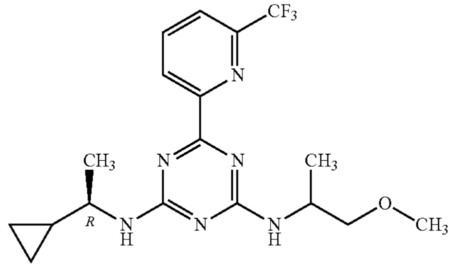 |
| 45 | 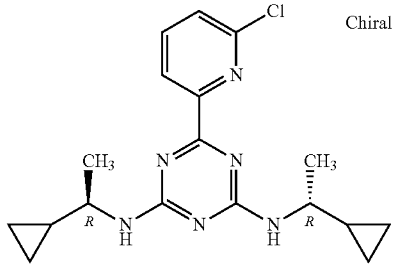 Chiral |

TABLE 1-continued
| Representative Compounds | |
|---|---|
| Compound Number | Structure |
| 46 | 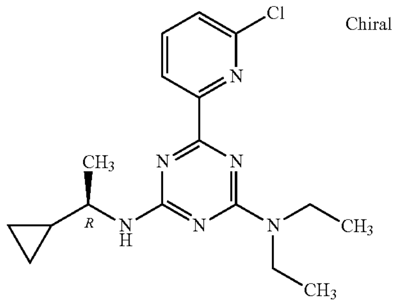 Chiral |
| 47 | 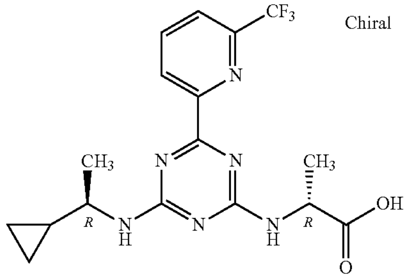 Chiral |
| 48 | 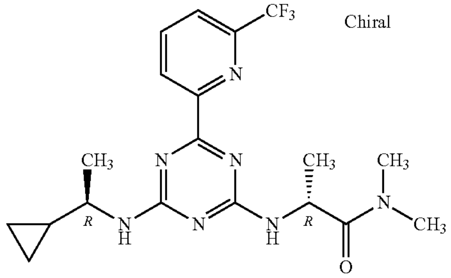 Chiral |
| 49 | 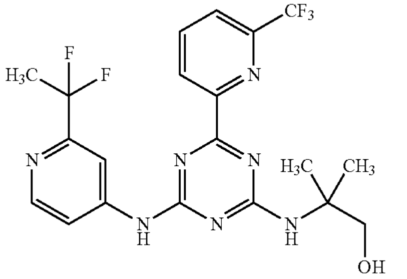 [SMILES: CC(C)(CO)Nc1nc(Nc2ccnc(C(C)(F)F)c2)nc(-c2cccc(C(F)(F)F)n2)n1] |
| 50 | 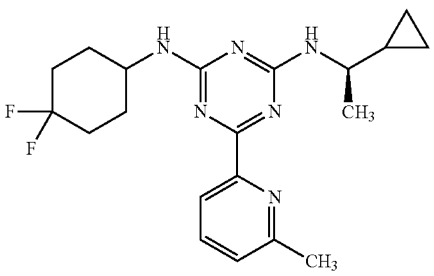 Chiral |

TABLE 1-continued
Representative Compounds
| Compound Number | Structure |
|---|---|
| 51 | 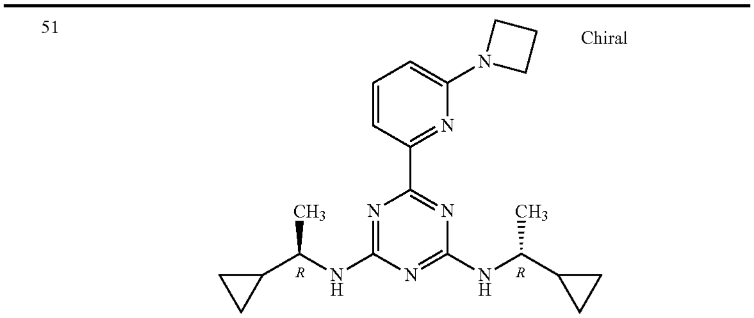 |
| 52 | 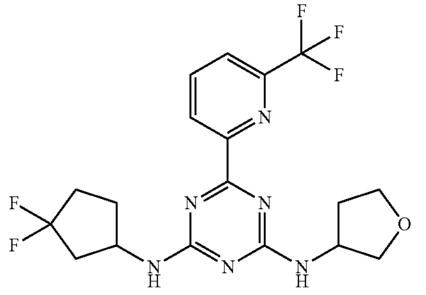 [SMILES: FC1(F)CCC(Nc2nc(NC3CCOC3)nc(-c3cccc(C(F)(F)F)n3)n2)C1] |
| 53 | 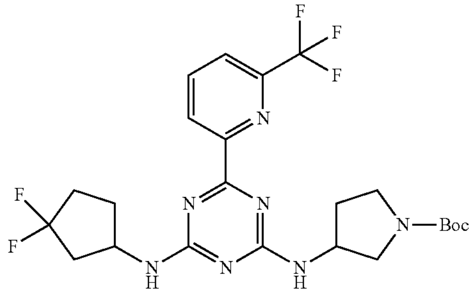 [SMILES: CC(C)(C)OC(=O)N1CCC(Nc2nc(NC3CCC(F)(F)C3)nc(-c3cccc(C(F)(F)F)n3)n2)C1] |
| 54 | 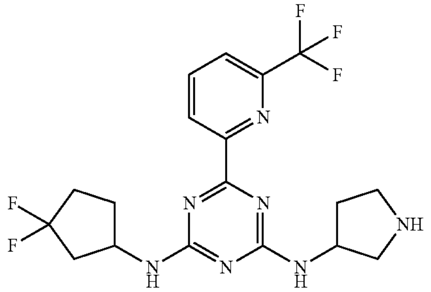 [SMILES: FC1(F)CCC(Nc2nc(NC3CCNC3)nc(-c3cccc(C(F)(F)F)n3)n2)C1] |
| 55 | 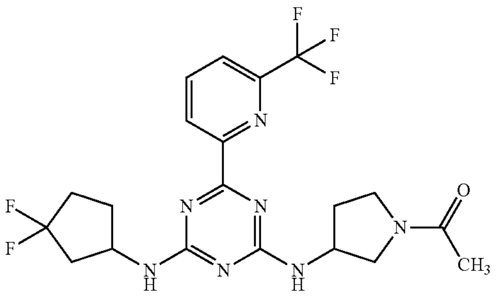 [SMILES: CC(=O)N1CCC(Nc2nc(NC3CCC(F)(F)C3)nc(-c3cccc(C(F)(F)F)n3)n2)C1] |

TABLE 1-continued
Representative Compounds
| Compound Number | Structure |
| --- | --- |
| 56 | 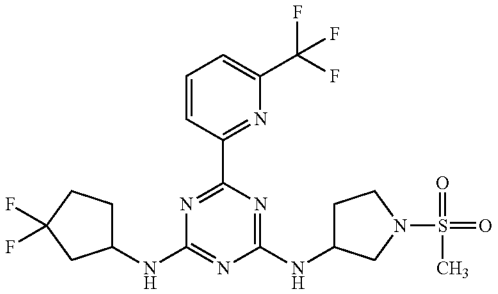 [SMILES: CS(=O)(=O)N1CCC(Nc2nc(NC3CCC(F)(F)C3)nc(-c3cccc(C(F)(F)F)n3)n2)C1] |
| 57 | 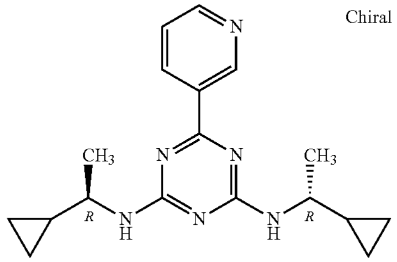 Chiral |
| 58 | 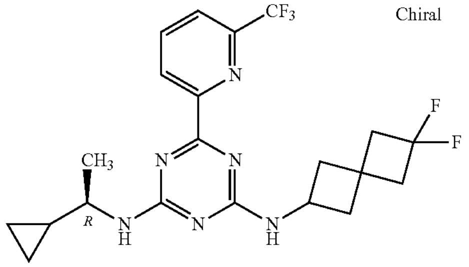 Chiral |
| 59 | 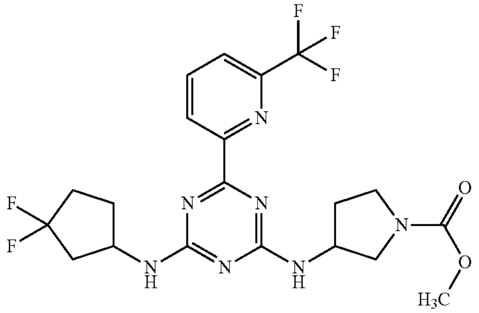 [SMILES: COC(=O)N1CCC(Nc2nc(NC3CCC(F)(F)C3)nc(-c3cccc(C(F)(F)F)n3)n2)C1] |
| 60 | 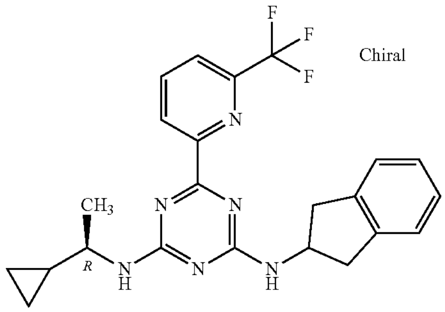 Chiral |

TABLE 1-continued
| Representative Compounds | | |
|---|---|---|
| Compound Number | Structure | |
| 61 | 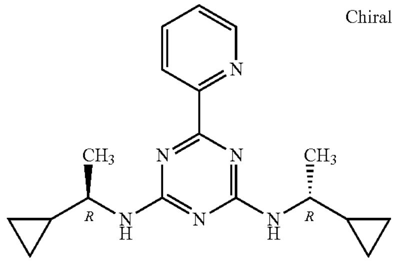 | Chiral |
| 63 | 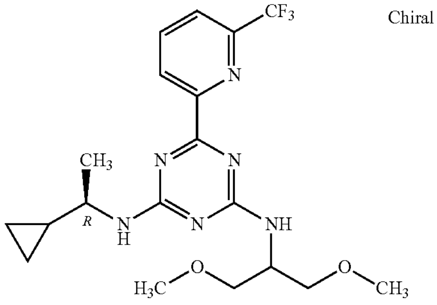 | Chiral |
| 64 | 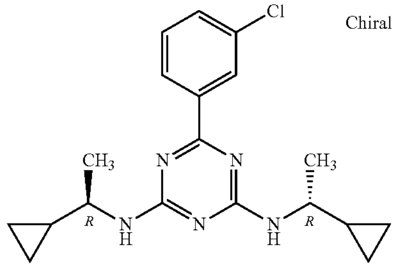 | Chiral |
| 65 | 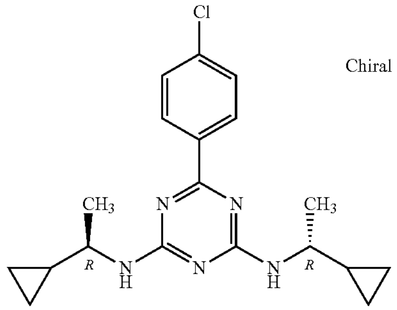 | Chiral |
| 66 | 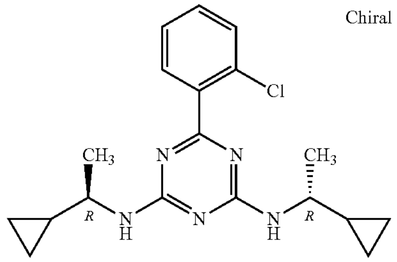 | Chiral |

TABLE 1-continued
| Representative Compounds | |
|---|---|
| Compound Number | Structure |
| 67 | 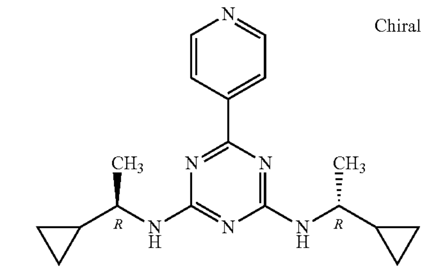 |
| 69 | 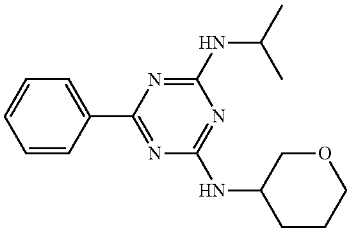 [SMILES: CC(C)Nc1nc(NC2CCCOC2)nc(-c2ccccc2)n1] |
| 70 | 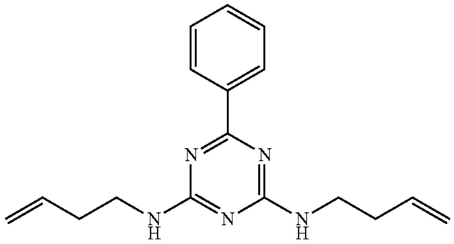 [SMILES: C=CCCNc1nc(NCCC=C)nc(-c2ccccc2)n1] |
| 71 | 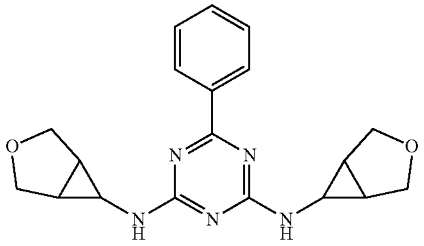 [SMILES: c1ccc(-c2nc(NC3C4COCC43)nc(NC3C4COCC43)n2)cc1] |
| 72 | 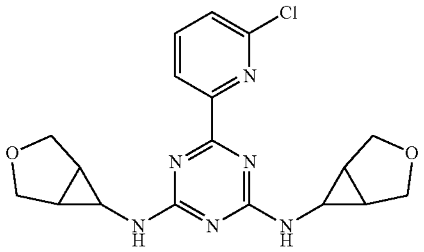 [SMILES: Clc1cccc(-c2nc(NC3C4COCC43)nc(NC3C4COCC43)n2)n1] |

TABLE 1-continued
| Representative Compounds | |
|---|---|
| Compound Number | Structure |
| 73 | 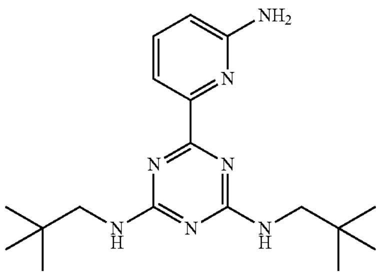 [SMILES: CC(C)(C)CNc1nc(NCC(C)(C)C)nc(-c2cccc(N)n2)n1] |
| 74 | 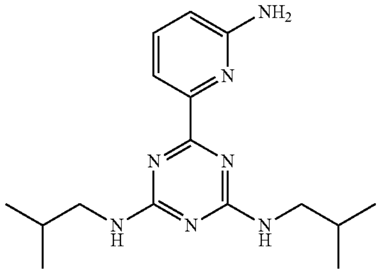 [SMILES: CC(C)CNc1nc(NCC(C)C)nc(-c2cccc(N)n2)n1] |
| 75 | 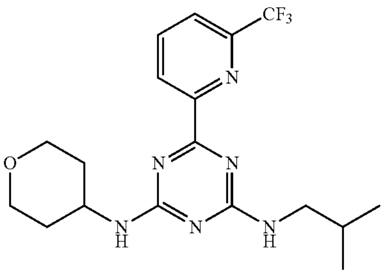 [SMILES: CC(C)CNc1nc(NC2CCOCC2)nc(-c2cccc(C(F)(F)F)n2)n1] |
| 76 | 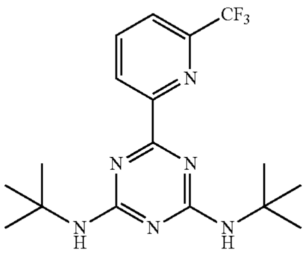 [SMILES: CC(C)(C)Nc1nc(NC(C)(C)C)nc(-c2cccc(C(F)(F)F)n2)n1] |
| 77 | 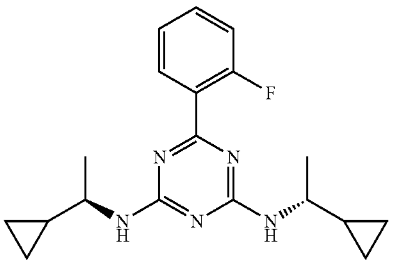 [SMILES: C[C@@H](Nc1nc(N[C@H](C)C2CC2)nc(-c2ccccc2F)n1)C1CC1] |

TABLE 1-continued
| Representative Compounds | |
|---|---|
| Compound Number | Structure |
| 78 | 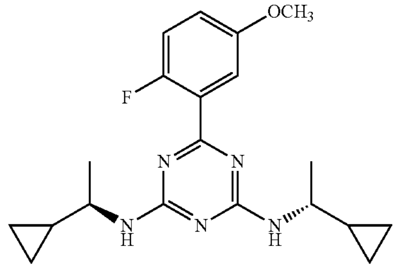 [SMILES: COc1ccc(F)c(-c2nc(N[C@H](C)C3CC3)nc(N[C@H](C)C3CC3)n2)c1] |
| 79 | 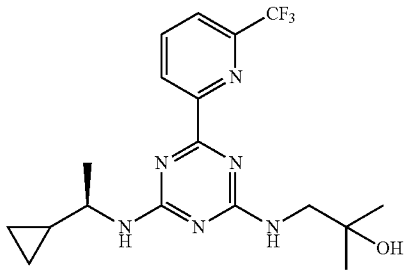 [SMILES: C[C@@H](Nc1nc(NCC(C)(C)O)nc(-c2cccc(C(F)(F)F)n2)n1)C1CC1] |
| 80 | 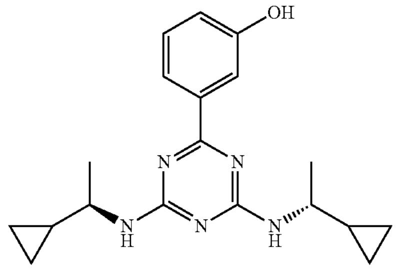 [SMILES: C[C@@H](Nc1nc(N[C@H](C)C2CC2)nc(-c2cccc(O)c2)n1)C1CC1] |
| 81 | 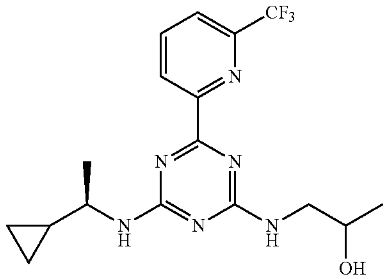 [SMILES: CC(O)CNc1nc(N[C@H](C)C2CC2)nc(-c2cccc(C(F)(F)F)n2)n1] |
| 82 | 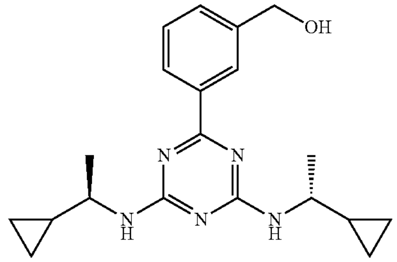 [SMILES: C[C@@H](Nc1nc(N[C@H](C)C2CC2)nc(-c2cccc(CO)c2)n1)C1CC1] |

TABLE 1-continued
| Representative Compounds | |
|---|---|
| Compound Number | Structure |
| 83 | 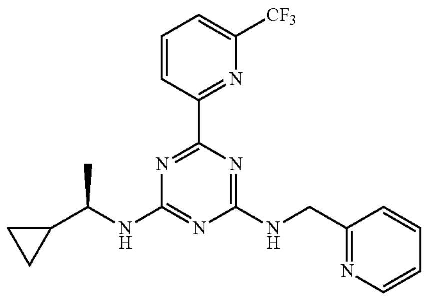 [SMILES: C[C@@H](Nc1nc(NCc2ccccn2)nc(-c2cccc(C(F)(F)F)n2)n1)C1CC1] |
| 84 | 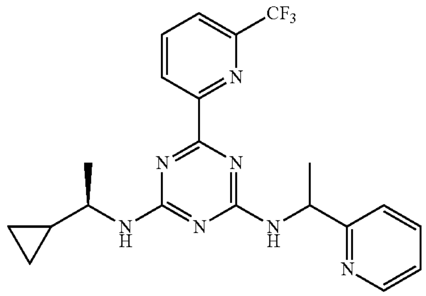 [SMILES: CC(Nc1nc(N[C@H](C)C2CC2)nc(-c2cccc(C(F)(F)F)n2)n1)c1ccccn1] |
| 85 | 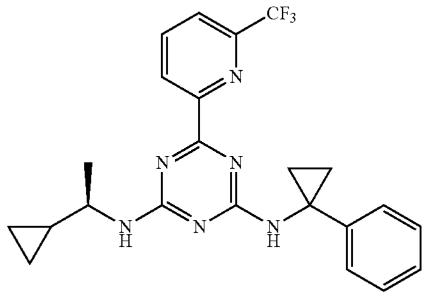 [SMILES: C[C@@H](Nc1nc(NC2(c3ccccc3)CC2)nc(-c2cccc(C(F)(F)F)n2)n1)C1CC1] |
| 86 | 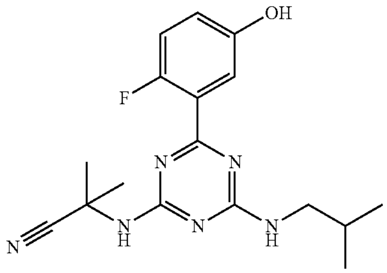 [SMILES: CC(C)CNc1nc(NC(C)(C)C#N)nc(-c2cc(O)ccc2F)n1] |
| 87 | 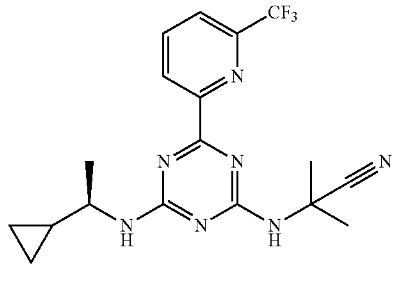 [SMILES: C[C@@H](Nc1nc(NC(C)(C)C#N)nc(-c2cccc(C(F)(F)F)n2)n1)C1CC1] |

TABLE 1-continued
| Representative Compounds | |
|---|---|
| Compound Number | Structure |
| 88 | 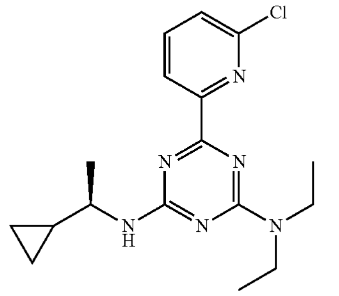 [SMILES: CCN(CC)c1nc(N[C@H](C)C2CC2)nc(-c2cccc(Cl)n2)n1] |
| 89 | 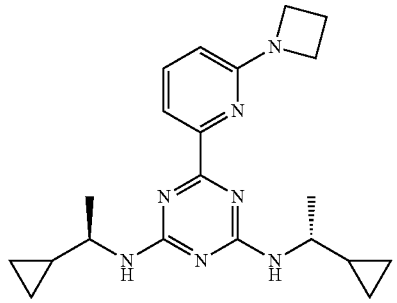 [SMILES: C[C@@H](Nc1nc(N[C@H](C)C2CC2)nc(-c2cccc(N3CCC3)n2)n1)C1CC1] |
| 90 | 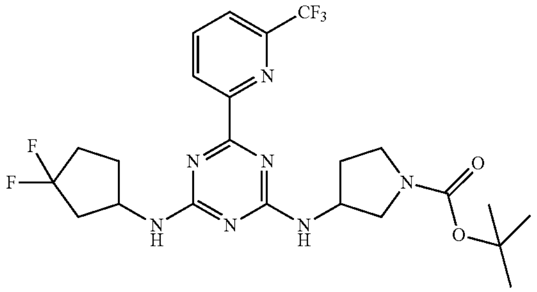 [SMILES: CC(C)(C)OC(=O)N1CCC(Nc2nc(NC3CCC(F)(F)C3)nc(-c3cccc(C(F)(F)F)n3)n2)C1] |
| 91 | 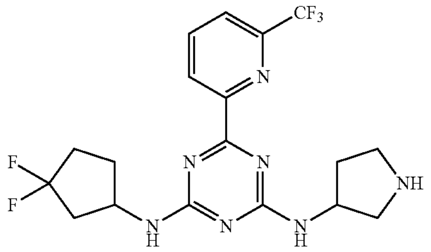 [SMILES: FC1(F)CCC(Nc2nc(NC3CCNC3)nc(-c3cccc(C(F)(F)F)n3)n2)C1] |
| 92 | 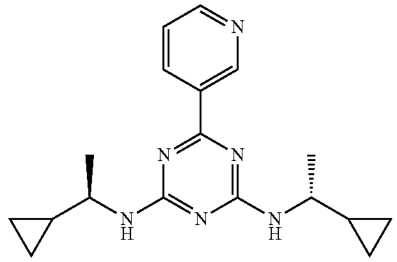 [SMILES: C[C@@H](Nc1nc(N[C@H](C)C2CC2)nc(-c2cccnc2)n1)C1CC1] |

TABLE 1-continued
| Representative Compounds | |
| --- | --- |
| Compound Number | Structure |
| 93 | 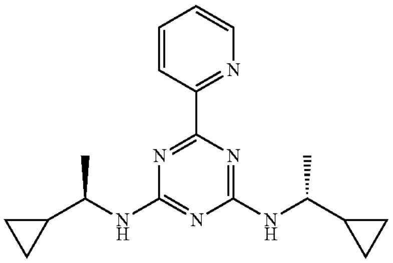 [SMILES: C[C@@H](Nc1nc(N[C@H](C)C2CC2)nc(-c2ccccn2)n1)C1CC1] |
| 94 | 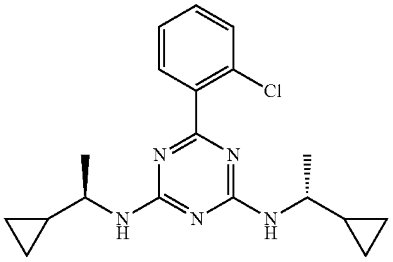 [SMILES: C[C@@H](Nc1nc(N[C@H](C)C2CC2)nc(-c2ccccc2Cl)n1)C1CC1] |
| 95 | 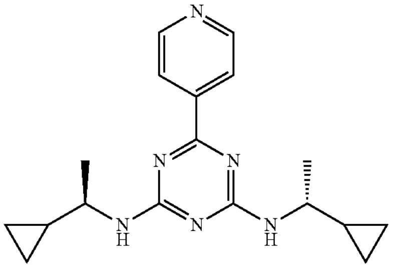 [SMILES: C[C@@H](Nc1nc(N[C@H](C)C2CC2)nc(-c2ccncc2)n1)C1CC1] |
| 96 | 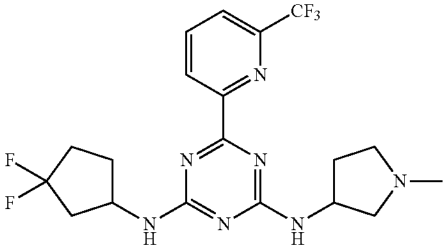 [SMILES: CN1CCC(Nc2nc(NC3CCC(F)(F)C3)nc(-c3cccc(C(F)(F)F)n3)n2)C1] |
| 100 | 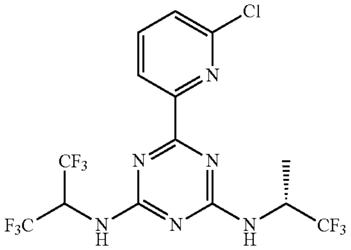 [SMILES: C[C@@H](Nc1nc(NC(C(F)(F)F)C(F)(F)F)nc(-c2cccc(Cl)n2)n1)C(F)(F)F] |

TABLE 1-continued
| Representative Compounds | |
|---|---|
| Compound Number | Structure |
| 101 | 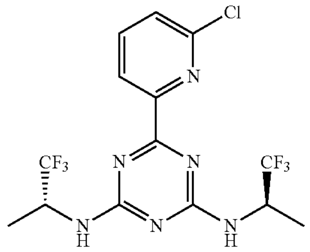 [SMILES: C[C@@H](Nc1nc(N[C@H](C)C(F)(F)F)nc(-c2cccc(Cl)n2)n1)C(F)(F)F] |
| 102 | 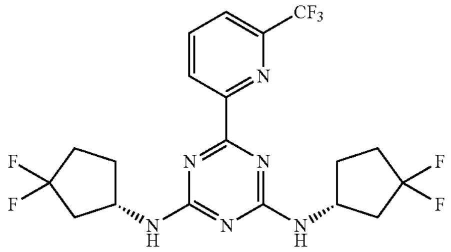 [SMILES: FC1(F)CC[C@@H](Nc2nc(N[C@H]3CCC(F)(F)C3)nc(-c3cccc(C(F)(F)F)n3)n2)C1] |
| 103 | 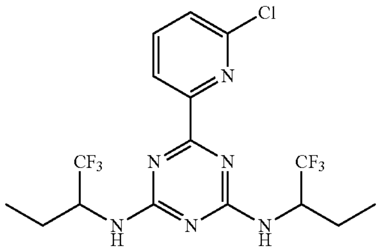 [SMILES: CCC(Nc1nc(NC(CC)C(F)(F)F)nc(-c2cccc(Cl)n2)n1)C(F)(F)F] |
| 104 | 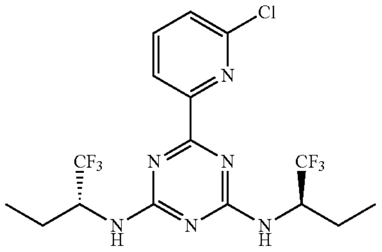 [SMILES: CC[C@@H](Nc1nc(N[C@H](CC)C(F)(F)F)nc(-c2cccc(Cl)n2)n1)C(F)(F)F] |
| 105 | 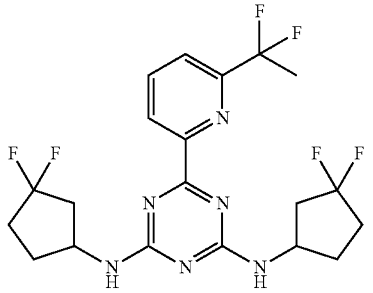 [SMILES: CC(F)(F)c1cccc(-c2nc(NC3CCC(F)(F)C3)nc(NC3CCC(F)(F)C3)n2)n1] |

TABLE 1-continued
| Representative Compounds | |
|---|---|
| Compound Number | Structure |
| 106 | 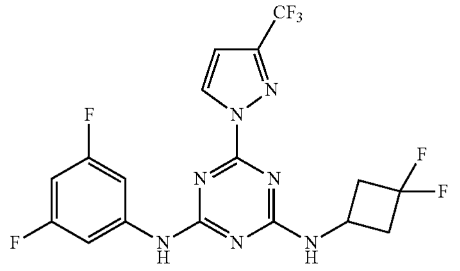 [SMILES: Fc1cc(F)cc(Nc2nc(NC3CC(F)(F)C3)nc(-n3ccc(C(F)(F)F)n3)n2)c1] |
| 107 | 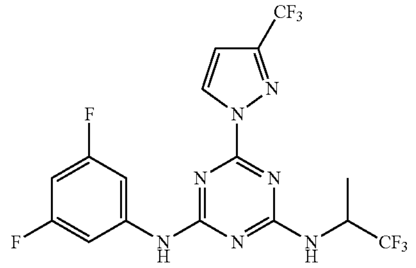 [SMILES: CC(Nc1nc(Nc2cc(F)cc(F)c2)nc(-n2ccc(C(F)(F)F)n2)n1)C(F)(F)F] |
| 108 | 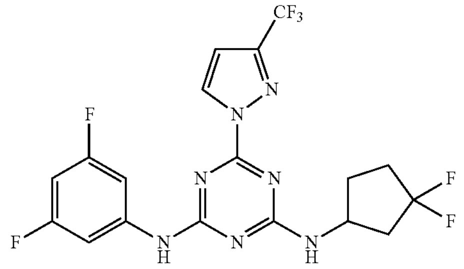 [SMILES: Fc1cc(F)cc(Nc2nc(NC3CCC(F)(F)C3)nc(-n3ccc(C(F)(F)F)n3)n2)c1] |
| 109 | 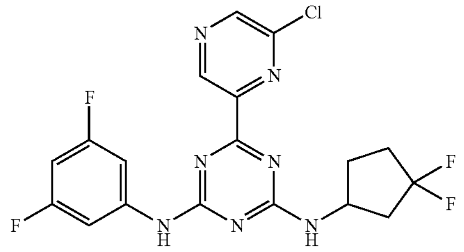 [SMILES: Fc1cc(F)cc(Nc2nc(NC3CCC(F)(F)C3)nc(-c3cncc(Cl)n3)n2)c1] |
| 110 | 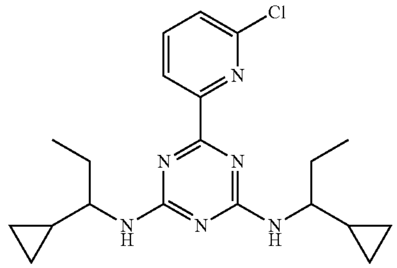 [SMILES: CCC(Nc1nc(NC(CC)C2CC2)nc(-c2cccc(Cl)n2)n1)C1CC1] |

TABLE 1-continued
| Representative Compounds | |
|---|---|
| Compound Number | Structure |
| 111 | 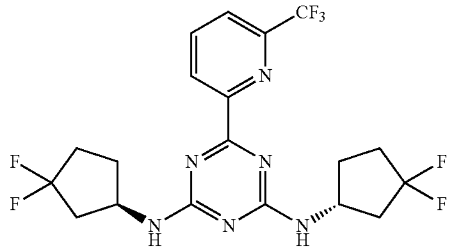 [SMILES: FC1(F)CC[C@@H](Nc2nc(N[C@@H]3CCC(F)(F)C3)nc(-c3cccc(C(F)(F)F)n3)n2)C1] |
| 112 | 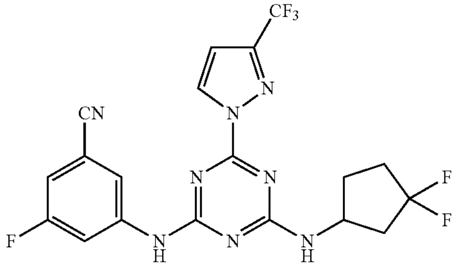 [SMILES: N#Cc1cc(F)cc(Nc2nc(NC3CCC(F)(F)C3)nc(-n3ccc(C(F)(F)F)n3)n2)c1] |
| 113 | 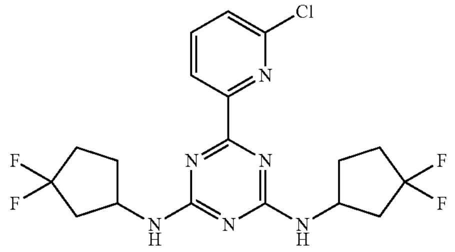 [SMILES: FC1(F)CCC(Nc2nc(NC3CCC(F)(F)C3)nc(-c3cccc(Cl)n3)n2)C1] |
| 114 | 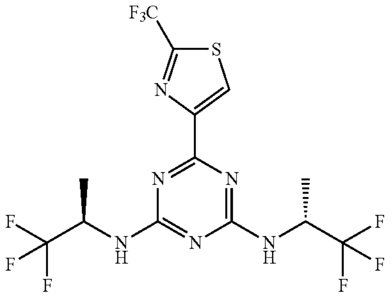 [SMILES: C[C@@H](Nc1nc(N[C@H](C)C(F)(F)F)nc(-c2csc(C(F)(F)F)n2)n1)C(F)(F)F] |
| 115 | 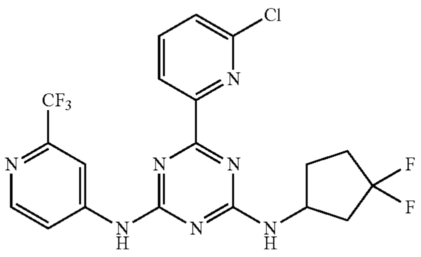 [SMILES: FC1(F)CCC(Nc2nc(Nc3ccnc(C(F)(F)F)c3)nc(-c3cccc(Cl)n3)n2)C1] |

TABLE 1-continued
| Representative Compounds | |
|---|---|
| Compound Number | Structure |
| 116 | 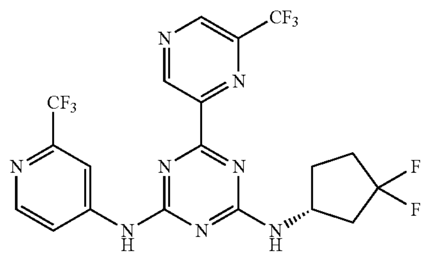 [SMILES: FC1(F)CC[C@@H](Nc2nc(Nc3ccnc(C(F)(F)F)c3)nc(-c3cncc(C(F)(F)F)n3)n2)C1] |
| 117 | 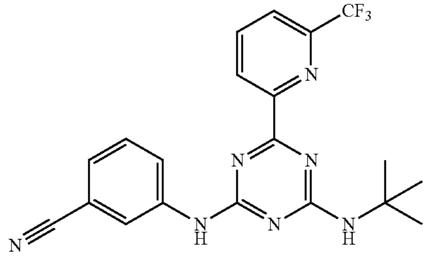 [SMILES: CC(C)(C)Nc1nc(Nc2cccc(C#N)c2)nc(-c2cccc(C(F)(F)F)n2)n1] |
| 118 | 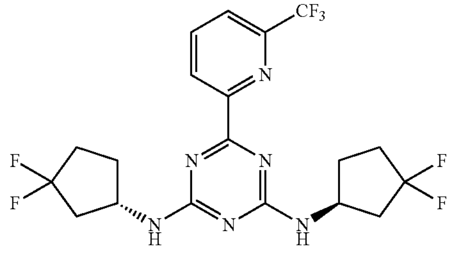 [SMILES: FC1(F)CC[C@H](Nc2nc(N[C@H]3CCC(F)(F)C3)nc(-c3cccc(C(F)(F)F)n3)n2)C1] |
| 119 | 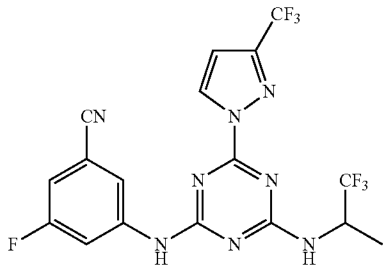 [SMILES: CC(Nc1nc(Nc2cc(F)cc(C#N)c2)nc(-n2ccc(C(F)(F)F)n2)n1)C(F)(F)F] |
| 120 | 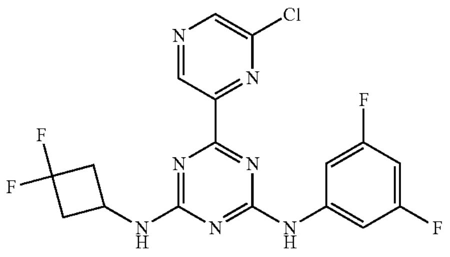 [SMILES: Fc1cc(F)cc(Nc2nc(NC3CC(F)(F)C3)nc(-c3cncc(Cl)n3)n2)c1] |

TABLE 1-continued
| Representative Compounds | |
|---|---|
| Compound Number | Structure |
| 121 | 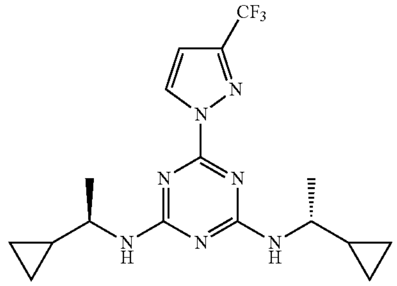 [SMILES: C[C@@H](Nc1nc(N[C@H](C)C2CC2)nc(-n2ccc(C(F)(F)F)n2)n1)C1CC1] |
| 122 | 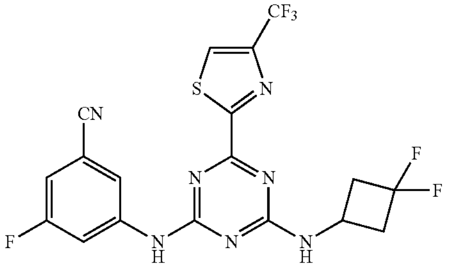 [SMILES: N#Cc1cc(F)cc(Nc2nc(NC3CC(F)(F)C3)nc(-c3nc(C(F)(F)F)cs3)n2)c1] |
| 123 | 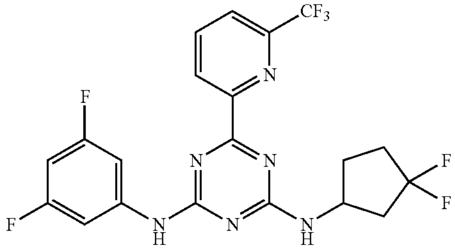 |
| 124 | 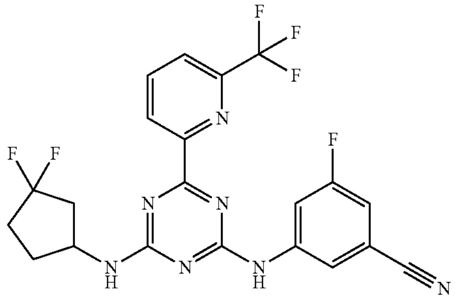 [SMILES: N#Cc1cc(F)cc(Nc2nc(NC3CCC(F)(F)C3)nc(-c3cccc(C(F)(F)F)n3)n2)c1] |
| 125 | 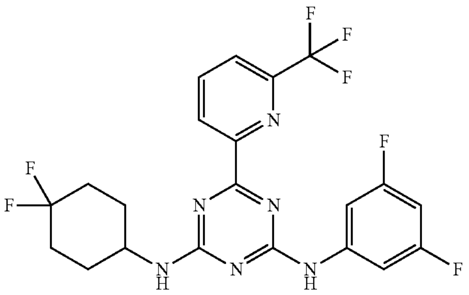 [SMILES: Fc1cc(F)cc(Nc2nc(NC3CCC(F)(F)CC3)nc(-c3cccc(C(F)(F)F)n3)n2)c1] |

TABLE 1-continued
| Representative Compounds | |
|---|---|
| Compound Number | Structure |
| 126 | 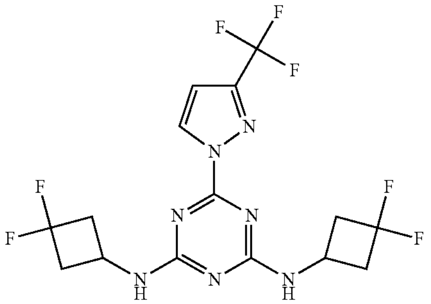 [SMILES: FC1(F)CC(Nc2nc(NC3CC(F)(F)C3)nc(-n3ccc(C(F)(F)F)n3)n2)C1] |
| 127 | 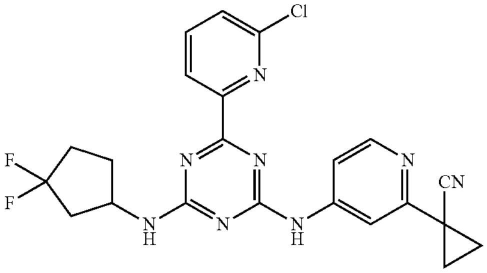 [SMILES: N#CC1(c2cc(Nc3nc(NC4CCC(F)(F)C4)nc(-c4cccc(Cl)n4)n3)ccn2)CC1] |
| 128 | 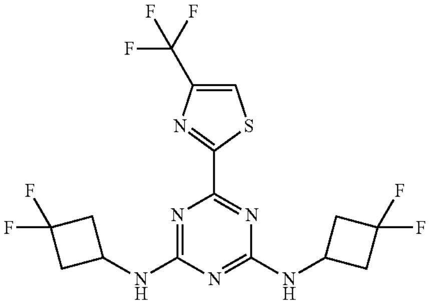 [SMILES: FC1(F)CC(Nc2nc(NC3CC(F)(F)C3)nc(-c3nc(C(F)(F)F)cs3)n2)C1] |
| 129 | 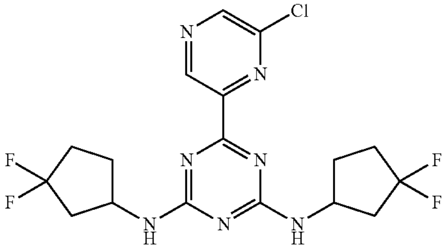 [SMILES: FC1(F)CCC(Nc2nc(NC3CCC(F)(F)C3)nc(-c3cncc(Cl)n3)n2)C1] |
| 130 | 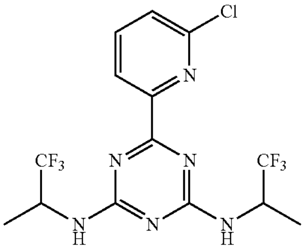 [SMILES: CC(Nc1nc(NC(C)C(F)(F)F)nc(-c2cccc(Cl)n2)n1)C(F)(F)F] |

TABLE 1-continued
| Representative Compounds | |
|---|---|
| Compound Number | Structure |
| 131 | 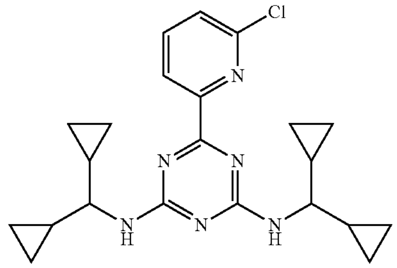 [SMILES: Clc1cccc(-c2nc(NC(C3CC3)C3CC3)nc(NC(C3CC3)C3CC3)n2)n1] |
| 132 | 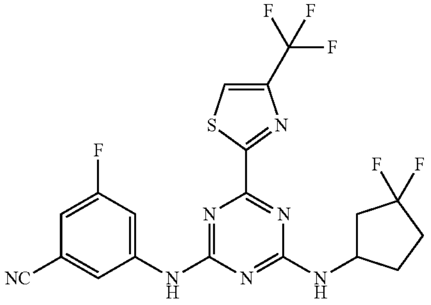 [SMILES: N#Cc1cc(F)cc(Nc2nc(NC3CCC(F)(F)C3)nc(-c3nc(C(F)(F)F)cs3)n2)c1] |
| 133 | 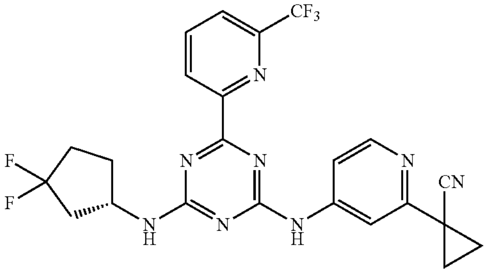 [SMILES: N#CC1(c2cc(Nc3nc(N[C@H]4CCC(F)(F)C4)nc(-c4cccc(C(F)(F)F)n4)n3)ccn2)CC1] |
| 134 | 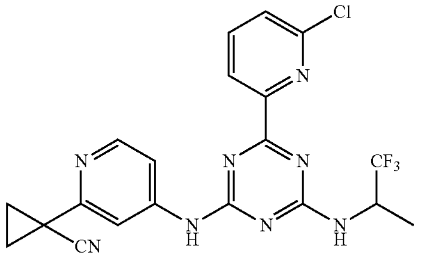 [SMILES: CC(Nc1nc(Nc2ccnc(C3(C#N)CC3)c2)nc(-c2cccc(Cl)n2)n1)C(F)(F)F] |
| 135 | 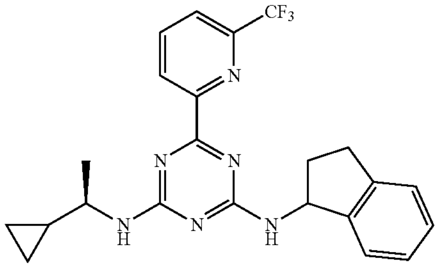 [SMILES: C[C@@H](Nc1nc(NC2CCc3ccccc32)nc(-c2cccc(C(F)(F)F)n2)n1)C1CC1] |

TABLE 1-continued
| Representative Compounds | |
|---|---|
| Compound Number | Structure |
| 136 | 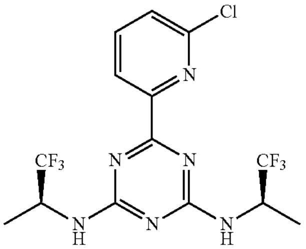 [SMILES: C[C@H](Nc1nc(N[C@H](C)C(F)(F)F)nc(-c2cccc(Cl)n2)n1)C(F)(F)F] |
| 137 | 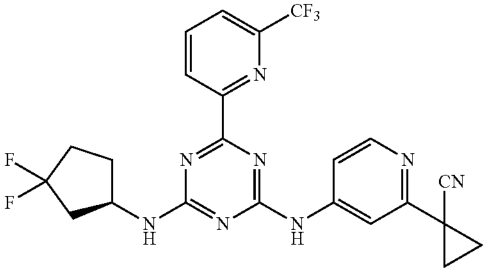 [SMILES: N#CC1(c2cc(Nc3nc(N[C@@H]4CCC(F)(F)C4)nc(-c4cccc(C(F)(F)F)n4)n3)ccn2)CC1] |
| 138 | 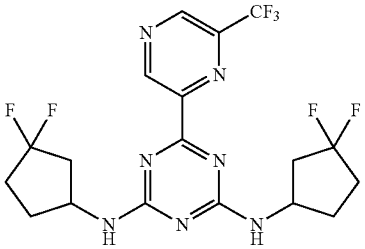 [SMILES: FC1(F)CCC(Nc2nc(NC3CCC(F)(F)C3)nc(-c3cncc(C(F)(F)F)n3)n2)C1] |
| 139 | 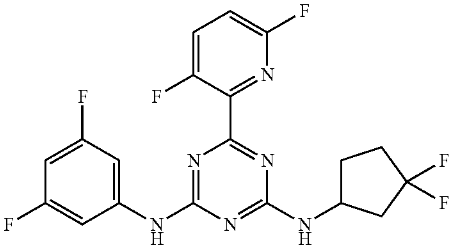 [SMILES: Fc1cc(F)cc(Nc2nc(NC3CCC(F)(F)C3)nc(-c3nc(F)ccc3F)n2)c1] |
| 140 | 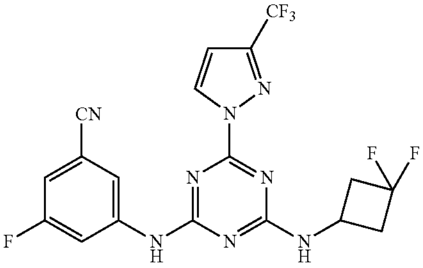 [SMILES: N#Cc1cc(F)cc(Nc2nc(NC3CC(F)(F)C3)nc(-n3ccc(C(F)(F)F)n3)n2)c1] |

TABLE 1-continued
| Representative Compounds | |
|---|---|
| Compound Number | Structure |
| 141 | 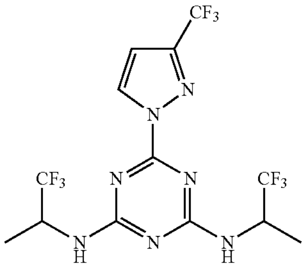 [SMILES: CC(Nc1nc(NC(C)C(F)(F)F)nc(-n2ccc(C(F)(F)F)n2)n1)C(F)(F)F] |
| 142 | 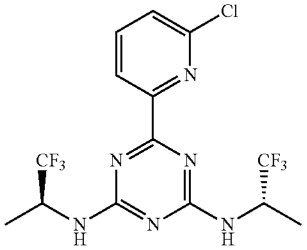 [SMILES: C[C@H](Nc1nc(N[C@@H](C)C(F)(F)F)nc(-c2cccc(Cl)n2)n1)C(F)(F)F] |
| 143 | 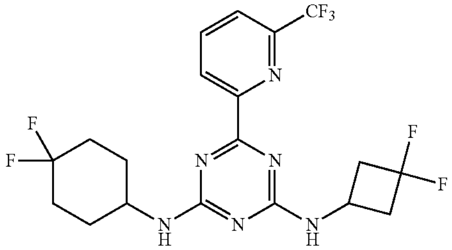 [SMILES: FC1(F)CCC(Nc2nc(NC3CC(F)(F)C3)nc(-c3cccc(C(F)(F)F)n3)n2)CC1] |
| 144 | 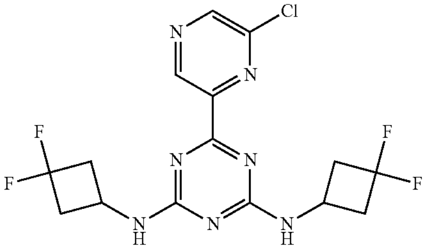 [SMILES: FC1(F)CC(Nc2nc(NC3CC(F)(F)C3)nc(-c3cncc(Cl)n3)n2)C1] |
| 145 | 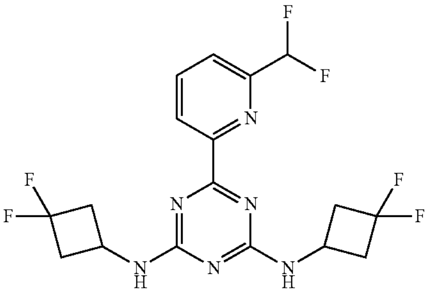 [SMILES: FC(F)c1cccc(-c2nc(NC3CC(F)(F)C3)nc(NC3CC(F)(F)C3)n2)n1] |

TABLE 1-continued
Representative Compounds
| Compound Number | Structure |
|---|---|
| 146 | 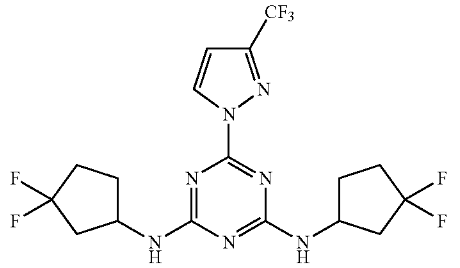 [SMILES: FC1(F)CCC(Nc2nc(NC3CCC(F)(F)C3)nc(-n3ccc(C(F)(F)F)n3)n2)C1] |
| 147 | 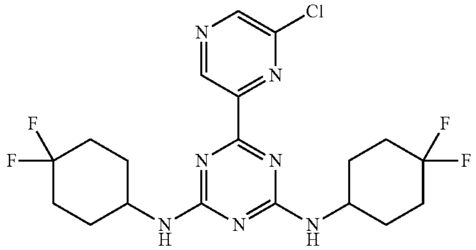 [SMILES: FC1(F)CCC(Nc2nc(NC3CCC(F)(F)CC3)nc(-c3cncc(Cl)n3)n2)CC1] |
| 148 | 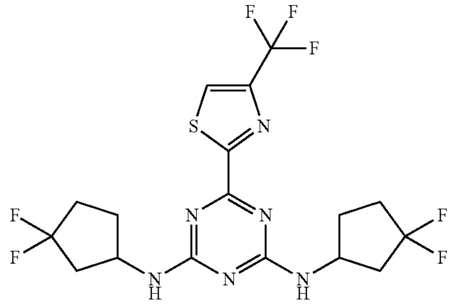 [SMILES: FC1(F)CCC(Nc2nc(NC3CCC(F)(F)C3)nc(-c3nc(C(F)(F)F)cs3)n2)C1] |
| 149 | 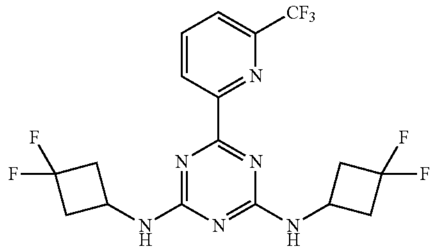 |
| 150 | 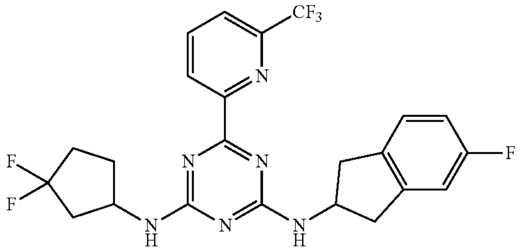 [SMILES: Fc1ccc2c(c1)CC(Nc1nc(NC3CCC(F)(F)C3)nc(-c3cccc(C(F)(F)F)n3)n1)C2] |

TABLE 1-continued
| Representative Compounds | |
|---|---|
| Compound Number | Structure |
| 151 | 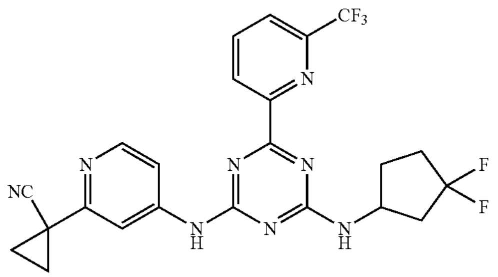 [SMILES: N#CC1(c2cc(Nc3nc(NC4CCC(F)(F)C4)nc(-c4cccc(C(F)(F)F)n4)n3)ccn2)CC1] |
| 152 | 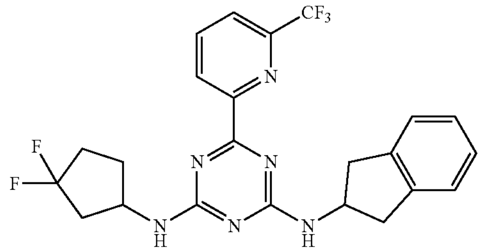 [SMILES: FC1(F)CCC(Nc2nc(NC3Cc4ccccc4C3)nc(-c3cccc(C(F)(F)F)n3)n2)C1] |
| 153 | 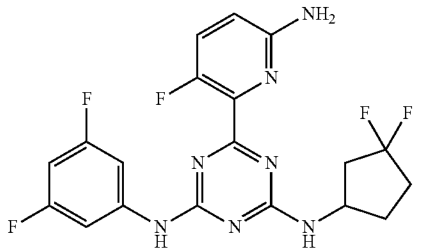 [SMILES: Nc1ccc(F)c(-c2nc(Nc3cc(F)cc(F)c3)nc(NC3CCC(F)(F)C3)n2)n1] |
| 154 | 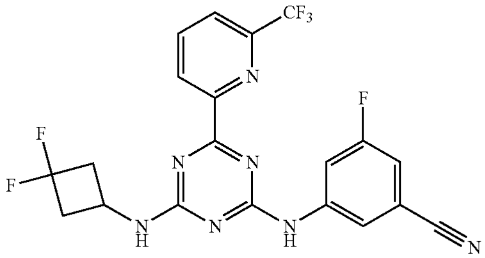 [SMILES: N#Cc1cc(F)cc(Nc2nc(NC3CC(F)(F)C3)nc(-c3cccc(C(F)(F)F)n3)n2)c1] |
| 155 | 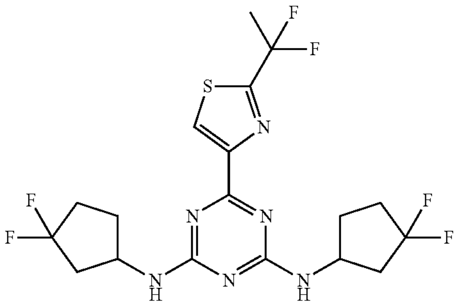 [SMILES: CC(F)(F)c1nc(-c2nc(NC3CCC(F)(F)C3)nc(NC3CCC(F)(F)C3)n2)cs1] |

TABLE 1-continued
| Representative Compounds | |
|---|---|
| Compound Number | Structure |
| 156 | 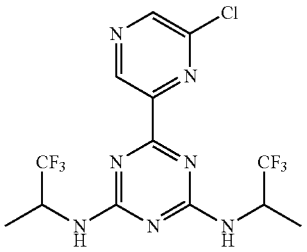 [SMILES: CC(Nc1nc(NC(C)C(F)(F)F)nc(-c2cncc(Cl)n2)n1)C(F)(F)F] |
| 157 | 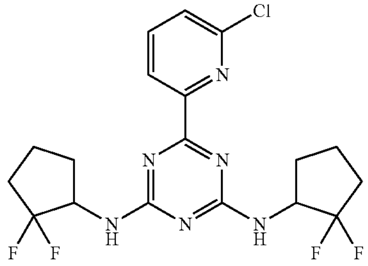 [SMILES: FC1(F)CCCC1Nc1nc(NC2CCCC2(F)F)nc(-c2cccc(Cl)n2)n1] |
| 158 | 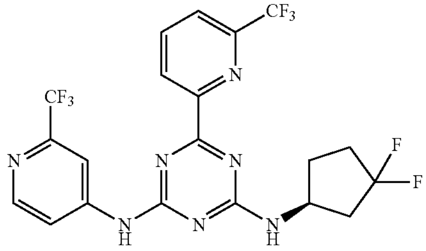 [SMILES: FC1(F)CC[C@H](Nc2nc(Nc3ccnc(C(F)(F)F)c3)nc(-c3cccc(C(F)(F)F)n3)n2)C1] |
| 159 | 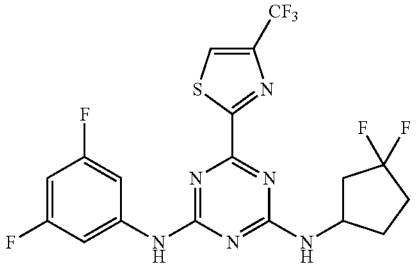 [SMILES: Fc1cc(F)cc(Nc2nc(NC3CCC(F)(F)C3)nc(-c3nc(C(F)(F)F)cs3)n2)c1] |
| 160 | 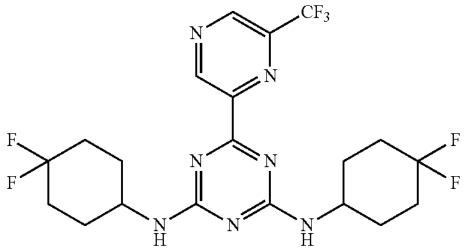 [SMILES: FC1(F)CCC(Nc2nc(NC3CCC(F)(F)CC3)nc(-c3cncc(C(F)(F)F)n3)n2)CC1] |

TABLE 1-continued
| Representative Compounds | |
| --- | --- |
| Compound Number | Structure |
| 161 | 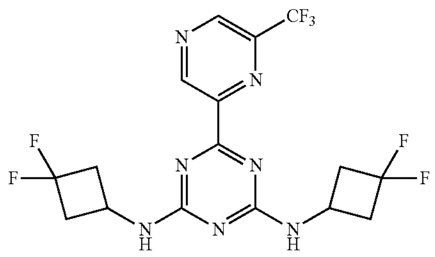 [SMILES: FC1(F)CC(Nc2nc(NC3CC(F)(F)C3)nc(-c3cncc(C(F)(F)F)n3)n2)C1] |
| 162 | 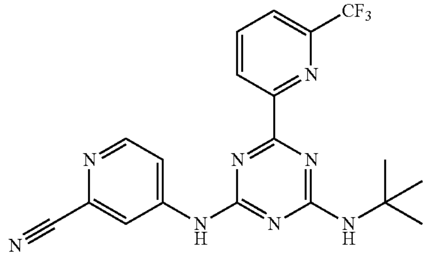 [SMILES: CC(C)(C)Nc1nc(Nc2ccnc(C#N)c2)nc(-c2cccc(C(F)(F)F)n2)n1] |
| 163 | 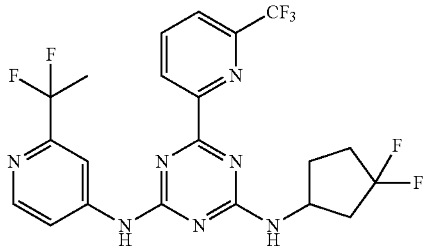 [SMILES: CC(F)(F)c1cc(Nc2nc(NC3CCC(F)(F)C3)nc(-c3cccc(C(F)(F)F)n3)n2)ccn1] |
| 164 | 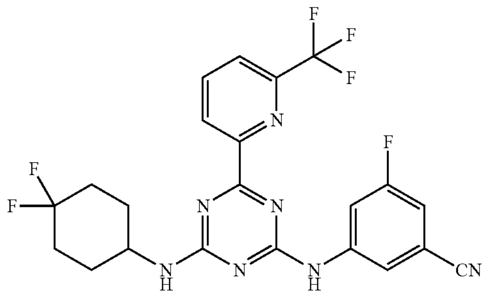 [SMILES: N#Cc1cc(F)cc(Nc2nc(NC3CCC(F)(F)CC3)nc(-c3cccc(C(F)(F)F)n3)n2)c1] |
| 165 | 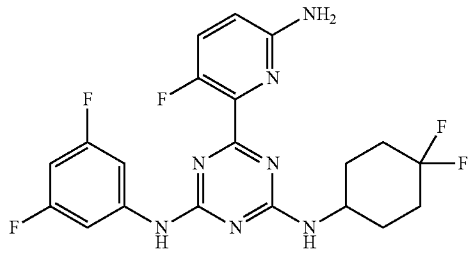 [SMILES: Nc1ccc(F)c(-c2nc(Nc3cc(F)cc(F)c3)nc(NC3CCC(F)(F)CC3)n2)n1] |

TABLE 1-continued
| Representative Compounds | |
|---|---|
| Compound Number | Structure |
| 166 | 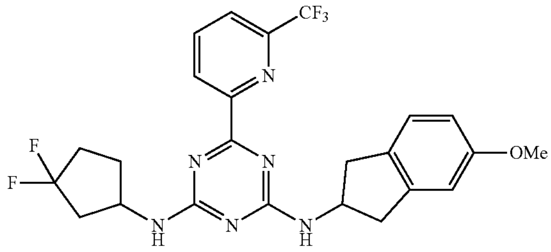 [SMILES: COc1ccc2c(c1)CC(Nc1nc(NC3CCC(F)(F)C3)nc(-c3cccc(C(F)(F)F)n3)n1)C2] |
| 167 | 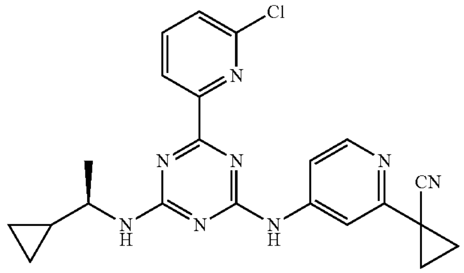 [SMILES: C[C@@H](Nc1nc(Nc2ccnc(C3(C#N)CC3)c2)nc(-c2cccc(Cl)n2)n1)C1CC1] |
| 168 | 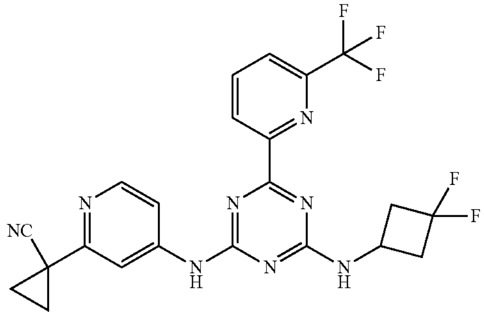 [SMILES: N#CC1(c2cc(Nc3nc(NC4CC(F)(F)C4)nc(-c4cccc(C(F)(F)F)n4)n3)ccn2)CC1] |
| 169 | 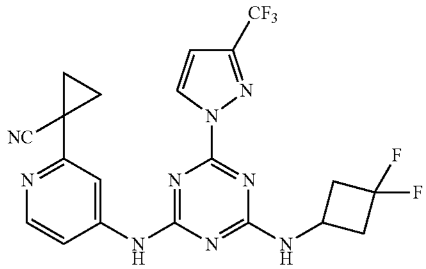 [SMILES: N#CC1(c2cc(Nc3nc(NC4CC(F)(F)C4)nc(-n4ccc(C(F)(F)F)n4)n3)ccn2)CC1] |
| 170 | 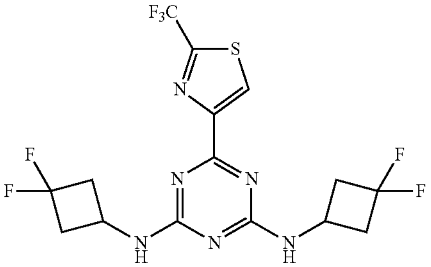 [SMILES: FC1(F)CC(Nc2nc(NC3CC(F)(F)C3)nc(-c3csc(C(F)(F)F)n3)n2)C1] |

TABLE 1-continued
| Representative Compounds | |
|---|---|
| Compound Number | Structure |
| 171 | 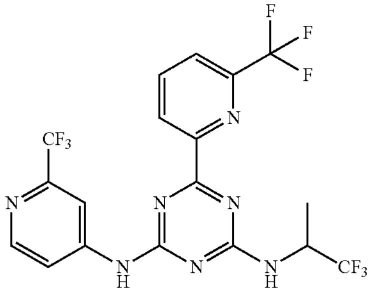 [SMILES: CC(Nc1nc(Nc2ccnc(C(F)(F)F)c2)nc(-c2cccc(C(F)(F)F)n2)n1)C(F)(F)F] |
| 172 | 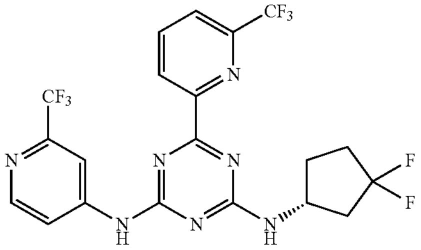 [SMILES: FC1(F)CC[C@@H](Nc2nc(Nc3ccnc(C(F)(F)F)c3)nc(-c3cccc(C(F)(F)F)n3)n2)C1] |
| 173 | 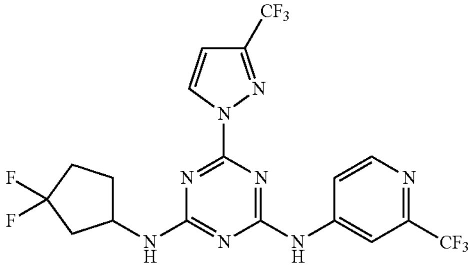 [SMILES: FC1(F)CCC(Nc2nc(Nc3ccnc(C(F)(F)F)c3)nc(-n3ccc(C(F)(F)F)n3)n2)C1] |
| 174 | 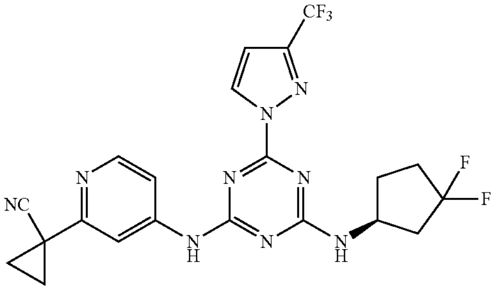 [SMILES: N#CC1(c2cc(Nc3nc(N[C@H]4CCC(F)(F)C4)nc(-n4ccc(C(F)(F)F)n4)n3)ccn2)CC1] |
| 175 | 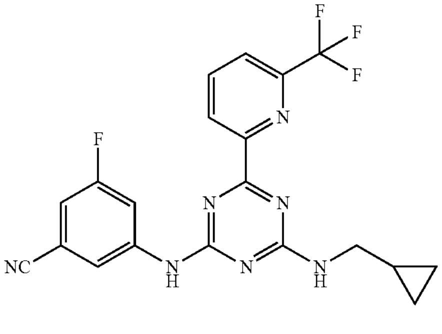 [SMILES: N#Cc1cc(F)cc(Nc2nc(NCC3CC3)nc(-c3cccc(C(F)(F)F)n3)n2)c1] |

TABLE 1-continued
| Representative Compounds | |
|---|---|
| Compound Number | Structure |
| 176 | 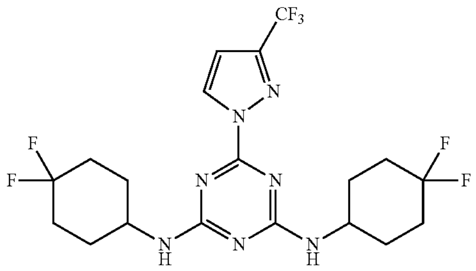 [SMILES: FC1(F)CCC(Nc2nc(NC3CCC(F)(F)CC3)nc(-n3ccc(C(F)(F)F)n3)n2)CC1] |
| 177 | 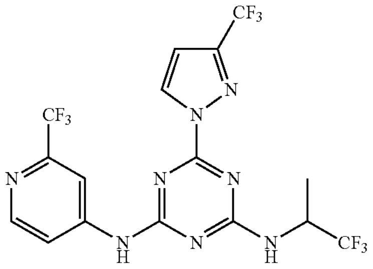 [SMILES: CC(Nc1nc(Nc2ccnc(C(F)(F)F)c2)nc(-n2ccc(C(F)(F)F)n2)n1)C(F)(F)F] |
| 178 | 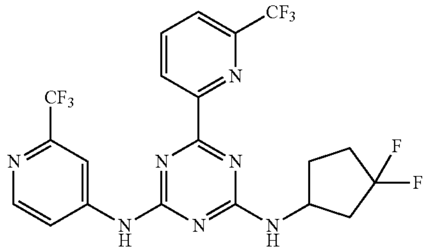 [SMILES: FC1(F)CCC(Nc2nc(Nc3ccnc(C(F)(F)F)c3)nc(-c3cccc(C(F)(F)F)n3)n2)C1] |
| 179 | 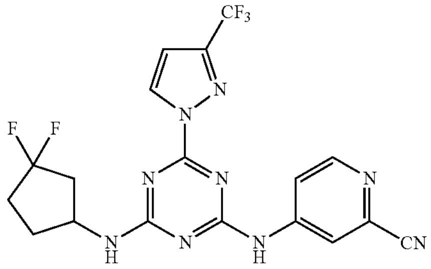 [SMILES: N#Cc1cc(Nc2nc(NC3CCC(F)(F)C3)nc(-n3ccc(C(F)(F)F)n3)n2)ccn1] |
| 180 | 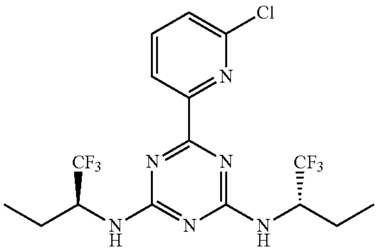 [SMILES: CC[C@H](Nc1nc(N[C@@H](CC)C(F)(F)F)nc(-c2cccc(Cl)n2)n1)C(F)(F)F] |

TABLE 1-continued
| Representative Compounds | |
|---|---|
| Compound Number | Structure |
| 181 | 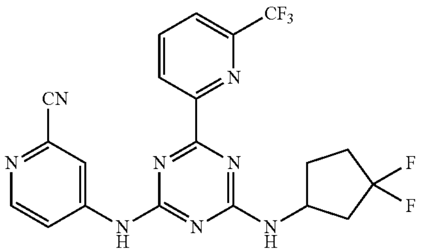 [SMILES: N#Cc1cc(Nc2nc(NC3CCC(F)(F)C3)nc(-c3cccc(C(F)(F)F)n3)n2)ccn1] |
| 182 | 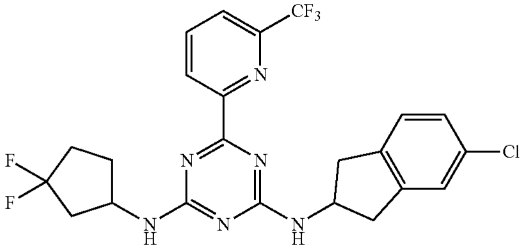 [SMILES: FC1(F)CCC(Nc2nc(NC3Cc4ccc(Cl)cc4C3)nc(-c3cccc(C(F)(F)F)n3)n2)C1] |
| 183 | 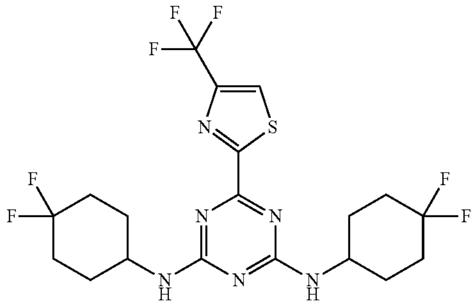 [SMILES: FC1(F)CCC(Nc2nc(NC3CCC(F)(F)CC3)nc(-c3nc(C(F)(F)F)cs3)n2)CC1] |
| 184 | 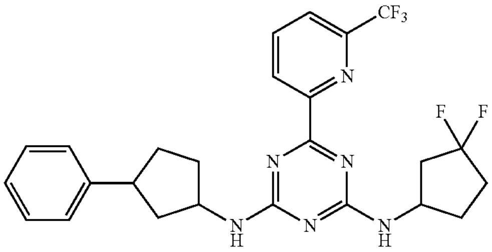 [SMILES: FC1(F)CCC(Nc2nc(NC3CCC(c4ccccc4)C3)nc(-c3cccc(C(F)(F)F)n3)n2)C1] |
| 185 | 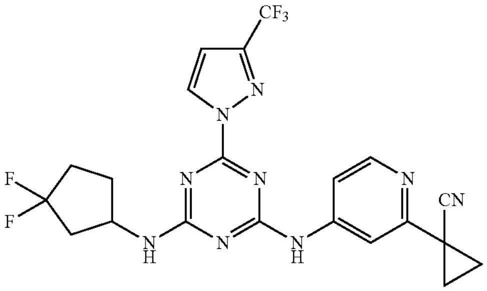 [SMILES: N#CC1(c2cc(Nc3nc(NC4CCC(F)(F)C4)nc(-n4ccc(C(F)(F)F)n4)n3)ccn2)CC1] |

TABLE 1-continued
| Representative Compounds | |
|---|---|
| Compound Number | Structure |
| 186 | 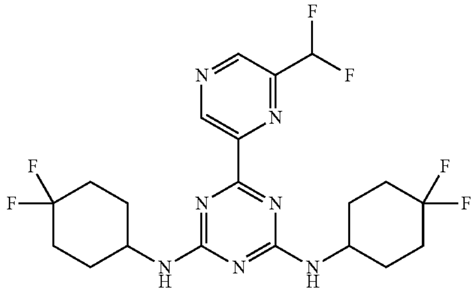 [SMILES: FC(F)c1cncc(-c2nc(NC3CCC(F)(F)CC3)nc(NC3CCC(F)(F)CC3)n2)n1] |
| 187 | 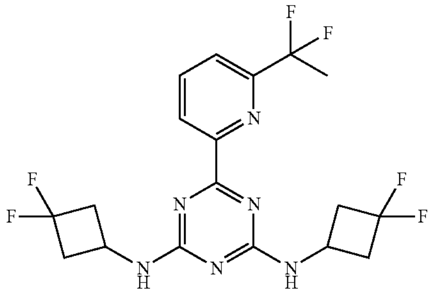 |
| 188 | 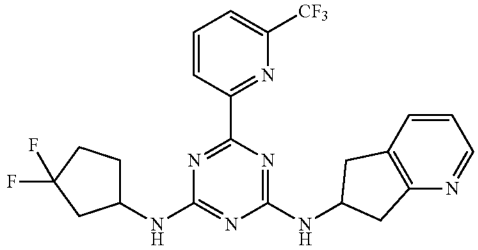 [SMILES: FC1(F)CCC(Nc2nc(NC3Cc4cccnc4C3)nc(-c3cccc(C(F)(F)F)n3)n2)C1] |
| 189 | 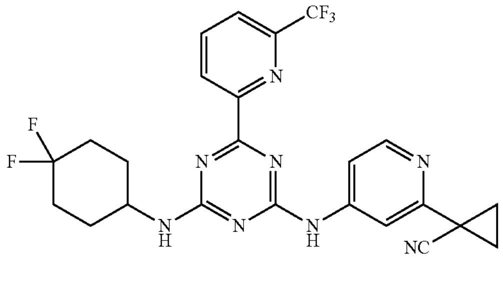 [SMILES: N#CC1(c2cc(Nc3nc(NC4CCC(F)(F)CC4)nc(-c4cccc(C(F)(F)F)n4)n3)ccn2)CC1] |
| 190 | 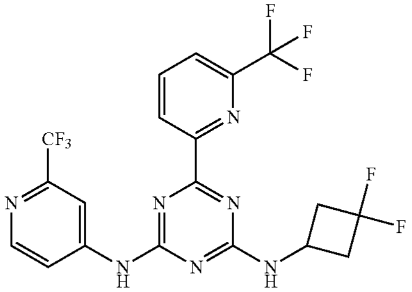 [SMILES: FC1(F)CC(Nc2nc(Nc3ccnc(C(F)(F)F)c3)nc(-c3cccc(C(F)(F)F)n3)n2)C1] |

TABLE 1-continued
| Representative Compounds | |
|---|---|
| Compound Number | Structure |
| 191 | 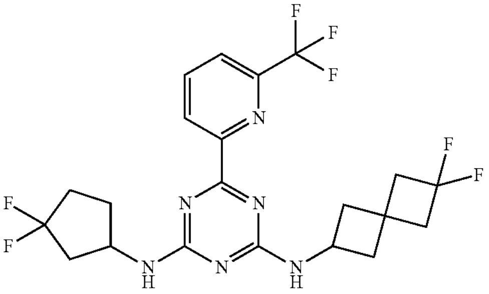 [SMILES: FC1(F)CCC(Nc2nc(NC3CC4(C3)CC(F)(F)C4)nc(-c3cccc(C(F)(F)F)n3)n2)C1] |
| 192 | 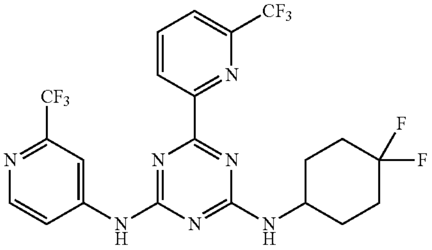 [SMILES: FC1(F)CCC(Nc2nc(Nc3ccnc(C(F)(F)F)c3)nc(-c3cccc(C(F)(F)F)n3)n2)CC1] |
| 193 | 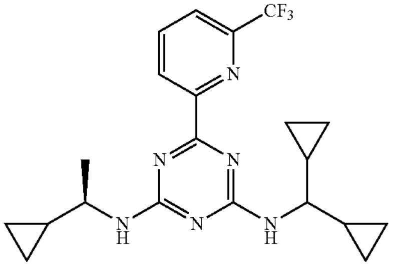 [SMILES: C[C@@H](Nc1nc(NC(C2CC2)C2CC2)nc(-c2cccc(C(F)(F)F)n2)n1)C1CC1] |
| 194 | 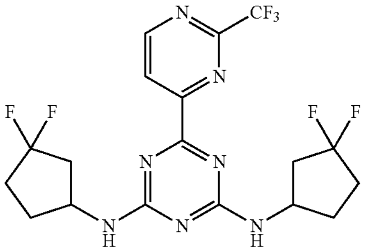 [SMILES: FC1(F)CCC(Nc2nc(NC3CCC(F)(F)C3)nc(-c3ccnc(C(F)(F)F)n3)n2)C1] |
| 195 | 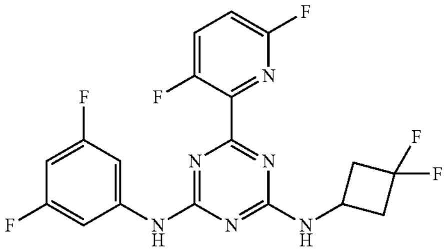 [SMILES: Fc1cc(F)cc(Nc2nc(NC3CC(F)(F)C3)nc(-c3nc(F)ccc3F)n2)c1] |

TABLE 1-continued
| Representative Compounds | |
|---|---|
| Compound Number | Structure |
| 196 | 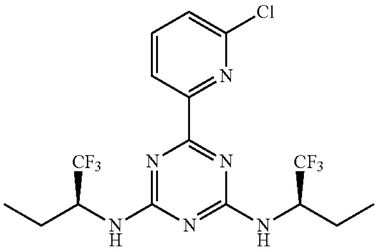 [SMILES: CC[C@H](Nc1nc(N[C@H](CC)C(F)(F)F)nc(-c2cccc(Cl)n2)n1)C(F)(F)F] |
| 197 | 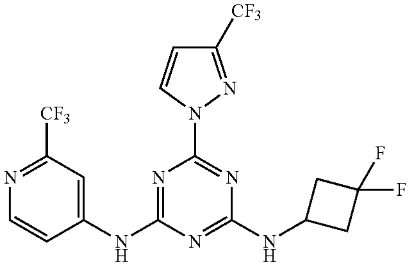 [SMILES: FC1(F)CC(Nc2nc(Nc3ccnc(C(F)(F)F)c3)nc(-n3ccc(C(F)(F)F)n3)n2)C1] |
| 198 | 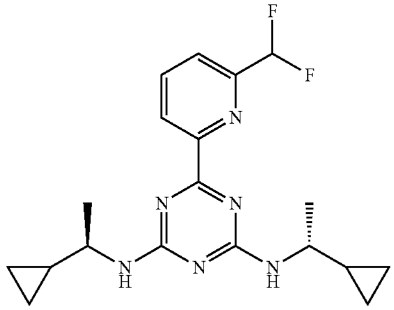 [SMILES: C[C@@H](Nc1nc(N[C@H](C)C2CC2)nc(-c2cccc(C(F)F)n2)n1)C1CC1] |
| 199 | 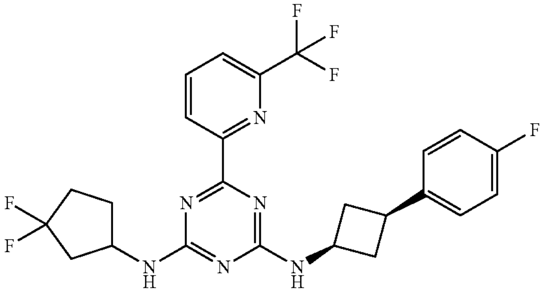 [SMILES: Fc1ccc([C@H]2C[C@@H](Nc3nc(NC4CCC(F)(F)C4)nc(-c4cccc(C(F)(F)F)n4)n3)C2)cc1] |
| 200 | 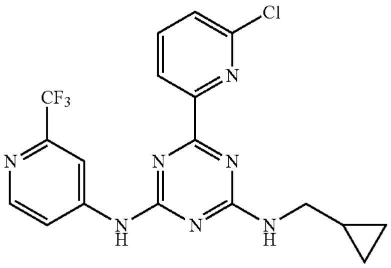 [SMILES: FC(F)(F)c1cc(Nc2nc(NCC3CC3)nc(-c3cccc(Cl)n3)n2)ccn1] |

TABLE 1-continued
| Representative Compounds | |
|---|---|
| Compound Number | Structure |
| 201 | 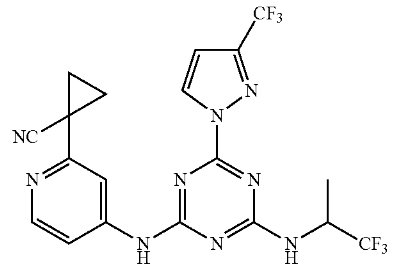 [SMILES: CC(Nc1nc(Nc2ccnc(C3(C#N)CC3)c2)nc(-n2ccc(C(F)(F)F)n2)n1)C(F)(F)F] |
| 202 | 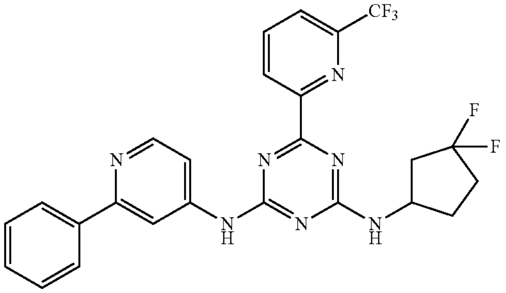 [SMILES: FC1(F)CCC(Nc2nc(Nc3ccnc(-c4ccccc4)c3)nc(-c3cccc(C(F)(F)F)n3)n2)C1] |
| 203 | 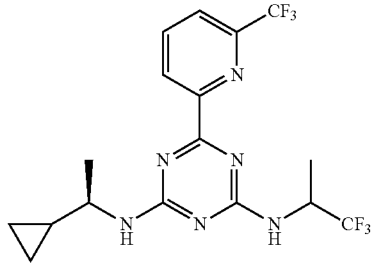 [SMILES: CC(Nc1nc(N[C@H](C)C2CC2)nc(-c2cccc(C(F)(F)F)n2)n1)C(F)(F)F] |
| 204 | 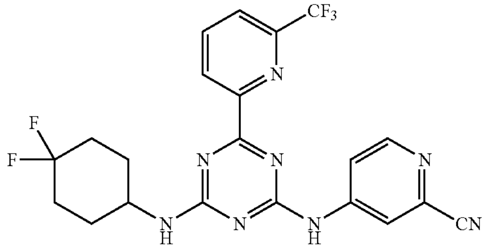 [SMILES: N#Cc1cc(Nc2nc(NC3CCC(F)(F)CC3)nc(-c3cccc(C(F)(F)F)n3)n2)ccn1] |
| 205 | 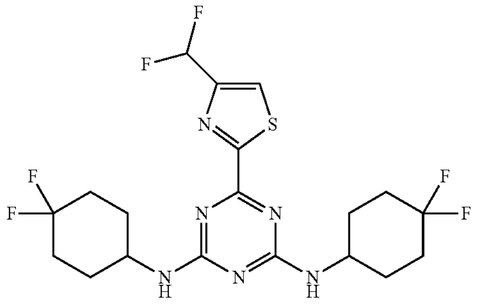 [SMILES: FC(F)c1csc(-c2nc(NC3CCC(F)(F)CC3)nc(NC3CCC(F)(F)CC3)n2)n1] |

TABLE 1-continued
Representative Compounds
| Compound Number | Structure |
| --- | --- |
| 206 | 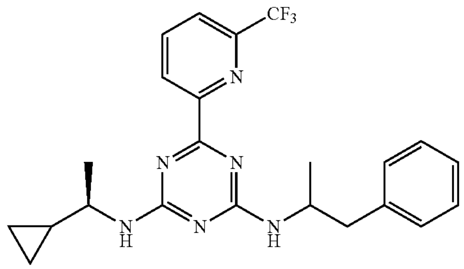 [SMILES: CC(Cc1ccccc1)Nc1nc(N[C@H](C)C2CC2)nc(-c2cccc(C(F)(F)F)n2)n1] |
| 207 | 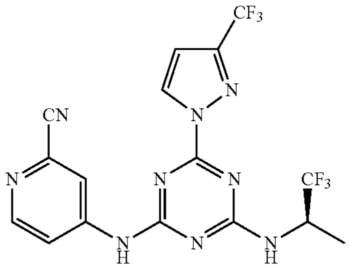 [SMILES: C[C@@H](Nc1nc(Nc2ccnc(C#N)c2)nc(-n2ccc(C(F)(F)F)n2)n1)C(F)(F)F] |
| 208 | 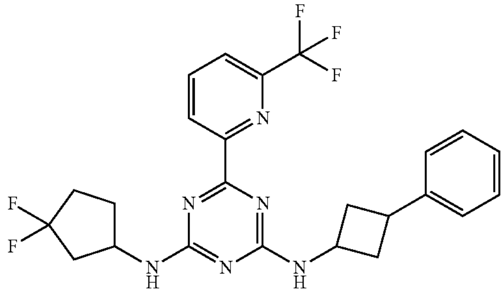 [SMILES: FC1(F)CCC(Nc2nc(NC3CC(c4ccccc4)C3)nc(-c3cccc(C(F)(F)F)n3)n2)C1] |
| 209 | 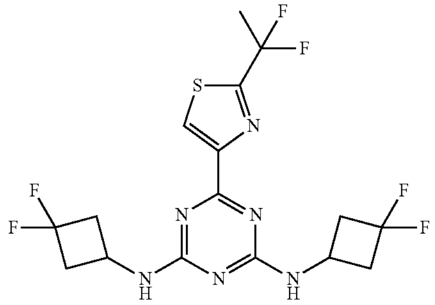 |
| 210 | 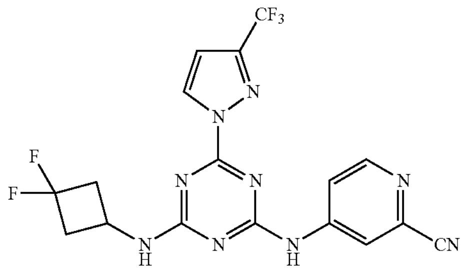 [SMILES: N#Cc1cc(Nc2nc(NC3CC(F)(F)C3)nc(-n3ccc(C(F)(F)F)n3)n2)ccn1] |

TABLE 1-continued
| Representative Compounds | |
|---|---|
| Compound Number | Structure |
| 211 | 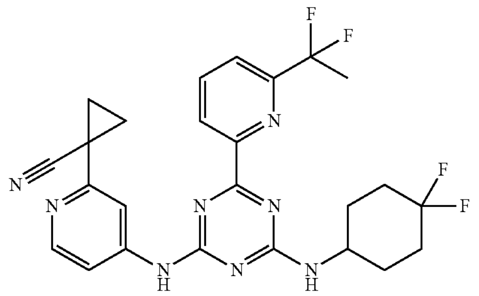 [SMILES: CC(F)(F)c1cccc(-c2nc(Nc3ccnc(C4(C#N)CC4)c3)nc(NC3CCC(F)(F)CC3)n2)n1] |
| 212 | 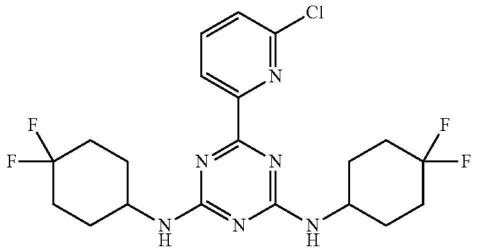 |
| 213 | 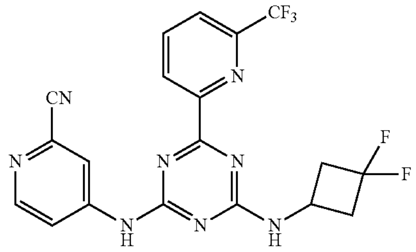 [SMILES: N#Cc1cc(Nc2nc(NC3CC(F)(F)C3)nc(-c3cccc(C(F)(F)F)n3)n2)ccn1] |
| 214 | 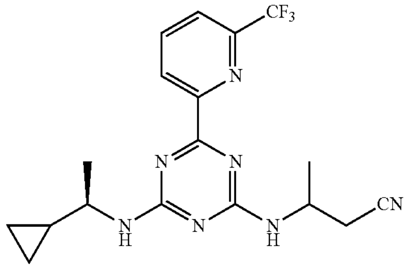 [SMILES: CC(CC#N)Nc1nc(N[C@H](C)C2CC2)nc(-c2cccc(C(F)(F)F)n2)n1] |
| 215 | 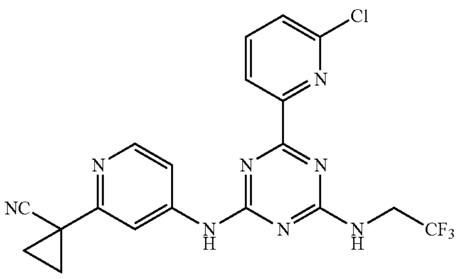 [SMILES: N#CC1(c2cc(Nc3nc(NCC(F)(F)F)nc(-c4cccc(Cl)n4)n3)ccn2)CC1] |

TABLE 1-continued
| Representative Compounds | |
|---|---|
| Compound Number | Structure |
| 216 | 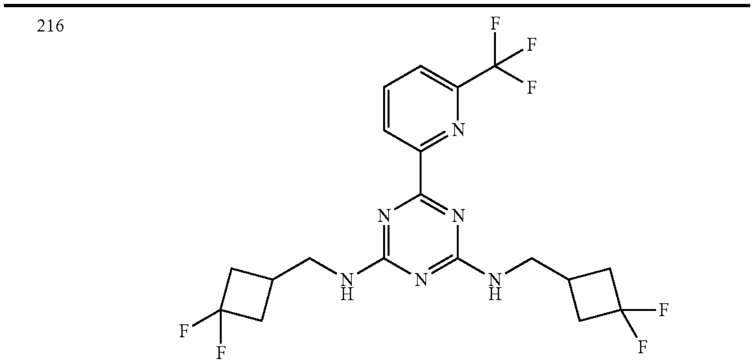 |
| 217 | 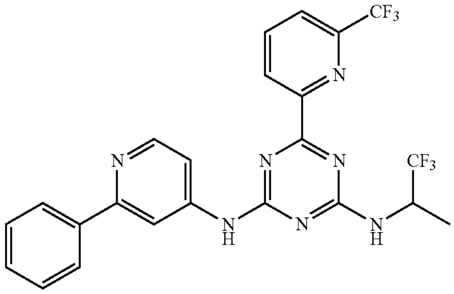 [SMILES: CC(Nc1nc(Nc2ccnc(-c3ccccc3)c2)nc(-c2cccc(C(F)(F)F)n2)n1)C(F)(F)F] |
| 218 | 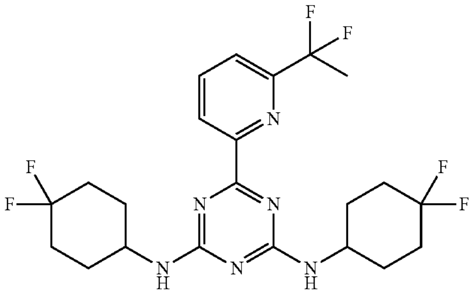 |
| 219 | 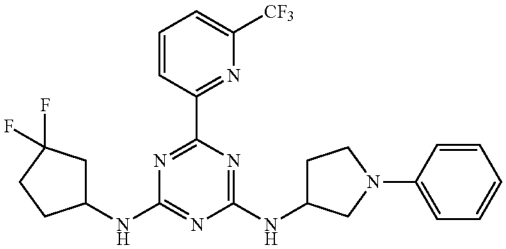 [SMILES: FC1(F)CCC(Nc2nc(NC3CCN(c4ccccc4)C3)nc(-c3cccc(C(F)(F)F)n3)n2)C1] |
| 220 | 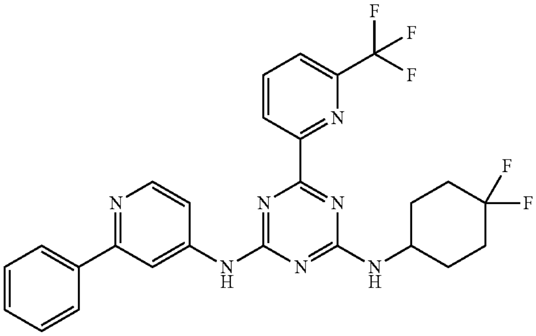 [SMILES: FC1(F)CCC(Nc2nc(Nc3ccnc(-c4ccccc4)c3)nc(-c3cccc(C(F)(F)F)n3)n2)CC1] |

TABLE 1-continued
| Representative Compounds | |
|---|---|
| Compound Number | Structure |
| 221 | 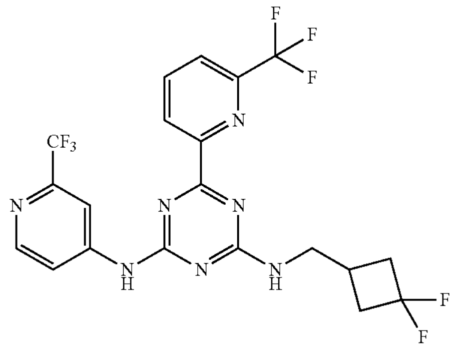 [SMILES: FC1(F)CC(CNc2nc(Nc3ccnc(C(F)(F)F)c3)nc(-c3cccc(C(F)(F)F)n3)n2)C1] |
| 222 | 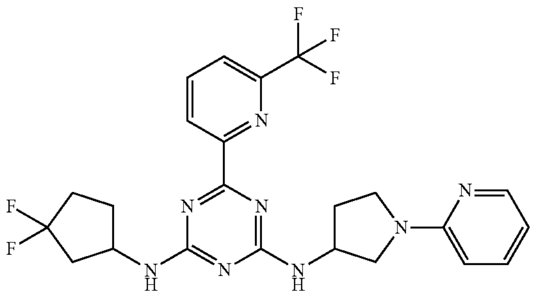 [SMILES: FC1(F)CCC(Nc2nc(NC3CCN(c4ccccn4)C3)nc(-c3cccc(C(F)(F)F)n3)n2)C1] |
| 223 | 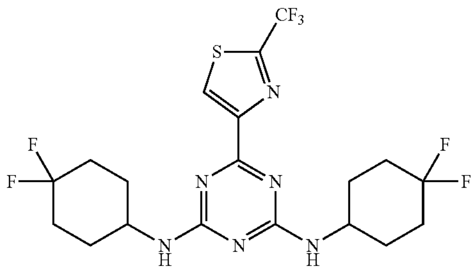 [SMILES: FC1(F)CCC(Nc2nc(NC3CCC(F)(F)CC3)nc(-c3csc(C(F)(F)F)n3)n2)CC1] |
| 224 | 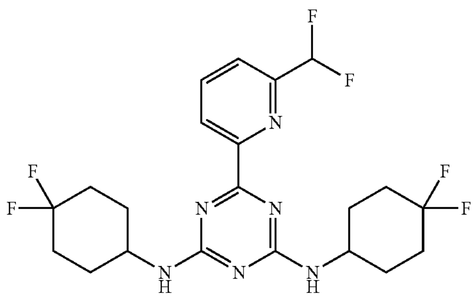 [SMILES: FC(F)c1cccc(-c2nc(NC3CCC(F)(F)CC3)nc(NC3CCC(F)(F)CC3)n2)n1] |

TABLE 1-continued
| Representative Compounds | |
|---|---|
| Compound Number | Structure |
| 225 | 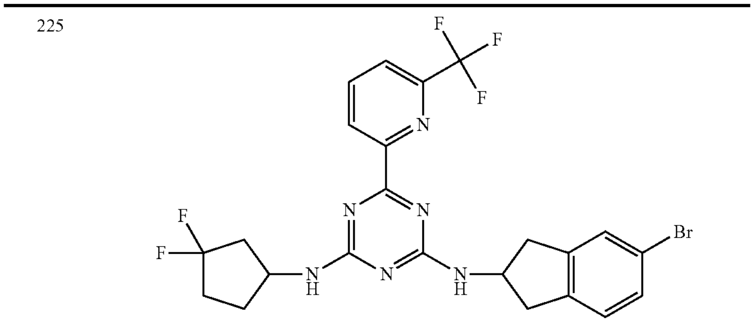 |
| 226 | 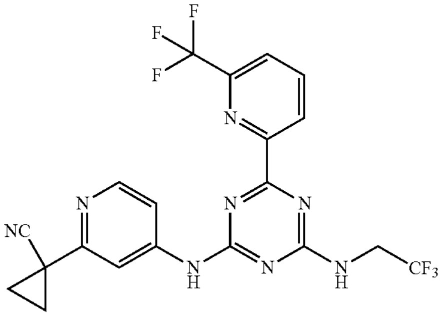 [SMILES: N#CC1(c2cc(Nc3nc(NCC(F)(F)F)nc(-c4cccc(C(F)(F)F)n4)n3)ccn2)CC1] |
| 227 | 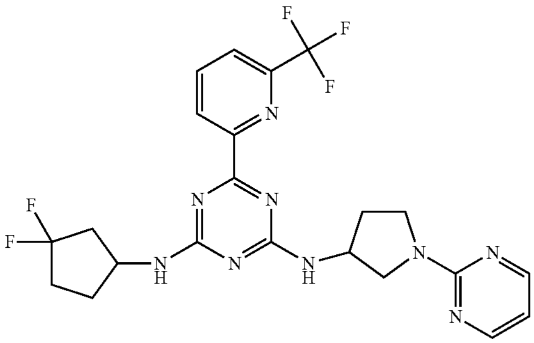 [SMILES: FC1(F)CCC(Nc2nc(NC3CCN(c4ncccn4)C3)nc(-c3cccc(C(F)(F)F)n3)n2)C1] |
| 228 | 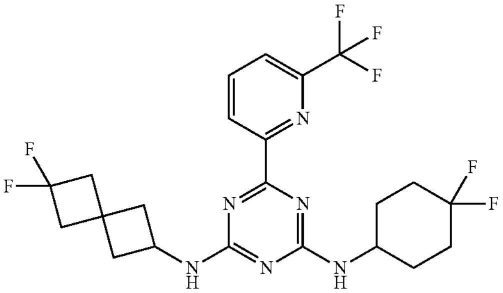 [SMILES: FC1(F)CCC(Nc2nc(NC3CC4(C3)CC(F)(F)C4)nc(-c3cccc(C(F)(F)F)n3)n2)CC1] |
| 229 | 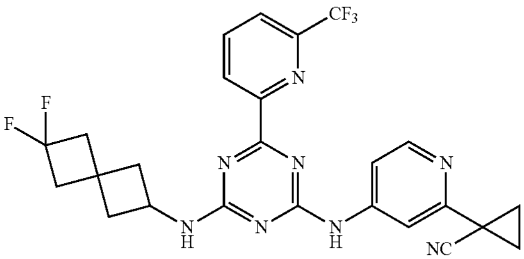 [SMILES: N#CC1(c2cc(Nc3nc(NC4CC5(C4)CC(F)(F)C5)nc(-c4cccc(C(F)(F)F)n4)n3)ccn2)CC1] |

TABLE 1-continued
| Compound Number | Structure |
| --- | --- |
| 230 | 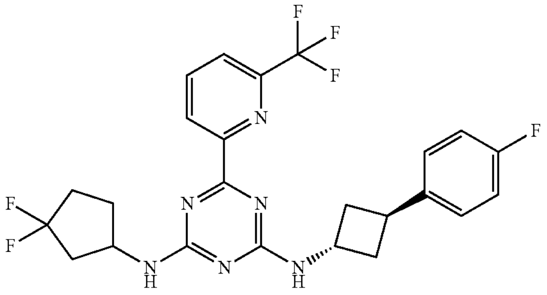 [SMILES: Fc1ccc([C@H]2C[C@H](Nc3nc(NC4CCC(F)(F)C4)nc(-c4cccc(C(F)(F)F)n4)n3)C2)cc1] |
| 231 | 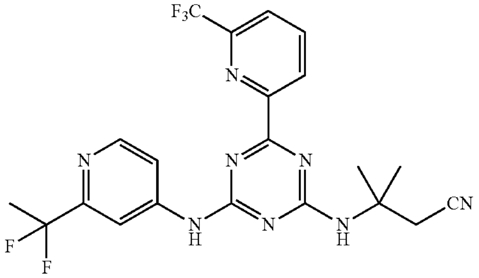 [SMILES: CC(C)(CC#N)Nc1nc(Nc2ccnc(C(C)(F)F)c2)nc(-c2cccc(C(F)(F)F)n2)n1] |
| 232 | 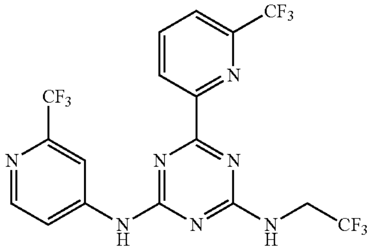 [SMILES: FC(F)(F)CNc1nc(Nc2ccnc(C(F)(F)F)c2)nc(-c2cccc(C(F)(F)F)n2)n1] |
| 233 | 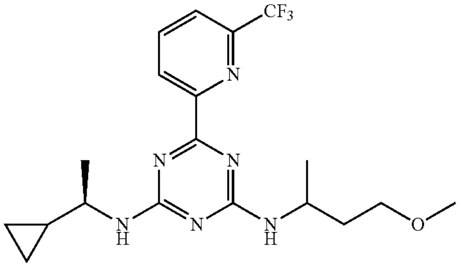 [SMILES: COCCC(C)Nc1nc(N[C@H](C)C2CC2)nc(-c2cccc(C(F)(F)F)n2)n1] |
| 234 | 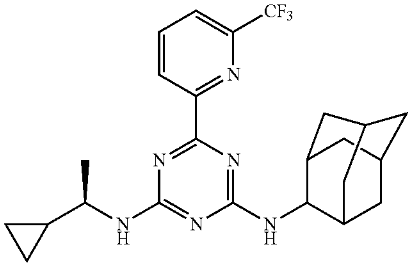 [SMILES: C[C@@H](Nc1nc(NC2C3CC4CC(C3)CC2C4)nc(-c2cccc(C(F)(F)F)n2)n1)C1CC1] |
Representative Compounds TABLE 1-continued
| Representative Compounds | |
|---|---|
| Compound Number | Structure |
| 235 | 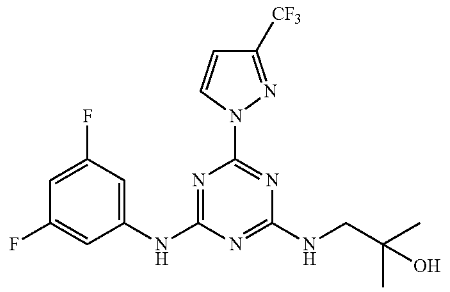 [SMILES: CC(C)(O)CNc1nc(Nc2cc(F)cc(F)c2)nc(-n2ccc(C(F)(F)F)n2)n1] |
| 236 | 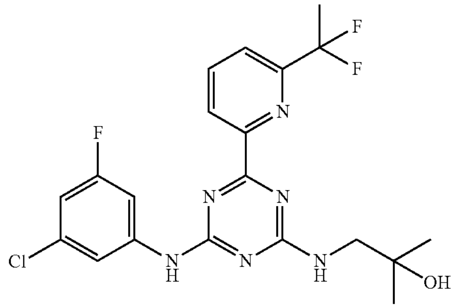 [SMILES: CC(C)(O)CNc1nc(Nc2cc(F)cc(Cl)c2)nc(-c2cccc(C(C)(F)F)n2)n1] |
| 237 | 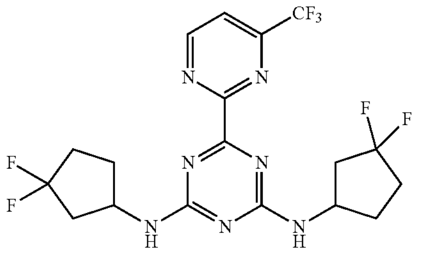 [SMILES: FC1(F)CCC(Nc2nc(NC3CCC(F)(F)C3)nc(-c3nccc(C(F)(F)F)n3)n2)C1] |
| 238 | 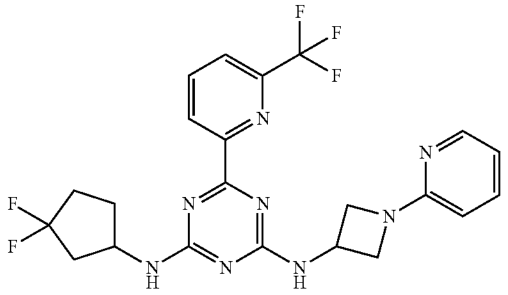 [SMILES: FC1(F)CCC(Nc2nc(NC3CN(c4ccccn4)C3)nc(-c3cccc(C(F)(F)F)n3)n2)C1] |
| 239 | 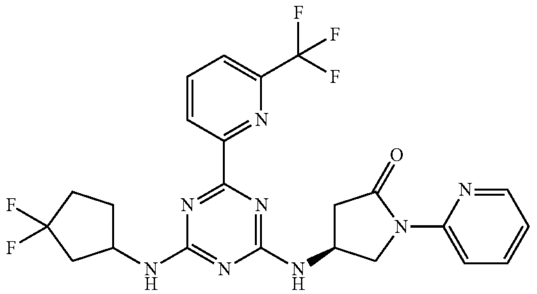 [SMILES: O=C1C[C@H](Nc2nc(NC3CCC(F)(F)C3)nc(-c3cccc(C(F)(F)F)n3)n2)CN1c1ccccn1] |

TABLE 1-continued
| Representative Compounds | |
|---|---|
| Compound Number | Structure |
| 240 | 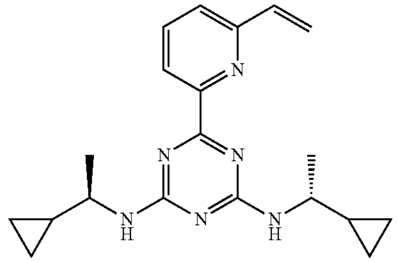 [SMILES: C=Cc1cccc(-c2nc(N[C@H](C)C3CC3)nc(N[C@H](C)C3CC3)n2)n1] |
| 241 | 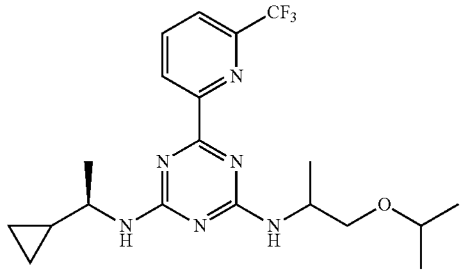 [SMILES: CC(COC(C)C)Nc1nc(N[C@H](C)C2CC2)nc(-c2cccc(C(F)(F)F)n2)n1] |
| 242 | 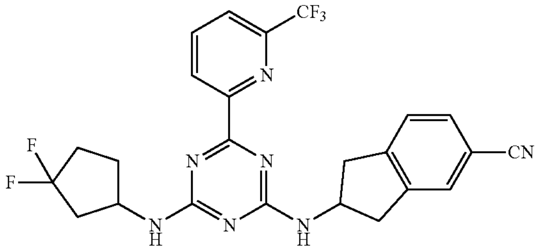 [SMILES: N#Cc1ccc2c(c1)CC(Nc1nc(NC3CCC(F)(F)C3)nc(-c3cccc(C(F)(F)F)n3)n1)C2] |
| 243 | 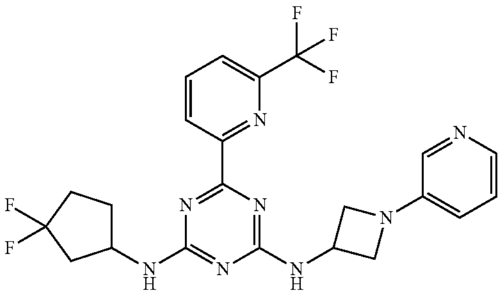 [SMILES: FC1(F)CCC(Nc2nc(NC3CN(c4cccnc4)C3)nc(-c3cccc(C(F)(F)F)n3)n2)C1] |
| 244 | 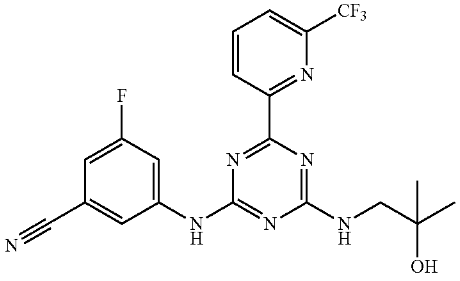 [SMILES: CC(C)(O)CNc1nc(Nc2cc(F)cc(C#N)c2)nc(-c2cccc(C(F)(F)F)n2)n1] |

TABLE 1-continued
| Representative Compounds | |
|---|---|
| Compound Number | Structure |
| 245 | 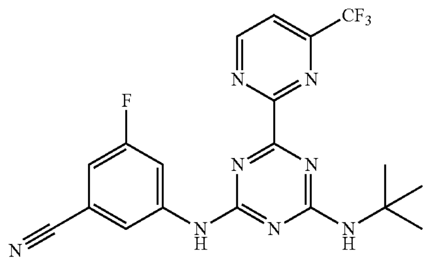 [SMILES: CC(C)(C)Nc1nc(Nc2cc(F)cc(C#N)c2)nc(-c2nccc(C(F)(F)F)n2)n1] |
| 246 | 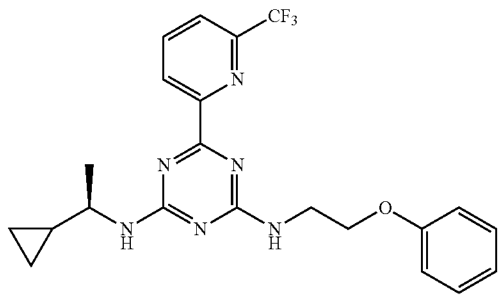 [SMILES: C[C@@H](Nc1nc(NCCOc2ccccc2)nc(-c2cccc(C(F)(F)F)n2)n1)C1CC1] |
| 247 | 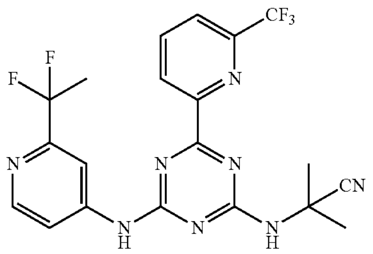 [SMILES: CC(C)(C#N)Nc1nc(Nc2ccnc(C(C)(F)F)c2)nc(-c2cccc(C(F)(F)F)n2)n1] |
| 248 | 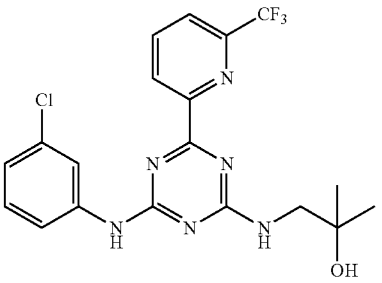 [SMILES: CC(C)(O)CNc1nc(Nc2cccc(Cl)c2)nc(-c2cccc(C(F)(F)F)n2)n1] |
| 249 | 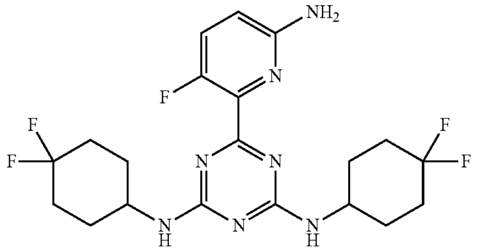 [SMILES: Nc1ccc(F)c(-c2nc(NC3CCC(F)(F)CC3)nc(NC3CCC(F)(F)CC3)n2)n1] |

TABLE 1-continued
| Representative Compounds | |
|---|---|
| Compound Number | Structure |
| 250 | 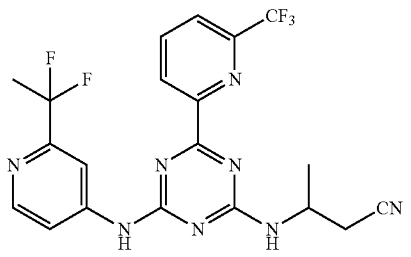 [SMILES: CC(CC#N)Nc1nc(Nc2ccnc(C(C)(F)F)c2)nc(-c2cccc(C(F)(F)F)n2)n1] |
| 251 | 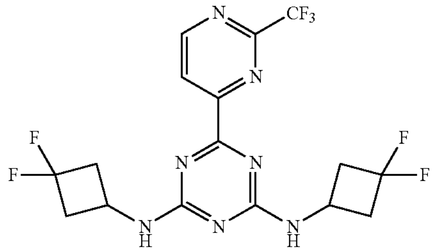 [SMILES: FC1(F)CC(Nc2nc(NC3CC(F)(F)C3)nc(-c3ccnc(C(F)(F)F)n3)n2)C1] |
| 252 | 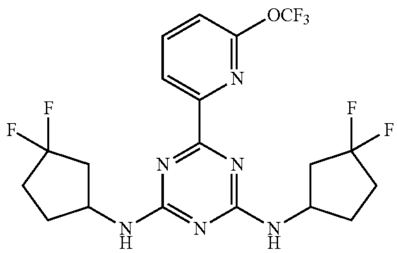 [SMILES: FC1(F)CCC(Nc2nc(NC3CCC(F)(F)C3)nc(-c3cccc(OC(F)(F)F)n3)n2)C1] |
| 253 | 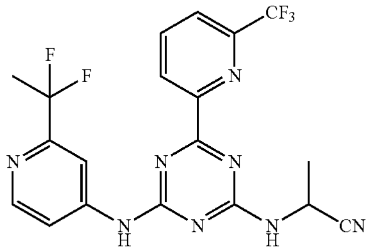 [SMILES: CC(C#N)Nc1nc(Nc2ccnc(C(C)(F)F)c2)nc(-c2cccc(C(F)(F)F)n2)n1] |
| 254 | 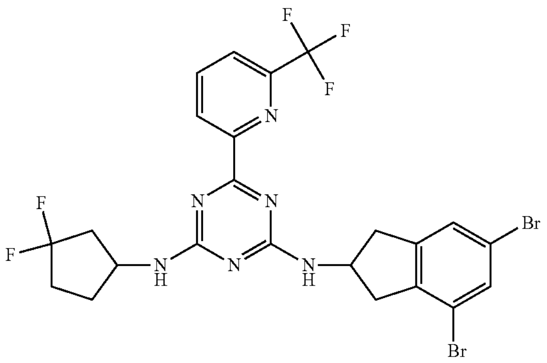 [SMILES: FC1(F)CCC(Nc2nc(NC3Cc4cc(Br)cc(Br)c4C3)nc(-c3cccc(C(F)(F)F)n3)n2)C1] |

TABLE 1-continued
| Compound Number | Structure |
|---|---|
| 255 | 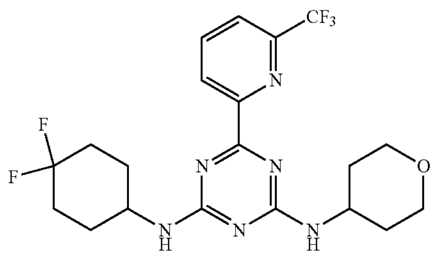 [SMILES: FC1(F)CCC(Nc2nc(NC3CCOCC3)nc(-c3cccc(C(F)(F)F)n3)n2)CC1] |
| 256 | 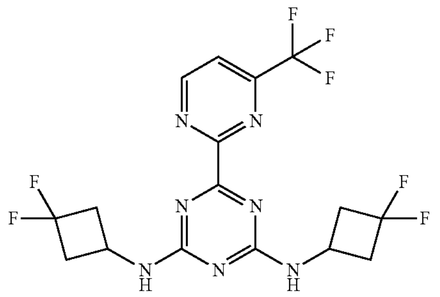 |
| 257 | 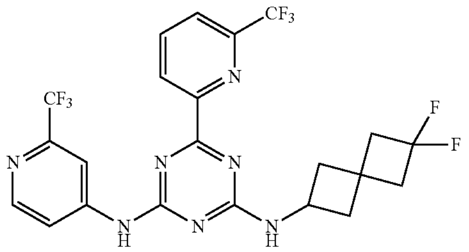 [SMILES: FC1(F)CC2(CC(Nc3nc(Nc4ccnc(C(F)(F)F)c4)nc(-c4cccc(C(F)(F)F)n4)n3)C2)C1] |
| 258 | 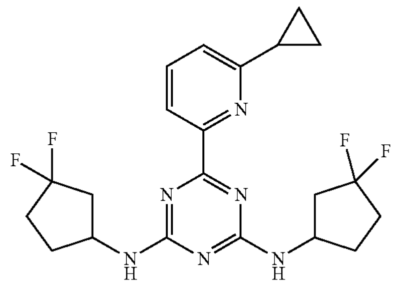 [SMILES: FC1(F)CCC(Nc2nc(NC3CCC(F)(F)C3)nc(-c3cccc(C4CC4)n3)n2)C1] |
| 259 | 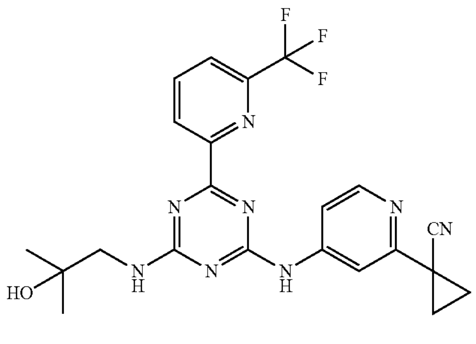 [SMILES: CC(C)(O)CNc1nc(Nc2ccnc(C3(C#N)CC3)c2)nc(-c2cccc(C(F)(F)F)n2)n1] |
Representative Compounds TABLE 1-continued
| Representative Compounds | |
| --- | --- |
| Compound Number | Structure |
| 260 | 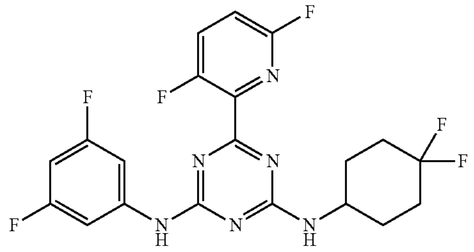 [SMILES: Fc1cc(F)cc(Nc2nc(NC3CCC(F)(F)CC3)nc(-c3nc(F)ccc3F)n2)c1] |
| 261 | 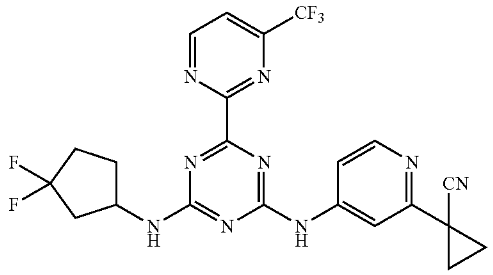 |
| 262 | 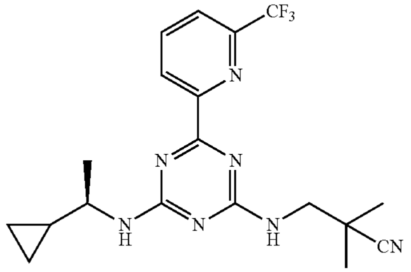 [SMILES: C[C@@H](Nc1nc(NCC(C)(C)C#N)nc(-c2cccc(C(F)(F)F)n2)n1)C1CC1] |
| 263 | 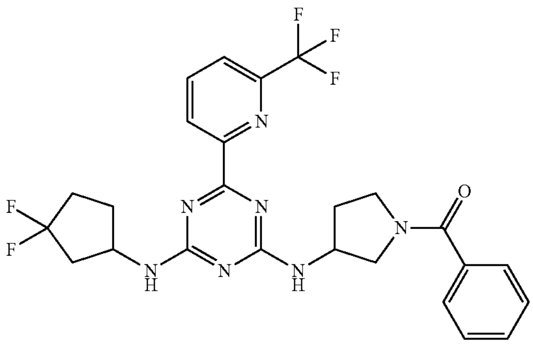 [SMILES: O=C(c1ccccc1)N1CCC(Nc2nc(NC3CCC(F)(F)C3)nc(-c3cccc(C(F)(F)F)n3)n2)C1] |
| 264 | 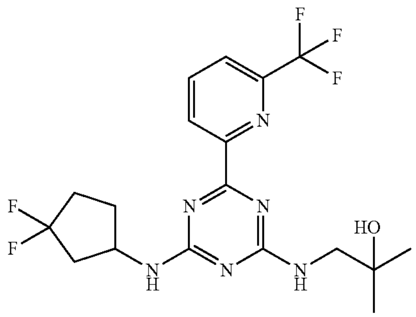 [SMILES: CC(C)(O)CNc1nc(NC2CCC(F)(F)C2)nc(-c2cccc(C(F)(F)F)n2)n1] |

TABLE 1-continued
| Representative Compounds | |
|---|---|
| Compound Number | Structure |
| 265 | 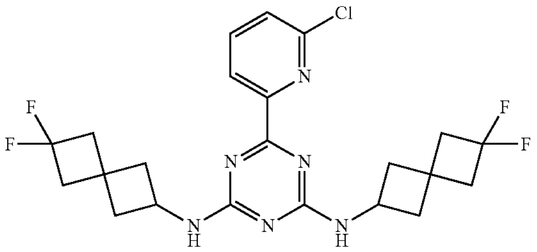 [SMILES: FC1(F)CC2(CC(Nc3nc(NC4CC5(C4)CC(F)(F)C5)nc(-c4cccc(Cl)n4)n3)C2)C1] |
| 266 | 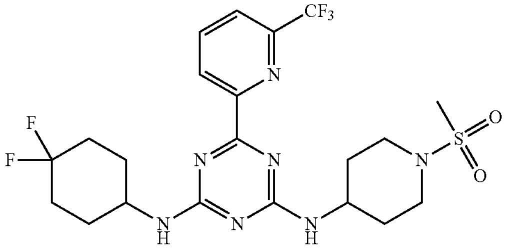 [SMILES: CS(=O)(=O)N1CCC(Nc2nc(NC3CCC(F)(F)CC3)nc(-c3cccc(C(F)(F)F)n3)n2)CC1] |
| 267 | 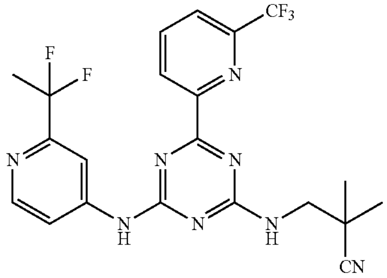 [SMILES: CC(C)(C#N)CNc1nc(Nc2ccnc(C(C)(F)F)c2)nc(-c2cccc(C(F)(F)F)n2)n1] |
| 268 | 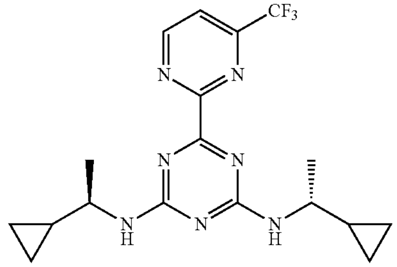 |
| 269 | 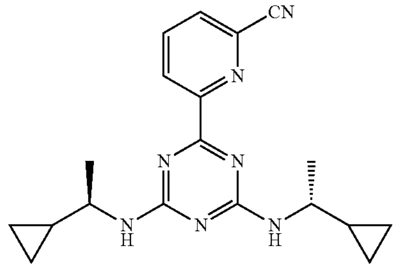 |

TABLE 1-continued
| Compound Number | Structure |
|---|---|
| | Representative Compounds |
| 270 | 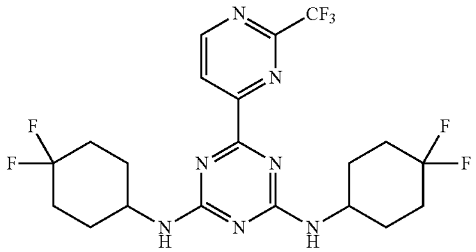 [SMILES: FC1(F)CCC(Nc2nc(NC3CCC(F)(F)CC3)nc(-c3ccnc(C(F)(F)F)n3)n2)CC1] |
| 271 | 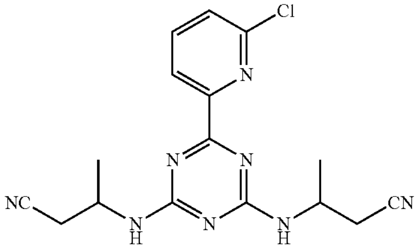 [SMILES: CC(CC#N)Nc1nc(NC(C)CC#N)nc(-c2cccc(Cl)n2)n1] |
| 272 | 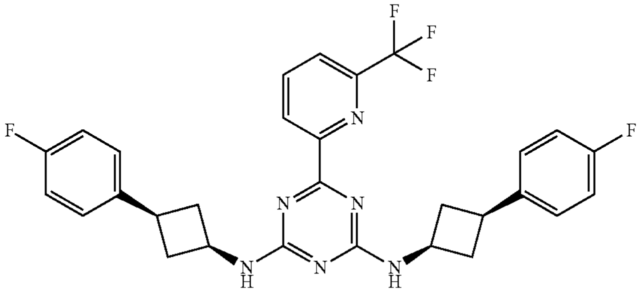 [SMILES: Fc1ccc([C@H]2C[C@@H](Nc3nc(N[C@H]4C[C@@H](c5ccc(F)cc5)C4)nc(-c4cccc(C(F)(F)F)n4)n3)C2)cc1] |
| 273 | 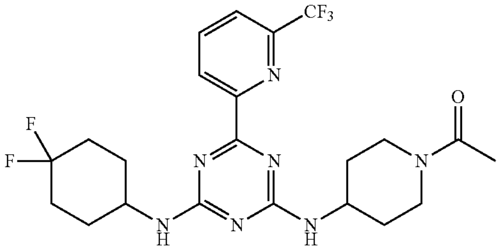 [SMILES: CC(=O)N1CCC(Nc2nc(NC3CCC(F)(F)CC3)nc(-c3cccc(C(F)(F)F)n3)n2)CC1] |
| 274 | 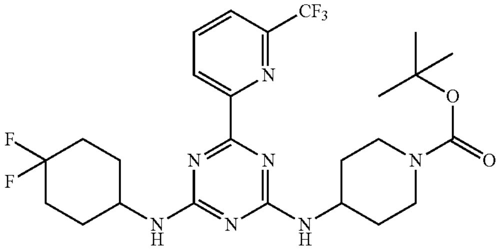 [SMILES: CC(C)(C)OC(=O)N1CCC(Nc2nc(NC3CCC(F)(F)CC3)nc(-c3cccc(C(F)(F)F)n3)n2)CC1] |

TABLE 1-continued
| Representative Compounds | |
|---|---|
| Compound Number | Structure |
| 275 | 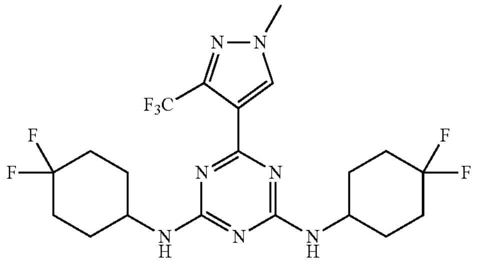 [SMILES: Cn1cc(-c2nc(NC3CCC(F)(F)CC3)nc(NC3CCC(F)(F)CC3)n2)c(C(F)(F)F)n1] |
| 276 | 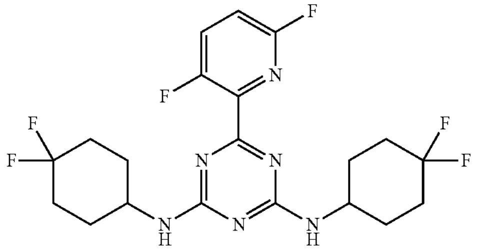 |
| 277 | 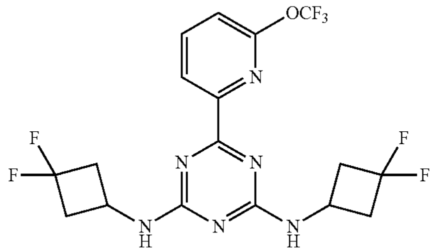 [SMILES: FC1(F)CC(Nc2nc(NC3CC(F)(F)C3)nc(-c3cccc(OC(F)(F)F)n3)n2)C1] |
| 278 | 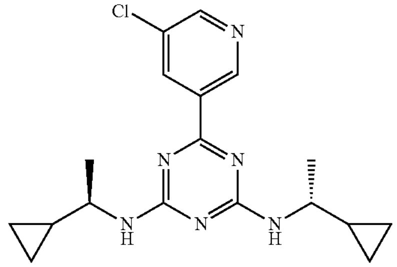 |
| 279 | 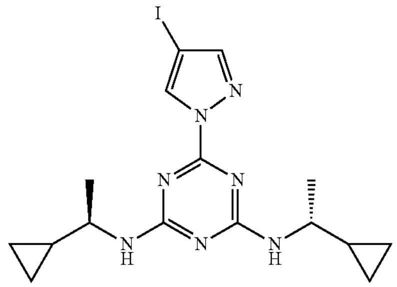 [SMILES: C[C@@H](Nc1nc(N[C@H](C)C2CC2)nc(-n2cc(I)cn2)n1)C1CC1] |

TABLE 1-continued
| Representative Compounds | |
|---|---|
| Compound Number | Structure |
| 280 | 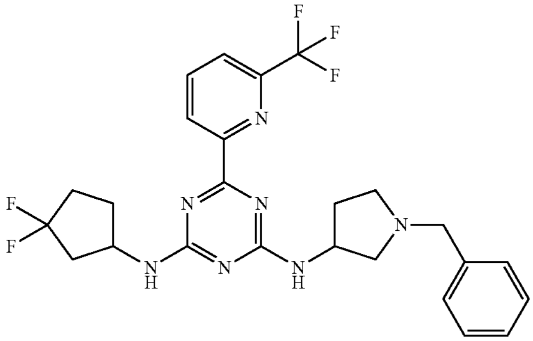 [SMILES: FC1(F)CCC(Nc2nc(NC3CCN(Cc4ccccc4)C3)nc(-c3cccc(C(F)(F)F)n3)n2)C1] |
| 281 | 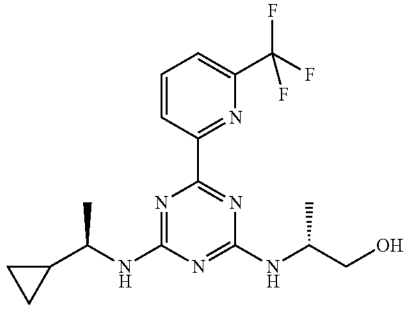 [SMILES: C[C@H](CO)Nc1nc(N[C@H](C)C2CC2)nc(-c2cccc(C(F)(F)F)n2)n1] |
| 282 | 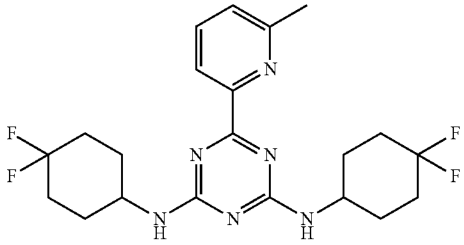 [SMILES: Cc1cccc(-c2nc(NC3CCC(F)(F)CC3)nc(NC3CCC(F)(F)CC3)n2)n1] |
| 283 | 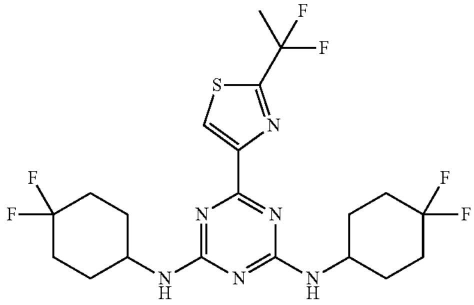 |
| 284 | 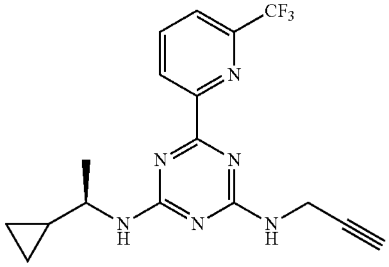 [SMILES: C#CCNc1nc(N[C@H](C)C2CC2)nc(-c2cccc(C(F)(F)F)n2)n1] |

TABLE 1-continued
| Representative Compounds | |
|---|---|
| Compound Number | Structure |
| 285 | 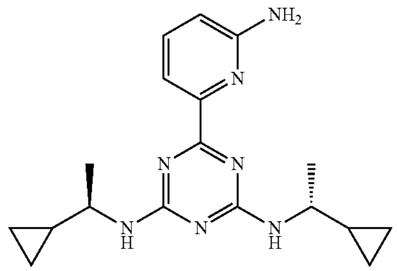 |
| 286 | 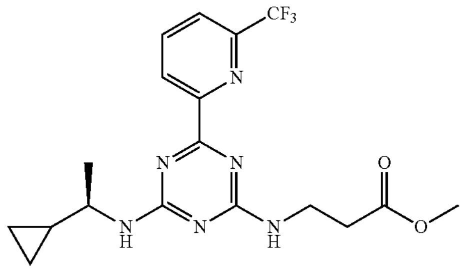 [SMILES: COC(=O)CCNc1nc(N[C@H](C)C2CC2)nc(-c2cccc(C(F)(F)F)n2)n1] |
| 287 | 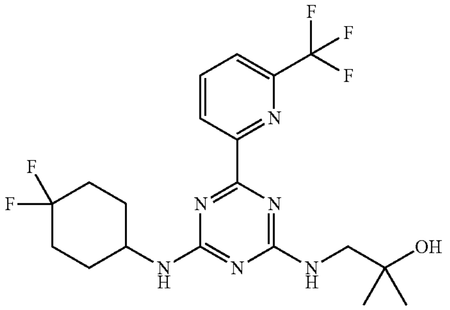 [SMILES: CC(C)(O)CNc1nc(NC2CCC(F)(F)CC2)nc(-c2cccc(C(F)(F)F)n2)n1] |
| 288 | 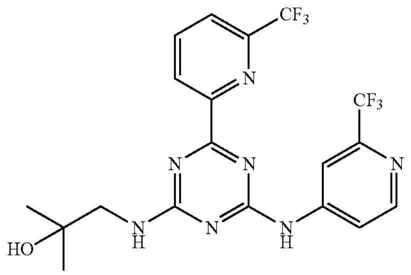 [SMILES: CC(C)(O)CNc1nc(Nc2ccnc(C(F)(F)F)c2)nc(-c2cccc(C(F)(F)F)n2)n1] |
| 289 | 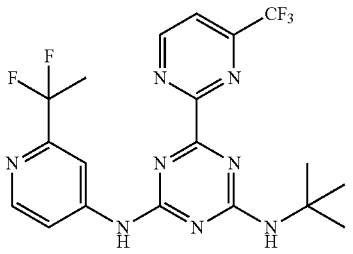 [SMILES: CC(C)(C)Nc1nc(Nc2ccnc(C(C)(F)F)c2)nc(-c2nccc(C(F)(F)F)n2)n1] |

TABLE 1-continued
| Representative Compounds | |
|---|---|
| Compound Number | Structure |
| 290 | 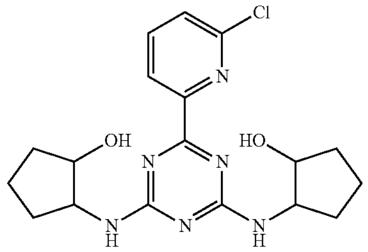 [SMILES: OC1CCCC1Nc1nc(NC2CCCC2O)nc(-c2cccc(Cl)n2)n1] |
| 291 | 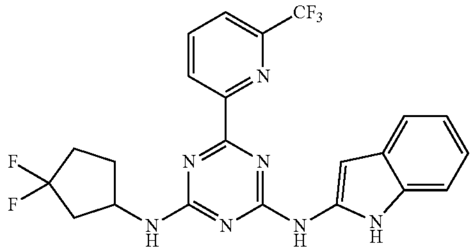 [SMILES: FC1(F)CCC(Nc2nc(Nc3cc4ccccc4[nH]3)nc(-c3cccc(C(F)(F)F)n3)n2)C1] |
| 292 | 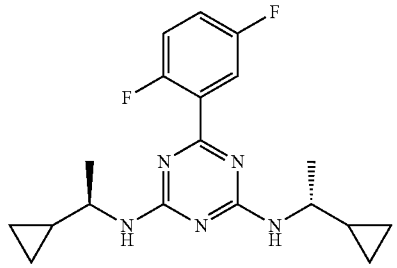 [SMILES: C[C@@H](Nc1nc(N[C@H](C)C2CC2)nc(-c2cc(F)ccc2F)n1)C1CC1] |
| 293 | 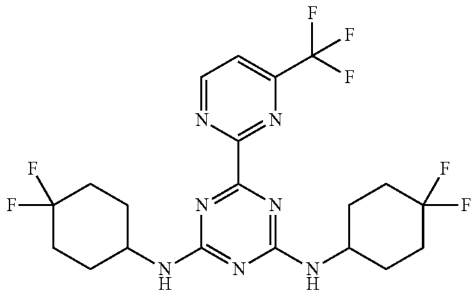 |
| 294 | 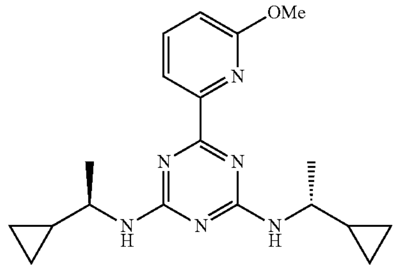 |

TABLE 1-continued
| Representative Compounds | |
|---|---|
| Compound Number | Structure |
| 295 | 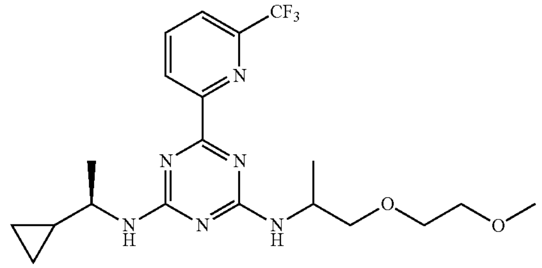 [SMILES: COCCOCC(C)Nc1nc(N[C@H](C)C2CC2)nc(-c2cccc(C(F)(F)F)n2)n1] |
| 296 | 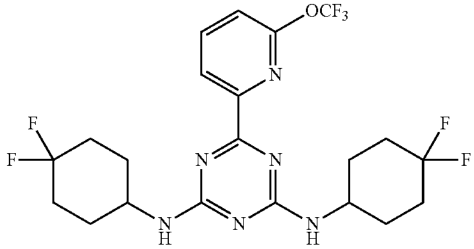 |
| 297 | 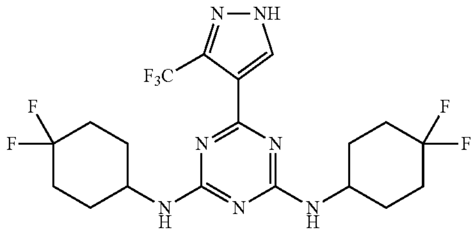 [SMILES: FC1(F)CCC(Nc2nc(NC3CCC(F)(F)CC3)nc(-c3c[nH]nc3C(F)(F)F)n2)CC1] |
| 298 | 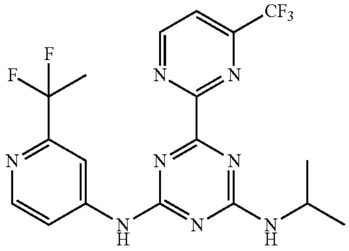 [SMILES: CC(C)Nc1nc(Nc2ccnc(C(C)(F)F)c2)nc(-c2nccc(C(F)(F)F)n2)n1] |
| 299 | 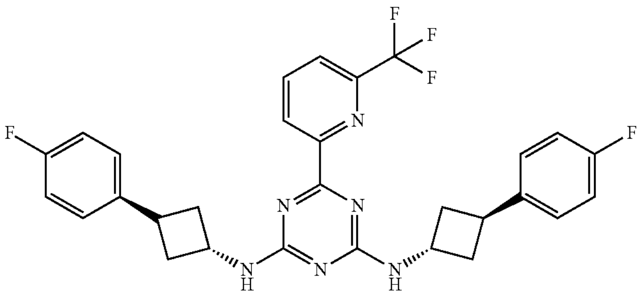 |

TABLE 1-continued
| Representative Compounds | |
|---|---|
| Compound Number | Structure |
| 300 | 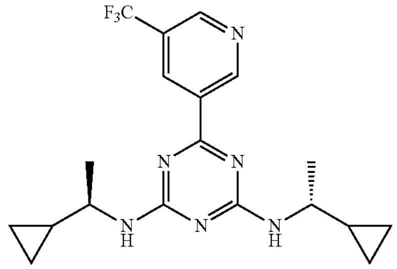 [SMILES: C[C@@H](Nc1nc(N[C@H](C)C2CC2)nc(-c2cncc(C(F)(F)F)c2)n1)C1CC1] |
| 301 | 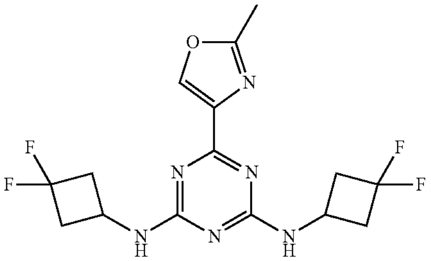 [SMILES: Cc1nc(-c2nc(NC3CC(F)(F)C3)nc(NC3CC(F)(F)C3)n2)co1] |
| 302 | 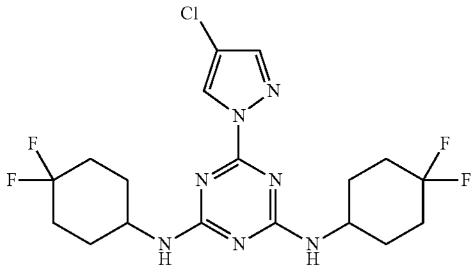 [SMILES: FC1(F)CCC(Nc2nc(NC3CCC(F)(F)CC3)nc(-n3cc(Cl)cn3)n2)CC1] |
| 303 | 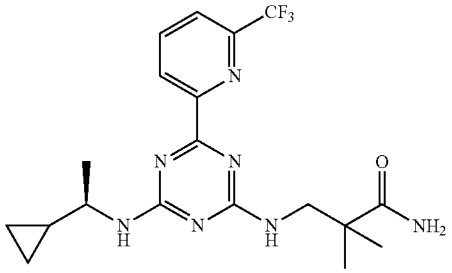 [SMILES: C[C@@H](Nc1nc(NCC(C)(C)C(N)=O)nc(-c2cccc(C(F)(F)F)n2)n1)C1CC1] |
| 304 | 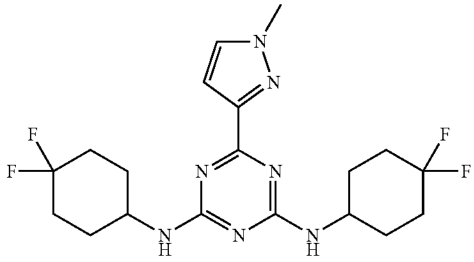 [SMILES: Cn1ccc(-c2nc(NC3CCC(F)(F)CC3)nc(NC3CCC(F)(F)CC3)n2)n1] |

TABLE 1-continued
| Representative Compounds | |
|---|---|
| Compound Number | Structure |
| 305 | 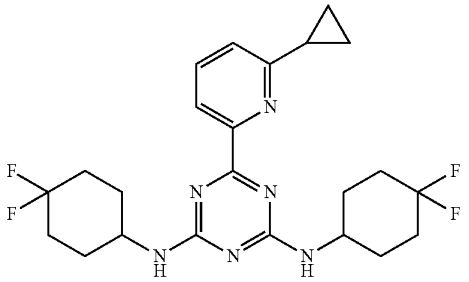 [SMILES: FC1(F)CCC(Nc2nc(NC3CCC(F)(F)CC3)nc(-c3cccc(C4CC4)n3)n2)CC1] |
| 306 | 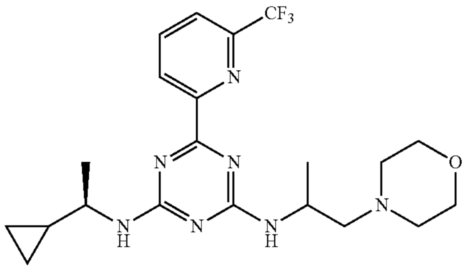 [SMILES: CC(CN1CCOCC1)Nc1nc(N[C@H](C)C2CC2)nc(-c2cccc(C(F)(F)F)n2)n1] |
| 307 | 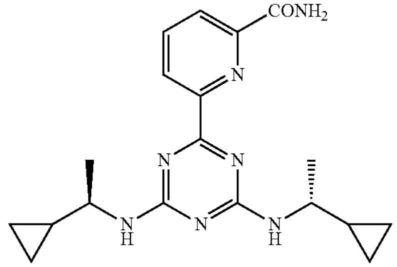 [SMILES: C[C@@H](Nc1nc(N[C@H](C)C2CC2)nc(-c2cccc(C(N)=O)n2)n1)C1CC1] |
| 308 | 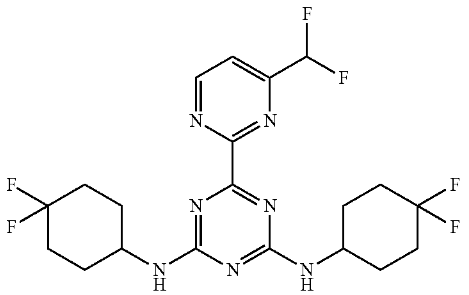 [SMILES: FC(F)c1ccnc(-c2nc(NC3CCC(F)(F)CC3)nc(NC3CCC(F)(F)CC3)n2)n1] |
| 309 | 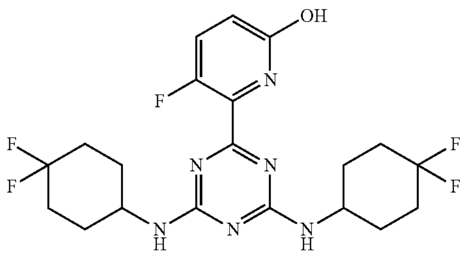 [SMILES: Oc1ccc(F)c(-c2nc(NC3CCC(F)(F)CC3)nc(NC3CCC(F)(F)CC3)n2)n1] |

TABLE 1-continued
| Compound Number | Structure |
| --- | --- |
| | Representative Compounds |
| 310 | 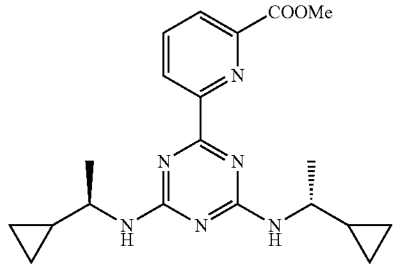 [SMILES: COC(=O)c1cccc(-c2nc(N[C@H](C)C3CC3)nc(N[C@H](C)C3CC3)n2)n1] |
| 311 | 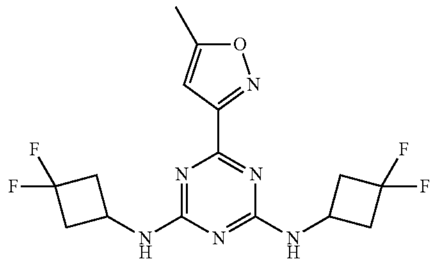 [SMILES: Cc1cc(-c2nc(NC3CC(F)(F)C3)nc(NC3CC(F)(F)C3)n2)no1] |
| 312 | 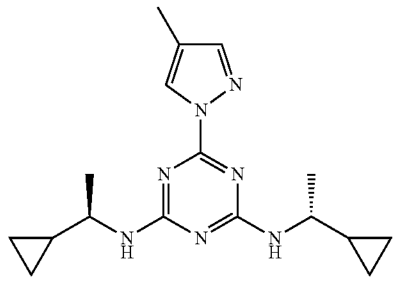 [SMILES: Cc1cnn(-c2nc(N[C@H](C)C3CC3)nc(N[C@H](C)C3CC3)n2)c1] |
| 313 | 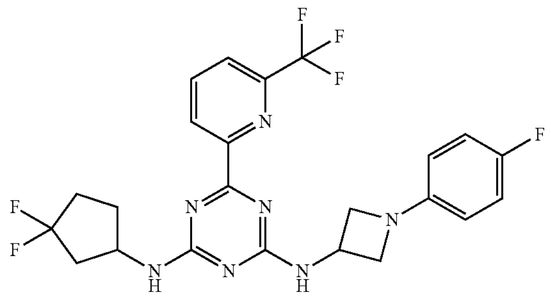 [SMILES: Fc1ccc(N2CC(Nc3nc(NC4CCC(F)(F)C4)nc(-c4cccc(C(F)(F)F)n4)n3)C2)cc1] |
| 314 | 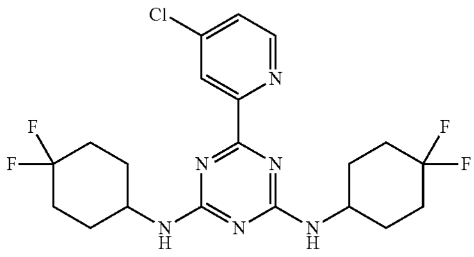 [SMILES: FC1(F)CCC(Nc2nc(NC3CCC(F)(F)CC3)nc(-c3cc(Cl)ccn3)n2)CC1] |

TABLE 1-continued
| Representative Compounds | |
|---|---|
| Compound Number | Structure |
| 315 | 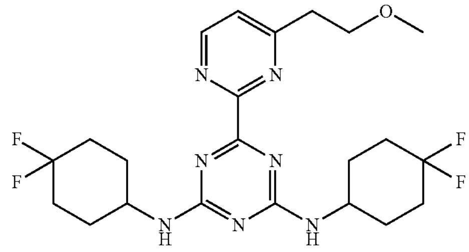 [SMILES: COCCc1ccnc(-c2nc(NC3CCC(F)(F)CC3)nc(NC3CCC(F)(F)CC3)n2)n1] |
| 316 | 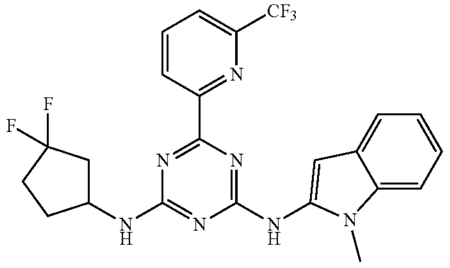 [SMILES: Cn1c(Nc2nc(NC3CCC(F)(F)C3)nc(-c3cccc(C(F)(F)F)n3)n2)cc2ccccc21] |
| 317 | 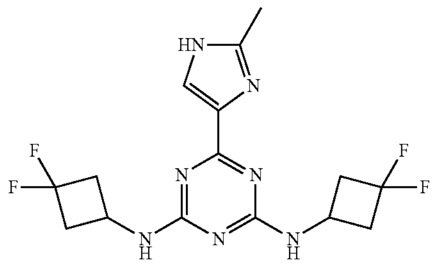 [SMILES: Cc1nc(-c2nc(NC3CC(F)(F)C3)nc(NC3CC(F)(F)C3)n2)c[nH]1] |
| 318 | 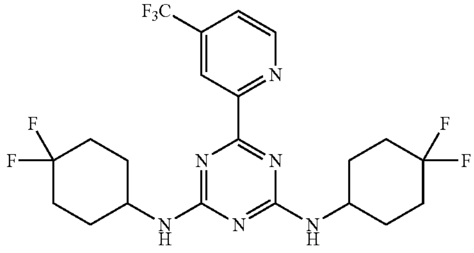 [SMILES: FC1(F)CCC(Nc2nc(NC3CCC(F)(F)CC3)nc(-c3cc(C(F)(F)F)ccn3)n2)CC1] |
| 319 | 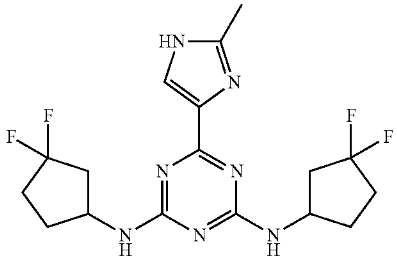 [SMILES: Cc1nc(-c2nc(NC3CCC(F)(F)C3)nc(NC3CCC(F)(F)C3)n2)c[nH]1] |

TABLE 1-continued
| Representative Compounds | |
|---|---|
| Compound Number | Structure |
| 320 | 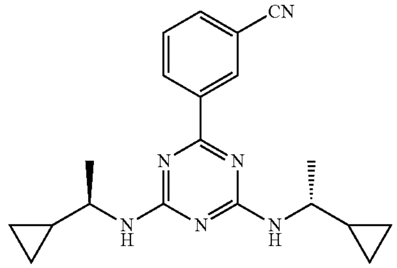 [SMILES: C[C@@H](Nc1nc(N[C@H](C)C2CC2)nc(-c2cccc(C#N)c2)n1)C1CC1] |
| 321 | 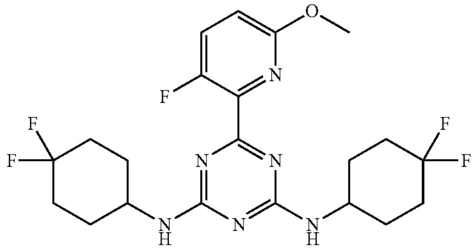 [SMILES: COc1ccc(F)c(-c2nc(NC3CCC(F)(F)CC3)nc(NC3CCC(F)(F)CC3)n2)n1] |
| 322 | 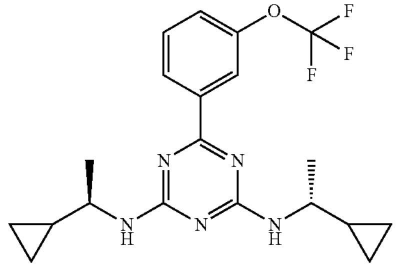 [SMILES: C[C@@H](Nc1nc(N[C@H](C)C2CC2)nc(-c2cccc(OC(F)(F)F)c2)n1)C1CC1] |
| 323 | 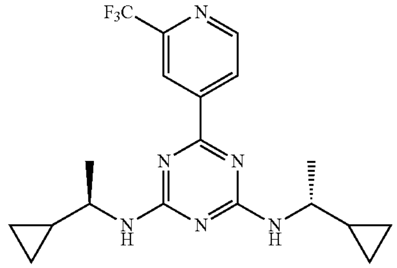 [SMILES: C[C@@H](Nc1nc(N[C@H](C)C2CC2)nc(-c2ccnc(C(F)(F)F)c2)n1)C1CC1] |
| 324 | 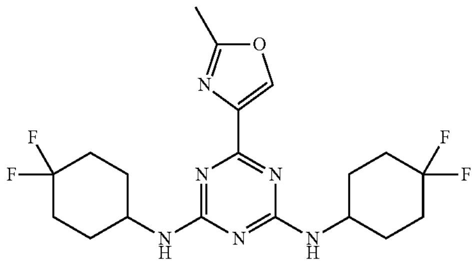 [SMILES: Cc1nc(-c2nc(NC3CCC(F)(F)CC3)nc(NC3CCC(F)(F)CC3)n2)co1] |

TABLE 1-continued
| Representative Compounds | |
| --- | --- |
| Compound Number | Structure |
| 325 | 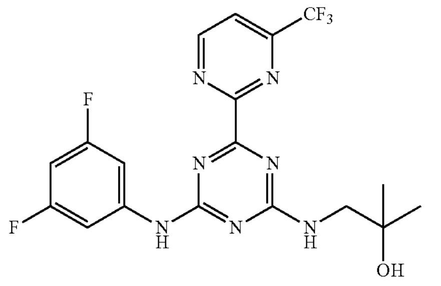 [SMILES: CC(C)(O)CNc1nc(Nc2cc(F)cc(F)c2)nc(-c2nccc(C(F)(F)F)n2)n1] |
| 326 | 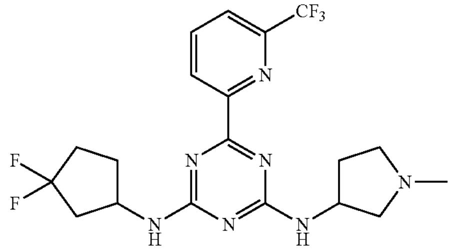 [SMILES: CN1CCC(Nc2nc(NC3CCC(F)(F)C3)nc(-c3cccc(C(F)(F)F)n3)n2)C1] |
| 327 | 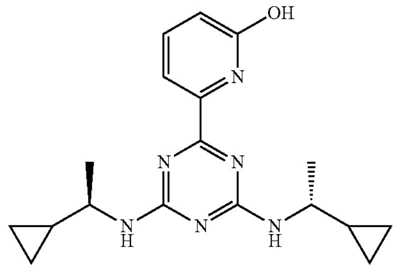 [SMILES: C[C@@H](Nc1nc(N[C@H](C)C2CC2)nc(-c2cccc(O)n2)n1)C1CC1] |
| 328 | 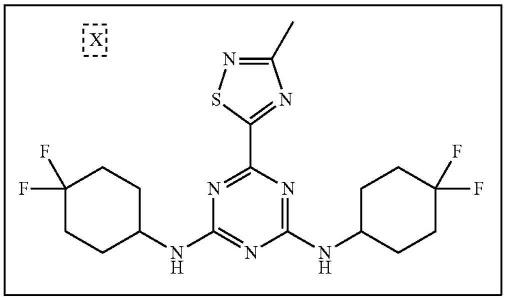 |
| 329 | 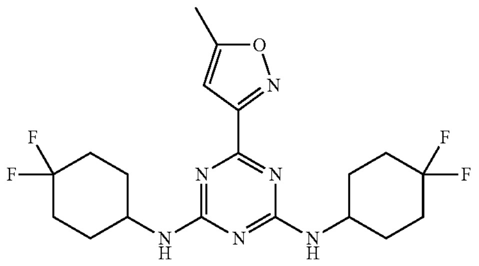 [SMILES: Cc1cc(-c2nc(NC3CCC(F)(F)CC3)nc(NC3CCC(F)(F)CC3)n2)no1] |

TABLE 1-continued
| Compound Number | Structure |
|---|---|
| Representative Compounds | |
| 330 | 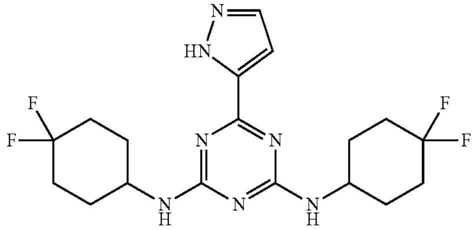 [SMILES: FC1(F)CCC(Nc2nc(NC3CCC(F)(F)CC3)nc(-c3ccn[nH]3)n2)CC1] |
| 331 | 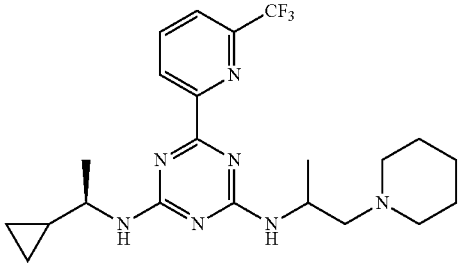 [SMILES: CC(CN1CCCCC1)Nc1nc(N[C@H](C)C2CC2)nc(-c2cccc(C(F)(F)F)n2)n1] |
| 332 | 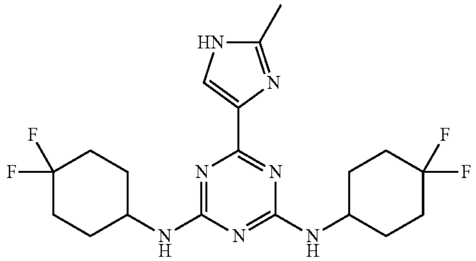 [SMILES: Cc1nc(-c2nc(NC3CCC(F)(F)CC3)nc(NC3CCC(F)(F)CC3)n2)c[nH]1] |
| 333 | 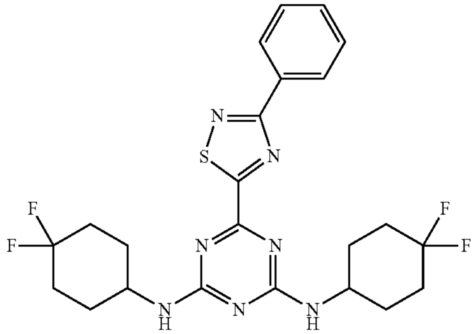 [SMILES: FC1(F)CCC(Nc2nc(NC3CCC(F)(F)CC3)nc(-c3nc(-c4ccccc4)ns3)n2)CC1] |
| 334 | 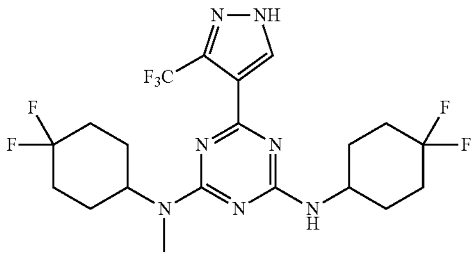 [SMILES: CN(c1nc(NC2CCC(F)(F)CC2)nc(-c2c[nH]nc2C(F)(F)F)n1)C1CCC(F)(F)CC1] |

TABLE 1-continued
| Representative Compounds | |
|---|---|
| Compound Number | Structure |
| 335 | 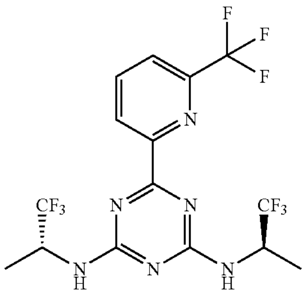 [SMILES: C[C@@H](Nc1nc(N[C@H](C)C(F)(F)F)nc(-c2cccc(C(F)(F)F)n2)n1)C(F)(F)F] |
| 336 | 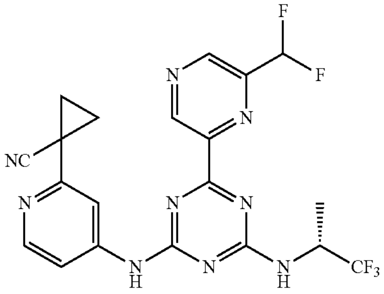 [SMILES: C[C@@H](Nc1nc(Nc2ccnc(C3(C#N)CC3)c2)nc(-c2cncc(C(F)F)n2)n1)C(F)(F)F] |
| 337 | 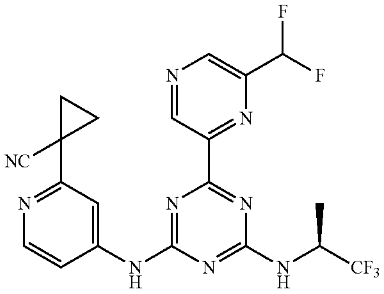 [SMILES: C[C@H](Nc1nc(Nc2ccnc(C3(C#N)CC3)c2)nc(-c2cncc(C(F)F)n2)n1)C(F)(F)F] |
| 338 | 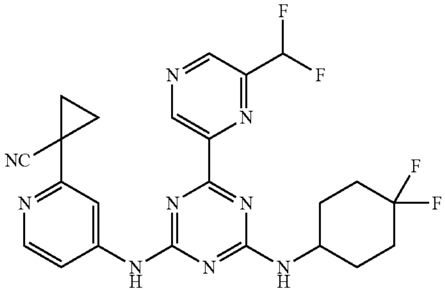 [SMILES: N#CC1(c2cc(Nc3nc(NC4CCC(F)(F)CC4)nc(-c4cncc(C(F)F)n4)n3)ccn2)CC1] |
| 339 | 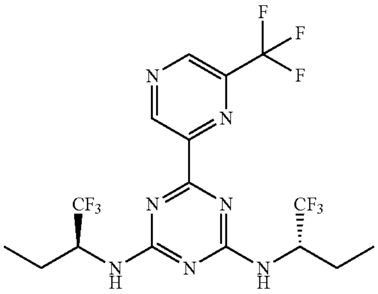 [SMILES: CC[C@H](Nc1nc(N[C@@H](CC)C(F)(F)F)nc(-c2cncc(C(F)(F)F)n2)n1)C(F)(F)F] |

TABLE 1-continued
| Representative Compounds | |
|---|---|
| Compound Number | Structure |
| 340 | 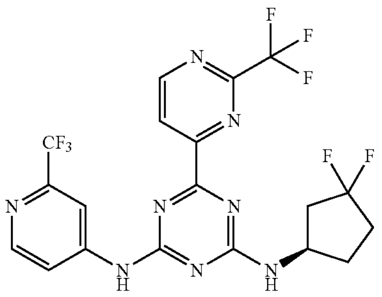 [SMILES: FC1(F)CC[C@@H](Nc2nc(Nc3ccnc(C(F)(F)F)c3)nc(-c3ccnc(C(F)(F)F)n3)n2)C1] |
| 341 | 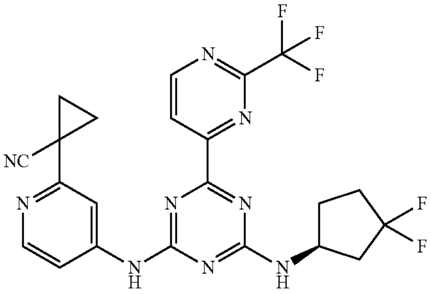 [SMILES: N#CC1(c2cc(Nc3nc(N[C@H]4CCC(F)(F)C4)nc(-c4ccnc(C(F)(F)F)n4)n3)ccn2)CC1] |
| 342 | 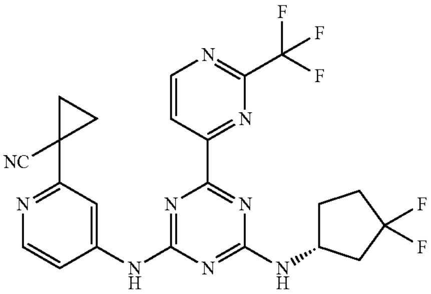 [SMILES: N#CC1(c2cc(Nc3nc(N[C@@H]4CCC(F)(F)C4)nc(-c4ccnc(C(F)(F)F)n4)n3)ccn2)CC1] |
| 343 | 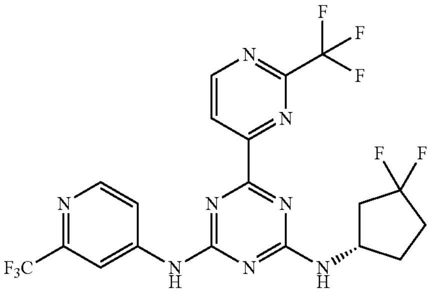 [SMILES: FC1(F)CC[C@H](Nc2nc(Nc3ccnc(C(F)(F)F)c3)nc(-c3ccnc(C(F)(F)F)n3)n2)C1] |
| 344 | 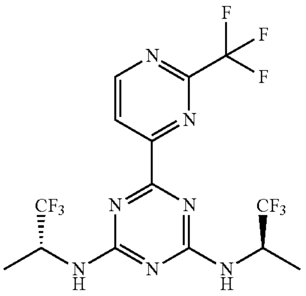 [SMILES: C[C@@H](Nc1nc(N[C@H](C)C(F)(F)F)nc(-c2ccnc(C(F)(F)F)n2)n1)C(F)(F)F] |

TABLE 1-continued
| Representative Compounds | |
|---|---|
| Compound Number | Structure |
| 345 | 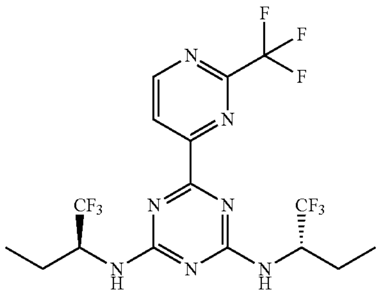 [SMILES: CC[C@H](Nc1nc(N[C@@H](CC)C(F)(F)F)nc(-c2ccnc(C(F)(F)F)n2)n1)C(F)(F)F] |
| 346 | 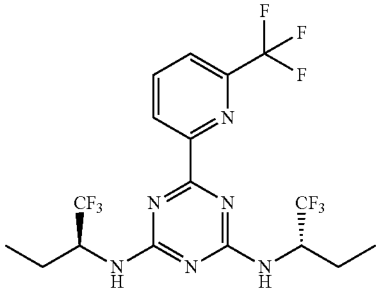 [SMILES: CC[C@H](Nc1nc(N[C@@H](CC)C(F)(F)F)nc(-c2cccc(C(F)(F)F)n2)n1)C(F)(F)F] |
| 347 | 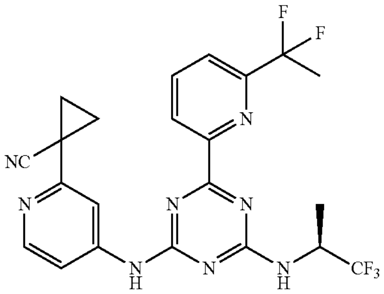 [SMILES: C[C@H](Nc1nc(Nc2ccnc(C3(C#N)CC3)c2)nc(-c2cccc(C(C)(F)F)n2)n1)C(F)(F)F] |
| 348 | 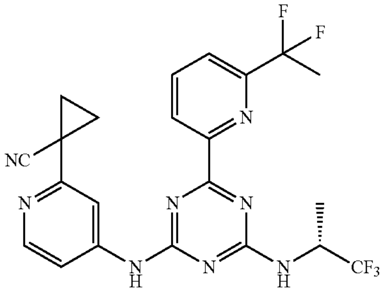 [SMILES: C[C@@H](Nc1nc(Nc2ccnc(C3(C#N)CC3)c2)nc(-c2cccc(C(C)(F)F)n2)n1)C(F)(F)F] |
| 349 | 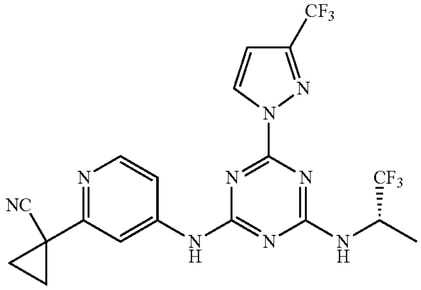 [SMILES: C[C@H](Nc1nc(Nc2ccnc(C3(C#N)CC3)c2)nc(-n2ccc(C(F)(F)F)n2)n1)C(F)(F)F] |

TABLE 1-continued
| Representative Compounds | |
|---|---|
| Compound Number | Structure |
| 350 | 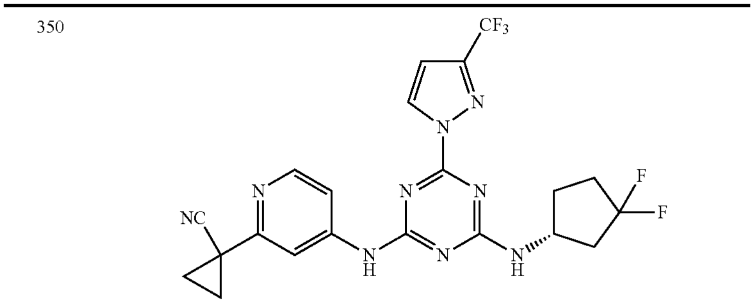 |
| 351 | 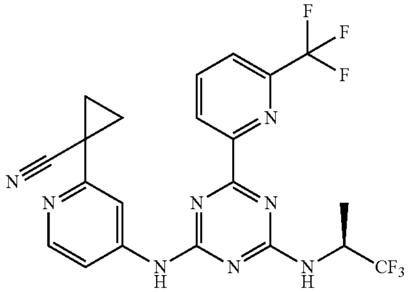 [SMILES: C[C@H](Nc1nc(Nc2ccnc(C3(C#N)CC3)c2)nc(-c2cccc(C(F)(F)F)n2)n1)C(F)(F)F] |
| 352 | 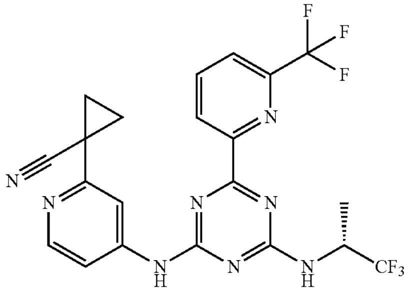 [SMILES: C[C@@H](Nc1nc(Nc2ccnc(C3(C#N)CC3)c2)nc(-c2cccc(C(F)(F)F)n2)n1)C(F)(F)F] |
| 353 | 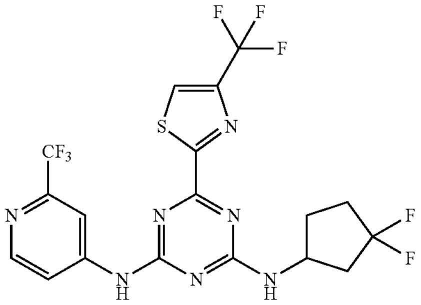 [SMILES: FC1(F)CCC(Nc2nc(Nc3ccnc(C(F)(F)F)c3)nc(-c3nc(C(F)(F)F)cs3)n2)C1] |
| 354 | 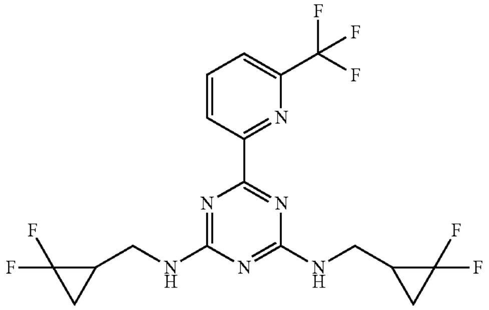 [SMILES: FC(F)(F)c1cccc(-c2nc(NCC3CC3(F)F)nc(NCC3CC3(F)F)n2)n1] |

TABLE 1-continued
| Representative Compounds | |
|---|---|
| Compound Number | Structure |
| 355 | 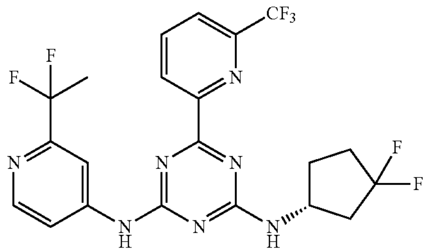 [SMILES: CC(F)(F)c1cc(Nc2nc(N[C@@H]3CCC(F)(F)C3)nc(-c3cccc(C(F)(F)F)n3)n2)ccn1] |
| 356 | 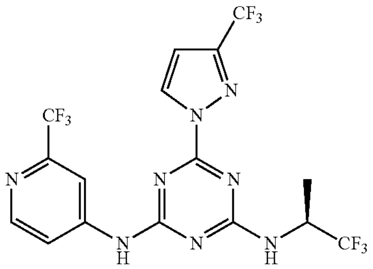 [SMILES: C[C@H](Nc1nc(Nc2ccnc(C(F)(F)F)c2)nc(-n2ccc(C(F)(F)F)n2)n1)C(F)(F)F] |
| 357 | 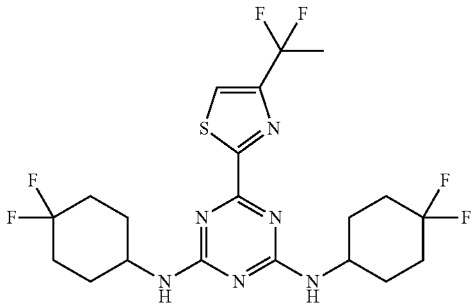 |
| 358 | 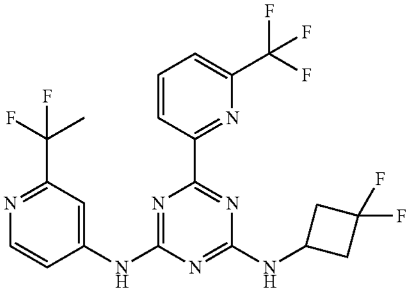 [SMILES: CC(F)(F)c1cc(Nc2nc(NC3CC(F)(F)C3)nc(-c3cccc(C(F)(F)F)n3)n2)ccn1] |
| 359 | 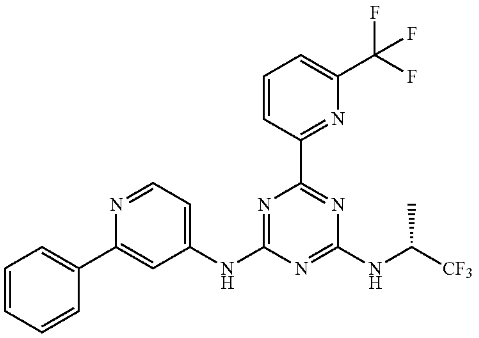 [SMILES: C[C@@H](Nc1nc(Nc2ccnc(-c3ccccc3)c2)nc(-c2cccc(C(F)(F)F)n2)n1)C(F)(F)F] |

TABLE 1-continued
| Representative Compounds | |
|---|---|
| Compound Number | Structure |
| 360 | 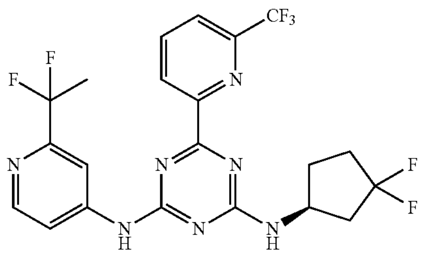 [SMILES: CC(F)(F)c1cc(Nc2nc(N[C@H]3CCC(F)(F)C3)nc(-c3cccc(C(F)(F)F)n3)n2)ccn1] |
| 361 | 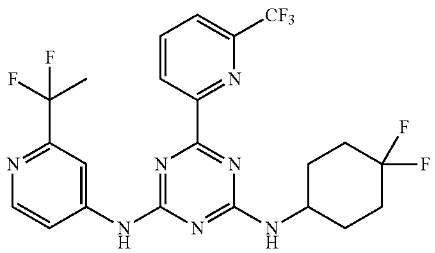 [SMILES: CC(F)(F)c1cc(Nc2nc(NC3CCC(F)(F)CC3)nc(-c3cccc(C(F)(F)F)n3)n2)ccn1] |
| 362 | 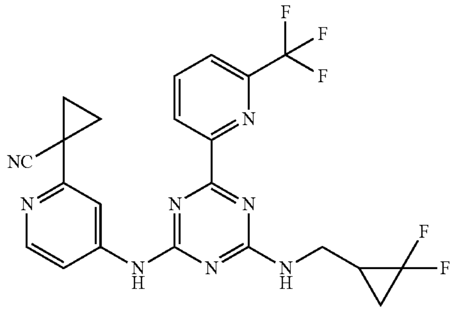 [SMILES: N#CC1(c2cc(Nc3nc(NCC4CC4(F)F)nc(-c4cccc(C(F)(F)F)n4)n3)ccn2)CC1] |
| 363 | 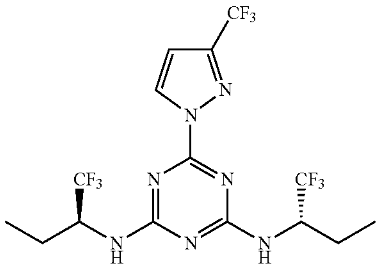 [SMILES: CC[C@H](Nc1nc(N[C@@H](CC)C(F)(F)F)nc(-n2ccc(C(F)(F)F)n2)n1)C(F)(F)F] |
| 364 | 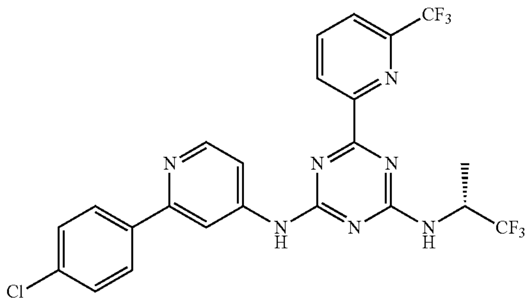 [SMILES: C[C@@H](Nc1nc(Nc2ccnc(-c3ccc(Cl)cc3)c2)nc(-c2cccc(C(F)(F)F)n2)n1)C(F)(F)F] |

TABLE 1-continued
| Representative Compounds | |
|---|---|
| Compound Number | Structure |
| 365 | 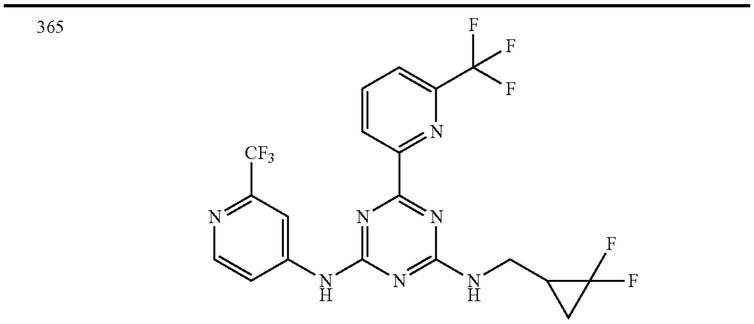 |
| 366 | 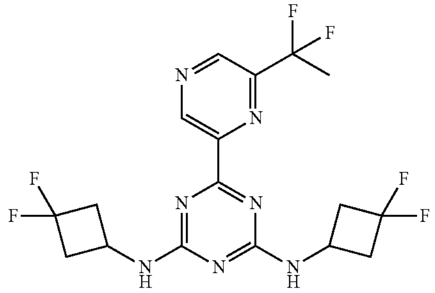 [SMILES: CC(F)(F)c1cncc(-c2nc(NC3CC(F)(F)C3)nc(NC3CC(F)(F)C3)n2)n1] |
| 367 | 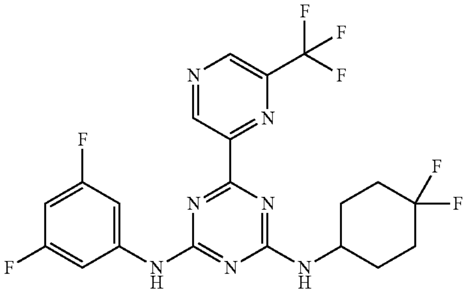 [SMILES: Fc1cc(F)cc(Nc2nc(NC3CCC(F)(F)CC3)nc(-c3cncc(C(F)(F)F)n3)n2)c1] |
| 368 | 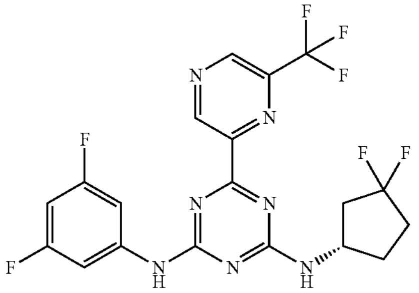 [SMILES: Fc1cc(F)cc(Nc2nc(N[C@H]3CCC(F)(F)C3)nc(-c3cncc(C(F)(F)F)n3)n2)c1] |
| 369 | 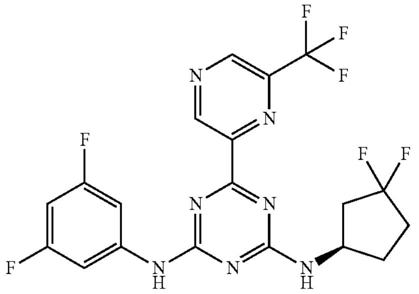 [SMILES: Fc1cc(F)cc(Nc2nc(N[C@@H]3CCC(F)(F)C3)nc(-c3cncc(C(F)(F)F)n3)n2)c1] |

TABLE 1-continued
| Representative Compounds | |
|---|---|
| Compound Number | Structure |
| 370 | 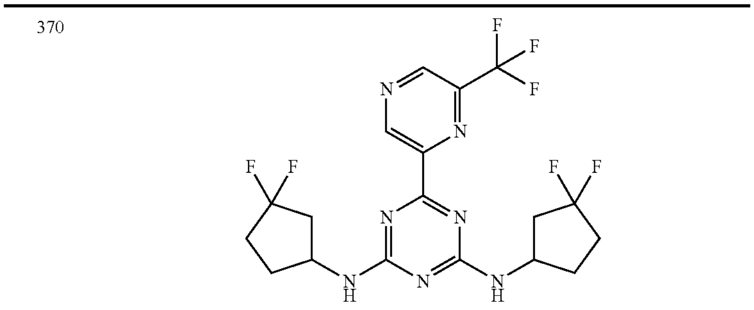 |
| 371 | 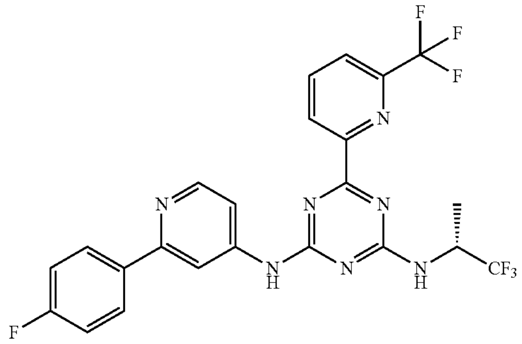 [SMILES: C[C@@H](Nc1nc(Nc2ccnc(-c3ccc(F)cc3)c2)nc(-c2cccc(C(F)(F)F)n2)n1)C(F)(F)F] |
| 372 | 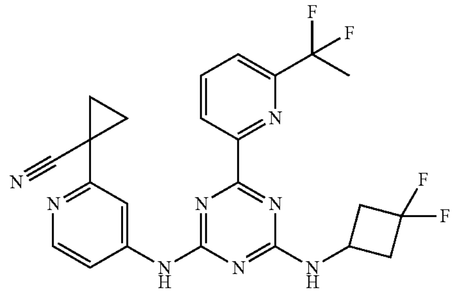 [SMILES: CC(F)(F)c1cccc(-c2nc(Nc3ccnc(C4(C#N)CC4)c3)nc(NC3CC(F)(F)C3)n2)n1] |
| 373 | 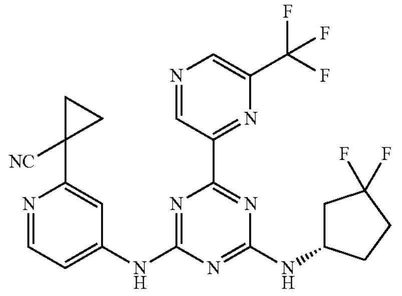 [SMILES: N#CC1(c2cc(Nc3nc(N[C@H]4CCC(F)(F)C4)nc(-c4cncc(C(F)(F)F)n4)n3)ccn2)CC1] |
| 374 | 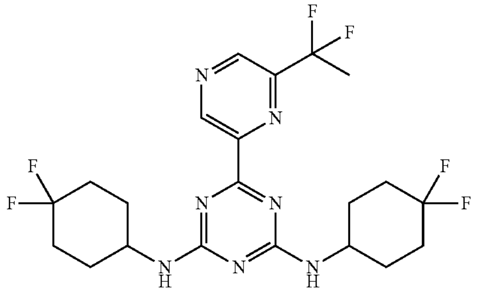 [SMILES: CC(F)(F)c1cncc(-c2nc(NC3CCC(F)(F)CC3)nc(NC3CCC(F)(F)CC3)n2)n1] |

TABLE 1-continued
| Representative Compounds | |
| --- | --- |
| Compound Number | Structure |
| 375 | 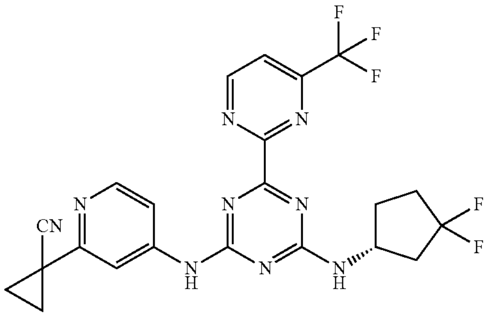 [SMILES: N#CC1(c2cc(Nc3nc(N[C@@H]4CCC(F)(F)C4)nc(-c4nccc(C(F)(F)F)n4)n3)ccn2)CC1] |
| 376 | 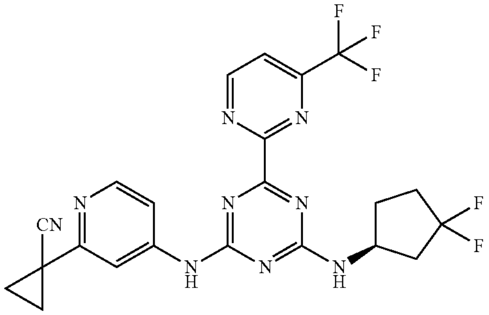 [SMILES: N#CC1(c2cc(Nc3nc(N[C@H]4CCC(F)(F)C4)nc(-c4nccc(C(F)(F)F)n4)n3)ccn2)CC1] |
| 377 | 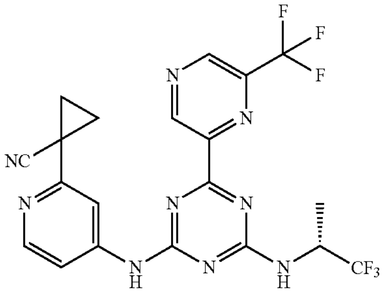 [SMILES: C[C@@H](Nc1nc(Nc2ccnc(C3(C#N)CC3)c2)nc(-c2cncc(C(F)(F)F)n2)n1)C(F)(F)F] |
| 378 | 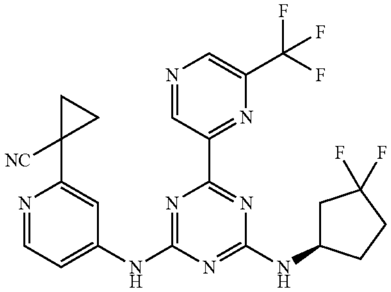 [SMILES: N#CC1(c2cc(Nc3nc(N[C@@H]4CCC(F)(F)C4)nc(-c4cncc(C(F)(F)F)n4)n3)ccn2)CC1] |
| 379 | 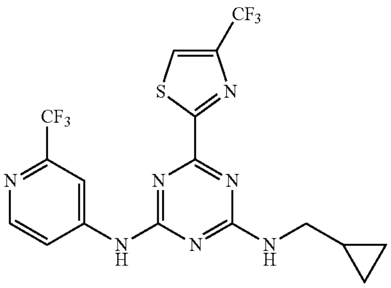 [SMILES: FC(F)(F)c1cc(Nc2nc(NCC3CC3)nc(-c3nc(C(F)(F)F)cs3)n2)ccn1] |

TABLE 1-continued
| Representative Compounds | |
|---|---|
| Compound Number | Structure |
| 380 | 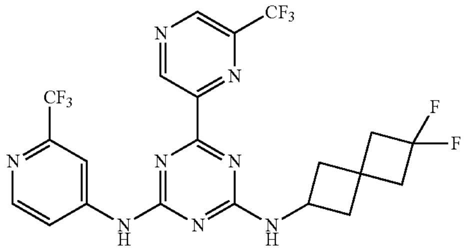 [SMILES: FC1(F)CC2(CC(Nc3nc(Nc4ccnc(C(F)(F)F)c4)nc(-c4cncc(C(F)(F)F)n4)n3)C2)C1] |
| 381 | 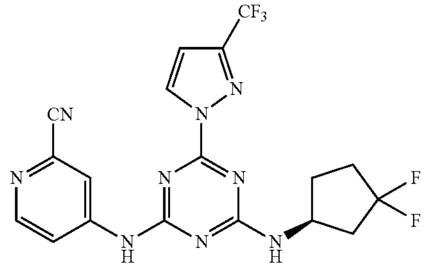 [SMILES: N#Cc1cc(Nc2nc(N[C@H]3CCC(F)(F)C3)nc(-n3ccc(C(F)(F)F)n3)n2)ccn1] |
| 382 | 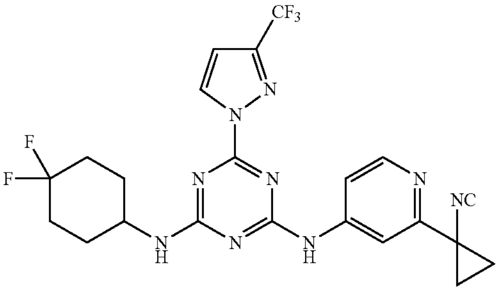 |
| 383 | 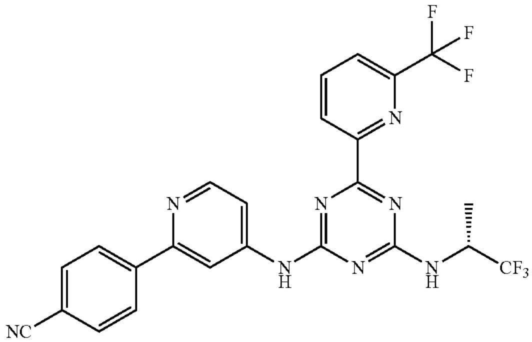 [SMILES: C[C@@H](Nc1nc(Nc2ccnc(-c3ccc(C#N)cc3)c2)nc(-c2cccc(C(F)(F)F)n2)n1)C(F)(F)F] |
| 384 | 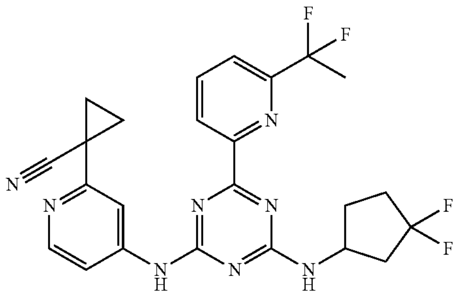 [SMILES: CC(F)(F)c1cccc(-c2nc(Nc3ccnc(C4(C#N)CC4)c3)nc(NC3CCC(F)(F)C3)n2)n1] |

TABLE 1-continued
| Representative Compounds | |
| --- | --- |
| Compound Number | Structure |
| 385 | 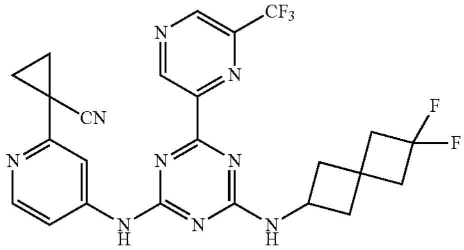 [SMILES: N#CC1(c2cc(Nc3nc(NC4CC5(C4)CC(F)(F)C5)nc(-c4cncc(C(F)(F)F)n4)n3)ccn2)CC1] |
| 386 | 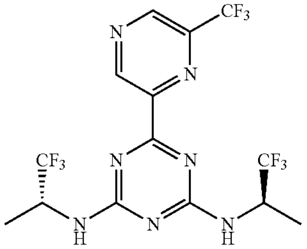 [SMILES: C[C@@H](Nc1nc(N[C@H](C)C(F)(F)F)nc(-c2cncc(C(F)(F)F)n2)n1)C(F)(F)F] |
| 387 | 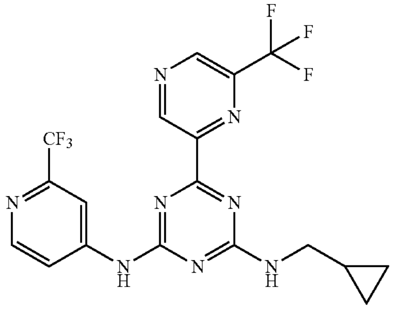 [SMILES: FC(F)(F)c1cc(Nc2nc(NCC3CC3)nc(-c3cncc(C(F)(F)F)n3)n2)ccn1] |
| 388 | 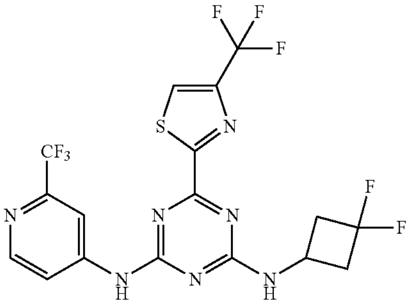 [SMILES: FC1(F)CC(Nc2nc(Nc3ccnc(C(F)(F)F)c3)nc(-c3nc(C(F)(F)F)cs3)n2)C1] |
| 389 | 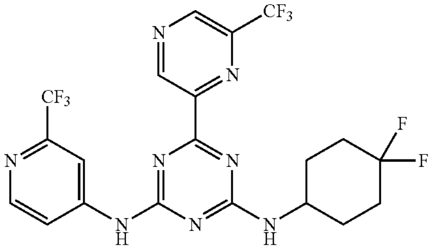 [SMILES: FC1(F)CCC(Nc2nc(Nc3ccnc(C(F)(F)F)c3)nc(-c3cncc(C(F)(F)F)n3)n2)CC1] |

TABLE 1-continued
| Representative Compounds | |
|---|---|
| Compound Number | Structure |
| 390 | 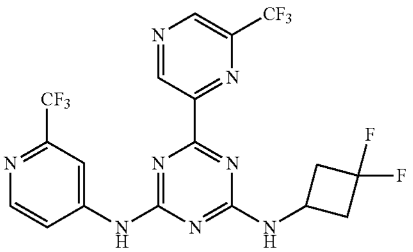 [SMILES: FC1(F)CC(Nc2nc(Nc3ccnc(C(F)(F)F)c3)nc(-c3cncc(C(F)(F)F)n3)n2)C1] |
| 391 | 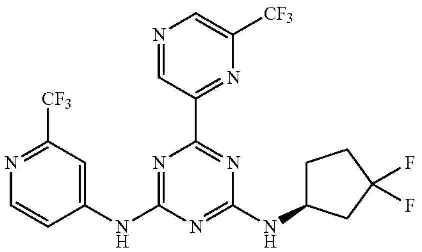 [SMILES: FC1(F)CC[C@H](Nc2nc(Nc3ccnc(C(F)(F)F)c3)nc(-c3cncc(C(F)(F)F)n3)n2)C1] |
| 392 | 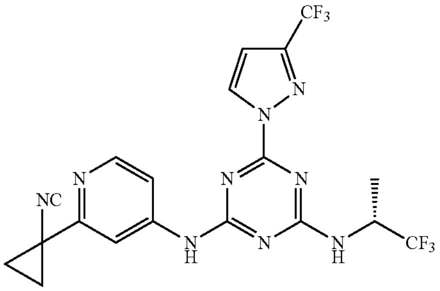 |
| 393 | 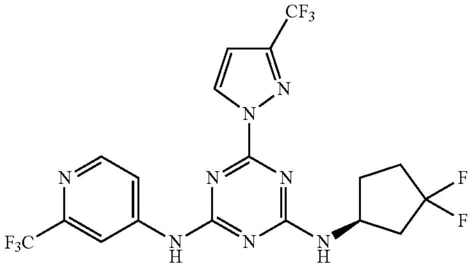 [SMILES: FC1(F)CC[C@H](Nc2nc(Nc3ccnc(C(F)(F)F)c3)nc(-n3ccc(C(F)(F)F)n3)n2)C1] |
| 394 | 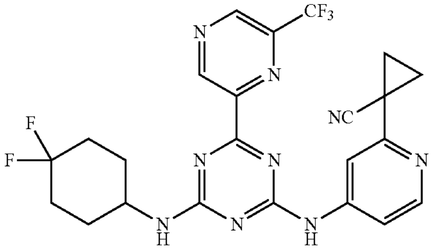 [SMILES: N#CC1(c2cc(Nc3nc(NC4CCC(F)(F)CC4)nc(-c4cncc(C(F)(F)F)n4)n3)ccn2)CC1] |

TABLE 1-continued
| Representative Compounds | |
|---|---|
| Compound Number | Structure |
| 395 | 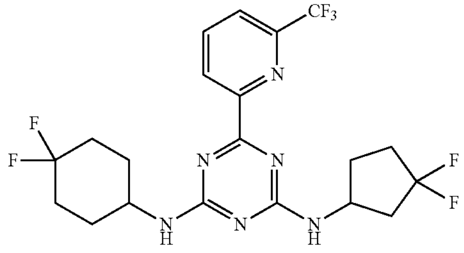 [SMILES: FC1(F)CCC(Nc2nc(NC3CCC(F)(F)C3)nc(-c3cccc(C(F)(F)F)n3)n2)CC1] |
| 397 | 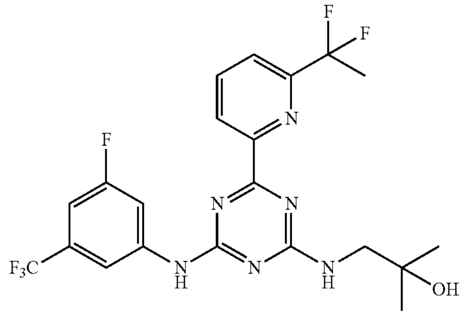 |
| 398 | 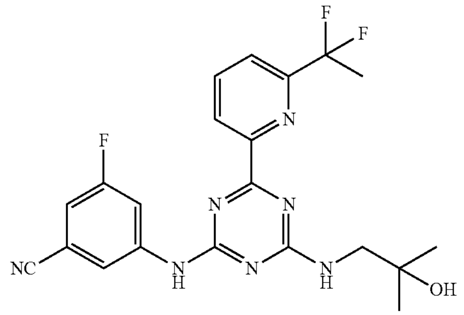 [SMILES: CC(C)(O)CNc1nc(Nc2cc(F)cc(C#N)c2)nc(-c2cccc(C(C)(F)F)n2)n1] |
| 399 | 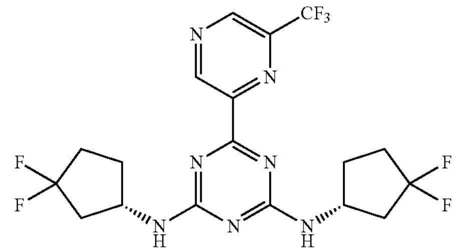 [SMILES: FC1(F)CC[C@@H](Nc2nc(N[C@H]3CCC(F)(F)C3)nc(-c3cncc(C(F)(F)F)n3)n2)C1] |
| 400 | 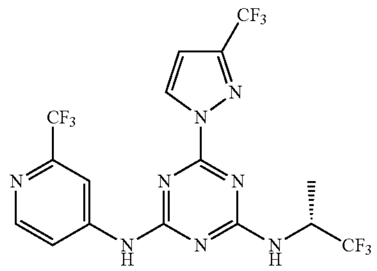 [SMILES: C[C@@H](Nc1nc(Nc2ccnc(C(F)(F)F)c2)nc(-n2ccc(C(F)(F)F)n2)n1)C(F)(F)F] |

TABLE 1-continued
| Representative Compounds | |
|---|---|
| Compound Number | Structure |
| 401 | 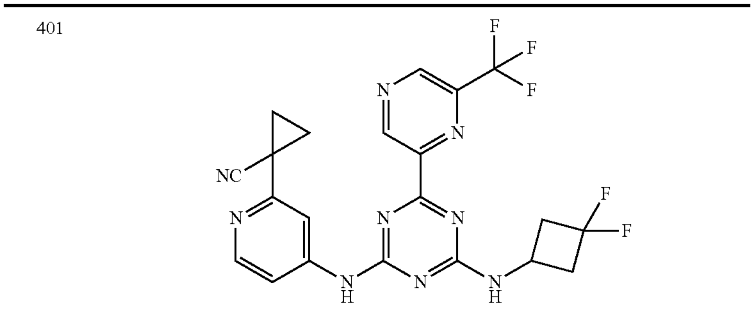 |
| 402 | 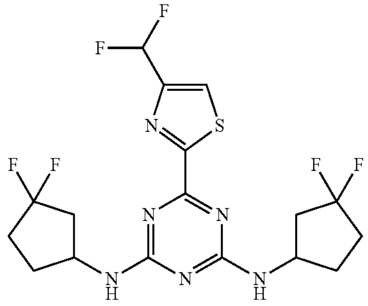 [SMILES: FC(F)c1csc(-c2nc(NC3CCC(F)(F)C3)nc(NC3CCC(F)(F)C3)n2)n1] |
| 403 | 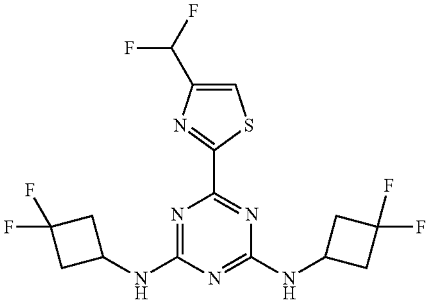 [SMILES: FC(F)c1csc(-c2nc(NC3CC(F)(F)C3)nc(NC3CC(F)(F)C3)n2)n1] |
| 404 | 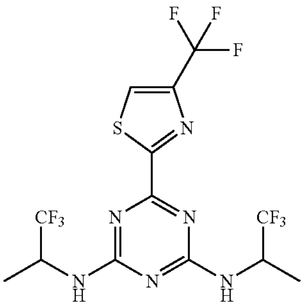 [SMILES: CC(Nc1nc(NC(C)C(F)(F)F)nc(-c2nc(C(F)(F)F)cs2)n1)C(F)(F)F] |
| 405 | 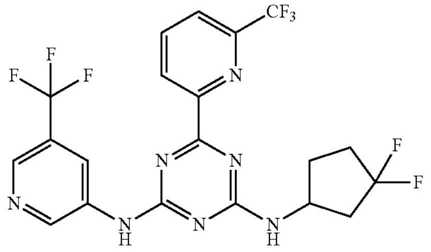 [SMILES: FC1(F)CCC(Nc2nc(Nc3cncc(C(F)(F)F)c3)nc(-c3cccc(C(F)(F)F)n3)n2)C1] |

TABLE 1-continued
| Representative Compounds | |
|---|---|
| Compound Number | Structure |
| 406 | 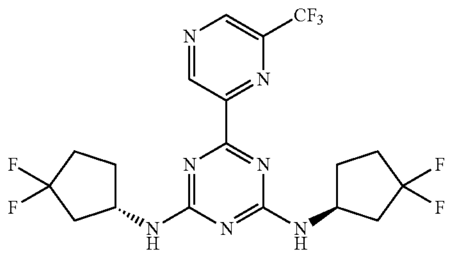 [SMILES: FC1(F)CC[C@H](Nc2nc(N[C@H]3CCC(F)(F)C3)nc(-c3cncc(C(F)(F)F)n3)n2)C1] |
| 407 | 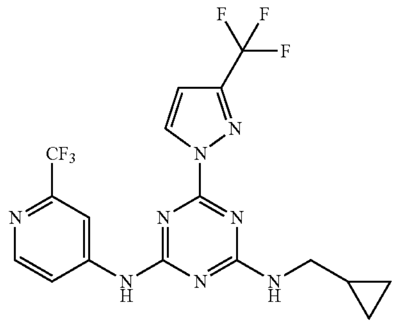 [SMILES: FC(F)(F)c1cc(Nc2nc(NCC3CC3)nc(-n3ccc(C(F)(F)F)n3)n2)ccn1] |
| 408 | 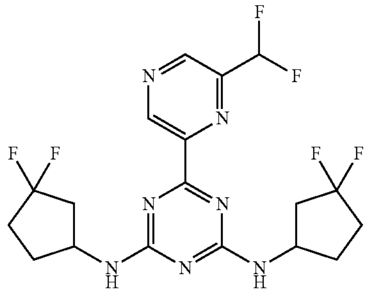 [SMILES: FC(F)c1cncc(-c2nc(NC3CCC(F)(F)C3)nc(NC3CCC(F)(F)C3)n2)n1] |
| 409 | 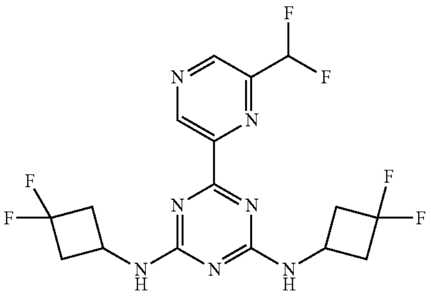 [SMILES: FC(F)c1cncc(-c2nc(NC3CC(F)(F)C3)nc(NC3CC(F)(F)C3)n2)n1] |
| 410 | 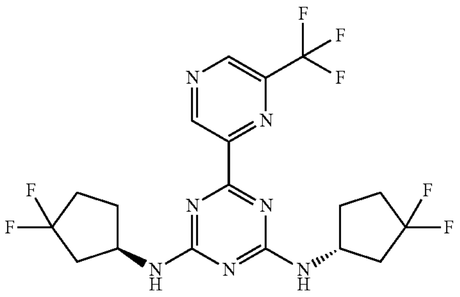 [SMILES: FC1(F)CC[C@@H](Nc2nc(N[C@@H]3CCC(F)(F)C3)nc(-c3cncc(C(F)(F)F)n3)n2)C1] |

TABLE 1-continued
| Representative Compounds | |
|---|---|
| Compound Number | Structure |
| 411 | 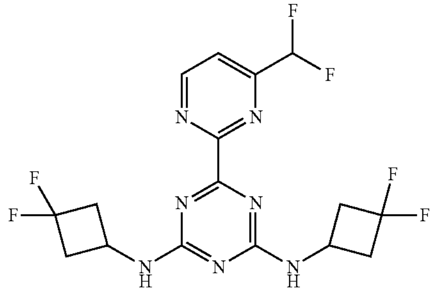 [SMILES: FC(F)c1ccnc(-c2nc(NC3CC(F)(F)C3)nc(NC3CC(F)(F)C3)n2)n1] |
| 412 | 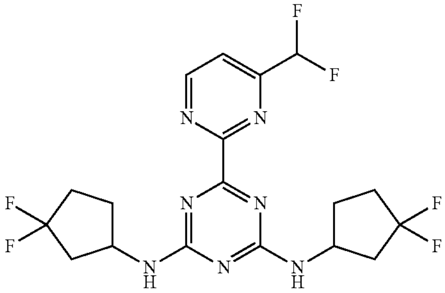 [SMILES: FC(F)c1ccnc(-c2nc(NC3CCC(F)(F)C3)nc(NC3CCC(F)(F)C3)n2)n1] |
| 413 | 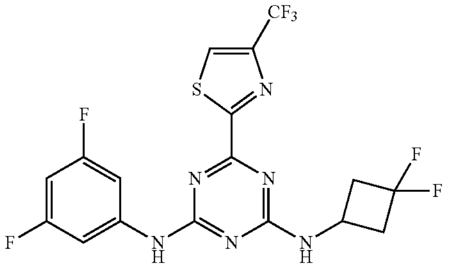 [SMILES: Fc1cc(F)cc(Nc2nc(NC3CC(F)(F)C3)nc(-c3nc(C(F)(F)F)cs3)n2)c1] |
| 414 | 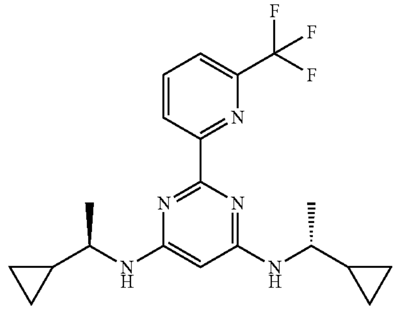 [SMILES: C[C@@H](Nc1cc(N[C@H](C)C2CC2)nc(-c2cccc(C(F)(F)F)n2)n1)C1CC1] |
| 415 | 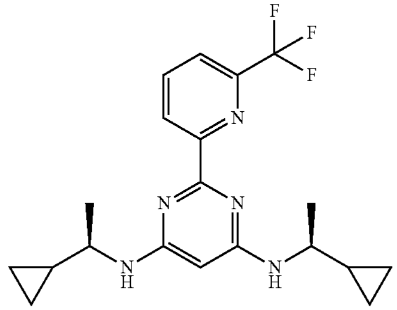 [SMILES: C[C@H](Nc1cc(N[C@H](C)C2CC2)nc(-c2cccc(C(F)(F)F)n2)n1)C1CC1] |

TABLE 1-continued
| Representative Compounds | |
|---|---|
| Compound Number | Structure |
| 416 | 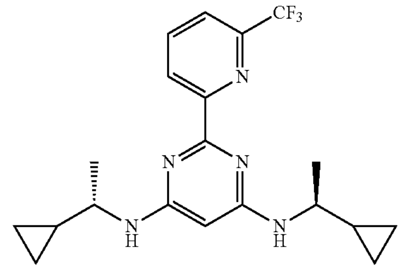 [SMILES: C[C@H](Nc1cc(N[C@@H](C)C2CC2)nc(-c2cccc(C(F)(F)F)n2)n1)C1CC1] |
| 417 | 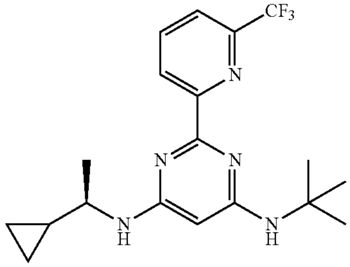 [SMILES: C[C@@H](Nc1cc(NC(C)(C)C)nc(-c2cccc(C(F)(F)F)n2)n1)C1CC1] |
| 418 | 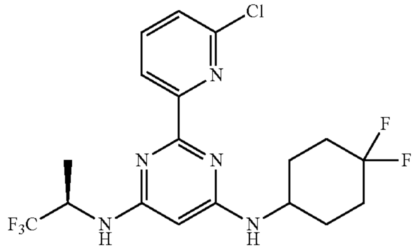 [SMILES: C[C@@H](Nc1cc(NC2CCC(F)(F)CC2)nc(-c2cccc(Cl)n2)n1)C(F)(F)F] |
| 419 | 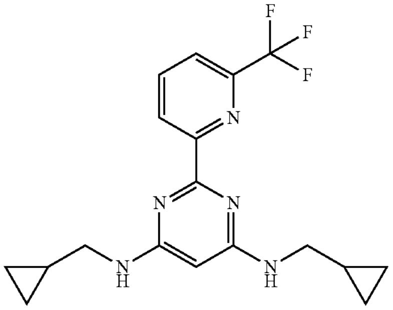 [SMILES: FC(F)(F)c1cccc(-c2nc(NCC3CC3)cc(NCC3CC3)n2)n1] |
| 420 | 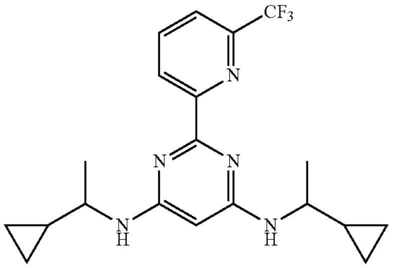 [SMILES: CC(Nc1cc(NC(C)C2CC2)nc(-c2cccc(C(F)(F)F)n2)n1)C1CC1] |

TABLE 1-continued
| Representative Compounds | |
|---|---|
| Compound Number | Structure |
| 421 | 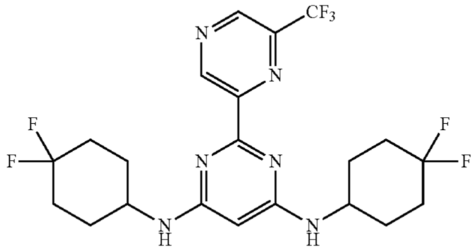 [SMILES: FC1(F)CCC(Nc2cc(NC3CCC(F)(F)CC3)nc(-c3cncc(C(F)(F)F)n3)n2)CC1] |
| 422 | 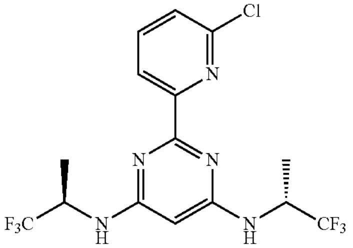 [SMILES: C[C@@H](Nc1cc(N[C@H](C)C(F)(F)F)nc(-c2cccc(Cl)n2)n1)C(F)(F)F] |
| 423 | 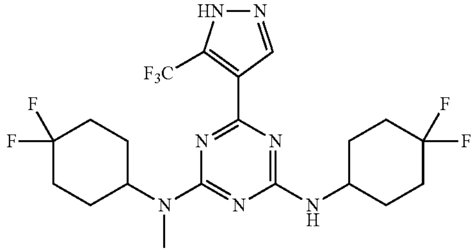 [SMILES: CN(c1nc(NC2CCC(F)(F)CC2)nc(-c2cn[nH]c2C(F)(F)F)n1)C1CCC(F)(F)CC1] |
| 424 | 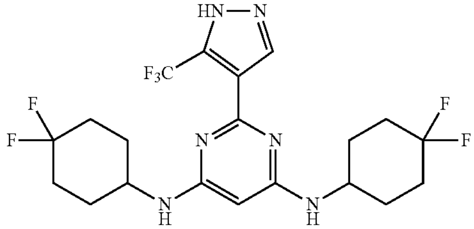 [SMILES: FC1(F)CCC(Nc2cc(NC3CCC(F)(F)CC3)nc(-c3cn[nH]c3C(F)(F)F)n2)CC1] |
Included herein are also methods for making compounds of Formula I or a compound of any one of the embodiments described herein comprising reacting
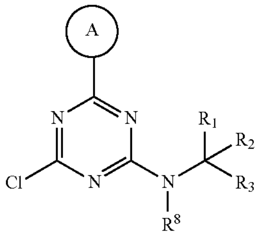
with
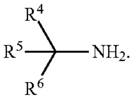
In some embodiments, the preceding methods comprise step (1) reacting
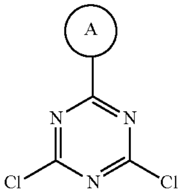

with
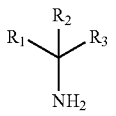
to give
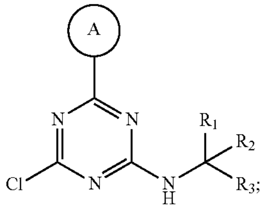
and step (2) reacting
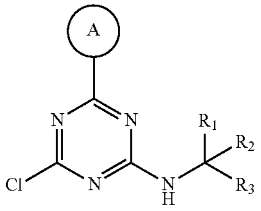
with
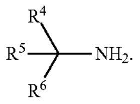
In other embodiments, the preceding methods comprise step (1) reacting
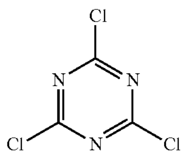
with
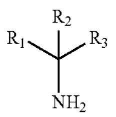
to give
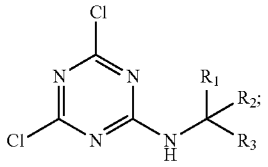
step (2) reacting
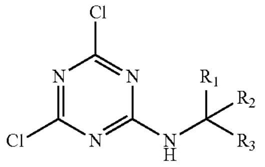
with
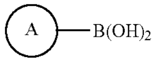
to give
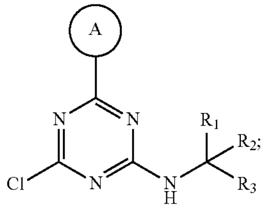
and step (3) reacting
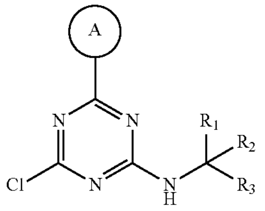
with
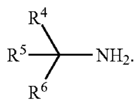
Also included are methods for making compounds of Formula I or a compound of any one of the embodiments described herein comprising reacting

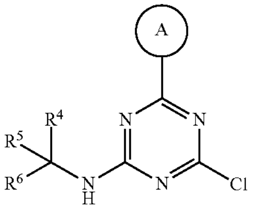

with

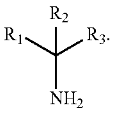

Also included are methods for making compounds of Formula I or a compound of any one of the embodiments described herein comprising reacting

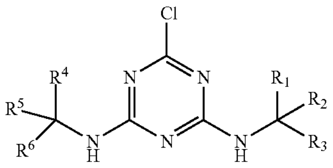

with

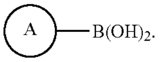

In some embodiments, the preceding methods comprise step (1) reacting

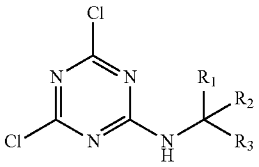

with

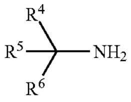

to give

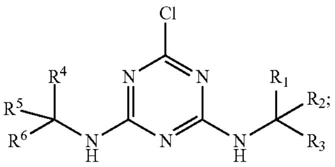

and step (2) reacting

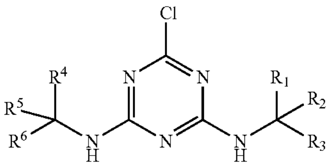

with

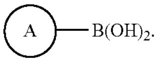

Also included are methods for making compounds of Formula I or a compound of any one of the embodiments described herein comprising reacting

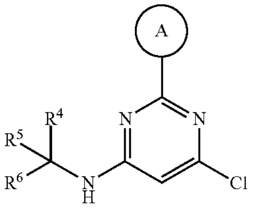

with

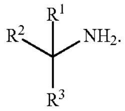

In other embodiments, the preceding methods comprise step (1) converting

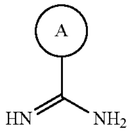

with

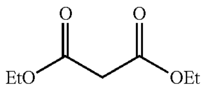

under basic conditions to give
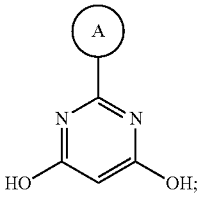
step (2) reacting
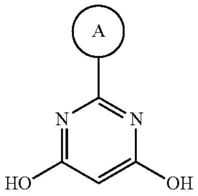
with $PCl_5$, $POCl_3$ to give
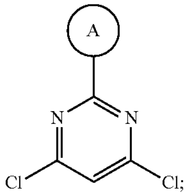
step (3) reacting
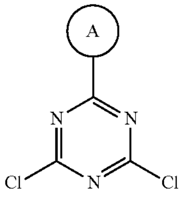
with
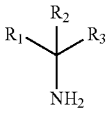
to give
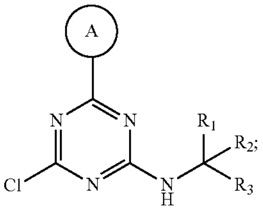
and step (4) reacting
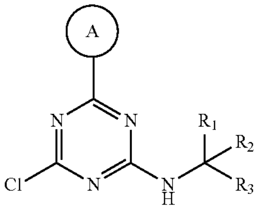
with
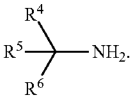
In other embodiments, the preceding methods comprise step (1) converting
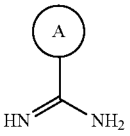
with
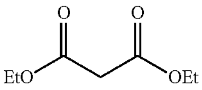
under basic conditions to give
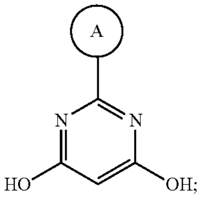

step (2) reacting
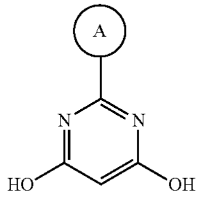
with $PCl_5$, $POCl_3$ to give
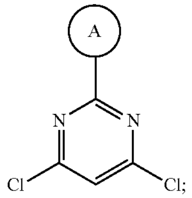
step (3) reacting
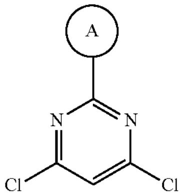
with
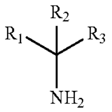
to give
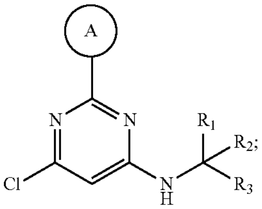
and step (4) reacting
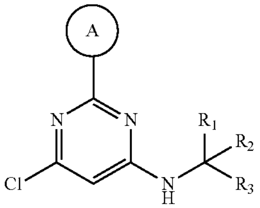
with
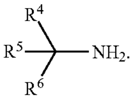
In other embodiments, the preceding methods comprise step (1) converting
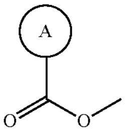
with
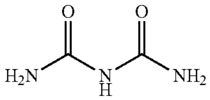
under basic conditions to give
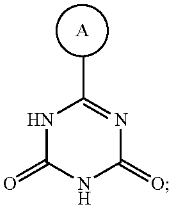
step (2) reacting
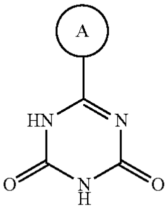

with $PCl_5$, $POCl_3$ to give
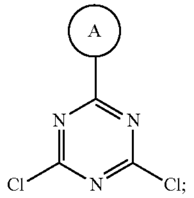
step (3) reacting
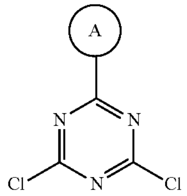
with
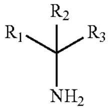
to give
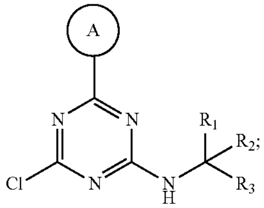
and step (4) reacting
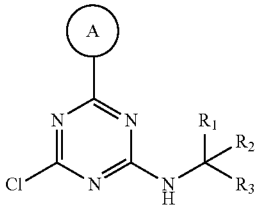
with
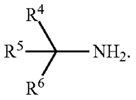
In other embodiments, the method comprises the step of reacting
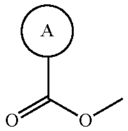
with
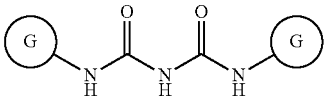
under basic conditions to give
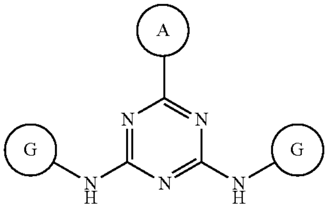
,
wherein ring G is a carbocyclyl or heterocyclyl ring. In other embodiments, the method comprises the steps of 1) reacting
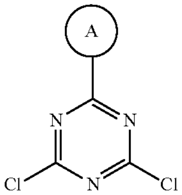
with
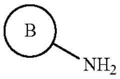
to give
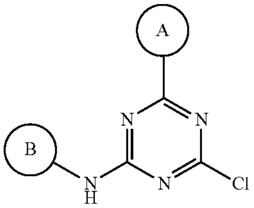

and 2) reacting

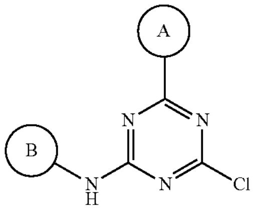

with

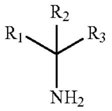

to give

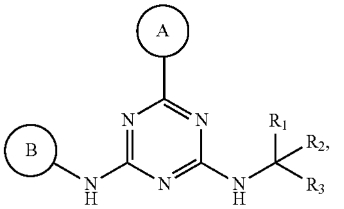

wherein ring B is an aryl or heteroaryl ring. In other embodiments, the method comprises the step of reacting

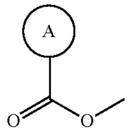

with

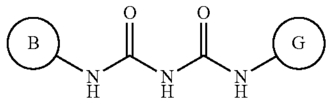

under basic conditions to give

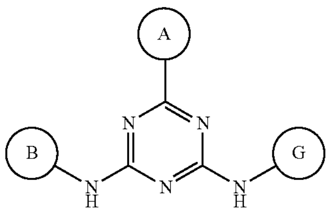
, wherein ring B is an aryl or heteroaryl ring, and ring G is a carbocyclyl or heterocyclyl ring. In other embodiments, the method comprises the step of reacting

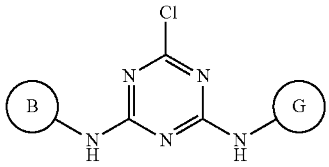

with ring A to form

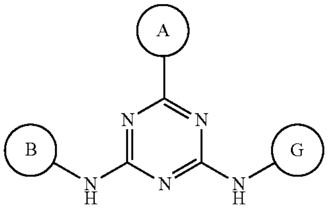
.

The compounds of one aspect of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, the compound of Formula I, Ia, Ib, B, C, Ic, Id, Ie, If, Ig, II, III, IIIa, IIIb, IIIc, or IIId, is enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

The compounds of Formula I, Ia, Ib, B, C, Ic, Id, Ie, If, Ig, II, III, IIIa, IIIb, IIIc, or IIId may also comprise one or more isotopic substitutions. For example, H may be in any isotopic form, including $^{1}H$, $^{2}H$ (D or deuterium), and $^{3}H$ (T or tritium); C may be in any isotopic form, including $^{11}C$, $^{12}C$, $^{13}C$, and $^{14}C$; N may be in any isotopic form, including $^{13}N$, $^{14}N$ and $^{15}N$; O may be in any isotopic form, including $^{15}O$, $^{16}O$ and $^{18}O$; F may be in any isotopic form, including $^{18}F$; and the like. For example, the compound is enriched in a specific isotopic form of H, C, N, O and/or F by at least about 60%, 65%, 70%, 75%, 80%, 85%, 90%, 95%, 96%, 97%, 98%, or 99%.

Unless otherwise indicated when a disclosed compound is named or depicted by a structure without specifying the stereochemistry and has one or more chiral centers, it is understood to represent all possible stereoisomers of the compound.

The compounds of one aspect of this invention may also be represented in multiple tautomeric forms, in such instances, one aspect of the invention expressly includes all tautomeric forms of the compounds described herein, even though only a single tautomeric form may be represented (e.g., alkylation of a ring system may result in alkylation at multiple sites, one aspect of the invention expressly includes all such reaction products; and keto-enol tautomers). All such isomeric forms of such compounds are expressly included herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4$+) and substituted ammonium ions (e.g., $NH_3R^+$, $NH_2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Mesylates of each compound in Table 1 are explicitly included herein. Examples of suitable polymeric organic anions include, but are not limited to, those derived from the following polymeric acids: tannic acid, carboxymethyl cellulose.

The compounds provided herein therefore include the compounds themselves, as well as their salts, hydrates and their prodrugs, if applicable. The compounds provided herein may be modified and converted to prodrugs by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds. Calcium and sodium phosphates of each compound in Table 1, if applicable, are explicitly included herein. Amino acid (e.g., valine) esters of each compound in Table 1, if applicable, are explicitly included herein.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of one aspect of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation.

Topically-transdermal patches are also included in one aspect of this invention.

The pharmaceutical compositions of one aspect of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of one aspect of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Formula I, Ia, Ib, B, C, Ic, Id, Ie, If, Ig, II, III, IIIa, IIIb, IIIc, or IIId or a compound described in any one of the embodiments herein, may further comprise another therapeutic agent useful for treating cancer.

Methods of Use

Provided is a method for inhibiting mutant IDH1 activity comprising contacting a subject in need thereof with a compound (including its tautomers and/or isotopologues) of Formula I, Ia, Ib, B, C, Ic, Id, Ie, If, Ig, II, III, IIIa, IIIb, IIIc, or IIId, or a compound described in any one of the embodiments herein, or a pharmaceutically acceptable salt thereof. In one embodiment, the cancer to be treated is characterized by a mutant allele of IDH1 wherein the IDH1 mutation results in a new ability of the enzyme to catalyze the NAPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H. Also provided are methods of treating a cancer characterized by the presence of a mutant allele of IDH1 comprising the step of administering to subject in need thereof (a) a compound of Formula I, Ia, Ib, B, C, Ic, Id, Ie, If, Ig, II, III, IIIa, IIIb, IIIc, or IIId, or a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation results in a new ability of the enzyme to catalyze the NAPH-dependent reduction of α-ketoglutarate to R(−)-2-hydroxyglutarate in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132 H or R132C. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NAPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such acitivity and in particular an IDH1 R132H or R132C mutation.

In one aspect of this embodiment, the efficacy of cancer treatment is monitored by measuring the levels of 2HG in the subject. Typically levels of 2HG are measured prior to treatment, wherein an elevated level is indicated for the use of the compound of Formula I, Ia, Ib, B, C, Ic, Id, Ie, If, Ig, II, III, IIIa, IIIb, IIIc, or IIId, or a compound described in any one of the embodiments described herein to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

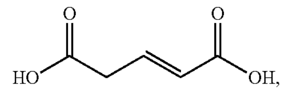
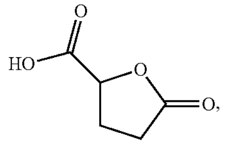
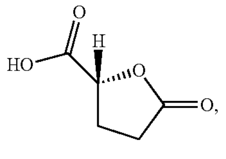
and
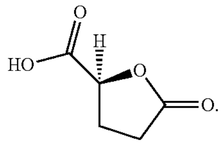

In one embodiment the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

IDH1 R132X mutations are known to occur in certain types of cancers as indicated in Table 2, below.

TABLE 2

| IDH mutations associated with certain cancers | | |
|---|---|---|
| Cancer Type | IDH1 R132X Mutation | Tumor Type |
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in glioblastoma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (glioblastoma), acute myelogenous leukemia, sarcoma, melanoma, non-small cell lung cancer (NSCLC), cholangiocarcinomas, chondrosarcoma, myelodysplastic syndromes (MDS), myeloproliferative neoplasm (MPN), colon cancer, or angio-immunoblastic non-Hodgkin's lymphoma (NHL) in a patient.

In another embodiment, the methods described herein are used to treat glioma (glioblastoma), acute myelogenous leukemia, sarcoma, melanoma, non-small cell lung cancer (NSCLC), cholangiocarcinomas (e.g., intrahepatic cholangiocarcinoma (IHCC)), chondrosarcoma, myelodysplastic syndromes (MDS), myeloproliferative neoplasm (MPN), prostate cancer, chronic myelomonocytic leukemia (CMML), B-acute lymphoblastic leukemias (B-ALL), B-acute lymphoblastic leukemias (B-ALL), myeloid sarcoma, multiple myeloma, lymphoma colon cancer, or angio-immunoblastic non-Hodgkin's lymphoma (NHL) in a patient.

In another embodiment, the advanced hematologic malignancy to be treated is lymphoma (e.g., Non-Hodgkin lymphoma (NHL) such B-cell lymphoma (e.g., Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma) and T-cell lymphoma (e.g., mycosis fungoides, anaplastic large cell lymphoma, and precursor T-lymphoblastic lymphoma).

Accordingly in one embodiment, the cancer is a cancer selected from any one of the cancer types listed in Table 2, and the IDH R132X mutation is one or more of the IDH1 R132X mutations listed in Table 2 for that particular cancer type.

Treatment methods described herein can additionally comprise various evaluation steps prior to and/or following treatment with a compound of Formula I, Ia, Ib, B, C, Ic, Id, Ie, If, Ig, TI, III, IIIa, IIIb, IIIc, or IIId or a compound described in any one of the embodiments described herein.

In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of evaluating the growth, size, weight, invasiveness, stage and/or other phenotype of the cancer.

In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of evaluating the IDH1 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Also provided is a method for inhibiting a mutant IDH2 activity comprising contacting a subject in need thereof with a compound of Formula I, Ia, Ib, B, C, Ic, Id, Ie, If, Ig, II, III, IIIa, IIIb, IIIc, or IIId, a compound described in any one of the embodiments herein, or a pharmaceutically acceptable salt thereof. In one embodiment, the cancer to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

Also provided are methods of treating a cancer characterized by the presence of a mutant allele of IDH2 comprising the step of administering to subject in need thereof (a) a compound of Formula I, Ia, Ib, B, C, Ic, Id, Ie, If, Ig, II, III, IIIa, IIIb, IIIc, or IIId or a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation results in a new ability of the enzyme to catalyze the NAPH-dependent reduction of α-ketoglutarate to R(−)-2-hydroxyglutarate, and in particular R140Q and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such acitivity and in particular an IDH2 R140Q and/or R172K mutation.

In one aspect of this embodiment, the efficacy of cancer treatment is monitored by measuring the levels of 2HG as described herein.

In one embodiment the cancer is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In another embodiment, one aspect of the invention provides a method of treating a cancer selected from glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma in a patient by administering to the patient a compound of Formula I, Ia, Ib, B, C, Ic, Id, Ie, If, Ig, II, III, IIIa, IIIb, IIIc, or IIId in an amount effective to treat the cancer. In a more specific embodiment the cancer to be treated is glioma, myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL).

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate HIF1-alpha levels.

Thus, according to another embodiment, one aspect of the invention provides a method of treating 2-hydroxyglutaric aciduria, particularly D-2-hydroxyglutaric aciduria, in a patient by administering to the patient a compound of Formula I, Ia, Ib, B, C, Ic, Id, Ie, If, Ig, II, III, IIIa, IIIb, IIIc, or IIId or a compound described in any one of the embodiments described herein.

Also provided are methods of treating a disease selected from Maffucci syndrome and Ollier disease, characterized by the presence of a mutant allele of IDH1 comprising the step of administering to subject in need thereof (a) a compound of Formula I, Ia, Ib, B, C, Ic, Id, Ie, If, Ig, II, III, IIIa, IIIb, IIIc, or IIId, or a compound described in any one of the embodiments herein, or a pharmaceutically acceptable salt thereof, or (b) a pharmaceutical composition comprising (a) and a pharmaceutically acceptable carrier.

Treatment methods described herein can additionally comprise various evaluation steps prior to and/or following treatment with a compound of Formula I, Ia, Ib, B, C, Ic, Id, Ie, If, Ig, II, III, IIIa, IIIb, IIIc, or IIId or a compound described in any one of the embodiments described herein.

In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of evaluating the growth, size, weight, invasiveness, stage and/or other phenotype of the cancer.

In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of evaluating the IDH2 genotype of the cancer. This may be achieved by ordinary methods in the art, such as DNA sequencing, immuno analysis, and/or evaluation of the presence, distribution or level of 2HG. In one embodiment, prior to and/or after treatment with a compound of Formula I, Ia, Ib, B, C, Ic, Id, Ie, If, Ig, II, III, IIIa, IIIb, IIIc, or IIId or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of one aspect of this invention as part of a single dosage form (such as a composition of one aspect of this invention comprising a compound of one aspect of the invention and an second therapeutic agent as described above) or as separate, multiple dosage forms. Alternatively, the additional cancer therapeutic agent may be administered prior to, consecutively with, or following the administration of a compound of one aspect of this invention. In such combination therapy treatment, both the compounds of one aspect of this invention and the second therapeutic agent(s) are administered by conventional methods. The administration of a composition of one aspect of this invention, comprising both a compound of one aspect of the invention and a second therapeutic agent, to a subject does not preclude the separate administration of that same therapeutic agent, any other second therapeutic agent or any compound of one aspect of this invention to said subject at another time during a course of treatment. The term "co-administering" as used herein with respect to an additional cancer treatment means that the additional cancer treatment may occur prior to, consecutively with, concurrently with or following the administration of a compound of one aspect of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein. Because some drugs work better together than alone, two or more drugs are often given at the same time. Often, two or more chemotherapy agents are used as combination chemotherapy. In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxyphenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®. In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

General Experimental Notes:

In the following examples, the reagents (chemicals) were purchased from commercial sources (such as Alfa, Acros, Sigma Aldrich, TCI and Shanghai Chemical Reagent Company), and used without further purification. Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA) or Shimadzu LCMS-2020 Mass Spectrometer (Shimadzu, Japan). Microwave reactions were run on an Initiator 2.5 Microwave Synthesizer (Biotage, Sweden).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%. The chemical name of each of the exemplary compound described below is generated by ChemDraw software.

ABBREVIATIONS LIST

General
- anhy. anhydrous
- aq. aqueous
- min minute(s)
- hrs hours
- mL milliliter
- mmol millimole(s)
- mol mole(s)
- MS mass spectrometry
- NMR nuclear magnetic resonance
- TLC thin layer chromatography
- HPLC high-performance liquid chromatography
- satd. saturated Spectrum
- Hz hertz
- δ chemical shift
- J coupling constant
- s singlet
- d doublet
- t triplet
- q quartet
- m multiplet
- br broad
- qd quartet of doublets
- dquin doublet of quintets
- dd doublet of doublets
- dt doublet of triplets Solvents and Reagents
- DAST diethylaminosulfurtrifluoride
- $CHCl_3$ chloroform
- DCM dichloromethane
- DMF dimethylformamide
- $Et_2O$ diethyl ether
- EtOH ethyl alcohol
- EtOAc ethyl acetate
- MeOH methyl alcohol
- MeCN acetonitrile
- PE petroleum ether
- THF tetrahydrofuran
- DMSO dimethyl sulfoxide
- AcOH acetic acid
- HCl hydrochloric acid
- $H_2SO_4$ sulfuric acid
- $NH_4Cl$ ammonium chloride
- KOH potassium hydroxide
- NaOH sodium hydroxide
- $K_2CO_3$ potassium carbonate
- $Na_2CO_3$ sodium carbonate
- TFA trifluoroacetic acid
- $Na_2SO_4$ sodium sulfate
- $NaBH_4$ sodium borohydride
- $NaHCO_3$ sodium bicarbonate
- NaHMDS sodium hexamethyldisilylamide
- LiHMDS lithium hexamethyldisilylamide
- LAH lithium aluminum hydride
- $NaBH_4$ sodium borohydride
- LDA lithium diisopropylamide
- $Et_3N$ triethylamine
- Py pyridine
- DMAP 4-(dimethylamino)pyridine
- DIPEA N,N-diisopropylethylamine
- Xphos 2-dicyclohexylphosphino-2,4,6-triisopropylbiphenyl
- BINAP 2,2'-bis(diphenylphosphanyl)-1,1'-binaphthyl
- dppf 1,1'-bis(diphenylphosphino)ferrocene
- TBTU 2-(1H-benzotriazole-1-yl)-1,1,3,3-tetramethyluronium tetrafluoroborate
- DPPA diphenylphosphoryl azide
- $NH_4OH$ ammonium hydroxide
- EDCI 1-ethyl-3-(3-dimethylaminopropyl)carbodiimide
- HOBt 1-hydroxybenzotriazole
- Py Pyridine
- Dppf 1,1'-bis(diphenylphosphino)ferrocene
- HATU O-(7-azabenzotriazol-1-yl)-N,N,N',N'-tetramethyluronium
- BINAP 2,2'-bis(diphenylphosphanyl)-1,1'-binaphthyl

Preparation of Intermediates

Preparation of 1-phenylcyclopropanamine

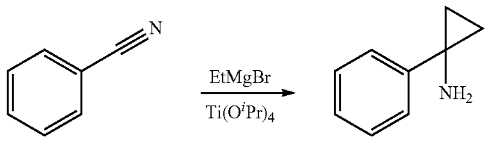 [SMILES: "EtMgBr" ; N#Cc1ccccc1 ; NC1(c2ccccc2)CC1 ; "Ti(OiPr)4"]

Ethylmagnesium bromide (48.5 mL, 146 mmol) was added dropwise over 30 min to a solution of benzonitrile (5 g, 48 mmol, 3 eq) and titanium tetraisopropanolate (21.5 mL, 73 mmol, 1.5 eq) in dry THF (140 mL) at −70° C. The solution was stirred at r.t. for 1.5 hr, followed by dropwise addition of boron trifluorideetherate (15 mL, 121 mmol, 2.5 eq) over 15 min. The mixture was stirred at r.t. for another 1.5 hr followed by addition of 1N aq. HCl and $Et_2O$. The resulting mixture was poured into 10% aq. NaOH, and extracted with $Et_2O$. Combined organic layers were dried over anhydrous $Na_2SO_4$, and concentrated. The residue was purified by column chromatography using PE/EtOAc/$NH_3 \cdot H_2O$ (4:1:0.1%) to afford the desired product. LC-MS: m/z 134.1 $(M+H)^+$.

Preparation of 2-amino-2-methylpropanenitrile

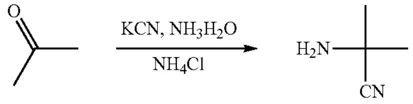

To a mixture of $NH_4Cl$(4.9 g, 92.3 mmol) and acetone (7 mL, 92.3 mmol) in ammonium hydroxide (40 mL, 230.7 mmol) was added KCN (5 g, 76.9 mmol) at r.t. The reaction mixture was stirred at r.t for 3 days. The mixture was extracted with DCM (2×30 mL). Combined organic layers were washed with brine, dried over anhydrous $Na_2SO_4$ and concentrated to afford the desired product which was used directly in the next step without any further purification.

Preparation of 2-aminopropanenitrile

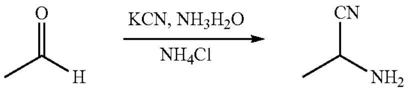

To a mixture of $NH_4Cl$ (981 mg, 18.5 mmol), acetaldehyde (1 mL, 18.5 mmol) in ammonium hydroxide (3 mL) was added KCN (1 g, 15.4 mmol) at room temperature. The reaction mixture was stirred at r.t for 2 days. The mixture was extracted with DCM (2×30 mL). Combined organic layers were washed with brine, dried over anhydrous $Na_2SO_4$ and concentrated to afford the desired product which was used directly in the next step without any further purification.

Preparation of dicyclopropylmethanamine

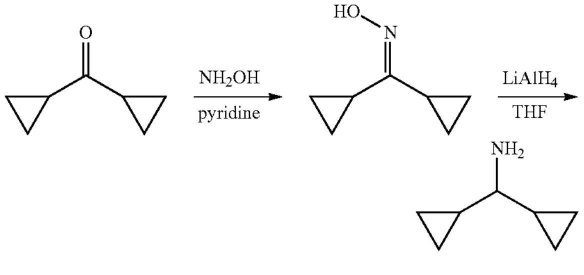

Step 1. Preparation of dicyclopropylmethanoneoxime. To a mixture of dicyclopropylmethanone (500 mg, 4.5 mmol) in pyridine (5 mL) was added hydroxylamine hydrochloride (469 mg, 6.75 mmol). The reaction mixture was stirred at 100° C. for 4 hr and cooled to r.t followed by addition of EtOAc. The resulting mixture was washed with 1 N aq. HCl and brine, dried over anhydrous $Na_2SO_4$, and concentrated under reduced pressure to give the desired product which was used directly in the next step without any further purification.

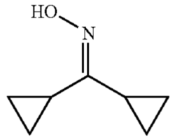

LC-MS: m/z 124.1 $(M-H)^-$.

Step 2. Preparation of dicyclopropylmethanamine. To a cooled solution of dicyclopropylmethanoneoxime (550 mg, 4.4 mmol) in THF (5 mL) was added $LiAlH_4$ (200 mg, 5.3 mmol). The mixture was then stirred at 80° C. for 6 hr and cooled to room temperature. The mixture was quenched by 1N aq.NaOH until gas evolution ceased and then filtered. The filtrate was extracted with EtOAc. Combined organic layers were dried over anhydrous $Na_2SO_4$, and concentrated under reduced pressure to give the desired product which was used directly in the next step without any further purification.

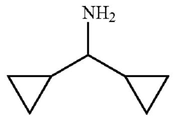

LC-MS: m/z 112.1 $(M+H)^+$.

Preparation of bicyclo[3.1.0]hexan-3-amine

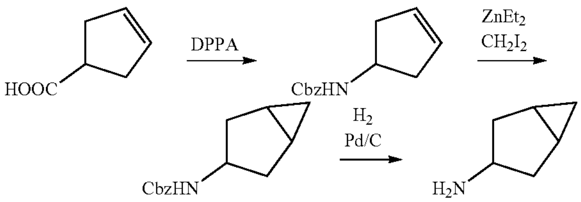

Step 1: Preparation of benzyl cyclopent-3-enylcarbamate. To a solution of cyclopent-3-enecarboxylic acid (5 g, 44.6 mmol, 1 eq) and DPPA (13.5 g, 49 mmol, 1.1 eq) in toluene (80 mL) was added $Et_3N$ (7.4 mL, 53.5 mmol, 1.2 eq) at r.t. The mixture was then stirred at reflux for 2 hr during which period a larger amount of nitrogen evolved. After BnOH (7 mL, 66.9 mmol, 1.5 eq) was added, the resulting mixture was stirred at 100° C. overnight and cooled to room temperature. After quenched with saturated aqueous $NaHCO_3$. The resulting mixture was extracted with EtOAc. Combined organic layers were washed with brine, dried over anhydrous $Na_2SO_4$, and concentrated under reduced pressure. The residue was purified by flash chromatography using PE/EtOAc (5:1) as eluent to give the desired product.

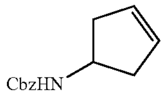 [SMILES: O=C(NC1CC=CC1)OCc1ccccc1]

LC-MS: m/z 218.0 $(M+H)^+$.

Step 2: Preparation of benzyl bicyclo[3.1.0]hexan-3-ylcarbamate. To a solution of benzyl cyclopent-3-enylcarbamate (1 g, 4.6 mmol, 1 eq) in anhydrous DCM at 0° C. under an atmosphere of nitrogen was added $ZnEt_2$ (9.7 mL, 9.7 mmol, 2.1 eq), followed by dropwise addition of $CH_2I_2$ (0.78 mL, 9.7 mmol, 2.1 eq). The reaction mixture was warmed to room temperature and stirred for 4 hr. The resulting reaction mixture was quenched with brine and extracted with DCM. The organic layer was dried over anhydrous $Na_2SO_4$, and concentrated. The residue was purified by column chromatography using PE/EtOAc (5:1) as eluent to give the desired product.

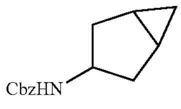 [SMILES: O=C(NC1CC2CC2C1)OCc1ccccc1]

LC-MS: m/z 232.1 $(M+H)^+$.

Step 3: Preparation of bicyclo[3.1.0]hexan-3-amine. To a solution of benzyl bicyclo[3.1.0]hexan-3-ylcarbamate (2 g) in MeOH (20 mL) at r.t. under an atmosphere of nitrogen was added Pd/C (0.2 g) in one portion. The resulting mixture was then stirred under a hydrogen balloon overnight. The reaction mixture was filtered and the filtrate was concentrated under reduced pressure to give the desired product which was used directly in the next step without any further purification.

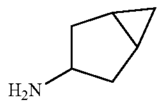

LC-MS: m/z 98.1 $(M+H)^+$.

Preparation of 2-(1,1-difluoroethyl)pyridin-4-amine

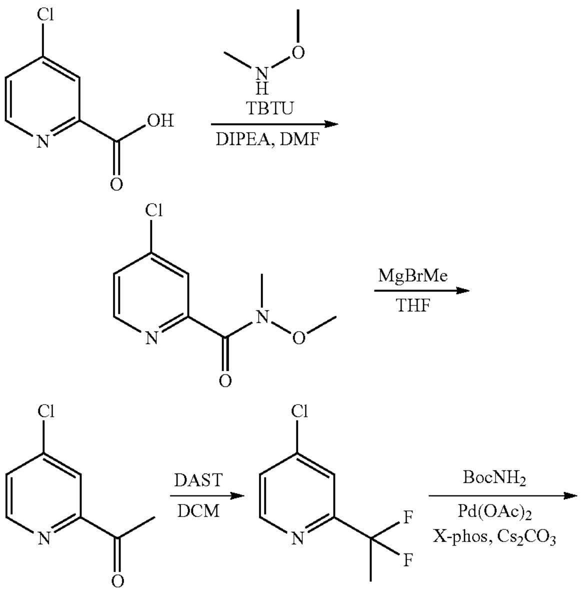

-continued

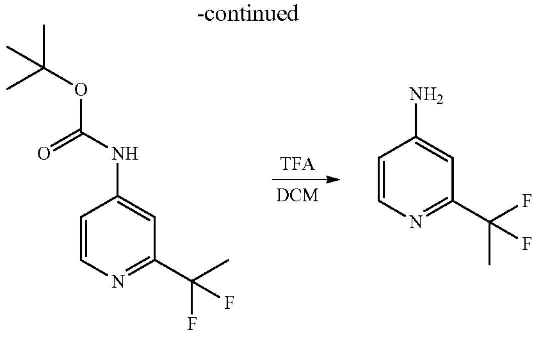

Step 1: Preparation of 4-chloro-N-methoxy-N-methylpicolinamide. To a solution of 4-chloropicolinic acid (10 g, 63.5 mmol) in DMF (150 mL) was added TBTU (30.6 g, 95.2 mmol), N,O-dimethylhydroxylamine (9.3 g, 95.2 mmol) and DIPEA (24.6 g, 190.4 mmol) at 0° C. The mixture was stirred at room temperature overnight. The reaction mixture was diluted with saturated aqueous $NH_4Cl$ and extracted with EtOAc. The organic layer was dried over $Na_2SO_4$ and concentrated. The residue was purified by flash chromatography to give the desired product.

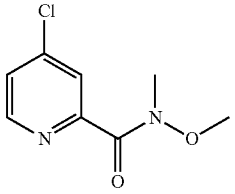

LC-MS: m/z 201.0 $(M+H)^+$.

Step 2: Preparation of 1-(4-chloropyridin-2-yl)ethanone. To a solution of 4-chloro-N-methoxy-N-methylpicolinamide (11.25 g, 56.08 mmol) in THF (50 mL) at 0° C. was added MeMgBr (28.04 mL, 84.12 mmol). The mixture was then stirred at r.t. overnight and quenched with saturated aqueous $NH_4Cl$. The resulting mixture was extracted with EtOAc. The organic layer was dried over anhydrous $Na_2SO_4$ and concentrated. The residue was purified by flash chromatography to give the desired product.

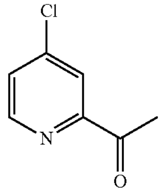

$^1H$ NMR (400 MHz, $CDCl_3$): δ8.52 (d, J=5.2 Hz, 1H), 7.96 (s, 1H), 7.40 (d, J=5.2 Hz, 1H), 2.64 (s, 3H). LC-MS: m/z 156.0 $(M+H)^+$.

Step 3: 4-chloro-2-(1,1-difluoroethyl)pyridine. To a solution of 1-(4-chloropyridin-2-yl)ethanone (6.3 g, 40.5 mmol) in DCM (30 mL) was added DAST (65.2 g, 405 mmol) at 0° C. The mixture was then stirred at r.t. overnight and quenched with saturated aqueous $NaHCO_3$. The resulting mixture was extracted with DCM. The organic layer was dried over anhydrous $Na_2SO_4$ and concentrated. The residue was purified by flash chromatography to give the desired product.

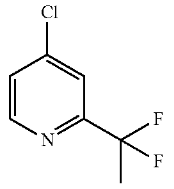

$^1$H NMR (400 MHz, $CDCl_3$): δ8.48 (d, J=5.2 Hz, 1H), 7.60 (s, 1H), 7.31 (d, J=5.2 Hz, 1H), 1.90-1.99 (m, 3H). LC-MS: m/z 178.0 $(M+H)^+$.

Step 4: Preparation of tert-butyl (2-(1,1-difluoroethyl)pyridin-4-yl)carbamate. To a solution of 4-chloro-2-(1,1-difluoroethyl)pyridine (6.0 g, 33.8 mmol) in dioxane (20 mL) was added $BocNH_2$(4.74 g, 40.5 mmol), X-phos (1.14 g, 1.7 mmol), $CsCO_3$ (16.5 g, 50.7 mmol) and $Pd(OAc)_2$ (1.32 g, 2.7 mmol) at room temperature. The mixture was then stirred at 80° C. overnight and then cooled to room temperature. The reaction mixture was diluted with Sat. aq. $NH_4Cl$ and extracted with EtOAc. The organic layer was dried over anhydrous $Na_2SO_4$ and concentrated. The residue was purified by flash chromatography to give the desired product.

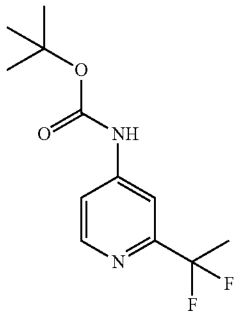 [SMILES: CC(C)(C)OC(=O)Nc1ccnc(C(C)(F)F)c1]

LC-MS: m/z 259.1$(M+H)^+$.

Step 5: Preparation of 2-(1,1-difluoroethyl)pyridin-4-amine. A solution of tert-butyl (2-(1,1-difluoroethyl)pyridin-4-yl)carbamate (7.97 g, 30.86 mmol) in DCM (30 mL) was cooled under ice-water bath. TFA (10 mL) was then added dropwise. The reaction mixture was stirred at room temperature for 4 hrs and monitored by TLC. Once the reaction completed, the mixture was diluted with water and adjusted pH>7 by saturated aqueous $NaHCO_3$. The resulting mixture was extracted with DCM. Combined organic layers were dried over anhydrous $Na_2SO_4$ and concentrated to give the desired product which was used in the next step without further purification.

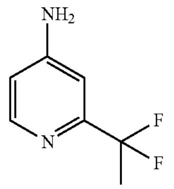

LC-MS: m/z 159.1 $(M+H)^+$.

Preparation of 1-(4-aminopyridin-2-yl)cyclopropanecarbonitrile

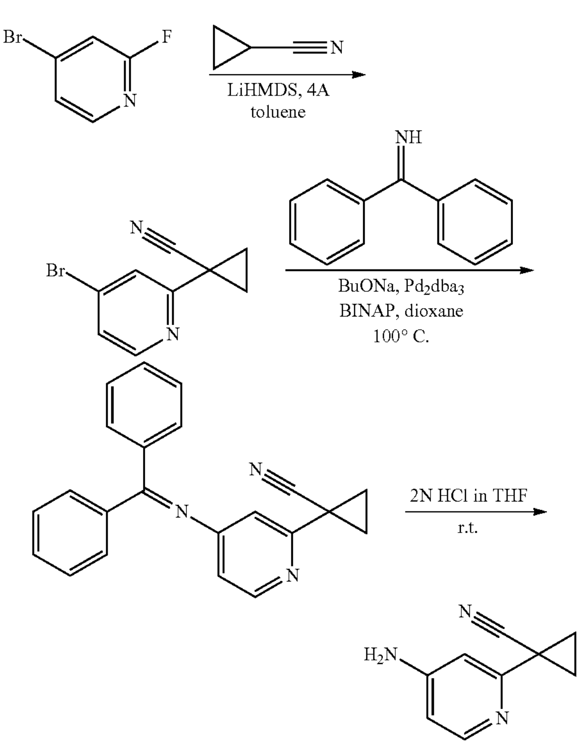

Step 1: Preparation of 1-(4-bromopyridin-2-yl)cyclopropanecarbonitrile. LiHMDS (1M in toluene, 17.6 mL, 17.6 mmol, 3.1 eq) was added dropwise to a cold (−5° C.) mixture of 4-bromo-2-fluoropyridine (1 g, 5.7 mmol), cyclopanecarbonitrile (1.25 mL, 17 mmol, 3 eq) and 4A MS in toluene (20 mL). The reaction mixture was allowed to warm to room temperature and stirred for 16 hr. After it was poured into water, the mixture was filtered. The filtrate was diluted with EtOAc and $H_2O$, and extracted with EtOAc. The organic phase was washed with water and brine, dried over anhydrous $Na_2SO_4$, and concentrated. The residue was purified by column chromatography using PE/EtOAc (9:1) as eluent to give the desired product.

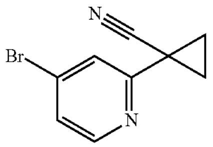 [SMILES: N#CC1(c2cc(Br)ccn2)CC1]

LC-MS: m/z 223.0 $(M+H)^+$.

Step 2: Preparation of 1-(4-(diphenylmethyleneamino)pyridin-2-yl) cyclopropanecarbonitrile. To a mixture of 1-(4-bromopyridin-2-yl)cyclopropanecarbonitrile (0.45 g, 2.1 mmol), BINAP (0.04 g, 0.063 mmol), $Pd_2(dba)_3$ (0.019 g, 0.021 mmol) and $NaO^tBu$ (0.282 g, 2.94 mmol) in toluene (6 mL) at r.t. under an atmosphere of nitrogen was added diphenylmethanimine (0.45 g, 2.51 mmol). The reaction mixture was stirred at reflux for 2 hr and then cooled to room temperature. The mixture was concentrated under reduced pressure and the residue was purified by column chromatography to give the desired product.

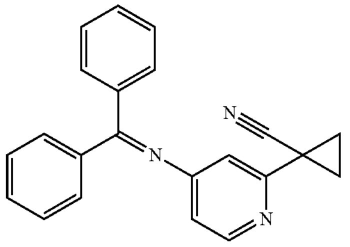 [SMILES: N#CC1(c2cc(N=C(c3ccccc3)c3ccccc3)ccn2)CC1]

LC-MS: m/z 324.1 $(M+H)^+$.

Step 3: Preparation of 1-(4-aminopyridin-2-yl)cyclopropanecarbonitrile. A mixture of 1-(4-(diphenylmethyleneamino)pyridin-2-yl)cyclopropanecarbonitrile (0.48 g, 1.49 mmol), THF (10 mL) and aq. HCl (2N, 2.0 mL) was stirred at room temperature for 1 hour. The mixture was then partitioned between EtOAc (15 mL) and water (15 mL). The aqueous phase was extracted with EtOAc (2×25 mL). Combined organic layers were dried over anhydrous $Na_2SO_4$ and concentrated. The residue was purified by column chromatography to give the desired product.

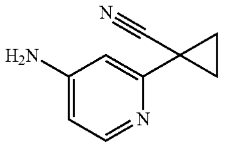 [SMILES: N#CC1(c2cc(N)ccn2)CC1]

LC-MS: m/z 160.1 $(M+H)^+$.

Example 1. Preparation of Di-aliphatic Triazine Compounds of Formula D Wherein Ring A is substituted Pyridin-2-yl or Phenyl. The compounds of this Example are prepared by general Scheme 1, set forth below.

Scheme 1

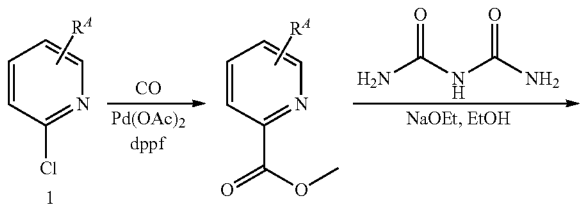

1 2

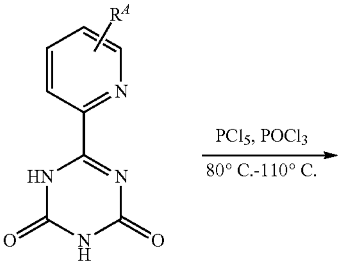

3

-continued

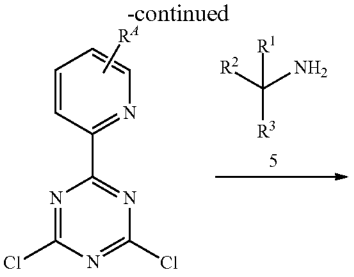

4

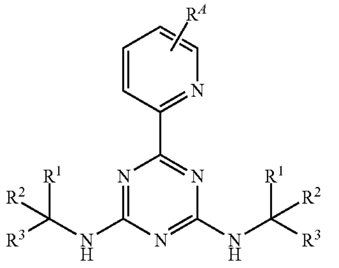

Formula D

Step 1: Preparation of 6-trifluomethyl-pyridine-2-carboxylic acid methyl ester (2). To a solution of 2-chloro-6-trifluoromethyl-pyridine (2 g, 11.1 mmol, 1.0 eq) in MeOH (20 mL) was add $Pd(OAc)_2$ (124 mg, 0.05 eq) and dppf (600 mg, 0.1 eq) under an atmosphere of nitrogen. $Et_3N$ (2.3 mL, 1.5 eq) was then added to the resulting orange solution. The reaction solution was then stirred under an atmosphere of carbon monoxide (40 psi) at 60° C. for 22 hr. Once the reaction completed, the mixture was filtered and the filtrate was concentrated in high vacuum. The residue was purified by column chromatography to afford the desired product.

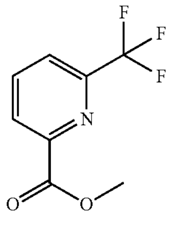

$^1$HNMR (400 MHz, $CDCl_3$): δ 8.32 (d, J=8 Hz, 1H), 8.06 (t, J=8 Hz, 1H), 8.88 (d, J=8 Hz, 1H), 4.04 (s, 3H). LC-MS: m/z 206 $(M+H)^+$.

Step 2: Preparation of 6-(6-trifluomethylpyridin-2-yl)-1,3,5-triazine-2,4-dione. To a solution of freshly prepared NaOEt from Na (3.84 g, 0.16 mol, 3 eq) in ethanol (500 mL) was added methyl 6-trifluoromethylpicolinate (33 g, 0.16 mol, 3 eq) and biuret (5.3 g, 0.052 mol). The resulting mixture was heated to reflux for 1 hr and then concentrated. The residue was poured into water and treated with Sat. aq. $NaHCO_3$ to adjust pH to 7. The precipitated solid was collected by filtration and dried under air to give the desired compound.

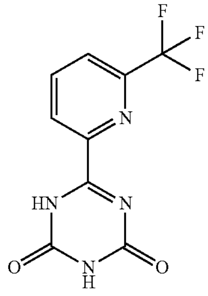 [SMILES: O=c1nc(-c2cccc(C(F)(F)F)n2)[nH]c(=O)[nH]1]

$^1$H NMR (400 MHz, DMSO-$d_6$): δ 10.88 (s, 1H), 8.46 (d, J=7.4 Hz, 1H), 8.28 (t, J=7.3 Hz, 1H), 8.11 (d, J=7.4 Hz, 1H). LC-MS: m/z 259 $(M+H)^+$.

Step 3: Preparation of 2,4-dichloro-6-(6-trifluomethyl-pyridin-2-yl)-1,3,5-triazine. To a solution of 6-(6-trifluomethyl-pyridin-2-yl)-1,3,5-triazine-2,4(1H,3H)-dione (3.37 g, 0.013 mol) in $POCl_3$ (48 mL) was added $PCl_5$ (23 g, 0.1 mol). The mixture was stirred at 100° C. for 2 hr and then concentrated. The residue was dissolved inEtOAc and then washed with Sat. aq. $NaHCO_3$. The organic layer was dried over anhydrous $Na_2SO_4$ and then concentrated to give the desired product.

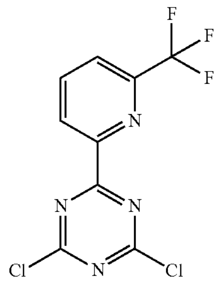 [SMILES: FC(F)(F)c1cccc(-c2nc(Cl)nc(Cl)n2)n1]

$^1$H NMR (400 MHz, $CDCl_3$): δ 8.76 (d, J=7.9 Hz, 1H), 8.19 (t, J=7.9 Hz, 1H), 7.97 (d, J=7.8 Hz, 1H). LC-MS: m/z 294.9 $(M+H)^+$.

Step 4: Preparation of $N^2$,$N^4$-bis((R)-1-cyclopropyl-ethyl)-6-(6-(trifluoromethyl)-pyridin-2-yl)-1,3,5-triazine-2, 4-diamine. To a mixture of 2,4-dichloro-6-(6-(trifluorom-ethyl)pyridine-2-yl)-1,3,5-triazine (600 mg, 2.0 mmol, 1.0 eq) and (R)-1-cyclopropylethanamine hydrochloride salt (536 mg, 4.4 mmol, 2.2 eq) in THF (12 mL) were added CsF (1.2 g, 8.0 mmol, 2 eq) and DIPEA (1.4 mL, 8.0 mmol, 4 eq) at room temperature. The mixture was stirred at 60° C. overnight and then filtered. The filtrate was concentrated under reduced pressure and the residue was purified by a standard method to give the desired product.

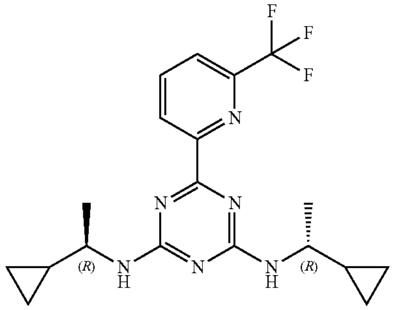

$^1$H NMR (400 MHz, $CD_3OD$): δ 8.70-8.68 (m, 1H), 8.34-8.32 (m, 1H), 8.16-8.14 (m, 1H), 3.61-3.57 (m, 2H), 1.36-1.32 (m, 6H), 1.06-1.01 (m, 2H), 0.61-0.39 (m, 8H). LC-MS: m/z 393.2 $(M+H)^+$.

The procedure set forth in Example 1 was used to produce the following compounds using the appropriate starting materials.

Compound $N^2$,$N^4$-bis((S)-1-cyclopropylethyl)-6-(6-(trifluoromethyl)pyridin-2-yl)-1,3,5-triazine-2,4-diamine

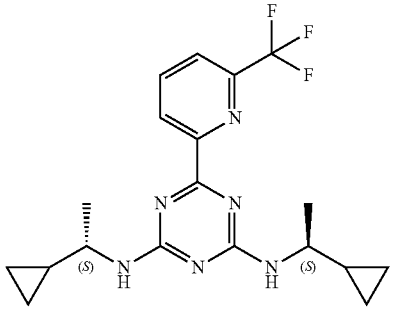

$^1$H NMR (400 MHz, $CDCl_3$): δ 8.50 (s, 1H), 7.99 (t, J=7.9 Hz, 1H), 7.77 (d, J=7.7 Hz, 1H), 5.44-5.18 (m, 2H), 3.66-3.57 (m, 2H), 1.27 (d, J=5.4 Hz, 6H), 0.93-0.88 (m, 2H), 0.52-0.27 (m, 8H). LC-MS: m/z 393.2 $(M+H)^+$.

Compound $N^2$—((R)-1-cyclopropylethyl)-$N^4$—((S)-1-cyclopropylethyl)-6-(6-(trifluoro methyl)pyridin-2-yl)-1,3,5-triazine-2,4-diamine

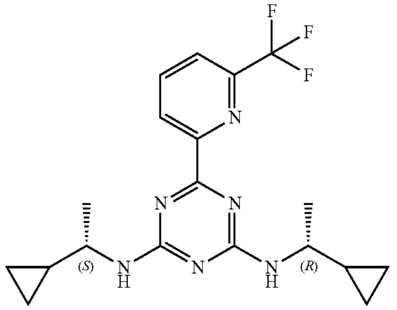

$^1$H NMR (400 MHz, $CDCl_3$): δ 8.51 (s, 1H), 7.99 (t, J=7.9 Hz, 1H), 7.77 (d, J=7.3 Hz, 1H), 5.46-5.19 (m, 2H), 3.67-

3.54 (m, 2H), 1.32-1.22 (m, 6H), 0.95-0.83 (m, 2H), 0.59-0.23 (m, 8H). LC-MS: m/z 393.2(M+H)$^+$.

Compound $N^2$,$N^4$-bis(1-cyclopropylethyl)-6-(6-(trifluoromethyl)pyridin-2-yl)-1,3,5-triazine-2,4-diamine

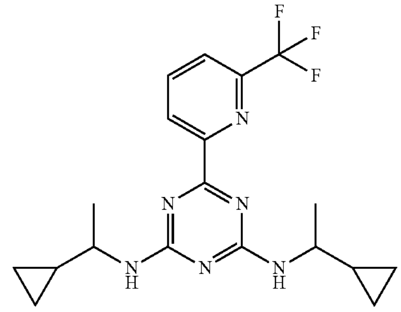 [SMILES: CC(Nc1nc(NC(C)C2CC2)nc(-c2cccc(C(F)(F)F)n2)n1)C1CC1]

$^1$HNMR (400 MHz, $CD_3OD$): δ8.6 (m, 1H), 8.2-8.1 (m, 1H), 8.0-7.9 (m, 1H), 4.0-3.52 (m, 2H), 1.4-1.2 (m, 6H), 1.0 (m, 2H), 0.6-0.35 (m, 6H), 0.35-0.2 (m, 2H). LC-MS: m/z 393.2 (M+H)$^+$.

Compound $N^2$,$N^4$-bis(cyclobutylmethyl)-6-(6-(trifluoromethyl)pyridin-2-yl)-1,3,5-triazine-2,4-diamine

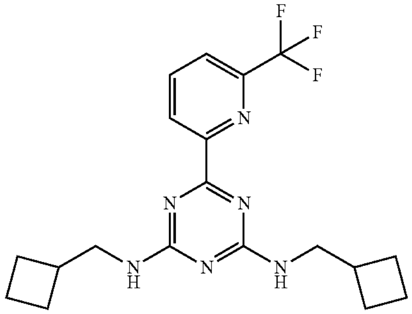 [SMILES: FC(F)(F)c1cccc(-c2nc(NCC3CCC3)nc(NCC3CCC3)n2)n1]

$^1$H NMR (400 MHz, $CDCl_3$): δ 8.54 (m, 1H), 8.00 (m, 1H), 7.78 (d, J=5.9 Hz, 1H), 5.27 (m, 2H), 3.69-3.32 (m, 4H), 2.59 (m, 2H), 2.10 (m, 4H), 1.92 (m, 4H), 1.84-1.62 (m, 4H). LC-MS: m/z 393.2 (M+H)$^+$.

Compound $N^2$,$N^4$-bis((R)-1-cyclobutylethyl)-6-(6-(trifluoromethyl)pyridin-2-yl)-1,3,5-triazine-2,4-diamine

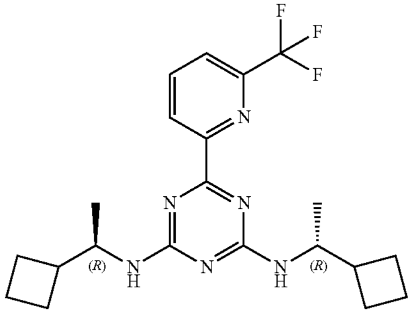

$^1$H NMR (400 MHz, $CDCl_3$): δ 8.71-8.41 (m, 1H), 7.99 (d, J=7.4 Hz, 1H), 7.77 (d, J=7.7 Hz, 1H), 5.34-4.84 (m, 2H), 4.30-3.96 (m, 2H), 2.44-2.28 (m, 2H), 2.09-1.96 (m, 4H), 1.93-1.78 (m, 8H), 1.14 (d, J=5.9 Hz, 6H). LC-MS: m/z 421.2 (M+H)$^+$.

Compound $N^2$,$N^4$-bis(2-methylcyclopropyl)-6-(6-(trifluoromethyl)pyridin-2-yl)-1,3,5-triazine-2,4-diamine

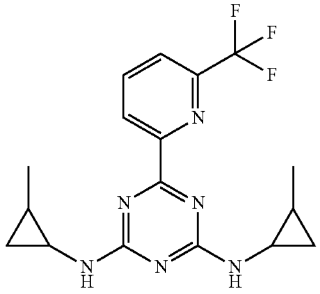 [SMILES: CC1CC1Nc1nc(NC2CC2C)nc(-c2cccc(C(F)(F)F)n2)n1]

$^1$HNMR (400 MHz, $CD_3OD$): δ8.65-8.4 (m, 1H), 8.1-7.75 (m, 2H), 2.55-2.25 (m, 2H), 1.2-1.0 (m, 6H), 0.9-0.8 (m, 2H), 0.7-0.6 (m, 2H), 0.5-0.38 (m, 2H). LC-MS: m/z 365.3 (M+H)$^+$.

Compound $N^2$,$N^4$-bis(cyclopropylmethyl)-6-(6-(trifluoromethyl)pyridin-2-yl)-1,3,5-triazine-2,4-diamine

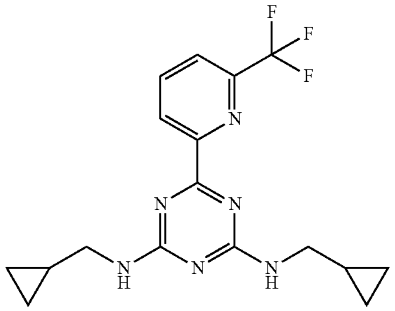 [SMILES: FC(F)(F)c1cccc(-c2nc(NCC3CC3)nc(NCC3CC3)n2)n1]

$^1$H NMR (400 MHz, $CD_3OD$): δ 8.60-8.68 (m, 1H), 8.21 (t, J=8.0 Hz, 1H), 7.93-8.00 (m, 1H), 3.26-3.42 (m, 4H), 1.08-1.19 (m, 2H), 0.51-0.58 (m, 4H), 0.25-0.34 (m, 4H). LC-MS: m/z 365.2 (M+H)$^+$.

Compound $N^2$,$N^4$-bis((1-methylcyclopropyl) methyl)-6-(6-(trifluoromethyl)pyridin-2-yl)-1,3,5-triazine-2,4-diamine

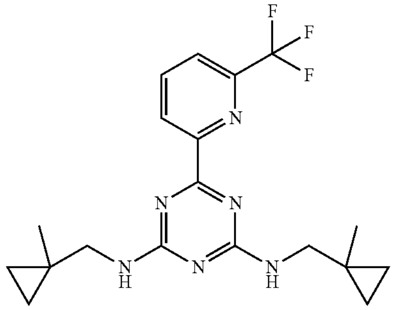 [SMILES: CC1(CNc2nc(NCC3(C)CC3)nc(-c3cccc(C(F)(F)F)n3)n2)CC1]

$^1$HNMR (400 MHz, $CD_3OD$): δ 8.61-8.59 (m, 1H), 8.17-8.15 (m, 1H), 7.94-7.92 (m, 1H), 3.43-3.33 (m, 4H), 1.14 (s, 6H), 0.55-0.53 (m, 4H), 0.34-0.32 (m, 4H). LC-MS: m/z 393.2 $(M+H)^+$.

Compound $N^2$,$N^4$-dicyclobutyl-6-(6-(trifluoromethyl)pyridin-2-yl)-1,3,5-triazine-2,4-diamine

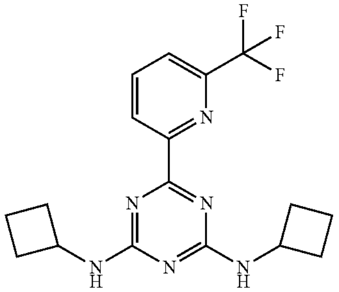 [SMILES: FC(F)(F)c1cccc(-c2nc(NC3CCC3)nc(NC3CCC3)n2)n1]

$^1$H NMR (400 MHz, $CDCl_3$): δ 8.67-8.38 (m, 1H), 7.99 (d, J=6.8 Hz, 1H), 7.78 (d, J=7.5 Hz, 1H), 5.52 (m 2H), 4.80-4.32 (m, 2H), 2.41 (s, 4H), 2.20 (s, 1H), 2.06-1.62 (m, 8H). LC-MS: m/z 365.2 $(M+H)^+$.

Compound $N^2$,$N^4$-di(bicyclo[3.1.0]hexan-3-yl)-6-(6-(trifluoromethyl)pyridin-2-yl)-1,3,5-triazine-2,4-diamine

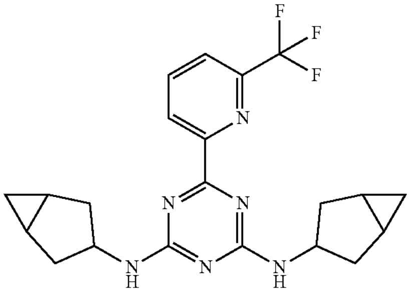 [SMILES: FC(F)(F)c1cccc(-c2nc(NC3CC4CC4C3)nc(NC3CC4CC4C3)n2)n1]

$^1$H NMR (400 MHz, $CD_3OD$): δ 8.66-8.57 (m, 1H), 8.14 (t, J=8.0 Hz, 1H), 7.92 (d, J=7.5 Hz, 1H), 4.60-4.44 (m, 2H), 2.44-2.21 (m, 4H), 1.80-1.69 (m, 4H), 1.35 (d, J=3.4 Hz, 4H), 0.69-0.53 (m, 2H), 0.32 (d, J=4.3 Hz, 2H). LC-MS: m/z 417.2 $(M+H)^+$.

Compound N,N'-dicyclopentyl-6-(6-trifluoromethyl-pyridin-2-yl)-[1,3,5]triazine-2,4-diamine

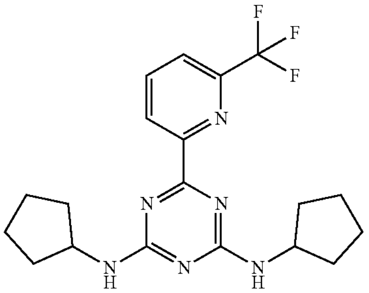 [SMILES: FC(F)(F)c1cccc(-c2nc(NC3CCCC3)nc(NC3CCCC3)n2)n1]

$^1$HNMR (400 MHz, $CD_3OD$): δ 8.60-8.68 (m, 1H), 8.20 (t, J=7.6 Hz, 1H), 7.95-8.01 (m, 1H), 4.29-4.55 (m, 2H), 2.00-2.15 (m, 4H), 1.75-1.84 (m, 4H), 1.51-1.74 (m, 8H). LC-MS: m/z 393.5 $(M+H)^+$.

Compound $N^2$,$N^4$-bis(3,3-difluorocyclopentyl)-6-(6-(trifluoromethyl)pyridin-2-yl)-1,3,5-triazine-2,4-diamine

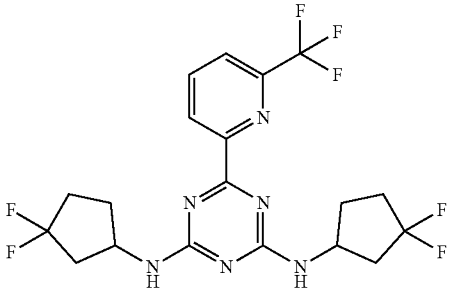 [SMILES: FC1(F)CCC(Nc2nc(NC3CCC(F)(F)C3)nc(-c3cccc(C(F)(F)F)n3)n2)C1]

$^1$H NMR (400 MHz, $CDCl_3$): δ 8.53 (m, 1H), 8.08-8.02 (m, 1H), 7.85-7.80 (m, 1H), 5.78-5.18 (m, 2H), 4.82-4.38 (m, 2H), 2.82-2.50 (m, 2H), 2.31-2.05 (m, 8H), 1.93-1.80 (m, 2H). LC-MS: m/z 465.2 $(M+H)^+$.

Compound $N^2$,$N^4$-bis(4,4-difluorocyclohexyl)-6-(6-(trifluoromethyl)pyridin-2-yl)-1,3,5-triazine-2,4-diamine

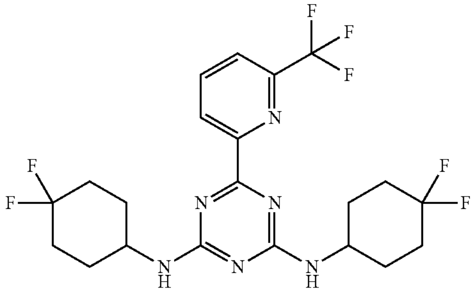 [SMILES: FC1(F)CCC(Nc2nc(NC3CCC(F)(F)CC3)nc(-c3cccc(C(F)(F)F)n3)n2)CC1]

$^1$H NMR (400 MHz, $CDCl_3$): δ 8.64-8.42 (m, 1H), 8.05 (t, J=7.8 Hz, 1H), 7.84 (d, J=6.6 Hz, 1H), 6.24-5.25 (m, 2H), 4.18-4.01 (m, 2H), 2.43-1.48 (m, 16H). LC-MS: m/z 493.2 $(M+H)^+$.

Compound N,N'-bis-(tetrahydro-pyran-4-yl)-6-(6-trifluoromethyl-pyridin-2-yl)-[1,3,5]triazine-2,4-diamine

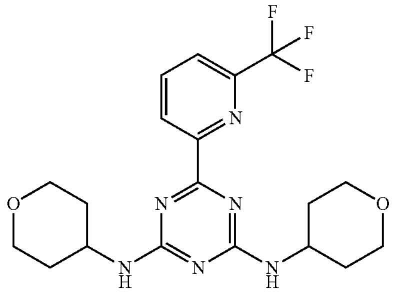 [SMILES: FC(F)(F)c1cccc(-c2nc(NC3CCOCC3)nc(NC3CCOCC3)n2)n1]

$^1$HNMR (400 MHz, DMSO-$d_6$): δ 7.43-8.55 (m, 5H), 3.82-4.15 (m, 6H), 3.48-3.50 (m, 4H), 1.75-1.87 (m, 4H), 1.46-1.60 (m, 4H). LC-MS: m/z 425.1 $(M+H)^+$.

Compound $N^2$,$N^4$-diisopropyl-6-(6-(trifluoromethyl)pyridin-2-yl)-1,3,5-triazine-2,4-diamine

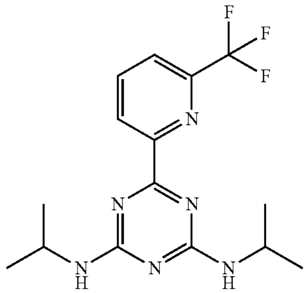 [SMILES: CC(C)Nc1nc(NC(C)C)nc(-c2cccc(C(F)(F)F)n2)n1]

$^1$H NMR (400 MHz, $CDCl_3$): δ 8.67-8.41 (m, 1H), 7.99 (s, 1H), 7.77 (d, J=7.7 Hz, 1H), 5.18 (m, 2H), 4.45-4.03 (m, 2H), 2.15 (m, 1H), 1.26 (d, J=4.5 Hz, 12H). LC-MS: m/z 341.2 $(M+H)^+$.

Compound $N^2$,$N^4$-di-tert-butyl-6-(6-(trifluoromethyl)pyridin-2-yl)-1,3,5-triazine-2,4-diamine

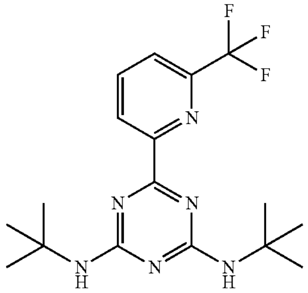 [SMILES: CC(C)(C)Nc1nc(NC(C)(C)C)nc(-c2cccc(C(F)(F)F)n2)n1]

$^1$H NMR (400 MHz, DMSO-$d_6$): δ 8.44-8.31 (m, 1H), 8.19-8.12 (m, 1H), 7.93 (d, J=7.3 Hz, 1H), 7.16-6.77 (m, 2H), 1.35 (s, 18H). LC-MS: m/z 369.2 $(M+H)^+$.

Compound N,N'-di-sec-butyl-6-(6-trifluoromethyl-pyridin-2-yl)-[1,3,5]triazine-2,4-diamine

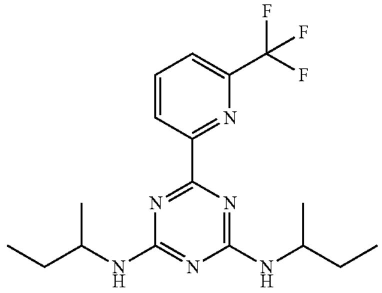 [SMILES: CCC(C)Nc1nc(NC(C)CC)nc(-c2cccc(C(F)(F)F)n2)n1]

$^1$HNMR (400 MHz, $CD_3OD$): δ 8.42-8.68 (m, 1H), 8.15-8.21 (m, 1H), 7.94 (d, J=8.0 Hz, 1H), 4.01-4.29 (m, 2H), 1.55-1.69 (m, 4H), 1.19-1.30 (m, 6H), 0.95-1.05 (m, 6H). LC-MS: m/z 369.5 $(M+H)^+$.

Compound N,N'-Di-sec-butyl-6-(6-trifluoromethyl-pyridin-2-yl)-[1,3,5]triazine-2,4-diamine

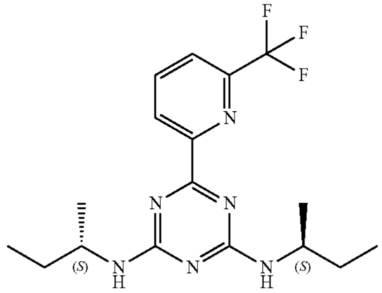

$^1$HNMR (400 MHz, $CD_3OD$): δ 8.72-8.79 (m, 1H), 8.38-8.43 (m, 1H), 8.20-8.23 (m, 1H), 4.13-4.45 (m, 2H), 1.67-1.74 (m, 4H), 1.29-1.33 (m, 6H), 1.01-1.05 (m, 6H). LC-MS: m/z 369.2 $(M+H)^+$.

Compound $N^2$,$N^4$-di-sec-butyl-6-(6-(trifluoromethyl)pyridin-2-yl)-1,3,5-triazine-2,4-diamine

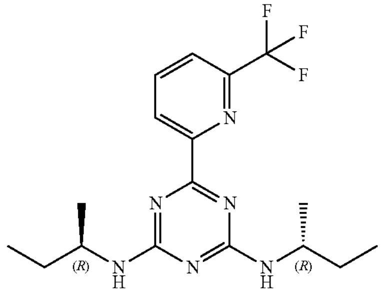

$^1$HNMR (400 MHz, $CD_3OD$): δ 8.72-8.79 (m, 1H), 8.38-8.43 (m, 1H), 8.20-8.23 (m, 1H), 4.13-4.45 (m, 2H), 1.67-1.74 (m, 4H), 1.29-1.33 (m, 6H), 1.01-1.05 (m, 6H). LC-MS: m/z 369.2 $(M+H)^+$.

Compound $N^2$—((R)-sec-butyl)-$N^4$—((S)-sec-butyl)-6-(6-(trifluoromethyl)pyridin-2-yl)-1,3,5-triazine-2,4-diamine

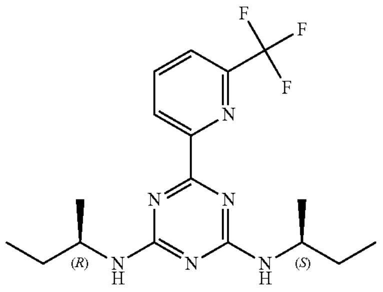

$^1$H NMR (400 MHz, $CD_3OD$): δ 8.59-8.65 (m, 1H), 8.15-8.19 (m, 1H), 7.94-7.95 (m, 1H), 4.06-4.24 (m, 2H), 1.58-1.65 (m, 4H), 1.21-1.26 (m, 6H), 0.98-1.01 (m, 6H). LC-MS: m/z 369.2 $(M+H)^+$.

Compound $N^2$,$N^4$-bis(3-methylbutan-2-yl)-6-(6-(trifluoromethyl)pyridin-2-yl)-1,3,5-triazine-2,4-diamine

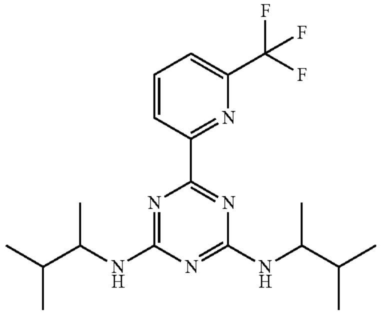 [SMILES: CC(C)C(C)Nc1nc(NC(C)C(C)C)nc(-c2cccc(C(F)(F)F)n2)n1]

$^1$H NMR (400 MHz, $CDCl_3$): δ 8.58-8.47 (m, 1H), 7.99 (t, J=7.2 Hz, 1H), 7.77 (d, J=7.7 Hz, 1H), 5.30-5.03 (m, 2H), 4.16-3.97 (m, 2H), 1.93-1.75 (m, 2H), 1.16 (d, J=6.6 Hz, 6H), 0.97-0.93 (m, 12H). LC-MS: m/z 397.2 $(M+H)^+$.

Compound $N^2$,$N^4$-bis((R)-3-methylbutan-2-yl)-6-(6-(trifluoromethyl)pyridin-2-yl)-1,3,5-triazine-2,4-diamine

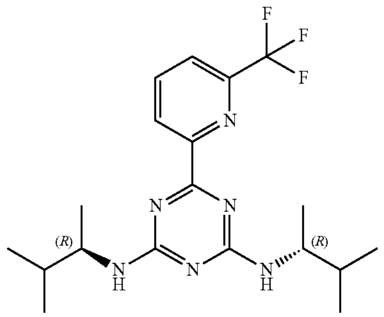

$^1$H NMR (400 MHz, DMSO-$d_6$): δ 8.46 (m, 1H), 8.21 (m, 1H), 8.00 (d, J=7.7 Hz, 1H), 7.36 (m, 2H), 3.90 (m 2H), 1.79 (m, 2H), 1.05 (t, J=7.6 Hz, 6H), 0.87 (t, J=7.6 Hz, 12H). LC-MS: m/z 397.2 $(M+H)^+$.

Compound $N^2$,$N^4$-bis((S)-3-methylbutan-2-yl)-6-(6-(trifluoromethyl)pyridin-2-yl)-1,3,5-triazine-2,4-diamine

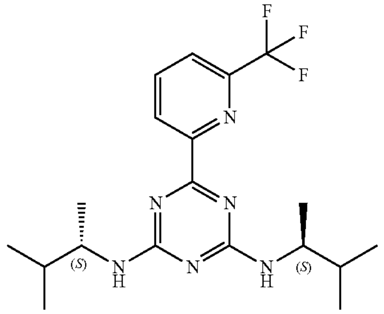

$^1$H NMR (400 MHz, DMSO-$d_6$): δ 8.46 (d, J=7.9 Hz, 1H), 8.24 (d, J=6.9 Hz, 1H), 8.03 (d, J=7.7 Hz, 1H), 7.55 (m, 2H), 4.25-3.78 (m, 1H), 1.93-1.65 (m, 1H), 1.15-1.00 (m, 6H), 0.89 (t, J=7.8 Hz, 12H). LC-MS: m/z 397.2 $(M+H)^+$.

Compound $N^2$,$N^4$-bis((R)-1-cyclopropylethyl)-6-(4-(trifluoromethyl)pyrimidin-2-yl)-1,3,5-triazine-2,4-diamine

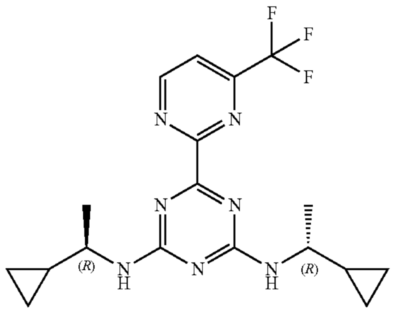

$^1$H NMR (400 MHz, $CDCl_3$): δ 9.20 (s, 1H), 7.74 (s, 1H), 5.46 (m, 2H), 3.59 (m, 2H), 1.26 (m, 8H), 0.91 (s, 2H), 0.65--0.27 (m, 8H). LC-MS: m/z 394.2 $(M+H)^+$.

Compound $N^2$—((R)-1-phenylethyl)-$N^4$—((S)-1-phenylethyl)-6-(6-(trifluoromethyl) pyridin-2-yl)-1,3,5-triazine-2,4-diamine

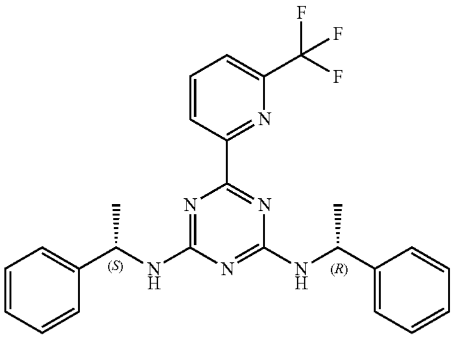

$^1$H NMR (400 MHz, $CDCl_3$): δ 8.52-8.33 (m, 1H), 8.05-7.86 (m, 1H), 7.76 (d, J=7.7 Hz, 1H), 7.52-7.18 (m, 10H), 5.82-5.40 (m, 2H), 5.37-4.92 (m, 2H), 1.65-1.39 (m, 6H). LC-MS: m/z 465.2 $(M+H)^+$.

Compound 6-(6-chloropyridin-2-yl)-$N^2$,$N^4$-bis((R)-1-cyclopropylethyl)-1,3,5-tria-zine-2,4-diamine

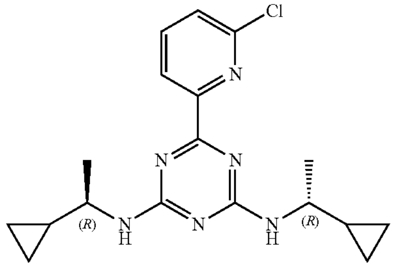

$^1$H NMR (400 MHz, $CD_3OD$): δ 8.37 (t, J=7.8 Hz, 1H), 8.02 (t, J=7.8 Hz, 1H), 7.71-7.65 (m, 1H), 3.74-3.54 (m, 2H), 1.32 (d, J=6.6 Hz, 6H), 1.08-0.94 (m, 2H), 0.63-0.21 (m, 8H). LC-MS: m/z 359.2 $(M+H)^+$.

Compound 6-(6-chloropyridin-2-yl)-$N^2$,$N^4$-di-isobutyl-1,3,5-triazine-2,4-diamine

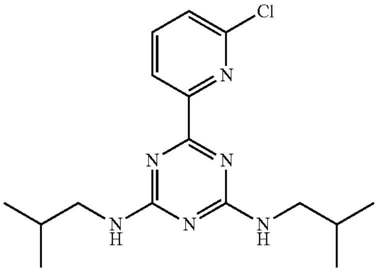 [SMILES: CC(C)CNc1nc(NCC(C)C)nc(-c2cccc(Cl)n2)n1]

$^1$HNMR (400 MHz, $CD_3OD$): δ8.5-8.38 (m, 1H), 8.0-7.9 (m, 1H), 7.6-7.5 (m, 1H), 3.35-3.16 (m, 4H), 2.0-1.9 (m, 2H), 1.0-0.9 (m, 12H). LC-MS: m/z 335.1 $(M+H)^+$.

Compound 6-(6-chloropyridin-2-yl)-$N^2$,$N^4$-diisopropyl-1,3,5-triazine-2,4-diamine

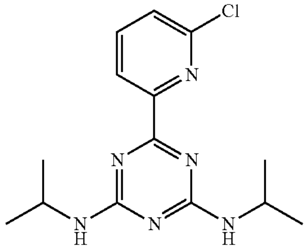 [SMILES: CC(C)Nc1nc(NC(C)C)nc(-c2cccc(Cl)n2)n1]

$^1$HNMR (400 MHz, $CD_3OD$): δ 8.25-8.19 (m, 1H), 7.81 (brs, 1H), 7.46 (d, J=7.6 Hz, 1H), 4.26-4.11 (m, 2H), 1.15 (d, J=6.0 Hz, 12H). LC-MS: m/z 307.1 $(M+H)^+$.

Compound $N^2$,$N^4$-di(but-3-en-1-yl)-6-phenyl-1,3,5-triazine-2,4-diamine

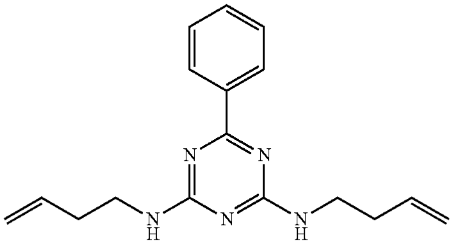 [SMILES: C=CCCNc1nc(NCCC=C)nc(-c2ccccc2)n1]

$^1$HNMR (400 MHz, $CD_3OD$): δ8.19-8.13 (m, 2H), 7.77-7.61 (m, 3H), 5.95-5.85 (m, 2H), 5.20-5.11 (m, 4H), 3.72-3.59 (m, 4H), 2.49-2.44 (m, 4H). LC-MS: m/z 296.3 $(M+H)^+$.

Compound $N^2$,$N^4$-di(3-oxabicyclo[3.1.0]hexan-6-yl)-6-phenyl-1,3,5-triazine-2,4-diamine

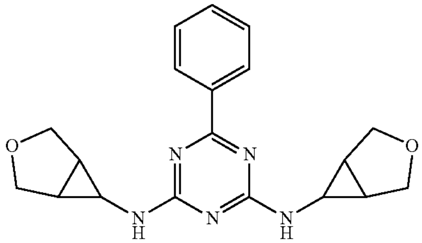 [SMILES: c1ccc(-c2nc(NC3C4COCC43)nc(NC3C4COCC43)n2)cc1]

$^1$HNMR (400 MHz, $CD_3OD$): δ 8.35-8.1 (m, 2H), 8.3-8.2 (m, 1H), 7.7-7.6 (m, 2H), 4.1-4.0 (m, 4H), 3.85-3.7 (m, 4H), 2.9-2.55 (m, 2H), 2.1-2.0 (m, 2H). LC-MS: m/z 352.2 $(M+H)^+$.

Compound $N^2$,$N^4$-bis((1S,3S)-3-(4-fluorophenyl)cyclobutyl)-6-(6-(trifluoromethyl)pyridin-2-yl)-1,3,5-triazine-2,4-diamine To a mixture of 2,4-dichloro-6-(6-(trifluoromethyl)pyridine-2-yl)-1,3,5-triazine (600 mg, 2.0 mmol, 1.0 eq) and (1s,3s)-3-(4-fluorophenyl)cyclobutanamine (726 mg, 4.4 mmol, 2.2 eq) in THF (12 mL) at r.t. were added CsF (0.6 g, 2.0 mmol, 1 eq.) and DIPEA (0.7 mL, 4.0 mmol, 2 eq). The resulting mixture was stirred at 60° C. overnight and then filtered. The filtrate was concentrated and purified via standard techniques to afford the desired product.

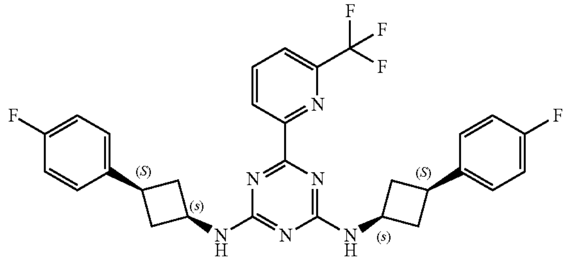

$^1$H NMR (400 MHz, $CDCl_3$) δ 8.48 (m, 1H), 7.95 (m, 1H), 7.75 (d, J=7.6 Hz, 1H), 7.16-7.04 (m, 4H), 6.93 (t, J=8.5 Hz, 4H), 6.46-5.32 (m, 2H), 4.47 (m, 2H), 3.28-3.02 (m, 2H), 2.81 (d, J=7.6 Hz, 4H), 2.01 (m, 4H). LC-MS: m/z 553.2 $(M+H)^+$.

Compound $N^2$,$N^4$-bis((1R,3R)-3-(4-fluorophenyl)cyclobutyl)-6-(6-(trifluoromethyl)pyridin-2-yl)-1,3,5-triazine-2,4-diamine

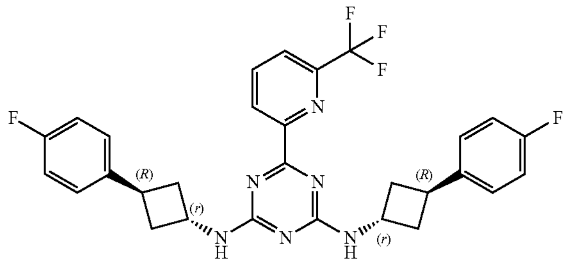

$^1$H NMR (400 MHz, $CDCl_3$) δ 8.56 (m, 1H), 8.01 (s, 1H), 7.80 (s, 1H), 7.25-6.93 (m, 8H), 5.64 (m, 2H), 4.82-4.37 (m, 2H), 3.68 (s, 1H), 3.24 (s, 1H), 2.89 (m, 2H), 2.54 (m, 4H), 2.09-1.98 (m, 2H). LC-MS: m/z 553.2 $(M+H)^+$.

Compound 6-(6-(Trifluoromethyl)pyridin-2-yl)-$N^2$,$N^4$-bis((R)-1,1,1-trifluoropropan-2-yl)-1,3,5-triazine-2,4-diamine

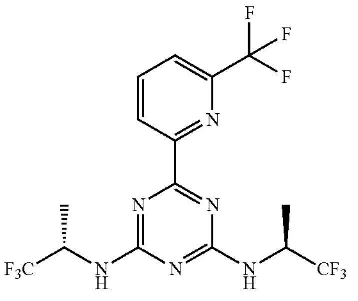 [SMILES: C[C@H](Nc1nc(N[C@@H](C)C(F)(F)F)nc(-c2cccc(C(F)(F)F)n2)n1)C(F)(F)F]

1H NMR (400 MHz, $CDCl_3$) δ 8.62 (m, 1H), 8.03 (d, J=7.8 Hz, 1H), 7.83 (d, J=7.7 Hz, 1H), 5.59 (d, J=9.4 Hz, 1H), 5.34 (m, 3H), 1.42 (m, 6H); LC-MS: m/z 449 $(M+H)^+$.

Compound $N^2$,$N^4$-bis((S)-1,1,1-trifluorobutan-2-yl)-6-(6-(trifluoromethyl)pyridin-2-yl)-1,3,5-triazine-2,4-diamine

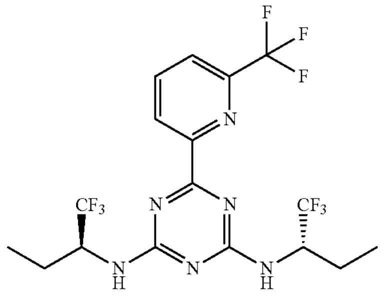

$^1$H NMR (400 MHz, $CDCl_3$) δ 8.55 (d, J=8 Hz, 1H), 8.06-8.02 (m, 1H), 7.83 (d, J=8 Hz, 1H), 5.64-5.15 (m, 2H), 4.93-4.71 (m, 2H), 2.0-1.94 (m, 2H), 1.69-1.57 (m, 2H), 1.08-1.02 (m, 6H). LCMS: m/z 477 $(M+H)^+$.

Compound $N^2$,$N^4$-bis((2,2-difluorocyclopropyl)methyl)-6-(6-(trifluoromethyl)pyridin-2-yl)-1,3,5-triazine-2,4-diamine

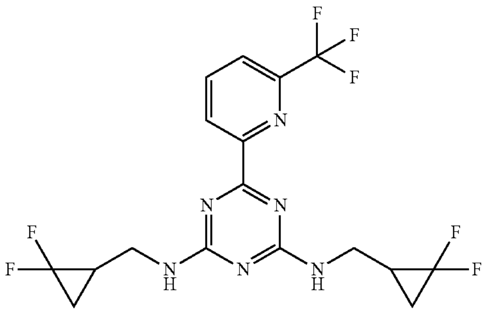 [SMILES: FC(F)(F)c1cccc(-c2nc(NCC3CC3(F)F)nc(NCC3CC3(F)F)n2)n1]

$^1$H NMR (400 MHz, $CDCl_3$) δ 8.59-8.51 (m, 1H), 8.02 (bs, 1H), 7.80 (d, J=7.6 Hz, 1H), 5.70-5.38 (m, 2H), 3.81-3.41 (m, 4H), 2.04-1.92 (m, 2H), 1.73-1.59 (m, 2H), 1.28-1.23 (m, 2H). LC-MS: m/z 437 $(M+H)^+$.

Compound $N^2$,$N^4$-bis((3,3-difluorocyclobutyl)methyl)-6-(6-(trifluoromethyl)pyridin-2-yl)-1,3,5-triazine-2,4-diamine

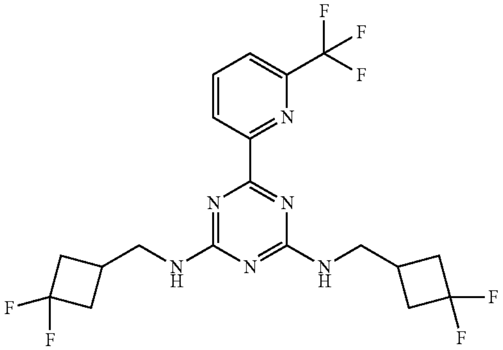 [SMILES: FC1(F)CC(CNc2nc(NCC3CC(F)(F)C3)nc(-c3cccc(C(F)(F)F)n3)n2)C1]

$^1$H NMR (400 MHz, $CDCl_3$) δ 8.54 (m, 1H), 8.02 (m, 1H), 7.80 (d, J=7.2 Hz, 1H), 5.84-5.11 (m, 2H), 3.95-3.27 (m, 4H), 2.94-1.99 (m, 10H). LC-MS: m/z 465 $(M+H)^+$.

Compound $N^2$,$N^4$-bis(3,3-difluorocyclobutyl)-6-(6-(trifluoromethyl)pyridin-2-yl)-1,3,5-triazine-2,4-diamine

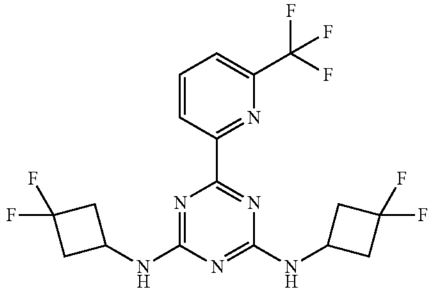 [SMILES: FC1(F)CC(Nc2nc(NC3CC(F)(F)C3)nc(-c3cccc(C(F)(F)F)n3)n2)C1]

$^1$H NMR (400 MHz, $CDCl_3$) δ8.56-8.48 (m, 1H), 8.04-8.02 (m, 1H), 7.82-7.80 (m, 1H), 5.76-5.41 (m, 2H), 4.52-4.37 (m, 2H), 3.06 (bs, 4H), 2.63-2.61 (m, 4H). LC-MS: m/z 437.1 $(M+H)^+$.

Compound $N^2$,$N^4$-bis((S)-3,3-difluorocyclopentyl)-6-(6-(trifluoromethyl)pyridin-2-yl)-1,3,5-triazine-2,4-diamine

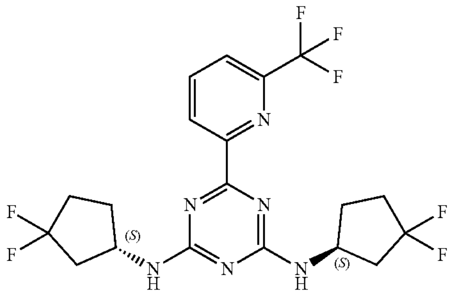

$^1$H NMR (400 MHz, $CDCl_3$) δ 8.54-8.38 (m, 1H), 7.95 (m 1H), 7.73 (m, 1H), 5.60-5.25 (m, 2H), 4.63-4.42 (m, 2H), 2.68-2.52 (m, 2H), 2.16-1.77 (m, 10H). LCMS: m/z 465.1 $(M+H)^+$.

Compound $N^2$,$N^4$-bis((R)-3,3-difluorocyclopentyl)-6-(6-(trifluoromethyl)pyridin-2-yl)-1,3,5-triazine-2,4-diamine

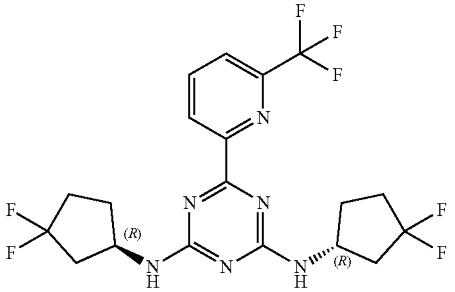

$^1$H NMR (400 MHz, $CDCl_3$) δ 57-8.48 (m, 1H), 8.02-8.01 (m, 1H), 7.80 (s, 1H), 5.66-5.32 (m, 2H), 4.71-4.49 (m, 2H), 2.64-2.61 (m, 2H), 2.31-2.05 (m, 8H), 1.86-1.79 (m, 2H). LC-MS: m/z 465 $(M+H)^+$.

Compound N2-((R)-3,3-difluorocyclopentyl)-N4-((S)-3,3-difluorocyclopentyl)-6-(6-(trifluoromethyl)pyridin-2-yl)-1,3,5-triazine-2,4-diamine

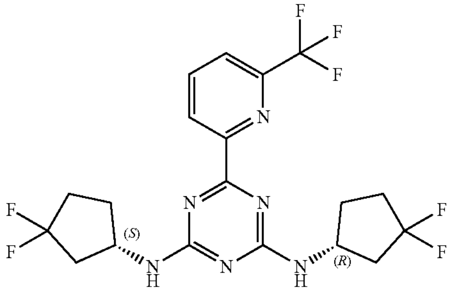

$^1$H NMR (400 MHz, $CDCl_3$) δ 8.56-8.48 (m, 1H), 8.02 (d, J=8 Hz, 1H), 7.80-7.81 (m, 1H), 5.66-5.32 (m, 2H), 4.71-4.54 (m, 2H), 2.65-2.60 (m, 2H), 2.31-2.05 (m, 8H), 1.86-1.81 (m, 2H). LC-MS: m/z 465 $(M+H)^+$.

Compound $N^2$,$N^4$-bis(4,4-difluorocyclohexyl)-6-(4-(trifluoromethyl)pyridin-2-yl)-1,3,5-triazine-2,4-diamine

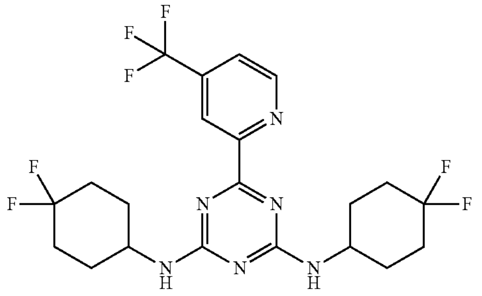 [SMILES: FC1(F)CCC(Nc2nc(NC3CCC(F)(F)CC3)nc(-c3cc(C(F)(F)F)ccn3)n2)CC1]

$^1$H NMR (400 MHz, $CDCl_3$) δ 8.70-8.62 (m, 2H), 7.62 (d, 1H), 6.70-6.43 (m, 1H), 5.22-3.95 (m, 3H), 2.11-1.69 (m, 16H). LCMS: m/z 493(M+H)$^+$.

Compound $N^2$,$N^4$-bis((R)-1-cyclopropylethyl)-6-(6-methoxypyridin-2-yl)-1,3,5-triazine-2,4-diamine

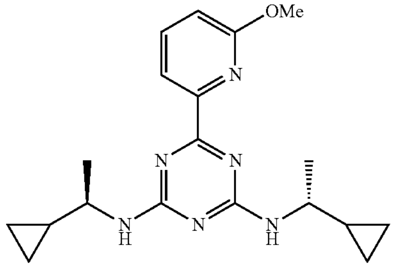

$^1$H NMR (400 MHz, $CDCl_3$) δ 8.18-7.65 (m, 2H), 7.15-6.98 (m, 1H), 6.34-5.67 (m, 2H), 4.15 (s, 3H), 3.71-3.48 (m, 2H), 1.33-1.25 (m, 6H), 0.98-0.86 (m, 2H), 0.62-0.26 (m, 8H). LCMS: m/z 355.2 (M+H)$^+$.

Compound $N^2$,$N^4$-bis(3,3-difluorocyclobutyl)-6-(6-(trifluoromethoxy)pyridin-2-yl)-1,3,5-triazine-2,4-diamine

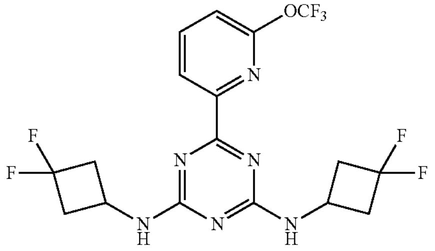 [SMILES: FC1(F)CC(Nc2nc(NC3CC(F)(F)C3)nc(-c3cccc(OC(F)(F)F)n3)n2)C1]

$^1$H NMR (400 MHz, $CDCl_3$) δ 8.34-8.27 (m, 1H), 7.96-7.92 (m, 1H), 7.22 (d, J=8 Hz, 1H), 5.83-5.41 (m, 2H), 4.49-4.35 (m, 2H), 3.05 (d, J=4 Hz, 4H), 2.63-2.54 (m, 4H). LCMS: m/z 453 (M+H)$^+$.

Compound $N^2$,$N^4$-bis(3,3-difluorocyclopentyl)-6-(6-(trifluoromethoxy)pyridin-2-yl)-1,3,5-triazine-2,4-diamine

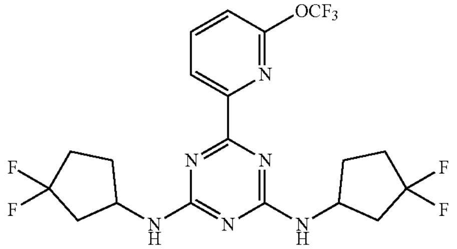 [SMILES: FC1(F)CCC(Nc2nc(NC3CCC(F)(F)C3)nc(-c3cccc(OC(F)(F)F)n3)n2)C1]

$^1$H NMR (400 MHz, $CDCl_3$) δ 8.33-8.26 (m, 1H), 7.95-7.92 (m, 1H), 7.22 (d, J=8 Hz, 1H), 5.65-5.28 (m, 2H), 4.67-4.52 (m, 2H), 2.64-2.59 (m, 2H), 2.30-1.79 (m, 10H). LCMS: m/z 481 (M+H)$^+$.

Compound $N^2$,$N^4$-bis(4,4-difluorocyclohexyl)-6-(6-(trifluoromethoxy)pyridin-2-yl)-1,3,5-triazine-2,4-diamine

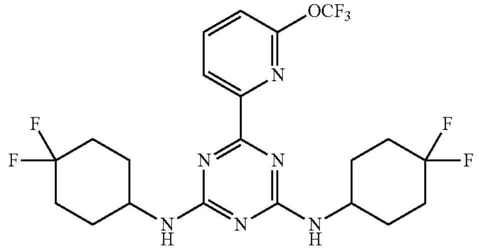 [SMILES: FC1(F)CCC(Nc2nc(NC3CCC(F)(F)CC3)nc(-c3cccc(OC(F)(F)F)n3)n2)CC1]

$^1$H NMR (400 MHz, $CDCl_3$) δ 8.31 (d, J=8 Hz, 1H), 7.98-7.92 (m, 1H), 7.24 (d, J=12 Hz, 1H), 5.44-5.08 (m, 2H), 4.16-3.98 (m, 2H), 2.15-1.65 (m, 16H). LCMS: m/z 509 (M+H).$^+$

Compound $N^2$,$N^4$-bis(4,4-difluorocyclohexyl)-6-(3-fluoro-6-methoxypyridin-2-yl)-1,3,5-triazine-2,4-diamine

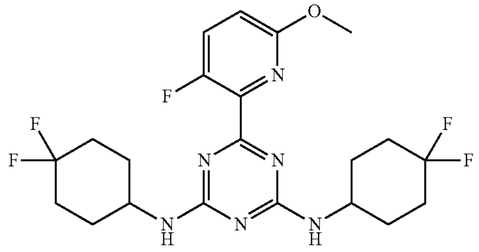 [SMILES: COc1ccc(F)c(-c2nc(NC3CCC(F)(F)CC3)nc(NC3CCC(F)(F)CC3)n2)n1]

$^1$H NMR (400 MHz, $CDCl_3$) δ 7.45-7.41 (t, 1H), 6.84 (d, 1H), 5.43-5.07 (m, 2H), 4.08-3.98 (m, 5H), 2.11-2.01 (m, 8H), 1.96-1.89 (m, 4H), 1.87-1.83 (m, 4H). LCMS: m/z 473(M+H)$^+$.

The following compounds were prepared by following the procedure described in Scheme 1 above.

| Compound No. | Name | Structure | LCMS Expected MW | LCMS Found (M + 1)+ |
|---|---|---|---|---|
| 72 | $N^2$,$N^4$-di((1R,5S)-3-oxabicyclo[3.1.0]hexan-6-yl)-6-(6-chloropyridin-2-yl)-1,3,5-triazine-2,4-diamine | 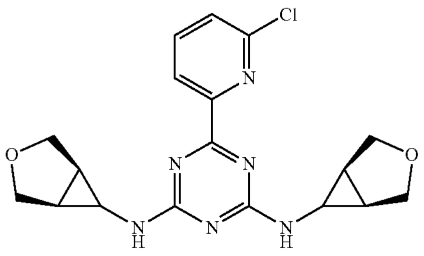 [SMILES: Clc1cccc(-c2nc(NC3[C@H]4COC[C@@H]34)nc(NC3[C@H]4COC[C@@H]34)n2)n1] | 386.1 | 387.1 |
| 73 | 6-(6-aminopyridin-2-yl)-$N^2$,$N^4$-dineopentyl-1,3,5-triazine-2,4-diamine | 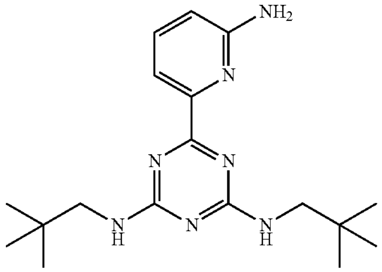 [SMILES: CC(C)(C)CNc1nc(NCC(C)(C)C)nc(-c2cccc(N)n2)n1] | 343.2 | 344.2 |
| 74 | 6-(6-aminopyridin-2-yl)-$N^2$,$N^4$-diisobutyl-1,3,5-triazine-2,4-diamine | 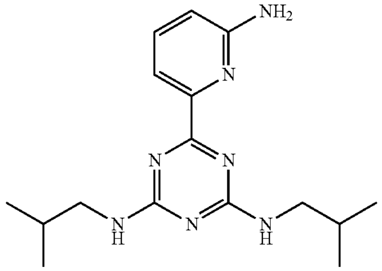 [SMILES: CC(C)CNc1nc(NCC(C)C)nc(-c2cccc(N)n2)n1] | 315.2 | 316.2 |
| | 6-(6-aminopyridin-2-yl)-$N^2$,$N^4$-bis(3-methylbutan-2-yl)-1,3,5-triazine-2,4-diamine | 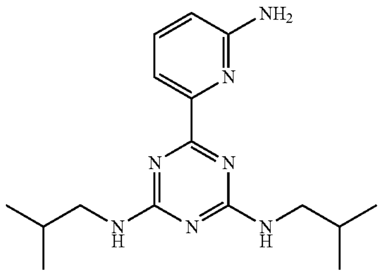 [SMILES: CC(C)CNc1nc(NCC(C)C)nc(-c2cccc(N)n2)n1] | 343.2 | 344.2 |

Example 2. Preparation of Di-aliphatic Triazine Compounds of Formula E Wherein Ring A is substituted Pyridin-2-yl or Phenyl. The compounds of this Example are prepared by general Scheme 2, set forth below.

Scheme 2

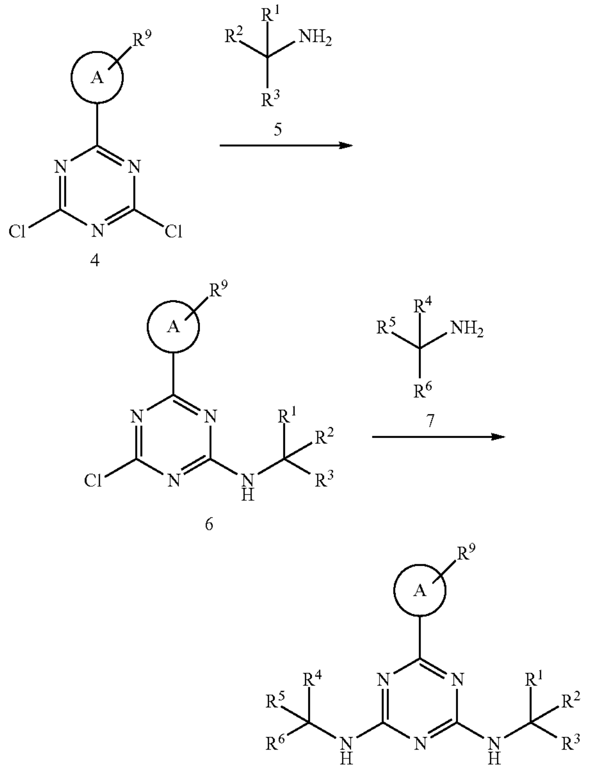

Formula E

Step 1: Preparation of (R)-4-chloro-N-(1-cyclopropylethyl)-6-(6-(trifluoromethyl) pyridin-2-yl)-1,3,5-triazin-2-amine. To a mixture of 2,4-dichloro-6-(6-(trifluoromethyl) pyridine-2-yl)-1,3,5-triazine (600 mg, 2.0 mmol, 1.0 eq) and (R)-1-cyclopropylethanamine hydrochloride salt (268 mg, 2.2 mmol, 1.1 eq) in THF (6 mL) were added CsF (608 mg, 4.0 mmol, 2 eq) and DIPEA (0.7 mL, 4.0 mmol, 2 eq) at room temperature. The mixture was stirred at 40° C. overnight and then filtered. The filtrate was concentrated under reduced pressure and the residue was purified by a standard method to give the desired product.

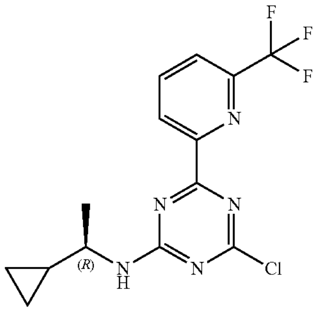

LC-MS: m/z 344.1 $(M+H)^+$.

Step 2: Preparation of $N^2$—((R)-1-cyclopropylethyl)-N4-(pentan-2-yl)-6-(6-(trifluoromethyl)pyridin-2-yl)-1,3,5-triazine-2,4-diamine. To a mixture of (R)-4-chloro-N-(1-cyclopropylethyl)-6-(6-(trifluoromethyl)pyridin-2-yl)-1,3,5-triazin-2-amine (80 mg, 0.23 mmol, 1.0 eq) and pentan-2-amine (25 mg, 0.28 mmol, 1.2 eq) in THF (2 mL) were added CsF (70 mg, 0.46 mmol, 2 eq) and DIPEA (0.08 mL, 0.46 mmol, 2 eq) at room temperature. The mixture was stirred at 60° C. overnight and filtered. The filtrate was concentrated under reduced pressure and then purified by a standard method to give the desired product.

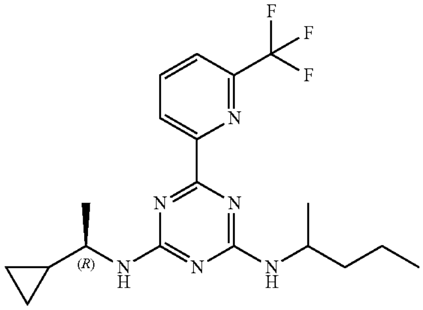

$^1H$ NMR (400 MHz, DMSO-$d_6$): δ 8.54-8.42 (m, 1H), 8.23 (t, J=7.8 Hz, 1H), 8.02 (d, J=7.7 Hz, 1H), 7.65 (d, J=8.4 Hz, 1H), 7.52 (t, J=9.5 Hz, 1H), 4.27-3.96 (m, 1H), 3.65-3.47 (m, 1H), 1.60-1.46 (m, 1H), 1.41-1.29 (m, 3H), 1.22 (d, 6.5 Hz, 3H), 1.12 (d, J=6.1 Hz, 3H), 1.01-0.96 (m, 1H), 0.88 (t, J=7.1 Hz, 3H), 0.50-0.29 (m, 3H), 0.26-0.07 (m, 1H). LC-MS: m/z 395.2 $(M+H)^+$.

The procedure set forth in Example 2 was used to produce the following compounds using the appropriate starting materials.

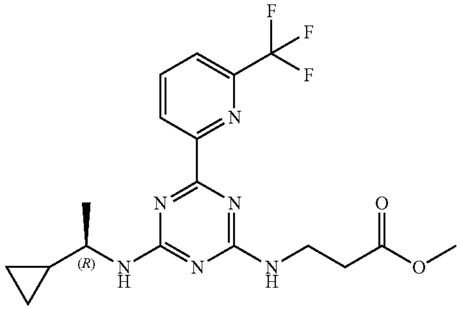

$^1H$ NMR (400 MHz, $CDCl_3$): δ 8.52 (m, 1H), 8.00 (t, J=7.6 Hz, 1H), 7.78 (d, J=7.7 Hz, 1H), 5.63 (m, 2H), 3.73 (m, 9H), 2.66 (d, J=5.9 Hz, 2H), 1.29 (m, 3H), 1.01-0.79 (m, 1H), 0.60-0.17 (m, 4H). LC-MS: m/z 411.2 $(M+H)^+$.

Compound (R)—$N^2$-(1-cyclopropylethyl)-$N^4$-(4,4-difluorocyclohexyl)-6-(6-(trifluoro methyl)pyridin-2-yl)-1,3,5-triazine-2,4-diamine

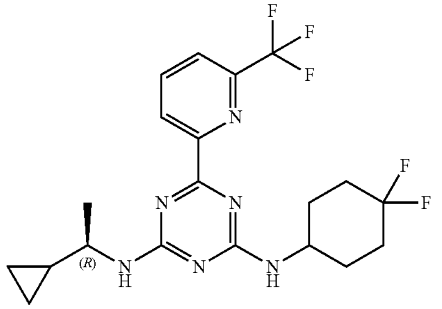

$^1$H NMR (400 MHz, $CDCl_3$): δ 8.66-8.39 (m, 1H), 8.02 (t, J=7.7 Hz, 1H), 7.80 (d, J=7.7 Hz, 1H), 5.34 (m, 2H), 4.11 (m, 1H), 3.63 (m, 1H), 2.32-1.54 (m, 9H), 1.29 (m, 3H), 0.95 (s, 1H), 0.70-0.16 (m, 4H). LC-MS: m/z 443.2 $(M+H)^+$.

Compound $N^2$—((R)-1-cyclopropylethyl)-$N^4$-(6,6-difluorospiro[3.3]heptan-2-yl)-6-(6-(trifluoromethyl)pyridin-2-yl)-1,3,5-triazine-2,4-diamine

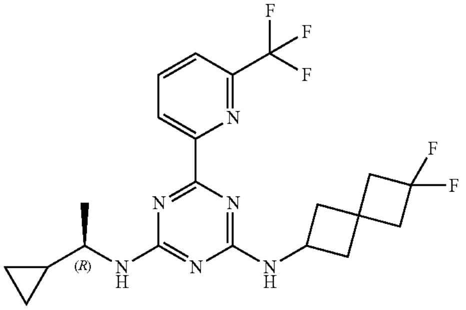

$^1$H NMR (400 MHz, $CDCl_3$): δ 8.54-8.49 (m, 1H), 8.01 (t, J=7.3 Hz, 1H), 7.78 (d, J=7.7 Hz, 1H), 5.60-5.27 (m, 2H), 4.57-4.37 (m, 1H), 3.67-3.57 (m, 1H), 2.70-2.65 (m, 2H), 2.57 (m, 3H), 2.22-1.92 (m, 4H), 1.30 (d, J=5.8 Hz, 2H), 0.93 (s, 1H), 0.54-0.29 (m, 4H). LC-MS: m/z 455.2 $(M+H)^+$.

Compound $N^2$-((1R,3R,5R,7R)-adamantan-2-yl)-$N^4$—((R)-1-cyclopropylethyl)-6-(6-(trifluoromethyl)pyridin-2-yl)-1,3,5-triazine-2,4-diamine

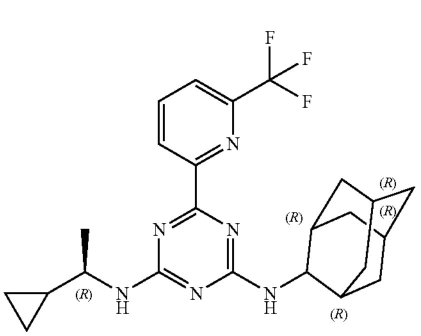

$^1$H NMR (400 MHz, $CDCl_3$): δ 8.63-8.34 (m, 1H), 8.00 (t, J=7.8 Hz, 1H), 7.78 (d, J=7.7 Hz, 1H), 5.57 (m, 2H), 4.21 (m, 1H), 3.85-3.32 (m, 1H), 2.22-1.57 (m, 15H), 1.25 (m, 4H), 0.90 (m, 1H), 0.66-0.24 (m, 4H). LC-MS: m/z 459.2 $(M+H)^+$.

Compound (R)—$N^2$-(1-cyclopropylethyl)-$N^4$-(dicyclopropylmethyl)-6-(6-(trifluoro methyl)pyridin-2-yl)-1,3,5-triazine-2,4-diamine

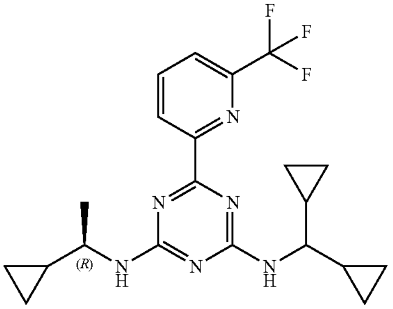

$^1$H NMR (400 MHz, $CDCl_3$): δ 8.49 (d, J=7.5 Hz, 1H), 7.99 (t, J=7.9 Hz, 1H), 7.77 (d, J=7.7 Hz, 1H), 5.71-5.05 (m, 2H), 3.59 (m, 2H), 1.25 (m, 3H), 1.07-0.80 (m, 3H), 0.64-0.19 (m, 12H). LC-MS: m/z 419.2 $(M+H)^+$.

Compound $N^2$—((R)-1-cyclopropylethyl)-6-(6-(trifluoromethyl)pyridin-2-yl)-$N^4$-(1,1,1-trifluoropropan-2-yl)-1,3,5-triazine-2,4-diamine

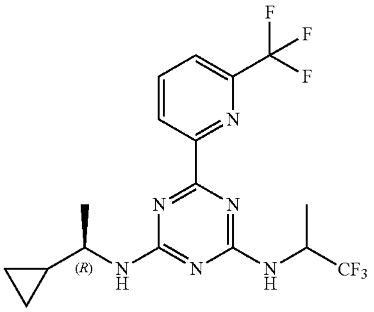

$^1$H NMR (400 MHz, $CDCl_3$): δ 8.53 (s, 1H), 8.01 (s, 1H), 7.80 (d, J=7.6 Hz, 1H), 5.91-4.65 (m, 3H), 3.67 (m, 1H), 1.51-1.15 (m, 6H), 0.93 (s, 1H), 0.74-0.10 (m, 4H). LC-MS: m/z 421.1 $(M+H)^+$.

Compound (R)—$N^2$-(1-cyclopropylethyl)-$N^4$-(2,3-dihydro-1H-inden-2-yl)-6-(6-(trifluoromethyl)pyridin-2-yl)-1,3,5-triazine-2,4-diamine

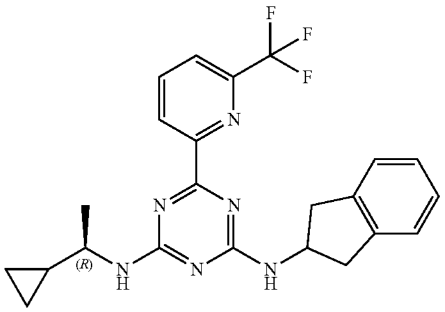

$^1H$ NMR (400 MHz, $CDCl_3$): δ 8.61-8.46 (m, 1H), 7.99 (t, J=8.1 Hz, 1H), 7.77 (d, J=7.7 Hz, 1H), 7.26-7.17 (m, 4H), 5.75-5.30 (m, 2H), 5.11-4.75 (m, 1H), 3.78-3.54 (m, 1H), 3.46-3.31 (m, 2H), 2.94-2.88 (m, 2H), 1.32 (d, J=6.4 Hz, 3H), 1.24-1.19 (m, 1H), 0.98-0.86 (m, 1H), 0.52-043(m, 3H), 0.29 (s, 1H). LC-MS: m/z 441.2 $(M+H)^+$.

Compound (R)—$N^2$-(1-cyclopropylethyl)-$N^4$-(prop-2-yn-1-yl)-6-(6-(trifluoromethyl) pyridin-2-yl)-1,3,5-triazine-2,4-diamine

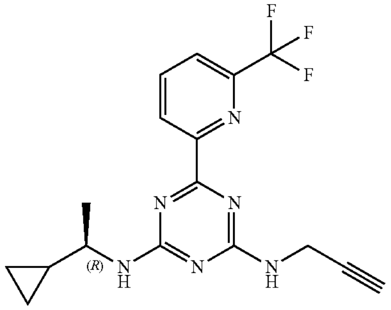

$^1H$ NMR (400 MHz, $CDCl_3$): δ 8.55 (m, 1H), 8.01 (t, J=7.8 Hz, 1H), 7.79 (d, J=7.7 Hz, 1H), 5.94-5.12 (m, 2H), 4.30 (m 2H), 3.59 (m, 1H), 2.23 (s, 1H), 2.01 (s, 3H), 0.90 (m, 1H), 0.59-0.16 (m, 4H). LC-MS: m/z 363.1 $(M+H)^+$.

Compound (R)—$N^2$-(1-cyclopropylethyl)-$N^4$-(2-phenoxyethyl)-6-(6-(trifluoromethyl)pyridin-2-yl)-1,3,5-triazine-2,4-diamine

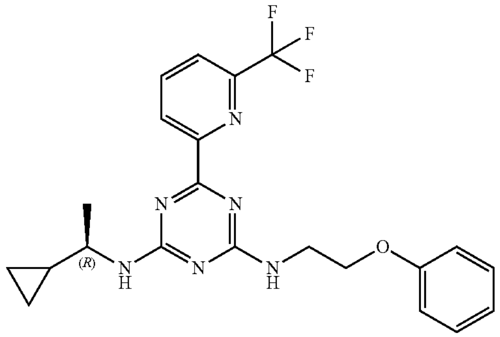

$^1H$ NMR (400 MHz, $CDCl_3$): δ 8.43 (d, J=8.0 Hz, 1H), 7.93 (t, J=7.6 Hz, 1H), 7.71 (d, J=7.7 Hz, 1H), 7.34-7.18 (m, 2H), 7.00-6.69 (m, 3H), 6.03-5.08 (m, 2H), 4.07 (s, 2H), 3.94-3.71 (m, 2H), 3.53 (d, J=6.8 Hz, 1H), 1.34-1.04 (m, 4H), 0.35 (m, 4H). LC-MS: m/z 445.2 $(M+H)^+$.

Compound $N^2$—((R)-1-cyclopropylethyl)-$N^4$-(1-methoxypropan-2-yl)-6-(6-(trifluoro methyl)pyridin-2-yl)-1,3,5-triazine-2,4-diamine

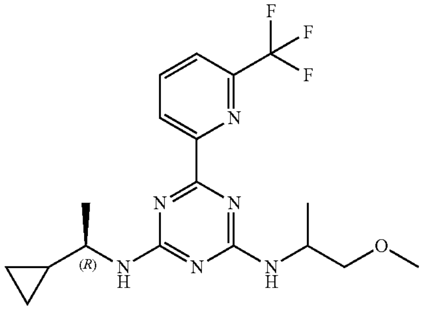

$^1H$ NMR (400 MHz, $CDCl_3$): δ 8.51 (m, 1H), 7.99 (t, J=7.9 Hz, 1H), 7.77 (d, J=7.7 Hz, 1H), 5.55-5.33 (m, 2H), 4.45-4.29 (m, 2H), 3.68-3.39 (m, 4H), 1.85 (s, 3H), 1.28-0.93 (m, 6H), 0.60-0.27 (m, 3H). LC-MS: m/z 397.2 $(M+H)^+$.

Compound (R)—$N^2$-(1-cyclopropylethyl)-$N^4$-(1,3-dimethoxypropan-2-yl)-6-(6-(trifluoromethyl)pyridin-2-yl)-1,3,5-triazine-2,4-diamine

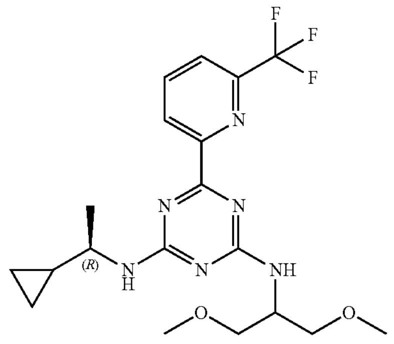

$^1$H NMR (400 MHz, $CDCl_3$): 8.47 (m, 1H), 8.05-7.80 (m, 1H), 7.71 (d, J=7.7 Hz, 1H), 5.90-5.06 (m, 2H), 4.57-4.05 (m, 1H), 3.65-3.38 (m, 4H), 3.33 (m, 6H), 1.23 (m, 4H), 0.84 (m, 1H), 0.61-0.05 (m, 4H). LC-MS: m/z 427.2 $(M+H)^+$.

Compound 2-((4-(((R)-1-cyclopropylethyl)amino)-6-(6-(trifluoromethyl)pyridine-2-yl)-1,3,5-triazin-2-yl)amino)propanenitrile

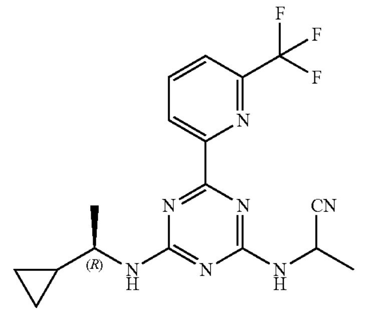

$^1$H NMR (400 MHz, $CDCl_3$): δ 8.56 (m, 1H), 8.03 (t, J=7.8 Hz, 1H), 7.81 (d, J=7.7 Hz, 1H), 5.52 (m, 2H), 5.16-4.85 (m, 1H), 3.76-3.44 (m, 1H), 1.72-1.55 (m, 3H), 1.39-1.21 (m, 3H), 0.95 (s, 1H), 0.65-0.16 (m, 4H). LC-MS: m/z 378.2 $(M+H)^+$.

Compound (R)-2-(4-(1-cyclopropylethylamino)-6-(6-(trifluoromethyl)pyridin-2-yl)-1,3,5-triazin-2-ylamino)-2-methylpropanenitrile

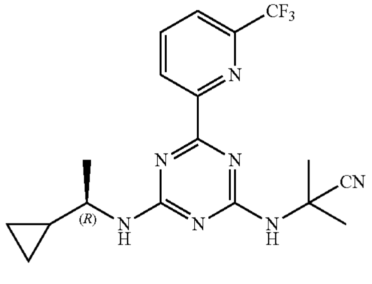

$^1$H NMR (400 MHz, $CDCl_3$): δ 8.56 (d, J=8.2 Hz, 1H), 8.03 (t, J=7.7 Hz, 1H), 7.80 (d, J=7.7 Hz, 1H), 5.71-5.54 (m, 2H), 3.70 (m, 1H), 1.82 (s, 6H), 1.36-1.25 (m, 4H), 0.97 (d, J=7.7 Hz, 1H), 0.62-0.26 (m, 4H). LC-MS: m/z 392 $(M+H)^+$.

Compound $N^2$—((R)-1-cyclopropylethyl)-$N^4$-(tetrahydrofuran-3-yl)-6-(6-(trifluoromethyl)pyridin-2-yl)-1,3,5-triazine-2,4-diamine

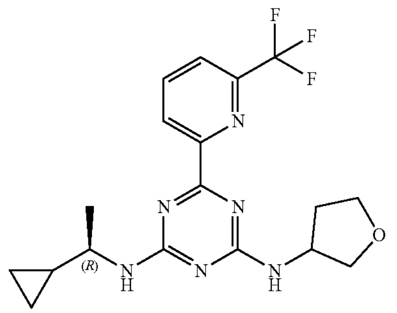

$^1$H NMR (400 MHz, $CDCl_3$): δ 8.57-8.47 (m, 1H), 7.99 (t, J=7.2 Hz, 1H), 7.78 (d, J=7.6 Hz, 1H), 5.73-5.32 (m, 2H), 4.79-4.60 (m, 1H), 3.99-3.49 (m, 5H), 2.29 (m, 2H), 1.91 (m, 1H), 1.30 (m, 3H), 0.56-0.23 (m, 4H). LC-MS: m/z 395.2 $(M+H)^+$.

Compound (1S,2S)-2-(4-((R)-1-cyclopropylethyl-amino)-6-(6-(trifluoro-methyl)pyridin-2-yl)-1,3,5-triazin-2-ylamino)cyclohexanol

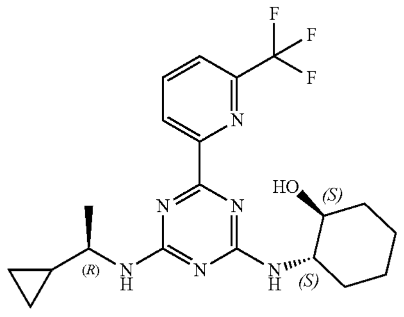

$^1$H NMR (400 MHz, $CDCl_3$): δ 8.48 (d, J=7.4 Hz, 1H), 8.01 (t, J=7.8 Hz, 1H), 7.79 (d, J=7.7 Hz, 1H), 5.67-5.28 (m, 2H), 3.65 (m, 4H), 2.09 (s, 3H), 1.47-1.23 (m, 8H), 0.92 (s, 1H), 0.62-0.40 (m, 3H), 0.30 (s, 1H). LC-MS: m/z 423.2 $(M+H)^+$.

Compound (1R,2S)-2-(4-((R)-1-cyclopropylethyl-amino)-6-(6-(trifluoromethyl)-pyridin-2-yl)-1,3,5-triazin-2-ylamino)cyclopentanol

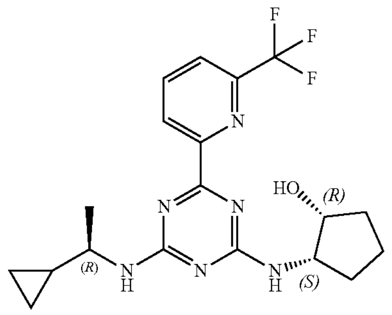

$^1$H NMR (400 MHz, $CDCl_3$): δ 8.51 (m, 1H), 8.01 (t, J=7.6 Hz, 1H), 7.80 (t, J=6.4 Hz, 1H), 5.40-5.31 (m, 1H), 4.10-3.97 (m, 2H), 3.69-3.52 (m, 1H), 2.25-2.09 (m, 2H), 1.95-1.55 (m, 7H), 1.29 (d, J=6.0 Hz, 2H), 0.93 (d, J=7.5 Hz, 1H), 0.66-0.16 (m, 4H). LC-MS: m/z 409.2 $(M+H)^+$.

Compound (R)—$N^2$-benzyl-$N^4$-(1-cyclopropyl-ethyl)-6-(6-(trifluoromethyl)pyridin-2-yl)-1,3,5-tri-azine-2,4-diamine

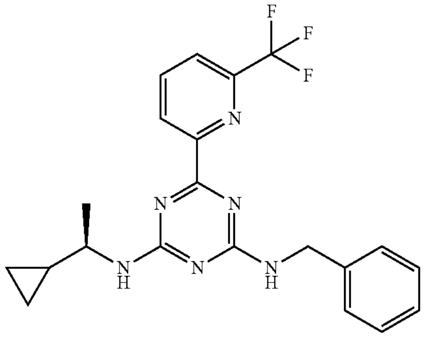 [SMILES: C[C@@H](Nc1nc(NCc2ccccc2)nc(-c2cccc(C(F)(F)F)n2)n1)C1CC1]

$^1$H NMR (400 MHz, $CDCl_3$): δ 8.49 (d, J=7.2 Hz, 1H), 7.98 (t, J=7.7 Hz, 1H), 7.77 (d, J=7.7 Hz, 1H), 7.31 (m, 5H), 5.51 (m, 2H), 4.67 (m, 2H), 3.63 (m, 1H), 1.27 (m, 3H), 0.91 (s, 1H), 0.38 (m, 4H). LC-MS: m/z 415.2 $(M+H)^+$.

Compound $N^2$—((R)-1-cyclopropylethyl)-$N^4$—((S)-1-phenylethyl)-6-(6-(trifluoromethyl) pyridin-2-yl)-1,3,5-triazine-2,4-diamine

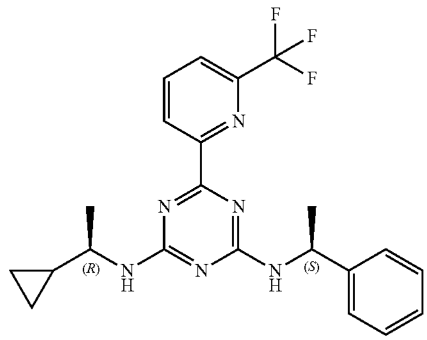

$^1$H NMR (400 MHz, $CDCl_3$): δ 8.45 (t, J=10.4 Hz, 1H), 7.98 (t, J=7.7 Hz, 1H), 7.77 (d, J=7.7 Hz, 1H), 7.54-7.03 (m, 5H), 5.70 (d, J=6.9 Hz, 1H), 5.45 (m, 1H), 5.15 (m, 1H), 3.50 (m, 1H), 1.55 (m, 3H), 1.28 (m, 1H), 0.96 (m, 3H), 0.64-0.18 (m, 4H). LC-MS: m/z 429.2 $(M+H)^+$.

Compound $N^2$—((R)-1-cyclopropylethyl)-$N^4$—((R)-1-phenylethyl)-6-(6-(trifluoro methyl) pyridin-2-yl)-1,3,5-triazine-2,4-diamine

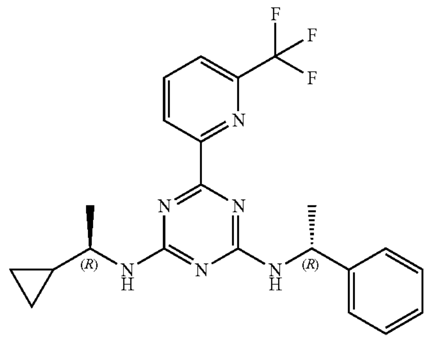

$^1$H NMR (400 MHz, $CDCl_3$): δ 8.47 (d, J=8.3 Hz, 1H), 7.98 (t, J=7.7 Hz, 1H), 7.76 (d, J=7.7 Hz, 1H), 7.50-7.02 (m, 5H), 5.78-5.07 (m, 3H), 3.55 (m, 1H), 1.72 (m, 1H), 1.56 (d, J=6.7 Hz, 3H), 0.97 (m, 3H), 0.58-0.15 (m, 4H). LC-MS: m/z 429.2 $(M+H)^+$.

Compound N$^2$—((R)-1-cyclopropylethyl)-N$^4$-(1-(3-fluorophenyl)ethyl)-6-(6-(trifluoromethyl)pyridin-2-yl)-1,3,5-triazine-2,4-diamine

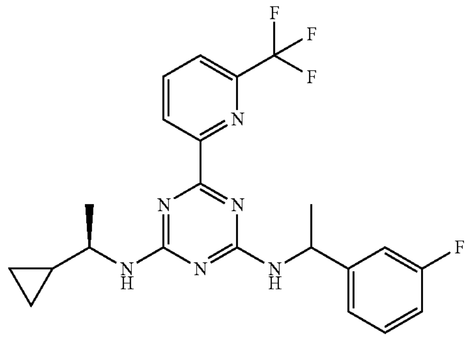 [SMILES: CC(Nc1nc(N[C@H](C)C2CC2)nc(-c2cccc(C(F)(F)F)n2)n1)c1cccc(F)c1]

$^1$H NMR (400 MHz, $CDCl_3$): δ 8.55-8.36 (m, 1H), 8.00 (t, J=7.7 Hz, 1H), 7.78 (d, J=7.7 Hz, 1H), 7.27 (d, J=7.8 Hz, 2H), 7.18-6.90 (m, 3H), 5.71-5.06 (m, 3H), 3.78-3.32 (m, 1H), 1.54 (d, J=6.8 Hz, 3H), 1.34-1.22 (m, 3H), 1.00 (d, J=6.3 Hz, 1H), 0.94-0.72 (m, 1H), 0.54-0.37 (m, 2H), 0.31-0.20 (m, 1H). LC-MS: m/z 447.2 $(M+H)^+$.

Compound N$^2$—((R)-1-cyclopropylethyl)-N$^4$-(1-(3-(trifluoromethyl)phenyl)ethyl)-6-(6-(trifluoromethyl)pyridin-2-yl)-1,3,5-triazine-2,4-diamine

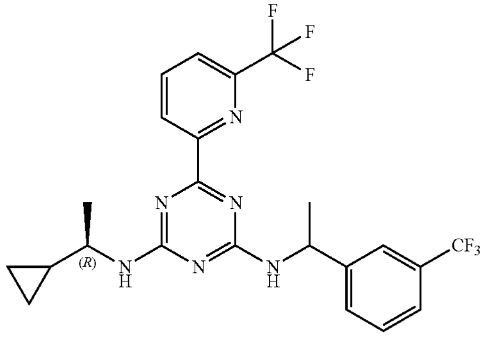

$^1$H NMR (400 MHz, $CDCl_3$): δ 8.42 (m, 1H), 8.08-7.93 (m, 1H), 7.79 (d, J=7.6 Hz, 1H), 7.67-7.38 (m, 4H), 5.84-5.49 (m, 1H), 5.49-5.03 (m, 2H), 3.72-3.16 (m, 1H), 1.57 (d, J=6.9 Hz, 3H), 1.26 (d, J=6.3 Hz, 3H), 0.92 (d, J=6.4 Hz, 1H), 0.73 (m, 1H), 0.53-0.41 (m, 1H), 0.37 (m, 1H), 0.25 (m, 1H). LC-MS: m/z 497.2 $(M+H)^+$.

Compound N$^2$—((R)-1-cyclopropylethyl)-N$^4$-((1R, 2S)-2-phenylcyclopropyl)-6-(6-(trifluoromethyl)pyridin-2-yl)-1,3,5-triazine-2,4-diamine

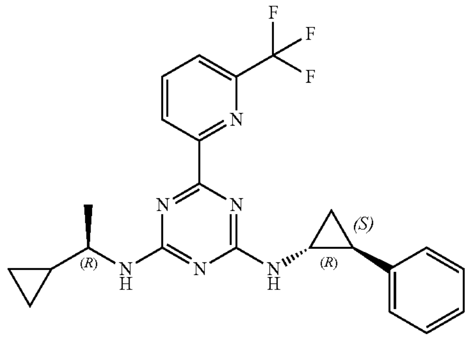

$^1$H NMR (400 MHz, $CDCl_3$): δ 8.47 (d, J=8.3 Hz, 1H), 7.98 (t, J=7.7 Hz, 1H), 7.76 (d, J=7.7 Hz, 1H), 7.37 (m, 4H), 7.23 (m, 1H), 5.81-5.05 (m, 3H), 3.55 (m 1H), 1.72 (s, 1H), 1.56 (d, J=6.7 Hz, 3H), 0.97 (m 3H), 0.63-0.18 (m, 4H). LC-MS: m/z 441.2 $(M+H)^+$.

Compound (R)—N$^2$-(1-cyclopropylethyl)-N$^4$-(1-phenylcyclopropyl)-6-(6-(trifluoro methyl)pyridin-2-yl)-1,3,5-triazine-2,4-diamine

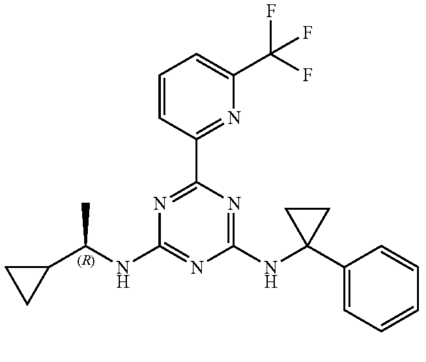

$^1$H NMR (400 MHz, DMSO-$d_6$): δ 8.53-8.13 (m, 3H), 7.99 (m, 1H), 7.70 (m, 1H), 7.45-7.04 (m, 5H), 3.30-3.19 (m, 1H), 1.38-1.09 (m, 5H), 1.07-0.75 (m, 3H), 0.43--0.09 (m, 4H). LC-MS: m/z 441.2 $(M+H)^+$.

Compound (R)-6-(6-chloropyridin-2-yl)-$N^2$-(1-cyclopropylethyl)-$N^4$,$N^4$-diethyl-1,3,5-triazine-2,4-diamine

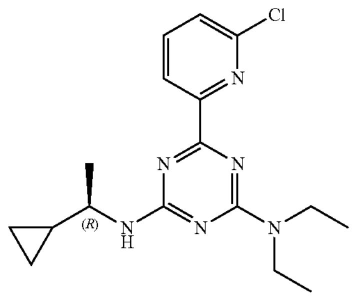

$^1$H NMR (400 MHz, $CDCl_3$): δ 8.32 (d, J=6.6 Hz, 1H), 7.75 (s, 1H), 7.42 (s, 1H), 5.51 (s, 1H), 3.62 (m, 5H), 1.42-1.03 (m, 9H), 0.92 (d, J=7.7 Hz, 1H), 0.63-0.17 (m, 4H). LC-MS: m/z 347.2 $(M+H)^+$.

Compound (R)-methyl 3-((4-((1-cyclopropylethyl)amino)-6-(6-(trifluoromethyl)pyri-din-2-yl)-1,3,5-triazin-2-yl)amino)propanoate

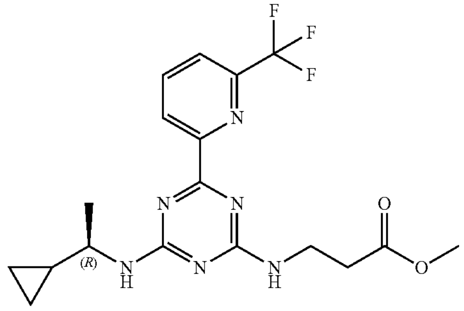

$^1$H NMR (400 MHz, $CDCl_3$): δ 8.52 (m, 1H), 8.00 (t, J=7.6 Hz, 1H), 7.78 (d, J=7.7 Hz, 1H), 5.63 (m, 2H), 3.73 (m, 9H), 2.66 (d, J=5.9 Hz, 2H), 1.29 (m, 3H), 1.01-0.79 (m, 1H), 0.60-0.17 (m, 4H). LC-MS: m/z 411.2 $(M+H)^+$.

Compound (R)—$N^2$-(1-cyclopropylethyl)-$N^4$-(2-phenoxyethyl)-6-(6-(trifluoromethyl) pyridin-2-yl)-1,3,5-triazine-2,4-diamine

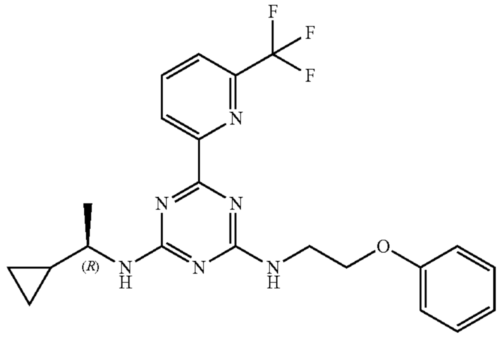

$^1$H NMR (400 MHz, $CDCl_3$): δ 8.43 (d, J=8.0 Hz, 1H), 7.93 (t, J=7.6 Hz, 1H), 7.71 (d, J=7.7 Hz, 1H), 7.34-7.18 (m, 2H), 7.00-6.69 (m, 3H), 6.03-5.08 (m, 2H), 4.07 (s, 2H), 3.94-3.71 (m, 2H), 3.53 (d, J=6.8 Hz, 1H), 1.34-1.04 (m, 4H), 0.35 (m, 4H). LC-MS: m/z 445.2 $(M+H)^+$.

Compound (1R,2S)-2-((4-(cyclopentylamino)-6-(6-(trifluoromethyl)pyridin-2-yl)-1,3,5-triazin-2-yl)amino)cyclopentanol

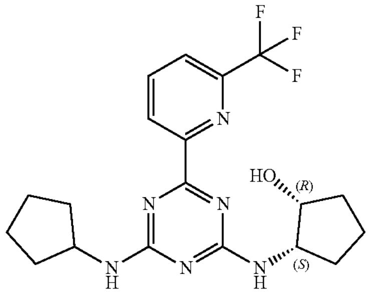

$^1$HNMR (400 MHz, $CD_3OD$): δ8.63-8.57 (m, 1H), 8.17-8.14 (m, 1H), 7.94-7.92 (m, 1H), 4.48-4.23 (m, 3H), 2.05-1.91 (m, 5H), 1.78-1.59 (m, 9H). LC-MS: m/z 409.3 (M+H).

Compound $N^2$-(3,3-difluorocyclopentyl)-$N^4$-(tetrahydrofuran-3-yl)-6-(6-(trifluoro methyl)pyridin-2-yl)-1,3,5-triazine-2,4-diamine

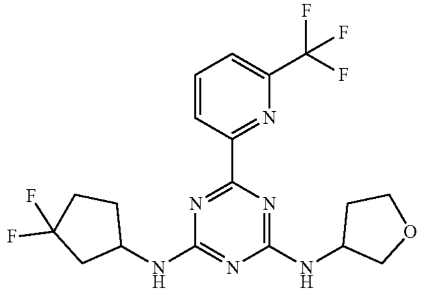 [SMILES: FC1(F)CCC(Nc2nc(NC3CCOC3)nc(-c3cccc(C(F)(F)F)n3)n2)C1]

$^1$H NMR (400 MHz, $CD_3OD$): δ 8.68-8.56 (m, 1H), 8.15 (t, J=8.3 Hz, 1H), 7.93 (d, J=7.5 Hz, 1H), 4.81-4.43 (m, 2H), 4.11-3.92 (m, 2H), 3.86 (m, 1H), 3.78-3.66 (m, 1H), 2.74-2.50 (m, 1H), 2.38-1.75 (m, 7H). LC-MS: m/z 431.2 $(M+H)^+$.

Compound tert-butyl 3-((4-((3,3-difluorocyclopentyl)amino)-6-(6-(trifluoromethyl) pyridin-2-yl)-1,3,5-triazin-2-yl)amino)pyrrolidine-1-carboxylate

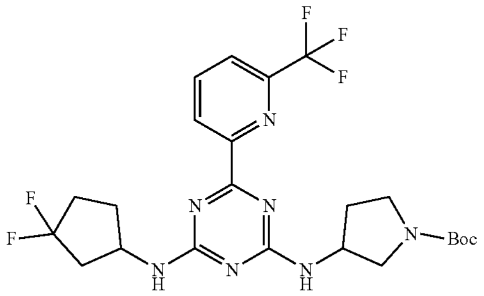 [SMILES: CC(C)(C)OC(=O)N1CCC(Nc2nc(NC3CCC(F)(F)C3)nc(-c3cccc(C(F)(F)F)n3)n2)C1]

$^1$H NMR (400 MHz, $CDCl_3$): δ 8.62-8.46 (m, 1H), 8.03 (d, J=6.9 Hz, 1H), 7.81 (d, J=7.7 Hz, 1H), 5.91-5.19 (m, 2H), 4.61 (m, 2H), 3.82-3.59 (m, 1H), 3.50 (s, 1H), 3.29 (m, 1H), 2.65 (m, 1H), 2.43-2.06 (m, 5H), 1.97 (s, 1H), 1.47 (s, 9H). LC-MS: m/z 530.2 $(M+H)^+$.

Compound $N^2$-isobutyl-$N^4$-(tetrahydro-2H-pyran-4-yl)-6-(6-(trifluoromethyl)-pyridin-2-yl)-1,3,5-triazine-2,4-diamine

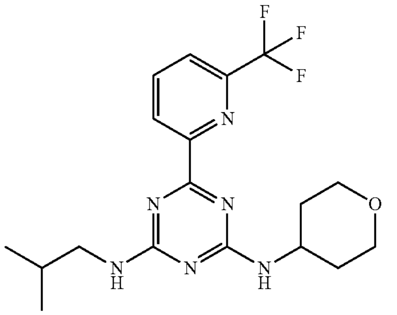 [SMILES: CC(C)CNc1nc(NC2CCOCC2)nc(-c2cccc(C(F)(F)F)n2)n1]

$^1$HNMR (400 MHz, $CD_3OD$): δ8.7-8.6 (m, 1H), 8.25-8.15 (m, 1H), 8.0-7.9 (m, 1H), 4.4-4.1 (m, 1H), 4.05-3.96 (m, 2H), 3.3-3.2 (m, 2H), 2.1-1.9 (m, 3H), 1.63-1.5 (m, 2H), 1.05-0.9 (m, 6H). LC-MS: m/z 397.3 $(M+H)^+$.

Compound $N^2$—((R)-1-cyclopropylethyl)-$N^4$-(1-(2-methoxyethoxy)propan-2-yl)-6-(6-(trifluoromethyl) pyridin-2-yl)-1,3,5-triazine-2,4-diamine

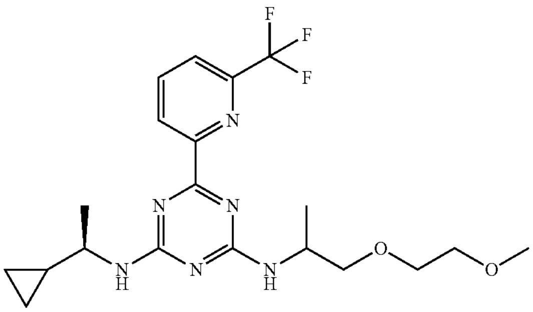 [SMILES: COCCOCC(C)Nc1nc(N[C@H](C)C2CC2)nc(-c2cccc(C(F)(F)F)n2)n1]

$^1$H NMR (400 MHz, $CDCl_3$) δ 8.61-8.42 (m, 1H), 7.99 (t, J=7.9 Hz, 1H), 7.77 (d, J=7.7 Hz, 1H), 5.78-5.37 (m, 2H), 4.52-4.22 (m, 1H), 3.79-3.47 (m, 7H), 3.40 (s, 3H), 1.29 (d, J=5.7 Hz, 6H), 0.99-0.80 (m, 1H), 0.61-0.21 (m, 4H). LC-MS: m/z 441 $(M+H)^+$.

Compound 2-((4-(((R)-1-cyclopropylethyl)amino)-6-(6-(trifluoromethyl)pyridin-2-yl)-1,3,5-triazin-2-yl)amino)propan-1-ol

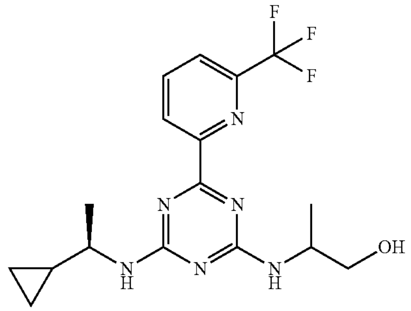 [SMILES: CC(CO)Nc1nc(N[C@H](C)C2CC2)nc(-c2cccc(C(F)(F)F)n2)n1]

$^1$H NMR (400 MHz, $CDCl_3$) δ 8.57-8.47 (m, 1H), 8.01 (t, J=7.6 Hz, 1H), 7.79 (d, J=7.6 Hz, 1H), 5.62-5.20 (m, 2H), 4.23 (m, 1H), 3.82-3.49 (m, 3H), 1.35-1.22 (m, 6H), 0.93 (m, 1H), 0.58-0.29 (m, 4H). LCMS: m/z 383.2 $(M+H)^+$.

Compound $N^2$—((R)-1-cyclopropylethyl)-$N^4$-(1-isopropoxypropan-2-yl)-6-(6-(trifluoromethyl)pyridin-2-yl)-1,3,5-triazine-2,4-diamine

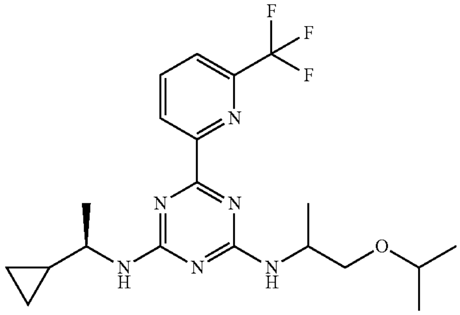 [SMILES: CC(COC(C)C)Nc1nc(N[C@H](C)C2CC2)nc(-c2cccc(C(F)(F)F)n2)n1]

$^1$H NMR (400 MHz, $CDCl_3$) δ 8.65-8.42 (m, 1H), 7.99 (t, J=7.9 Hz, 1H), 7.78 (d, J=7.3 Hz, 1H), 5.92-5.08 (m, 2H), 4.44-4.13 (m, 1H), 3.73-3.27 (m, 4H), 1.27 (m, 6H), 1.17 (d, J=6.1 Hz, 6H), 1.04-0.84 (m, 1H), 0.63-0.16 (m, 4H). LC-MS: m/z 425 $(M+H)^+$.

Compound $N^2$—((R)-1-cyclopropylethyl)-$N^4$-(4-methoxybutan-2-yl)-6-(6-(trifluoromethyl)pyridin-2-yl)-1,3,5-triazine-2,4-diamine

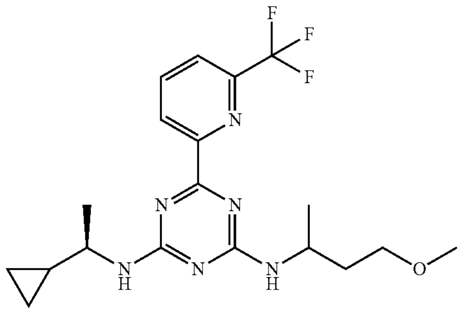 [SMILES: COCCC(C)Nc1nc(N[C@H](C)C2CC2)nc(-c2cccc(C(F)(F)F)n2)n1]

$^1$H NMR (400 MHz, $CDCl_3$) δ 8.63-8.48 (m, 1H), 8.01-7.97 (m, 1H), 7.77 (d, J=7.6 Hz, 1H), 5.54-5.25 (m, 2H), 4.44-4.22 (m, 1H), 3.64-3.49 (m, 3H), 3.33 (d, J=2.4 Hz, 3H), 1.89-1.78 (m, 2H), 1.30-1.25 (m, 5H), 0.93-0.83 (m, 2H), 0.53-0.28 (m, 4H). LCMS: m/z 411 $(M+H)^+$.

Compound $N^2$—((R)-1-cyclopropylethyl)-$N^4$-(1-phenylpropan-2-yl)-6-(6-(trifluoromethyl)pyridin-2-yl)-1,3,5-triazine-2,4-diamine

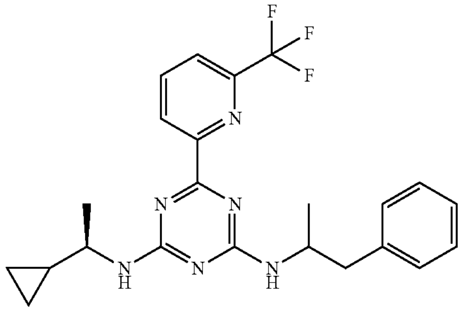 [SMILES: CC(Cc1ccccc1)Nc1nc(N[C@H](C)C2CC2)nc(-c2cccc(C(F)(F)F)n2)n1]

$^1$H NMR (400 MHz, $CDCl_3$) δ 8.41 (d, J=7.6 Hz, 1H), 7.92 (t, J=7.8 Hz, 1H), 7.70 (d, J=7.6 Hz, 1H), 7.25-7.14 (m, 5H), 5.50-4.92 (m, 2H), 4.25 (m, 1H), 3.68-3.39 (m, 1H), 2.99 (m, 1H), 2.61 (m, 1H), 1.26-1.06 (m, 8H), 0.52-0.28 (m, 3H). LC-MS: m/z 443 $(M+H)^+$.

Compound $N^2$—((R)-1-cyclopropylethyl)-$N^4$-(1-morpholinopropan-2-yl)-6-(6-(trifluoromethyl)pyridin-2-yl)-1,3,5-triazine-2,4-diamine

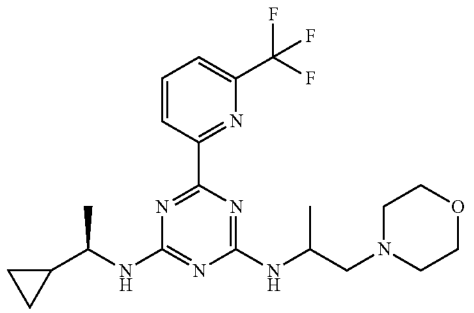 [SMILES: CC(CN1CCOCC1)Nc1nc(N[C@H](C)C2CC2)nc(-c2cccc(C(F)(F)F)n2)n1]

$^1$H NMR (400 MHz, $CDCl_3$) δ 8.51-8.50 (m, 1H), 8.22 (s, 1H), 8.03-7.99 (m, 1H), 7.83-7.79 (m, 1H), 6.39-5.86 (m, 2H), 4.44 (m, 7H), 3.79-3.52 (m, 5H), 3.25-2.53 (m, 5H), 0.95 (s, 1H), 0.54-0.26 (m, 4H). LCMS: m/z 452 $(M+H)^+$.

Compound $N^2$—((R)-1-cyclopropylethyl)-$N^4$-(1-(piperidin-1-yl)propan-2-yl)-6-(6-(trifluoromethyl)pyridin-2-yl)-1,3,5-triazine-2,4-diamine

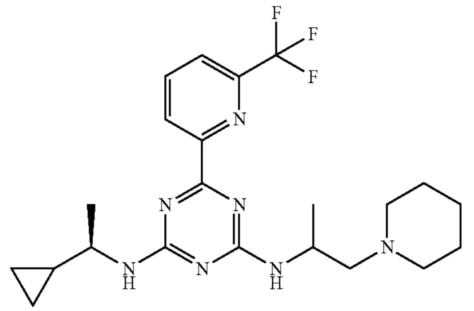 [SMILES: CC(CN1CCCCC1)Nc1nc(N[C@H](C)C2CC2)nc(-c2cccc(C(F)(F)F)n2)n1]

$^1$H NMR (400 MHz, $CDCl_3$): δ 8.54-8.51 (m, 2H), 8.01-7.98 (m, 1H), 7.77 (d, J=7.6 Hz, 1H), 6.66-6.17 (m, 1H), 5.72-5.54 (m, 1H), 4.84-4.44 (m, 1H), 4.21 (s, 5H), 3.67-2.63 (m, 7H), 1.77 (d, J=5.2 Hz, 4H), 1.53 (s, 2H), 0.93 (d, J=4 Hz, 1H), 0.52-0.27 (m, 4H). LCMS: m/z 450 $(M+H)^+$.

Compound (R)-3-((4-((1-cyclopropylethyl)amino)-6-(6-(trifluoromethyl)pyridin-2-yl)-1,3,5-triazin-2-yl)amino)-2,2-dimethylpropanamide

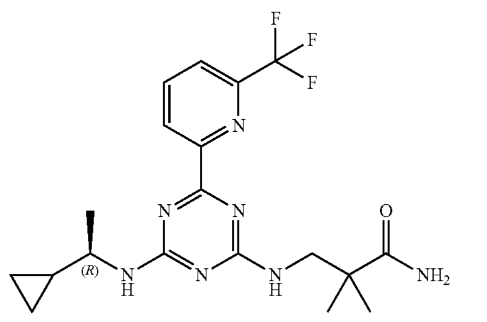

$^1H$ NMR (400 MHz, $CDCl_3$) δ 8.52-8.37 (m, 1H), 8.00-7.96 (m, 1H), 7.87-7.75 (m, 1H), 6.01-5.22 (m, 2H), 4.26-3.53 (m, 3H), 2.32-1.45 (m, 2H), 1.41-1.29 (m, 8H), 1.23-1.21 (m, 1H), 0.97-0.28 (m, 5H). LCMS: m/z 424 (M+H)+.

Compound 3-((4-(((R)-1-cyclopropylethyl)amino)-6-(6-(trifluoromethyl)pyridin-2-yl)-1,3,5-triazin-2-yl)amino)butanenitrile

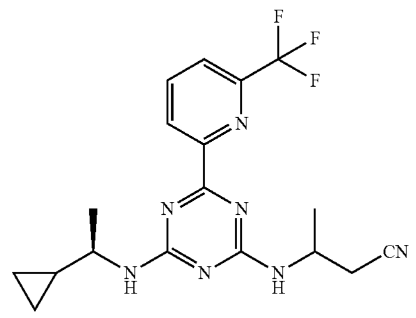 [SMILES: CC(CC#N)Nc1nc(N[C@H](C)C2CC2)nc(-c2cccc(C(F)(F)F)n2)n1]

$^1H$ NMR (400 MHz, $CDCl_3$) δ 8.50 (d, J=7.6 Hz, 1H), 8.03-7.99 (m, 1H), 7.80 (d, J=7.6 Hz, 1H), 5.64-5.17 (m, 2H), 4.55-4.32 (m, 1H), 3.70-3.51 (m, 1H), 2.87-2.69 (m, 2H), 1.46 (d, J=6.8 Hz, 3H), 1.33-1.25 (m, 3H), 0.96-0.89 (m, 1H), 0.55-0.30 (m, 4H). LCMS: m/z 392 $(M+H)^+$.

Compound (R)-3-((4-((1-cyclopropylethyl)amino)-6-(6-(trifluoromethyl)pyridin-2-yl)-1,3,5-triazin-2-yl)amino)-2,2-dimethylpropanenitrile

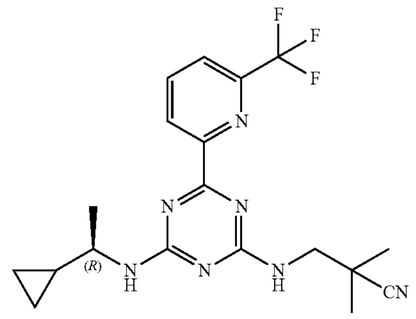

$^1H$ NMR (400 MHz, $CDCl_3$) δ 8.55 (s, 1H), 8.11 (s, 1H), 7.91 (d, J=8 Hz, 1H), 3.73-3.62 (m, 4H), 1.47-1.42 (m, 7H), 1.37-1.35 (m, 3H), 0.75-0.69 (m, 1H), 0.58 (m, 2H), 0.40-0.34 (m, 2H). LCMS: m/z 406 $(M+H)^+$.

Compound 1-((4-((3,3-Difluorocyclopentyl)amino)-6-(6-(trifluoromethyl)pyridin-2-yl)-1,3,5-triazin-2-yl)amino)-2-methylpropan-2-ol

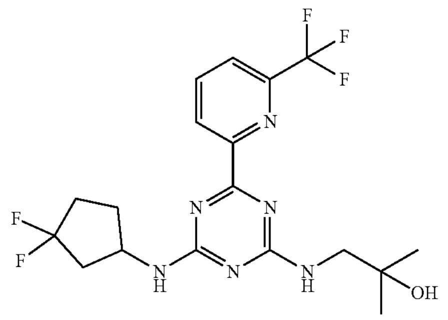 [SMILES: CC(C)(O)CNc1nc(NC2CCC(F)(F)C2)nc(-c2cccc(C(F)(F)F)n2)n1]

$^1H$ NMR (400 MHz, $CDCl_3$) δ 8.50 (s, 1H), 8.03 (d, J=7.3 Hz, 1H), 7.80 (d, J=7.4 Hz, 1H), 5.68 (m, 2H), 4.60 (m, 1H), 3.83-3.03 (m, 3H), 2.74-2.56 (m, 1H), 2.31 (s, 2H), 2.19-1.97 (m, 2H), 1.83 (m, 1H), 1.30 (s, 6H). LCMS: m/z 433 $(M+H)^+$.

Compound $N^2$-(3,3-difluorocyclopentyl)-$N^4$-(1-(4-fluorophenyl)azetidin-3-yl)-6-(6-(trifluoromethyl)pyridin-2-yl)-1,3,5-triazine-2,4-diamine

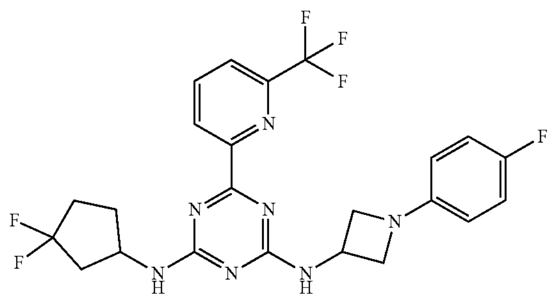 [SMILES: Fc1ccc(N2CC(Nc3nc(NC4CCC(F)(F)C4)nc(-c4cccc(C(F)(F)F)n4)n3)C2)cc1]

$^1H$ NMR (400 MHz, $CDCl_3$) δ 10.05-8.37 (m, 1H), 8.31-7.54 (m, 2H), 7.60-6.68 (m, 4H), 5.49-4.41 (m, 4H), 3.80-3.35 (m, 2H), 2.55-2.12 (m, 6H). LC-MS: m/z 510 $(M+H)^+$.

Compound $N^2$-(3,3-difluorocyclopentyl)-$N^4$-(1-(pyridin-2-yl)azetidin-3-yl)-6-(6-(trifluoromethyl)pyridin-2-yl)-1,3,5-triazine-2,4-diamine

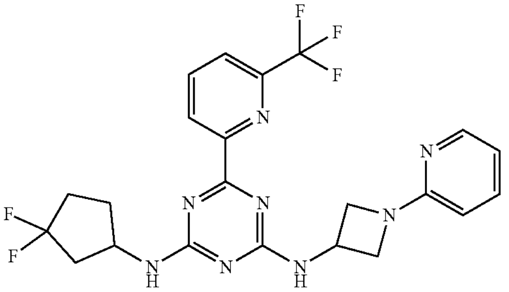 [SMILES: FC1(F)CCC(Nc2nc(NC3CN(c4ccccn4)C3)nc(-c3cccc(C(F)(F)F)n3)n2)C1]

$^1$H NMR (400 MHz, $CDCl_3$) δ 8.50 (s, 1H), 8.09 (m, 2H), 7.80 (s, 1H), 7.49 (s, 1H), 6.66 (s, 1H), 6.26 (m, 2H), 5.77 (m, 1H), 4.99-4.34 (m, 4H), 3.96 (m, 2H), 2.42-1.71 (m, 6H). LCMS: m/z 493 $(M+H)^+$.

Compound $N^2$-(3,3-difluorocyclopentyl)-$N^4$-(1-(pyridin-3-yl)azetidin-3-yl)-6-(6-(trifluoromethyl)pyridin-2-yl)-1,3,5-triazine-2,4-diamine

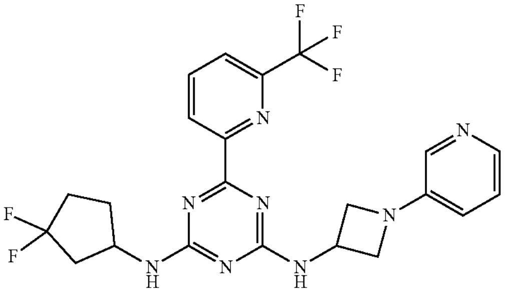 [SMILES: FC1(F)CCC(Nc2nc(NC3CN(c4cccnc4)C3)nc(-c3cccc(C(F)(F)F)n3)n2)C1]

$^1$H NMR (400 MHz, $CDCl_3$): δ 8.50 (d, J=8 Hz, 1H), 8.07-8.01 (m, 2H), 7.92 (s, 1H), 7.80 (d, J=8 Hz, 1H), 7.17-7.14 (m, 1H), 6.80-6.79 (m, 1H), 6.15-5.34 (m, 2H), 5.14-4.51 (m, 2H), 4.39-4.35 (m, 2H), 3.89-3.78 (m, 2H), 2.62-2.57 (m, 1H), 2.30-2.11 (m, 5H). LCMS: m/z 493 $(M+H)^+$.

Compound $N^2$-(3,3-difluorocyclopentyl)-$N^4$-((1r,3r)-3-(4-fluorophenyl)cyclobutyl)-6-(6-(trifluoromethyl)pyridin-2-yl)-1,3,5-triazine-2,4-diamine

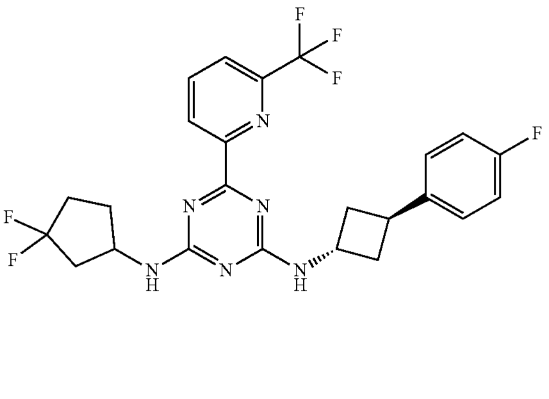 [SMILES: Fc1ccc([C@H]2C[C@H](Nc3nc(NC4CCC(F)(F)C4)nc(-c4cccc(C(F)(F)F)n4)n3)C2)cc1]

$^1$H NMR (400 MHz, $CDCl_3$) δ 8.55 (d, J=7.6 Hz, 1H), 8.21-8.01 (m, 1H), 7.88 (m, 1H), 7.26-7.15 (m, 2H), 7.04 (t, J=8.4 Hz, 2H), 4.89-4.35 (m, 2H), 3.88-3.40 (m, 1H), 3.00-1.75 (m, 11H). LC-MS: m/z 509 $(M+H)^+$.

Compound $N^2$-(3,3-difluorocyclopentyl)-$N^4$-((1s,3s)-3-(4-fluorophenyl)cyclobutyl)-6-(6-(trifluoromethyl)pyridin-2-yl)-1,3,5-triazine-2,4-diamine

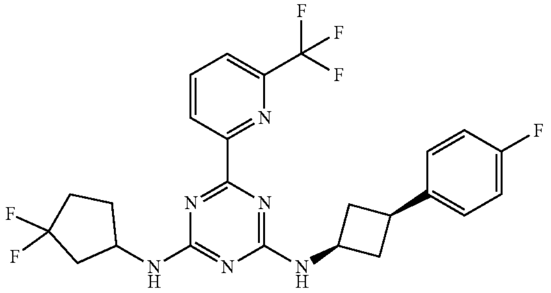 [SMILES: Fc1ccc([C@H]2C[C@@H](Nc3nc(NC4CCC(F)(F)C4)nc(-c4cccc(C(F)(F)F)n4)n3)C2)cc1]

$^1$H NMR (400 MHz, $CDCl_3$) δ 8.65-8.42 (m, 1H), 8.02 (t, J=7.3 Hz, 1H), 7.80 (d, J=7.6 Hz, 1H), 7.20-7.12 (m, 2H), 7.01 (t, J=8.6 Hz, 2H), 5.82-5.20 (m, 2H), 4.83-4.37 (m, 2H), 3.40-3.11 (m, 1H), 3.00-1.75 (m, 10H). LC-MS: m/z 509 $(M+H)^+$.

Compound N2-(3,3-difluorocyclopentyl)-N4-(3-phenylcyclobutyl)-6-(6-(trifluoromethyl)pyridin-2-yl)-1,3,5-triazine-2,4-diamine

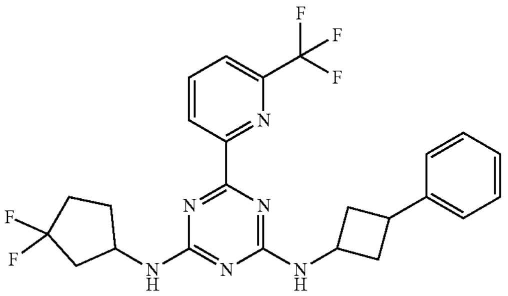 [SMILES: FC1(F)CCC(Nc2nc(NC3CC(c4ccccc4)C3)nc(-c3cccc(C(F)(F)F)n3)n2)C1]

$^1$H NMR (400 MHz, $CDCl_3$) δ 8.65-8.42 (m, 1H), 8.01 (t, J=7.8 Hz, 1H), 7.80 (d, J=7.4 Hz, 1H), 7.42-7.29 (m, 3H), 7.23 (t, J=6.4 Hz, 1H), 6.07-5.20 (m, 2H), 4.90-4.40 (m, 2H), 4.13-3.56 (m, 1H), 2.75-1.75 (m, 10H). LC-MS: m/z 491 $(M+H)^+$.

Compound $N^2$-(3,3-difluorocyclopentyl)-$N^4$-(1-methylpyrrolidin-3-yl)-6-(6-(trifluoromethyl)pyridin-2-yl)-1,3,5-triazine-2,4-diamine

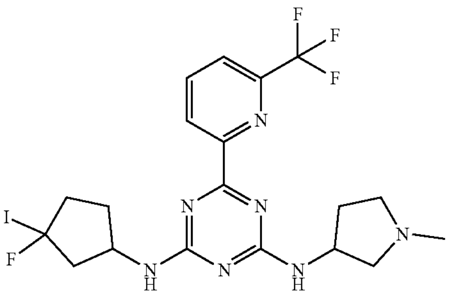 [SMILES: CN1CCC(Nc2nc(NC3CCC(F)(I)C3)nc(-c3cccc(C(F)(F)F)n3)n2)C1]

$^1$H NMR (400 MHz, $CDCl_3$) δ 8.62-8.48 (m, 1H), 8.09-7.94 (m, 1H), 7.80 (t, J=7.4 Hz, 1H), 4.91-4.27 (m, 2H), 3.42-2.56 (m, 9H), 2.44-2.22 (m, 4H), 2.00-1.57 (m, 4H). LC-MS: m/z 444 $(M+H)^+$.

Compound (3-((4-((3,3-Difluorocyclopentyl)amino)-6-(6-(trifluoromethyl)pyridin-2-yl)-1,3,5-triazin-2-yl)amino)pyrrolidin-1-yl)(phenyl)methanone

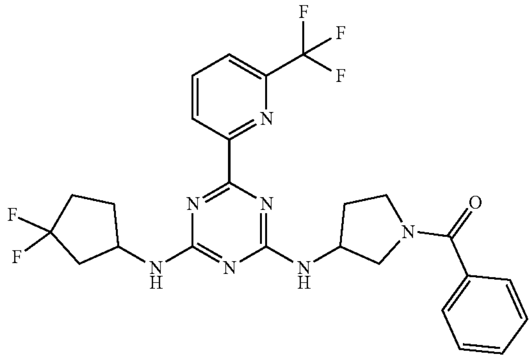 [SMILES: O=C(c1ccccc1)N1CCC(Nc2nc(NC3CCC(F)(F)C3)nc(-c3cccc(C(F)(F)F)n3)n2)C1]

$^1$H NMR (400 MHz, $CDCl_3$) δ 8.76-8.35 (m, 1H), 8.10-7.91 (m, 1H), 7.84 (s, 1H), 7.53 (d, J=7.4 Hz, 2H), 7.43 (d, J=6.5 Hz, 3H), 5.75-5.29 (m, 2H), 4.86-3.77 (m, 4H), 3.70-3.23 (m, 2H), 2.79-1.74 (m, 8H). LC-MS: m/z 534 $(M+H)^+$.

Compound $N^2$-(1-benzylpyrrolidin-3-yl)-$N^4$-(3,3-difluorocyclopentyl)-6-(6-(trifluoromethyl)pyridin-2-yl)-1,3,5-triazine-2,4-diamine

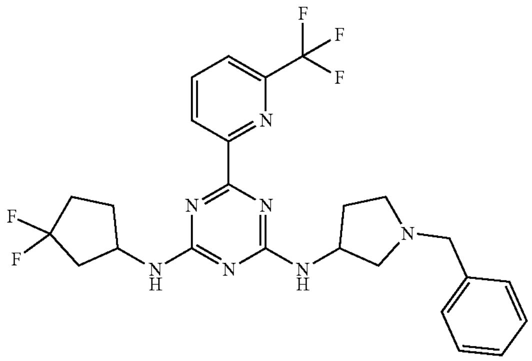 [SMILES: FC1(F)CCC(Nc2nc(NC3CCN(Cc4ccccc4)C3)nc(-c3cccc(C(F)(F)F)n3)n2)C1]

$^1$H NMR (400 MHz, $CDCl_3$) δ: 8.62-8.40 (m, 1H), 8.12-7.93 (m, 1H), 7.79 (d, J=7.3 Hz, 1H), 7.57-7.28 (m, 5H), 6.23-5.45 (m, 2H), 5.07-3.75 (m, 4H), 3.06-2.40 (m, 4H), 2.38-1.60 (m, 8H). LC-MS: m/z 520 $(M+H)^+$.

Compound (4S)-4-((4-((3,3-difluorocyclopentyl)amino)-6-(6-(trifluoromethyl)pyridin-2-yl)-1,3,5-triazin-2-yl)amino)-1-(pyridin-2-yl)pyrrolidin-2-one

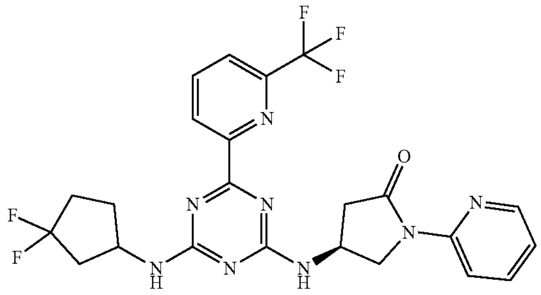 [SMILES: O=C1C[C@H](Nc2nc(NC3CCC(F)(F)C3)nc(-c3cccc(C(F)(F)F)n3)n2)CN1c1ccccn1]

$^1$H NMR (400 MHz, $CDCl_3$) δ 8.66-8.29 (m, 3H), 8.00 (s, 1H), 7.73 (m, 2H), 7.12-7.01 (m, 1H), 5.73 (m, 2H), 5.00-4.40 (m, 3H), 4.24-4.05 (m, 1H), 3.15 (m, 6.3 Hz, 1H), 2.85-2.51 (m, 2H), 2.21 (m, 5H). LCMS: m/z 521 $(M+H)^+$.

Compound $N^2$-(3,3-difluorocyclopentyl)-$N^4$-(3-phenylcyclopentyl)-6-(6-(trifluoromethyl)pyridin-2-yl)-1,3,5-triazine-2,4-diamine

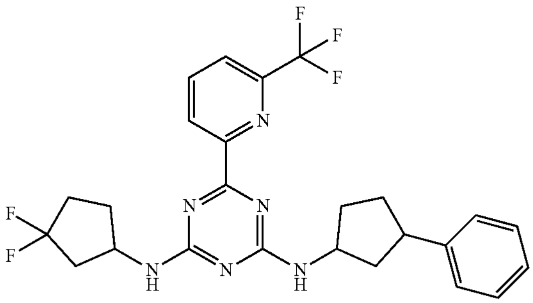 [SMILES: FC1(F)CCC(Nc2nc(NC3CCC(c4ccccc4)C3)nc(-c3cccc(C(F)(F)F)n3)n2)C1]

$^1$H NMR (400 MHz, $CDCl_3$) δ 8.59-8.48 (m, 1H), 8.03-7.99 (m, 1H), 7.80 (d, J=4 Hz, 1H), 7.34-7.30 (m, 3H), 7.23-7.19 (m, 2H), 5.63-5.31 (m, 2H), 4.70-4.56 (m, 2H), 3.29-3.17 (m, 1H), 2.65-2.04 (m, 9H), 1.81 (m, 3H). LCMS: m/z 505 $(M+H)^+$.

Compound $N^2$-(3,3-difluorocyclopentyl)-$N^4$-(2,3-dihydro-1H-inden-2-yl)-6-(6-(trifluoromethyl)pyridin-2-yl)-1,3,5-triazine-2,4-diamine

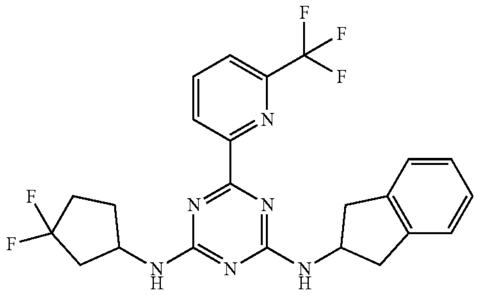 [SMILES: FC1(F)CCC(Nc2nc(NC3Cc4ccccc4C3)nc(-c3cccc(C(F)(F)F)n3)n2)C1]

1H NMR (400 MHz, $CDCl_3$): δ 8.64-8.46 (m, 1H), 8.01 (d, J=12.8 Hz, 1H), 7.78 (d, J=7.6 Hz, 1H), 7.21 (m, 3H), 5.76-5.31 (m, 2H), 5.02-4.44 (m, 2H), 3.45-3.36 (m, 2H), 2.97-2.91 (m, 2H), 2.68-2.58 (m, 1H), 2.31-2.09 (m, 4H), 1.85-1.84 (m, 1H), 1.25 (m, 1H). LCMS: m/z 477$(M+H)^+$.

Compound $N^2$-(5-chloro-2,3-dihydro-1H-inden-2-yl)-$N^4$-(3,3-difluorocyclopentyl)-6-(6-(trifluoromethyl)pyridin-2-yl)-1,3,5-triazine-2,4-diamine

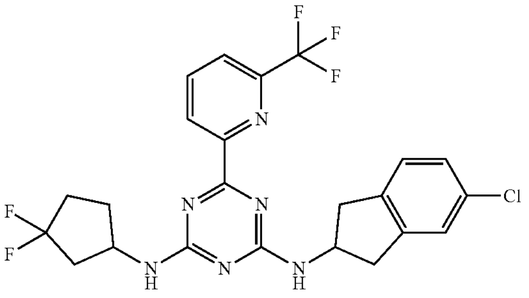 [SMILES: FC1(F)CCC(Nc2nc(NC3Cc4ccc(Cl)cc4C3)nc(-c3cccc(C(F)(F)F)n3)n2)C1]

$^1$H NMR (400 MHz, $CDCl_3$) δ 8.57-8.48 (m, 1H), 8.01 (d, J=8 Hz, 1H), 7.81 (d, J=8 Hz, 1H), 7.26-7.18 (m, 3H), 6.02-5.36 (m, 2H), 5.05-4.43 (m, 2H), 3.48-3.32 (m, 2H), 3.04-2.87 (m, 2H), 2.70-2.58 (m, 1H), 2.36-2.10 (m, 4H), 1.99-1.82 (m, 1H). LCMS: m/z 511 $(M+H)^+$.

Compound $N^2$-(3,3-difluorocyclopentyl)-$N^4$-(5-fluoro-2,3-dihydro-1H-inden-2-yl)-6-(6-(trifluoromethyl)pyridin-2-yl)-1,3,5-triazine-2,4-diamine

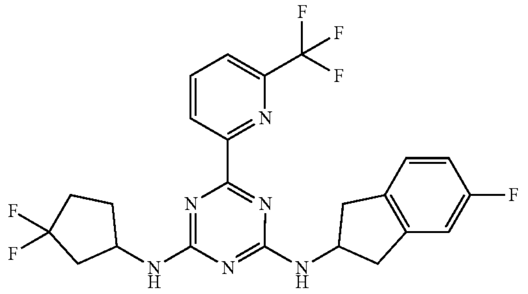 [SMILES: Fc1ccc2c(c1)CC(Nc1nc(NC3CCC(F)(F)C3)nc(-c3cccc(C(F)(F)F)n3)n1)C2]

$^1$H NMR (400 MHz, $CDCl_3$) δ 8.59-8.47 (m, 1H), 8.04-7.97 (m, 1H), 7.79 (d, J=7.2 Hz, 1H), 7.26-7.17 (m, 1H), 6.96-6.87 (m, 2H), 5.75-5.30 (m, 2H), 5.06-4.44 (m, 2H), 3.39-3.32 (m, 2H), 2.95-2.62 (m, 3H), 2.33-2.05 (m, 4H), 1.87-1.82 (m, 1H). LCMS: m/z 495 $(M+H)^+$.

Compound $N^2$-(5-bromo-2,3-dihydro-1H-inden-2-yl)-$N^4$-(3,3-difluorocyclopentyl)-6-(6-(trifluoromethyl)pyridin-2-yl)-1,3,5-triazine-2,4-diamine

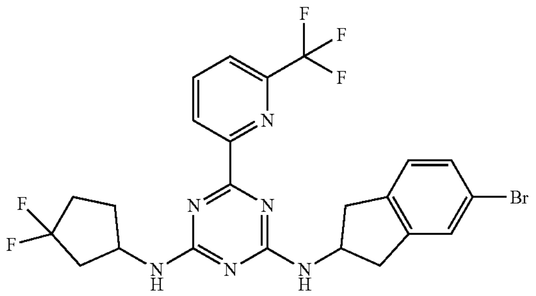 [SMILES: FC1(F)CCC(Nc2nc(NC3Cc4ccc(Br)cc4C3)nc(-c3cccc(C(F)(F)F)n3)n2)C1]

$^1$H NMR (400 MHz, $CDCl_3$) δ 8.57-8.47 (m, 1H), 8.04-7.99 (m, 1H), 7.82-7.78 (m, 1H), 7.52-7.29 (m, 2H), 7.18-7.00 (m, 1H), 5.70-5.30 (m, 2H), 5.03-4.48 (m, 2H), 3.40-3.30 (m, 2H), 2.96-2.63 (m, 3H), 2.35-2.07 (m, 4H), 1.87-1.25 (m, 1H). LCMS: m/z 556 $(M+H)^+$.

Compound 2-((4-((3,3-Difluorocyclopentyl)amino)-6-(6-(trifluoromethyl)pyridin-2-yl)-1,3,5-triazin-2-yl)amino)-2,3-dihydro-1H-indene-5-carbonitrile

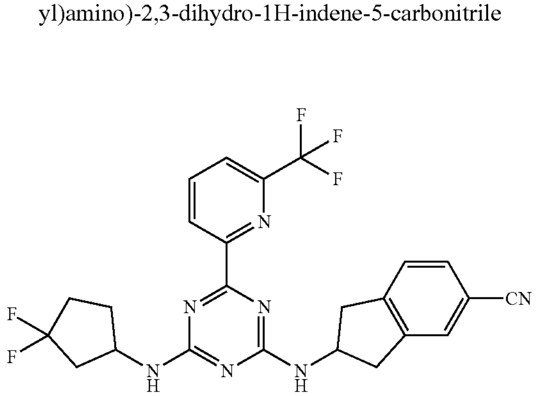

$^1H$ NMR (400 MHz, $CDCl_3$) δ 8.57-8.47 (m, 1H), 8.01 (d, J=8 Hz, 1H), 7.80 (d, J=4 Hz, 1H), 7.54-7.50 (m, 2H), 7.37-7.33 (m, 1H), 5.77-5.34 (m, 2H), 5.07-4.56 (m, 2H), 3.43 (m, 2H), 3.03-2.99 (m, 2H), 2.70-2.58 (m, 1H), 2.32-2.04 (m, 5H). LCMS: m/z 502 $(M+H)^+$.

Compound $N^2$-(3,3-difluorocyclopentyl)-$N^4$-(5-methoxy-2,3-dihydro-1H-inden-2-yl)-6-(6-(trifluoromethyl)pyridin-2-yl)-1,3,5-triazine-2,4-diamine

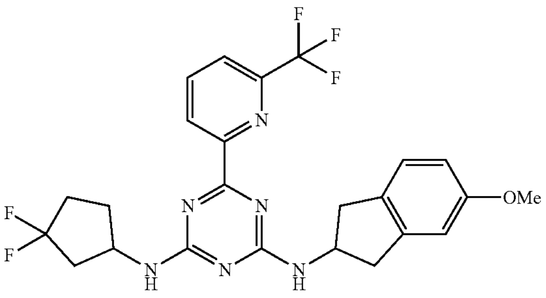 [SMILES: COc1ccc2c(c1)CC(Nc1nc(NC3CCC(F)(F)C3)nc(-c3cccc(C(F)(F)F)n3)n1)C2]

$^1H$ NMR (400 MHz, $CDCl_3$) δ 8.69-8.46 (m, 1H), 8.00 (d, J=8 Hz, 1H), 7.79-7.74 (m, 1H), 7.14 (s, 1H), 6.81-6.75 (m, 2H), 5.76-5.33 (m, 2H), 5.02-4.78 (m, 1H), 4.58-4.47 (m, 1H), 3.80 (s, 3H), 3.39-3.33 (m, 2H), 2.93-2.62 (m, 4H), 2.31-2.10 (m, 4H). LCMS: m/z 507 $(M+H)^+$.

Compound $N^2$-(3,3-difluorocyclopentyl)-$N^4$-(6,7-dihydro-5H-cyclopenta[b]pyridin-6-yl)-6-(6-(trifluoromethyl)pyridin-2-yl)-1,3,5-triazine-2,4-diamine

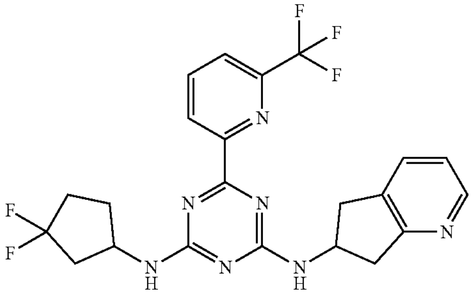 [SMILES: FC1(F)CCC(Nc2nc(NC3Cc4cccnc4C3)nc(-c3cccc(C(F)(F)F)n3)n2)C1]

$^1H$ NMR (400 MHz, $CDCl_3$) δ: 8.64-8.35 (m, 2H), 8.07-7.76 (m, 2H), 7.53 (m, 1H), 7.11 (m, 1H), 5.86-5.30 (m, 2H), 5.01-4.54 (m, 2H), 3.62-2.60 (m, 5H), 2.40-1.86 (m, 5H). LCMS: m/z 478.2 $(M+H)^+$.

Compound $N^2$-(4,6-dibromo-2,3-dihydro-1H-inden-2-yl)-$N^4$-(3,3-difluorocyclopentyl)-6-(6-(trifluoromethyl)pyridin-2-yl)-1,3,5-triazine-2,4-diamine

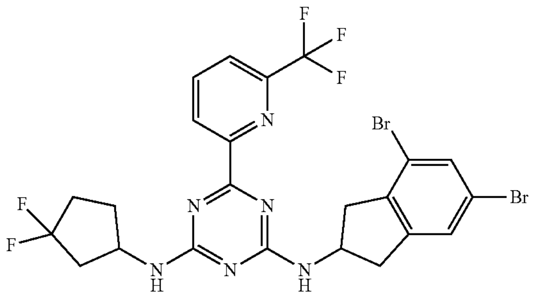 [SMILES: FC1(F)CCC(Nc2nc(NC3Cc4cc(Br)cc(Br)c4C3)nc(-c3cccc(C(F)(F)F)n3)n2)C1]

$^1H$ NMR (400 MHz, $CDCl_3$) δ 8.55-8.46 (m, 1H), 8.07-7.99 (m, 1H), 7.80 (d, J=8 Hz, 1H), 7.51-7.44 (m, 2H), 7.09-7.04 (m, 2H), 6.03-5.38 (m, 2H), 5.03-4.43 (m, 2H), 3.48-3.25 (m, 2H), 3.06-2.88 (m, 2H), 2.69-2.58 (m, 1H), 2.31-2.29 (d, J=8 Hz, 2H), 2.17-2.01 (m, 2H), 1.90-1.77 (m, 1H). LCMS: m/z 635 $(M+H)^+$.

Compound $N^2$-(3,3-difluorocyclopentyl)-$N^4$-(1-phenylpyrrolidin-3-yl)-6-(6-(trifluoromethyl)pyridin-2-yl)-1,3,5-triazine-2,4-diamine

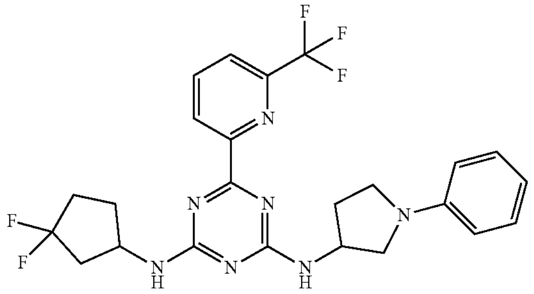 [SMILES: FC1(F)CCC(Nc2nc(NC3CCN(c4ccccc4)C3)nc(-c3cccc(C(F)(F)F)n3)n2)C1]

$^1H$ NMR (400 MHz, $CDCl_3$) δ 8.61-8.49 (m, 1H), 8.04-7.98 (m, 1H), 7.80-7.78 (m, 1H), 7.27-7.23 (m, 2H), 6.74-6.70 (t, 1H), 6.59 (d, 2H), 5.73-5.33 (m, 2H), 4.91-4.48 (m, 2H), 3.75-3.28 (m, 4H), 2.62-1.87 (m, 8H). LCMS: m/z 506 $(M+H)^+$.

Compound $N^2$-(3,3-difluorocyclopentyl)-$N^4$-(1-(pyridin-2-yl)pyrrolidin-3-yl)-6-(6-(trifluoromethyl)pyridin-2-yl)-1,3,5-triazine-2,4-diamine

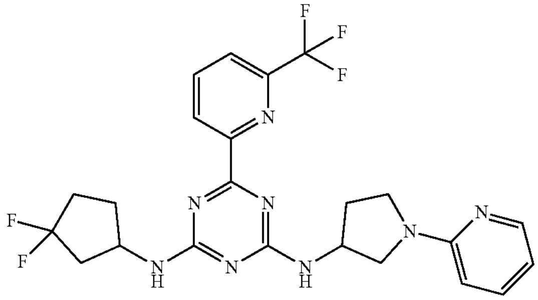 [SMILES: FC1(F)CCC(Nc2nc(NC3CCN(c4ccccn4)C3)nc(-c3cccc(C(F)(F)F)n3)n2)C1]

$^1$H NMR (400 MHz, $CDCl_3$) δ 8.67-8.44 (m, 1H), 8.17 (s, 1H), 8.01 (d, J=8.8 Hz, 1H), 7.79 (d, J=6.4 Hz, 1H), 7.48 (t, J=7.7 Hz, 1H), 6.59 (t, J=5.9 Hz, 1H), 6.39 (d, J=8.1 Hz, 1H), 5.84-4.30 (m, 4H), 4.07-3.51 (m, 4H), 2.83-1.97 (m, 8H). LC-MS: m/z 507 $(M+H)^+$.

Compound $N^2$-(3,3-difluorocyclopentyl)-$N^4$-(1-(pyrimidin-2-yl)pyrrolidin-3-yl)-6-(6-(trifluoromethyl)pyridin-2-yl)-1,3,5-triazine-2,4-diamine

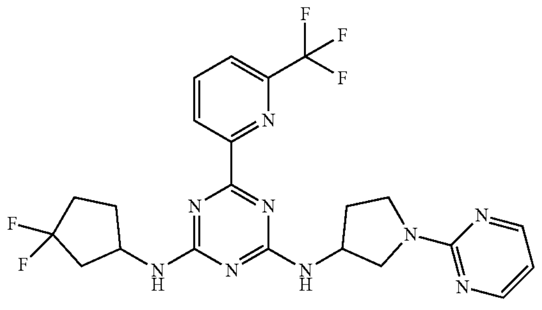 [SMILES: FC1(F)CCC(Nc2nc(NC3CCN(c4ncccn4)C3)nc(-c3cccc(C(F)(F)F)n3)n2)C1]

$^1$H NMR (400 MHz, $CDCl_3$) δ 8.64-8.48 (m, 1H), 8.34-8.33 (m, 2H), 8.04-7.38 (m, 1H), 7.80-7.79 (m, 1H), 6.54-6.52 (m, 1H), 5.73-5.35 (m, 2H), 4.61-4.58 (m, 2H), 4.00-3.93 (m, 1H), 3.79-3.58 (m, 3H), 2.90-2.61 (m, 1H), 2.38-2.12 (m, 6H), 1.88-1.82 (m, 1H). LCMS: m/z 508 $(M+H)^+$.

Compound $N^2$-(3,3-difluorocyclopentyl)-$N^4$-(6,6-difluorospiro[3.3]heptan-2-yl)-6-(6-(trifluoromethyl)pyridin-2-yl)-1,3,5-triazine-2,4-diamine

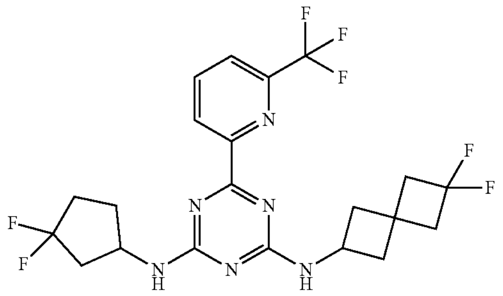 [SMILES: FC1(F)CCC(Nc2nc(NC3CC4(C3)CC(F)(F)C4)nc(-c3cccc(C(F)(F)F)n3)n2)C1]

$^1$H NMR (400 MHz, $CDCl_3$) δ 8.66-8.39 (m, 1H), 8.02 (d, J=7.2 Hz, 1H), 7.80 (d, J=6.6 Hz, 1H), 5.73-5.20 (m, 2H), 4.80-4.30 (m, 2H), 2.83-1.78 (m, 14H). LC-MS: m/z 491 $(M+H)^+$.

Compound 1-((4-((4,4-Difluorocyclohexyl)amino)-6-(6-(trifluoromethyl)pyridin-2-yl)-1,3,5-triazin-2-yl)amino)-2-methylpropan-2-ol

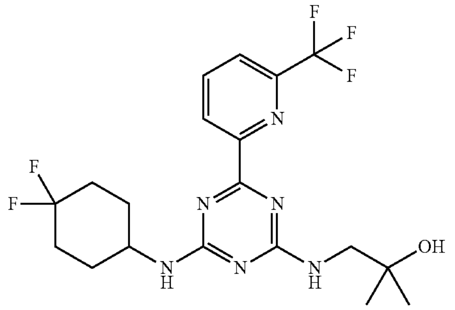 [SMILES: CC(C)(O)CNc1nc(NC2CCC(F)(F)CC2)nc(-c2cccc(C(F)(F)F)n2)n1]

$^1$H NMR (400 MHz, DMSO-$d_6$) δ 8.63-8.45 (m, 1H), 8.24 (t, J=7.7 Hz, 1H), 8.03 (d, J=7.5 Hz, 1H), 7.83 (d, J=7.2 Hz, 1H), 7.57-7.10 (m, 1H), 4.62 (m, 1H), 4.03-4.04 (m, 1H), 3.37 (s, 2H), 2.08 (s, 2H), 1.93-1.85 (m, 4H), 1.62 (d, J=12.2 Hz, 2H), 1.12 (s, 6H). LC-MS: m/z 447 $(M+H)^+$.

Compound $N^2$-(4,4-difluorocyclohexyl)-$N^4$-(tetrahydro-2H-pyran-4-yl)-6-(6-(trifluoromethyl)pyridin-2-yl)-1,3,5-triazine-2,4-diamine

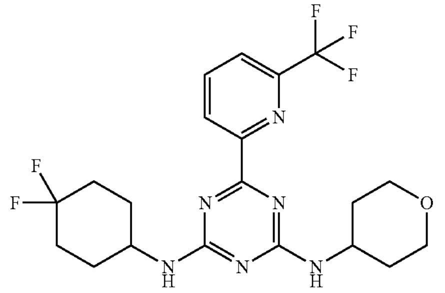 [SMILES: FC1(F)CCC(Nc2nc(NC3CCOCC3)nc(-c3cccc(C(F)(F)F)n3)n2)CC1]

$^1$H NMR (400 MHz, $CDCl_3$) δ 8.55-8.48 (m, 1H), 8.05-7.99 (m, 1H), 7.80 (d, J=7.6 Hz, 1H), 5.44-5.12 (m, 2H), 4.26-4.01 (m, 4H), 3.74-3.52 (m, 2H), 2.20-1.83 (m, 8H), 1.73-1.50 (m, 4H); LCMS: m/z 459.2 $(M+H)^+$.

Compound Tert-butyl 4-((4-((4,4-difluorocyclohexyl)amino)-6-(6-(trifluoromethyl)pyridin-2-yl)-1,3,5-triazin-2-yl)amino)piperidine-1-carboxylate

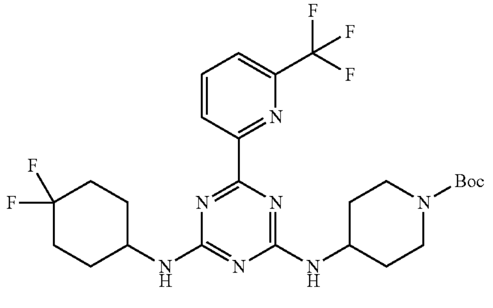 [SMILES: CC(C)(C)OC(=O)N1CCC(Nc2nc(NC3CCC(F)(F)CC3)nc(-c3cccc(C(F)(F)F)n3)n2)CC1]

$^1$H NMR (400 MHz, $CDCl_3$) δ 8.48-8.40 (m, 1H), 7.97-7.91 (m, 1H), 7.74-7.69 (m, 1H), 5.56-5.15 (m, 2H), 4.18-3.85 (m, 4H), 2.95-2.82 (m, 2H), 2.10-1.54 (m, 9H), 1.40 (m, 12H).

LCMS: m/z 558.3 $(M+H)^+$.

Compound 1-(4-((4-((4,4-Difluorocyclohexyl)amino)-6-(6-(trifluoromethyl)pyridin-2-yl)-1,3,5-triazin-2-yl)amino)piperidin-1-yl)ethanone

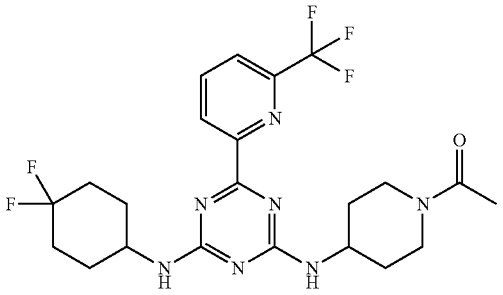 [SMILES: CC(=O)N1CCC(Nc2nc(NC3CCC(F)(F)CC3)nc(-c3cccc(C(F)(F)F)n3)n2)CC1]

$^1$H NMR (400 MHz, $CDCl_3$) δ 8.54-8.48 (m, 1H), 8.06-7.97 (m, 1H), 7.81 (d, J=7.2 Hz, 1H), 5.57-5.14 (m, 2H), 4.54-3.83 (m, 4H), 3.25-2.83 (m, 4H), 2.24-2.05 (m, 7H), 1.77-1.44 (m, 6H). LCMS: m/z 500.2 $(M+H)^+$.

Compound $N^2$-(4,4-difluorocyclohexyl)-$N^4$-(1-(methylsulfonyl)piperidin-4-yl)-6-(6-(trifluoromethyl)pyridin-2-yl)-1,3,5-triazine-2,4-diamine

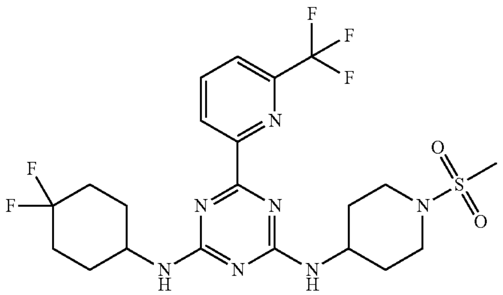 [SMILES: CS(=O)(=O)N1CCC(Nc2nc(NC3CCC(F)(F)CC3)nc(-c3cccc(C(F)(F)F)n3)n2)CC1]

1H NMR (400 MHz, $CDCl_3$) δ 8.58-8.48 (m, 1H), 8.05-7.96 (m, 1H), 7.80 (d, J=6.8 Hz, 1H), 5.56-5.18 (m 2H), 4.25-3.95 (m, 4H), 3.64-3.45 (m, 2H), 2.26-1.55 (m, 15H). LCMS: m/z 536.2 $(M+H)^+$.

Compound $N^2$-(4,4-difluorocyclohexyl)-$N^4$-(6,6-difluorospiro[3.3]heptan-2-yl)-6-(6-(trifluoromethyl)pyridin-2-yl)-1,3,5-triazine-2,4-diamine

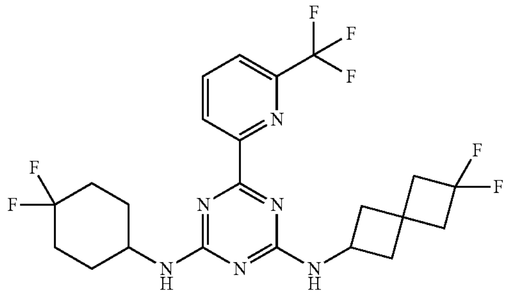 [SMILES: FC1(F)CCC(Nc2nc(NC3CC4(C3)CC(F)(F)C4)nc(-c3cccc(C(F)(F)F)n3)n2)CC1]

$^1$H NMR (400 MHz, $CDCl_3$) δ 8.66-8.39 (m, 1H), 8.14-7.94 (m, 1H), 7.81 (d, J=7.7 Hz, 1H), 6.04-5.01 (m, 2H), 4.74-3.74 (m, 2H), 2.79-2.42 (m, 6H), 2.31-1.96 (m, 6H), 1.85-1.50 (m, 4H). LC-MS: m/z 505 $(M+H)^+$.

Compound $N^2$-(3,3-difluorocyclobutyl)-$N^4$-(4,4-difluorocyclohexyl)-6-(6-(trifluoromethyl)pyridin-2-yl)-1,3,5-triazine-2,4-diamine

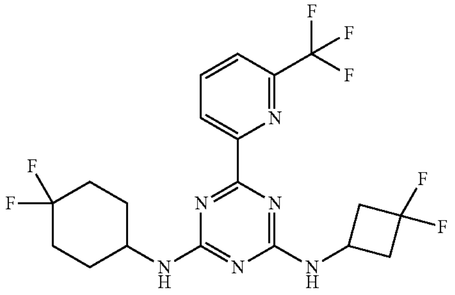 [SMILES: FC1(F)CCC(Nc2nc(NC3CC(F)(F)C3)nc(-c3cccc(C(F)(F)F)n3)n2)CC1]

$^1$H NMR (400 MHz, $CDCl_3$) δ 8.54-8.48 (m, 1H), 8.02 (d, J=8 Hz, 1H), 7.81 (d, J=4 Hz, 1H), 5.77-5.14 (m, 2H), 4.53-3.96 (m, 2H), 3.11-3.03 (m, 2H), 2.70-2.54 (m, 2H), 2.15-2.09 (m, 4H), 1.93 (m, 2H), 1.69 (m, 2H). LCMS: m/z 465 $(M+H)^+$.

Compound $N^2$-(4,4-difluorocyclohexyl)-$N^4$-(3,3-difluorocyclopentyl)-6-(6-(trifluoromethyl)pyridin-2-yl)-1,3,5-triazine-2,4-diamine

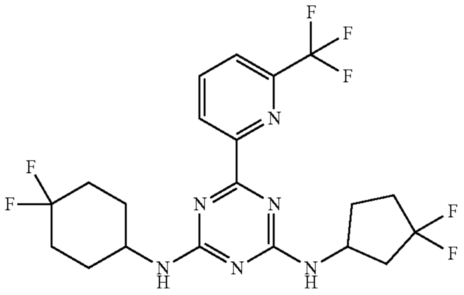 [SMILES: FC1(F)CCC(Nc2nc(NC3CCC(F)(F)C3)nc(-c3cccc(C(F)(F)F)n3)n2)CC1]

$^1$H NMR (400 MHz, $CDCl_3$) δ 8.48-8.56 (m, 1H), 8.01 (d, J=4 Hz, 1H), 7.80 (d, J=4 Hz, 1H), 5.63-5.13 (m, 2H), 4.72-3.97 (m, 2H), 2.62 (m, 1H), 2.31 (m, 2H), 2.14-1.86 (m, 9H), 1.74 (m, 2H). LCMS: m/z 479 $(M+H)^+$.

Compound (R)-6-(6-chloropyridin-2-yl)-$N^2$-(1,1,1,3,3,3-hexafluoropropan-2-yl)-$N^4$-(1,1,1-trifluoropropan-2-yl)-1,3,5-triazine-2,4-diamine

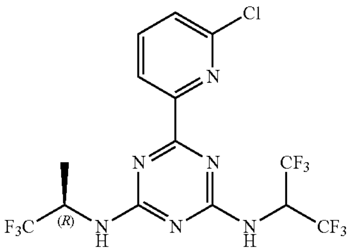

$^1$H NMR (400 MHz, $CDCl_3$) δ 8.40-8.34 (m, 1H), 7.87-7.84 (m, 1H), 7.53 (d, J=8 Hz, 1H),-6.15-5.83 (m, 1H), 5.77-5.31 (m, 2H), 5.17-4.76 (m, 1H), 1.51-1.43 (m, 3H); LC-MS: m/z 469 $(M+H)^+$.

Compound (R)-6-(6-chloropyridin-2-yl)-$N^2$-(4,4-difluorocyclohexyl)-$N^4$-(1,1,1-trifluoropropan-2-yl)-1,3,5-triazine-2,4-diamine

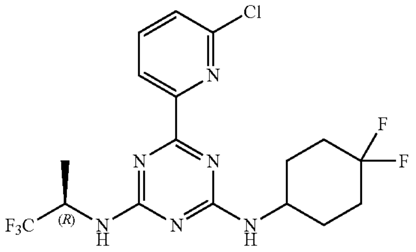

$^1$H NMR (400 MHz, DMSO-$d_6$) δ 8.33 (m, 2H), 8.13-7.92 (m, 2H), 7.78-7.59 (m, 1H), 5.21-4.76 (m, 1H), 4.06 (m, 1H), 2.23-1.45 (m, 8H), 1.42-1.25 (m, 3H). LCMS: m/z 437 $(M+H)^+$.

TABLE 2

The following targets were prepared by the procedure described in Scheme 2 above.

| Compound ID | Name | Structure | LCMS Expected MW | LCMS Found $(M + 1)^+$ |
|---|---|---|---|---|
| 12 | 1-(4-((R)-1-cyclopropylethylamino)-6-(6-(trifluoromethyl)pyridin-2-yl)-1,3,5-triazin-2-ylamino)propan-2-ol | 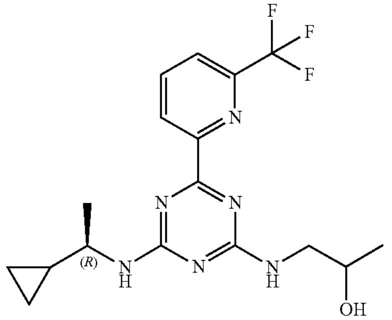 | 382.2 | 383.2 |
| 10 | 1-(4-(1-cyclopropylethylamino)-6-(6-(trifluoromethyl)pyridin-2-yl)-1,3,5-triazin-2-ylamino)-2-methylpropan-2-ol | 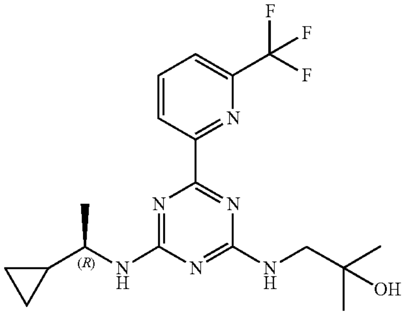 | 396.2 | 397.2 |

TABLE 2-continued

The following targets were prepared by the procedure described in Scheme 2 above.

| Compound ID | Name | Structure | LCMS Expected MW | LCMS Found $(M+1)^+$ |
|---|---|---|---|---|
| 24 | (R)-$N^2$-(1-cyclopropylethyl)-$N^4$-(pyridin-2-ylmethyl)-6-(6-(trifluoro methyl)pyridin-2-yl)-1,3,5-triazine-2,4-diamine | 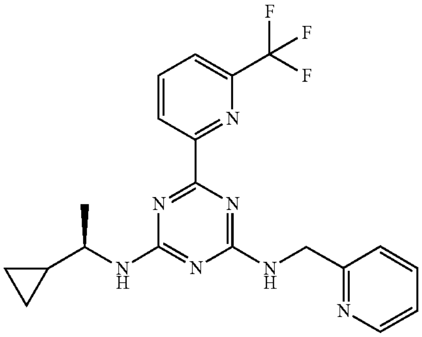 | 415.2 | 416.2 |
| 25 | $N^2$-((R)-1-cyclopropylethyl)-$N^4$-(1-(pyridin-2-yl)ethyl)-6-(6-(trifluoro methyl)pyridin-2-yl)-1,3,5-triazine-2,4-diamine | 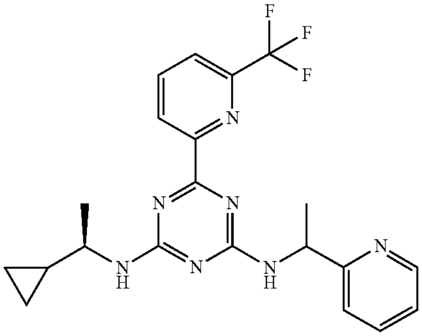 [SMILES: CC(Nc1nc(N[C@H](C)C2CC2)nc(-c2cccc(C(F)(F)F)n2)n1)c1ccccn1] | 429.2 | 430.2 |
| | $N^2$-cyclohexyl-$N^4$-isopropyl-6-phenyl-1,3,5-triazine-2,4-diamine | 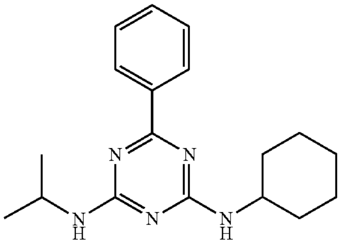 [SMILES: CC(C)Nc1nc(NC2CCCCC2)nc(-c2ccccc2)n1] | 311.2 | 312.2 |
| 69 | $N^2$-isopropyl-6-phenyl-$N^4$-(tetrahydro-2H-pyran-3-yl)-1,3,5-triazine-2,4-diamine | 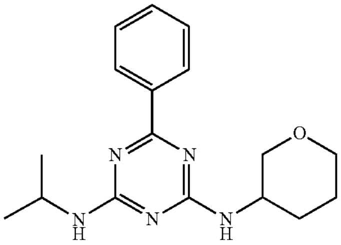 [SMILES: CC(C)Nc1nc(NC2CCCOC2)nc(-c2ccccc2)n1] | 313.2 | 314.2 |

Example 3. Preparation of Di-aliphatic Triazine Compounds of Formula F. The compounds of this Example are prepared by general Scheme 3, set forth below.

Scheme 3

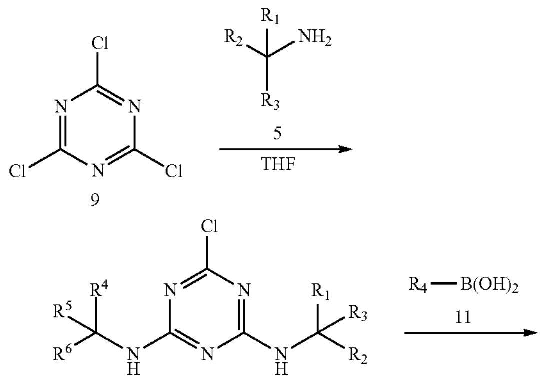

9

10

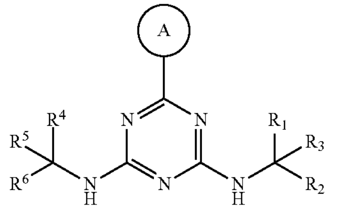

Formula F

Step 1: Preparation of 6-chloro-$N^2$,$N^4$-bis((R)-1-cyclopropylethyl)-1,3,5-triazine-2,4-diamine. To a mixture of 2,4,6-trichloro-1,3,5-triazine (2 g, 10.9 mmol, 1 eq) and (R)-1-cyclopropylethanamine hydrochloride (2.7 g, 22.8 mmol, 2.1 eq) in acetone (50 mL) was added DIPEA (4.5 mL, 27.3 mmol, 2.5 eq) and CsF (3.3 g, 21.8 mmol, 2.0 eq). The mixture was stirred at 40° C. for 3 hr and then at 50° C. for another 3 hr. The mixture was filtered and the filtrate was concentrated under reduced pressure. The residue was purified by a standard method to afford the desired product.

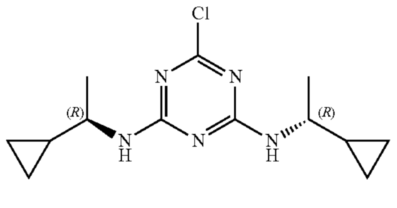

LC-MS: m/z 282.1 $(M+H)^+$.

Step 2: Preparation of $N^2$,$N^4$-bis((R)-1-cyclopropylethyl)-6-(pyridin-4-yl)-1,3,5-triazine-2,4-diamine. To a mixture of 6-chloro-$N^2$,$N^4$-bis((R)-1-cyclo-propylethyl)-1,3,5-triazine-2,4-diamine (100 mg, 0.36 mmol), pyridin-4-ylboronic acid (66 mg, 0.52 mmol), and $K_2CO_3$ (99 mg, 0.72 mmol) in 1,4-dioxane (3 mL) and water (1 mL) stirred at r.t. under the atmosphere of nitrogen was added $Pd(PPh_3)_4$(42 mg, 0.036 mmol) in one portion. The reaction mixture was stirred at 80° C. overnight. The mixture was partitioned between water and EtOAc. The organic layer was dried over anhydrous $Na_2SO_4$ and concentrated. The residue was purified by a standard method to give the desired product.

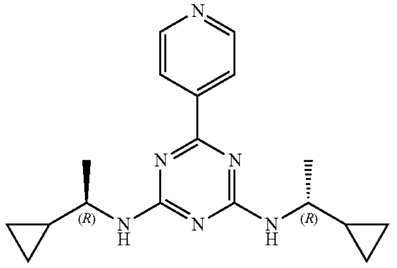

$^1H$ NMR (400 MHz, DMSO-$d_6$): δ 7.61-7.28 (m, 6H), 3.58-3.39 (m, 2H), 1.23-1.10 (m, 3H), 1.02-0.89 (m, 2H), 0.48-0.26 (m, 6H), 0.20-0.10 (m, 2H). LC-MS: m/z 325.2 $(M+H)^+$.

The procedure set forth above was used to produce the following compounds using the appropriate starting materials.

Compound 6-(3-chlorophenyl)-$N^2$,$N^4$-bis((R)-1-cyclopropylethyl)-1,3,5-triazine-2,4-diamine

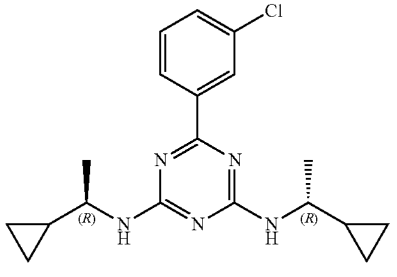

$^1H$ NMR (400 MHz, DMSO-$d_6$): δ 8.30-8.14 (m, 2H), 7.58 (d, J=7.7 Hz, 1H), 7.52 (t, J=7.8 Hz, 1H), 7.41 (d, J=8.2 Hz, 1H), 7.35-7.26 (m, 1H), 3.70-3.43 (m, 2H), 1.26-1.15 (m, 6H), 1.02-0.92 (m, 2H), 0.49-0.30 (m, 6H), 0.26-0.11 (m, 2H). LC-MS: m/z 358.2 $(M+H)^+$.

Compound 3-(4,6-bis((R)-1-cyclopropylethylamino)-1,3,5-triazin-2-yl)phenol

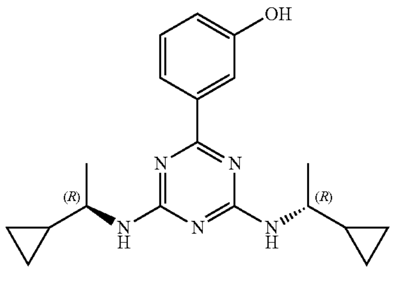

$^1H$ NMR (400 MHz, $CDCl_3$): δ 7.99-7.64 (m, 2H), 7.29 (d, J=7.9 Hz, 1H), 6.96 (d, J=7.8 Hz, 1H), 5.78-5.04 (m, 2H), 4.07 (s, 1H), 3.60 (m, 2H), 1.27 (d, J=4.3 Hz, 6H), 0.89 (d, J=3.6 Hz, 2H), 0.43 (m, 8H). LC-MS: m/z 340.2 $(M+H)^+$.

TABLE 3

| The following targets were prepared by the procedure described in Scheme 3 above. | | | | |
|---|---|---|---|---|
| | | | LCMS | |
| Compound ID | Name | Structure | Expected MW | Found $(M + 1)^+$ |
| 92 | $N^2$,$N^4$-bis((R)-1-cyclopropylethyl)-6-(pyridin-3-yl)-1,3,5-triazine-2,4-diamine | 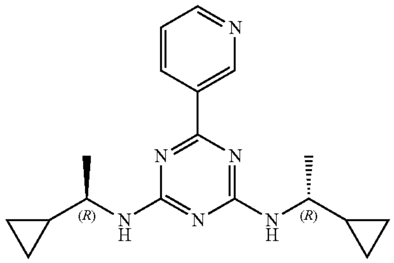 | 324.2 | 325.2 |
| 78 | $N^2$,$N^4$-bis((R)-1-cyclopropylethyl)-6-(2-fluoro-5-methoxyphenyl)-1,3,5-triazine-2,4-diamine | 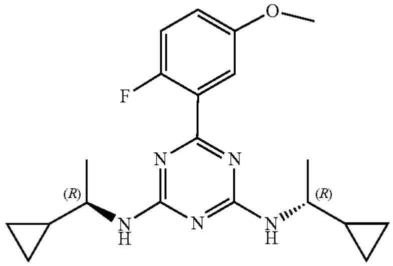 | 371.2 | 372.2 |
| 66 | 6-(2-chlorophenyl)-$N^2$,$N^4$-bis((R)-1-cyclopropylethyl)-1,3,5-triazine-2,4-diamine | 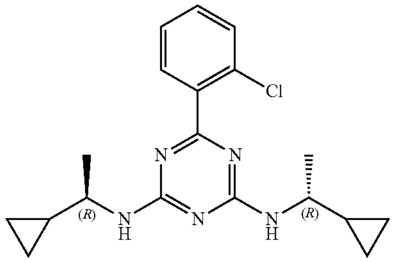 | 357.2 | 358.2 |
| 77 | 6-(2-fluorophenyl)-$N^2$,$N^4$-bis((R)-1-cyclopropylethyl)-1,3,5-triazine-2,4-diamine | 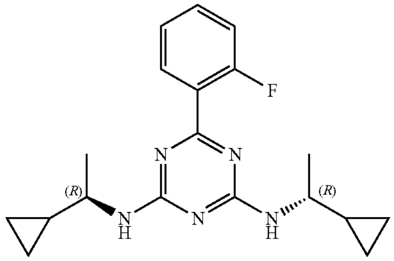 | 341.2 | 342.2 |
| 82 | (3-(4,6-bis((R)-1-cyclopropylethylamino)-1,3,5-triazin-2-yl)phenyl)methanol | 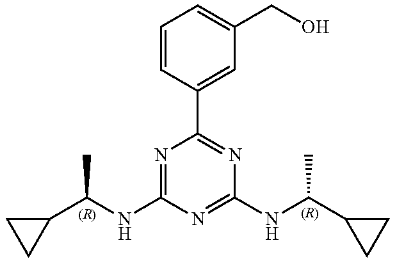 | 353.2 | 354.2 |

TABLE 3-continued

The following targets were prepared by the procedure described in Scheme 3 above.

| Compound ID | Name | Structure | LCMS Expected MW | LCMS Found (M + 1)$^+$ |
|---|---|---|---|---|
| | $N^2$,$N^4$-bis(1-cyclopropylethyl)-6-(1H-indol-4-yl)-1,3,5-triazine-2,4-diamine | 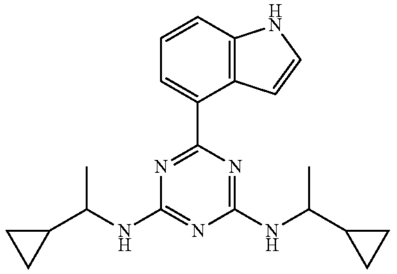 [SMILES: CC(Nc1nc(NC(C)C2CC2)nc(-c2cccc3[nH]ccc23)n1)C1CC1] | 362.2 | 363.2 |
| | $N^2$,$N^4$-bis((R)-1-cyclopropylethyl)-6-(1H-indol-4-yl)-1,3,5-triazine-2,4-diamine | 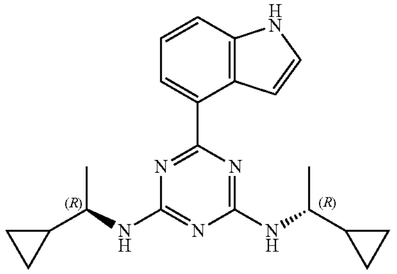 | 362.2 | 363.2 |

Example 4. Preparation of Di-aliphatic Triazine Compounds of Formula G. The compounds of this Example are prepared by general Scheme 4, set forth below.

Scheme 4

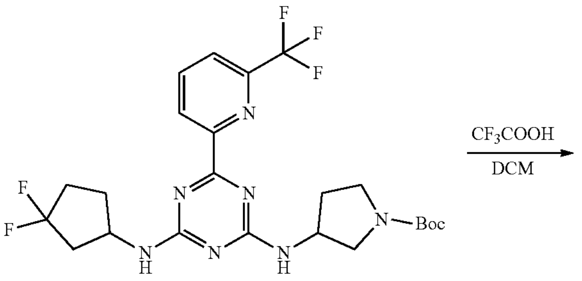

12

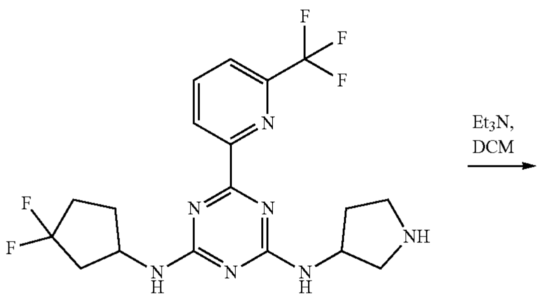

13

-continued

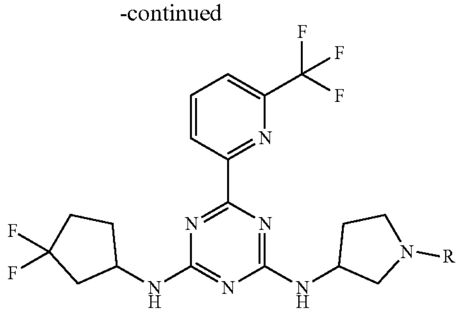

Formula G

Step 1. Preparation of $N^2$-(3,3-difluorocyclopentyl)-$N^4$-(pyrrolidin-3-yl)-6-(6-(trifluoro methyl)pyridin-2-yl)-1,3,5-triazine-2,4-diamine. To a solution of tert-butyl 3-(4-(3,3-difluorocyclopentylamino)-6-(6-(trifluoromethyl)pyridin-2-yl)-1,3,5-triazin-2-ylamino)pyrrolidine-1-carboxylate (160 mg, 0.3 mmol) in DCM (3 mL) at 0° C. was added TFA (1 mL). The mixture was stirred at room temperature for 2 hrs and then concentrated. The residue was extracted with EtOAc. Combined organic layers were washed with saturated aqueous $NaHCO_3$ and brine, dried over anhydrous $Na_2SO_4$ and then concentrated to afford the desired product which was used in the next step without any further purification.

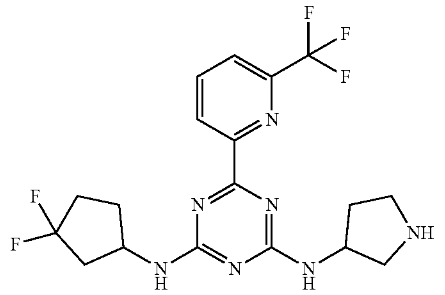 [SMILES: FC1(F)CCC(Nc2nc(NC3CCNC3)nc(-c3cccc(C(F)(F)F)n3)n2)C1]

LC-MS: m/z 430.2 $(M+H)^+$.

Step 2. Preparation of $N^2$-(3,3-difluorocyclopentyl)-$N^4$-(1-(methylsulfonyl)pyrroli-din-3-yl)-6-(6-(trifluoromethyl) pyridin-2-yl)-1,3,5-triazine-2,4-diamine. A mixture of $N^2$-(3,3-difluorocyclopentyl)-$N^4$-(pyrrolidin-3-yl)-6-(6-(trifluoromethyl) pyridin-2-yl)-1,3,5-triazine-2,4-diamine (20 mg, 0.05 mmol), $Et_3N$ (9.4 mg, 0.09 mmol), MsCl (6 mg, 0.06 mmol) in DCM (2 mL) was stirred at room temperature overnight. The mixture was concentrated and the residue was purified by a standard method to afford the desired product.

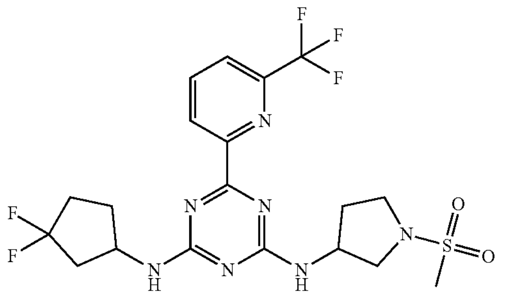 [SMILES: CS(=O)(=O)N1CCC(Nc2nc(NC3CCC(F)(F)C3)nc(-c3cccc(C(F)(F)F)n3)n2)C1]

$^1H$ NMR (400 MHz, $CDCl_3$): δ 8.62-8.46 (m, 1H), 8.04 (d, J=7.5 Hz, 1H), 7.81 (d, J=7.6 Hz, 1H), 5.79-5.38 (m, 2H), 4.80-4.53 (m, 2H), 3.76-3.52 (m, 2H), 3.39-3.23 (m, 1H), 2.91 (s, 3H), 2.69-2.57 (m, 1H), 2.45-2.25 (m, 3H), 2.20-1.98 (m, 3H), 1.95-1.81 (m, 1H), 1.22-1.18 (m, 1H). LC-MS: m/z 508.1 $(M+H)^+$.

The procedure set forth above was used to produce the following compounds using the appropriate starting material.

Coumpound methyl 3-((4-((3,3-difluorocyclopentyl) amino)-6-(6-(trifluoro methyl)pyridin-2-yl)-1,3,5-triazin-2-yl)amino)pyrrolidine-1-carboxylate

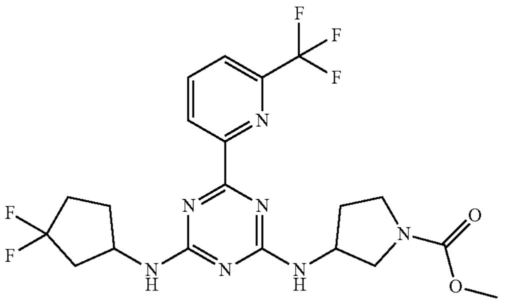 [SMILES: COC(=O)N1CCC(Nc2nc(NC3CCC(F)(F)C3)nc(-c3cccc(C(F)(F)F)n3)n2)C1]

$^1H$ NMR (400 MHz, $CDCl_3$): δ 8.58-8.48 (m, 1H), 8.02 (d, J=7.5 Hz, 1H), 7.81 (d, J=7.5 Hz, 1H), 5.94-5.18 (m, 2H), 4.72-4.47 (m, 2H), 3.83-3.74 (m, 1H), 3.72 (s, 3H), 3.65-3.51 (m, 2H), 3.44-3.28 (m, 1H), 2.45-1.80 (m, 7H). LC-MS: m/z 488.2 $(M+H)^+$.

Compound 1-(3-((4-((3,3-difluorocyclopentyl) amino)-6-(6-(trifluoromethyl)pyridin-2-yl)-1,3,5-triazin-2-yl)amino)pyrrolidin-1-yl)ethanone

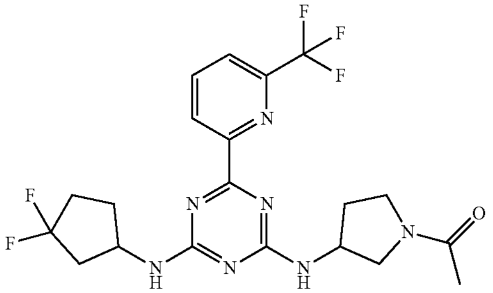 [SMILES: CC(=O)N1CCC(Nc2nc(NC3CCC(F)(F)C3)nc(-c3cccc(C(F)(F)F)n3)n2)C1]

$^1H$ NMR (400 MHz, $CDCl_3$): δ 8.55 (m, 1H), 8.07 (d, J=6.8 Hz, 1H), 7.85 (t, J=6.7 Hz, 1H), 4.84-4.30 (m, 2H), 3.97-3.52 (m, 4H), 2.62 (m, 1H), 2.50-2.22 (m, 3H), 2.22-1.98 (m, 3H), 1.25 (s, 3H). LC-MS: m/z 472.2 $(M+H)^+$.

Compound $N^2$-(3,3-difluorocyclopentyl)-$N^4$-(1-methylpyrrolidin-3-yl)-6-(6-(trifluoromethyl)pyridin-2-yl)-1,3,5-triazine-2,4-diamine. To a solution of tert-butyl 3-(4-(3,3-difluorocyclopentylamino)-6-(6-(trifluoromethyl)pyridin-2-yl)-1,3,5-triazin-2-ylamino)pyrrolidine-1-carboxylate (25 mg, 0.05 mmol) in THF (3 mL) at 0° C. was added $LiAlH_4$(5 mg, 0.14 mmol). The mixture was stirred at 0° C. for 2 hr, then at r.t for 30 min, and finally at 60° C. for 2 hr. The reaction mixture was quenched with water and extracted by EtOAc. Combined organic layers were washed with brine, dried over anhydrous $Na_2SO_4$, and concentrated. The residue was purified by a standard method to give the desired product.

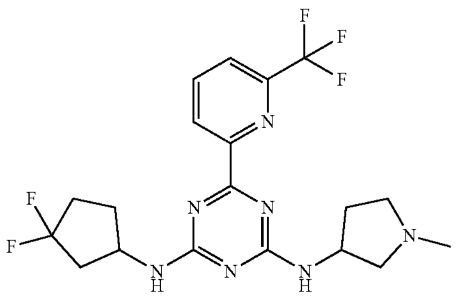 [SMILES: CN1CCC(Nc2nc(NC3CCC(F)(F)C3)nc(-c3cccc(C(F)(F)F)n3)n2)C1]

$^1H$ NMR (400 MHz, $CDCl_3$): δ 8.55 (m, 1H), 8.08-7.93 (m, 1H), 7.80 (t, J=7.4 Hz, 1H), 4.63 (m, 2H), 3.47-2.87 (m, 3H), 2.69 (m, 6H), 2.28 (m, 4H), 1.84 (m, 4H). LC-MS: m/z 444.2 $(M+H)^+$.

Example 5. Preparation of Di-aliphatic Triazine Compounds. The compounds of this Example are prepared by general Scheme 5, set forth below.

Scheme 5

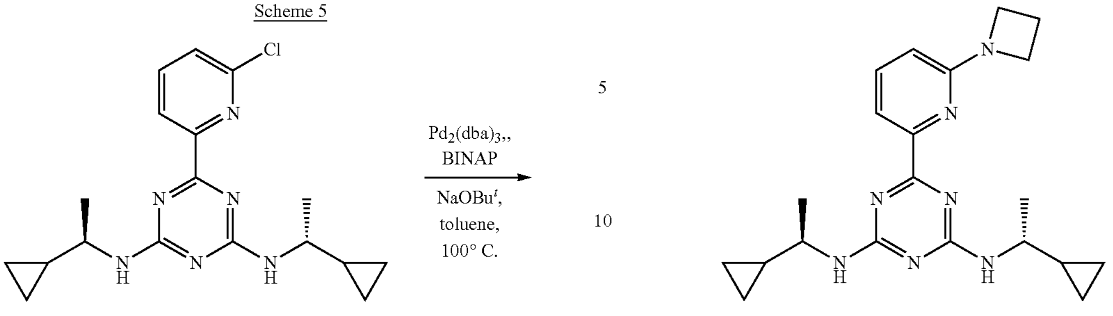

14

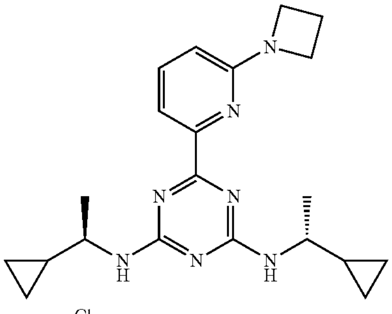

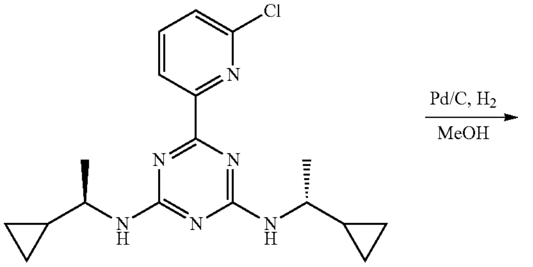

14

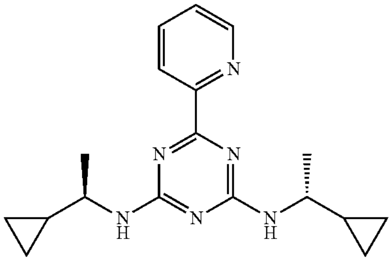 [SMILES: C[C@@H](Nc1nc(N[C@H](C)C2CC2)nc(-c2ccccn2)n1)C1CC1]

Step 1: Preparation of 6-(6-(azetidin-1-yl)pyridin-2-yl)-$N^2$,$N^4$-bis((R)-1-cyclopropyl-ethyl)-1,3,5-triazine-2,4-diamine. A mixture of 6-(6-chloropyridin-2-yl)-$N^2$,$N^4$-bis((R)-1-cyclopropylethyl)-1,3,5-triazine-2,4-diamine (40 mg, 0.11 mmol), azetidine (7.6 mg, 0.13 mmol), 2,2'-bis-(diphenylphosphino)-1,1'-binaphthyl (6.9 mg, 0.01 mmol), sodium tert-butoxide (15 mg, 0.16 mmol) and tris(dibenzylideneacetone)-dipalladium (10.2 mg, 0.01 mmol) in toluene (3 mL) was stirred at 100° C. under an atmosphere of nitrogen overnight. The mixture was cooled to room temperature and filtered. The filtrate was concentrated under reduced pressure and the residue was purified by a standard method to afford the desired product.

$^1$H NMR (400 MHz, $CD_3OD$): δ 8.49 (s, 1H), 7.72-7.53 (m, 2H), 6.56 (d, J=7.4, 1H), 4.11 (t, J=7.4, 4H), 3.59 (m, 2H), 2.42 (p, J=7.4, 2H), 1.30 (d, J=6.5, 6H), 0.98 (s, 2H), 0.67-0.13 (m, 8H). LC-MS: m/z 380.2 $(M+H)^+$.

Step 2: Preparation of $N^2$,$N^4$-bis((R)-1-cyclopropyl-ethyl)-6-(pyridin-2-yl)-1,3,5-triazine-2,4-diamine. To a solution of 6-(6-chloropyridin-2-yl)-$N^2$,$N^4$-bis((R)-1-cyclopropylethyl)-1,3,5-triazine-2,4-diamine (20 mg, 0.05 mmol) in methanol (2 mL) was added Pd/C (2 mg) under an atmosphere of nitrogen. The mixture was then stirred at room temperature under a hydrogen balloon overnight. The mixture was filtered and the filtrate was concentrated. The residue was purified by a standard method to afford the desired product.

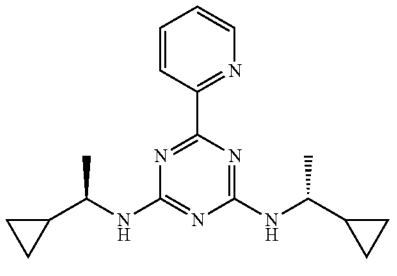

$^1$H NMR (400 MHz, DMSO-$d_6$): δ 8.82-8.03 (m, 4H), 7.75 (m, 2H), 3.79-3.45 (m, 2H), 1.21 (d, J=6.3 Hz, 6H), 1.07-0.84 (m, 2H), 0.55-0.05 (m, 8H). LC-MS: m/z 325.2 $(M+H)^+$.

Example 6. Preparation of Di-aliphatic Triazine Compounds of Formula H. The compounds of this Example are prepared by general Scheme 6, set forth below.

Scheme 6

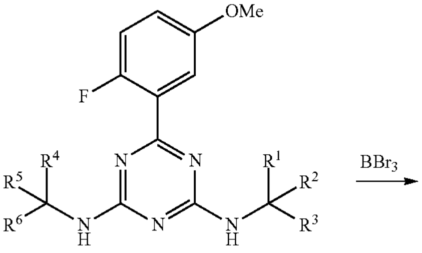

18

-continued

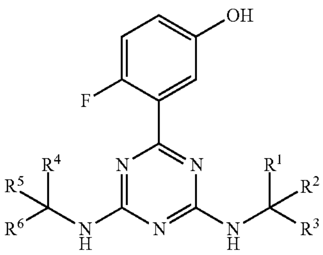

Formula H

Step 1: Preparation of 2-((4-(2-fluoro-5-hydroxyphenyl)-6-(isopropylamino)-1,3,5-triazin-2-yl)amino)-2-methylpropanenitrile. To a solution of 2-((4-(2-fluoro-5-methoxyphenyl)-6-(isopropylamino)-1,3,5-triazin-2-yl)amino)-2-methylpropanenitrile (200 mg, 0.6 mmol) in anhydrous DCM (3 mL) at −65° C. was added dropwise $BBr_3$ (0.6 mL) and the reaction mixture was stirred at this temperature for 20 min. The mixture was slowly warmed up to 0° C. and stirred for 10 min. and then stirred at room temperature for 1 hr. The reaction was quenched with icy Sat. aq. $NaHCO_3$ till pH=8. The resulting mixture was extracted with EtOAc (2×10 mL). Combined organic layers were washed with brine, dried over anhydrous $Na_2SO_4$ and concentrated under reduced pressure. The residue was purified by a standard method to afford the desired product.

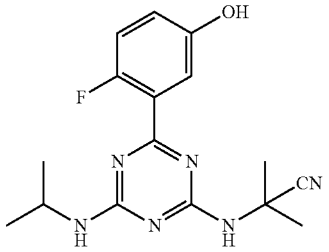 [SMILES: CC(C)Nc1nc(NC(C)(C)C#N)nc(-c2cc(O)ccc2F)n1]

$^1$H NMR (400 MHz, $CDCl_3$): δ 7.20 (s, 1H), 6.96 (t, J=9.6 Hz, 1H), 6.83 (d, J=8.6 Hz, 1H), 5.72 (m, 2H), 4.26 (s, 1H), 1.79 (s, 6H), 1.26 (d, J=6.1 Hz, 6H). LC-MS: m/z 331.2 $(M+H)^+$.

Example 7. Preparation of Di-aliphatic Pyrimidine Compounds of Formula J. The compounds of this Example are prepared by general Scheme 7, set forth below.

Scheme 7

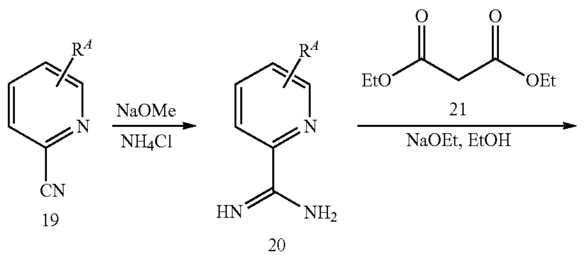

-continued

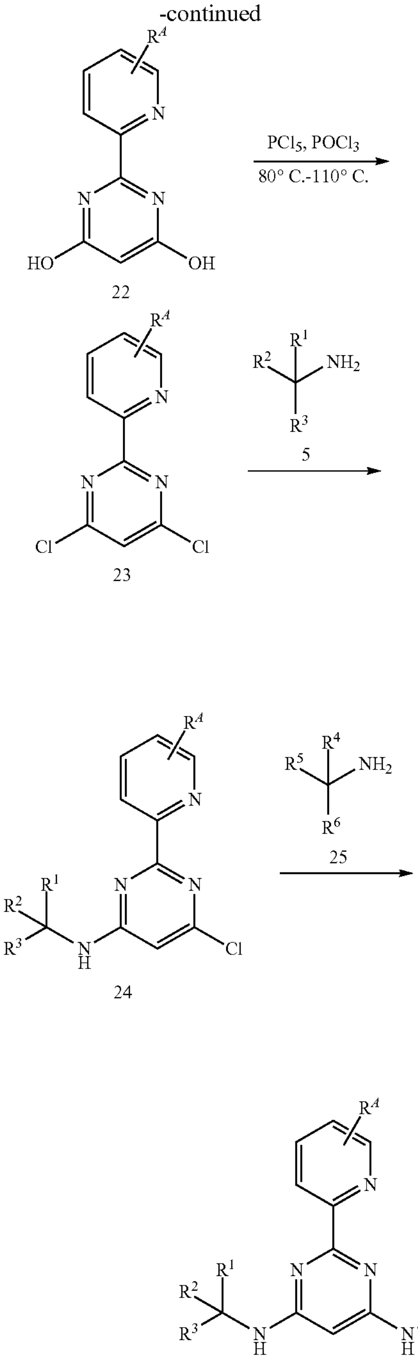

Formula J

Step 1: Preparation of 6-(trifluoromethyl)picolinimidamide. To a solution of 6-(trifluoromethyl)picolinonitrile (50 mg, 0.3 mmol, 1 eq) in EtOH (3 mL) was added NaOMe (1.6 mg, 0.03 mmol, 0.1 eq) at 0° C. The mixture was stirred at r.t. for 1 hr, followed by addition of $NH_4Cl$ (21 mg, 0.39 mmol, 13 eq). The resulting mixture was stirred at 90° C. for 1 hr and cooled to room temperature. The mixture was adjusted pH to 9 with saturated aqueous $NaHCO_3$ and then extracted with EtOAc. Combined organic layers were washed with brine, dried over anhydrous $Na_2SO_4$, and concentrated. The residue was purified by a standard method to afford the desired product.

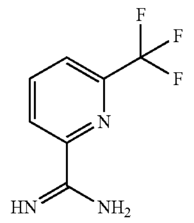 [SMILES: N=C(N)c1cccc(C(F)(F)F)n1]

LC-MS: m/z 190.1 $(M+H)^+$.

Step 2: Preparation of 2-(6-(trifluoromethyl)pyridin-2-yl) pyrimidine-4,6-diol. To a solution of sodium (366 mg, 15.9 mmol, 5.0 eq) in anhydrous EtOH (6 mL) was added dropwise a solution of 6-(trifluoromethyl)picolinimidamide (600 mg, 3.2 mmol) in EtOH. The reaction mixture was stirred at r.t. for 1 hr, followed by addition of diethyl malonate (1 mL, 6.4 mmol, 2.0 eq). The mixture was stirred at reflux overnight and then cooled to room temperature. The resulting mixture was adjusted pH to 7 by 1 N aq. HCl solution. The suspension was filtered and the filter cake was washed with water. The solid was suspended in MeOH and filtered. The filtrate was concentrated under reduced pressure to give the desired product which was used directly in the next step without any further purification.

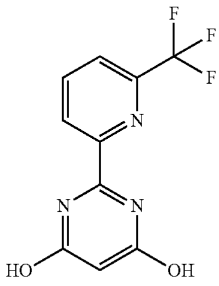 [SMILES: Oc1cc(O)nc(-c2cccc(C(F)(F)F)n2)n1]

LC-MS: m/z 256.0 $(M-H)^-$.

Step 3: Preparation of 4,6-dichloro-2-(6-(trifluoromethyl) pyridin-2-yl)pyrimidine. A solution of 2-(6-(trifluoromethyl)pyridin-2-yl)pyrimidine-4,6-diol (1 g, 3.9 mmol) in $POCl_3$ (6 mL) was stirred at 90° C. overnight and then concentrated to remove the volatile. The residue was purified by a standard method to afford the desired product.

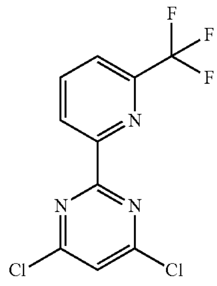 [SMILES: FC(F)(F)c1cccc(-c2nc(Cl)cc(Cl)n2)n1]

LC-MS: m/z 294.0 $(M+H)^+$.

Step 4: Preparation of (R)-6-chloro-N-(1-cyclopropylethyl)-2-(6-(trifluoromethyl)-pyridin-2-yl)pyrimidin-4-amine. To a solution of 4,6-dichloro-2-(6-(trifluoromethyl) pyridin-2-yl)pyrimidine (80 mg, 0.27 mmol, 1 eq) in THF (3 mL) was added (R)-1-cyclopropylethanamine (0.06 mL, 0.6 mmol, 2.2 eq) and $Et_3N$ (0.07 mL, 0.54 mmol, 2 eq). The reaction mixture was stirred at room temperature overnight and concentrated. The residue was purified by a standard method to give the desired product.

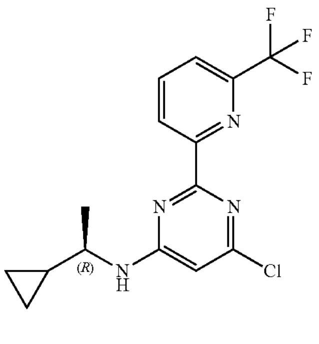

LC-MS: m/z 343.1 $(M+H)^+$.

Step 5: Preparation of N4,N6-bis((R)-1-cyclopropylethyl)-2-(6-(trifluoromethyl)pyri din-2-yl)pyrimidine-4,6-diamine. To a solution of (R)-6-chloro-N-(1-cyclopropylethyl)-2-(6-(trifluoromethyl)-pyridin-2-yl)pyrimidin-4-amine (50 mg, 0.15 mmol, 1 eq) in DMSO (2 mL) was added (R)-1-cyclopropylethanamine hydrochloride (22 mg, 0.18 mmol, 1.2 eq) and DIPEA (0.08 mL, 0.45 mmol, 3 eq). The mixture was irradiated under microwave at 160° C. for 1.5 hr. After addition of (R)-1-cyclopropylethanamine (0.18 mmol, 1.2 eq), the resulting mixture was stirred and irradiated under microwave at 160° C. for another 2 hr. The mixture was cooled to r.t. and then partitioned between EtOAc and water. The organic layer was washed with water and brine, dried over anhydrous $Na_2SO_4$, and concentrated. The residue was purified by a standard method to give the desired product.

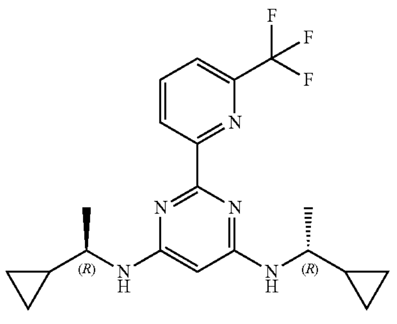

$^1$H NMR (400 MHz, $CDCl_3$): δ 8.40 (d, J=7.9 Hz, 1H), 7.87 (t, J=7.9 Hz, 1H), 7.62 (d, J=7.8 Hz, 1H), 5.19 (m, 3H), 3.13 (d, J=6.3 Hz, 2H), 1.19 (d, J=6.4 Hz, 6H), 0.96-0.72 (m, 2H), 0.52-0.33 (m, 4H), 0.33-0.10 (m, 4H). LC-MS: m/z 392.2 $(M+H)^+$.

The procedure set forth above was used to produce the following compounds using the appropriate starting materials.

Compound $N^4$,$N^6$-bis((S)-1-cyclopropylethyl)-2-(6-(trifluoromethyl)pyridin-2-yl) pyrimidine-4,6-diamine

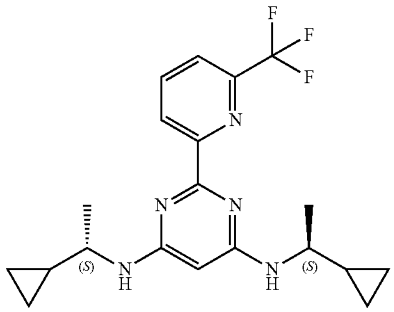

$^1$H NMR (400 MHz, $CDCl_3$): δ 8.49 (d, J=7.8 Hz, 1H), 7.95 (t, J=7.9 Hz, 1H), 7.71 (d, J=7.8 Hz, 1H), 5.22 (m, 3H), 3.22 (d, J=6.5 Hz, 2H), 1.40-1.15 (m, 6H), 0.95 (m, 2H), 0.61-0.44 (m, 4H), 0.31 (m, 4H). LC-MS: m/z 392.2 $(M+H)^+$.

Compound $N^4$—((R)-1-cyclopropylethyl)-$N^6$—((S)-1-cyclopropylethyl)-2-(6-(trifluoro methyl)pyridin-2-yl)pyrimidine-4,6-diamine

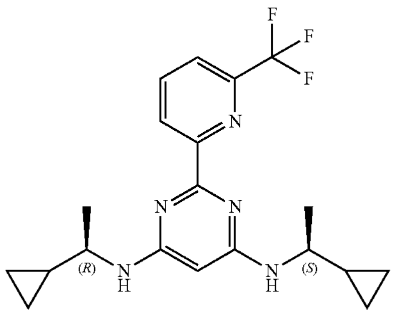

$^1$H NMR (400 MHz, $CDCl_3$): δ 8.49 (d, J=7.8 Hz, 1H), 7.97 (t, J=7.9 Hz, 1H), 7.72 (d, J=7.8 Hz, 1H), 5.22 (m, 3H), 3.22 (d, J=6.5 Hz, 2H), 1.68-1.25 (m, 6H), 0.97 (m 2H), 0.61-0.44 (m, 4H), 0.31 (m, 4H). LC-MS: m/z 392.2 $(M+H)^+$.

TABLE 7

The following compounds were prepared by the procedure described in Scheme 7 above.

| Compound ID | Name | Structure | LCMS Expected MW | LCMS Found $(M + 1)^+$ |
|---|---|---|---|---|
| | $N^4$,$N^6$-bis(-1-cyclopropylethyl)-2-(6-(trifluoromethyl)pyridin-2-yl)pyrimidine-4,6-diamine | 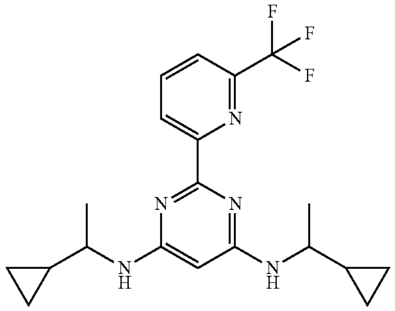 [SMILES: CC(Nc1cc(NC(C)C2CC2)nc(-c2cccc(C(F)(F)F)n2)n1)C1CC1] | 391.2 | 392.2 |

Example 9. Preparation of Symmetric Di-aliphatic Triazine Compounds of Formula K. The compounds of this Example are prepared by general Scheme 9, set forth below.

Scheme 9

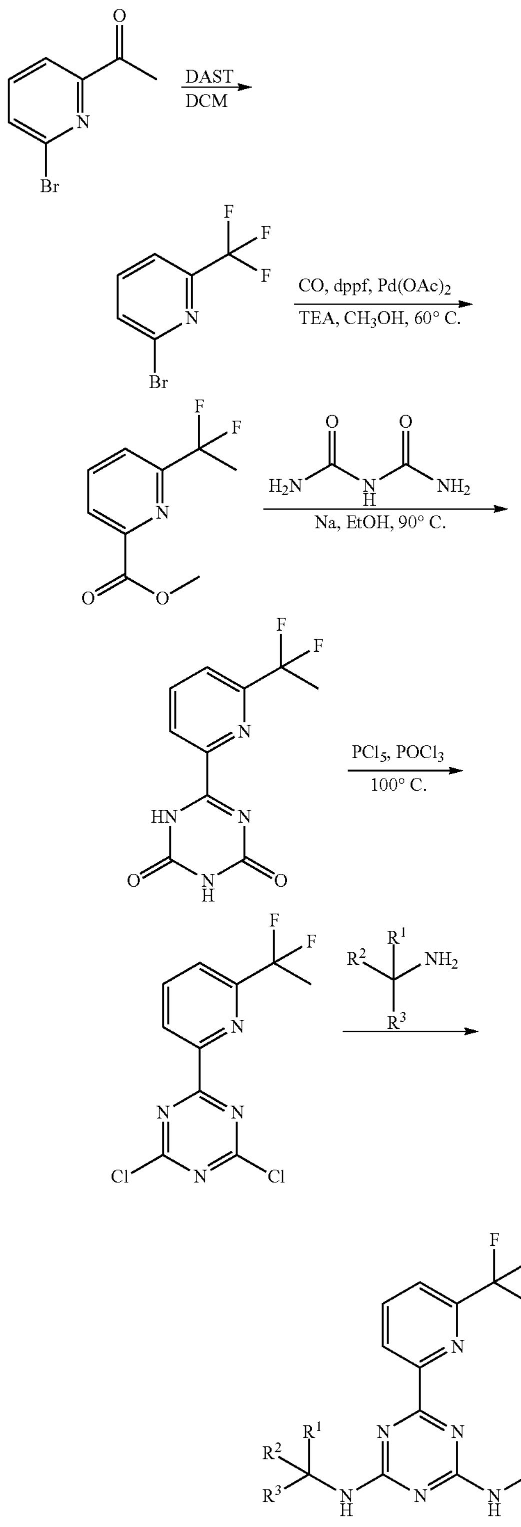

Formula K

Step 1: Preparation of 2-bromo-6-(1,1-difluoroethyl)pyridine

To a solution of 1-(6-bromopyridin-2-yl)ethanone (26 g, 130 mmol) in dry DCM (150 mL) at 0° C. was added dropwise DAST (84 mL, 650 mmol) over 30 min. The reaction mixture was then slowly allowed to warm up to r.t., and stirred until the reaction was complete. The resulting mixture was slowly poured into ice (300 g) and extracted with DCM (2×50 mL). The combined organic layers were washed with water, dried over anhydrous $Na_2SO_4$ and concentrated under reduced pressure. The residue was purified by standard methods to afford 2-bromo-6-(1,1-difluoroethyl)pyridine. LC-MS: m/z 222.0 $(M+H)^+$.

Step 2: Preparation of methyl 6-(1,1-difluoroethyl)picolinate

To a solution of 2-bromo-6-(1,1-difluoroethyl)pyridine (30.2 g, 136 mmol) in MeOH (300 mL) were added 1,1'-bis(diphenylphosphino)-ferrocene (7.5 g, 13.6 mmol), triethylamine (28.4 mL, 204 mmol), and $Pd(OAc)_2$ (1.52 g, 6.7 mmol). The mixture was stirred at 60° C. under CO atmosphere (60 psi) for 16 hr. The resulting mixture was filtered and concentrated under reduced pressure. The residue was purified by standard methods to afford methyl 6-(1,1-difluoroethyl) picolinate. LC-MS: m/z 202.2 $(M+H)^+$.

Step 3: Preparation of 6-(6-(1,1-difluoroethyl)pyridin-2-yl)-1,3,5-triazine-2,4 (1H,3H)-dione To a solution of NaOEt in EtOH (freshly prepared from sodium (1.9 g, 82.6 mmol and EtOH (150 mL)) was added methyl 6-(1,1-difluoroethyl)picolinate (2.8 g, 28 mmol) and biuret (14.0 g, 70 mmol). The mixture was stirred at 90° C. for 16 hr and concentrated under reduced pressure. To the residue was added water (50 mL). The resulting mixture was adjusted the pH to 7 with 1N HCl, and then filtered. The filter cake was washed with water, and dried under high vacuum to afford 6-(6-(1,1-difluoroethyl)pyridin-2-yl)-1,3,5-triazine-2,4(1H,3H)-dione. LC-MS: m/z 255.1 $(M+H)^+$.

Step 4: Preparation of 2,4-dichloro-6-(6-(1,1-difluoroethyl)pyridin-2-yl)-1,3,5-triazine To a solution of 6-(6-(1,1-difluoroethyl)pyridin-2-yl)-1,3,5-triazine-2,4 (1H,3H)-dione (6 g, 25 mmol) in $POCl_3$ (60 mL) was added $PCl_5$ (26 g, 125 mmol). The mixture was stirred at 100° C. for 16 hr and concentrated under reduced pressure. The residue was purified by standard methods to afford 2,4-dichloro-6-(6-(1,1-difluoroethyl)pyridin-2-yl)-1,3,5-triazine. $^1H$ NMR (400 MHz, $CDCl_3$) δ 8.62 (d, 1H), 8.07 (t, 1H), 7.94 (d, 1H), 2.16 (q, 3H). LC-MS: m/z 292.1 $(M+H)^+$.

Step 5: Preparation of $N^2$,$N^4$-bis(4,4-difluorocyclohexyl)-6-(6-(1,1-difluoroethyl) pyridin-2-yl)-1,3,5-triazine-2,4-diamine To a mixture of 2,4-dichloro-6-(6-(1,1-difluoroethyl) pyridin-2-yl)-1,3,5-triazine (582 mg, 2.0 mmol, 1.0 eq) and 4,4-difluorocyclohexanamine hydrochloride (752 mg, 4.4 mmol, 2.2 eq) in THF (12 mL) at r.t. were added CsF (1.2 g, 8.0 mmol, 2 eq) and DIPEA (1.4 mL, 8.0 mmol, 4 eq). The mixture was stirred at 60° C. overnight and then filtered. The filtrate was concentrated under reduced pressure and the residue was purified by standard methods to give the desired product.

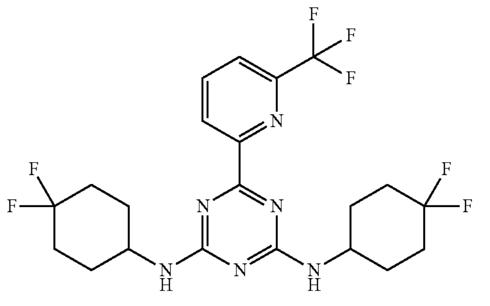 [SMILES: FC1(F)CCC(Nc2nc(NC3CCC(F)(F)CC3)nc(-c3cccc(C(F)(F)F)n3)n2)CC1]

$^1H$ NMR (400 MHz, $CDCl_3$) δ 8.32-8.40 (m, 1H), 7.94 (bs, 1H), 7.78 (bs, 1H), 5.07-5.46 (m, 2H), 3.99-4.18 (m, 2H), 1.71-2.17 (m, 19H). LC-MS: m/z 489.2 $(M+H)^+$.

The procedure set forth in Example 9 was used to produce the following compounds using the appropriate starting materials.

Compound $N^2$,$N^4$-bis(3,3-difluorocyclopentyl)-6-(6-(1,1-difluoroethyl)pyridin-2-yl)-1,3,5-triazine-2,4-diamine

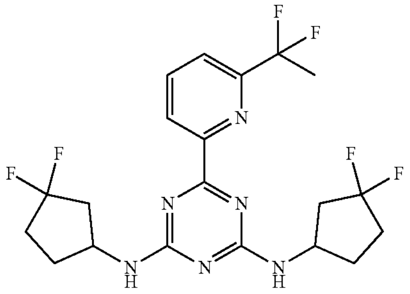 [SMILES: CC(F)(F)c1cccc(-c2nc(NC3CCC(F)(F)C3)nc(NC3CCC(F)(F)C3)n2)n1]

$^1H$ NMR (400 MHz, $CDCl_3$) δ 8.32-8.43 (m, 1H), 7.93-7.95 (m, 1H), 7.78 (bs, 1H), 5.28-5.70 (m, 2H), 4.54-4.71 (m, 2H), 1.72-2.65 (m, 15H). LC-MS: m/z 461.2 $(M+H)^+$.

Compound $N^2$,$N^4$-bis(3,3-difluorocyclobutyl)-6-(6-(1,1-difluoroethyl)pyridin-2-yl)-1,3,5-triazine-2,4-diamine

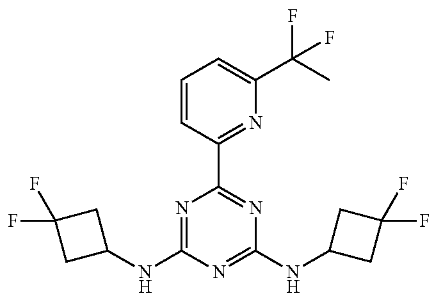 [SMILES: CC(F)(F)c1cccc(-c2nc(NC3CC(F)(F)C3)nc(NC3CC(F)(F)C3)n2)n1]

$^1H$ NMR (400 MHz, $CDCl_3$) δ 8.35-8.42 (m, 1H), 7.95 (bs, 1H), 7.80 (bs, 1H), 5.42-5.85 (m, 2H), 4.35-4.52 (m, 2H), 3.04 (bs, 4H), 2.62 (bs, 4H), 2.04-2.16 (m, 3H). LC-MS: m/z 433.2 $(M+H)^+$.

Example 10. Preparation of Symmetric Di-aliphatic Triazine Compounds of Formula L. The compounds of this Example are prepared by general Scheme 10, set forth below.

Scheme 10

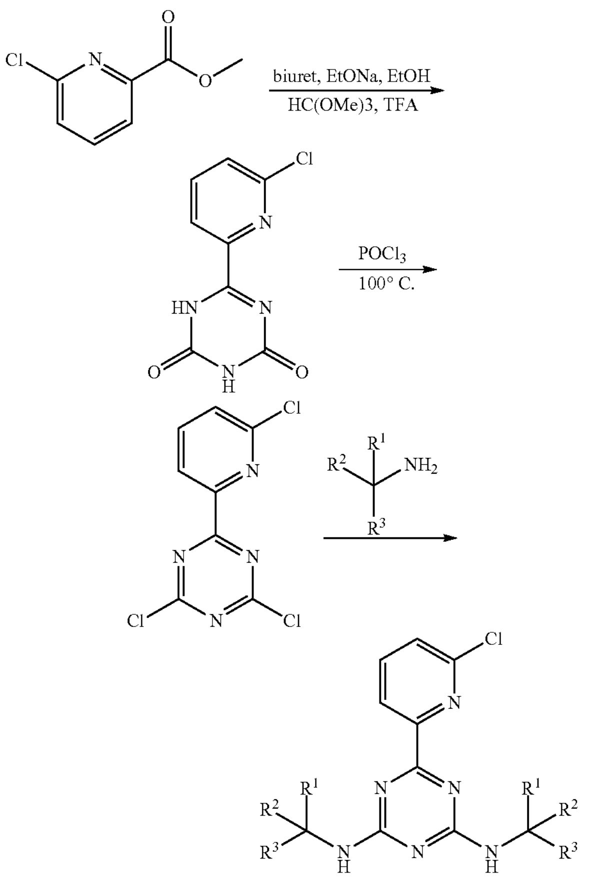

Formula L

Step 1: Preparation of 6-(6-chloropyridin-2-yl)-1,3,5-triazine-2,4(1H,3H)-dione. To a dried three-necked round bottom flask were added biuret (14.8 g, 0.14 mol), methyl 6-chloropicolinate (21 g, 0.12 mol) and EtOH (250 mL). The mixture was degassed with N2 three times and then stirred at 25° C. for 20 min. Then the temperature was allowed to rise to 50° C., followed by addition of $HC(OMe)_3$ (17 mL, 0.14 mol) and TFA (1.37 g, 0.01 mol). The reaction mixture (pale yellow slurry) was stirred at this temperature for 30 min, followed by dropwise addition of a solution of NaOEt in EtOH (20% wt, 163 g, 0.48 mol). The resulting yellowish thick slurry was heated to reflux for 2 hr until the reaction was complete. The mixture was cooled to r.t. and concentrated under reduced pressure. The residue was treated with water (200 mL) and concentrated under reduced pressure to remove the remaining ethanol. Then water (300 mL) was added to the residue (while stirring) to form a clear brown solution. The solution was cooled to 10° C. and slowly adjusted to pH 1 by 6N HCl. The resulting mixture was stirred for another 2 hr and filtered. The filter cake was washed with aq. HCl (pH=1), collected and suspended in DCM (300 mL). The suspension was stirred at r.t. for 2 hr, filtered and dried to afford the desired product. LC-MS: m/z 225.0 $(M+H)^+$.

Step 2: Preparation of 2,4-dichloro-6-(6-chloropyridin-2-yl)-1,3,5-triazine. The procedure is the same as Example 1 Step 3 described above. LC-MS: m/z 260.9 $(M+H)^+$.

Step 3: Preparation of 6-(6-chloropyridin-2-yl)-$N^2$,$N^4$-bis((R)-1,1,1-trifluoro propan-2-yl)-1,3,5-triazine-2,4-diamine. A mixture of 2,4-dichloro-6-(6-chloro-pyridin-2-yl)-1,3,5-triazine (0.27 g, 1.04 mol), (R)-1,1,1-trifluoropropan-2-amine hydrochloride (0.39 g, 2.6 mol), and potassium carbonate (0.43 g, 3.1 mol) in dry 1,4-dioxane (2.5 mL) was stirred under the atmosphere of $N_2$ at 50° C. for 36 hr then at 100° C. for another 36 hr until the reaction was complete. The resulting mixture was filtered through Celite and the cake was washed with EtOAc. The filtrate was concentrated and the residue was purified by standard methods to give the desired product.

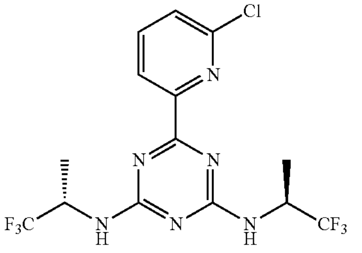 [SMILES: C[C@H](Nc1nc(N[C@@H](C)C(F)(F)F)nc(-c2cccc(Cl)n2)n1)C(F)(F)F]

$^1$H NMR (400 MHz, $CDCl_3$) δ 8.32 (m, 1H), 7.80 (m, 1H), 7.48 (d, J=7.9 Hz, 1H), 5.61 (m, 1.5H), 5.25 (m, 0.5H), 5.09 (m, 0.5H), 4.88 (m, 1.5H), 1.54-1.26 (m, 6H). LC-MS: m/z 415 $(M+H)^+$.

The procedure set forth in Example 10 was used to produce the following compounds using the appropriate starting materials.

Compound 6-(6-Chloropyridin-2-yl)-$N^2$,$N^4$-bis((S)-1,1,1-trifluoropropan-2-yl)-1,3,5-triazine-2,4-diamine

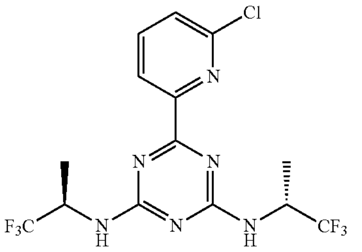 [SMILES: C[C@@H](Nc1nc(N[C@H](C)C(F)(F)F)nc(-c2cccc(Cl)n2)n1)C(F)(F)F]

$^1$H NMR (400 MHz, $CDCl_3$) δ 8.29-8.16 (m, 1H), 7.72 (d, J=7.6 Hz, 1H), 7.41 (d, J=7.9 Hz, 1H), 5.70-5.13 (m, 2H), 5.09-4.71 (m, 2H), 1.34 (m, 6H). LC-MS: m/z 415 $(M+H)^+$.

Compound 6-(6-Chloropyridin-2-yl)-$N^2$—((R)-1,1,1-trifluoropropan-2-yl)-$N^4$—((S)-1,1,1-trifluoropropan-2-yl)-1,3,5-triazine-2,4-diamine

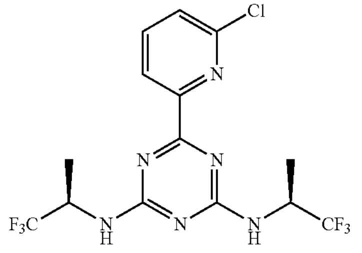 [SMILES: C[C@H](Nc1nc(N[C@H](C)C(F)(F)F)nc(-c2cccc(Cl)n2)n1)C(F)(F)F]

$^1$H NMR (400 MHz, $CDCl_3$) δ 8.41-8.23 (m, 1H), 7.83 (s, 1H), 7.51 (d, J=6.2 Hz, 1H), 5.68-5.20 (m, 2H), 5.18-4.81 (m, 2H), 1.48-1.39 (m, 6H). LC-MS: m/z 415 $(M+H)^+$.

Compound 6-(6-Chloropyridin-2-yl)-$N^2$,$N^4$-bis(1,1,1-trifluoropropan-2-yl)-1,3,5-triazine-2,4-diamine

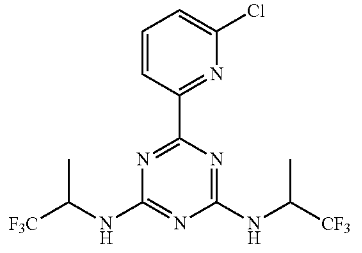 [SMILES: CC(Nc1nc(NC(C)C(F)(F)F)nc(-c2cccc(Cl)n2)n1)C(F)(F)F]

$^1$H NMR (400 MHz, $CDCl_3$) δ 8.29-8.16 (m, 1H), 7.72 (d, J=7.6 Hz, 1H), 7.41 (d, J=7.9 Hz, 1H), 5.70-5.13 (m, 2H), 5.09-4.71 (m, 2H), 1.34 (m, 6H). LC-MS: m/z 415 $(M+H)^+$.

Compound 6-(6-Chloropyridin-2-yl)-$N^2$,$N^4$-bis(1,1,1-trifluorobutan-2-yl)-1,3,5-triazine-2,4-diamine

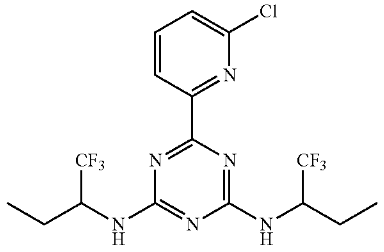 [SMILES: CCC(Nc1nc(NC(CC)C(F)(F)F)nc(-c2cccc(Cl)n2)n1)C(F)(F)F]

$^1$H NMR (400 MHz, $CDCl_3$) δ 8.39-8.31 (m, 1H), 7.86-7.79 (m, 1H), 7.50 (d, J=7.8 Hz, 1H), 5.67-5.12 (m, 2H), 4.98-4.65 (m, 2H), 2.07-1.91 (m, 2H), 1.70-1.55 (m, 2H), 1.06 (dd, J=8.6, 6.0 Hz, 6H). LC-MS: m/z 443 $(M+H)^+$.

Compound 6-(6-Chloropyridin-2-yl)-$N^2$,$N^4$-bis((S)-1,1,1-trifluorobutan-2-yl)-1,3,5-triazine-2,4-diamine

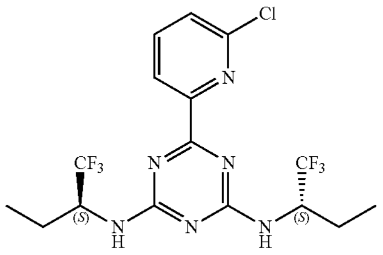

$^1$H NMR (400 MHz, $CDCl_3$) δ 8.30-8.35 (t, 1H), 7.78-7.82 (t, 1H), 7.47-7.52 (m, 1H), 5.49-5.63 (m, 2H), 4.72-4.89 (m, 2H), 1.95-1.99 (m, 2H), 1.59 (m, 2H), 1.02-1.08 (t, 6H). LC-MS: m/z 443 $(M+H)^+$.

Compound 6-(6-Chloropyridin-2-yl)-$N^2$,$N^4$-bis((R)-1,1,1-trifluorobutan-2-yl)-1,3,5-triazine-2,4-diamine

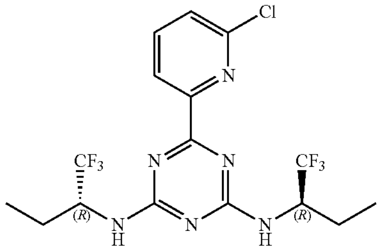

$^1$H NMR (400 MHz, $CDCl_3$) δ 8.31-8.35 (t, 1H), 7.78-7.82 (t, 1H), 7.47-7.49 (m, 1H), 5.16-5.71 (m, 2H), 4.72-4.74 (m, 2H), 1.94-2.01 (m, 2H), 1.62-1.64 (m, 2H), 1.02-1.08 (t, 6H). LC-MS: m/z 443 $(M+H)^+$.

Compound 6-(6-Chloropyridin-2-yl)-$N^2$—((R)-1,1,1-trifluorobutan-2-yl)-$N^4$—((S)-1,1,1-trifluorobutan-2-yl)-1,3,5-triazine-2,4-diamine

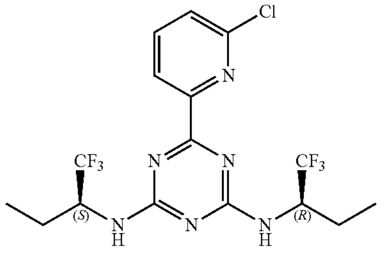

$^1$HNMR (400 MHz, $CDCl_3$) δ 8.30-8.35 (m, 1H), 7.81 (s, 1H), 7.47-7.49 (d, 1H), 5.35-5.66 (m, 2H), 4.91-5.13 (d, 1H), 4.72 (s, 1H), 2.00-2.23 (d, 3H), 1.31-1.42 (d, 1H), 1.03-1.07 (m, 6H). LC-MS: m/z 443 $(M+H)^+$.

Compound 3,3'-((6-(6-Chloropyridin-2-yl)-1,3,5-triazine-2,4-diyl)bis(azanediyl))dibutanenitrile

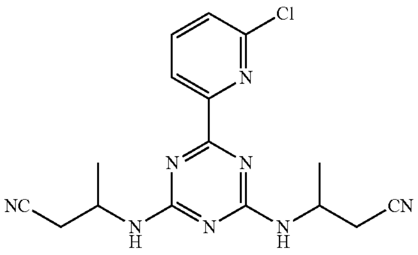 [SMILES: CC(CC#N)Nc1nc(NC(C)CC#N)nc(-c2cccc(Cl)n2)n1]

$^1$H NMR (400 MHz, $CDCl_3$) δ 8.21 (s, 1H), 7.73 (t, J=7.6 Hz, 1H), 7.41 (d, J=7.8 Hz, 1H), 5.61-5.18 (m, 2H), 4.59-4.20 (m, 2H), 2.85-2.60 (m, 4H), 1.44-1.36 (m, 6H). LC-MS: m/z 357 $(M+H)^+$.

Compound 6-(6-Chloropyridin-2-yl)-$N^2$,$N^4$-bis(1-cyclopropylpropyl)-1,3,5-triazine-2,4-diamine

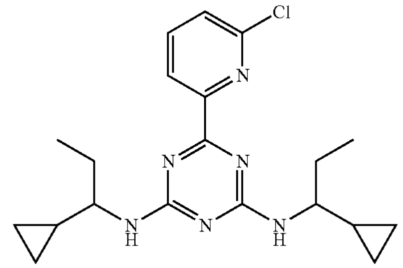 [SMILES: CCC(Nc1nc(NC(CC)C2CC2)nc(-c2cccc(Cl)n2)n1)C1CC1]

$^1$H NMR (400 MHz, $CDCl_3$) δ 8.26 (d, J=7.3 Hz, 1H), 7.76 (t, J=7.8 Hz, 1H), 7.43 (d, J=7.8 Hz, 1H), 5.37-5.08 (m, 2H), 3.48-3.37 (m, 2H), 1.73-1.56 (m, 4H), 0.98 (t, J=7.3 Hz, 6H), 0.92-0.80 (m, 2H), 0.66-0.20 (m, 8H). LC-MS (m/z): 387.2 $(M+H)^+$.

Compound 6-(6-Chloropyridin-2-yl)-$N^2$,$N^4$-bis(dicyclopropylmethyl)-1,3,5-triazine-2,4-diamine

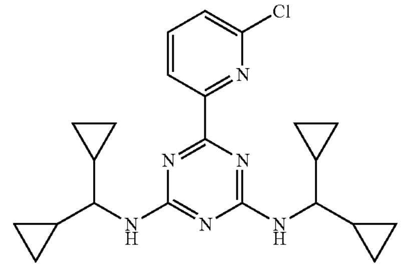 [SMILES: Clc1cccc(-c2nc(NC(C3CC3)C3CC3)nc(NC(C3CC3)C3CC3)n2)n1]

$^1$H NMR (400 MHz, $CDCl_3$) δ 8.18 (d, J=7.6 Hz, 1H), 7.69 (t, J=7.8 Hz, 1H), 7.36 (d, J=7.8 Hz, 1H), 5.50-5.01 (m, 2H), 3.30 (s, 2H), 0.89 (m, 4H), 0.50-0.21 (m, 16H). LC-MS: m/z 411.2 $(M+H)^+$.

Compound 6-(6-Chloropyridin-2-yl)-$N^2$,$N^4$-bis(4,4-difluorocyclohexyl)-1,3,5-triazine-2,4-diamine

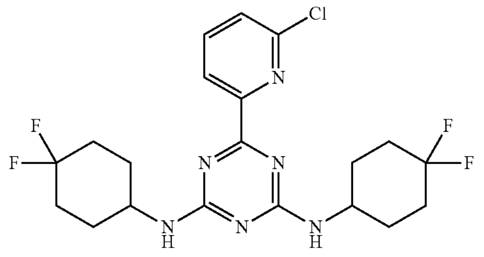

$^1H$ NMR (400 MHz, $CDCl_3$) δ 8.28 (d, J=8.2 Hz, 1H), 7.80 (t, J=7.5 Hz, 1H), 7.44 (d, J=8.0 Hz, 1H), 6.64-6.12 (m, 2H), 4.17-3.98 (m, 2H), 2.17-1.70 (m, 16H). LC-MS: m/z 459 $(M+H)^+$.

Compound 6-(6-Chloropyridin-2-yl)-$N^2$,$N^4$-bis(3,3-difluorocyclopentyl)-1,3,5-triazine-2,4-diamine

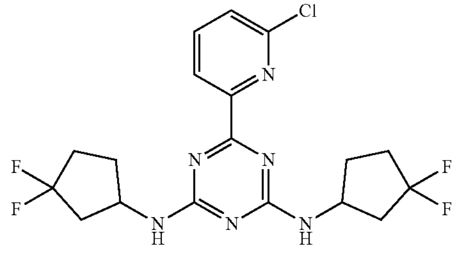 [SMILES: FC1(F)CCC(Nc2nc(NC3CCC(F)(F)C3)nc(-c3cccc(Cl)n3)n2)C1]

1H NMR (400 MHz, $CDCl_3$) δ 8.41-8.25 (m, 1H), 7.85 (t, J=7.6 Hz, 1H), 7.53 (d, J=7.6 Hz, 1H), 5.78-5.37 (m, 2H), 4.69-4.53 (m, 2H), 2.65-2.55 (m, 2H), 2.51-1.98 (m, 8H), 1.85-1.76 (m, 2H). LCMS: m/z 431.1 $(M+H)^+$.

Compound 6-(6-Chloropyridin-2-yl)-$N^2$,$N^4$-bis(2,2-difluorocyclopentyl)-1,3,5-triazine-2,4-diamine

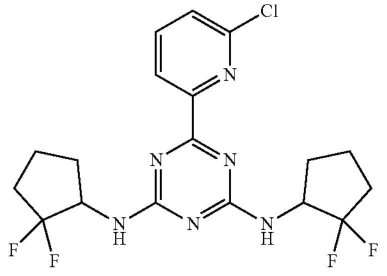 [SMILES: FC1(F)CCCC1Nc1nc(NC2CCCC2(F)F)nc(-c2cccc(Cl)n2)n1]

$^1H$ NMR (400 MHz, $CDCl_3$) δ 8.48-8.26 (m, 1H), 7.82 (s, 1H), 7.49 (s, 1H), 5.63 (m, 2H), 4.70 (m, 2H), 2.41-2.08 (m, 6H), 1.83 (m, 4H), 1.66 (s, 2H). LCMS: m/z 431$(M+H)^+$.

Compound 2,2'-((6-(6-Chloropyridin-2-yl)-1,3,5-triazine-2,4-diyl)bis(azanediyl))dicyclopentanol

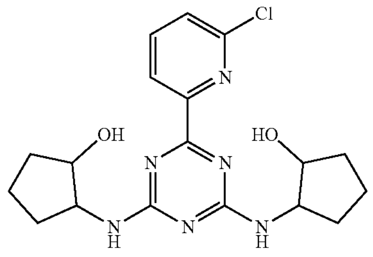 [SMILES: OC1CCCC1Nc1nc(NC2CCCC2O)nc(-c2cccc(Cl)n2)n1]

$^1H$ NMR (400 MHz, $CDCl_3$) δ 8.27-8.17 (m, 1H), 7.77 (t, J=7.8 Hz, 1H), 7.45 (d, J=7.9 Hz, 1H), 6.30-5.83 (m, 1H), 5.52 (m, 2H), 5.00 (m, 1H), 4.05-3.88 (m, 2H), 2.32-2.17 (m, 2H), 2.10 (m, 1H), 2.01 (s, 1H), 1.88-1.65 (m, 6H), 1.51 (m, 2H). LCMS: m/z 391$(M+H)^+$.

Compound 6-(6-Chloropyridin-2-yl)-$N^2$,$N^4$-bis(6,6-difluorospiro[3.3]heptan-2-yl)-1,3,5-triazine-2,4-diamine

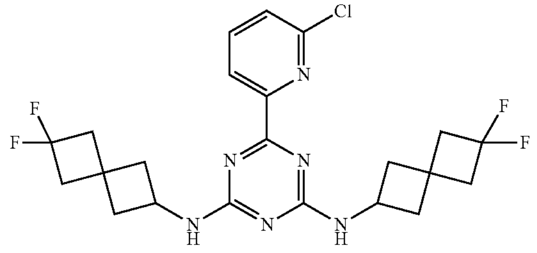 [SMILES: FC1(F)CC2(CC(Nc3nc(NC4CC5(C4)CC(F)(F)C5)nc(-c4cccc(Cl)n4)n3)C2)C1]

$^1H$ NMR (400 MHz, $CDCl_3$) δ 8.25-7.78 (m, 4H), 7.64 (m, 1H), 4.45-4.24 (m, 2H), 2.72-2.66 (m, 4H), 2.61-2.50 (m, 4H), 2.46-2.41 (m, 4H), 2.22-2.19 (m, 4H). LCMS: m/z 483$(M+H)^+$.

Compound 6-(4-Chloropyridin-2-yl)-N2,N4-bis(4,4-difluorocyclohexyl)-1,3,5-triazine-2,4-diamine

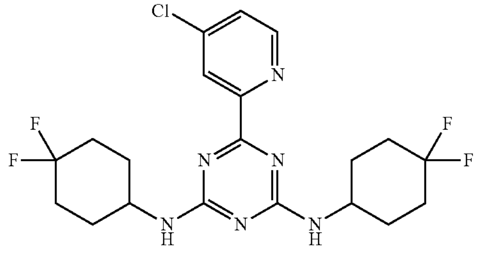 [SMILES: FC1(F)CCC(Nc2nc(NC3CCC(F)(F)CC3)nc(-c3cc(Cl)ccn3)n2)CC1]

$^1H$ NMR (400 MHz, $CDCl_3$) δ 8.68 (d, J=8.0 Hz, 1H), 8.48 (s, 1H), 7.62 (d, J=8.0 Hz, 1H), 5.28 (d, J=8.0 Hz, 2H), 4.20-4.02 (m, 2H), 1.98-1.61 (m, 16H). LC-MS: m/z 459.1 $(M+H)^+$.

Compound 6-(5-Chloropyridin-3-yl)-$N^2$,$N^4$-bis((R)-1-cyclopropylethyl)-1,3,5-triazine-2,4-diamine

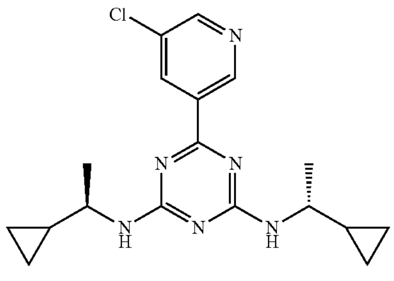 [SMILES: C[C@@H](Nc1nc(N[C@H](C)C2CC2)nc(-c2cncc(Cl)c2)n1)C1CC1]

$^1$H NMR (400 MHz, $CDCl_3$) δ 9.36 (m, 1H), 8.65 (d, J=2.1 Hz, 1H), 8.54 (t, J=1.9 Hz, 1H), 5.46-5.06 (m, 2H), 3.78-3.40 (m, 2H), 1.29 (s, 6H), 0.95-0.87 (m, 2H), 0.56-0.38 (m, 6H), 0.29 (s, 2H). LC-MS: m/z 359 $(M+H)^+$.

Example 11 The compounds of this Example are prepared by general Scheme 11, set forth below.

Scheme 11

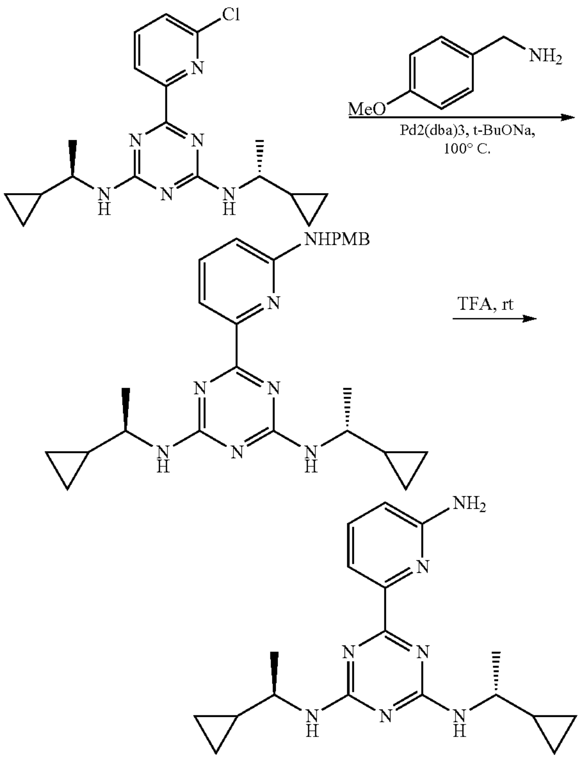

Step 1. Preparation of $N^2$,$N^4$-bis((R)-1-cyclopropylethyl)-6-(6-((4-methoxybenzyl) amino)pyridin-2-yl)-1,3,5-triazine-2,4-diamine. To a solution of 6-(6-chloropyridin-2-yl)-N2,N4-bis((R)-1-cyclopropylethyl)-1,3,5-triazine-2,4-diamine (120 mg, 0.33 mmol), (4-methoxyphenyl) methanamine (69 mg, 0.51 mmol), BINAP (42 mg, 0.66 mmol) and t-BuONa (63 mg, 0.66 mmol) in anhydrous dioxane (2 mL) at r.t. under N2 atmosphere was added $Pd_2(dba)_3$ (30 mg, 0.033 mmol) in one portion. The reaction mixture was then stirred at 100° C. overnight then concentrated under reduced pressure to afford the desired product.

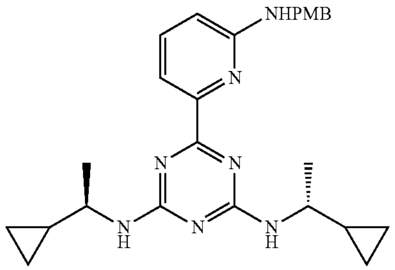

LCMS: m/z 460 $(M+H)^+$.

Step 2. Preparation of 6-(6-aminopyridin-2-yl)-$N^2$,$N^4$-bis ((R)-1-cyclopropyl ethyl)-1,3,5-triazine-2,4-diamine. $N^2$,$N^4$-bis((R)-1-cyclopropylethyl)-6-(6-(4-methoxybenzylamino) pyridin-2-yl)-1,3,5-triazine-2,4-diamine (80 mg, 0.17 mmol) was dissolved in TFA (0.5 mL) under $N_2$ atmosphere. The solution mixture was then stirred at r.t. overnight then concentrated under reduced pressure. The residue was purified by standard methods to afford the desired product.

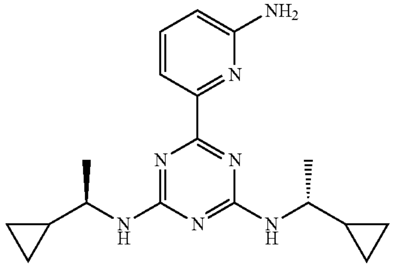

1H NMR (400 MHz, $CDCl_3$) δ 7.71-7.54 (m, 2H), 6.74-6.69 (m, 1H), 6.24-5.30 (m, 2H), 3.70-3.54 (m, 2H), 1.29-1.25 (m, 6H), 0.95-0.90 (m, 2H), 0.58-0.26 (m, 8H). LCMS: m/z 340.2 $(M+H)^+$.

Example 12 The compounds of this example are prepared by general Scheme 12, set forth below.

Scheme 12

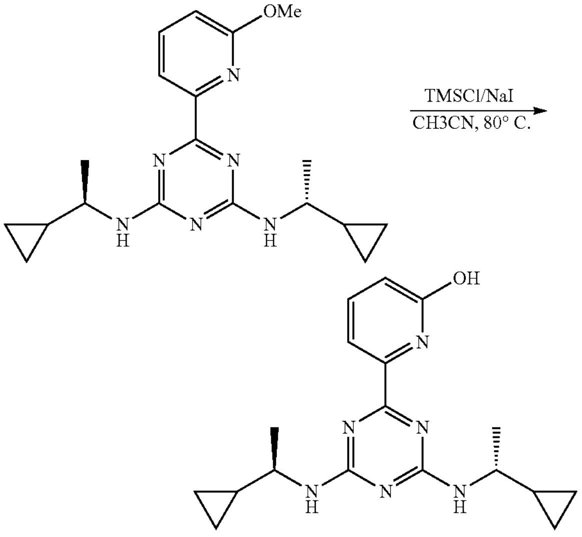

Step 1. Preparation of 6-(4,6-bis((R)-1-cyclopropyl-ethylamino)-1,3,5-triazin-2-yl) pyridin-2-ol To a mixture of $N^2$,$N^4$-bis((R)-1-cyclopropylethyl)-6-(6-methoxypyridin-2-yl)-1,3,5-triazine-2,4-diamine (50 mg, 0.14 mmol) and NaI (63 mg, 0.42 mmol) in anhydrous $CH_3CN$ (1 mL) at r.t. was added TMSCl (46 mg, 0.42 mmol) in one portion. The reaction mixture was stirred 80° C. for 6 hr then concentrated under reduced pressure. The residue was purified by standard methods to afford the desired product. $^1H$ NMR (400 MHz, $CDCl_3$) δ 10.24 (br s, 1H), 7.51 (t, J=8.0 Hz, 1H), 7.29-7.20 (m, 1H), 6.71 (d, J=8.0 Hz, 1H), 5.42-5.31 (m, 2H), 3.63-3.52 (m, 2H), 1.30-1.25 (m, 6H), 0.98-0.87 (m, 2H), 0.62-0.21 (m, 8H). LCMS: m/z 341.2 $(M+H)^+$.

Example 13 The compounds of this Example are prepared by general Scheme 13, set forth below.

Scheme 13

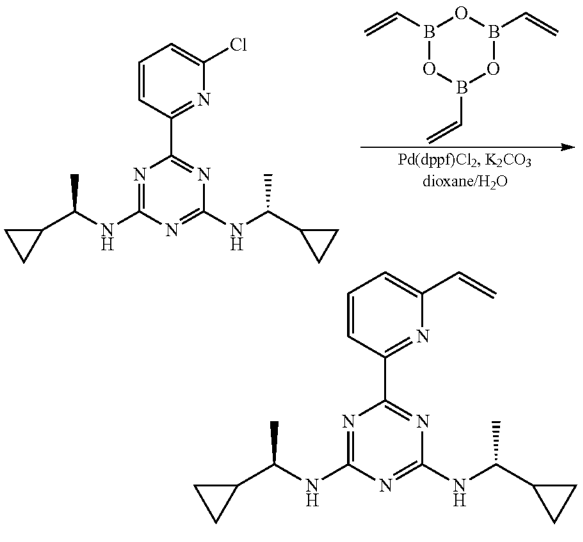

Step 1. Preparation of $N^2$,$N^4$-bis((R)-1-cyclopropyl-ethyl)-6-(6-vinylpyridin-2-yl)-1,3,5-triazine-2,4-diamine. To a suspension of 6-(6-chloropyridin-2-yl)-N2,N4-bis ((R)-1-cyclopropylethyl)-1,3,5-triazine-2,4-diamine (200 mg, 0.56 mmol), 2,4,6-trivinyl-1,3,5,2,4,6-trioxatriborinane (135 mg, 0.84 mmol) and $K_2CO_3$ (154 mg, 1.11 mmol) in dioxane (2 mL) and $H_2O$ (0.8 mL) under an atmosphere of $N_2$ was added Pd(dppf)$Cl_2$ (41 mg, 0.06 mmol) in one portion. The reaction mixture was stirred at 100° C. overnight then cooled to r.t. and quenched with water. The resulting mixture was extracted with EtOAc (20 mL×2). The combined organic layers were washed with water and brine, dried over anhydrous $Na_2SO_4$, and concentrated under reduced pressure. The residue was purified by standard methods to afford the desired product. $^1H$ NMR (400 MHz, $CDCl_3$) δ 8.28-8.15 (m, 1H), 7.77 (t, J=7.6 Hz, 1H), 7.58 (d, J=7.6 Hz, 1H), 7.05-6.99 (m, 1H), 6.15 (d, J=17.6 Hz, 1H), 5.42 (d, J=17.6 Hz, 1H), 5.44-5.16 (m, 2H), 3.72-3.52 (m, 2H), 1.35-1.22 (m, 6H), 0.98-0.86 (m, 2H), 0.58-0.21 (m, 8H). LCMS: m/z 351.1 $(M+H)^+$.

Example 14 The compounds of this Example are prepared by general Scheme 14, set forth below.

Scheme 14

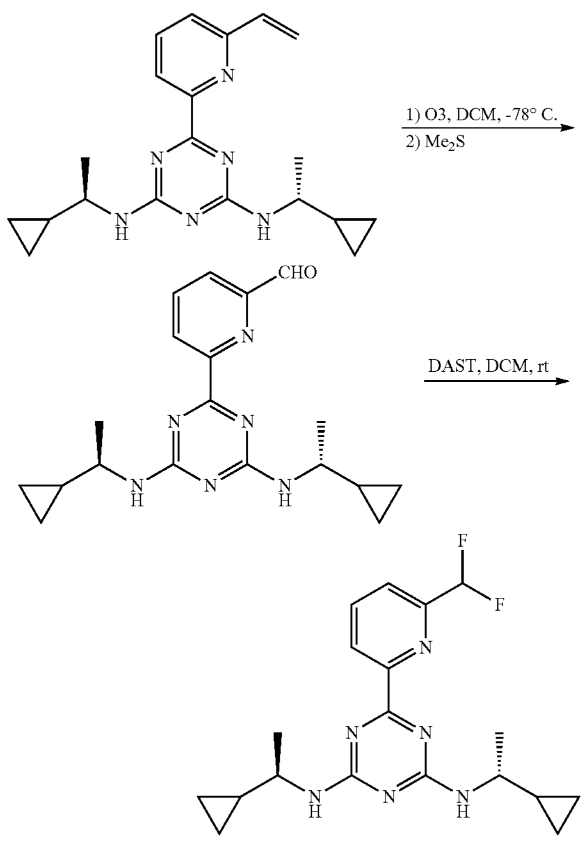

Step 1. Preparation of 6-(4,6-bis(((R)-1-cyclopropylethyl) amino)-1,3,5-triazin-2-yl) picolinaldehyde. Ozone was bubbled into a solution of $N^2$,$N^4$-bis((R)-1-cyclopropyl-ethyl)-6-(6-vinylpyridin-2-yl)-1,3,5-triazine-2,4-diamine (120 mg, 0.34 mmol) in DCM (2 mL) at −78° C. for 1 hr. After excess ozone was purged by $N_2$, $Me_2S$ (0.2 mL) was added into the reaction mixture at 0° C. The resulting mixture was concentrated and the residue was purified by standard methods to afford the desired product. LCMS: m/z 353 $(M+H)^+$.

Step 2. Preparation of $N^2$,$N^4$-bis((R)-1-cyclopropyl-ethyl)-6-(6-(difluoromethyl) pyridin-2-yl)-1,3,5-triazine-2,4-diamine. To a solution of 6-(4,6-bis((R)-1-cyclo propyl-ethylamino)-1,3,5-triazin-2-yl)picolinaldehyde (50 mg, 0.14 mmol) in anhydrous DCM (2 mL) at 0° C. was added dropwise DAST (68 mg, 0.43 mmol). The reaction mixture was stirred at r.t overnight. The resulting mixture was slowly quenched with satd. aq. $NaHCO_3$(5 mL) at 0° C., then extracted with DCM (40 mL). The combined organic layers were washed with water and brine, dried over anhydrous $Na_2SO_4$, concentrated, and purified by standard methods to afford the desired product.

$^1H$ NMR (400 MHz, $CDCl_3$) δ 8.46 (s, 1H), 7.97 (t, J=7.6 Hz, 1H), 7.77 (d, J=7.6 Hz, 1H), 6.98-6.70 (m, 1H), 5.47-5.21 (m, 2H), 3.67-3.50 (m, 2H), 1.32-1.25 (m, 6H), 0.92-0.86 (m, 2H), 0.58-0.21 (m, 8H). LCMS: m/z 375 $(M+H)^+$.

The procedure set forth in Example 14 was used to produce the following compounds using the appropriate starting materials.

Compound $N^2$,$N^4$-bis(4,4-difluorocyclohexyl)-6-(6-(difluoromethyl)pyridin-2-yl)-1,3,5-triazine-2,4-diamine

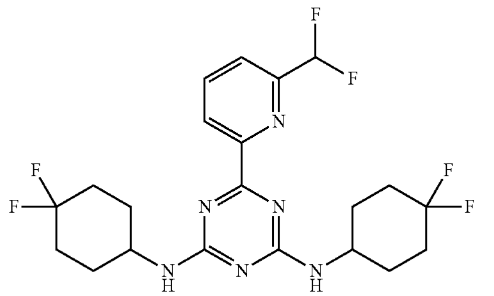 [SMILES: FC(F)c1cccc(-c2nc(NC3CCC(F)(F)CC3)nc(NC3CCC(F)(F)CC3)n2)n1]

$^1$H NMR (400 MHz, $CDCl_3$) δ 8.48 (, 1H), 8.01 (br s., 1H), 7.81 (d, J=8.0 Hz, 1H), 6.67-7.01 (m, 1H), 5.02-5.55 (m, 2H), 3.95-4.20 (m, 2H), 2.14 (m, 8H), 1.86-1.98 (m, 4H), 1.77 (m, 4H).

LC-MS: m/z 475 $(M+H)^+$.

Compound $N_2$,$N_4$-bis(3,3-difluorocyclobutyl)-6-(6-(difluoromethyl)pyridin-2-yl)-1,3,5-triazine-2,4-diamine

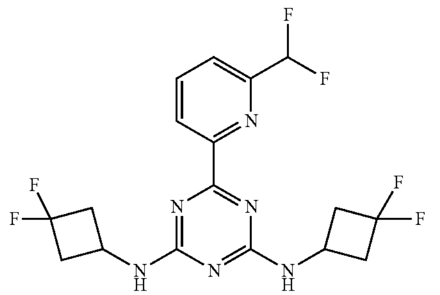 [SMILES: FC(F)c1cccc(-c2nc(NC3CC(F)(F)C3)nc(NC3CC(F)(F)C3)n2)n1]

$^1$H NMR (400 MHz, $CDCl_3$) δ 8.64-8.35 (m, 1H), 8.10-7.92 (m, 1H), 7.81 (d, J=7.7 Hz, 1H), 6.82 (m, 1H), 5.98-5.29 (m, 2H), 4.70-4.16 (m, 2H), 3.24-2.92 (m, 4H), 2.79-2.44 (m, 4H).

LC-MS: m/z 419 $(M+H)^+$.

Example 15 The compounds of this Example are prepared by general Scheme 15, set forth below.

Scheme 15

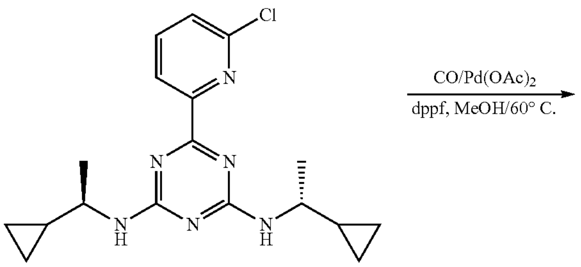

-continued

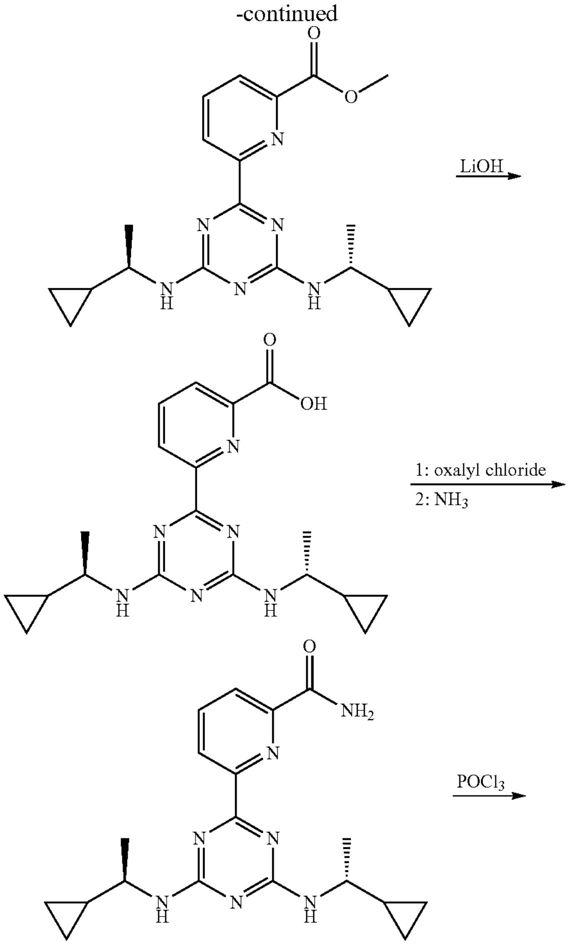

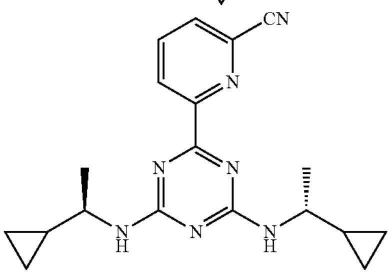

Step 1: Preparation of methyl 6-(4,6-bis((R)-1-cyclopropylethylamino)-1,3,5-triazin-2-yl)picolinate. To a mixture of 6-(6-chloropyridin-2-yl)-$N^2$,$N^4$-bis((R)-1-cyclopropylethyl)-1,3,5-triazine-2,4-diamine (0.25 g, 0.7 mmol) in MeOH (10 mL) were added dppf (80 mg, 0.15 mmol), $Pd(OAc)_2$ (60 mg, 0.27 mmol) and $Et_3N$ (150 mg, 1.5 mmol). The reaction mixture was degassed and back-filled with CO three times and then stirred under an atmosphere of CO (60 psi) at 70° C. for 12 hr. The resulting mixture was cooled to r.t. and concentrated under reduced pressure. The residue was triturated with EtOAc (100 mL) and filtered. The filtrate was concentrated and purified by standard methods to afford methyl 6-(4,6-bis((R)-1-cyclopropylethylamino)-1,3,5-triazin-2-yl)picolinate. $^1$H NMR (400 MHz, $CDCl_3$) δ 8.50 (m, 1H), 8.24-8.22 (dd, 1H), 7.99-7.95 (t, 1H), 5.49 (m, 2H), 4.02 (s, 3H), 3.57 (m, 2H), 1.92 (s, 6H), 0.96-0.87 (m, 2H), 0.52-0.26 (m, 8H).

LCMS: m/z 383 $(M+H)^+$.

Step 2: Preparation of 6-(4,6-bis(((R)-1-cyclopropylethyl) amino)-1,3,5-triazin-2-yl) picolinic acid. To a mixture of methyl 6-(4,6-bis((R)-1-cyclopropylethyl amino)-1,3,5-triazin-2-yl)picolinate (150 mg, 0.40 mmol) in water (2.0 mL) and THF (3.0 mL) was added lithium hydroxide (47 mg, 2.0 mmol). The reaction mixture was stirred at r.t. overnight then acidified with aq. HCl (1 N) to pH 5-6 and extracted with EtOAc. The combined organic layers were dried over anhydrous $Na_2SO_4$, and concentrated under reduced pressure to give the desired product. LCMS: m/z 367 $(M-H)^-$.

Step 3: Preparation of 6-(4,6-bis((R)-1-cyclopropylethyl-amino)-1,3,5-triazin-2-yl)picolinamide. To an ice cold mixture of 6-(4,6-bis(((R)-1-cyclopropylethyl)amino)-1,3,5-triazin-2-yl)picolinic acid (120 mg, 0.32 mmol) in dry DCM (5.0 mL) and DMF (0.1 mL) was added dropwise oxalyl chloride (65 mg, 0.5 mmol). The reaction mixture was stirred at r.t. for 2 hr then treated with ammonia. The resulting mixture was stirred for 10 min at 0° C., and then concentrated and purified by standard methods to give 6-(4,6-bis((R)-1-cyclopropylethylamino)-1,3,5-triazin-2-yl) picolinamide. $^1H$ NMR (400 MHz, $CDCl_3$) δ 13.59 (s, 1H), 9.30-9.14 (m, 3H), 8.58-8.30 (m, 3H), 7.95 (s, 1H), 3.77-3.54 (m, 2H), 1.29 (d, 6H), 1.02 (m, 2H), 0.50-0.30 (m, 8H). LCMS: m/z 368 $(M+H)^+$.

Step 4: Preparation of 6-(4,6-bis((R)-1-cyclopropylethyl-amino)-1,3,5-triazin-2-yl)picolinonitrile. To a mixture of 6-(4,6-bis((R)-1-cyclopropylethylamino)-1,3,5-triazin-2-yl) picolinamide (36 mg, 0.1 mmol) in dry pyridine (3.0 mL) was added phosphorous trichloride (0.1 mL). The reaction mixture was stirred at r.t. for 2 hr then concentrated under reduced pressure. The residue was purified by standard methods to give 6-(4,6-bis((R)-1-cyclopropylethylamino)-1,3,5-triazin-2-yl) picolinonitrile. $^1H$ NMR (400 MHz, $CDCl_3$) δ 8.50-8.48 (m, 1H), 8.24-8.22 (t, 1H), 7.73-7.71 (dd, 1H), 5.46-5.14 (m, 2H), 3.62-3.50 (m, 2H), 1.22-1.18 (m, 6H), 0.89-0.84 (m, 2H), 0.46-0.20 (m, 8H). LCMS: m/z 350 $(M+H)^+$.

Example 16 The compounds of this Example are prepared by general Scheme 16, set forth below.

Scheme 16

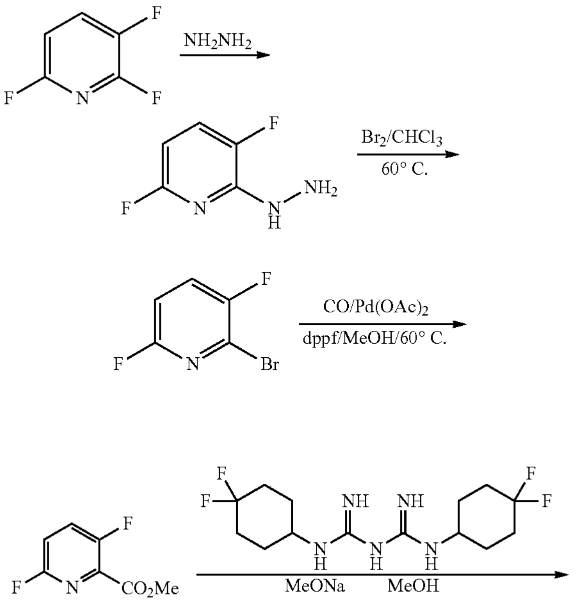

-continued

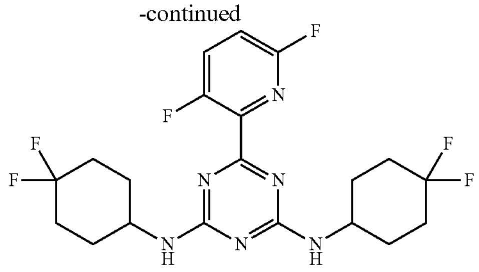

Step 1: Preparation of 3,6-difluoro-2-hydrazinylpyridine. To an ice-cold solution of 2,3,6-trifluoropyridine (1.0 g, 7.5 mmol) in ethanol (10 mL) was added hydrazine hydrate (0.75 g, 15.0 mmol). The reaction mixture was warmed up to r.t. and then heated at reflux for 2 hr. After it was cooled to r.t., the reaction mixture was diluted with water (10 mL) and extracted with DCM (2×20 mL). The combined organic layers were dried over anhydrous $Na_2SO_4$ and concentrated under reduced pressure to afford 3,6-difluoro-2-hydrazinylpyridine. LC-MS (m/z): 146 $(M+H)^+$.

Step 2: Preparation of 2-bromo-3,6-difluoropyridine. To a stirred solution of 3,6-difluoro-2-hydrazinylpyridine(1.1 g, 7.0 mmol) in chloroform (20 mL) at r.t. was added dropwise bromine (1.8 g, 11.2 mmol). The reaction mixture was heated to 60° C. for 1.5 hr. The resulting mixture was cooled to r.t., quenched with satd. aq. $NaHCO_3$, and extracted with dichloromethane (2×20 mL). The combined organic layers were dried over anhydrous $Na_2SO_4$ and concentrated and purified by standard methods to afford 2-bromo-3,6-difluoropyridine. LC-MS: m/z 194 $(M+H)^+$.

Step 3: Preparation of methyl 3,6-difluoropicolinate. To a solution of 2-bromo-3,6-difluoropyridine (0.8 g, 4.1 mmol) in MeOH (10 mL) were added dppf (0.3 g, 0.56 mmol), $Pd(OAc)_2$ (0.1 g, 0.45 mmol) and $Et_3N$ (1.6 mL, 8.2 mmol). The suspension was degassed and back-filled with CO atmosphere three times. The resulting mixture was stirred under CO atmosphere (60 psi) at 70° C. for 12 hr, then cooled to r.t. and concentrated under reduced pressure. The residue was triturated with EtOAc (150 mL) and filtered. The filtrate was concentrated and purified by standard methods to afford methyl 3,6-difluoropicolinate. LC-MS: m/z 174 $(M+H)^+$.

Step 4: Preparation of $N^2$,$N^4$-bis(4,4-difluorocyclohexyl)-6-(3,6-difluoropyridin-2-yl)-1,3,5-triazine-2,4-diamine. To a suspension of $N^1$,$N^5$-bis(4,4-difluorocyclo hexyl)-biguanide (167 mg, 0.50 mmol) and methyl 3,6-difluoropicolinate (130 mg, 0.75 mmol) in MeOH (5 mL) was added NaOMe (81 mg, 1.5 mmol). The reaction mixture was stirred at r.t. overnight, then poured into water, and extracted with EtOAc. The combined organic extracts were dried over anhydrous $Na_2SO_4$, and concentrated under reduced pressure. The residue was purified by standard methods to afford $N^2$,$N^4$-bis (4,4-difluorocyclohexyl)-6-(3,6-difluoropyridin-2-yl)-1,3,5-triazine-2,4-diamine. $^1H$ NMR (400 MHz, $CDCl_3$) δ 7.67-7.61 (m, 1H), 7.07-7.03 (m, 1H), 5.46-5.10 (m, 2H), 4.08-3.97 (m, 2H), 2.17-2.09 (m, 8H), 1.96-1.83 (m, 4H), 1.73-1.63 (m, 4H). LC-MS: m/z 461 $(M+H)^+$.

Example 17 The compounds of this Example are prepared by general Scheme 17, set forth below.

Scheme 17

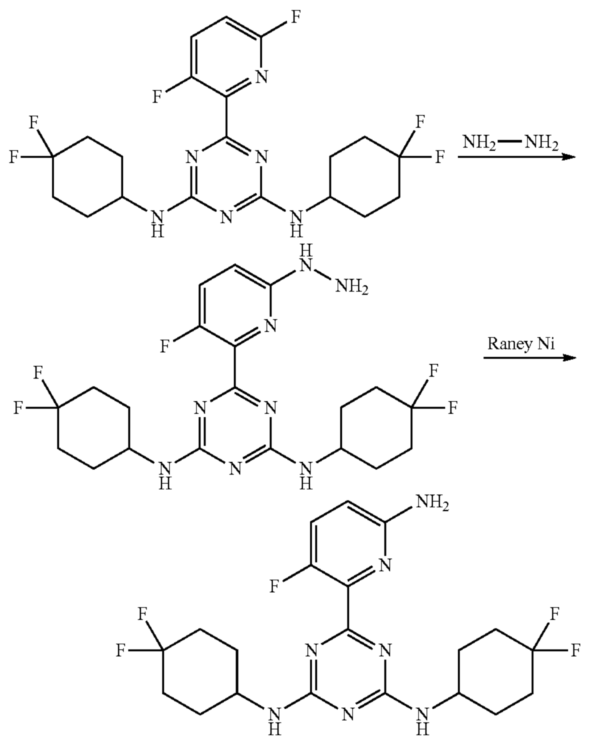

Step 1: Preparation of $N^2$,$N^4$-bis(4,4-difluorocyclohexyl)-6-(3-fluoro-6-hydrazinyl pyridin-2-yl)-1,3,5-triazine-2,4-diamine. To a solution of $N^2$,$N^4$-bis(4,4-difluoro-cyclohexyl)-6-(3,6-difluoropyridin-2-yl)-1,3,5-triazine-2,4-diamine (230 mg, 0.50 mmol) in THF (20 mL) was added hydrazine hydrate (150 mg, 3.0 mmol). The reaction mixture was stirred at 60° C. for 2.5 hr. After cooling to r.t., the reaction mixture was diluted with DCM and washed with water. The organic phase was separated, dried over anhydrous $Na_2SO_4$, and concentrated under reduced pressure to give the desired product. LC-MS (m/z): 473.2 $(M+H)^+$.

Step 2: Preparation of 6-(6-amino-3-fluoropyridin-2-yl)-$N_2$,$N_4$-bis(4,4-difluoro cyclohexyl)-1,3,5-triazine-2,4-diamine. To a solution of $N^2$,$N^4$-bis(4,4-difluoro-cyclohexyl)-6-(3-fluoro-6-hydrazinylpyridin-2-yl)-1,3,5-triazine-2,4-diamine (47 mg, 0.1 mmol) in methanol (5.0 mL) was added Raney Ni (100 mg). The reaction mixture was stirred under $H_2$ atmosphere overnight at r.t. then filtered. The filtrate was concentrated and purified by standard methods to afford the desired product. $^1H$ NMR (400 MHz, $CDCl_3$) δ 7.43-7.39 (m, 1H), 7.03-7.01 (m, 1H), 4.59 (s, 2H), 4.10-4.05 (m, 2H), 2.09-1.93 (m, 12H), 1.76-1.68 (m, 4H). LC-MS: m/z 458.2 $(M+H)^+$.

Example 18 The compounds of this Example are prepared by general Scheme 18, set forth below.

Scheme 18

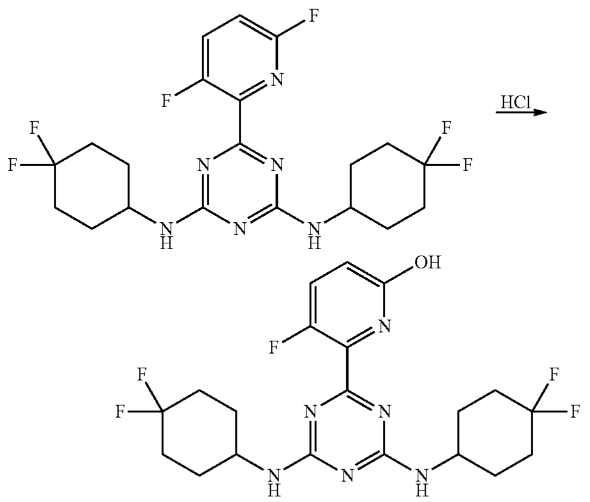

Step 1: Preparation of 6-(4,6-bis((4,4-difluorocyclohexyl) amino)-1,3,5-triazin-2-yl)-5-fluoropyridin-2-ol. A mixture of $N_2$,$N_4$-bis(4,4-difluorocyclohexyl)-6-(3,6-difluoropyridin-2-yl)-1,3,5-triazine-2,4-diamine (100 mg, 0.22 mmol) in conc. HCl (5.0 mL) was stirred at 100° C. overnight. The resulting mixture was concentrated and purified by standard methods to afford the desired product. $^1H$ NMR (400 MHz, $CDCl_3$) δ 9.96 (m, 1H), 7.40-7.27 (m, 2H), 6.73-6.67 (m, 1H), 5.47-5.17 (m, 2H), 4.02-3.92 (m, 2H), 2.11-1.66 (m, 16H). LCMS: m/z 459 $(M+H)^+$.

Example 19 The compounds of this Example are prepared by general Scheme 19, set forth below.

Scheme 19

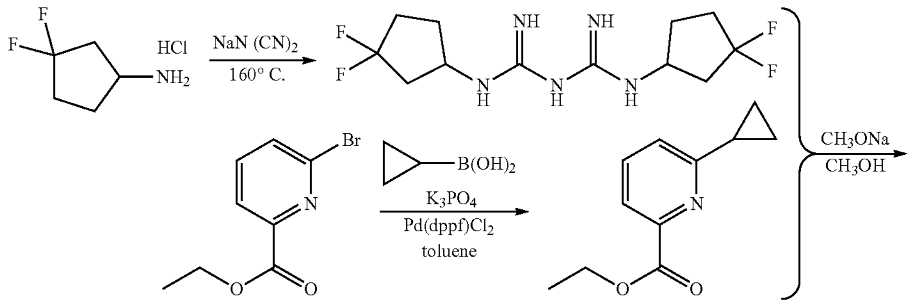

-continued

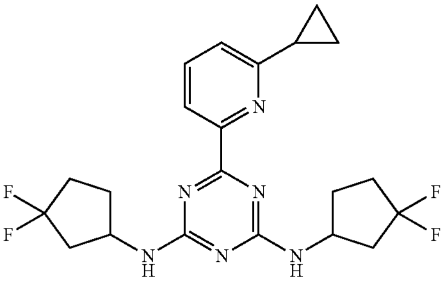

Step 1: Preparation of $N^1$,$N^5$-bis(3,3-difluorocyclopentyl)-biguanide. A mixture of 3,3-difluorocyclopentanamine hydrochloride (3 g, 19.1 mmol) and sodium dicyanamide (1.7 g, 19.1 mmol) was heated at 160° C. for 1 hr. The resulting product was dissolved in MeOH then filtered. The filtrate was concentrated to afford the desired product. LC-MS: m/z 310.2 $(M+H)^+$.

Step 2: Preparation of ethyl 6-cyclopropylpicolinate. To a mixture of ethyl 6-bromopicolinate (200 mg, 0.87 mmol) and cyclopropylboronic acid (149 mg, 1.74 mmol) in toluene (15 mL) were added $K_3PO_4$ (369 mg, 1.74 mmol) and dichloro(diphenylphosphinoferrocene)palladium (11 mg, 0.017 mmol). The resulting mixture was stirred under $N_2$ atmosphere at 100° C. overnight, then cooled to r.t. and filtered. The filtrate was concentrated and purified by standard methods to afford the desired product. LC-MS: m/z 192.1 $(M+H)^+$.

Step 3: 6-(6-cyclopropylpyridin-2-yl)-$N^2$,$N^4$-bis(3,3-difluorocyclopentyl)-1,3,5-triazine-2,4-diamine. To a mixture of $N^1$,$N^5$-bis(3,3-difluorocyclopentyl)-biguanide (50 mg, 0.16 mmol) and ethyl 6-cyclopropylpicolinate (62 mg, 0.33 mmol) in methanol (5 mL) was added NaOMe (44 mg, 0.80 mmol). The reaction mixture was stirred at r.t. overnight, and then concentrated under reduced pressure. The residue was partitioned between EtOAc and water. The organic layer was separated, washed with brine, and dried over anhydrous $Na_2SO_4$, concentrated, and purified by standard methods to afford the desired product. $^1$H NMR (400 MHz, $CDCl_3$) δ 8.43-8.33 (m, 1H), 8.06-7.99 (m, 1H), 7.25-7.23 (d, J=8 Hz, 1H), 6.66-6.52 (m, 1H), 5.90-5.79 (m, 1H), 4.74-4.45 (m, 2H), 2.66-2.54 (m, 2H), 2.38-2.16 (m, 8H), 1.90-1.88 (m, 2H), 1.42-1.40 (m, 2H), 1.29-1.25 (m, 1H), 1.25-1.01 (m, 2H). LC-MS: m/z 437.2 $(M+H)^+$.

The procedure set forth in Example 19 was used to produce the following compounds using the appropriate starting materials.

Compound 6-(6-Cyclopropylpyridin-2-yl)-$N^2$,$N^4$-bis (4,4-difluorocyclohexyl)-1,3,5-triazine-2,4-diamine

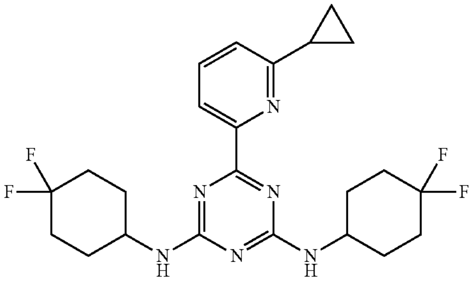 [SMILES: FC1(F)CCC(Nc2nc(NC3CCC(F)(F)CC3)nc(-c3cccc(C4CC4)n3)n2)CC1]

$^1$H NMR (400 MHz, $CDCl_3$) δ 8.21 (s, 1H), 7.87 (s, 1H), 7.14 (s, 1H), 5.16 (s, 1H), 4.17-4.01 (m, 2H), 2.43 (s, 1H), 2.16-1.74 (m, 16H), 1.25 (s, 2H), 1.02 (s, 2H), 0.87 (m, 1H). LCMS: m/z 465 $(M+H)^+$.

Compound $N^2$,$N^4$-bis(4,4-difluorocyclohexyl)-6-(6-methylpyridin-2-yl)-1,3,5-triazine-2,4-diamine

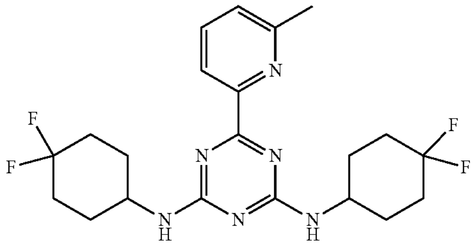 [SMILES: Cc1cccc(-c2nc(NC3CCC(F)(F)CC3)nc(NC3CCC(F)(F)CC3)n2)n1]

$^1$H NMR (400 MHz, $CDCl_3$) δ 8.181-8.11 (m, 1H), 7.71 (s, 1H), 7.29 (s, 1H), 5.46-5.07 (m, 2H), 4.19-3.99 (m, 2H), 2.69 (s, 3H), 2.17-2.12 (m, 9H), 1.97-1.84 (m, 4H), 1.63-1.55 (m, 3H). LCMS: m/z 439 $(M+H)^+$.

Example 20 Preparation of Symmetric Di-aliphatic Triazine Compounds of Formula M. The compounds of this Example are prepared by general Scheme 20, set forth below.

Scheme 20

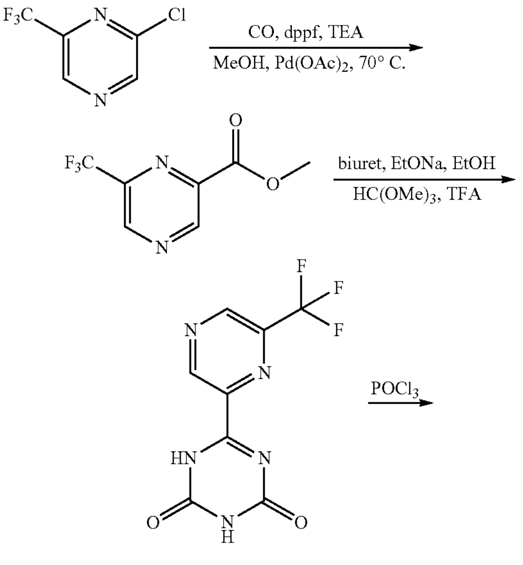

-continued

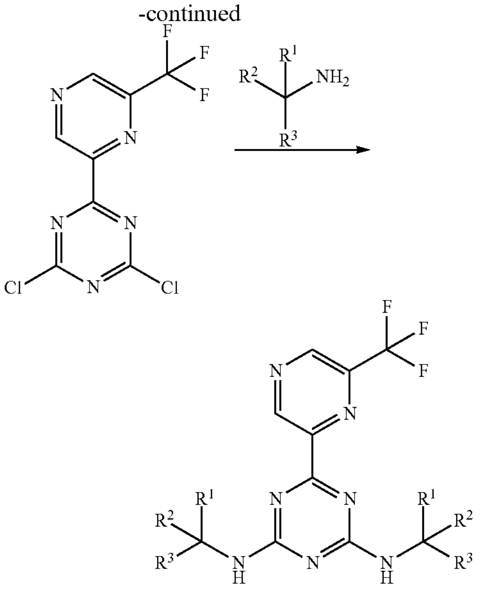

Formula M

Step 1: Preparation of methyl 6-(trifluoromethyl)pyrazine-2-carboxylate. To a mixture of 2-chloro-6-(trifluoromethyl)pyrazine (1 g, 5.5 mol) in MeOH (5.5 mL) was added dppf (0.16 g, 0.29 mmol), $Pd(OAc)_2$ (0.1 g, 0.44 mmol) and $Et_3N$ (0.12 mL, 8.2 mmol). The suspension was degassed under vacuum and then backfilled with CO three times. The resulting mixture was stirred under CO atmosphere (80 psi) at 70° C. for 2 days until the reaction was completed. The mixture was cooled to r.t. and concentrated under reduced pressure at 30° C. To the residue was added EtOAc (150 mL). The suspension was filtered and the filtrate was concentrated and purified by standard methods to afford the desired product. LC-MS: m/z 207 $(M+H)^+$.

Step 2: Preparation of 6-(6-(trifluoromethyl)pyrazin-2-yl)-1,3,5-triazine-2,4(1H,3H)-dione. The procedure is the same as Example 1 Step 2 described above. LC-MS: m/z 260 $(M+H)^+$.

Step 3: Preparation of 2,4-dichloro-6-(6-(trifluoromethyl)pyrazin-2-yl)-1,3,5-triazine. To a solution of 6-(6-(trifluoromethyl)pyrazin-2-yl)-1,3,5-triazine-2,4 (1H,3H)-dione (2.8 g, 0.011 mol) in $POCl_3$ (30 mL) was added $Et_3N$ (0.3 mL). The mixture was stirred at 100° C. for 16 hr until the reaction was completed. The resulting mixture was concentrated and purified by standard methods to afford the desired product. LC-MS: m/z 296 $(M+H)^+$.

Step 4: Preparation of $N^2$,$N^4$-bis(4,4-difluorocyclohexyl)-6-(6-(trifluoromethyl) pyrazin-2-yl)-1,3,5-triazine-2,4-diamine. The procedure is the same as Example 1 Step 4.

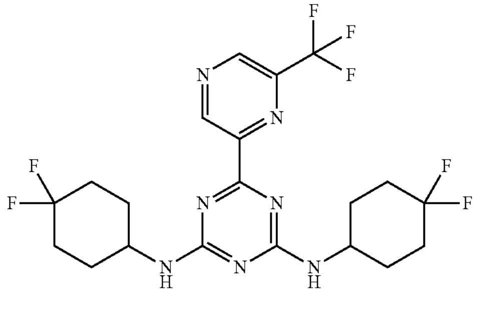

$^1$H NMR (400 MHz, $CDCl_3$) δ 9.73 (m, 1H), 9.07 (s, 1H), 5.49-5.15 (m, 2H), 4.17-3.99 (m, 2H), 2.17-1.58 (m, 16H). LC-MS: m/z 494 $(M+H)^+$.

The procedure set forth in Example 20 above was used to produce the following compounds using the appropriate starting materials.

$N^2$,$N^4$-bis(3,3-difluorocyclopentyl)-6-(6-(trifluoromethyl)pyrazin-2-yl)-1,3,5-triazine-2,4-diamine

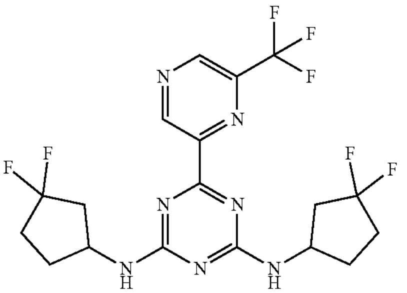 [SMILES: FC1(F)CCC(Nc2nc(NC3CCC(F)(F)C3)nc(-c3cncc(C(F)(F)F)n3)n2)C1]

$^1$H NMR (400 MHz, $CDCl_3$) δ 9.74 (m, 1H), 9.07 (d, J=3.2 Hz, 1H), 5.68-5.37 (m, 2H), 4.71-4.53 (m, 2H), 2.66-2.61 (m, 2H), 2.32-1.85 (m, 10H). LC-MS: m/z 466 $(M+H)^+$.

$N^2$,$N^4$-bis((R)-3,3-difluorocyclopentyl)-6-(6-(trifluoromethyl)pyrazin-2-yl)-1,3,5-triazine-2,4-diamine

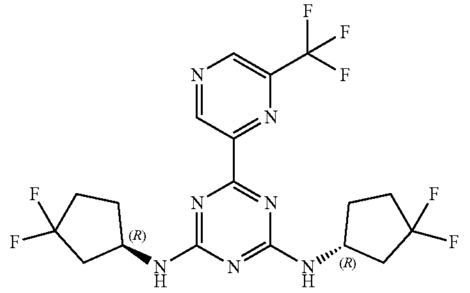

$^1$H NMR (400 MHz, $CDCl_3$) δ 9.77-9.71 (m, 1H), 9.06 (s, 1H), 5.68-5.37 (m, 2H), 5.54-4.72 (m, 2H), 3.12 (m, 1H), 2.64 (m, 1H), 2.32 (m, 3H), 2.17-2.13 (m, 6H). LC-MS: m/z 466 $(M+H)^+$.

$N^2$,$N^4$-bis((S)-3,3-difluorocyclopentyl)-6-(6-(trifluoromethyl)pyrazin-2-yl)-1,3,5-triazine-2,4-diamine

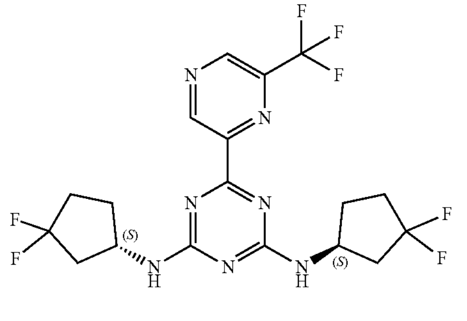

$^1$H NMR (400 MHz, $CDCl_3$) δ 9.74 (m, 1H), 9.07 (d, J=3.6 Hz, 1H), 5.70-5.38 (m, 2H), 4.83-4.38 (m, 2H), 2.80-1.76 (m, 12H). LC-MS: m/z 466 $(M+H)^+$.

$N^2$—((R)-3,3-difluorocyclopentyl)-$N^4$—((S)-3,3-difluorocyclopentyl)-6-(6-(trifluoromethyl)pyrazin-2-yl)-1,3,5-triazine-2,4-diamine

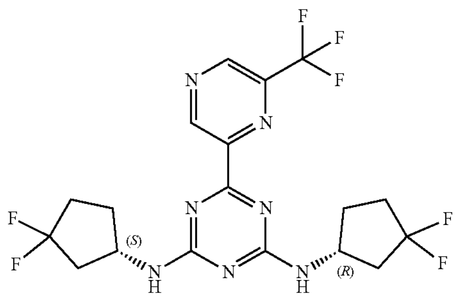

$^1$H NMR (400 MHz, $CDCl_3$) δ 9.74 (m, 1H), 9.07 (d, J=3.3 Hz, 1H), 5.68-5.37 (m, 2H), 4.81-4.40 (m, 2H), 2.79-1.73 (m, 12H). LC-MS: m/z 466 $(M+H)^+$.

$N^2$,$N^4$-bis(3,3-difluorocyclobutyl)-6-(6-(trifluoromethyl)pyrazin-2-yl)-1,3,5-triazine-2,4-diamine

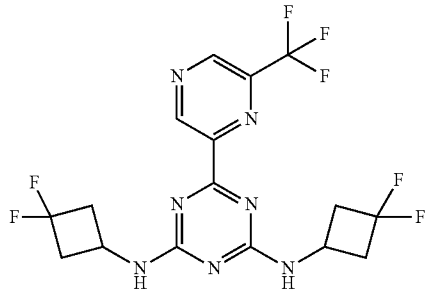 [SMILES: FC1(F)CC(Nc2nc(NC3CC(F)(F)C3)nc(-c3cncc(C(F)(F)F)n3)n2)C1]

$^1$H NMR (400 MHz, $CDCl_3$) δ 9.74 (m, 1H), 9.08 (s, 1H), 5.84-5.49 (m, 2H), 4.53-4.37 (m, 2H), 3.12-3.02 (m, 4H), 2.70-2.57 (m, 4H). LC-MS: m/z 438 $(M+H)^+$.

6-(6-(Trifluoromethyl)pyrazin-2-yl)-$N^2$,$N^4$-bis((R)-1,1,1-trifluoropropan-2-yl)-1,3,5-triazine-2,4-diamine

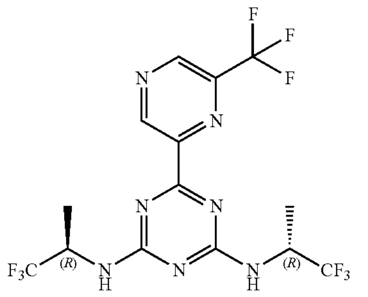

1H NMR (400 MHz, $CD_3OD$) δ 9.80 (s, 1H), 9.17 (s, 1H), 5.22-4.88 (m, 2H), 1.43-1.38 (m, 6H). LC-MS: m/z 450.1 $(M+H)^+$.

$N^2$,$N^4$-bis((S)-1,1,1-trifluorobutan-2-yl)-6-(6-(trifluoromethyl)pyrazin-2-yl)-1,3,5-triazine-2,4-diamine

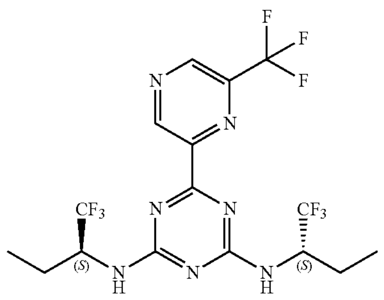

$^1$H NMR (400 MHz, DMSO-$d_6$) δ 9.86-9.69 (m, 1H), 9.37 (d, 1H), 8.68-8.28 (m, 2H), 5.04-4.71 (m, 2H), 1.81-1.68 (m, 4H), 0.97-0.90, 6H). LC-MS: m/z 478.1 $(M+H)^+$.

Example 21 Preparation of Symmetric Di-aliphatic Triazine Compounds of Formula N. The compounds of this Example are prepared by general Scheme 21, set forth below.

Scheme 21

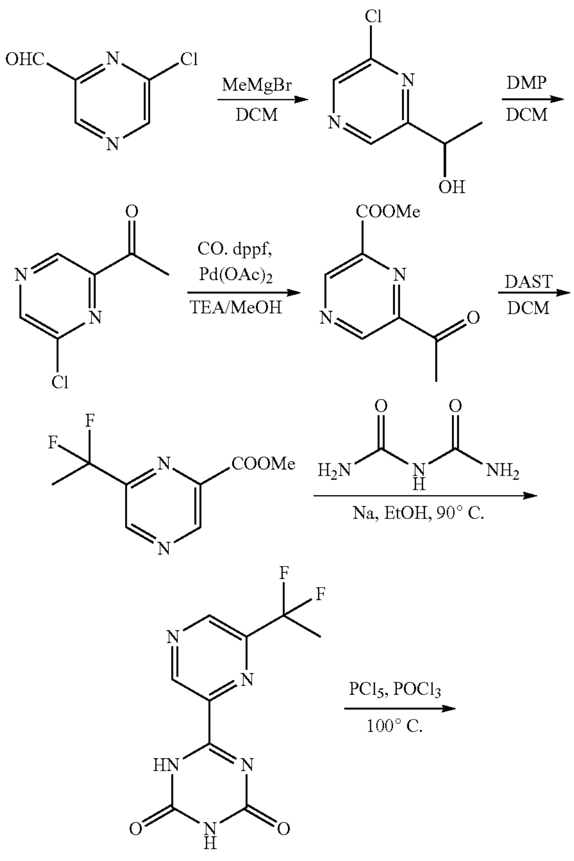

-continued

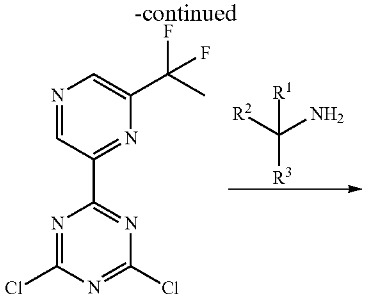

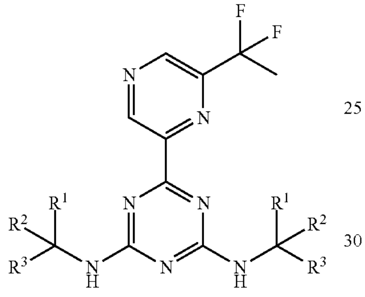

Formula N

Step 1: Preparation of 1-(6-chloropyrazin-2-yl)ethanol. To a solution of methyl 6-formylpyrazine-2-carboxylate (590 mg, 4.15 mmol) in anhydrous THF (5 mL) at −5° C. was added dropwise $CH_3MgBr$ (2.1 mL, 6.2 mmol). The reaction mixture was stirred at r.t. for 1 hr, then quenched with satd. a.q. $NH_4Cl$ at 0° C. and extracted with DCM (3×10 mL). The combined organic layers were washed with brine, dried over anhydrous $Na_2SO_4$ and concentrated to afford the desired product. LC-MS: m/z 159.0 $(M+H)^+$.

Step 2: Preparation of 1-(6-chloropyrazin-2-yl)ethanone. To a solution of 1-(6-chloropyrazin-2-yl) ethanol (370 mg, 2.3 mmol) in DCM (5 mL) at r.t. was added DMP (1.5 g, 3.5 mmol). The reaction mixture was stirred at r.t. for 3 hr then filtered. The filtrate was concentrated and purified by standard methods to afford the desired product. $^1H$ NMR (400 MHz, $CDCl_3$) δ 9.12 (s, 1H), 8.78 (s, 1H), 2.72 (s, 3H). LC-MS: m/z 157.1 $(M+H)^+$.

Step 3: Preparation of methyl 6-acetylpyrazine-2-carboxylate. To a solution of 1-(6-chloropyrazin-2-yl)ethanone (260.0 mg, 1.7 mmol) in MeOH (3 mL) were added dppf (94.0 mg, 0.17 mmol), $Pd(OAc)_2$ (20 mg, 0.1 mmol) and $Et_3N$ (0.4 mL, 2.6 mmol). The mixture was stirred under CO (60 psi) atmosphere at 60° C. overnight. The resulting mixture was cooled to r.t. and filtered. The filtrate was concentrated and purified by standard methods to afford the desired product. LC-MS: m/z 181.0 $(M+H)^+$.

Step 4: Preparation of methyl 6-(1,1-difluoroethyl)pyrazine-2-carboxylate. To a solution of methyl 6-acetylpyrazine-2-carboxylate (240 mg, 1.3 mmol) in anhydrous DCM (3 mL) at 0° C. was slowly added DAST (0.86 mL, 6.5 mmol). The reaction mixture was stirred at r.t. for 3 hr, then quenched with cold satd. aq. $NaHCO_3$ at 0° C. and extracted with DCM (3×10 mL). The combined organic layers were dried over anhydrous $Na_2SO_4$ and concentrated to afford the desired product.

LC-MS: m/z 203.1 $(M+H)^+$.

Step 5: Preparation of 6-(6-(1,1-difluoroethyl)pyrazin-2-yl)-1,3,5-triazine-2,4 (1H,3H)-dione. The procedure is the same as Example 1 Step 2 described above. LC-MS: m/z 256.1 $(M+H)^+$.

Step 6: Preparation of 2,4-dichloro-6-(6-(1,1-difluoroethyl)pyrazin-2-yl)-1,3,5-triazine. The procedure is the same as Example 1 Step 3 described above. LC-MS: m/z 292.0 $(M+H)^+$.

Step 7: Preparation of $N^2$,$N^4$-bis(4,4-difluorocyclohexyl)-6-(6-(1,1-difluoroethyl) pyrazin-2-yl)-1,3,5-triazine-2,4-diamine. The procedure is the same as Example 1 Step 4 described above.

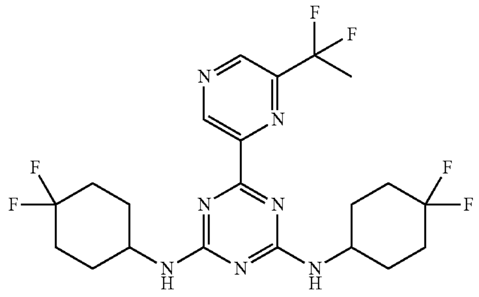 [SMILES: CC(F)(F)c1cncc(-c2nc(NC3CCC(F)(F)CC3)nc(NC3CCC(F)(F)CC3)n2)n1]

$^1H$ NMR (400 MHz, $CDCl_3$) δ 9.59 (m, 1H), 9.05 (s, 1H), 5.46 (s, 1H), 5.06 (m, 1H), 4.07 (m, 2H), 2.17 (s, 3H), 2.09 (s, 4H), 1.93 (m, 4H), 1.79-1.55 (m, 8H). LC-MS: m/z 490.2 $(M+H)^+$.

The procedure set forth in Example 21 was used to produce the following compounds using the appropriate starting materials.

$N^2$,$N^4$-bis(3,3-difluorocyclopentyl)-6-(6-(1,1-difluoroethyl)pyrazin-2-yl)-1,3,5-triazine-2,4-diamine

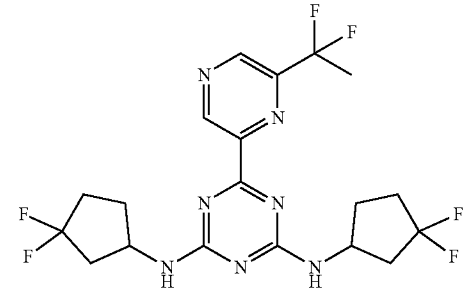 [SMILES: CC(F)(F)c1cncc(-c2nc(NC3CCC(F)(F)C3)nc(NC3CCC(F)(F)C3)n2)n1]

$^1H$ NMR (400 MHz, $CDCl_3$) δ 9.60 (m, 1H), 9.04 (d, J=6.0 Hz, 1H), 5.66-5.34 (m, 2H), 4.70-4.52 (m, 2H), 2.65-2.60 (m, 2H), 2.32-2.08 (m, 10H), 1.90-1.74 (m, 3H). LC-MS: m/z 462.2 $(M+H)^+$.

$N^2$,$N^4$-bis(3,3-difluorocyclobutyl)-6-(6-(1,1-difluoroethyl)pyrazin-2-yl)-1,3,5-triazine-2,4-diamine

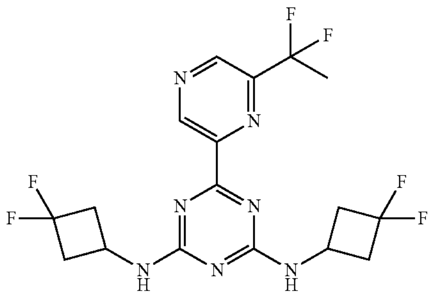 [SMILES: CC(F)(F)c1cncc(-c2nc(NC3CC(F)(F)C3)nc(NC3CC(F)(F)C3)n2)n1]

$^1$H NMR (400 MHz, $CDCl_3$) δ 9.62-9.57 (m, 1H), 9.05 (s, 1H), 5.75-5.44 (m, 2H), 4.51-4.37 (m, 2H), 3.07 (s, 4H), 2.65-2.61 (m, 4H), 2.17-2.08 (m, 3H). LC-MS: m/z 434.2 $(M+H)^+$.

Example 22 Preparation of Symmetric Di-aliphatic Triazine Compounds of Formula O. The compounds of this Example are prepared by general Scheme 22, set forth below.

Scheme 22

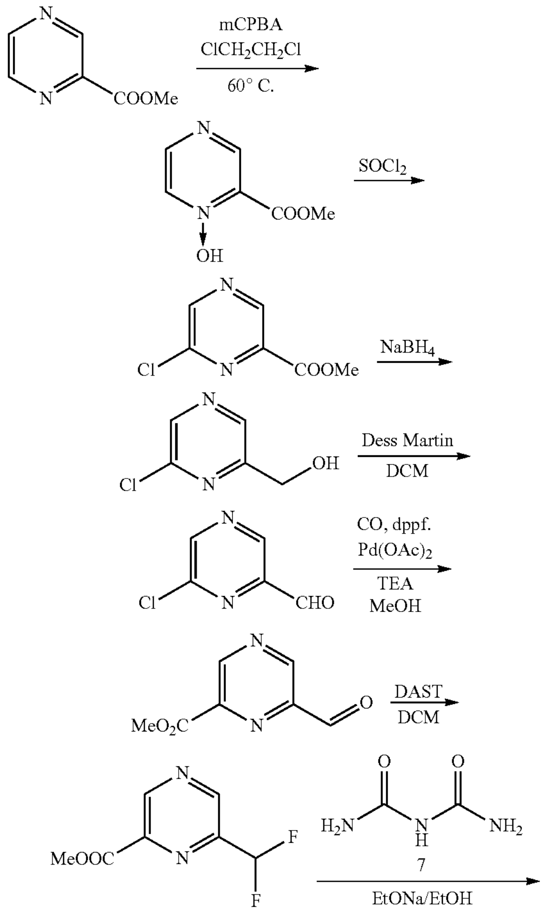

-continued

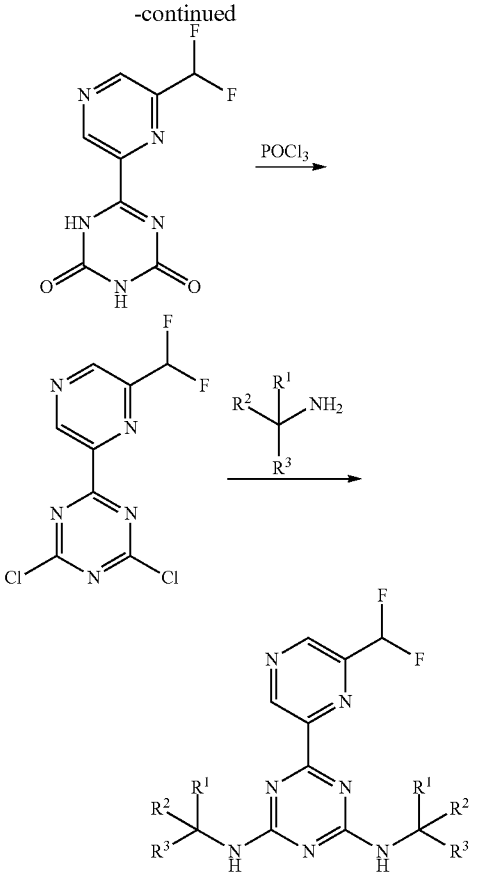

Formula O

Step 1: Preparation of 2-(methoxycarbonyl)pyrazine 1-oxide. To a solution of methyl pyrazine-2-carboxylate (10.0 g, 70 mmol) in 1,2-dichloroethane (120 mL) was added 3-chloroperoxybenzoic acid (25.0 g, 140 mmol). The reaction mixture was stirred at 60° C. overnight. The resulting mixture was cooled to r.t. and filtered. The filtrate was dried over anhydrous $K_2CO_3$ and concentrated under reduced pressure. The residue was triturated with hexane and filtered and dried to afford 2-(methoxycarbonyl)pyrazine 1-oxide. LC-MS: m/z 155.0 $(M+H)^+$.

Step 2: Preparation of methyl 6-chloropyrazine-2-carboxylate. A mixture of 2-(methoxycarbonyl)pyrazine 1-oxide (4.8 g, 30 mmol) in $SOCl_2$ (50 mL) was stirred at 85° C. overnight. The mixture was cooled to r.t. and concentrated under reduced pressure. The residue was neutralized by satd. aq. $NaHCO_3$ and extracted with DCM (3×20 mL). The combined organic layers were washed with brine, dried over anhydrous $Na_2SO_4$ and concentrated and purified by standard methods to afford methyl 6-chloropyrazine-2-carboxylate. $^1$H NMR (600 MHz, $CDCl_3$) δ 8.59 (s, 1H), 8.53 (s, 1H), 4.84 (s, 2H), 3.01 (s, 1H). LC-MS: m/z 173.0 $(M+H)^+$.

Step 3: Preparation of (6-chloropyrazin-2-yl)methanol. To a solution of methyl 6-chloropyrazine-2-carboxylate (2.0 g, 11.6 mmol) in water (20 mL) at 0° C. was added $NaBH_4$ (2.3 g, 58.0 mmol) portionwise. The reaction mixture was warmed to r.t. and stirred for 30 min, followed by addition of satd. aq. $K_2CO_3$ (40 mL) and EtOH (20 mL). The resulting mixture was stirred for another 1 hr and extracted with EA (2×20 mL). The combined organic layers were dried over anhydrous $Na_2SO_4$ and concentrated and purified by standard methods to afford (6-chloropyrazin-2-yl)methanol. LC-MS: m/z 145.0 $(M+H)^+$.

Step 4: Preparation of 6-chloropyrazine-2-carbaldehyde. To a solution of (6-chloropyrazin-2-yl)methanol (600 mg, 4.2 mmol) in DCM (10 mL) was added Dess-Martin reagent (2.6 g, 6.3 mmol). The reaction mixture was stirred at r.t. for 3 hr, and then filtered. The filtrate was concentrated and purified by standard methods to afford 6-chloropyrazine-2-carbaldehyde.

LC-MS: m/z 143.0 $(M+H)^+$.

Step 5: Preparation of methyl 6-formylpyrazine-2-carboxylate. To a mixture of 6-chloropyrazine-2-carbaldehyde (1.0 g, 7.0 mmol) in MeOH (10 mL) were added dppf (388 mg, 0.7 mmol), $Pd(OAc)_2$ (90 mg, 0.4 mmol) and $Et_3N$ (1.5 mL, 10.5 mmol). The suspension was stirred under CO atmosphere (60 psi) at 60° C. overnight. The resulting mixture was cooled to r.t. and filtered. The filtrate was concentrated and purified by standard methods to afford methyl 6-formylpyrazine-2-carboxylate. LC-MS: m/z 167.0 $(M+H)^+$.

Step 6: Preparation of methyl 6-(difluoromethyl)pyrazine-2-carboxylate. To a mixture of methyl 6-formylpyrazine-2-carboxylate (4.1 g, 24.7 mmol) in anhydrous DCM (40 mL) at 0° C. was slowly added DAST (16.3 mL, 123.5 mmol). The reaction mixture was stirred at r.t. for 3 hrs, then quenched with cold satd. aq. $NaHCO_3$ at 0° C. and extracted with DCM (2×20 mL). Combined organic layers were dried over anhydrous $Na_2SO_4$ and concentrated to afford the desired product.

LC-MS: m/z 189.0 $(M+H)^+$.

Step 7: Preparation of 6-(6-(difluoromethyl)pyrazin-2-yl)-1,3,5-triazine-2,4 (1H,3H)-dione. To a flame-dried three necked round bottom flask was added biuret (659 mg, 6.4 mmol) and methyl 6-(difluoromethyl)pyrazine-2-carboxylate (1.0 g, 5.3 mmol), followed by addition of EtOH (12 mL). The mixture was degassed and back-filled with $N_2$ three times. The mixture was stirred at 25° C. for 20 min, and then heated to 50° C. Then $HC(OMe)_3$ (0.7 mL, 6.4 mmol) and TFA (0.04 mL, 0.53 mmol) were added to the above mixture. The mixture (pale yellow slurry) was stirred at this temperature for 30 min, followed by dropwise addition of a solution of NaOEt in EtOH (20% wt, 7.2 g, 21.2 mmol). The resulting mixture was heated at reflux for 2 hr, then cooled to r.t. and concentrated under reduced pressure. The residue was treated with water (10 mL) and concentrated again to remove the remaining ethanol. The final residue was suspended in water (30 mL), cooled to 10° C. when the acidity was adjusted to pH=1 by slow addition of 6N HCl (solid precipitated out), and then stirred for 2 hr. The mixture was filtered and the filter cake was washed with aq. HCl (pH=1). The solid was collected and suspended in DCM (30 mL). The suspension was stirred at r.t. for 2 hr and then filtered again. The filter cake was collected and dried to afford the desired product. LC-MS: m/z 242.0 $(M+H)^+$.

Step 8: Preparation of 2,4-dichloro-6-(6-(difluoromethyl) pyrazin-2-yl)-1,3,5-triazine. The procedure is the same as Example 1 Step 3 described above. LC-MS: m/z 2782.0 $(M+H)^+$.

Step 8: Preparation of $N^2$,$N^4$-bis(4,4-difluorocyclohexyl)-6-(6-(difluoromethyl) pyrazin-2-yl)-1,3,5-triazine-2,4-diamine. The procedure is the same as Example 1 Step 4 described above.

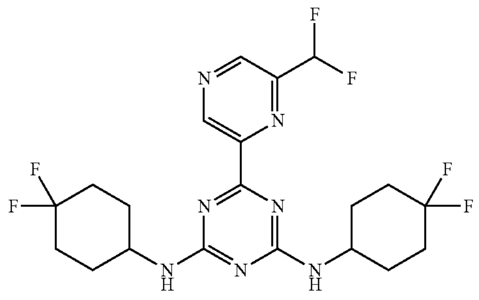

$^1H$ NMR (400 MHz, $CDCl_3$) δ 9.69 (m, 1H), 9.07 (s, 1H), 6.89 (m, 1H), 5.53-5.12 (m, 2H), 4.08 (m, 2H), 2.23-1.67 (m, 16H). LC-MS: m/z 476.2 $(M+H)^+$.

The procedure set forth in Example 22 was used to produce the following compounds using the appropriate starting materials.

$N^2$,$N^4$-bis(3,3-difluorocyclopentyl)-6-(6-(difluoromethyl)pyrazin-2-yl)-1,3,5-triazine-2,4-diamine

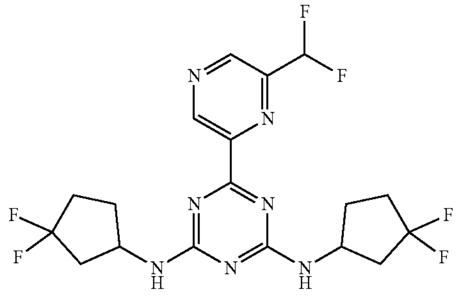 [SMILES: FC(F)c1cncc(-c2nc(NC3CCC(F)(F)C3)nc(NC3CCC(F)(F)C3)n2)n1]

$^1H$ NMR (400 MHz, $CDCl_3$) δ 9.73-9.67 (m, 1H), 9.07 (s, 1H), 7.03-6.76 (m, 1H), 5.63-5.35 (m, 2H), 4.73-4.55 (m, 2H), 2.66-2.61 (m, 2H), 2.32 (s, 4H), 2.13-1.57 (m, 6H). LC-MS: m/z 448.2 $(M+H)^+$.

$N^2$,$N^4$-bis(3,3-difluorocyclobutyl)-6-(6-(difluoromethyl)pyrazin-2-yl)-1,3,5-triazine-2,4-diamine

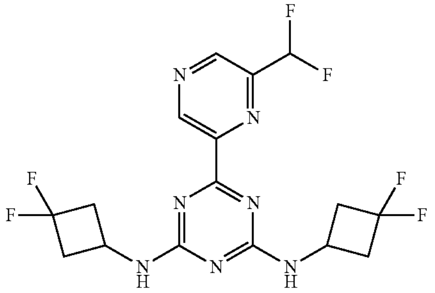 [SMILES: FC(F)c1cncc(-c2nc(NC3CC(F)(F)C3)nc(NC3CC(F)(F)C3)n2)n1]

$^1H$ NMR (400 MHz, $CDCl_3$) δ 9.72-9.67 (m, 1H), 9.07 (s, 1H), 6.85 (d, 1H), 5.76-5.48 (m, 2H), 4.54-4.38 (m, 2H), 3.08 (s, 4H), 2.66-2.61 (m, 4H). LC-MS: m/z 420.1 $(M+H)^+$.

N[2],N[4]-bis(3,3-difluorocyclobutyl)-6-(4-(difluoromethyl)pyrimidin-2-yl)-1,3,5-triazine-2,4-diamine

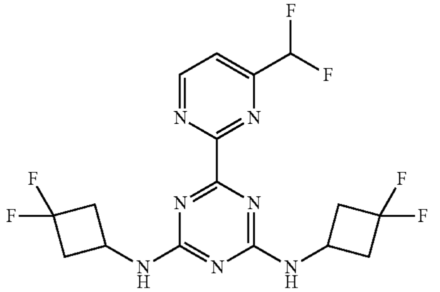 [SMILES: FC(F)c1ccnc(-c2nc(NC3CC(F)(F)C3)nc(NC3CC(F)(F)C3)n2)n1]

$^1$H NMR (400 MHz, $CDCl_3$) δ 9.17 (d, J=4.9 Hz, 1H), 7.77 (d, J=4.9 Hz, 1H), 6.77 (m, 1H), 5.76 (m, 2H), 4.55 (m, 2H), 3.07 m, 4H), 2.61 (m, 4H). LC-MS: m/z 420 $(M+H)^+$.

N[2],N[4]-bis(3,3-difluorocyclopentyl)-6-(4-(difluoromethyl)pyrimidin-2-yl)-1,3,5-triazine-2,4-diamine

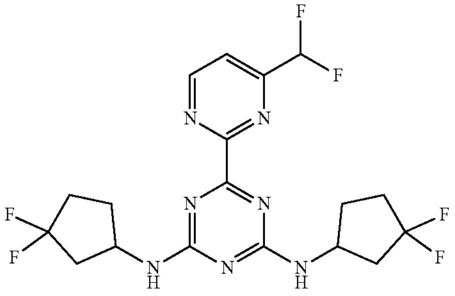 [SMILES: FC(F)c1ccnc(-c2nc(NC3CCC(F)(F)C3)nc(NC3CCC(F)(F)C3)n2)n1]

$^1$H NMR (400 MHz, DMSO-$d_6$) δ 9.19 (m, 1H), 8.16 (m, 1H), 7.88 (m, 1H), 7.04 (m, 1H), 4.47 (m, 2H), 2.63 (m, 1H), 2.25 (m, 9H), 1.83 (m, 2H). LC-MS: m/z 448 $(M+H)^+$.

N[2],N[4]-bis(4,4-difluorocyclohexyl)-6-(4-(difluoromethyl)pyrimidin-2-yl)-1,3,5-triazine-2,4-diamine

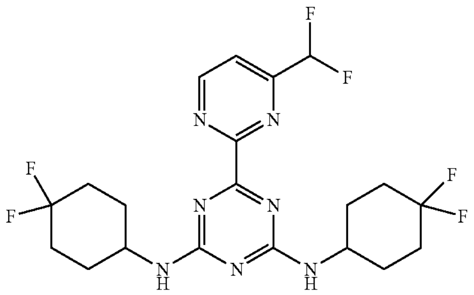 [SMILES: FC(F)c1ccnc(-c2nc(NC3CCC(F)(F)CC3)nc(NC3CCC(F)(F)CC3)n2)n1]

$^1$H NMR (400 MHz, $CDCl_3$) δ (m, 1H), 7.79-7.78 (m, 1H), 6.91-6.64 (m, 1H), 5.72-5.20 (m, 2H), 4.26-4.02 (m, 2H), 2.13-2.10 (m, 8H), 1.98-1.87 (m, 4H), 1.76-1.73 (m, 4H). LC-MS: m/z 476 $(M+H)^+$.

Example 23 The compounds of this Example are prepared by general Scheme 23, set forth below.

Scheme 23

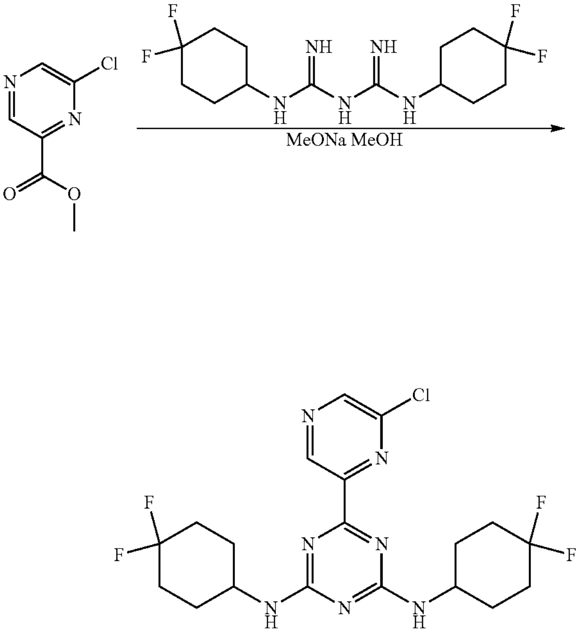

Step 1: Preparation of 6-(6-chloropyrazin-2-yl)-N[2],N[4]-bis(4,4-difluorocyclo hexyl)-1,3,5-triazine-2,4-diamine. To a mixture of methyl 6-chloropyrazine-2-carboxylate (300 mg, 1.74 mmol) and N[1],N[5]-di-(4,4-difluorocyclohexanamine)-biguanide (700 mg, 2.10 mmol) in MeOH (8 mL) was added MeONa (340 mg, 6.28 mmol). The reaction mixture was stirred at r.t. overnight, and then partitioned between EtOAc (30 mL) and $H_2O$ (30 mL). The organic layer was separated, washed with brine (30 mL), dried over anhydrous $Na_2SO_4$, and concentrated and purified by standard methods to afford the desired product. $^1$H NMR (400 MHz, DMSO-$d_6$) δ 9.48-9.32 (m, 1H), 8.93 (d, J=8 Hz, 1H), 7.92-7.59 (m, 2H), 4.15-3.95 (m, 2H), 2.08-1.60 (m, 16H). LCMS: m/z 460 $(M+H)^+$.

The procedure set forth in Example 23 was used to produce the following compounds using the appropriate starting materials.

6-(6-Chloropyrazin-2-yl)-N[2],N[4]-bis(3,3-difluorocyclopentyl)-1,3,5-triazine-2,4-diamine

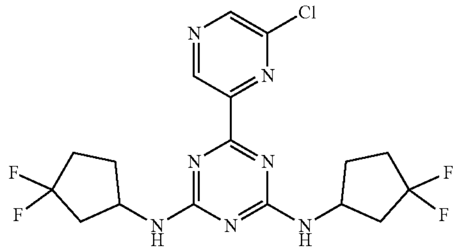 [SMILES: FC1(F)CCC(Nc2nc(NC3CCC(F)(F)C3)nc(-c3cncc(Cl)n3)n2)C1]

$^1$H NMR (400 MHz, $CDCl_3$) δ 9.45 (d, 1H), 8.72 (s, 1H), 5.65 (d, 2H), 4.53-4.37 (m, 2H), 3.07-2.60 (m, 8H). LC-MS: m/z 432 $(M+H)^+$.

6-(6-Chloropyrazin-2-yl)-$N^2$,$N^4$-bis(3,3-difluorocyclobutyl)-1,3,5-triazine-2,4-diamine

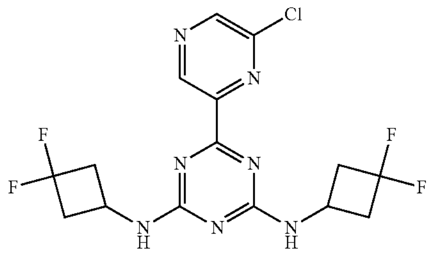 [SMILES: FC1(F)CC(Nc2nc(NC3CC(F)(F)C3)nc(-c3cncc(Cl)n3)n2)C1]

$^1$H NMR (400 MHz, $CDCl_3$) δ 9.45 (d, 1H), 8.71 (s, 1H), 5.69-5.36 (m, 2H), 4.70-4.52 (m, 2H), 2.65-2.05 (m, 12H). LC-MS: m/z 404 $(M+H)^+$.

6-(6-chloropyrazin-2-yl)-$N_2$,$N_4$-bis(1,1,1-trifluoropropan-2-yl)-1,3,5-triazine-2,4-diamine

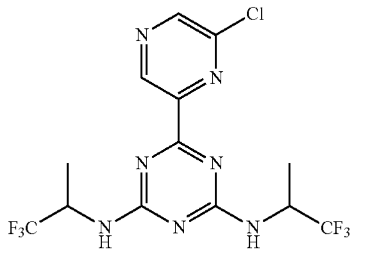 [SMILES: CC(Nc1nc(NC(C)C(F)(F)F)nc(-c2cncc(Cl)n2)n1)C(F)(F)F]

$^1$H NMR (400 MHz, $CDCl_3$) δ 9.42 (d, 1H), 8.66 (s, 1H), 5.61-5.24 (m, 2H), 5.01-4.78 (m, 2H), 1.41-1.34 (m, 6H). LCMS: m/z 416$(M+H)^+$.

Example 24 Preparation of Symmetric Di-aliphatic Triazine Compounds of Formula P. The compounds of this Example are prepared by general Scheme 24, set forth below.

Scheme 24

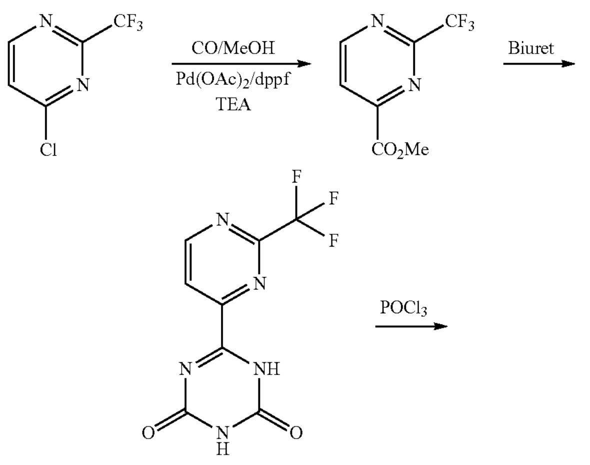

-continued

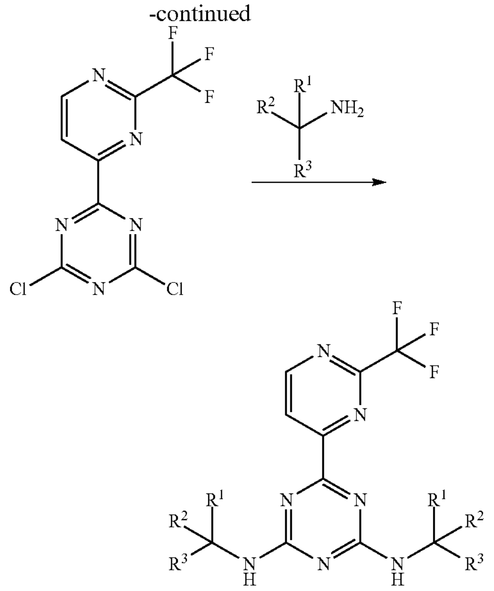

Formula P

Step 1: Preparation of methyl 2-(trifluoromethyl)pyrimidine-4-carboxylate. To a solution of 4-chloro-2-(trifluoromethyl)pyrimidine (10 g, 54.9 mmol) in MeOH (60 mL) was added dppf (3.0 g, 5.5 mmol), $Pd(OAc)_2$ (630 mg, 2.8 mmol) and $Et_3N$ (11.4 mL, 41.2 mmol). The mixture was stirred under CO atmosphere (60 psi) at 60° C. overnight. The resulting mixture was cooled to r.t. and filtered. The filtrate was concentrated and purified by standard methods to afford the desired product. LC-MS: m/z 207.0 $(M+H)^+$.

Step 2: Preparation of 6-(2-(trifluoromethyl)pyrimidin-4-yl)-1,3,5-triazine-2,4(1H, 3H)-dione. The procedure is the same as Example 1 Step 2 described above. LC-MS: m/z 260.0 $(M+H)^+$.

Step 3: Preparation of 2,4-dichloro-6-(2-(trifluoromethyl) pyrimidin-4-yl)-1,3,5-triazine. The procedure is the same as Example 1 Step 3 described above. LC-MS: m/z 296.0 $(M+H)^+$.

Step 4: Preparation of $N^2$,$N^4$-bis(4,4-difluorocyclohexyl)-6-(2-(trifluoromethyl)pyri midin-4-yl)-1,3,5-triazine-2,4-diamine. The procedure is the same as Example 1 Step 4 described above.

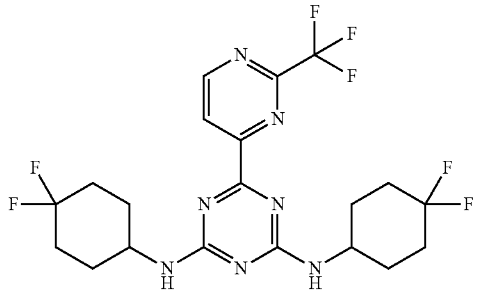

$^1$H NMR (400 MHz, $CDCl_3$) δ 9.08 (m, 1H), 8.42 (m, 1H), 5.54-5.19 (m, 2H), 4.16-3.99 (m, 2H), 2.29-1.73 (m, 16H). LC-MS: m/z 494.2 $(M+H)^+$.

The procedure set forth in Example 24 was used to produce the following compounds using the appropriate starting materials.

N$^2$,N$^4$-bis(3,3-difluorocyclopentyl)-6-(2-(trifluoromethyl)pyrimidin-4-yl)-1,3,5-triazine-2,4-diamine

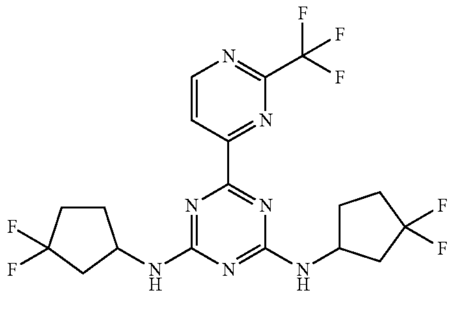 [SMILES: FC1(F)CCC(Nc2nc(NC3CCC(F)(F)C3)nc(-c3ccnc(C(F)(F)F)n3)n2)C1]

$^1$H NMR (400 MHz, $CDCl_3$) δ 9.06-9.10 (m, 1H), 8.39-8.45 (m, 1H), 5.66-5.68 (d, J=8.0 Hz, 2H), 4.52-4.70 (m, 2H), 2.60-2.65 (m, 2H), 2.13-2.32 (m, 8H), 1.67-1.87 (m, 2H). LC-MS: m/z 466.2 $(M+H)^+$.

N$^2$,N$^4$-bis(3,3-difluorocyclobutyl)-6-(2-(trifluoromethyl)pyrimidin-4-yl)-1,3,5-triazine-2,4-diamine

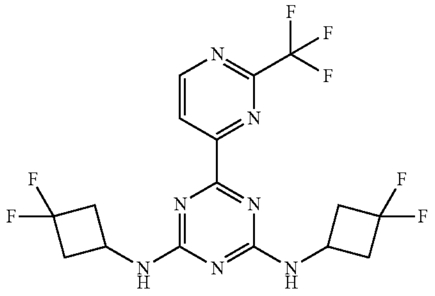 [SMILES: FC1(F)CC(Nc2nc(NC3CC(F)(F)C3)nc(-c3ccnc(C(F)(F)F)n3)n2)C1]

$^1$H NMR (400 MHz, $CDCl_3$) δ 9.10 (m, 1H), 8.51-8.37 (m, 1H), 5.93-5.48 (m, 2H), 4.44 (m, 2H), 3.07 (m, 4H), 2.75-2.49 (m, 4H). LC-MS: m/z 438.1 $(M+H)^+$.

6-(2-(Trifluoromethyl)pyrimidin-4-yl)-N$^2$,N$^4$-bis((R)-1,1,1-trifluoropropan-2-yl)-1,3,5-triazine-2,4-diamine

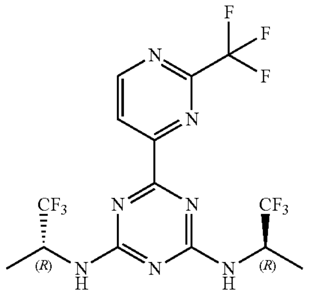

$^1$H NMR (400 MHz, $CDCl_3$) δ 9.11 (m, 1H), 8.45 (t, J=5.6 Hz, 1H), 5.74-5.32 (m, 2H), 5.16-4.79 (m, 2H), 1.43 (m, 6H). LC-MS: m/z 450.1 $(M+H)^+$.

N$^2$,N$^4$-bis((S)-1,1,1-trifluorobutan-2-yl)-6-(2-(trifluoromethyl)pyrimidin-4-yl)-1,3,5-triazine-2,4-diamine

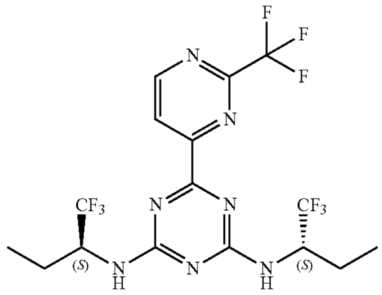

$^1$H NMR (400 MHz, $CDCl_3$) δ 9.11 (m, 1H), 8.46 (d, J=5.0 Hz, 1H), 5.78-5.22 (m, 2H), 4.97-4.63 (m, 2H), 2.12-1.90 (m, 2H), 1.61-1.69 (m, 2H), 1.05 (t, J=7.5 Hz, 6H). LC-MS: m/z 478.1 $(M+H)^+$.

N$^2$,N$^4$-bis(4,4-difluorocyclohexyl)-6-(4-(trifluoromethyl)pyri midin-2-yl)-1,3,5-triazine-2,4-diamine

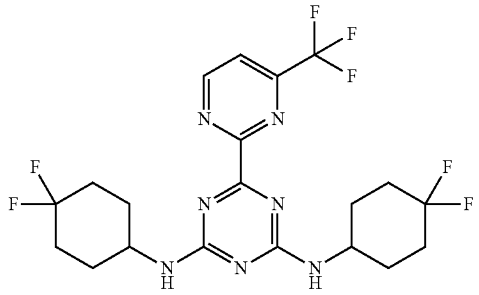 [SMILES: FC1(F)CCC(Nc2nc(NC3CCC(F)(F)CC3)nc(-c3nccc(C(F)(F)F)n3)n2)CC1]

$^1$H NMR (400 MHz, $CDCl_3$) δ 9.22 (d, J=4.9 Hz, 1H), 7.77 (d, J=4.9 Hz, 1H), 5.64-5.16 (m, 2H), 4.21-4.01 (m, 2H), 2.28-1.52 (m, 16H). LC-MS: m/z 494.2 $(M+H)^+$.

N$^2$,N$^4$-bis(3,3-difluorocyclopentyl)-6-(4-(trifluoromethyl)pyrimidin-2-yl)-1,3,5-triazine-2,4-diamine

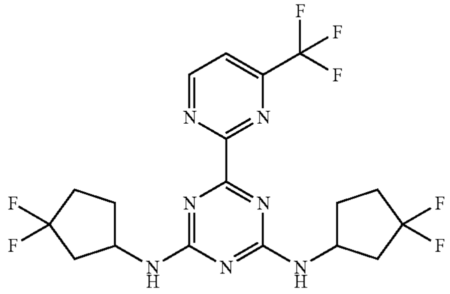 [SMILES: FC1(F)CCC(Nc2nc(NC3CCC(F)(F)C3)nc(-c3nccc(C(F)(F)F)n3)n2)C1]

$^1$H NMR (400 MHz, $CDCl_3$) δ 9.22 (d, 1H), 7.77 (d, 1H), 5.87 (d, 2H), 4.58-4.53 (m, 2H), 2.69-2.56 (m, 2H), 2.31-2.29 (m, 4H), 2.17-2.08 (m, 4H), 1.87-1.68 (m, 2H). LC-MS: m/z 466.2 $(M+H)^+$.

$N^2$,$N^4$-bis(3,3-difluorocyclobutyl)-6-(4-(trifluoromethyl)pyrimidin-2-yl)-1,3,5-triazine-2,4-diamine

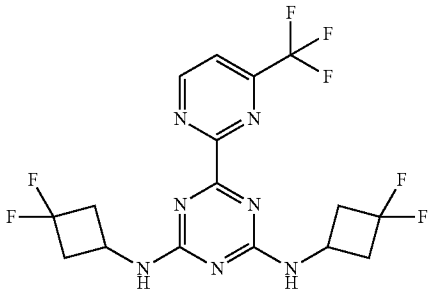 [SMILES: FC1(F)CC(Nc2nc(NC3CC(F)(F)C3)nc(-c3nccc(C(F)(F)F)n3)n2)C1]

$^1$H NMR (400 MHz, DMSO-$d_6$) δ 9.34 (m, 1H), 8.64-8.00 (m, 3H), 4.46-4.10 (m, 2H), 3.07-2.83 (m, 4H), 2.74-2.62 (m, 4H). LC-MS: m/z 438.1 $(M+H)^+$.

$N^2$,$N^4$-bis((R)-1-cyclopropylethyl)-6-(4-(trifluoromethyl)pyrimidin-2-yl)-1,3,5-triazine-2,4-diamine

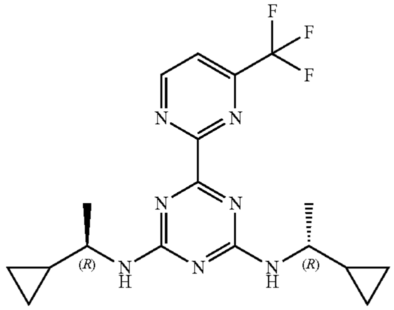

$^1$H NMR (400 MHz, $CDCl_3$) δ 9.19 (s, 0.6H), 7.74-7.73 (m, 0.6H), 5.63-5.43 (m, 2H), 3.61-3.58 (m, 2H), 1.27-1.26 (m, 8H), 0.90 (m, 2H), 0.50-0.26 (m, 8H). LCMS: m/z 394 $(M+H)^+$.

$N^2$,$N^4$-bis(4,4-difluorocyclohexyl)-6-(4-(2-methoxyethyl)pyrimidin-2-yl)-1,3,5-triazine-2,4-diamine

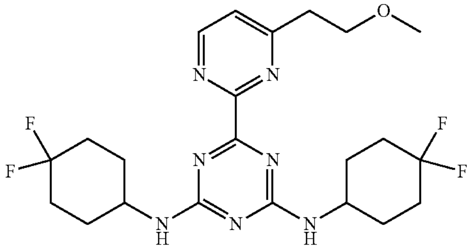 [SMILES: COCCc1ccnc(-c2nc(NC3CCC(F)(F)CC3)nc(NC3CCC(F)(F)CC3)n2)n1]

$^1$H NMR (400 MHz, $CDCl_3$) δ 8.83-8.82 (m, 1H), 7.40-7.39 (m, 1H), 5.60-5.58 (m, 2H), 4.26-4.01 (m, 2H), 3.81-3.77 (t, J=8 Hz, 2H), 3.35 (s, 3H), 3.21-3.18 (m, J=8 Hz, 2H), 2.11-2.05 (m, 8H), 1.94-1.86 (m, 4H), 1.74-1.69 (m, 4H). LC-MS: m/z 484 $(M+H)^+$.

Example 25 The compounds of this Example are prepared by general Scheme 25, set forth below.

Scheme 25

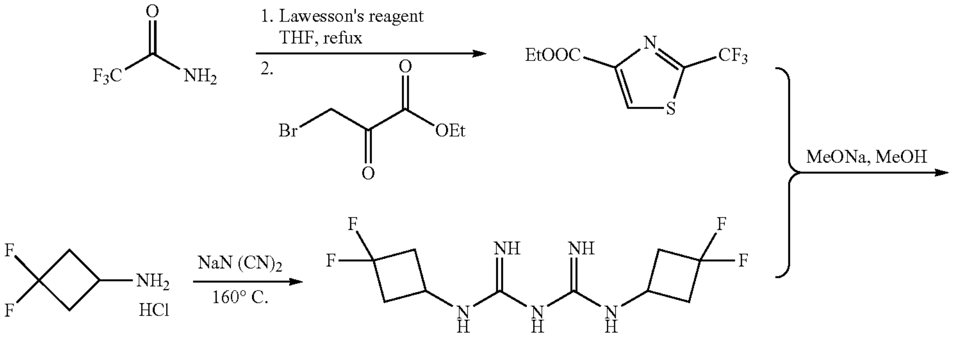

-continued

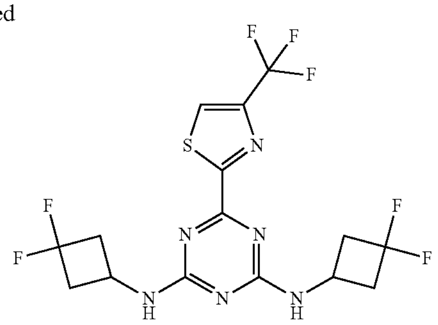

Step 1: Preparation of ethyl 2-(trifluoromethyl)thiazole-4-carboxylate. To a solution of 2,2,2-trifluoroacetamide (1.42 g, 12.6 mmol) in dry THF (60 mL) was added Lawesson's reagent (3.06 g, 7.56 mmol). The reaction mixture was heated at reflux for 18 hr and then cooled, followed by addition of ethyl 3-bromo-2-oxopropanoate (1.6 mL, 12.6 mmol). The mixture was refluxed for another 18 hr and then cooled to r.t. The resulting mixture was partitioned between EtOAc and water. The organic layer was separated, dried over anhydrous $Na_2SO_4$ and concentrated and purified by standard methods to afford ethyl 2-(trifluoromethyl) thiazole-4-carboxylate. $^1H$ NMR (400 MHz, $CDCl_3$) δ 8.42 (s, 1H) 4.47 (q, J=7.1 Hz, 2H), 1.45 (t, J=7.2 Hz, 3H). LC-MS: m/z 226 $(M+H)^+$.

Step 2: Preparation of $N^1$,$N^5$-bis (3,3-difluorocyclobutyl)-biguanide. A mixture of 3,3-difluorocyclobutanamine hydrochloride (3.024 g, 0.021 mol) and $NaN(CN)_2$ (890 mg, 0.01 mol) was vigorously stirred at 160° C. for 2 hr then cooled to r.t. The resulting mixture was dissolved in MeOH and filtered. The filtrate was concentrated to afford the desired product. LC-MS: m/z 282 $(M+H)^+$.

Step 3: Preparation of $N^2$,$N^4$-bis(3,3-difluorocyclobutyl)-6-(4-(trifluoromethyl) thiazol-2-yl)-1,3,5-triazine-2,4-diamine. To a mixture of $N^1$,$N^5$-bis(3,3-difluoro cyclobutyl)-biguanide (60 mg, 0.22 mmol) in MeOH (5 mL) were added ethyl 2-(trifluoromethyl)thiazole-4-carboxylate (58.5 mg, 0.26 mmol) and NaOMe (23.7 mg, 0.44 mmol). The reaction mixture was then stirred at r.t. for 48 hr then partitioned between EtOAc and $H_2O$. The organic layer was separated, washed with brine, dried over anhydrous $Na_2SO_4$, and concentrated and purified by standard methods to afford the $N^2$,$N^4$-bis(3,3-difluorocyclobutyl)-6-(4-(trifluoromethyl) thiazol-2-yl)-1,3,5-triazine-2,4-diamine.

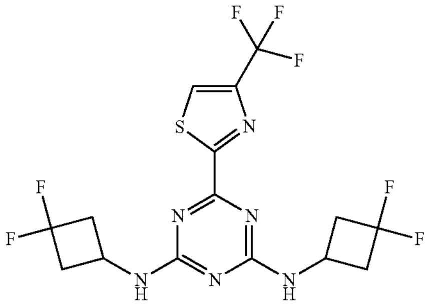 [SMILES: FC1(F)CC(Nc2nc(NC3CC(F)(F)C3)nc(-c3nc(C(F)(F)F)cs3)n2)C1]

$^1H$ NMR (400 MHz, $CDCl_3$) δ 7.83 (d, J=5.2 Hz, 1H), 7.01-6.74 (m, 1H), 5.74-5.43 (m, 2H), 4.45-4.32 (m, 2H), 3.11-3.04 (m, 4H), 2.63-2.48 (m, 4H). LC-MS: m/z 443 $(M+H)^+$.

The procedure set forth in Example 25 was used to produce the following compounds using the appropriate starting materials.

$N^2$,$N^4$-bis(4,4-difluorocyclohexyl)-6-(4-(trifluoromethyl)thiazol-2-yl)-1,3,5-triazine-2,4-diamine

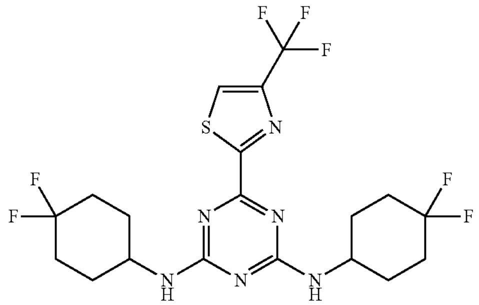 [SMILES: FC1(F)CCC(Nc2nc(NC3CCC(F)(F)CC3)nc(-c3nc(C(F)(F)F)cs3)n2)CC1]

$^1H$ NMR (400 MHz, $CDCl_3$) δ 7.84 (s, 1H), 5.42-5.07 (m, 2H), 3.89-3.79 (m, 2H), 2.06-1.79 (m, 13H), 1.67-1.57 (m, 3H). LCMS: m/z 499 $(M+H)^+$.

$N^2$,$N^4$-bis(3,3-difluorocyclopentyl)-6-(4-(trifluoromethyl)thiazol-2-yl)-1,3,5-triazine-2,4-diamine

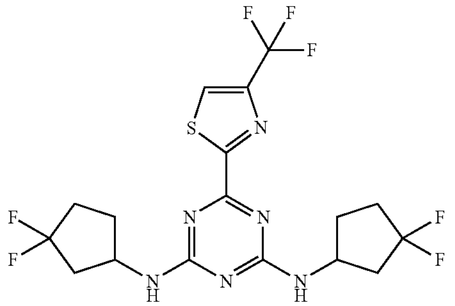 [SMILES: FC1(F)CCC(Nc2nc(NC3CCC(F)(F)C3)nc(-c3nc(C(F)(F)F)cs3)n2)C1]

$^1H$ NMR (400 MHz, $CDCl_3$) δ 7.91 (d, J=4 Hz, 1H), 5.66-5.34 (m, 2H), 4.64-4.51 (m, 2H), 2.69-2.59 (m, 2H), 2.31-2.04 (m, 8H), 1.86-1.80 (m, 2H). LCMS: m/z 471 $(M+H)^+$.

6-(4-(trifluoromethyl)thiazol-2-yl)-$N^2$,$N^4$-bis(1,1,1-trifluoropropan-2-yl)-1,3,5-triazine-2,4-diamine

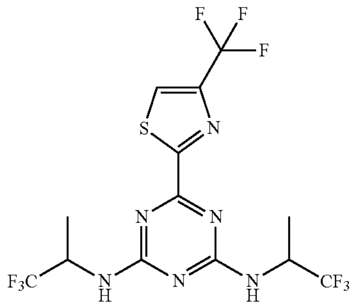 [SMILES: CC(Nc1nc(NC(C)C(F)(F)F)nc(-c2nc(C(F)(F)F)cs2)n1)C(F)(F)F]

$^1H$ NMR (400 MHz, $CDCl_3$) δ 7.94 (s, 1H), 5.81-5.31 (m, 2H), 5.01-4.83 (m, 2H), 1.47-1.39 (m, 6H). LCMS: m/z 455 $(M+H)^+$.

$N^2$,$N^4$-bis(4,4-difluorocyclohexyl)-6-(2-(trifluoromethyl)thiazol-4-yl)-1,3,5-triazine-2,4-diamine

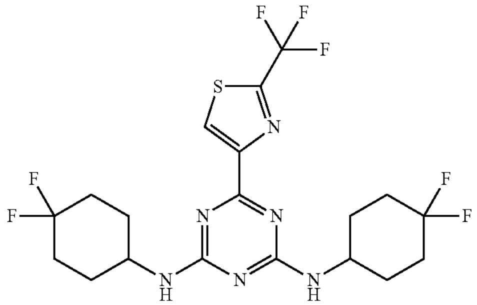 [SMILES: FC1(F)CCC(Nc2nc(NC3CCC(F)(F)CC3)nc(-c3csc(C(F)(F)F)n3)n2)CC1]

$^1H$ NMR (400 MHz, $CDCl_3$) δ 8.48 (m, 1H), 5.41-5.09 (m, 2H), 4.16-3.99 (m, 2H), 2.28-1.66 (m, 16H). LC-MS: m/z 499 $(M+H)^+$.

$N^2$,$N^4$-bis(3,3-difluorocyclobutyl)-6-(2-(trifluoromethyl)thiazol-4-yl)-1,3,5-triazine-2,4-diamine

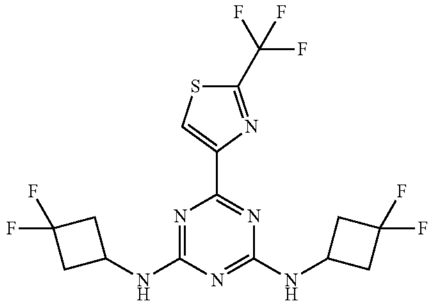 [SMILES: FC1(F)CC(Nc2nc(NC3CC(F)(F)C3)nc(-c3csc(C(F)(F)F)n3)n2)C1]

$^1H$ NMR (400 MHz, $CDCl_3$) δ 8.50 (m, 1H), 6.73-6.38 (m, 2H), 4.46-4.36 (m, 2H), 3.06 (s, 4H), 2.61 (s, 4H). LC-MS: m/z 443 $(M+H)^+$.

6-(2-(trifluoromethyl)thiazol-4-yl)-$N^2$,$N^4$-bis((R)-1,1,1-trifluoropropan-2-yl)-1,3,5-triazine-2,4-diamine

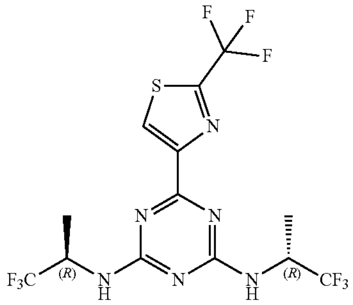

$^1H$ NMR (400 MHz, $CDCl_3$) δ 8.49 (d, 1H), 5.57-5.12 (m, 2H), 4.97-4.49 (m, 2H), 1.36-1.25 (m, 6H). LCMS: m/z 455 $(M+H)^+$.

$N^2$,$N^4$-bis(4,4-difluorocyclohexyl)-6-(2-methyloxazol-4-yl)-1,3,5-triazine-2,4-diamine

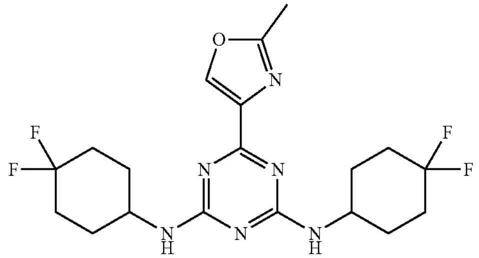 [SMILES: Cc1nc(-c2nc(NC3CCC(F)(F)CC3)nc(NC3CCC(F)(F)CC3)n2)co1]

$^1H$ NMR (400 MHz, $CDCl_3$) δ 8.11 (s, 1H), 5.27-4.92 (m, 2H), 4.02-3.81 (m, 2H), 2.47 (s, 3H), 2.03-1.79 (m, 12H), 1.63-1.54 (m, 4H). LCMS: m/z 429 $(M+H)^+$.

$N^2$,$N^4$-bis(3,3-difluorocyclobutyl)-6-(2-methyloxazol-4-yl)-1,3,5-triazine-2,4-diamine

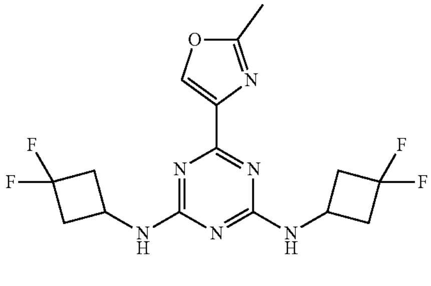 [SMILES: Cc1nc(-c2nc(NC3CC(F)(F)C3)nc(NC3CC(F)(F)C3)n2)co1]

$^1H$ NMR (400 MHz, $CDCl_3$) δ 8.24 (m, 1H), 5.66 (m, 2H), 4.31 (s, 2H), 3.13-2.95 (m, 4H), 2.60 (m, 7H). LC-MS: m/z 373 $(M+H)^+$.

N$^2$,N$^4$-bis(4,4-difluorocyclohexyl)-6-(5-methylisoxazol-3-yl)-1,3,5-triazine-2,4-diamine

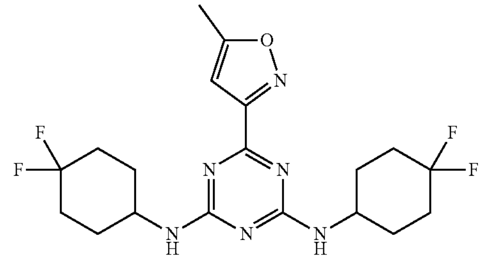 [SMILES: Cc1cc(-c2nc(NC3CCC(F)(F)CC3)nc(NC3CCC(F)(F)CC3)n2)no1]

$^1$H NMR (400 MHz, $CDCl_3$) δ 6.52-6.48 (m, 1H), 5.44-5.09 (m, 2H), 4.15-3.96 (m, 2H), 2.49 (s, 3H), 2.11-1.89 (m, 13H), 1.70-1.63 (m, 3H). LCMS: m/z 429 $(M+H)^+$.

N$^2$,N$^4$-bis(3,3-difluorocyclobutyl)-6-(5-methylisoxazol-3-yl)-1,3,5-triazine-2,4-diamine

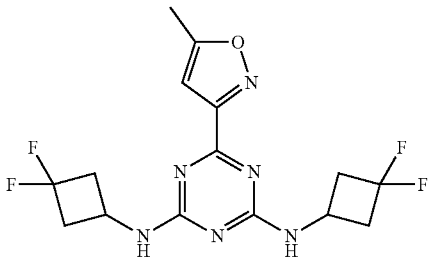 [SMILES: Cc1cc(-c2nc(NC3CC(F)(F)C3)nc(NC3CC(F)(F)C3)n2)no1]

$^1$H NMR (400 MHz, DMSO-$d_6$) δ 6.51 (m, 1H), 5.86-5.33 (m, 2H), 4.65-4.13 (m, 2H), 3.04 (dd, J=6.2, 5.4 Hz, 4H), 2.70-2.55 (m, 4H), 2.50 (s, 3H). LC-MS: m/z 373 $(M+H)^+$.

Example 26 The compounds of this Example are prepared by general Scheme 26, set forth below.

Scheme 26

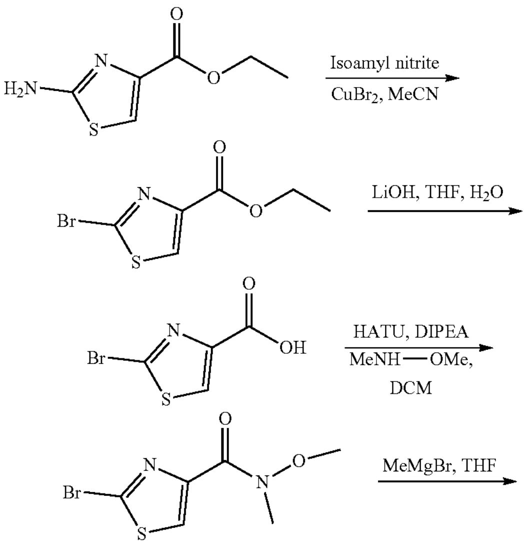

-continued

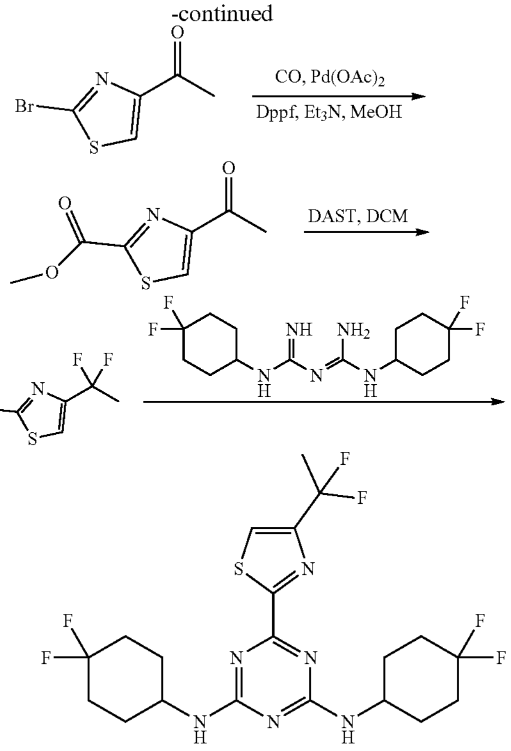

Step 1: Preparation of ethyl 2-bromothiazole-4-carboxylate. To a solution of ethyl 2-aminothiazole-4-carboxylate (15.0 g, 87.1 mmol) in MeCN (100 mL) was added isoamyl nitrite (24.5 g, 209 mmol) and $CuBr_2$ (27.5 g, 122 mmol). The mixture was stirred at 70° C. overnight, then cooled to r.t., diluted with water (200 mL), and extracted with EtOAc (2×200 mL). The combined organic layers were dried over anhydrous $Na_2SO_4$ and concentrated and purified by standard methods to afford ethyl 2-bromothiazole-4-carboxylate. LC-MS: m/z 236 $(M+H)^+$.

Step 2: Preparation of 2-bromothiazole-4-carboxylic acid. To a solution of ethyl 2-bromothiazole-4-carboxylate (18.0 g, 76.0 mmol) in THF (90 mL) and $H_2O$ (90 mL) was added LiOH (4.8 g, 114 mmol). The mixture was stirred at r,t for 3 hr and extracted with EtOAc (2×150 mL). The aqueous layer was separated, adjusted to pH 2-3 with satd. aq. $NH_4Cl$, and filtered. The solid was collected and dried under high vacuum to afford 2-bromothiazole-4-carboxylic acid. LC-MS: m/z 206 $(M-H)^-$.

Step 3: Preparation of 2-bromo-N-methoxy-N-methylthiazole-4-carboxamide. To a solution of 2-bromothiazole-4-carboxylic acid (11.4 g, 55.0 mmol) in DCM (100 mL) were added N,O-dimethylhydroxylamine (6.9 g, 71.0 mmol), HATU (27.0 g, 71.0 mmol) and DIPEA (21.2 g, 164.0 mmol). The mixture was stirred at r,t. overnight, then quenched with water (200 mL) and extracted with DCM (2×200 mL). The combined organic layers were dried over anhydrous $Na_2SO_4$, and concentrated and purified by standard methods to afford 2-bromo-N-methoxy-N-methylthiazole-4-carboxamide. LC-MS: m/z 251 $(M+H)^+$.

Step 4: Preparation of 1-(2-bromothiazol-4-yl)ethanone. To a solution of 2-bromo-N-methoxy-N-methylthiazole-4-carboxamide (6.8 g, 27.0 mmol) in THF (60 mL) under $N_2$ atomsphere at 0° C. was slowly added dropwise MeMgBr (9.9 mL, 29.7 mmol, 3M in THF). The mixture was slowly warmed to r,t and stirred at this temperature for 30 min. The reaction mixture was quenched with satd. aq. $NH_4Cl$ (100 mL) and extracted with EtOAc (2×100 mL). The combined organic layers were dried over anhydrous $Na_2SO_4$, and concentrated and purified by standard methods to afford 1-(2-bromothiazol-4-yl)ethanone. LC-MS: m/z 206 $(M+H)^+$.

Step 5: Preparation of methyl 4-acetylthiazole-2-carboxylate. To a solution of 1-(2-bromothiazol-4-yl)ethanone (340 mg, 1.65 mmol) in MeOH (10 mL) were added $Pd(OAc)_2$ (20.0 mg, 0.08 mmol), dppf (95.0 mg, 0.16 mmol) and $Et_3N$ (250 mg, 2.5 mmol). The mixture was heated at 60° C. under CO atmosphere (0.4 mPa) overnight. The resulting mixture was cooled to r.t. and filtered. The filtrate was concentrated and the residue purified by standard methods to afford methyl 4-acetylthiazole-2-carboxylate. LC-MS: m/z 186 $(M+H)^+$.

Step 6: Preparation of methyl 4-(1,1-difluoroethyl)thiazole-2-carboxylate. To a solution of 4-acetylthiazole-2-carboxylate (200 mg, 1.07 mmol) in DCM (10 mL) at 0° C. was slowly added dropwise DAST (1.64 g, 10.2 mmol). The mixture was then warmed to r,t and stirred at r.t. overnight. The mixture was slowly quenched with satd. aq. $NaHCO_3$ (20 mL) and extracted with DCM (2×20 mL). The combined organic layers were dried over anhydrous $Na_2SO_4$, and concentrated and purified by standard methods to give methyl 4-(1,1-difluoroethyl)thiazole-2-carboxylate. LC-MS: m/z 208 $(M+H)^+$.

Step 7: Preparation of $N^2$,$N^4$-bis(4,4-difluorocyclohexyl)-6-(4-(1,1-difluoroethyl) thiazol-2-yl)-1,3,5-triazine-2,4-diamine. To a mixture of $N^1$,$N^5$-bis(3,3-difluoro cyclobutyl)-biguanide (60 mg, 0.22 mmol) in MeOH (5 mL) were added ethyl 4-(1,1-difluoroethyl)thiazole-2-carboxylate (50 mg, 0.26 mmol) and NaOMe (23.7 mg, 0.44 mmol). The reaction mixture was then stirred at r.t. for 48 hr, and then partitioned between EtOAc and $H_2O$. The organic layer was separated, washed with brine, dried over anhydrous $Na_2SO_4$, concentrated and purified by standard methods to afford $N^2$,$N^4$-bis(4,4-difluorocyclohexyl)-6-(4-(1,1-difluoroethyl)thiazol-2-yl)-1,3,5-triazine-2,4-diamine.

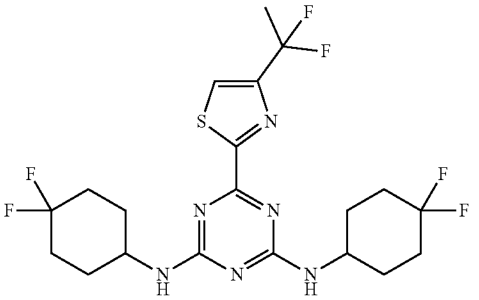 [SMILES: CC(F)(F)c1csc(-c2nc(NC3CCC(F)(F)CC3)nc(NC3CCC(F)(F)CC3)n2)n1]

$^1H$ NMR (400 MHz, $CDCl_3$) δ 7.75 (d, J=3.7 Hz, 1H), 5.30 (m, 2H), 4.05 (d, J=49.4 Hz, 2H), 2.30-2.01 (m, 11H), 1.94 (d, J=9.2 Hz, 4H), 1.81-1.68 (m, 3H). LC-MS: m/z 495 $(M+H)^+$.

The procedure set forth in Example 26 was used to produce the following compounds using the appropriate starting materials.

$N^2$,$N^4$-bis(4,4-difluorocyclohexyl)-6-(2-(1,1-difluoroethyl)thiazol-4-yl)-1,3,5-triazine-2,4-diamine

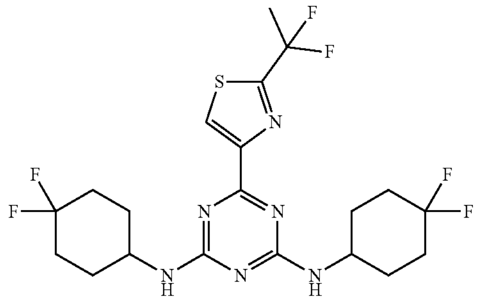 [SMILES: CC(F)(F)c1nc(-c2nc(NC3CCC(F)(F)CC3)nc(NC3CCC(F)(F)CC3)n2)cs1]

$^1H$ NMR (400 MHz, DMSO-$d_6$) δ 8.59 (d, 1H), 7.52 (m, 2H), 4.09 (m, 2H), 3.25 (m, 3H), 2.34 (m, 1H), 1.58 (m, 16H). LC-MS: m/z 494 $(M+H)^+$.

$N^2$,$N^4$-bis(3,3-difluorocyclopentyl)-6-(2-(1,1-difluoroethyl)thiazol-4-yl)-1,3,5-triazine-2,4-diamine

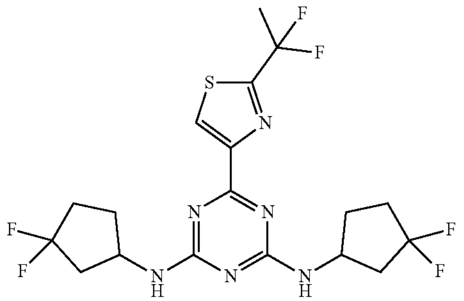 [SMILES: CC(F)(F)c1nc(-c2nc(NC3CCC(F)(F)C3)nc(NC3CCC(F)(F)C3)n2)cs1]

$^1H$ NMR (400 MHz, $CDCl_3$) δ 8.44-8.36 (m, 1H), 5.54-5.24 (m, 2H), 4.67-4.53 (m, 2H), 2.63-2.60 (m, 2H), 2.31-2.02 (m, 11H), 1.82-1.75 (m, 2H). LCMS: m/z 467$(M+H)^+$.

$N^2$,$N^4$-bis(3,3-difluorocyclobutyl)-6-(2-(1,1-difluoroethyl)thiazol-4-yl)-1,3,5-triazine-2,4-diamine

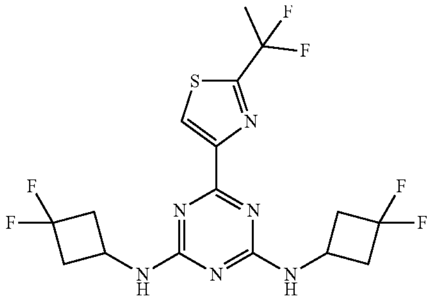 [SMILES: CC(F)(F)c1nc(-c2nc(NC3CC(F)(F)C3)nc(NC3CC(F)(F)C3)n2)cs1]

$^1H$ NMR (400 MHz, $CDCl_3$) δ 8.45-8.36 (m, 1H), 5.71-5.36 (m, 2H), 4.47-4.35 (m, 2H), 3.05 (s, 4H), 3.6 1(s, 4H), 2.24-2.03 (m, 3H). LCMS: m/z 439 $(M+H)^+$.

Example 27 The compounds of this Example are prepared by general Scheme 27, set forth below.

Scheme 27

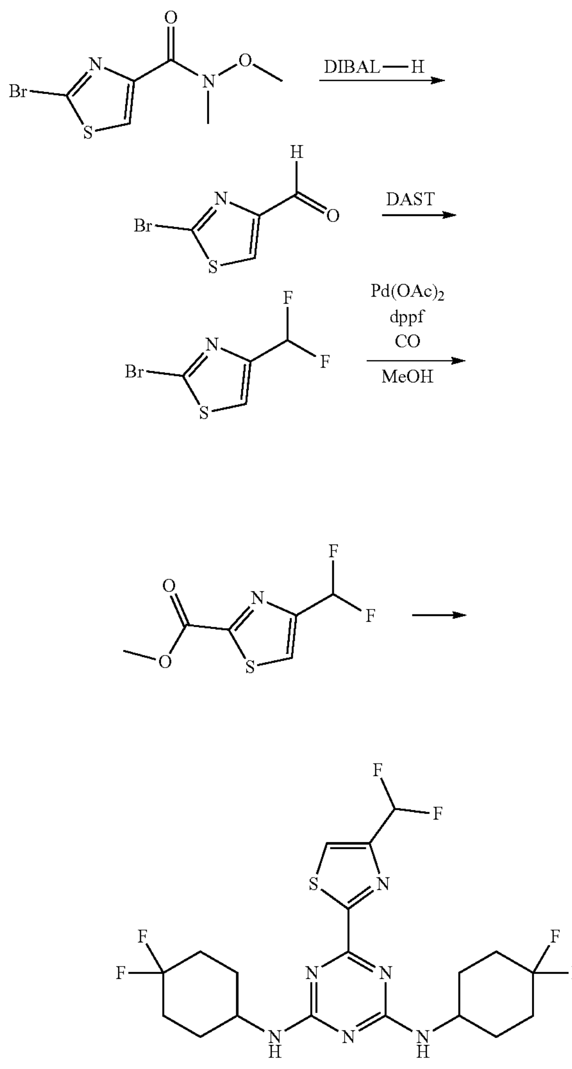

Step 1: Preparation of 2-bromothiazole-4-carbaldehyde. To a mixture of 2-bromo-N-methoxy-N-methyl thiazole-4-carboxamide (10 g, 0.04 mol) in THF (80 mL) at −78° C. was slowly added DIBAL-H (7.35 g, 0.052 mol). The reaction mixture was stirred at −78° C. for 2 hr, then adjusted pH to 5-6. The mixture was partitioned between EtOAc (80 mL) and $H_2O$ (60 mL). The organic layer was separated, washed with brine (40 mL), dried over anhydrous $Na_2SO_4$, concentrated and purified by standard methods to afford the desired product. LC-MS: m/z 192 $(M+H)^+$.

Step 2: Preparation of 2-bromo-4-(difluoromethyl)thiazole. To a mixture of 2-bromothiazole-4-carbaldehyde (0.764 g, 0.004 mol) in DCM (7 mL) at 0° C. was added dropwise DAST (3.22 g, 0.02 mol). The mixture was stirred at 25° C. for 48 hr, then quenched with satd. aq. $NaHCO_3$ and adjusted pH to 8-10. The resulting mixture was extracted with DCM (2×40 mL). The combined organic layers were washed with brine (30 mL), dried over anhydrous $Na_2SO_4$ and concentrated and purified by standard methods to afford the desired product. LC-MS: m/z 214 $(M+H)^+$.

Step 3: Preparation of methyl 4-(difluoromethyl)thiazole-2-carboxylate. A mixture of 2-bromo-4-(difluoromethyl)thiazole (0.6 g, 2.82 mmol), dppf (0.14 g, 0.28 mmol), $Et_3N$ (0.43 g, 4.23 mmol) and $Pd(OAc)_2$ (0.13 g, 0.56 mmol) in MeOH (10 mL) was stirred at 60° C. under an atmosphere of CO for 16 hr. The resulting mixture was filtered, the filtrate was concentrated and the residue was partitioned between DCM (30 mL) and $H_2O$. The organic layer was separated, washed with brine (30 mL), dried over anhydrous $Na_2SO_4$, and concentrated and purified by standard methods to afford the desired product. LC-MS: m/z 194 $(M+H)^+$.

Step 4: Preparation of $N^2$,$N^4$-bis(4,4-difluorocyclohexyl)-6-(4-(difluoromethyl) thiazol-2-yl)-1,3,5-triazine-2,4-diamine. To a suspension of $N^1$,$N^5$-bis(3,3-difluoro cyclobutyl)-biguanide (45 mg, 13.3 mmol) and methyl 4-(difluoromethyl)thiazole-2-carboxylate (40 mg, 20.7 mmol) in MeOH (10 mL) was added NaOMe (20 mg, 37.0 mmol). The reaction mixture was stirred at r.t. overnight, then poured into water and extracted with EtOAc. Combined organic layers were over anhydrous $Na_2SO_4$, concentrated and purified by standard methods to afford the desired product.

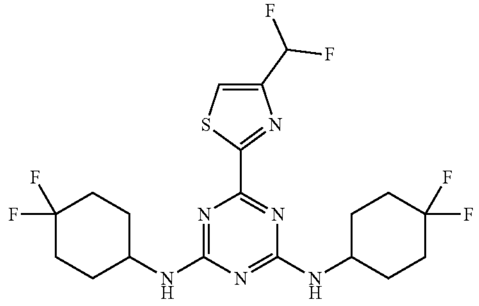 [SMILES: FC(F)c1csc(-c2nc(NC3CCC(F)(F)CC3)nc(NC3CCC(F)(F)CC3)n2)n1]

$^1$H NMR (400 MHz, $CDCl_3$) δ 7.75 (s, 1H), 6.94-6.67 (t, 1H), 5.40-5.08 (m, 2H), 4.04-3.90 (m, 2H), 2.05-1.84 (m, 8H), 1.79-1.64 (m, 4H), 1.62-1.54 (m, 4H). LC-MS: m/z 481 $(M+H)^+$.

The procedure set forth in Example 27 was used to produce the following compounds using the appropriate starting materials.

$N^2$,$N^4$-bis(3,3-difluorocyclobutyl)-6-(4-(difluoromethyl)thiazol-2-yl)-1,3,5-triazine-2,4-diamine

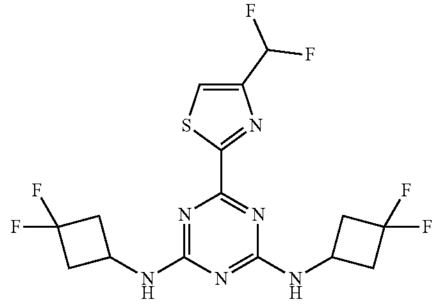 [SMILES: FC(F)c1csc(-c2nc(NC3CC(F)(F)C3)nc(NC3CC(F)(F)C3)n2)n1]

$^1$H NMR (400 MHz, $CDCl_3$) δ 7.84 (d, J=8 Hz, 1H), 7.02-6.74 (m, 1H), 5.74-5.44 (m, 2H), 4.46-4.36 (m, 2H), 3.06 (d, J=8 Hz, 4H), 2.63-2.59 (m, 4H). LCMS: m/z 425 $(M+H)^+$.

$N^2$,$N^4$-bis(3,3-difluorocyclopentyl)-6-(4-(difluoromethyl)thiazol-2-yl)-1,3,5-triazine-2,4-diamine

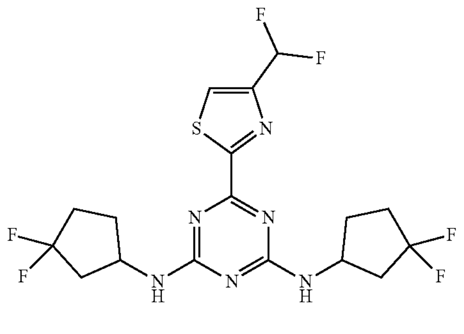 [SMILES: FC(F)c1csc(-c2nc(NC3CCC(F)(F)C3)nc(NC3CCC(F)(F)C3)n2)n1]

$^1$H NMR (400 MHz, $CDCl_3$) δ 7.84 (s, 1H), 7.04-6.76 (m, 1H), 5.65-5.36 (m, 2H), 4.66-4.55 (m, 2H), 2.66-1.85 (m, 12H). LCMS: m/z 453 $(M+H)^+$.

Example 28 The compounds of this Example are prepared by general Scheme 28, set forth below.

Scheme 28

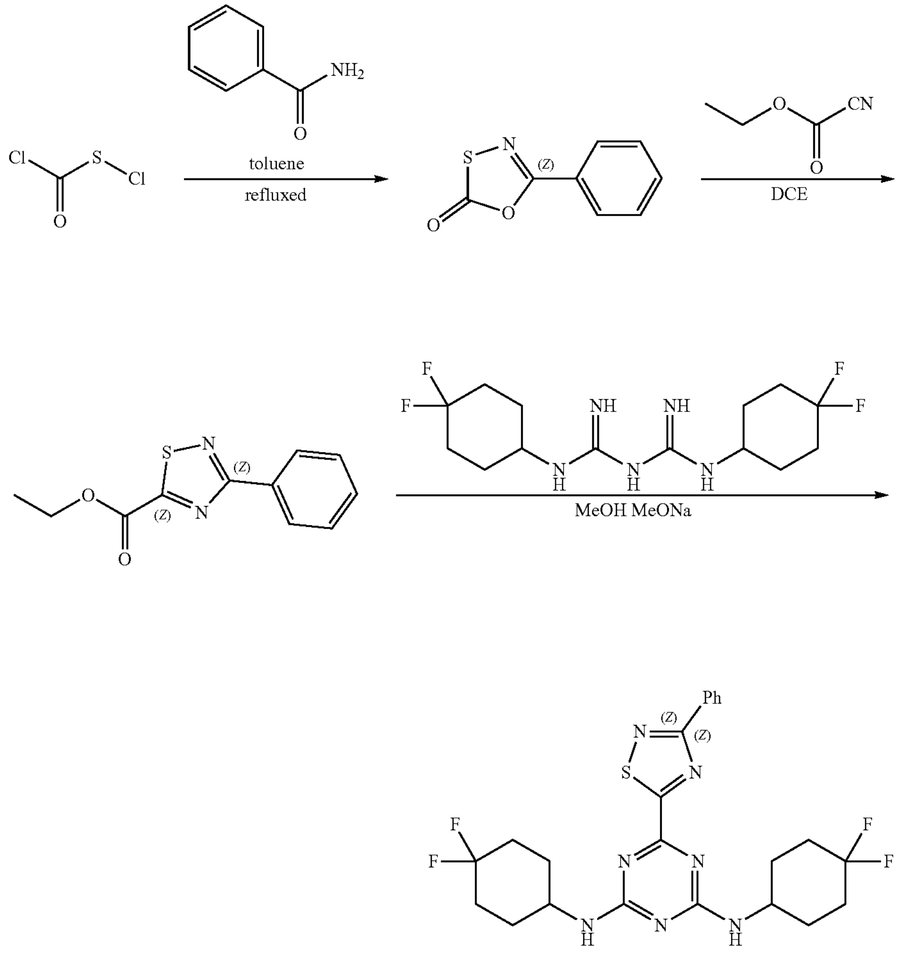

Step 1: Preparation of 5-phenyl-1,3,4-oxathiazol-2-one. To a solution of benzamide (200 mg, 1.65 mmol) in toluene (2 mL) under $N_2$ atmosphere was added carbonyl chloride thiohypochlorite (0.16 mL, 1.98 mmol). The mixture was stirred at 120° C. for 3 hr. The resulting mixture was cooled to r.t., then quenched with $H_2O$ and extracted with EtOAc (2×10 mL). The combined organic layers were washed with brine, dried over anhydrous $Na_2SO_4$, concentrated and purified by standard methods to afford the desired product. LC-MS: m/z 180 $(M+H)^+$.

Step 2: Preparation of 3-phenyl-1,2,4-thiadiazole-5-carboxylate. A mixture of 5-phenyl-1,3,4-oxathiazol-2-one (270 mg, 1.5 mmol) and ethyl carbonocyanidate (790 mg, 6.0 mmol) in DCE (2 mL) was stirred in a sealed vial under microwave irradiation at 160° C. for 0.5 hr. The resulting mixture was concentrated and purified by standard methods to afford the desired product. LC-MS: m/z 235 $(M+H)^+$.

Step 3: Preparation of $N^2$,$N^4$-bis(4,4-difluorocyclohexyl)-6-(3-phenyl-1,2,4-thiadiazol-5-yl)-1,3,5-triazine-2,4-diamine. To a mixture of $N^1$,$N^5$-bis(4,4-difluoro cyclohexyl)-biguanide (90 mg, 0.27 mmol) and ethyl 3-phenyl-1,2,4-thiadiazole-5-carboxylate (75 mg, 0.32 mmol) in MeOH (2 mL) was added NaOMe (43 mg, 0.8 mmol). The reaction mixture was then stirred at r.t. overnight. The resulting mixture was poured into water and extracted with EtOAc. The combined organic layers were dried over anhydrous $Na_2SO_4$ and concentrated and purified by standard methods to afford the desired product.

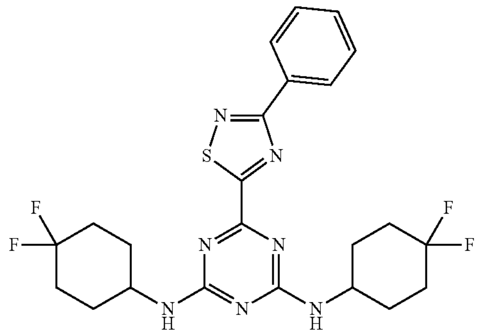 [SMILES: FC1(F)CCC(Nc2nc(NC3CCC(F)(F)CC3)nc(-c3nc(-c4ccccc4)ns3)n2)CC1]

$^1$H NMR (400 MHz, $CDCl_3$) δ 8.40 (d, J=3.3 Hz, 2H), 7.48 (s, 3H), 5.68-5.01 (m, 2H), 4.27-3.87 (m, 2H), 2.26-1.63 (m, 8H). LC-MS: m/z 508.2 $(M+H)^+$.

The procedure set forth in Example 28 was used to produce the following compounds using the appropriate starting materials.

$N^2$,$N^4$-bis(4,4-difluorocyclohexyl)-6-(3-methyl-1,2,4-thiadiazol-5-yl)-1,3,5-triazine-2,4-diamine

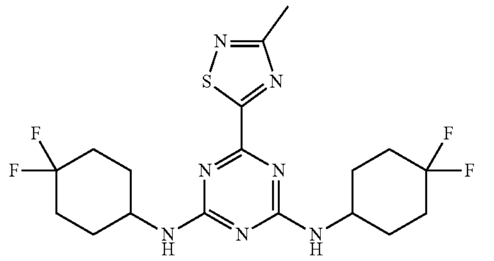 [SMILES: Cc1nsc(-c2nc(NC3CCC(F)(F)CC3)nc(NC3CCC(F)(F)CC3)n2)n1]

$^1$H NMR (400 MHz, $CDCl_3$) δ 5.58-5.10 (m, 2H), 4.20-3.84 (m, 2H), 2.77 (s, 3H), 2.23-1.63 (m, 16H). LC-MS: m/z 446 $(M+H)^+$.

Example 29 The compounds of this Example are prepared by general Scheme 29, set forth below.

Scheme 29

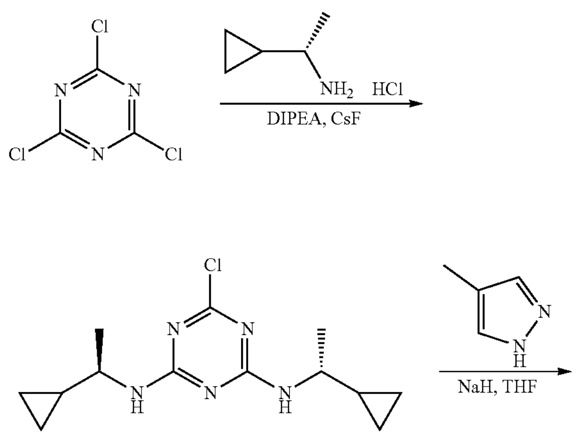

-continued

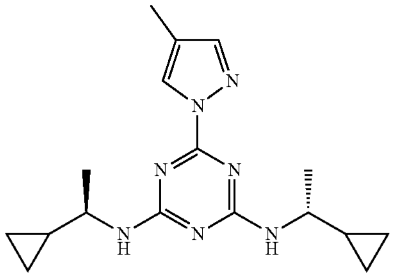

Step 1. Preparation of 6-chloro-$N^2$,$N^4$-bis((R)-1-cyclopropylethyl)-1,3,5-triazine-2,4-diamine. To a solution of 2,4,6-trichloro-1,3,5-triazine (2 g, 10.9 mmol) in acetone (35 mL) were added (S)-1-cyclopropylethanamine hydrochloride (2.7 mg, 22.8 mmol), DIPEA (3.5 mg, 27 mmol) and CsF (3.3 mg, 21.8 mmol). The mixture was stirred at 50° C. overnight, and then filtered. The filtrate was concentrated and purified by standard methods to give the desired product. LC-MS: m/z 282 $(M+H)^+$.

Step B. Preparation of $N^2$,$N^4$-bis((R)-1-cyclopropylethyl)-6-(4-methyl-1H-pyrazol-1-yl)-1,3,5-triazine-2,4-diamine. To an ice-cold solution of 4-methyl-1H-pyrazole (207 mg, 1.07 mmol) in dry THF (5 mL) was slowly added NaH (34 mg, 1.42 mmol) over 30 min, followed by addition of a solution of 6-chloro-$N^2$,$N^4$-bis((R)-1-cyclo-propylethyl)-1,3,5-triazine-2,4-diamine (200 mg, 0.71 mmol) in THF (3 mL). The reaction mixture was stirred at r.t. overnight, and then concentrated and purified by standard methods to afford $N^2$,$N^4$-bis((R)-1-cyclopropylethyl)-6-(4-methyl-1H-pyrazol-1-yl)-1,3,5-triazine-2,4-diamine.

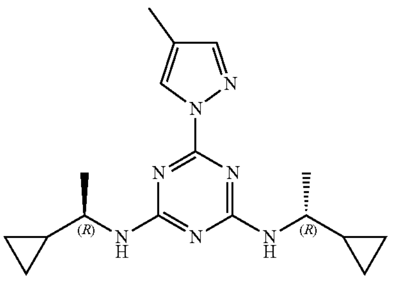

$^1$H NMR (400 MHz, $CDCl_3$) δ 8.17 (s, 1H), 7.56 (s, 1H), 5.50-5.12 (m, 2H), 3.56 (d, J=6.0 Hz, 2H), 2.12 (s, 3H), 1.25 (s, 6H), 0.94-0.84 (m, 2H), 0.54-0.32 (m, 6H), 0.26 (d, J=4.1 Hz, 2H).

LC-MS: m/z 328 $(M+H)^+$.

The procedure set forth in Example 29 was used to produce the following compounds using the appropriate starting materials.

Compound $N^2$,$N^4$-bis((R)-1-cyclopropylethyl)-6-(4-iodo-1H-pyrazol-1-yl)-1,3,5-triazine-2,4-diamine

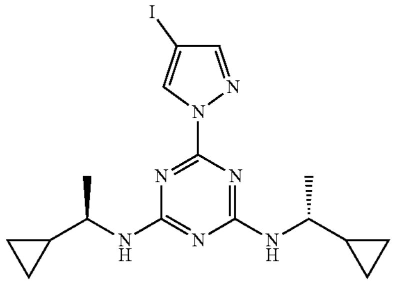 [SMILES: C[C@@H](Nc1nc(N[C@H](C)C2CC2)nc(-n2cc(I)cn2)n1)C1CC1]

$^1$H NMR (400 MHz, $CDCl_3$) δ 8.51 (s, 1H), 7.73 (s, 1H), 5.49-5.20 (m, 2H), 3.56 (d, J=6.8 Hz, 2H), 1.26 (d, J=6.5 Hz, 6H), 0.90 (s, 2H), 0.55-0.24 (m, 8H). LC-MS: m/z 440 $(M+H)^+$.

Compound 6-(4-Chloro-1H-pyrazol-1-yl)-N2,N4-bis(4,4-difluorocyclohexyl)-1,3,5-triazine-2,4-diamine

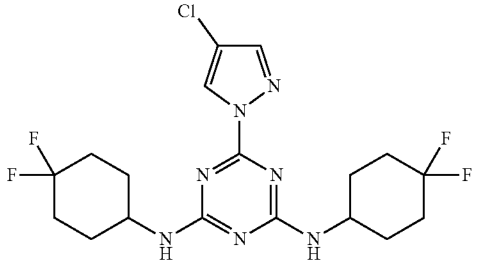 [SMILES: FC1(F)CCC(Nc2nc(NC3CCC(F)(F)CC3)nc(-n3cc(Cl)cn3)n2)CC1]

$^1$H NMR (400 MHz, $CDCl_3$) δ 8.43-8.38 (m, 1H), 7.68 (d, J=9.2 Hz, 1H), 5.41-5.18 (m, 2H), 4.10-3.98 (m, 2H), 2.14-1.91 (m, 13H), 1.86-1.73 (m, 1.2H), 1.68-1.61 (m, 1.8H). LCMS: m/z 448 $(M+H)^+$.

Compound $N^2$,$N^4$-bis((R)-1-cyclopropylethyl)-6-(3-(trifluoromethyl)-1H-pyrazol-1-yl)-1,3,5-triazine-2,4-diamine

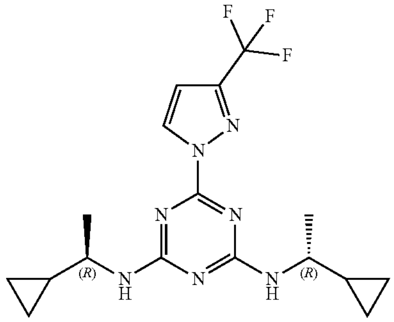

$^1$H NMR (400 MHz, $CDCl_3$) δ 8.53 (d, J=10.0 Hz, 1H), 6.66 (d, J=2.5 Hz, 1H), 5.63-5.23 (m, 2H), 3.63-3.45 (m, 2H), 1.27 (d, J=6.5 Hz, 6H), 0.91 (d, J=7.6 Hz, 2H), 0.58-0.26 (m, 8H).

LC-MS: m/z 382 $(M+H)^+$.

Compound 6-(3-(Trifluoromethyl)-1H-pyrazol-1-yl)-$N^2$,$N^4$-bis(1,1,1-trifluoropropan-2-yl)-1,3,5-triazine-2,4-diamine

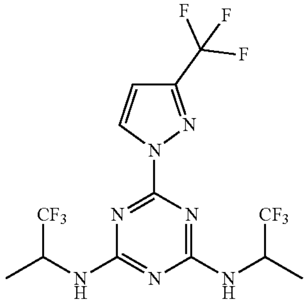 [SMILES: CC(Nc1nc(NC(C)C(F)(F)F)nc(-n2ccc(C(F)(F)F)n2)n1)C(F)(F)F]

$^1$H NMR (400 MHz, $CDCl_3$) δ 8.55 (m, 1H), 6.70 (d, J=2.7 Hz, 1H), 5.77-5.30 (m, 2H), 5.05-4.78 (m, 2H), 1.49-1.37 (m, 6H). LC-MS: m/z 438.1$(M+H)^+$.

Compound $N^2$,$N^4$-bis((S)-1,1,1-trifluorobutan-2-yl)-6-(3-(trifluoromethyl)-1H-pyrazol-1-yl)-1,3,5-triazine-2,4-diamine

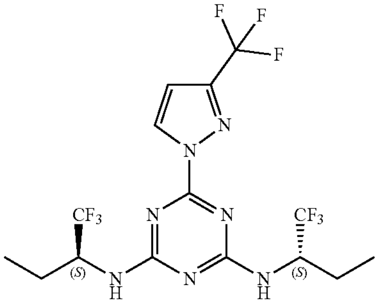

$^1$H NMR (400 MHz, $CDCl_3$) δ 8.60-8.57 (m, 1H), 7.80-5.29 (m, 3H), 4.76-4.69 (m, 2H), 2.03-1.95 (m, 2H), 1.72-1.63 (m, 2H), 1.09-1.02 (m, 6H). LCMS: m/z 466 $(M+H)^+$.

Compound $N^2$,$N^4$-bis(3,3-difluorocyclopentyl)-6-(3-(trifluoromethyl)-1H-pyrazol-1-yl)-1,3,5-triazine-2,4-diamine

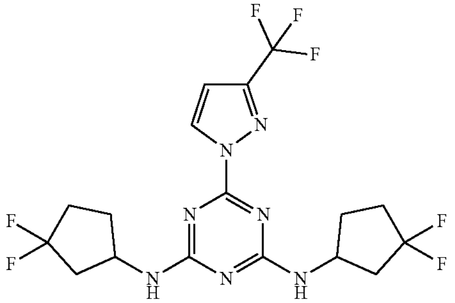 [SMILES: FC1(F)CCC(Nc2nc(NC3CCC(F)(F)C3)nc(-n3ccc(C(F)(F)F)n3)n2)C1]

$^1H$ NMR (400 MHz, $CDCl_3$) δ 8.57-8.50 (m, 1H), 6.68 (d, J=4 Hz, 1H), 5.74-5.44 (m, 2H), 4.76-4.47 (m, 2H), 2.66-2.57 (m, 2H), 2.08-2.31 (m, 8H), 1.81-1.86 (m, 2H). LCMS: m/z 454 $(M+H)^+$.

Compound $N^2$,$N^4$-bis(4,4-difluorocyclohexyl)-6-(3-(trifluoromethyl)-1H-pyrazol-1-yl)-1,3,5-triazine-2,4-diamine

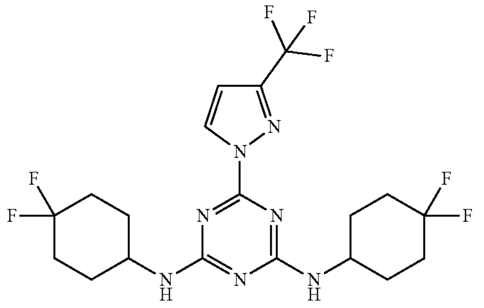 [SMILES: FC1(F)CCC(Nc2nc(NC3CCC(F)(F)CC3)nc(-n3ccc(C(F)(F)F)n3)n2)CC1]

$^1H$ NMR (400 MHz, DMSO-$d_6$) δ 8.86-8.50 (m, 1H), 8.13-7.76 (m, 2H), 7.00 (d, J=9.7 Hz, 1H), 4.18-3.92 (m, 2H), 2.14-1.82 (m, 12H), 1.62 (s, 4H). LC-MS: m/z 482 $(M+H)^+$.

Compound $N^2$,$N^4$-bis(3,3-difluorocyclobutyl)-6-(3-(trifluoromethyl)-1H-pyrazol-1-yl)-1,3,5-triazine-2,4-diamine

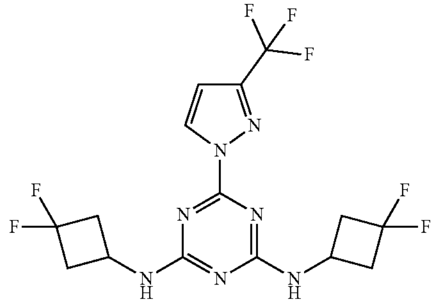 [SMILES: FC1(F)CC(Nc2nc(NC3CC(F)(F)C3)nc(-n3ccc(C(F)(F)F)n3)n2)C1]

$^1H$ NMR (400 MHz, $CDCl_3$) δ 8.56-8.50 (m, 1H), 6.69 (d, J=6 Hz, 1H), 5.85-5.52 (m, 2H), 4.37 (m, 2H), 3.05-3.12 (m, 4H), 2.50-2.67 (m, 4H). LCMS: m/z 426 $(M+H)^+$.

Example 30 The compounds of this Example are prepared by general Scheme 30, set forth below.

Scheme 30

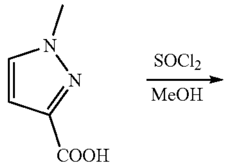

-continued

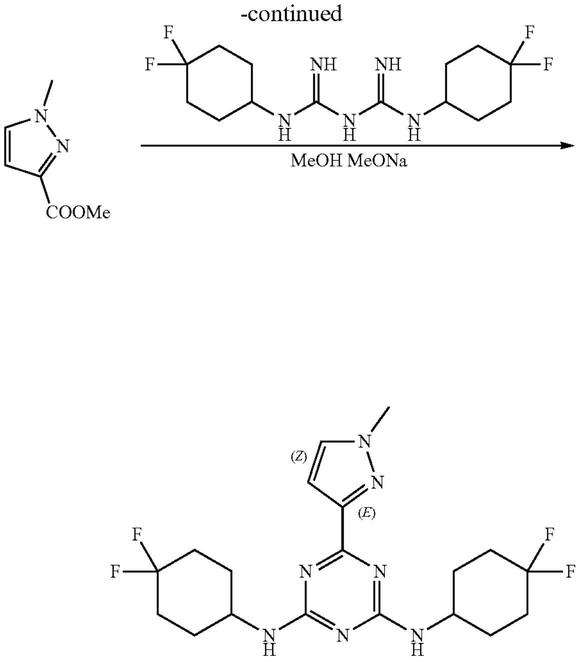

Step 1: Preparation of methyl 1-methyl-1H-pyrazole-3-carboxylate. To a solution of 1-methyl-1H-pyrazole-3-carboxylic acid (504 mg, 4 mmol) in MeOH (5 mL) was added $SOCl_2$ (1.4 mL, 20 mmol) at 0° C. The mixture was stirred at r.t overnight then concentrated under reduced pressure. The residue was dissolved in EtOAc, washed with satd. aq. $NaHCO_3$ and concentrated to afford methyl 1-methyl-1H-pyrazole-3-carboxylate. LC-MS: m/z 141 $(M+H)^+$.

Step 2: Preparation of $N^2$,$N^4$-bis(4,4-difluorocyclohexyl)-6-(1-methyl-1H-pyrazol-3-yl)-1,3,5-triazine-2,4-diamine. To a solution of $N^1$,$N^5$-bis(4,4-difluoro cyclohexyl)-biguanide (120 mg, 0.36 mmol) and methyl 1-methyl-1H-pyrazole-3-carboxylate (60 mg, 0.43 mmol) in MeOH (2 mL) was added NaOMe (28 mg, 1.07 mmol). The reaction mixture was stirred at r.t. overnight, then poured into water and extracted with EtOAc. Combined organic layers were dried over anhydrous $Na_2SO_4$, and concentrated and purified by standard methods to afford $N^2$,$N^4$-bis(4,4-difluorocyclohexyl)-6-(1-methyl-1H-pyrazol-3-yl)-1,3,5-triazine-2,4-diamine.

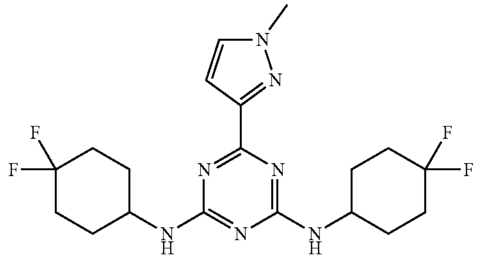 [SMILES: Cn1ccc(-c2nc(NC3CCC(F)(F)CC3)nc(NC3CCC(F)(F)CC3)n2)n1]

$^1H$ NMR (400 MHz, $CDCl_3$) δ 7.40 (d, J=2.1 Hz, 1H), 6.92 (s, 1H), 5.75-4.94 (m, 2H), 4.28-3.85 (m, 5H), 2.26-1.54 (m, 16H). LC-MS: m/z 428 $(M+H)^+$.

The procedure set forth in Example 30 was used to produce the following compounds using the appropriate starting materials.

Compound $N^2$,$N^4$-bis(4,4-difluorocyclohexyl)-6-(1H-pyrazol-3-yl)-1,3,5-triazine-2,4-diamine

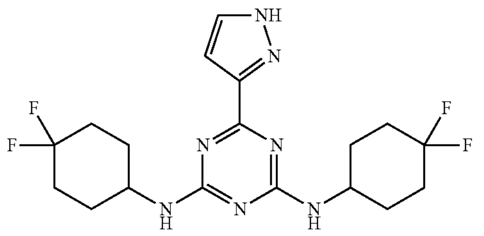 [SMILES: FC1(F)CCC(Nc2nc(NC3CCC(F)(F)CC3)nc(-c3cc[nH]n3)n2)CC1]

$^1H$ NMR (400 MHz, $CDCl_3$) δ 7.57 (s, 1H), 6.89 (s, 1H), 5.55-4.84 (m, 2H), 4.15-3.80 (m, 2H), 2.05-1.56 (m, 16H). LC-MS: m/z 414 $(M+H)^+$.

Compound $N^2$,$N^4$-bis(3,3-difluorocyclopentyl)-6-(2-methyl-1H-imidazol-4-yl)-1,3,5-triazine-2,4-diamine

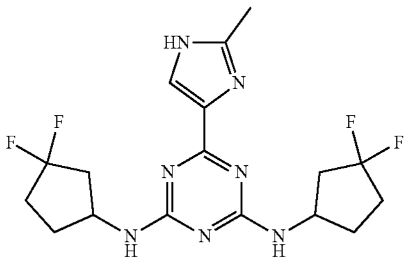 [SMILES: Cc1nc(-c2nc(NC3CCC(F)(F)C3)nc(NC3CCC(F)(F)C3)n2)c[nH]1]

$^1H$ NMR (400 MHz, $CDCl_3$) δ 7.71 (s, 1H), 5.65-5.07 (m, 2H), 4.63-4.61 (m, 2H), 2.61-2.49 (m, 3H), 2.29 (s, 3H), 2.09-1.92 (m, 9H). LC-MS: m/z 400.1 $(M+H)^+$.

Compound $N^2$,$N^4$-bis(3,3-difluorocyclobutyl)-6-(2-methyl-1H-imidazol-4-yl)-1,3,5-triazine-2,4-diamine

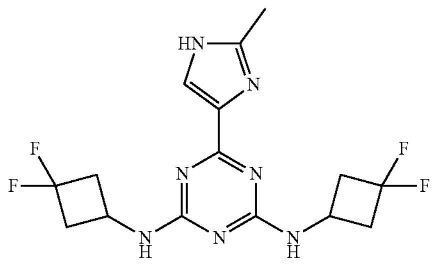 [SMILES: Cc1nc(-c2nc(NC3CC(F)(F)C3)nc(NC3CC(F)(F)C3)n2)c[nH]1]

$^1H$ NMR (400 MHz, $CDCl_3$) δ 7.62 (s, 1H), 6.49-6.34 (m, 2H), 4.36-4.33 (m, 2H), 3.04 (s, 3H), 2.69-2.49 (m, 8H). LC-MS: m/z 372 $(M+H)^+$.

Compound $N^2$,$N^4$-bis(4,4-difluorocyclohexyl)-6-(2-methyl-1H-imidazol-4-yl)-1,3,5-triazine-2,4-diamine

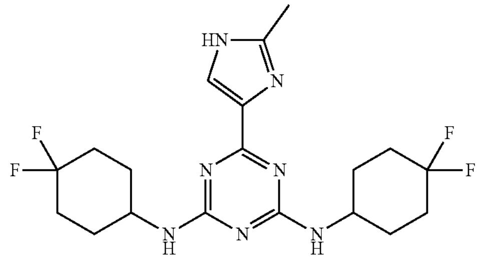 [SMILES: Cc1nc(-c2nc(NC3CCC(F)(F)CC3)nc(NC3CCC(F)(F)CC3)n2)c[nH]1]

$^1H$ NMR (400 MHz, $CDCl_3$) δ 8.67-7.66 (m, 1H), 6.26-5.84 (m, 1H), 5.11-4.81 (m, 1H), 3.49-3.11 (m, 7H), 2.48 (s, 2H), 2.10-1.66 (m, 12H). LC-MS: m/z 428.3 $(M+H)^+$.

Example 31 The compounds of this Example are prepared by general Scheme 31, set forth below.

Scheme 31

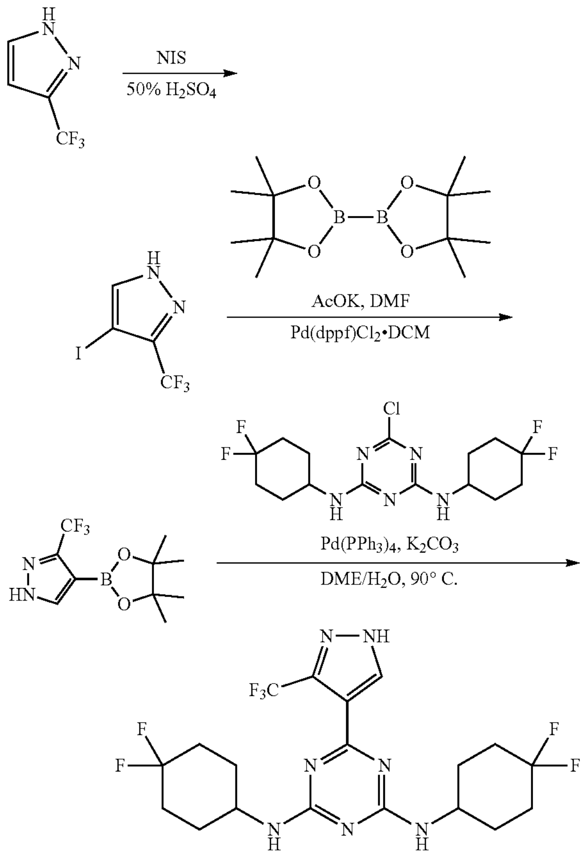

Step 1: Preparation of 4-iodo-3-(trifluoromethyl)-1H-pyrazole. To a solution of 3-(trifluoromethyl)-1H-pyrazole (500 mg, 3.7 mmol) in 50% $H_2SO_4$ at 0° C. was added NIS (992 mg, 4.4 mmol). The suspension was stirred at 0° C. for 10 min and then at r.t. for 3 hr. The resulting mixture was quenched with water (50 mL), and then stirred overnight. The precipitate was collected by filtration and dried to afford 4-iodo-3-(trifluoromethyl)-1H-pyrazole. LC-MS: m/z 263 $(M+H)^+$.

Step 2: Preparation of 4-(4,4,5,5-tetramethyl-1,3,2-dioxaborolan-2-yl)-3-(trifluoromethyl)-1H-pyrazole. To a mixture of 4-iodo-3-(trifluoromethyl)-1H-pyrazole (100 mg, 0.38 mmol) and (4,4,4',4',5,5,5',5'-octamethyl-2,2'-bi(1,3,2-dioxaborolane) (397 mg, 0.57 mmol) in DMF (3 mL) were added 1,1'-bis-(diphenylphosphino)ferrocene-palladium(II) dichloride dichloromethane complex (31 mg, 0.04 mmol) and potassium acetate (509 mg, 0.76). The reaction mixture was stirred at 90° C. for 2 hr, then quenched with water and extracted with $Et_2O$. The combined organic layers were washed with brine, dried over anhydrous $Na_2SO_4$, and concentrated to afford 4-(4,4,5,5-tetramethyl-1,3,2-dioxaborolan-2-yl)-3-(trifluoromethyl)-1H-pyrazole. LC-MS: m/z 263 $(M+H)^+$.

Step 3: Preparation of $N^2$,$N^4$-bis(4,4-difluorocyclohexyl)-6-(3-(trifluoromethyl)-1H-pyrazol-4-yl)-1,3,5-triazine-2,4-diamine. To a solution of 6-chloro-$N^2$,$N^4$-bis (4,4-difluorocyclohexyl)-1,3,5-triazine-2,4-diamine (145 mg, 0.38 mmol) and 4-(4,4,5,5-tetramethyl-1,3,2-dioxaborolan-2-yl)-3-(trifluoromethyl)-1H-pyrazole (100 mg, 0.38 mmol) in DME (3 mL) and $H_2O$ (1 mL) were added $K_2CO_3$ (158 mg, 1.15 mmol) and $Pd(PPh_3)_4$(44 mg, 0.04 mmol) under $N_2$ atmosphere. The mixture was stirred at 90° C. for 16 hr, and then filtered. The filtrate was partitioned between EtOAc and $H_2O$. The aqueous layer was separated and extracted with EtOAc. The combined organic layers were washed with brine, dried over anhydrous $Na_2SO_4$, and concentrated and purified by standard methods to afford $N^2$,$N^4$-bis(4,4-difluorocyclohexyl)-6-(3-(trifluoromethyl)-1H-pyrazol-4-yl)-1,3,5-triazine-2,4-diamine.

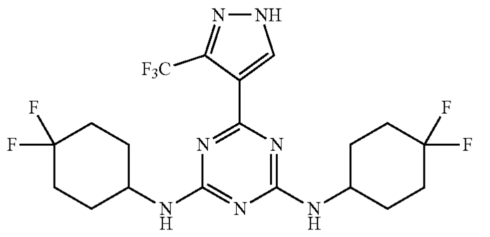 [SMILES: FC1(F)CCC(Nc2nc(NC3CCC(F)(F)CC3)nc(-c3c[nH]nc3C(F)(F)F)n2)CC1]

$^1$H NMR (400 MHz, DMSO-$d_6$) δ 8.09-7.47 (m, 3H), 7.29-7.00 (m, 1H), 4.11-3.76 (m, 2H), 2.19-1.46 (m, 16H). LC-MS: m/z 482 $(M+H)^+$.

The procedure set forth Example 31 was used to produce the following compounds using the appropriate starting materials.

Compound $N^2$,$N^4$-bis(4,4-difluorocyclohexyl)-$N^2$-methyl-6-(3-(trifluoromethyl)-1H-pyrazol-4-yl)-1,3,5-triazine-2,4-diamine

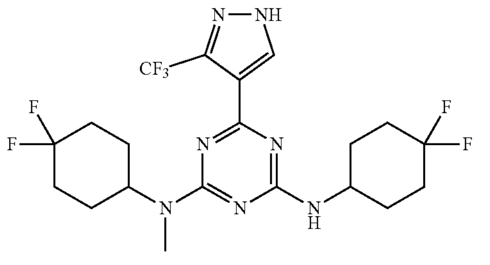 [SMILES: CN(c1nc(NC2CCC(F)(F)CC2)nc(-c2c[nH]nc2C(F)(F)F)n1)C1CCC(F)(F)CC1]

$^1$H NMR (400 MHz, $CDCl_3$) δ 7.75 (s, 1H), 6.90 (s, 1H), 5.45 (d, J=7.1 Hz, 1H), 4.94-4.44 (m, 1H), 4.09-3.84 (m, 1H), 3.07 (d, J=11.0 Hz, 3H), 2.35-2.02 (m, 6H), 2.03-1.66 (m, 10H).

LC-MS: m/z 496 $(M+H)^+$.

Compound $N^2$,$N^4$-bis(4,4-difluorocyclohexyl)-6-(1-methyl-3-(trifluoromethyl)-1H-pyrazol-4-yl)-1,3,5-triazine-2,4-diamine

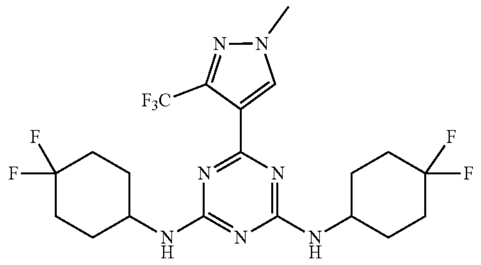 [SMILES: Cn1cc(-c2nc(NC3CCC(F)(F)CC3)nc(NC3CCC(F)(F)CC3)n2)c(C(F)(F)F)n1]

$^1$H NMR (400 MHz, $CDCl_3$) δ 7.57-7.37 (m, 1H), 5.18-4.88 (m, 2H), 4.01-3.79 (m, 5H), 2.21-1.46 (m, 16H). LC-MS: m/z 496 $(M+H)^+$.

Compound $N^2$,$N^4$-bis((R)-1-cyclopropylethyl)-6-(5-(trifluoromethyl)pyridin-3-yl)-1,3,5-triazine-2,4-diamine

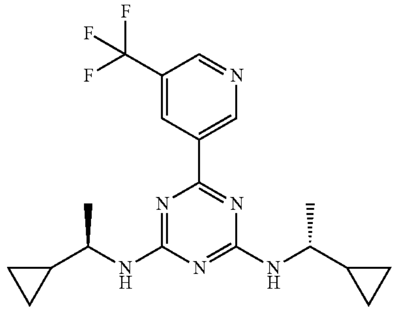 [SMILES: C[C@@H](Nc1nc(N[C@H](C)C2CC2)nc(-c2cncc(C(F)(F)F)c2)n1)C1CC1]

$^1$H NMR (400 MHz, DMSO-$d_6$) δ 9.60 (s, 1H), 9.13 (s, 1H), 8.75 (s, 1H), 7.60 (s, 1H), 7.46 (s, 1H), 3.64-3.50 (m, 2H), 1.21 (d, J=4 Hz, 6H), 0.96 (s, 2H), 0.43-0.33 (m, 6H), 0.14 (s, 2H).

LCMS: m/z 393 $(M+H)^+$.

Compound $N^2$,$N^4$-bis((R)-1-cyclopropylethyl)-6-(2-(trifluoromethyl)pyridin-4-yl)-1,3,5-triazine-2,4-diamine

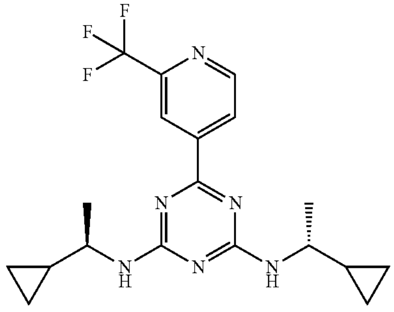 [SMILES: C[C@@H](Nc1nc(N[C@H](C)C2CC2)nc(-c2ccnc(C(F)(F)F)c2)n1)C1CC1]

$^1$H NMR (400 MHz, $CDCl_3$) δ 9.04-8.82 (m, 1H), 8.68-8.28 (m, 2H), 3.83-3.64 (m, 1H), 3.60-3.51 (m, 1H), 1.36 (m, 6H), 0.91-0.85 (m, 2H), 0.67-0.48 (m, 4H), 0.34 (m, 4H). LCMS: m/z 393 $(M+H)^+$.

Compound $N^2$,$N^4$-bis((R)-1-cyclopropylethyl)-6-(2,5-difluorophenyl)-1,3,5-triazine-2,4-diamine

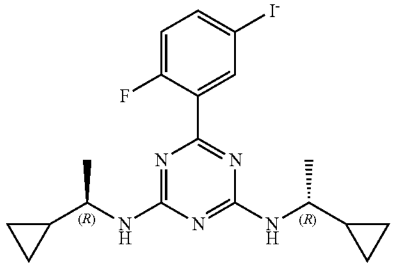

$^1$H NMR (400 MHz, $CDCl_3$) δ 7.76-7.55 (m, 1H), 7.08 (dd, J=7.6, 5.8 Hz, 2H), 5.43-5.02 (m, 2H), 3.55 (s, 2H), 1.27 (d, J=5.8 Hz, 6H), 0.90 (d, J=7.4 Hz, 2H), 0.55-0.37 (m, 6H), 0.30-0.23 (m, 2H). LC-MS: m/z 360 $(M+H)^+$.

Compound $N^2$,$N^4$-bis((R)-1-cyclopropylethyl)-6-(3-(trifluoromethoxy)phenyl)-1,3,5-triazine-2,4-diamine

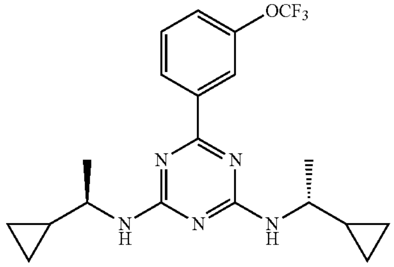 [SMILES: C[C@@H](Nc1nc(N[C@H](C)C2CC2)nc(-c2cccc(OC(F)(F)F)c2)n1)C1CC1]

$^1$H NMR (400 MHz, $CDCl_3$): δ 8.25-8.18 (m, 2H), 7.46-7.42 (m, 1H), 7.32-7.26 (m, 1H), 5.28-5.13 (m, 2H), 3.68-3.55 (m, 2H), 1.29-1.25 (m, 6H), 0.95-0.88 (m, 2H), 0.56-0.41 (m, 6H), 0.28 (s, 2H). LCMS: m/z 408 $(M+H)^+$.

Compound 3-(4,6-bis(((R)-1-cyclopropylethyl)amino)-1,3,5-triazin-2-yl)benzonitrile

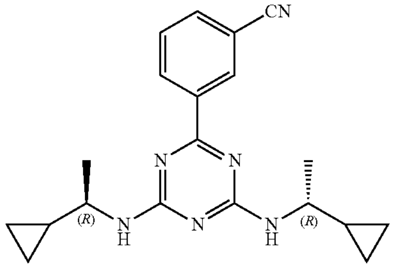

$^1$H NMR (400 MHz, CDC13) δ 8.63-8.55 (m, 2H), 7.75 (d, J=8 Hz, 1H), 7.57-7.53 (m, 1H), 5.53-5.21 (m, 2H), 3.69-3.55 (m, 2H), 1.25 (s, 2H), 0.90-8.86 (m, 2H), 0.57-0.30 (m, 1H).

LCMS: m/z 349 $(M+H)^+$.

Example 32. Preparation of Aromatic-Aliphatic Triazine Compounds of Formula Q. The compounds of this Example are prepared by general Scheme 32, set forth below.

Scheme 32

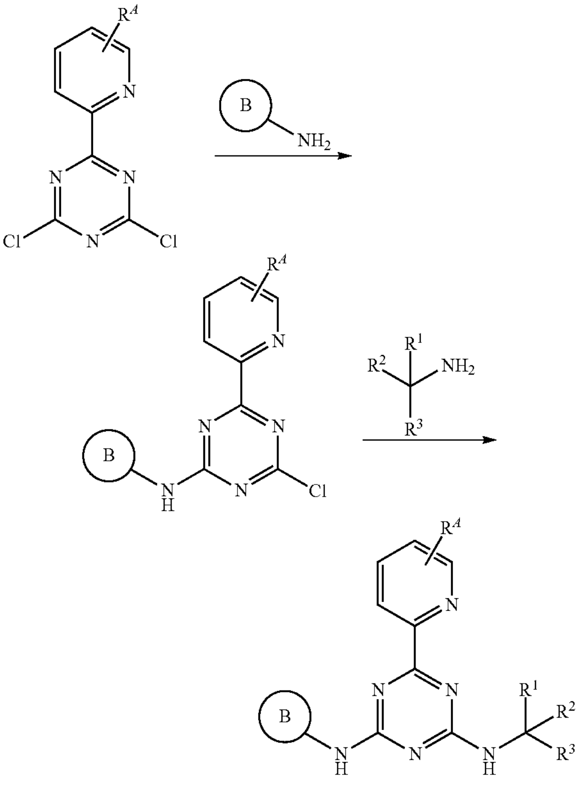

Formula Q

Step 1: Preparation of 4-chloro-N-(6-(1,1-difluoroethyl)pyridin-3-yl)-6-(6-(trifluoro methyl)pyridin-2-yl)-1,3,5-triazin-2-amine. To a mixture of 2,4-dichloro-6-(6-(trifluoromethyl)pyridin-2-yl)-1,3,5-triazine (188 mg, 0.64 mmol) and 2-(1,1-difluoroethyl)pyridin-4-amine (50 mg, 0.32 mmol) in 1,4-dioxane (4 mL) were added $^t$BuONa (61 mg, 0.64 mmol) and Pd(dppf)$Cl_2$ (22 mg, 0.03 mmol) under an atmosphere of nitrogen. The reaction mixture was then stirred at 80° C. overnight, and then filtered. The filtrate was concentrated and purified by standard methods to afford the desired product.

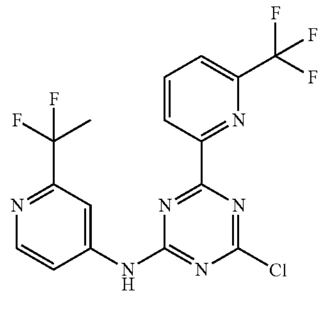 [SMILES: CC(F)(F)c1cc(Nc2nc(Cl)nc(-c3cccc(C(F)(F)F)n3)n2)ccn1]

LC-MS: m/z 417.1 $(M+H)^+$.

Step 2: Preparation of $N^2$-(3,3-difluorocyclopentyl)-$N^4$-(2-(1,1-difluoroethyl)pyridin-4-yl)-6-(6-(trifluoromethyl) pyridin-2-yl)-1,3,5-triazine-2,4-diamine To a mixture of 4-chloro-N-(6-(1,1-difluoroethyl)pyridin-3-yl)-6-(6-(trifluoromethyl)pyridine-2-yl)-1,3,5-triazin-2-amine (35 mg, 0.08 mmol) and 3,3-difluorocyclopentanamine (16 mg, 0.13 mmol) in THF (2 mL) were added CsF (24 mg, 0.16 mmol) and DIPEA (0.03 mL, 0.16 mmol). The reaction mixture was then stirred at 50° C. overnight. The mixture was filtered and the filtrate was concentrated and purified by standard methods to afford the desired product.

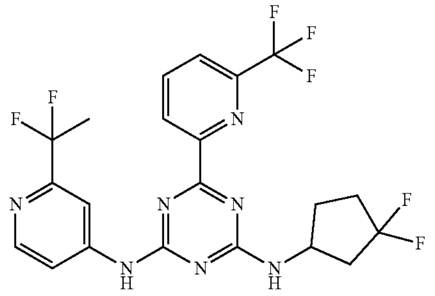 [SMILES: CC(F)(F)c1cc(Nc2nc(NC3CCC(F)(F)C3)nc(-c3cccc(C(F)(F)F)n3)n2)ccn1]

$^1H$ NMR (400 MHz, $CDCl_3$) δ 8.61 (m, 1H), 8.52 (d, J=5.4 Hz, 1H), 8.43 (s, 1H), 8.08 (d, J=7.7 Hz, 1H), 8.03-7.73 (m, 2H), 7.73-7.34 (m, 1H), 6.08-5.52 (m, 1H), 4.88-4.55 (m, 1H), 2.82-2.64 (m, 1H), 2.46-2.12 (m, 4H), 2.11-1.98 (m, 3H), 1.94-1.81 (m, 1H). LC-MS: m/z 502 $(M+H)^+$.

The procedure set forth in Example 32 was used to produce the following compounds using the appropriate starting materials.

(S)—$N^2$-(3,3-difluorocyclopentyl)-$N^4$-(2-(1,1-difluoroethyl)pyridin-4-yl)-6-(6-(trifluoromethyl)pyridin-2-yl)-1,3,5-triazine-2,4-diamine

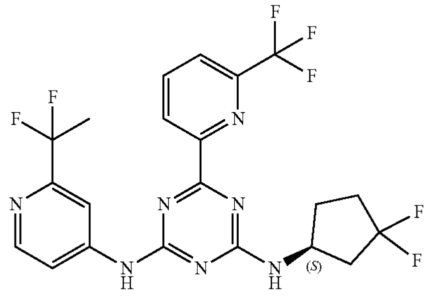

$^1H$ NMR (400 MHz, $CDCl_3$) δ 8.61 (m, 1H), 8.53 (d, J=5.4 Hz, 1H), 8.46-7.94 (m, 2H), 7.91-7.32 (m, 3H), 5.77 (m, 1H), 4.70 (m, 1H), 2.79-2.60 (m, 1H), 2.50-2.11 (m, 4H), 2.04 (m, 3H), 1.87 (m, 1H). LC-MS: m/z 502 $(M+H)^+$.

(R)—$N^2$-(3,3-difluorocyclopentyl)-$N^4$-(2-(1,1-difluoroethyl)pyridin-4-yl)-6-(6-(trifluoromethyl)pyridin-2-yl)-1,3,5-triazine-2,4-diamine

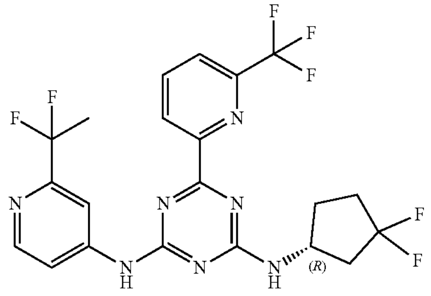

$^1H$ NMR (400 MHz, $CDCl_3$) δ 8.62 (m, 1H), 8.53 (d, J=5.4 Hz, 1H), 8.47-7.94 (m, 2H), 7.93-7.33 (m, 3H), 5.90-5.60 (m, 1H), 4.96-4.46 (m, 1H), 2.80-2.61 (m, 1H), 2.50-2.10 (m, 4H), 2.04 (m, 3H), 1.87 (m, 1H). LC-MS: m/z 502 $(M+H)^+$.

$N^2$-(4,4-difluorocyclohexyl)-$N^4$-(2-(1,1-difluoroethyl)pyridin-4-yl)-6-(6-(trifluoromethyl)pyridin-2-yl)-1,3,5-triazine-2,4-diamine

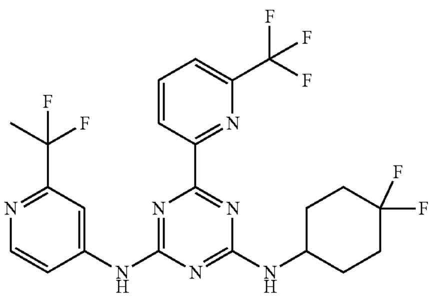 [SMILES: CC(F)(F)c1cc(Nc2nc(NC3CCC(F)(F)CC3)nc(-c3cccc(C(F)(F)F)n3)n2)ccn1]

$^1$H NMR (400 MHz, $CDCl_3$) δ 8.69-8.43 (m, 3H), 8.07 (t, J=7.8 Hz, 1H), 8.01-7.73 (m, 2H), 7.49 (m, 1H), 5.61 (m, 1H), 4.19 (m, 1H), 2.24-2.13 (m, 4H), 2.12-1.93 (m, 5H), 1.76-1.65 (m, 2H). LC-MS: m/z 516 $(M+H)^+$.

$N^2$-(3,3-difluorocyclobutyl)-$N^4$-(2-(1,1-difluoroethyl)pyridin-4-yl)-6-(6-(trifluoromethyl)pyridin-2-yl)-1,3,5-triazine-2,4-diamine

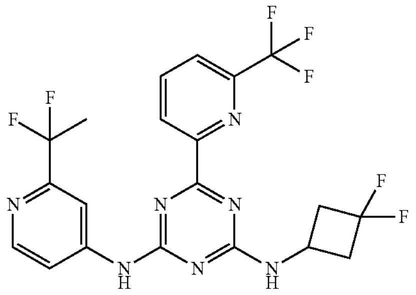 [SMILES: CC(F)(F)c1cc(Nc2nc(NC3CC(F)(F)C3)nc(-c3cccc(C(F)(F)F)n3)n2)ccn1]

$^1$H NMR (400 MHz, $CDCl_3$) δ 8.72-8.26 (m, 3H), 8.18-7.75 (m, 3H), 7.72-7.33 (m, 1H), 6.03 (m, 1H), 4.53 (m, 1H), 3.16 (d, J=8.2 Hz, 2H), 2.59 (m, 2H), 2.05 (m, 3H). LCMS: m/z 488 $(M+H)^+$.

2-((4-((2-(1,1-Difluoroethyl)pyridin-4-yl)amino)-6-(6-(trifluoromethyl)pyridin-2-yl)-1,3,5-triazin-2-yl)amino)propanenitrile

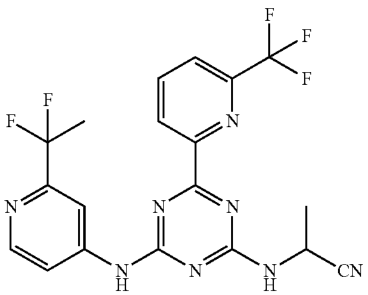 [SMILES: CC(C#N)Nc1nc(Nc2ccnc(C(C)(F)F)c2)nc(-c2cccc(C(F)(F)F)n2)n1]

$^1$H NMR (400 MHz, DMSO-$d_6$) δ 11.25-10.25 (m, 1H), 9.16-8.47 (m, 3H), 8.41-8.19 (m, 2H), 8.15-7.80 (m, 2H), 5.40-4.80 (m, 1H), 2.00 (t, J=19.0 Hz, 3H), 1.63 (d, J=7.2 Hz, 3H).

LCMS: m/z 451 $(M+H)^+$.

2-((4-((2-(1,1-Difluoroethyl)pyridin-4-yl)amino)-6-(6-(trifluoromethyl)pyridin-2-yl)-1,3,5-triazin-2-yl)amino)-2-methylpropanenitrile

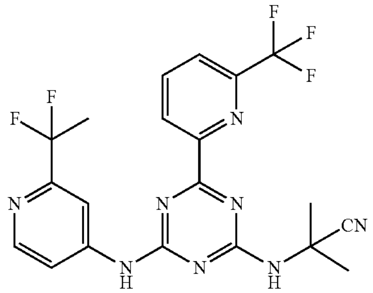 [SMILES: CC(C)(C#N)Nc1nc(Nc2ccnc(C(C)(F)F)c2)nc(-c2cccc(C(F)(F)F)n2)n1]

$^1$H NMR (400 MHz, $CDCl_3$) δ 8.88-8.43 (m, 2H), 8.03 (m, 4H), 7.67 (s, 1H), 5.97 (m, 1H), 2.02 (m, 3H), 1.86 (s, 6H). LCMS: m/z 465 $(M+H)^+$.

3-((4-((2-(1,1-Difluoroethyl)pyridin-4-yl)amino)-6-(6-(trifluoromethyl)pyridin-2-yl)-1,3,5-triazin-2-yl)amino)-2,2-dimethylpropanenitrile

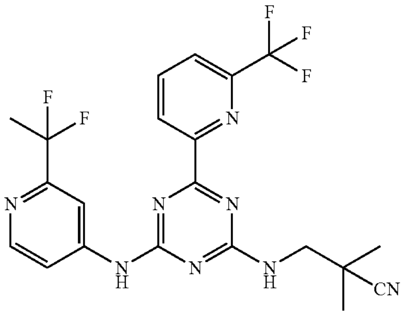 [SMILES: CC(C)(C#N)CNc1nc(Nc2ccnc(C(C)(F)F)c2)nc(-c2cccc(C(F)(F)F)n2)n1]

$^1$H NMR (400 MHz, DMSO-$d_6$) δ 10.65 (s, 1H), 8.91-8.38 (m, 4H), 8.33 (t, J=7.9 Hz, 1H), 8.21-7.51 (m, 2H), 3.80-3.60 (m, 2H), 2.00 (m, 3H), 1.40 (d, J=3.9 Hz, 6H). LCMS: m/z 479 $(M+H)^+$.

3-((4-((2-(1,1-Difluoroethyl)pyridin-4-yl)amino)-6-(6-(trifluoromethyl)pyridin-2-yl)-1,3,5-triazin-2-yl)amino)butanenitrile

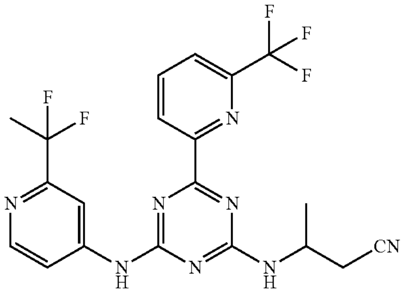 [SMILES: CC(CC#N)Nc1nc(Nc2ccnc(C(C)(F)F)c2)nc(-c2cccc(C(F)(F)F)n2)n1]

$^1$H NMR (400 MHz, DMSO-$d_6$) δ: 10.90-10.25 (m, 1H), 8.75-8.52 (m, 2H), 8.52-8.20 (m, 3H), 8.18-7.75 (m, 2H), 4.67-4.26 (m, 1H), 3.09-2.72 (m, 2H), 2.00 (m, 3H), 1.35 (t, J=5.5 Hz, 3H). LCMS: m/z 465 $(M+H)^+$.

3-((4-((2-(1,1-Difluoroethyl)pyridin-4-yl)amino)-6-(6-(trifluoromethyl)pyridin-2-yl)-1,3,5-triazin-2-yl)amino)-3-methylbutanenitrile

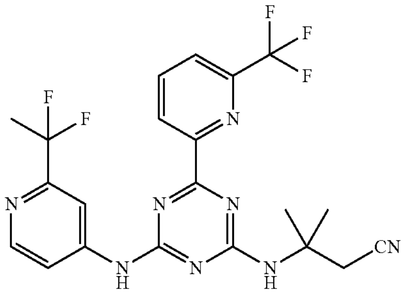 [SMILES: CC(C)(CC#N)Nc1nc(Nc2ccnc(C(C)(F)F)c2)nc(-c2cccc(C(F)(F)F)n2)n1]

$^1$H NMR (400 MHz, DMSO-$d_6$) δ 8.65-8.44 (m, 2H), 8.42-7.96 (m, 3H), 7.92-7.35 (m, 2H), 6.00-5.60 (m, 1H), 3.40-3.10 (m, 2H), 2.10-1.90 (m, 3H), 1.75-1.50 (m, 6H). LCMS: m/z 479 $(M+H)^+$.

$N^2$-(3,3-difluorocyclopentyl)-6-(6-(trifluoromethyl)pyridin-2-yl)-$N^4$-(2-(trifluoromethyl)pyridin-4-yl)-1,3,5-triazine-2,4-diamine

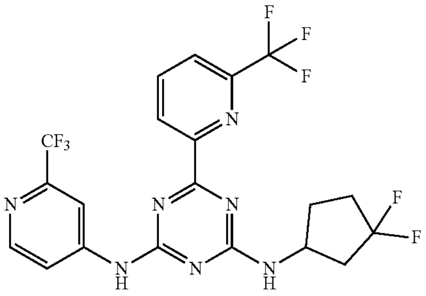 [SMILES: FC1(F)CCC(Nc2nc(Nc3ccnc(C(F)(F)F)c3)nc(-c3cccc(C(F)(F)F)n3)n2)C1]

$^1$H NMR (400 MHz, $CDCl_3$) δ 8.67-8.57 (m, 2H), 8.53 (d, J=1.7 Hz, 1H), 8.19-7.38 (m, 4H), 6.03-5.53 (m, 1H), 4.85-4.55 (m, 1H), 2.81-2.58 (m, 1H), 2.51-2.07 (m, 4H), 1.98-1.81 (m, 1H), 1.32-1.16 (m, 1H). LC-MS: m/z 506 $(M+H)^+$.

(R)—$N^2$-(3,3-difluorocyclopentyl)-6-(6-(trifluoromethyl)pyridin-2-yl)-$N^4$-(2-(trifluoromethyl)pyridin-4-yl)-1,3,5-triazine-2,4-diamine

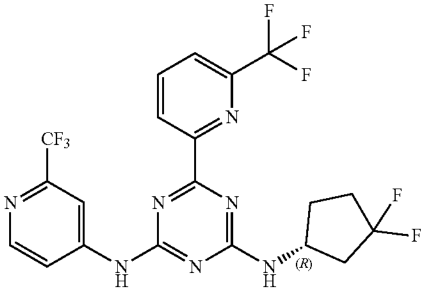

$^1$H NMR (400 MHz, $CDCl_3$) δ 8.65-8.52 (m, 3H), 8.10-8.06 (m, 2H), 7.86-7.85 (m, 1H), 7.48-7.42 (m, 1H), 6.00-5.86 (m, 1H), 4.81-4.60 (m, 1H), 2.77-2.62 (m, 1H), 2.41-2.32 (m, 2H), 2.12-2.19 (m, 2H), 1.93-1.86 (m, 1H). LCMS: m/z 506 $(M+H)^+$.

(S)—$N^2$-(3,3-difluorocyclopentyl)-6-(6-(trifluoromethyl)pyridin-2-yl)-$N^4$-(2-(trifluoromethyl)pyridin-4-yl)-1,3,5-triazine-2,4-diamine

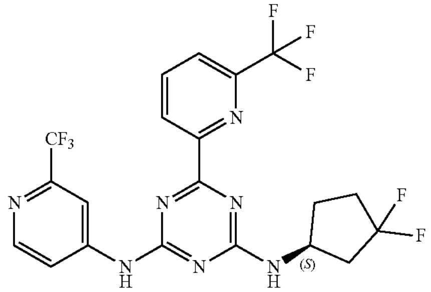

$^1$H NMR (400 MHz, $CDCl_3$) δ 8.67-8.56 (m, 2H), 8.53 (d, J=1.8 Hz, 1H), 8.20-7.82 (m, 3H), 7.77-7.40 (m, 1H), 6.09-5.51 (m, 1H), 4.92-4.46 (m, 1H), 2.80-2.59 (m, 1H), 2.46-2.29 (m, 2H), 2.29-2.08 (m, 2H), 1.97-1.85 (m, 1H). LC-MS: m/z 506 $(M+H)^+$.

$N^2$-(4,4-difluorocyclohexyl)-6-(6-(trifluoromethyl)pyridin-2-yl)-$N^4$-(2-(trifluoromethyl)pyridin-4-yl)-1,3,5-triazine-2,4-diamine

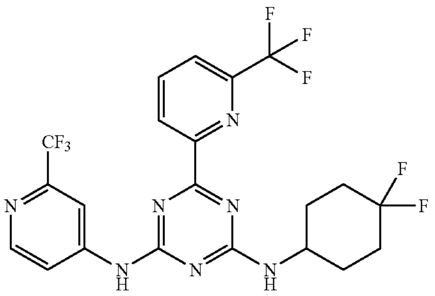

1H NMR (400 MHz, $CDCl_3$) δ 8.57-8.62 (m, 3H), 7.85-8.17 (m, 3H), 7.37-7.72 (m, 1H), 5.45-5.82 (m, 1H), 4.10-4.26 (m, 1H), 2.17-2.19 (d, J=9.2 Hz, 4H), 1.88-2.04 (m, 2H), 1.66-1.81 (m, 2H); LC-MS: m/z 520 $(M+H)^+$.

N[2]-(3,3-difluorocyclobutyl)-6-(6-(trifluoromethyl) pyridin-2-yl)-N[4]-(2-(trifluoromethyl)pyridin-4-yl)-1,3,5-triazine-2,4-diamine

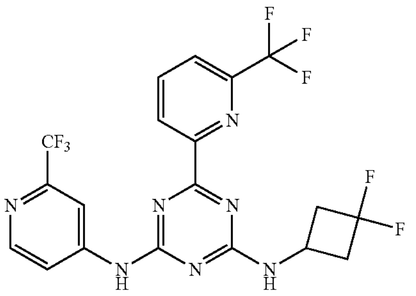 [SMILES: FC1(F)CC(Nc2nc(Nc3ccnc(C(F)(F)F)c3)nc(-c3cccc(C(F)(F)F)n3)n2)C1]

$^1$H NMR (400 MHz, $CDCl_3$) δ 8.65-8.55 (m, 2H), 8.51-8.32 (m, 1H) 8.11-8.04 (m, 1H), 7.86-7.83 (m, 1H), 7.68-7.47 (m, 1H), 6.33-6.06 (m, 1H), 4.58-4.42 (m, 1H), 3.17-3.10 (m, 2H), 2.75-2.53 (m, 2H), 2.29 (s, 1H). LCMS: m/z 492 $(M+H)^+$.

N[2]-(6,6-difluorospiro[3.3]heptan-2-yl)-6-(6-(trifluoromethyl)pyridin-2-yl)-N[4]-(2-(trifluoromethyl)pyridin-4-yl)-1,3,5-triazine-2,4-diamine

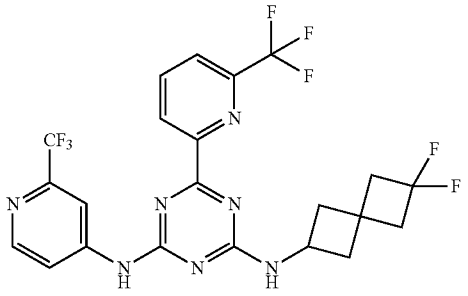

1H NMR (400 MHz, $CDCl_3$) δ 8.55-8.70 (m, 3H), 7.84-8.20 (m, 3H), 7.31-7.66 (m, 1H), 5.68-6.00 (m, 1H), 4.49-4.55 (m, 1H), 2.57-2.76 (m, 6H), 1.83-2.27 (m, 2H). LC-MS: m/z 532 $(M+H)^+$.

6-(6-(Trifluoromethyl)pyridin-2-yl)-N[2]-(2-(trifluoromethyl)pyridin-4-yl)-N[4]-(1,1,1-trifluoropropan-2-yl)-1,3,5-triazine-2,4-diamine

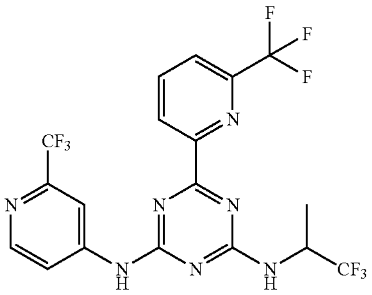 [SMILES: CC(Nc1nc(Nc2ccnc(C(F)(F)F)c2)nc(-c2cccc(C(F)(F)F)n2)n1)C(F)(F)F]

$^1$H NMR (400 MHz, $CDCl_3$) δ 8.62-8.59 (m, 1H), 8.44 (s, 1H), 8.16-8.07 (m, 1H), 7.87 (d, J=8 Hz, 1H), 7.75-7.50 (m, 1H), 1.53-1.49 (m, 3H). LCMS: m/z 498 $(M+H)^+$.

N[2]-(2,2,2-trifluoroethyl)-6-(6-(trifluoromethyl)pyridin-2-yl)-N[4]-(2-(trifluoromethyl)pyridin-4-yl)-1,3,5-triazine-2,4-diamine

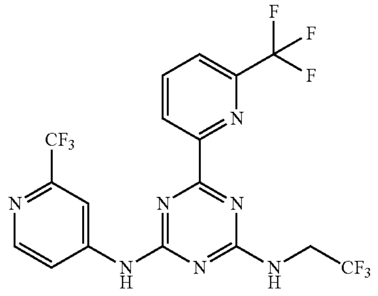 [SMILES: FC(F)(F)CNc1nc(Nc2ccnc(C(F)(F)F)c2)nc(-c2cccc(C(F)(F)F)n2)n1]

$^1$H NMR (400 MHz, DMSO-$d_6$) δ 10.91 (s, 1H), 8.75-8.71 (m, 2H), 8.61-8.57 (m, 2H), 8.36-8.33 (m, 1H), 8.21-7.83 (m, 2H), 4.41-4.24 (m, 2H). LCMS: m/z 484 $(M+H)^+$.

N[2]-((3,3-difluorocyclobutyl)methyl)-6-(6-(trifluoromethyl)pyridin-2-yl)-N[4]-(2-(trifluoromethyl)pyridin-4-yl)-1,3,5-triazine-2,4-diamine

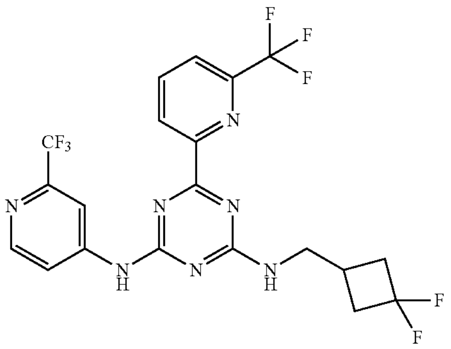 [SMILES: FC1(F)CC(CNc2nc(Nc3ccnc(C(F)(F)F)c3)nc(-c3cccc(C(F)(F)F)n3)n2)C1]

$^1$H NMR (400 MHz, $CDCl_3$) δ 8.70-8.41 (m, 3H), 7.96 (m, 4H), 7.52 (m, 1H), 5.95-5.58 (m, 1H), 3.67 (m, 2H), 2.77-2.13 (m, 5H). LCMS: m/z 506 $(M+H)^+$.

$N^2$-((2,2-difluorocyclopropyl)methyl)-6-(6-(trifluoromethyl)pyridin-2-yl)-$N^4$-(2-(trifluoromethyl)pyridin-4-yl)-1,3,5-triazine-2,4-diamine

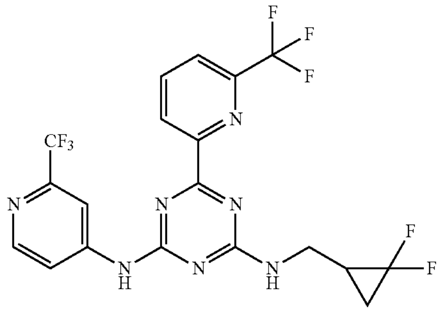 [SMILES: FC(F)(F)c1cc(Nc2nc(NCC3CC3(F)F)nc(-c3cccc(C(F)(F)F)n3)n2)ccn1]

$^1$H NMR (400 MHz, DMSO-$d_6$) δ 10.76-10.69 (m, 1H), 8.74-8.66 (m, 2H), 8.58-8.55 (m, 2H), 8.34-8.30 (m, 1H), 8.11 (d, J=8 Hz, 1H), 7.96-7.86 (m, 1H), 3.61-3.43 (m, 2H), 2.17-2.09 (m, 1H), 1.67-1.32 (m, 2H). LCMS: m/z 492 $(M+H)^+$.

$N^2$-(3,3-difluorocyclopentyl)-6-(6-(trifluoromethyl) pyridin-2-yl)-$N^4$-(5-(trifluoromethyl)pyridin-3-yl)-1,3,5-triazine-2,4-diamine

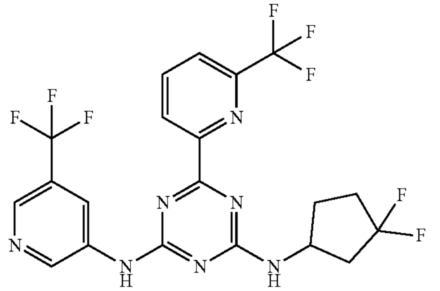 [SMILES: FC1(F)CCC(Nc2nc(Nc3cncc(C(F)(F)F)c3)nc(-c3cccc(C(F)(F)F)n3)n2)C1]

$^1$H NMR (400 MHz, $CDCl_3$) δ 8.86 (t, J=6.0 Hz, 1H), 8.83-8.73 (m, 1H), 8.64-8.55 (m, 2H), 8.09-8.03 (m, 1H), 7.89-7.83 (m, 1H), 6.00-5.88 (m, 1H), 4.80-4.55 (m, 1H), 2.74-2.57 (m, 1H), 2.47-2.05 (m, 4H), 1.94-1.82 (m, 1H). LC-MS: m/z 506 $(M+H)^+$.

1-(4-((4-((3,3-Difluorocyclopentyl)amino)-6-(6-(trifluoromethyl)pyridin-2-yl)-1,3,5-triazin-2-yl) amino)pyridin-2-yl)cyclopropanecarbonitrile

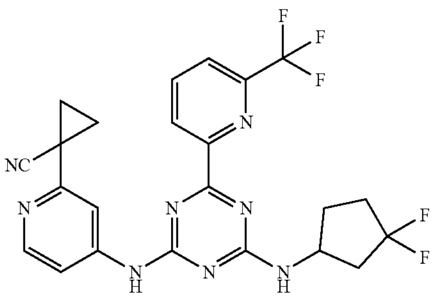 [SMILES: N#CC1(c2cc(Nc3nc(NC4CCC(F)(F)C4)nc(-c4cccc(C(F)(F)F)n4)n3)ccn2)CC1]

$^1$H NMR (600 MHz, $CDCl_3$) δ 8.67 (s, 2H), 8.29 (t, J=5.9 Hz, 1H), 8.07 (t, J=7.6 Hz, 1H), 7.91-7.79 (m, 2H), 7.05 (s, 1H), 5.97 (d, J=7.9 Hz, 1H), 5.06-4.61 (m, 1H), 2.81-2.66 (m, 1H), 2.43-1.36 (m, 1H), 2.34-2.18 (m, 2H), 2.14-2.04 (m, 1H), 1.87-1.77 (m, 3H), 1.72 (m, 2H). LC-MS: m/z 503 (M+H)+

(R)-1-(4-((4-((3,3-difluorocyclopentyl)amino)-6-(6-(trifluoromethyl)pyridin-2-yl)-1,3,5-triazin-2-yl) amino)pyridin-2-yl)cyclopropanecarbonitrile

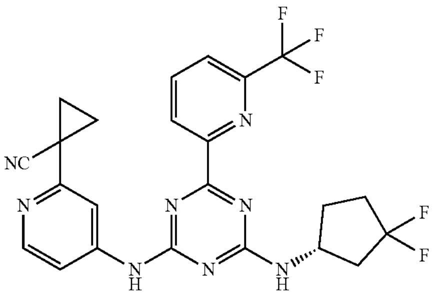

$^1$H NMR (400 MHz, DMSO-$d_6$) δ 10.47 (s, 1H), 8.77-8.59 (m, 2H), 8.49 (s, 1H), 8.36-8.20 (m, 2H), 8.11 (d, J=7.8 Hz, 1H), 7.55 (d, J=4.6 Hz, 1H), 4.86-4.47 (m, 1H), 2.75-2.57 (m, 1H), 2.29-2.06 (m, 4H), 1.97-1.82 (m, 1H), 1.80-1.74 (m, 2H), 1.71-1.63 (m, 2H). LC-MS: m/z 503 $(M+H)^+$.

(S)-1-(4-((4-((3,3-difluorocyclopentyl)amino)-6-(6-(trifluoromethyl)pyridin-2-yl)-1,3,5-triazin-2-yl) amino)pyridin-2-yl)cyclopropanecarbonitrile

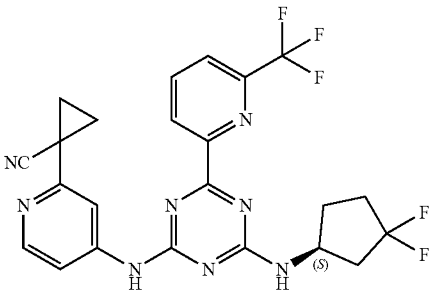

$^1$H NMR (400 MHz, DMSO-$d_6$) δ 10.47 (s, 1H), 8.79-8.60 (m, 2H), 8.49 (s, 1H), 8.38-8.19 (m, 2H), 8.11 (d, J=7.7 Hz, 1H), 7.55 (d, J=4.4 Hz, 1H), 4.80-4.54 (m, 1H), 2.75-2.55 (m, 1H), 2.37-2.06 (m, 4H), 1.96-1.82 (m, 1H), 1.76-1.67 (m, 4H). LC-MS: m/z 503 $(M+H)^+$.

1-(4-((4-((4,4-Difluorocyclohexyl)amino)-6-(6-(trifluoromethyl)pyridin-2-yl)-1,3,5-triazin-2-yl)amino)pyridin-2-yl)cyclopropanecarbonitrile

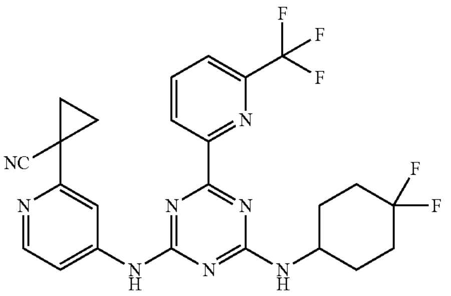 [SMILES: N#CC1(c2cc(Nc3nc(NC4CCC(F)(F)CC4)nc(-c4cccc(C(F)(F)F)n4)n3)ccn2)CC1]

$^1$H NMR (400 MHz, $CDCl_3$) δ 8.83-8.65 (m, 1H), 8.58 (m, 1H), 8.32 (d, J=5.4 Hz, 1H), 8.10 (t, J=7.8 Hz, 1H), 7.86 (d, J=7.7 Hz, 1H), 7.62 (m, 1H), 7.09 (s, 1H), 5.65 (m, 1H), 4.29 (s, 1H), 2.12 (m, 6H), 1.89-1.91 (m, 2H), 1.82-1.63 (m, 4H). LC-MS: m/z 517 $(M+H)^+$.

1-(4-((4-((3,3-Difluorocyclobutyl)amino)-6-(6-(trifluoromethyl)pyridin-2-yl)-1,3,5-triazin-2-yl)amino)pyridin-2-yl)cyclopropanecarbonitrile

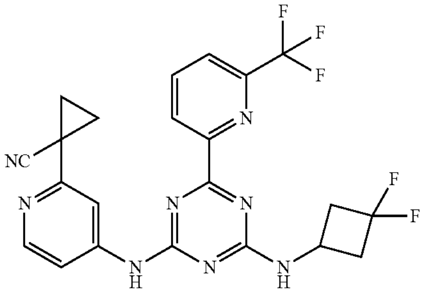

$^1$H NMR (400 MHz, DMSO-$d_6$) δ 10.48 (brs, 1H), 8.89 (d, J=6.5 Hz, 1H), 8.78-8.56 (m, 1H), 8.42 (s, 1H), 8.37-8.24 (m, 2H), 8.10 (d, J=7.8 Hz, 1H), 7.58 (d, J=4.1 Hz, 1H), 4.45 (s, 1H), 3.13-2.97 (m, 2H), 2.71-2.56 (m, 2H), 1.83-1.59 (m, 4H). LC-MS: m/z 489 $(M+H)^+$.

1-(4-((4-((6,6-Difluorospiro[3.3]heptan-2-yl)amino)-6-(6-(trifluoromethyl)pyridin-2-yl)-1,3,5-triazin-2-yl)amino)pyridin-2-yl)cyclopropanecarbonitrile

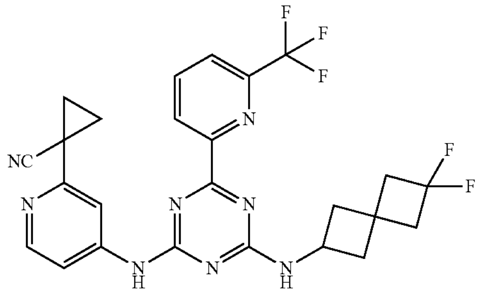 [SMILES: N#CC1(c2cc(Nc3nc(NC4CC5(C4)CC(F)(F)C5)nc(-c4cccc(C(F)(F)F)n4)n3)ccn2)CC1]

$^1$H NMR (400 MHz, $CDCl_3$) δ 8.70-8.53 (m, 2H), 8.31-8.28 (m, 1H), 8.10-8.06 (m, 1H), 7.85-7.83 (d, J=8 Hz, 1H), 7.66-7.52 (m, 1H), 7.20-7.07 (m, 1H), 5.94-5.66 (m, 1H), 4.67-4.63 (m, 1H), 2.75-2.55 (m, 6H), 2.25-2.10 (m, 2H), 1.89-1.83 (m, 2H), 1.74-1.71 (m, 2H). LCMS: m/z 529 $(M+H).^+$ 1-(4-((4-(((2,2-Difluorocyclopropyl)methyl)amino)-6-(6-(trifluoromethyl)pyridin-2-yl)-1,3,5-triazin-2-yl)amino)pyridin-2-yl)cyclopropanecarbonitrile

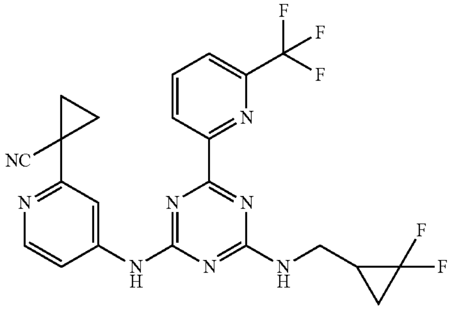 [SMILES: N#CC1(c2cc(Nc3nc(NCC4CC4(F)F)nc(-c4cccc(C(F)(F)F)n4)n3)ccn2)CC1]

$^1$H NMR (400 MHz, $CDCl_3$) δ 8.72 (m, 2H), 8.31 (d, J=5.5 Hz, 1H), 8.09 (d, J=7.8 Hz, 1H), 7.85 (d, J=7.8 Hz, 1H), 7.58 (m, 1H), 7.05 (m, 1H), 5.92 (m, 1H), 4.00 (s, 1H), 3.61 (m, 1H), 2.08 (m, 1H), 1.83 (m, 2H), 1.72 (m, 2H), 1.52 (m, 2H). LC-MS: m/z 489 $(M+H)^+$.

1-(4-((4-((2,2,2-Trifluoroethyl)amino)-6-(6-(trifluoromethyl)pyridin-2-yl)-1,3,5-triazin-2-yl)amino)pyridin-2-yl)cyclopropanecarbonitrile

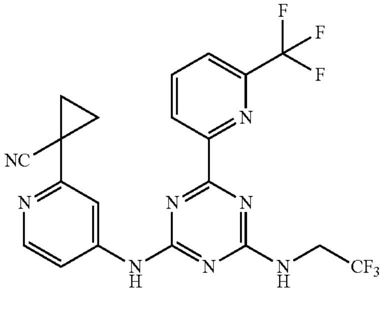 [SMILES: N#CC1(c2cc(Nc3nc(NCC(F)(F)F)nc(-c4cccc(C(F)(F)F)n4)n3)ccn2)CC1]

$^1$H NMR (400 MHz, $CDCl_3$) δ 8.93-8.42 (m, 2H), 8.34-8.29 (m, 1H), 8.10 (t, J=7.8 Hz, 1H), 8.03-7.58 (m, 2H), 7.13 (d, J=4.2 Hz, 1H), 6.34-6.03 (m, 1H), 4.36-4.29 (m, 2H), 1.74 (s, 4H). LC-MS: m/z 481.2 $(M+H)^+$.

1-(4-((4-((2-Hydroxy-2-methylpropyl)amino)-6-(6-(trifluoromethyl)pyridin-2-yl)-1,3,5-triazin-2-yl)amino)pyridin-2-yl)cyclopropanecarbonitrile

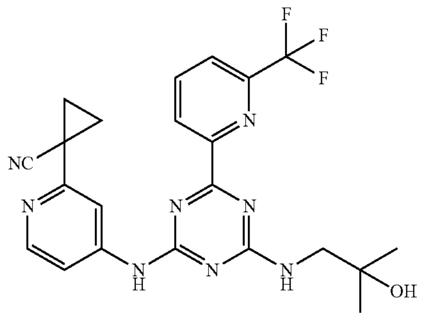 [SMILES: CC(C)(O)CNc1nc(Nc2ccnc(C3(C#N)CC3)c2)nc(-c2cccc(C(F)(F)F)n2)n1]

$^1$H NMR (400 MHz, $CDCl_3$) δ 8.77-8.44 (m, 2H), 8.29 (d, J=5.5 Hz, 1H), 8.07 (t, J=7.7 Hz, 1H), 7.77 (m, 2H), 6.96 (s, 1H), 6.14 (m, 1H), 3.79-3.55 (m, 2H), 1.91-1.84 (m, 2H), 1.73-1.69 (m, 2H), 1.35 (s, 6H). LC-MS: m/z 471 $(M+H)^+$.

(R)-1-(4-((4-(6-(trifluoromethyl)pyridin-2-yl)-6-((1,1,1-trifluoropropan-2-yl)amino)-1,3,5-triazin-2-yl)amino)pyridin-2-yl)cyclopropanecarbonitrile

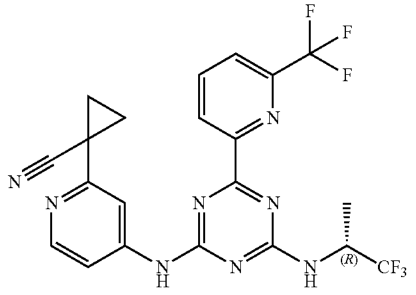

$^1$H NMR (400 MHz, $CDCl_3$) δ 8.73 (m, 2H), 8.36 (m, 1H), 8.11 (d, J=7.3 Hz, 1H), 7.87 (d, J=7.8 Hz, 1H), 7.52 (s, 1H), 7.07 (m, 1H), 5.82 (m, 1H), 5.09 (s, 1H), 4.81 (m, 4H), 1.50 (m, J=8.5 Hz, 3H). LC-MS: m/z 495 $(M+H)^+$.

(S)-1-(4-((4-(6-(trifluoromethyl)pyridin-2-yl)-6-((1,1,1-trifluoropropan-2-yl)amino)-1,3,5-triazin-2-yl)amino)pyridin-2-yl)cyclopropanecarbonitrile

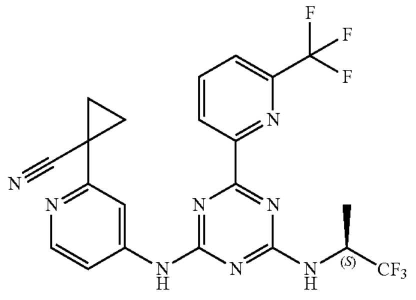

$^1$H NMR (400 MHz, $CDCl_3$) δ 8.77 (d, J=9.2 Hz, 2H), 8.66 (m, J=8 Hz, 1H), 8.57 (s, 1H), 8.10 (m, 1H), 7.52 (m,

1H), 7.10 (d, J=4 Hz, 1H), 5.86 (m, 1H), 5.05 (m, 1H), 1.8 (m, 4H), 1.62 (m, 3H). LC-MS: m/z 495 $(M+H)^+$.

4-((4-(Tert-butylamino)-6-(6-(trifluoromethyl)pyridin-2-yl)-1,3,5-triazin-2-yl)amino)picolinonitrile

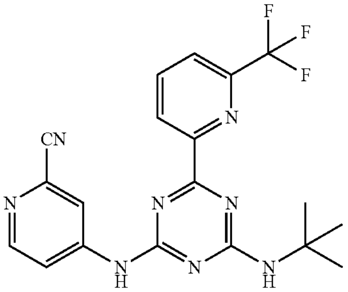 [SMILES: CC(C)(C)Nc1nc(Nc2ccnc(C#N)c2)nc(-c2cccc(C(F)(F)F)n2)n1]

$^1$H NMR (400 MHz, DMSO-$d_6$) δ 8.66-8.41 (m, 3H), 8.12-8.00 (m, 1H), 7.91-7.80 (m, 1H), 7.65-7.55 (m, 1H), 5.80-5.20 (m, 1H), 1.58 (m, 9H). LCMS: m/z 415 $(M+H)^+$.

4-((4-((3,3-Difluorocyclobutyl)amino)-6-(6-(trifluoromethyl)pyridin-2-yl)-1,3,5-triazin-2-yl)amino)picolinonitrile

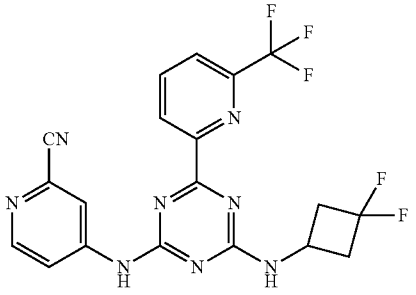 [SMILES: N#Cc1cc(Nc2nc(NC3CC(F)(F)C3)nc(-c3cccc(C(F)(F)F)n3)n2)ccn1]

$^1$H NMR (400 MHz, DMSO-$d_6$) δ 10.78 (s, 1H), 8.97-8.52 (m, 4H), 8.38-8.25 (m, 1H), 8.13 (d, J=7.8 Hz, 1H), 8.01-7.80 (m, 1H), 4.56-4.24 (m, 1H), 3.17-2.95 (m, 2H), 2.80-2.60 (m, 2H). LCMS: m/z 449 $(M+H)^+$.

4-((4-((3,3-Difluorocyclopentyl)amino)-6-(6-(trifluoromethyl)pyridin-2-yl)-1,3,5-triazin-2-yl)amino)picolinonitrile

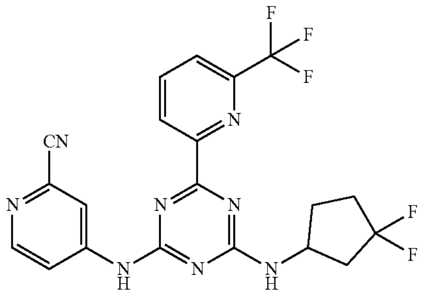 [SMILES: N#Cc1cc(Nc2nc(NC3CCC(F)(F)C3)nc(-c3cccc(C(F)(F)F)n3)n2)ccn1]

$^1$H NMR (400 MHz, $CDCl_3$) δ 8.07-8.66 (m, 4H), 7.86 (d, J=8.0 Hz, 2H), 7.53-7.68 (m, 1H), 5.85-6.03 (m, 1H), 4.58-4.79 (m, 1H), 2.66-2.75 (m, 1H), 1.95-2.47 (m, 1H), 1.88-1.93 (m, 1H). LC-MS: m/z 463 $(M+H)^+$.

4-((4-((4,4-Difluorocyclohexyl)amino)-6-(6-(trifluoromethyl)pyridin-2-yl)-1,3,5-triazin-2-yl)amino)picolinonitrile

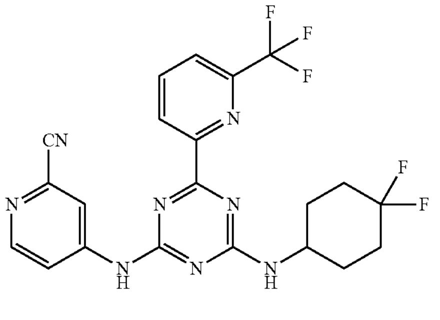 [SMILES: N#Cc1cc(Nc2nc(NC3CCC(F)(F)CC3)nc(-c3cccc(C(F)(F)F)n3)n2)ccn1]

$^1$H NMR (400 MHz, DMSO-$d_6$) δ 10.72-10.76 (m, 1H), 7.93-8.72 (m, 5H), 4.03-4.23 (m, 1H), 1.94-2.16 (m, 6H), 1.64-1.73 (m, 2H). LC-MS: m/z 477 $(M+H)^+$.

4-((4-((2-Hydroxy-2-methylpropyl)amino)-6-(6-(trifluoromethyl)pyridin-2-yl)-1,3,5-triazin-2-yl)amino)picolinonitrile

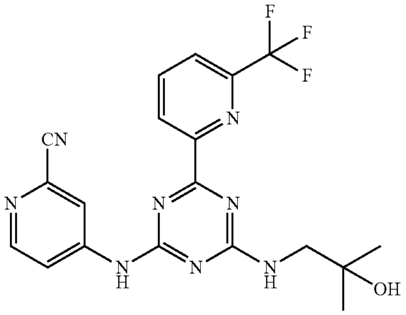 [SMILES: CC(C)(O)CNc1nc(Nc2ccnc(C#N)c2)nc(-c2cccc(C(F)(F)F)n2)n1]

$^1$H NMR (400 MHz, $CDCl_3$) δ 8.57-8.50 (m, 2H), 8.43-8.36 (m, 1H), 8.22-8.02 (m, 2H), 7.85 (m, 1H), 7.60 (s, 1H), 6.32-6.23 (m, 1H), 3.74-3.58 (m, 2H), 1.37 (s, 6H). LCMS: m/z 431 $(M+H)^+$.

3-((4-((3,3-Difluorocyclopentyl)amino)-6-(6-(trifluoromethyl)pyridin-2-yl)-1,3,5-triazin-2-yl)amino)-5-fluorobenzonitrile

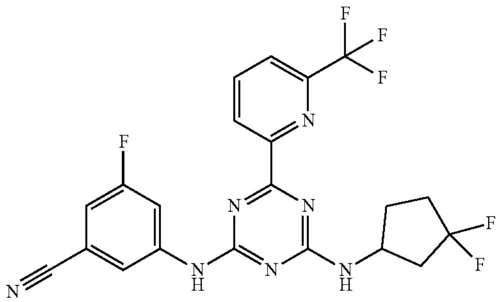 [SMILES: N#Cc1cc(F)cc(Nc2nc(NC3CCC(F)(F)C3)nc(-c3cccc(C(F)(F)F)n3)n2)c1]

$^1$H NMR (400 MHz, $CDCl_3$) δ 8.64-8.55 (m, 1H), 8.16-7.74 (m, 5H), 7.08-7.02 (m, 1H), 5.97-5.71 (m, 1H), 4.79-4.55 (m, 1H), 2.69-2.64 (m, 1H), 2.41-2.14 (m, 4H), 2.01 (s, 1H). LCMS: m/z 480 $(M+H)^+$.

3-((4-((4,4-Difluorocyclohexyl)amino)-6-(6-(trifluoromethyl)pyridin-2-yl)-1,3,5-triazin-2-yl)amino)-5-fluorobenzonitrile

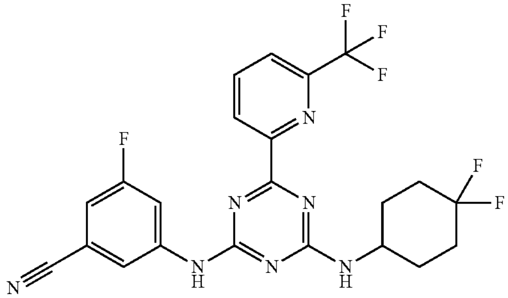 [SMILES: N#Cc1cc(F)cc(Nc2nc(NC3CCC(F)(F)CC3)nc(-c3cccc(C(F)(F)F)n3)n2)c1]

$^1$H NMR (400 MHz, $CDCl_3$): δ 8.60-8.54 (m, 1H), 8.08-8.07 (m, 1H), 7.85-7.81 (m, 4H), 7.08-7.03 (m, 1H), 5.76-5.48 (m, 1H), 4.22-4.04 (m, 1H), 2.21-2.18 (m, 4H), 2.02-1.92 (m, 2H), 1.78-1.71 (m, 2H). LCMS: m/z 494 $(M+H)^+$.

3-((4-((3,3-Difluorocyclobutyl)amino)-6-(6-(trifluoromethyl)pyridin-2-yl)-1,3,5-triazin-2-yl)amino)-5-fluorobenzonitrile

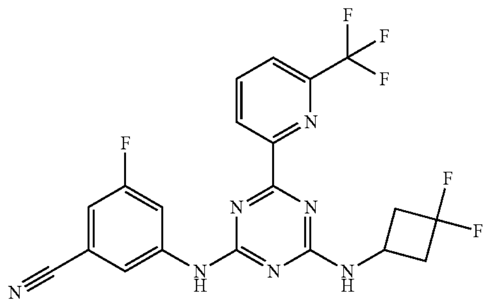 [SMILES: N#Cc1cc(F)cc(Nc2nc(NC3CC(F)(F)C3)nc(-c3cccc(C(F)(F)F)n3)n2)c1]

$^1$H NMR (400 MHz, DMSO-$d_6$) δ 10.50 (s, 1H), 8.81-8.67 (m, 1H), 8.55 (d, J=8 Hz, 1H), 8.24-8.09 (m, 3H), 7.46-7.42 (m, 1H), 4.45-4.28 (m, 2H), 3.05-3.01 (m, 2H), 2.77 (d, J=8 Hz, 2H). LCMS: m/z 466 $(M+H)^+$.

3-((4-((Cyclopropylmethyl)amino)-6-(6-(trifluoromethyl)pyridin-2-yl)-1,3,5-triazin-2-yl)amino)-5-fluorobenzonitrile

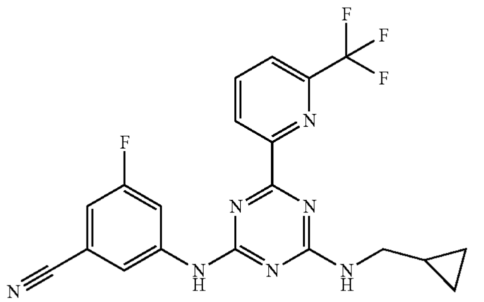 [SMILES: N#Cc1cc(F)cc(Nc2nc(NCC3CC3)nc(-c3cccc(C(F)(F)F)n3)n2)c1]

$^1$H NMR (400 MHz, $CDCl_3$) δ 8.59-8.49 (m, 1H), 8.01-7.97 (m, 1H), 7.83-7.74 (m, 3H), 7.56 (s, 1H), 6.99-6.96 (m, 1H), 5.83-5.62 (m, 1H), 3.43-3.30 (m, 2H), 1.07 (d, J=4 Hz, 1H), 0.57-0.52 (m, 2H), 0.29-0.24 (m, 2H). LCMS: m/z 430 $(M+H)^+$.

3-Fluoro-5-((4-((2-hydroxy-2-methylpropyl)amino)-6-(6-(trifluoromethyl)pyridin-2-yl)-1,3,5-triazin-2-yl)amino)benzonitrile

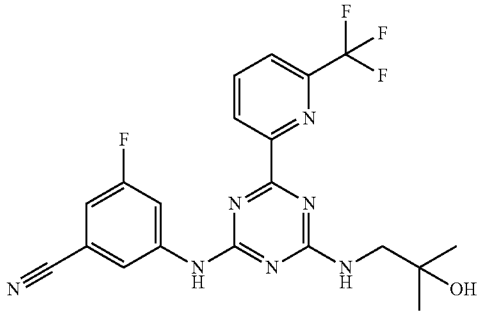 [SMILES: CC(C)(O)CNc1nc(Nc2cc(F)cc(C#N)c2)nc(-c2cccc(C(F)(F)F)n2)n1]

$^1$H NMR (400 MHz, DMSO-$d_6$) δ 10.44 (s, 1H), 8.61 (m, 1H), 8.24 (m, 5H), 7.43 (t, J=8.8 Hz, 1H), 4.61 (m, 1H), 3.45 (m, 2H), 1.18 (d, J=4.4 Hz, 6H). LCMS: m/z 448 $(M+H)^+$.

1-((4-((3-Chlorophenyl)amino)-6-(6-(trifluoromethyl)pyridin-2-yl)-1,3,5-triazin-2-yl)amino)-2-methylpropan-2-ol

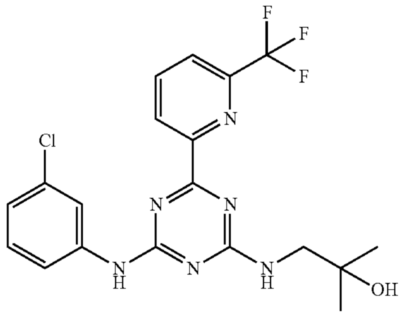 [SMILES: CC(C)(O)CNc1nc(Nc2cccc(Cl)c2)nc(-c2cccc(C(F)(F)F)n2)n1]

$^1$H NMR (400 MHz, DMSO-$d_6$) δ 10.11 (m 1H), 8.67-8.52 (m, 1H), 8.40-8.20 (m, 2H), 8.09 (d, J=7.8 Hz, 1H), 7.90 (s, 1H), 7.67 (d, J=7.7 Hz, 1H), 7.40-7.22 (m, 1H), 7.05 (t, J=7.2 Hz, 1H), 4.75-4.40 (m, 1H), 3.44 (m 2H), 1.17 (d, J=6.4 Hz, 6H). LCMS: m/z 439 $(M+H)^+$.

3-((4-(Tert-butylamino)-6-(6-(trifluoromethyl)pyridin-2-yl)-1,3,5-triazin-2-yl)amino)benzonitrile

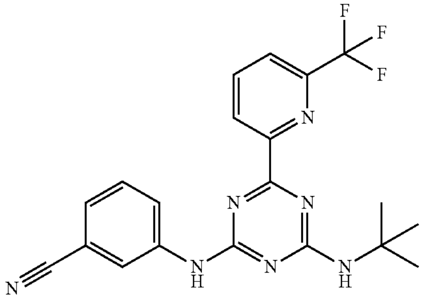 [SMILES: CC(C)(C)Nc1nc(Nc2cccc(C#N)c2)nc(-c2cccc(C(F)(F)F)n2)n1]

$^1$H NMR (400 MHz, DMSO-$d_6$) δ 10.80-10.20 (m, 1H), 9.50-9.25 (m, 1H), 8.36-7.96 (m, 4H), 7.50-7.40 (m, 1H), 1.47 (s, 9H). LCMS: m/z 414 $(M+H)^+$.

$N^2$-(3,3-difluorocyclopentyl)-$N^4$-(3,5-difluorophenyl)-6-(6-(trifluoromethyl)pyridin-2-yl)-1,3,5-triazine-2,4-diamine

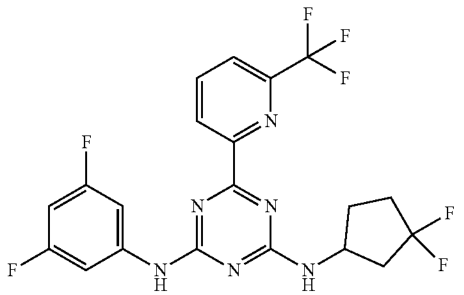 [SMILES: Fc1cc(F)cc(Nc2nc(NC3CCC(F)(F)C3)nc(-c3cccc(C(F)(F)F)n3)n2)c1]

$^1$H NMR (400 MHz, $CDCl_3$) δ 8.59 (m, 1H), 8.06 (t, J=7.8 Hz, 1H), 7.84 (d, J=7.7 Hz, 1H), 7.41 (m, 3H), 6.56 (t, J=8.8 Hz, 1H), 5.74 (m, 1H), 4.83-4.53 (m, 1H), 2.79-2.60 (m, 1H), 2.46-2.06 (m, 4H), 1.95-1.81 (m, 1H). LC-MS: m/z 473 $(M+H)^+$.

$N^2$-(4,4-difluorocyclohexyl)-$N^4$-(3,5-difluorophenyl)-6-(6-(trifluoromethyl)pyridin-2-yl)-1,3,5-triazine-2,4-diamine

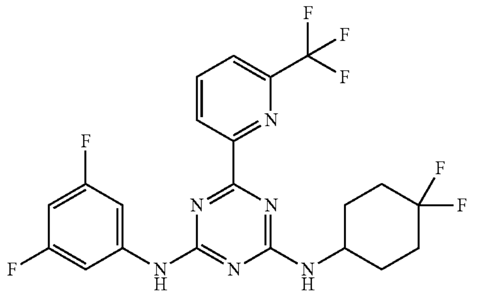

$^1$H NMR (400 MHz, $CDCl_3$) δ 8.50 (d, J=10.5 Hz, 1H), 7.98 (t, J=7.7 Hz, 1H), 7.76 (d, J=7.7 Hz, 1H), 7.25 (d, J=7.6 Hz, 2H), 6.48 (t, J=8.9 Hz, 1H), 5.67-5.34 (m, 1H), 4.14-3.96 (m, 1H), 2.13-2.11 (m, 4H), 2.00-1.74 (m, 5H). LC-MS: m/z 487.2 $(M+H)^+$.

$N^2$-(4,4-difluorocyclohexyl)-$N^4$-(2-phenylpyridin-4-yl)-6-(6-(trifluoromethyl)pyridin-2-yl)-1,3,5-triazine-2,4-diamine

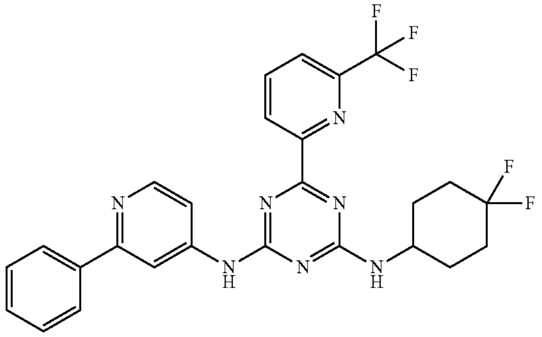 [SMILES: FC1(F)CCC(Nc2nc(Nc3ccnc(-c4ccccc4)c3)nc(-c3cccc(C(F)(F)F)n3)n2)CC1]

$^1$H NMR (400 MHz, $CDCl_3$) δ 8.59-8.58 (m, 2H), 8.30 (s, 1H), 8.08-7.81 (m, 5H), 7.50-7.42 (m, 4H), 5.87-5.85 (m, 1H), 4.22-4.10 (m, 1H), 2.15-1.68 (m, 8H). LC-MS: m/z 528 $(M+H)^+$.

$N^2$-(3,3-difluorocyclopentyl)-$N^4$-(2-phenylpyridin-4-yl)-6-(6-(trifluoromethyl)pyridin-2-yl)-1,3,5-triazine-2,4-diamine

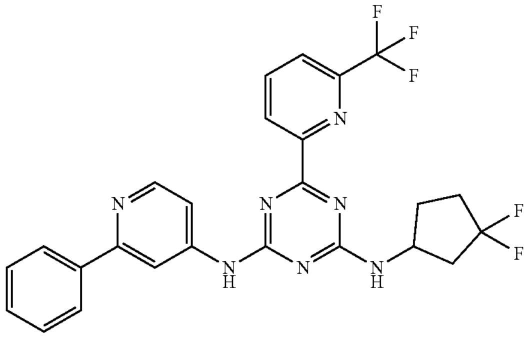 [SMILES: FC1(F)CCC(Nc2nc(Nc3ccnc(-c4ccccc4)c3)nc(-c3cccc(C(F)(F)F)n3)n2)C1]

$^1$H NMR (400 MHz, $CDCl_3$) δ 8.61 (m, 2H), 8.31-7.69 (m, 6H), 7.69-7.40 (m, 4H), 5.87 (m, 1H), 4.72 (m, 1H), 2.69 (m, 1H), 2.34 (m, 2H), 2.14 (m, 2H), 1.86-1.80 (m, 1H). LC-MS: m/z 514 $(M+H)^+$.

$N^2$-(2-phenylpyridin-4-yl)-6-(6-(trifluoromethyl)pyridin-2-yl)-$N^4$-(1,1,1-trifluoropropan-2-yl)-1,3,5-triazine-2,4-diamine

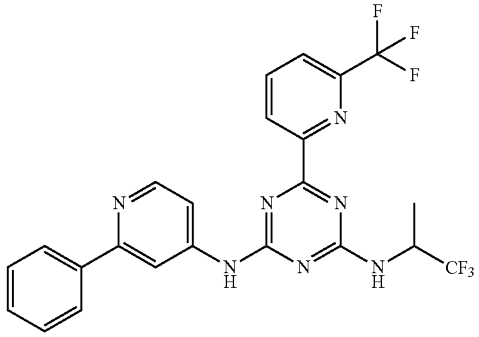 [SMILES: CC(Nc1nc(Nc2ccnc(-c3ccccc3)c2)nc(-c2cccc(C(F)(F)F)n2)n1)C(F)(F)F]

$^1$H NMR (400 MHz, $CDCl_3$) δ 8.63 (m, 2H), 8.04 (m, 6H), 7.62-7.30 (m, 5H), 5.81 (d, J=9.1 Hz, 1H), 5.39 (m, 1H), 5.00 (m, 1H), 1.50 (d, J=7.0 Hz, 3H). LC-MS: m/z 506 $(M+H)^+$.

(R)—$N^2$-(2-phenylpyridin-4-yl)-6-(6-(trifluoromethyl)pyridin-2-yl)-$N^4$-(1,1,1-trifluoropropan-2-yl)-1,3,5-triazine-2,4-diamine

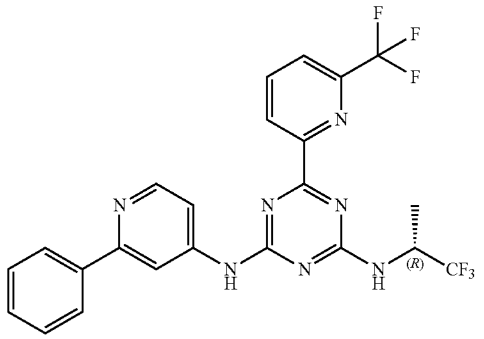

$^1$H NMR (400 MHz, $CDCl_3$) δ 8.67-8.58 (m, 2H), 8.14 (m, 2H), 8.01 (d, J=7.0 Hz, 2H), 7.88 (d, J=7.6 Hz, 1H), 7.71-7.34 (m, 5H), 5.69 (m, 1H), 5.22-4.92 (m, 1H), 1.49 (d, J=7.1 Hz, 3H). LC-MS: m/z 506 $(M+H)^+$.

(R)-4-(4-((4-(6-(trifluoromethyl)pyridin-2-yl)-6-((1,1,1-trifluoropropan-2-yl)amino)-1,3,5-triazin-2-yl)amino)pyridin-2-yl)benzonitrile

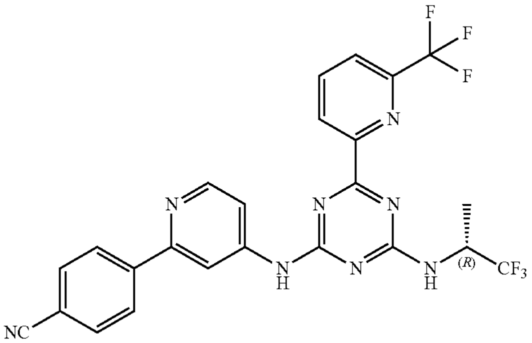

$^1$H NMR (400 MHz, $CDCl_3$) δ 8.87-8.53 (m, 2H), 8.42 (s, 1H), 8.11 (d, J=8.0 Hz, 3H), 7.96-7.76 (m, 4H), 7.40 (s, 1H), 5.86-5.67 (m, 1H), 5.18-4.91 (m, 1H), 1.62-1.47 (m, 3H). LC-MS: m/z 531 $(M+H)^+$.

(R)—$N^2$-(2-(4-fluorophenyl)pyridin-4-yl)-6-(6-(trifluoromethyl)pyridin-2-yl)-$N^4$-(1,1,1-trifluoropropan-2-yl)-1,3,5-triazine-2,4-diamine

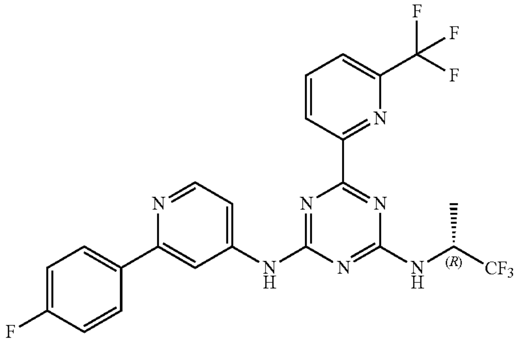

$^1$H NMR (400 MHz, $CDCl_3$) δ 8.61 (d, J=8.0 Hz, 2H), 8.27 (s, 1H), 8.13-7.64 (m, 5H), 7.36 (s, 1H), 7.17 (t, J=8.6 Hz, 2H), 6.83-6.64 (m, 1H), 6.16-4.96 (m, 1H), 1.50 (d, J=7.5 Hz, 3H). LC-MS: m/z 524.1 $(M+H)^+$.

(R)—$N^2$-(2-(4-chlorophenyl)pyridin-4-yl)-6-(6-(trifluoromethyl)pyridin-2-yl)-$N^4$-(1,1,1-trifluoropropan-2-yl)-1,3,5-triazine-2,4-diamine

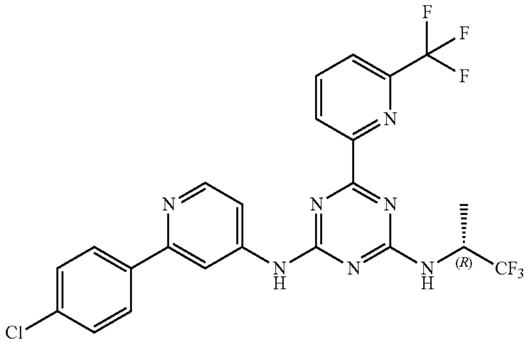

$^1$H NMR (400 MHz, $CDCl_3$) δ 8.61 (t, J=6.4 Hz, 2H), 8.31-8.05 (m, 2H), 7.95 (d, J=8.5 Hz, 2H), 7.89 (d, J=7.8 Hz, 1H), 7.46 (d, J=8.4 Hz, 2H), 6.10-5.91 (m, 1H), 5.22-4.91 (m, 1H), 1.51 (t, J=7.7 Hz, 3H). LC-MS: m/z 540 $(M+H)^+$.

N$^2$-(3,3-difluorocyclopentyl)-N$^4$-(1H-indol-2-yl)-6-(6-(trifluoromethyl)pyridin-2-yl)-1,3,5-triazine-2,4-diamine

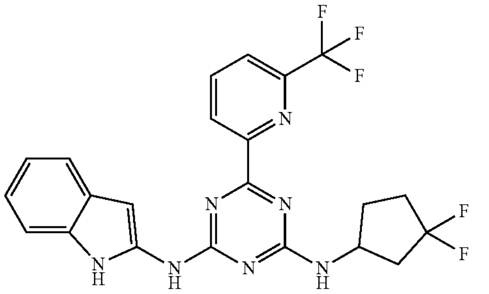 [SMILES: FC1(F)CCC(Nc2nc(Nc3cc4ccccc4[nH]3)nc(-c3cccc(C(F)(F)F)n3)n2)C1]

$^1$H NMR (400 MHz, DMSO-d$_6$) δ 10.76 (s, 1H), 8.82-8.55 (m, 1H), 8.16 (m, 4H), 7.68 (m, 2H), 7.02 (m, 3H), 4.98 (m, 1H), 2.68 (s, 1H), 2.23 (m, 4H), 1.97 (m, 1H). LC-MS: m/z 476 (M+H)$^+$.

N$^2$-(3,3-difluorocyclopentyl)-N$^4$-(1-methyl-1H-indol-2-yl)-6-(6-(trifluoromethyl)pyridin-2-yl)-1,3,5-triazine-2,4-diamine

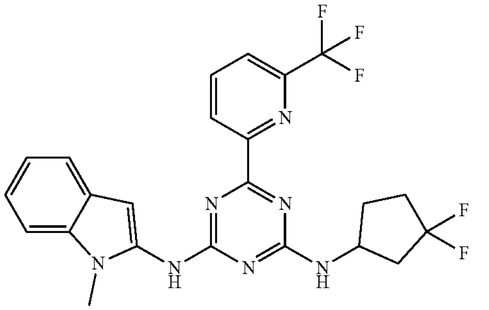 [SMILES: Cn1c(Nc2nc(NC3CCC(F)(F)C3)nc(-c3cccc(C(F)(F)F)n3)n2)cc2ccccc21]

$^1$H NMR (400 MHz, CDCl$_3$) δ 8.54 (s, 1H), 8.35 (d, J=6.8 Hz, 1H), 8.10 (s, 1H), 7.81 (d, J=7.5 Hz, 1H), 7.17 (m, 4H), 5.57 (m, 1H), 4.83 (m, 1H), 3.59 (s, 3H), 2.94-2.06 (m, 7H). LCMS: m/z 490 (M+H)$^+$.

1-(4-((4-((4,4-difluorocyclohexyl)amino)-6-(6-(1,1-difluoroethyl)pyridin-2-yl)-1,3,5-triazin-2-yl)amino)pyridin-2-yl)cyclopropanecarbonitrile

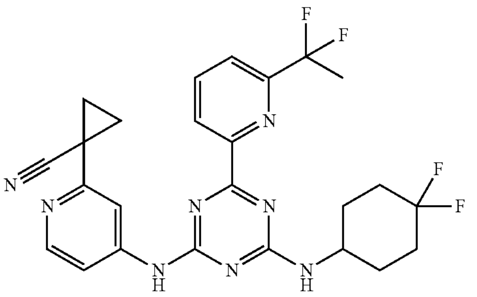 [SMILES: CC(F)(F)c1cccc(-c2nc(Nc3ccnc(C4(C#N)CC4)c3)nc(NC3CCC(F)(F)CC3)n2)n1]

$^1$H NMR (400 MHz, CDCl$_3$) δ 8.54 (m, 2H), 8.32 (d, J=5.5 Hz, 1H), 8.02 (d, J=7.8 Hz, 1H), 7.84 (d, J=8.0 Hz, 1H), 7.59 (m, 1H), 7.20 (s, 1H), 5.71 (d, J=7.9 Hz, 1H), 4.34 (m, 1H), 2.15 (m, 9H), 1.85 (m, 2H), 1.23 (m, 1H). LC-MS: m/z 513 (M+H)$^+$.

1-(4-((4-((3,3-Difluorocyclopentyl)amino)-6-(6-(1,1-difluoroethyl)pyridin-2-yl)-1,3,5-triazin-2-yl)amino)pyridin-2-yl)cyclopropanecarbonitrile

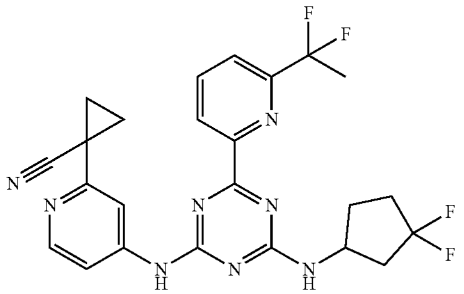 [SMILES: CC(F)(F)c1cccc(-c2nc(Nc3ccnc(C4(C#N)CC4)c3)nc(NC3CCC(F)(F)C3)n2)n1]

$^1$H NMR (400 MHz, CDCl$_3$) δ 8.61 (s, 1H), 8.53 (s, 1H), 8.30 (d, J=4 Hz, 1H), 8.02-7.98 (m, 1H), 7.82 (d, J=8 Hz, 1H), 7.52-7.10 (m, 2H), 5.93-5.60 (m, 1H), 4.87-4.75 (m, 1H), 2.74-2.71 (m, 1H), 2.44 (m, 1H), 2.18-2.04 (m, 5H), 1.89-1.85 (m, 3H), 1.72 (m, 3H). LCMS: m/z 499 (M+H)$^+$.

1-(4-((4-((3,3-Difluorocyclobutyl)amino)-6-(6-(1,1-difluoroethyl)pyridin-2-yl)-1,3,5-triazin-2-yl)amino)pyridin-2-yl)cyclopropanecarbonitrile

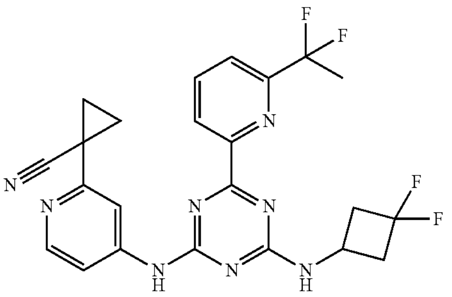 [SMILES: CC(F)(F)c1cccc(-c2nc(Nc3ccnc(C4(C#N)CC4)c3)nc(NC3CC(F)(F)C3)n2)n1]

$^1$H NMR (400 MHz, CDCl$_3$) δ10.43 (m, 1H), 8.78 (d, J=4.1 Hz, 1H), 8.61 (d, J=7.8 Hz, 1H), 8.32 (d, J=5.6 Hz, 2H), 8.12 (m, 1H), 7.9 (m, 1H), 7.88 (m, 1H), 4.45 (s, 1H), 3.03 (m, 2H), 2.78 (m, 2H), 2.13 (m, 3H), 1.43 (m, 4H). LC-MS: m/z 485 (M+H)$^+$.

(R)-1-(4-((4-(6-(1,1-difluoroethyl)pyridin-2-yl)-6-((1,1,1-trifluoropropan-2-yl)amino)-1,3,5-triazin-2-yl)amino)pyridin-2-yl)cyclopropanecarbonitrile

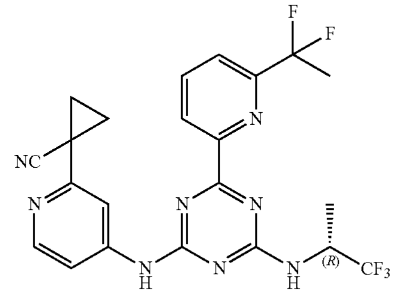

$^1$H NMR (400 MHz, $CDCl_3$) δ 8.59-8.52 (m, 1H), 8.46-8.45 (d, J=4 Hz, 1H), 8.32-8.25 (m, 1H), 8.02-7.98 (m, 1H), 7.82 (d, J=8 Hz, 1H), 7.69-7.50 (m, 1H), 7.21-7.00 (m, 1H), 5.83-5.56 (m, 1H), 5.18-5.07 (m, 1H), 2.18-2.07 (m, 3H), 1.87-1.85 (m, 2H), 1.73-1.71 (m, 2H), 1.50-1.46 (m, 3H). LCMS: m/z 491 $(M+H)^+$.

(S)-1-(4-((4-(6-(1,1-difluoroethyl)pyridin-2-yl)-6-((1,1,1-trifluoropropan-2-yl)amino)-1,3,5-triazin-2-yl)amino)pyridin-2-yl)cyclopropanecarbonitrile

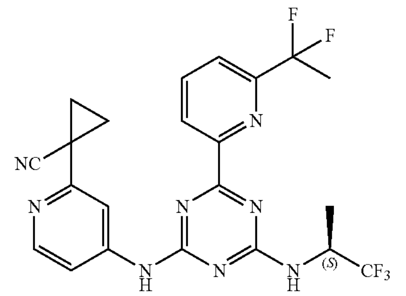

$^1$H NMR (400 MHz, $CDCl_3$) δ 8.59-8.52 (m, 1H), 8.46 (s, 1H), 8.33-8.32 (d, J=4 Hz, 1H) 8.03-7.99 (m, 1H), 7.92-7.84 (m, 1H), 7.52 (s, 1H), 7.26-7.22 (d, J=16 Hz, 1H), 5.85-5.59 (m, 1H), 5.18-5.09 (m, 1H), 2.18-2.09 (m, 3H), 1.88-1.85 (m, 4H), 1.51-1.48 (m, 3H). LCMS: m/z 491 $(M+H)^+$.

1-((4-((3-Chloro-5-fluorophenyl)amino)-6-(6-(1,1-difluoroethyl)pyridin-2-yl)-1,3,5-triazin-2-yl)amino)-2-methylpropan-2-ol

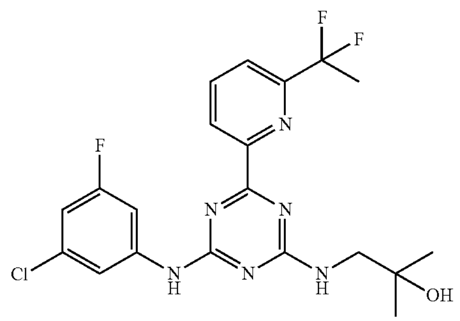 [SMILES: CC(C)(O)CNc1nc(Nc2cc(F)cc(Cl)c2)nc(-c2cccc(C(C)(F)F)n2)n1]

$^1$H NMR (400 MHz, DMSO-$d_6$) δ 10.19 (s, 1H), 8.43 (m, 1H), 8.17 (m, 1H), 7.88 (m, 3H), 7.00 (d, J=7.9 Hz, 1H), 4.54 (s, 1H), 3.45 (m, 2H), 2.10 (m, 3H), 1.17 (m, J=7.0 Hz, 6H). LC-MS: m/z 453 $(M+H)^+$.

3-((4-(6-(1,1-Difluoroethyl)pyridin-2-yl)-6-((2-hydroxy-2-methylpropyl)amino)-1,3,5-triazin-2-yl)amino)-5-fluorobenzonitrile

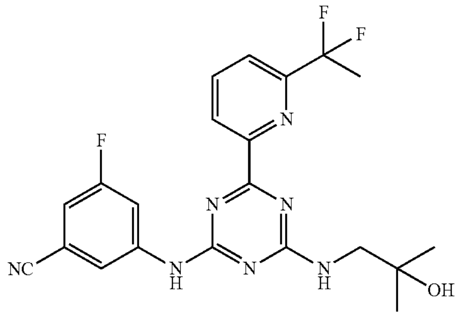 [SMILES: CC(C)(O)CNc1nc(Nc2cc(F)cc(C#N)c2)nc(-c2cccc(C(C)(F)F)n2)n1]

1H NMR (400 MHz, $CDCl_3$) δ8.40-8.42 (d, J=8 Hz, 1H), 7.74-7.99 (m, 5H), 7.03 (m, 1H), 6.16-6.25 (m, 1H), 3.49-3.64 (m, 2H), 2.05-2.21 (m, 3H), 1.33 (s, 6H); LC-MS: m/z 444 $(M+H)^+$.

1-((4-(6-(1,1-Difluoroethyl)pyridin-2-yl)-6-((3-fluoro-5-(trifluoromethyl)phenyl)amino)-1,3,5-triazin-2-yl)amino)-2-methylpropan-2-ol

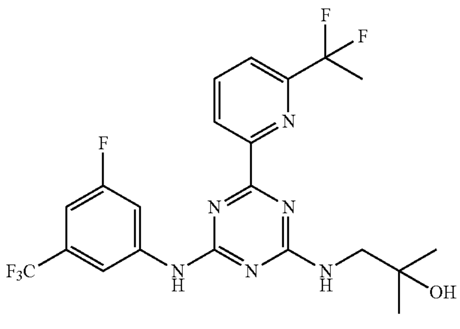

$^1$H NMR (400 MHz, $CDCl_3$) δ 8.42 (bs, 1H), 7.57-7.96 (m, 5H), 6.99-7.03 (m, 1H), 6.16-6.28 (m, 1H), 3.54-3.62 (m, 2H), 2.00-2.21 (m, 3H), 2.07-2.22 (m, 3H), 1.28 (s, 6H). LC-MS: m/z 487 $(M+H)^+$.

1-(4-((4-(6-Chloropyridin-2-yl)-6-((3,3-difluorocyclopentyl)amino)-1,3,5-triazin-2-yl)amino)pyridin-2-yl)cyclopropanecarbonitrile

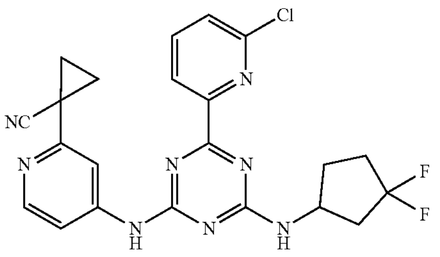 [SMILES: N#CC1(c2cc(Nc3nc(NC4CCC(F)(F)C4)nc(-c4cccc(Cl)n4)n3)ccn2)CC1]

$^1$H NMR (400 MHz, $CDCl_3$) δ 8.68 (s, 1H), 8.53-8.43 (m, 1H), 8.30 (d, J=4 Hz, 1H), 7.86-7.72 (m, 1H), 7.59-7.49 (m, 2H), 7.27-6.99 (m, 1H), 5.96-5.71 (m, 1H), 4.96-4.88 (m, 1H), 2.76-2.70 (m, 1H), 2.43-2.07 (m, 4H), 1.89-1.79 (m, 3H), 1.75-1.72 (m, 2H). LCMS: m/z 469 $(M+H)^+$.

(R)-1-(4-((4-(6-chloropyridin-2-yl)-6-((1-cyclopropylethyl)amino)-1,3,5-triazin-2-yl)amino)pyridin-2-yl)cyclopropanecarbonitrile

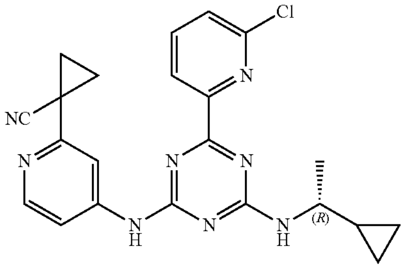

$^1$H NMR (400 MHz, $CDCl_3$) δ 8.43 (s, 2H), 8.23 (d, J=8 Hz, 1H), 7.80-7.76 (m, 1H), 7.43 (d, J=8 Hz, 2H), 7.05-7.03 (m, 1H), 5.79-5.50 (m, 1H), 3.70-3.67 (m, 1H), 1.80-1.77 (m, 2H), 1.66-1.59 (m, 2H), 1.29-1.18 (m, 4H), 0.93-0.78 (m, 1H), 0.48-0.33 (m, 4H). LCMS: m/z 433 $(M+H)^+$.

1-(4-((4-(6-Chloropyridin-2-yl)-6-((2,2,2-trifluoroethyl)amino)-1,3,5-triazin-2-yl)amino)pyridin-2-yl) cyclopropanecarbonitrile

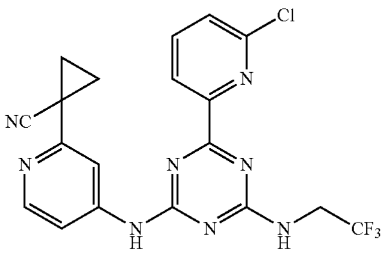 [SMILES: N#CC1(c2cc(Nc3nc(NCC(F)(F)F)nc(-c4cccc(Cl)n4)n3)ccn2)CC1]

$^1$H NMR (400 MHz, $CDCl_3$) δ 8.54-8.42 (m, 2H), 8.33-8.29 (m, 1H), 7.88-7.50 (m, 3H), 7.14-7.08 (m, 1H), 6.19-5.99 (m, 1H), 4.31 (s, 2H), 1.88-1.71 (m, 4H). LCMS: m/z 447 $(M+H)^+$.

1-(4-((4-(6-Chloropyridin-2-yl)-6-((1,1,1-trifluoropropan-2-yl)amino)-1,3,5-triazin-2-yl)amino)pyridin-2-yl)cyclopropanecarbonitrile

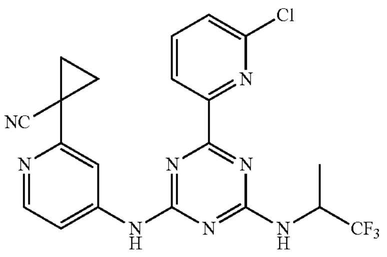 [SMILES: CC(Nc1nc(Nc2ccnc(C3(C#N)CC3)c2)nc(-c2cccc(Cl)n2)n1)C(F)(F)F]

$^1$H NMR (400 MHz, $CDCl_3$) δ 8.56-8.43 (m, 2H), 8.32 (d, J=4 Hz, 1H), 7.88-7.84 (m, 1H), 7.73-7.50 (m, 2H), 7.07-7.00 (m, 1H), 5.85-5.57 (m, 1H), 5.30-5.07 (m, 1H), 1.90-1.73 (m, 4H), 1.50-1.46 (m, 3H). LCMS: m/z 461 $(M+H)^+$.

6-(6-Chloropyridin-2-yl)-$N^2$-(3,3-difluorocyclopentyl)-$N^4$-(2-(trifluoromethyl)pyridin-4-yl)-1,3,5-triazine-2,4-diamine

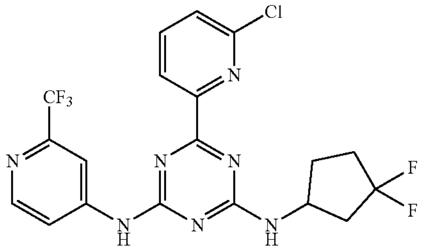 [SMILES: FC1(F)CCC(Nc2nc(Nc3ccnc(C(F)(F)F)c3)nc(-c3cccc(Cl)n3)n2)C1]

$^1$H NMR (400 MHz, $CDCl_3$) δ 8.61-8.53 (m, 2H), 8.41-8.33 (m, 1H), 8.13-7.78 (m, 2H), 7.68-7.27 (m, 2H), 5.95-5.61 (m, 1H), 4.79-4.60 (m, 1H), 2.74-2.65 (m, 1H), 2.44-2.29 (m, 2H), 2.25-2.09 (m, 2H), 1.92-1.83 (m, 1H). LCMS: m/z 472 $(M+H)^+$.

6-(6-Chloropyridin-2-yl)-N2-(cyclopropylmethyl)-N4-(2-(trifluoromethyl)pyridin-4-yl)-1,3,5-triazine-2,4-diamine

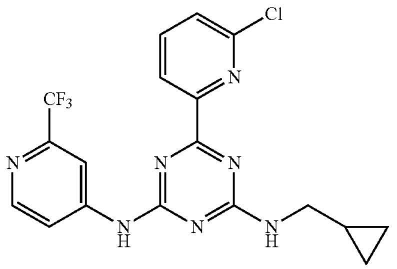 [SMILES: FC(F)(F)c1cc(Nc2nc(NCC3CC3)nc(-c3cccc(Cl)n3)n2)ccn1]

$^1$H NMR (400 MHz, $CDCl_3$) δ 8.60-8.57 (m, 1H), 8.52-8.42 (m, 1H), 8.36-8.19 (m, 1H), 7.86-7.68 (m, 2H), 7.51 (d, J=8 Hz, 2H), 5.96-5.65 (m, 1H), 3.51-3.39 (m, 2H), 1.16 (d, J=8 Hz, 1H), 0.63-0.60 (m, 2H), 0.35-0.30 (m, 2H). LCMS: m/z 422 $(M+H)^+$.

1-(4-((4-((3,3-Difluorocyclobutyl)amino)-6-(6-(trifluoromethyl)pyrazin-2-yl)-1,3,5-triazin-2-yl)amino)pyridin-2-yl)cyclopropanecarbonitrile

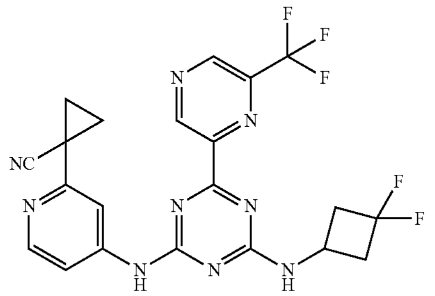 [SMILES: N#CC1(c2cc(Nc3nc(NC4CC(F)(F)C4)nc(-c4cncc(C(F)(F)F)n4)n3)ccn2)CC1]

$^1$H NMR (400 MHZz, $CDCl_3$) δ 9.84 (s, 1H), 9.12 (s, 1H), 8.49-8.31 (m, 2H), 7.78-7.68 (m, 1H), 7.15 (s, 1H), 6.16-5.98 (m, 1H), 4.73-4.58 (m, 1H), 3.22 (d, J=8 Hz, 2H), 2.62-2.54 (m, 2H), 1.89-1.79 (m, 4H). LCMS: m/z 490 $(M+H)^+$.

1-(4-((4-((4,4-Difluorocyclohexyl)amino)-6-(6-(trifluoromethyl)pyrazin-2-yl)-1,3,5-triazin-2-yl)amino)pyridin-2-yl)cyclopropanecarbonitrile

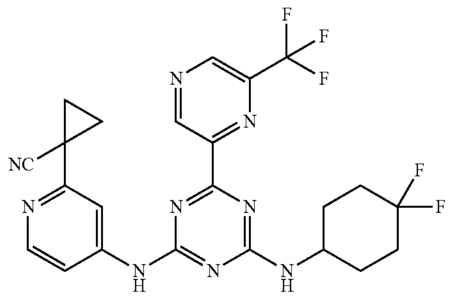 [SMILES: N#CC1(c2cc(Nc3nc(NC4CCC(F)(F)CC4)nc(-c4cncc(C(F)(F)F)n4)n3)ccn2)CC1]

$^1$H NMR (400 MHz, $CDCl_3$) δ 9.84 (d, J=4 Hz, 1H), 9.12 (s, 1H), 8.49 (s, 1H), 8.34-8.31 (m, 1H), 7.72-7.63 (m, 1H), 7.27-7.13 (m, 1H), 5.79-5.58 (m, 1H), 4.36-4.26 (m, 1H), 2.20-2.13 (m, 4H), 1.90-1.72 (m, 8H). LCMS: m/z 518 $(M+H)^+$.

1-(4-((4-((6,6-Difluorospiro[3.3]heptan-2-yl)amino)-6-(6-(trifluoromethyl)pyrazin-2-yl)-1,3,5-triazin-2-yl)amino)pyridin-2-yl)cyclopropanecarbonitrile

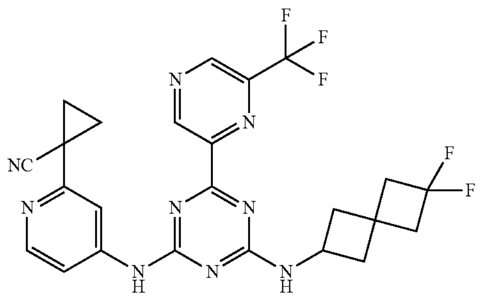 [SMILES: N#CC1(c2cc(Nc3nc(NC4CC5(C4)CC(F)(F)C5)nc(-c4cncc(C(F)(F)F)n4)n3)ccn2)CC1]

$^1$H NMR (400 MHz, DMSO-$d_6$) δ 10.53 (s, 1H), 9.84-9.75 (m, 1H), 9.39 (d, J=8 Hz, 1H), 8.80 (d, J=8 Hz, 1H), 8.41-8.21 (m, 2H), 7.83-7.56 (m, 1H), 4.57 (d, J=8 Hz, 1H), 2.71-2.57 (m, 6H), 2.27-2.22 (m, 2H), 1.81-1.67 (m, 4H). LCMS: m/z 530 $(M+H)^+$.

(R)-1-(4-((4-((3,3-difluorocyclopentyl)amino)-6-(6-(trifluoromethyl)pyrazin-2-yl)-1,3,5-triazin-2-yl)amino)pyridin-2-yl)cyclopropanecarbonitrile

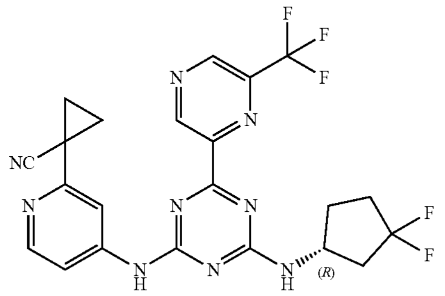

$^1$H NMR (400 MHz, DMSO-$d_6$) δ 10.58 (s, 1H), 9.87-9.77 (m, 1H), 9.39 (d, J=4 Hz, 1H), 8.77 (d, J=4 Hz, 1H), 8.42-8.32 (m, 2H), 7.82-7.57 (m, 1H), 4.67 (m, 1H), 2.67-1.69 (m, 10H).

LCMS: m/z 504 $(M+H)^+$.

(S)-1-(4-((4-((3,3-difluorocyclopentyl)amino)-6-(6-(trifluoromethyl)pyrazin-2-yl)-1,3,5-triazin-2-yl)amino)pyridin-2-yl)cyclopropanecarbonitrile

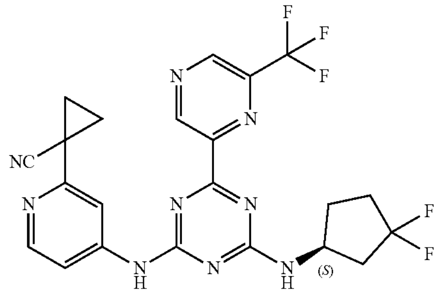

$^1$H NMR (400 MHz, $CDCl_3$) δ 9.85 (s, 1H), 9.12 (s, 1H), 8.61-8.44 (m, 1H), 8.33 (d, J=8 Hz, 1H), 7.52 (s, 1H), 7.00 (s, 1H), 5.97-5.75 (m, 1H), 4.94-4.75 (m, 1H), 2.75-1.73 (m, 10H).

LCMS: m/z 504 $(M+H)^+$.

(R)-1-(4-((4-(6-(trifluoromethyl)pyrazin-2-yl)-6-((1,1,1-trifluoropropan-2-yl)amino)-1,3,5-triazin-2-yl)amino)pyridin-2-yl)cyclopropanecarbonitrile

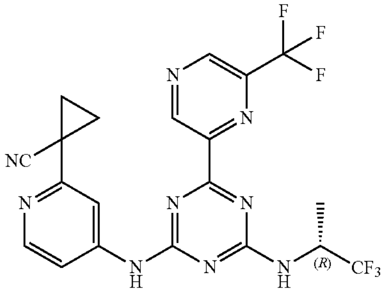

$^1$H NMR (400 MHz, $CDCl_3$) δ 9.90-9.84 (m, 1H), 9.14 (s, 1H), 8.43-8.35 (m, 2H), 7.52-7.15 (m, 2H), 5.86-5.60 (m, 1H), 5.14-4.80 (m, 1H), 1.87 (d, J=8 Hz, 2H), 1.74 (m, 2H), 1.50-1.57 (m, 3H). LCMS: m/z 496 $(M+H)^+$.

(R)—$N^2$-(3,3-difluorocyclopentyl)-6-(6-(trifluoromethyl)pyrazin-2-yl)-$N^4$-(2-(trifluoromethyl)pyridin-4-yl)-1,3,5-triazine-2,4-diamine

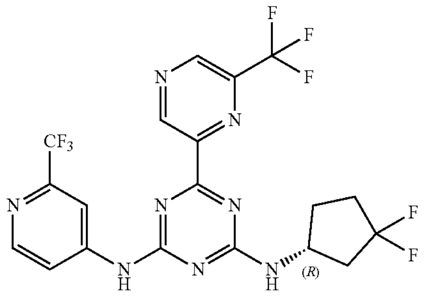

$^1$H NMR (400 MHz, $CDCl_3$) δ 9.81 (m 1H), 9.14 (d, J=3.6 Hz, 1H), 8.81-8.14 (m, 2H), 8.07-7.37 (m, 2H), 6.30-5.59 (m, 1H), 4.82-4.62 (m, 1H), 2.70 (m, 1H), 2.57-2.09 (m, 4H), 2.01-1.84 (m, 1H). LC-MS: m/z 507 $(M+H)^+$.

(S)—$N^2$-(3,3-difluorocyclopentyl)-6-(6-(trifluoromethyl)pyrazin-2-yl)-$N^4$-(2-(trifluoromethyl)pyridin-4-yl)-1,3,5-triazine-2,4-diamine

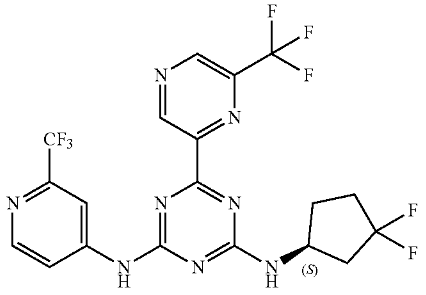

$^1$H NMR (400 MHz, $CDCl_3$) δ 9.81 (m, 1H), 9.14 (d, J=3.1 Hz, 1H), 8.74-8.08 (m, 2H), 8.06-7.29 (m, 2H), 6.22-5.58 (m, 1H), 4.85-4.50 (m, 1H), 2.70 (m, 1H), 2.52-2.09 (m, 4H), 2.01-1.82 (m, 1H). LC-MS: m/z 507 $(M+H)^+$.

$N^2$-(3,3-difluorocyclobutyl)-6-(6-(trifluoromethyl)pyrazin-2-yl)-$N^4$-(2-(trifluoromethyl)pyridin-4-yl)-1,3,5-triazine-2,4-diamine

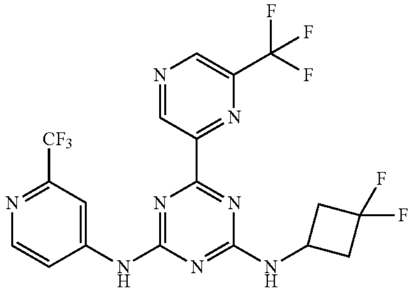 [SMILES: FC1(F)CC(Nc2nc(Nc3ccnc(C(F)(F)F)c3)nc(-c3cncc(C(F)(F)F)n3)n2)C1]

$^1$H NMR (400 MHz, $CDCl_3$) δ 9.81 (d, J=13.8 Hz, 1H), 9.14 (d, J=3.5 Hz, 1H), 8.80-8.19 (m, 2H), 7.99-7.41 (m, 2H), 6.31-5.71 (m, 1H), 4.70-4.39 (m, 1H), 3.29-3.06 (m, 2H), 2.88-2.47 (m, 2H). LC-MS: m/z 493 $(M+H)^+$.

$N^2$-(4,4-difluorocyclohexyl)-6-(6-(trifluoromethyl)pyrazin-2-yl)-$N^4$-(2-(trifluoromethyl)pyridin-4-yl)-1,3,5-triazine-2,4-diamine

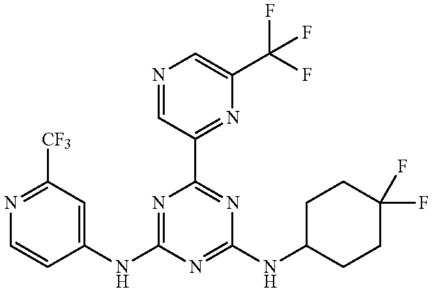 [SMILES: FC1(F)CCC(Nc2nc(Nc3ccnc(C(F)(F)F)c3)nc(-c3cncc(C(F)(F)F)n3)n2)CC1]

$^1$H NMR (400 MHz, $CDCl_3$) δ 9.80 (d, J=8.8 Hz, 1H), 9.14 (d, J=3.4 Hz, 1H), 8.62 (d, J=5.5 Hz, 1H), 8.59-8.20 (m, 1H), 5.83-5.49 (m, 1H), 4.25-4.11 (m, 1H), 2.33-1.71 (m, 6H). LC-MS: m/z 521 $(M+H)^+$.

$N^2$-(cyclopropylmethyl)-6-(6-(trifluoromethyl)pyrazin-2-yl)-N4-(2-(trifluoromethyl)pyridin-4-yl)-1,3,5-triazine-2,4-diamine

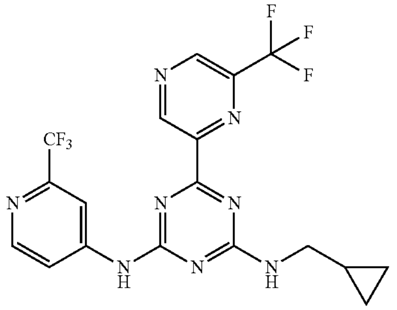 [SMILES: FC(F)(F)c1cc(Nc2nc(NCC3CC3)nc(-c3cncc(C(F)(F)F)n3)n2)ccn1]

$^1$H NMR (400 MHz, DMSO-$d_6$) 82 (s, 4H), 9.20 (s, 4H), 8.73 (s, 3H), 8.49 (t, J=6.2 Hz, 4H), 8.37 (s, 1H), 8.13 (s, 1H), 7.79 (d, J=4.4 Hz, 3H), 3.45-3.30 (m, 8H), 1.29-1.16 (m, 5H), 0.57 (m 8H), 0.39-0.30 (m, 8H). LC-MS: m/z 457 $(M+H)^+$.

N$^2$-(6,6-difluorospiro[3.3]heptan-2-yl)-6-(6-(trifluoromethyl)pyrazin-2-yl)-N$^4$-(2-(trifluoromethyl)pyridin-4-yl)-1,3,5-triazine-2,4-diamine

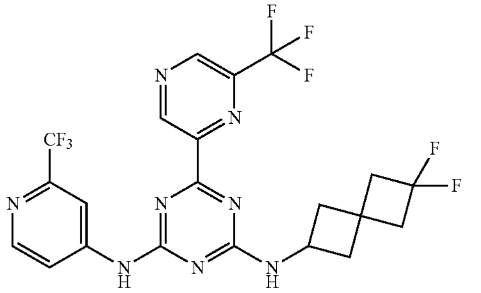 [SMILES: FC1(F)CC2(CC(Nc3nc(Nc4ccnc(C(F)(F)F)c4)nc(-c4cncc(C(F)(F)F)n4)n3)C2)C1]

$^1$H NMR (400 MHz, $CD_3OD$) δ9.84 (d, J=9.0 Hz, 1H), 9.22 (d, J=5.1 Hz, 1H), 8.93-8.35 (m, 2H), 8.14-7.72 (m, 2H), 4.77-4.35 (m, 1H), 2.67 (m, 6H), 2.43-2.15 (m, 2H). LC-MS: m/z 533 $(M+H)^+$.

(S)—N$^2$-(3,3-difluorocyclopentyl)-N$^4$-(3,5-difluorophenyl)-6-(6-(trifluoromethyl)pyrazin-2-yl)-1,3,5-triazine-2,4-diamine

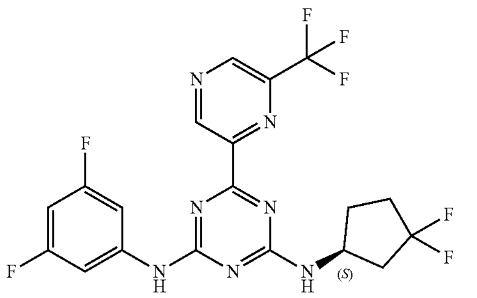

$^1$H NMR (400 MHz, $CDCl_3$) δ 9.80 (m, 1H), 9.12 (d, J=3.1 Hz, 1H), 7.71-7.27 (m, 3H), 6.73-6.44 (m, 1H), 5.98-5.48 (m, 1H), 4.68 (m, 1H), 2.81-2.59 (m, 1H), 2.50-2.02 (m, 4H), 1.97-1.78 (m, 1H). LC-MS: m/z 474 $(M+H)^+$.

(R)—N$^2$-(3,3-difluorocyclopentyl)-N$^4$-(3,5-difluorophenyl)-6-(6-(trifluoromethyl)pyrazin-2-yl)-1,3,5-triazine-2,4-diamine

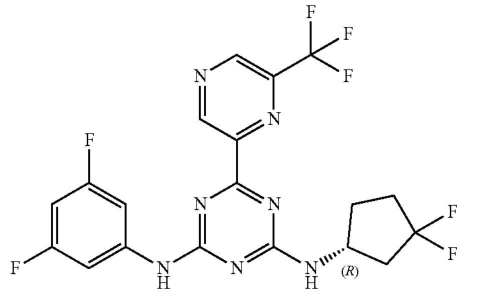

$^1$H NMR (400 MHz, $CDCl_3$) δ 9.80 (m, 1H), 9.12 (d, J=3.1 Hz, 1H), 7.71-7.27 (m, 3H), 6.73-6.44 (m, 1H), 5.98-5.48 (m, 1H), 4.68 (m, 1H), 2.81-2.59 (m, 1H), 2.50-2.02 (m, 4H), 1.97-1.78 (m, 1H). LC-MS: m/z 474 $(M+H)^+$.

N$^2$-(4,4-difluorocyclohexyl)-N$^4$-(3,5-difluorophenyl)-6-(6-(trifluoromethyl)pyrazin-2-yl)-1,3,5-triazine-2,4-diamine

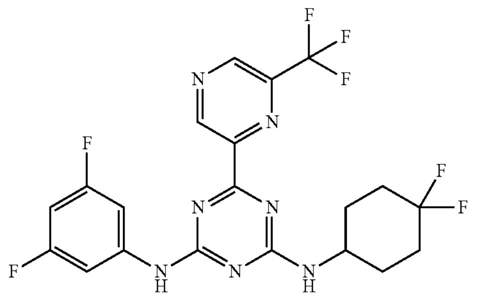 [SMILES: Fc1cc(F)cc(Nc2nc(NC3CCC(F)(F)CC3)nc(-c3cncc(C(F)(F)F)n3)n2)c1]

$^1$H NMR (400 MHz, $CDCl_3$) δ 9.78 (d, J=7.6 Hz, 1H), 9.11 (s, 1H), 7.39 (m, 3H), 6.58 (t, J=8.8 Hz, 1H), 5.76-5.39 (m, 1H), 4.22-4.06 (m, 1H), 2.21 (m, 4H), 1.95 (m, 2H), 1.80-1.68 (m, 2H). LC-MS: m/z 488 $(M+H)^+$.

1-(4-((4-((4,4-Difluorocyclohexyl)amino)-6-(6-(difluoromethyl)pyrazin-2-yl)-1,3,5-triazin-2-yl)amino)pyridin-2-yl)cyclopropanecarbonitrile

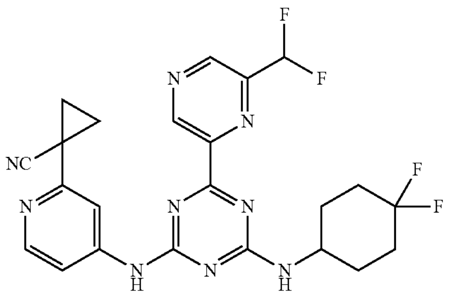 [SMILES: N#CC1(c2cc(Nc3nc(NC4CCC(F)(F)CC4)nc(-c4cncc(C(F)F)n4)n3)ccn2)CC1]

1H NMR (400 MHz, $CDCl_3$) δ 9.79 (d, J=7.0 Hz, 1H), 9.12 (s, 1H), 8.54 (m, 1H), 8.32 (d, J=6.0 Hz, 1H), 7.52 (d,

J=6.1 Hz, 1H), 7.14 (m, 1H), 6.85 (m, 1H), 5.68 (m, 1H), 4.30 (m, 1H), 2.18 (m, 6H), 1.85 (m, 2H), 1.73 (m, 4H). LC-MS: m/z 500 $(M+H)^+$.

(S)-1-(4-((4-(6-(difluoromethyl)pyrazin-2-yl)-6-((1,1,1-trifluoropropan-2-yl)amino)-1,3,5-triazin-2-yl)amino)pyridin-2-yl)cyclopropanecarbonitrile

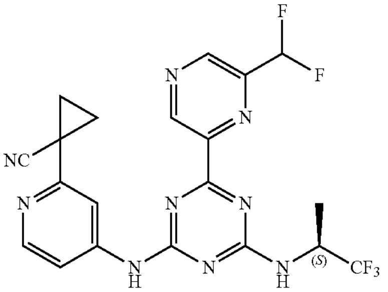

$^1$H NMR (400 MHz, $CDCl_3$) δ 9.83 (m, 1H), 9.16 (s, 1H), 8.42 (m, 2H), 7.60 (s, 1H), 7.13 (m, 1H), 6.88 (m, 1H), 5.88 (m, J=9.5 Hz, 1H), 5.16 (s, 1H), 1.89 (m, J=4.5 Hz, 2H), 1.76 (s, 2H), 1.52 (d, J=7.0 Hz, 3H). LC-MS: m/z 478 $(M+H)^+$.

(R)-1-(4-((4-(6-(difluoromethyl)pyrazin-2-yl)-6-((1,1,1-trifluoropropan-2-yl)amino)-1,3,5-triazin-2-yl)amino)pyridin-2-yl)cyclopropanecarbonitrile

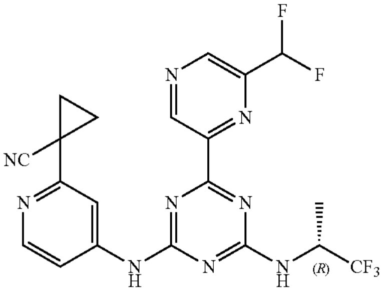

$^1$H NMR (400 MHz, $CDCl_3$) δ 9.81 (m, 1H), 9.12 (d, J=10.5 Hz, 1H), 8.34 (m, 2H), 7.54 (d, J=13.1 Hz, 1H), 7.08 (m, 1H), 6.86 (m, 1H), 5.85 (d, J=9.8 Hz, 1H), 5.14 (s, 1H), 1.92 (m, 2H), 1.71 (m, 2H), 1.51 (m, J=7.7 Hz, 3H). LC-MS: m/z 478 $(M+H)^+$.

6-(6-Chloropyrazin-2-yl)-$N^2$-(3,3-difluorocyclopentyl)-$N^4$-(3,5-difluorophenyl)-1,3,5-triazine-2,4-diamine

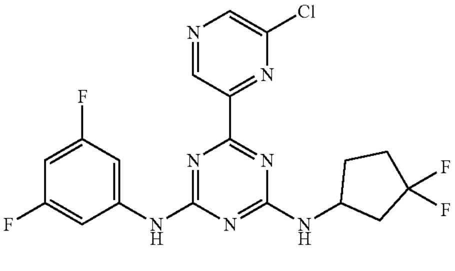 [SMILES: Fc1cc(F)cc(Nc2nc(NC3CCC(F)(F)C3)nc(-c3cncc(Cl)n3)n2)c1]

$^1$H NMR (400 MHz, $CDCl_3$) δ 9.51 (d, J=17.3 Hz, 1H), 8.76 (s, 1H), 7.64-7.11 (m, 3H), 6.57 (t, J=8.8 Hz, 1H), 5.95-5.50 (m, 1H), 4.86-4.50 (m, 1H), 2.85-1.80 (m, 6H). LC-MS: m/z 440 $(M+H)^+$.

6-(6-Chloropyrazin-2-yl)-$N^2$-(3,3-difluorocyclobutyl)-$N^4$-(3,5-difluorophenyl)-1,3,5-triazine-2,4-diamine

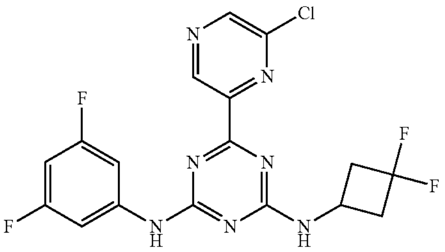 [SMILES: Fc1cc(F)cc(Nc2nc(NC3CC(F)(F)C3)nc(-c3cncc(Cl)n3)n2)c1]

$^1$H NMR (400 MHz, $CDCl_3$) δ 9.53-9.49 (m, 1H), 8.76 (s, 1H), 7.60-7.50 (m, 1H), 7.29 (s, 1H), 7.26 (s, 1H), 6.61-6.56 (m, 1H), 6.01-5.74 (m, 1H), 4.59-4.42 (m, 1H), 3.16 (s, 2H), 3.16-2.55 (m, 2H). LCMS: m/z 426 $(M+H)^+$.

(S)—$N^2$-(3,3-difluorocyclopentyl)-$N^4$-(2-(trifluoromethyl)pyridin-4-yl)-6-(2-(trifluoromethyl)pyrimidin-4-yl)-1,3,5-triazine-2,4-diamine

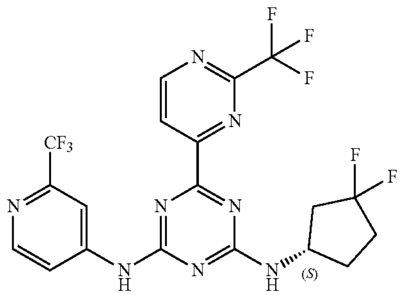

$^1$H NMR (400 MHz, $CDCl_3$) δ 9.16 (t, J=6.1 Hz, 1H), 8.68-7.76 (m, 4H), 7.72-7.45 (m, 1H), 5.86 (m, 1H), 4.70 (m, 1H), 2.86-1.84 (m, 6H). LCMS: m/z 507 $(M+H)^+$.

(R)—$N^2$-(3,3-difluorocyclopentyl)-$N^4$-(2-(trifluoromethyl)pyridin-4-yl)-6-(2-(trifluoromethyl)pyrimidin-4-yl)-1,3,5-triazine-2,4-diamine

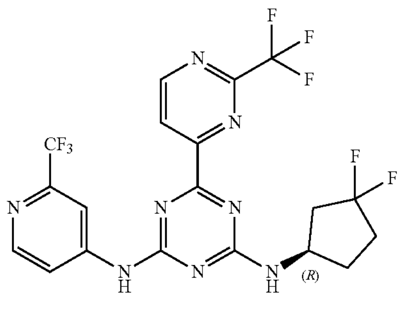

$^1$H NMR (400 MHz, $CDCl_3$) δ 9.18-9.15 (m, 1H), 8.64-8.61 (m, 1H), 8.53-8.51 (m, 1H), 8.48 (d, J=4 Hz, 1H), 8.17-7.80 (m, 1H) 7.72-7.48 (m, 1H), 6.02-5.71 (m, 1H), 4.80-4.61 (m, 1H), 2.76-2.63 (m, 4H), 1.95-1.88 (m, 1H). LCMS: m/z 507 $(M+H)^+$.

(S)-1-(4-((4-((3,3-difluorocyclopentyl)amino)-6-(2-(trifluoromethyl)pyrimidin-4-yl)-1,3,5-triazin-2-yl)amino)pyridin-2-yl)cyclopropanecarbonitrile

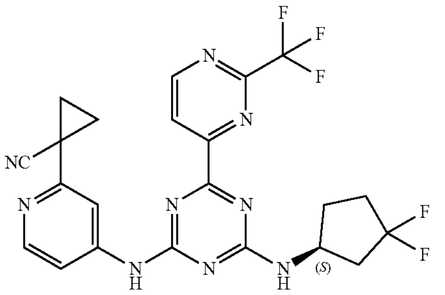

1H NMR (400 MHz, $CDCl_3$) δ 9.15 (d, J=5.4 Hz, 1H), 7.62 (m, 2H), 8.33 (d, J=5.5 Hz, 1H), 7.57 (s, 1H), 7.00 (s, 1H), 6.00 (d, J=8.0 Hz, 1H), 4.76 (d, J=8.6 Hz, 1H), 2.71 (s, 1H), 2.32 (m, 4H), 1.83 (m, 5H). LC-MS: m/z 504 $(M+H)^+$.

(R)-1-(4-((4-((3,3-difluorocyclopentyl)amino)-6-(2-(trifluoromethyl)pyrimidin-4-yl)-1,3,5-triazin-2-yl)amino)pyridin-2-yl)cyclopropanecarbonitrile

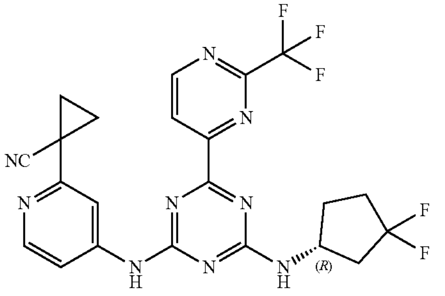

$^1$H NMR (400 MHz, $CDCl_3$) δ 9.14 (d, J=5.1 Hz, 1H), 8.35 (m, 2H), 8.33 (d, J=5.5 Hz, 1H), 7.56 (s, 1H), 7.00 (s, 1H), 5.99 (d, J=8.0 Hz, 1H), 4.76 (d, J=7.1 Hz, 1H), 2.73 (m, 1H), 2.23 (m, 4H), 1.78 (m, 5H). LC-MS: m/z 504 $(M+H)^+$.

1-(4-((4-((3,3-Difluorocyclopentyl)amino)-6-(4-(trifluoromethyl)pyrimidin-2-yl)-1,3,5-triazin-2-yl)amino)pyridin-2-yl)cyclopropanecarbonitrile

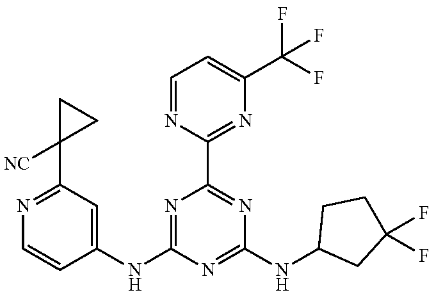 [SMILES: N#CC1(c2cc(Nc3nc(NC4CCC(F)(F)C4)nc(-c4nccc(C(F)(F)F)n4)n3)ccn2)CC1]

$^1$H NMR (400 MHz, $CDCl_3$) δ 9.27 (d, J=4.8 Hz, 1H), 8.67 (s, 1H), 8.29 (d, J=5.2 Hz, 1H), 8.06 (s, 1H), 7.81 (d, J=5.2 Hz, 1H), 6.97 (s, 1H), 6.19 (d, J=7.6 Hz, 1H), 2.85-2.69 (m, 1H), 2.53-2.05 (m, 5H), 1.92-1.68 (m, 5H). LCMS: m/z 504 $(M+H)^+$.

(S)-1-(4-((4-((3,3-difluorocyclopentyl)amino)-6-(4-(trifluoromethyl)pyrimidin-2-yl)-1,3,5-triazin-2-yl)amino)pyridin-2-yl)cyclopropanecarbonitrile

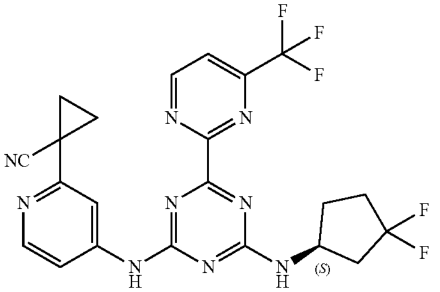

$^1$H NMR (400 MHz, $CDCl_3$) δ 9.29 (d, J=4.9 Hz, 1H), 8.58 (m, 1H), 8.33 (d, J=5.5 Hz, 1H), 7.82 (t, J=14.2 Hz, 2H), 7.00 (d, J=13.0 Hz, 1H), 6.14 (d, J=8.0 Hz, 1H), 4.94 (m, 1H), 2.89-2.69 (m, 1H), 2.51 (m, 1H), 2.34-2.07 (m, 3H), 1.94-1.72 (m, 5H). LCMS: m/z 504 $(M+H)^+$.

(R)-1-(4-((4-((3,3-difluorocyclopentyl)amino)-6-(4-(trifluoromethyl)pyrimidin-2-yl)-1,3,5-triazin-2-yl)amino)pyridin-2-yl)cyclopropanecarbonitrile

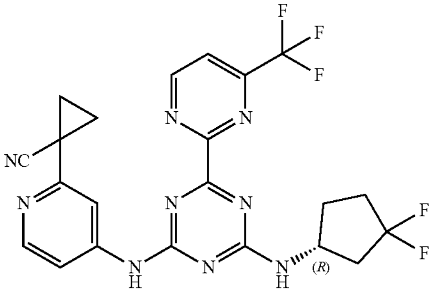

$^1$H NMR (400 MHz, $CDCl_3$) δ9.27 (d, J=4.9 Hz, 1H), 8.68 (s, 1H), 8.31 (d, J=5.5 Hz, 1H), 7.80 (dd, J=20.2, 12.7 Hz, 2H), 6.95 (s, 1H), 6.12 (d, J=8.1 Hz, 1H), 5.02 (s, 1H), 2.77 (m, 1H), 2.56-2.41 (m, 1H), 2.32-2.05 (m, 3H), 1.95-1.69 (m, 5H). LCMS: m/z 504 $(M+H)^+$.

$N^2$-(tert-butyl)-$N^4$-(2-(1,1-difluoroethyl)pyridin-4-yl)-6-(4-(trifluoromethyl)pyrimidin-2-yl)-1,3,5-triazine-2,4-diamine

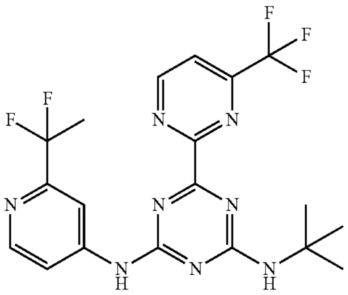 [SMILES: CC(C)(C)Nc1nc(Nc2ccnc(C(C)(F)F)c2)nc(-c2nccc(C(F)(F)F)n2)n1]

$^1$H NMR (400 MHz, $CDCl_3$) δ 9.24 (d, J=5.0 Hz, 1H), 8.50 (d, J=5.5 Hz, 1H), 8.38 (d, J=1.4 Hz, 1H), 7.97 (s, 1H), 7.80 (d, J=5.0 Hz, 1H), 7.37 (s, 1H), 6.05 (s, 1H), 2.04 (d, J=18.6 Hz, 3H), 1.55 (s, 9H). LCMS: m/z 455 $(M+H)^+$.

$N^2$-(2-(1,1-difluoroethyl)pyridin-4-yl)-$N^4$-isopropyl-6-(4-(trifluoromethyl)pyrimidin-2-yl)-1,3,5-triazine-2,4-diamine

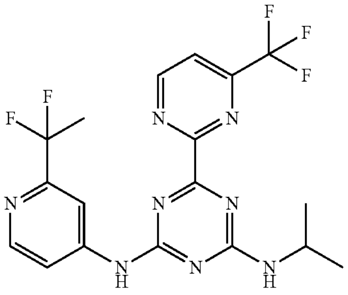 [SMILES: CC(C)Nc1nc(Nc2ccnc(C(C)(F)F)c2)nc(-c2nccc(C(F)(F)F)n2)n1]

$^1$H NMR (400 MHz, $CDCl_3$) δ 9.26 (d, J=5.0 Hz, 1H), 8.52 (d, J=5.5 Hz, 1H), 8.41 (d, J=1.5 Hz, 1H), 7.84 (m, 2H), 7.41 (s, 1H), 5.86 (d, J=7.5 Hz, 1H), 4.32 (m, 1H), 2.04 (m, 3H), 1.36 (d, J=6.5 Hz, 6H). LCMS: m/z 441 $(M+H)^+$.

3-((4-(Tert-butylamino)-6-(4-(trifluoromethyl)pyrimidin-2-yl)-1,3,5-triazin-2-yl)amino)-5-fluorobenzonitrile

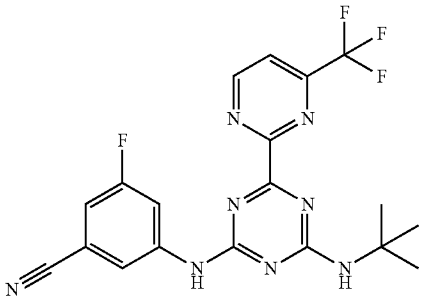 [SMILES: CC(C)(C)Nc1nc(Nc2cc(F)cc(C#N)c2)nc(-c2nccc(C(F)(F)F)n2)n1]

$^1$H NMR (400 MHz, DMSO-$d_6$) δ 10.80-10.20 (m, 1H), 9.50-9.25 (m, 1H), 8.36-7.96 (m, 4H), 7.50-7.40 (m, 1H), 1.47 (s, 9H). LCMS: m/z 433 $(M+1)^+$.

1-((4-((3,5-Difluorophenyl)amino)-6-(4-(trifluoromethyl)pyrimidin-2-yl)-1,3,5-triazin-2-yl)amino)-2-methylpropan-2-ol

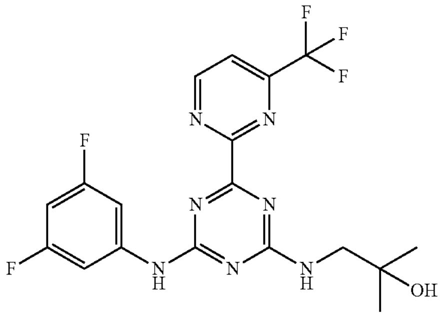 [SMILES: CC(C)(O)CNc1nc(Nc2cc(F)cc(F)c2)nc(-c2nccc(C(F)(F)F)n2)n1]

$^1$H NMR (400 MHz, DMSO-$d_6$) δ 10.70-10.20 (m, 1H), 9.50-9.27 (m, 1H), 8.37-7.94 (m, 2H), 7.80-7.50 (m, 2H), 6.98-6.71 (m, 1H), 4.75-4.48 (m, 1H), 3.47-3.38 (m, 2H), 1.14 (s, 6H). LCMS: m/z 442 $(M+H)^+$.

Example 33. Preparation of Aromatic-aliphatic Triazine Compounds. The compounds of this Example are prepared by general Scheme 33, set forth below.

Scheme 33

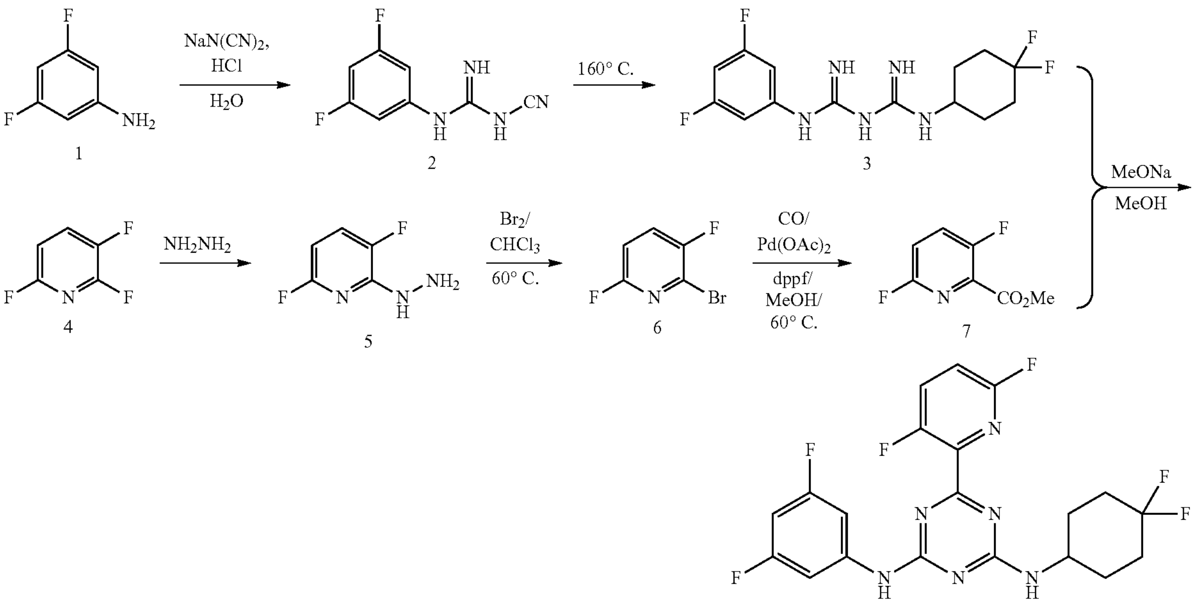

Step 1: Preparation of $N^1$-(3,5-difluorophenyl)-$N^3$-nitrile-guanidine. To a solution of $NaN(CN)_2$ (4.1 g, 46.5 mmol) in water (34 mL) at 80° C. was added a solution of 3,5-difluoroaniline (3 g, 23.2 mmol) in a mixed solvent of water and conc. HCl (2M, 2 mL). The reaction mixture was then stirred at 90° C. for 16 hours. The resulting mixture was cooled to r.t. and quenched by satd. aq. $NaHCO_3$ and adjusted to pH 7-8. The mixture was filtered and the filter cake was collected and dried to afford the desired product. LC-MS: m/z 197 $(M+H)^+$.

Step 2: Preparation of $N^1$-(3,5-difluorophenyl)-$N^5$-(4,4-difluorocyclohexyl)-guanidine. A mixture of $N^1$-(3,5-difluorophenyl)-$N^3$-nitrile-guanidine (300 mg, 1.53 mmol) and 4,4-difluorocyclohexanamine hydrochloride (262 mg, 1.53 mmol) was well mixed together and then stirred at 160° C. for 1 hr. The resulting mixture was cooled to r.t. and then triturated with a mixed solvent of EtOAc and PE. The solid was collected by filtration and dried to afford the desired product. LC-MS: m/z 332 $(M+H)^+$.

Step 3: Preparation of 3,6-difluoro-2-hydrazinylpyridine. To an ice-cold mixture of 2,3,6-trifluoropyridine (1.0 g, 7.5 mmol) in ethanol (10 mL) was added hydrazine hydrate (0.75 g, 15.0 mmol). The reaction mixture was warmed to r.t. then heated to reflux for 2 hr. After cooling to r.t., the reaction mixture was diluted with water (10 mL) and extracted with DCM (2×20 mL). The combined organic layers were dried over anhydrous $Na_2SO_4$ and concentrated under reduced pressure to afford 3,6-difluoro-2-hydrazinylpyridine. LC-MS: m/z 146 $(M+H)^+$.

Step 4: Preparation of 2-bromo-3,6-difluoropyridine. To a stirred solution of 3,6-difluoro-2-hydrazinylpyridine (1.1 g, 7.0 mmol) in chloroform (20 mL) at r.t. was added dropwise bromine (1.8 g, 11.2 mmol). The reaction mixture was then stirred at 60° C. for 1.5 hr. The resulting mixture was cooled to r.t., then quenched with satd. aq. $NaHCO_3$, and extracted with dichloromethane (2×20 mL). The combined organic layers were dried over anhydrous $Na_2SO_4$, and concentrated and purified by standard methods to afford 2-bromo-3,6-difluoropyridine. LC-MS: m/z 194 $(M+H)^+$.

Step 5: Preparation of methyl 3,6-difluoropicolinate. To a solution of 2-bromo-3,6-difluoropyridine (0.8 g, 4.1 mmol) in MeOH (10 mL) were added dppf (0.3 g, 0.56 mmol), $Pd(OAc)_2$ (0.1 g, 0.45 mmol) and $Et_3N$ (1.6 mL, 8.2 mmol). The suspension was degassed and back-filled with CO atmosphere three times. The mixture was then stirred under CO atmosphere (60 psi) at 70° C. for 12 hr. The resulting mixture was cooled to r.t. and concentrated under reduced pressure. The residue was triturated with EtOAc (150 mL). The solid was filtered off and the filtrate was concentrated and purified by standard methods to afford methyl 3,6-difluoropicolinate.

LC-MS: m/z 174 $(M+H)^+$.

Step 6: Preparation of $N^2$-(4,4-difluorocyclohexyl)-$N^4$-(3,5-difluorophenyl)-6-(3,6-difluoropyridin-2-yl)-1,3,5-triazine-2,4-diamine. To a suspension of $N^1$-(3,5-difluorophenyl)-$N^5$-(4,4-difluorocyclohexyl)-guanidine (191 mg, 0.58 mmol) and methyl 3,6-difluoropicolinate (100 mg, 0.58 mmol) in MeOH (3 mL) was added NaOMe (94 mg, 1.73 mmol). The reaction mixture was stirred at r.t. overnight, then poured into water and extracted with EtOAc. Combined organic layers were dried over anhydrous $Na_2SO_4$, and concentrated and purified by standard methods to afford $N^2$-(4,4-difluorocyclohexyl)-$N^4$-(3,5-difluoro phenyl)-6-(3,6-difluoropyridin-2-yl)-1,3,5-triazine-2,4-diamine.

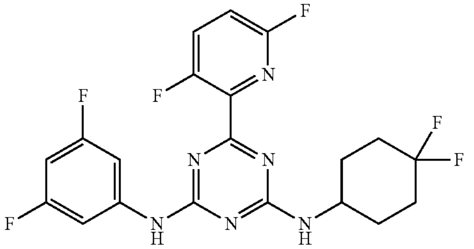 [SMILES: Fc1cc(F)cc(Nc2nc(NC3CCC(F)(F)CC3)nc(-c3nc(F)ccc3F)n2)c1]

$^1H$ NMR (400 MHz, $CDCl_3$) δ 7.70 (td, J=8.8, 5.8 Hz, 1H), 7.49-7.38 (m, 1H), 7.37-7.17 (m, 2H), 7.17-7.05 (m,

1H), 6.55 (t, J=8.9 Hz, 1H), 5.67-5.37 (m, 1H), 4.13-4.02 (m, 1H), 2.18 (d, J=8.3 Hz, 4H), 2.03-1.87 (m, 2H), 1.73-1.70 (d, J=11.2 Hz, 2H). LC-MS: m/z 455 $(M+H)^+$.

The procedure set forth in Example 33 was used to produce the following compounds using the appropriate starting materials.

Compound $N^2$-(3,3-difluorocyclopentyl)-$N^4$-(3,5-difluorophenyl)-6-(3,6-difluoropyridin-2-yl)-1,3,5-triazine-2,4-diamine

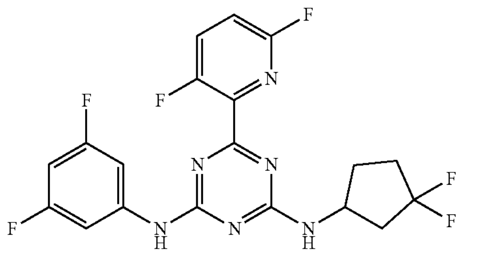 [SMILES: Fc1cc(F)cc(Nc2nc(NC3CCC(F)(F)C3)nc(-c3nc(F)ccc3F)n2)c1]

$^1H$ NMR (400 MHz, $CDCl_3$) δ 7.77-7.62 (m, 1H), 7.47-7.27 (m, 2H), 7.24 (d, J=7.7 Hz, 1H), 7.11 (ddd, J=8.8, 3.9, 2.7 Hz, 1H), 6.55 (t, J=8.7 Hz, 1H), 5.94-5.29 (m, 1H), 4.76-4.48 (m, 1H), 2.90-1.72 (m, 6H). LC-MS: m/z 441 $(M+H)^+$.

Compound $N^2$-(3,3-difluorocyclobutyl)-$N^4$-(3,5-difluorophenyl)-6-(3,6-difluoropyridin-2-yl)-1,3,5-triazine-2,4-diamine

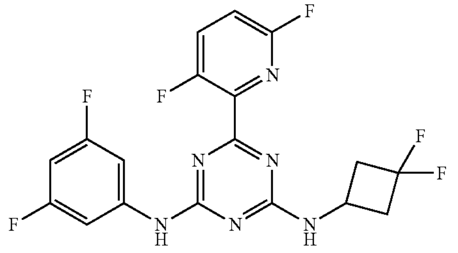 [SMILES: Fc1cc(F)cc(Nc2nc(NC3CC(F)(F)C3)nc(-c3nc(F)ccc3F)n2)c1]

$^1H$ NMR (400 MHz, $CDCl_3$) δ 7.70 (m, 1H), 7.58-7.28 (m, 2H), 7.25-7.19 (m, 1H), 7.16-7.06 (m, 1H), 6.73-6.30 (m, 1H), 6.18-5.37 (m, 1H), 4.63-4.31 (m, 1H), 3.40-2.93 (m, 2H), 2.88-2.19 (m, 2H). LC-MS: m/z 427 $(M+H)^+$.

Example 34. The compounds of this Example are prepared by general Scheme 34, set forth below.

Scheme 34

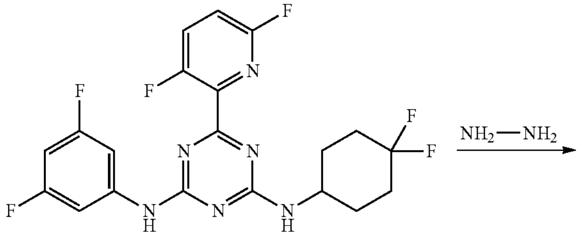

-continued

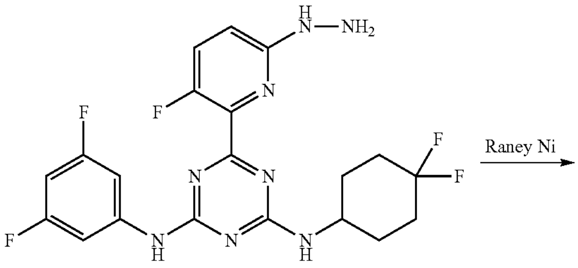

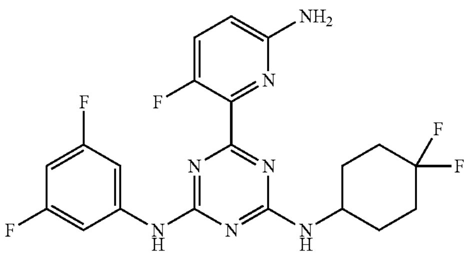

Step 1: Preparation of $N^2$-(4,4-difluorocyclohexyl)-$N^4$-(3,5-difluorophenyl)-6-(3-fluoro-6-hydrazinylpyridin-2-yl)-1,3,5-triazine-2,4-diamine. To a solution of $N^2$-(4,4-difluorocyclohexyl)-$N^4$-(3,5-difluorophenyl)-6-(3,6-difluoropyridin-2-yl)-1,3,5-triazine-2,4-diamine (225 mg, 0.49 mmol) in THF (20 mL) was added hydrazine hydrate (150 mg, 3.0 mmol). The reaction mixture was then stirred at 60° C. for 2.5 hr. After cooling to r.t., the reaction mixture was diluted with DCM (20 mL) and washed with brine (2×10 mL). The organic phase was separated, dried over anhydrous $Na_2SO_4$ and concentrated under reduced pressure to give the desired product.

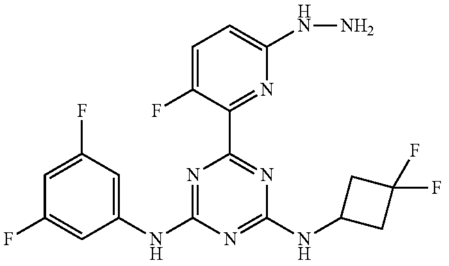 [SMILES: NNc1ccc(F)c(-c2nc(Nc3cc(F)cc(F)c3)nc(NC3CC(F)(F)C3)n2)n1]

LC-MS: m/z 467 $(M+H)^+$.

Step 2: Preparation of 6-(6-amino-3-fluoropyridin-2-yl)-$N^2$-(4,4-difluorocyclo hexyl)-$N^4$-(3,5-difluorophenyl)-1,3,5-triazine-2,4-diamine. To a solution of $N^2$-(4,4-difluorocyclohexyl)-$N^4$-(3,5-difluorophenyl)-6-(3-fluoro-6-hydrazinylpyridin-2-yl)-1,3,5-triazine-2,4-diamine (46 mg, 0.1 mmol) in methanol (5.0 mL) was added Raney Ni (100 mg). The mixture was stirred at r.t. under $H_2$ atmosphere overnight. The resulting mixture was filtered and the filtrate was concentrated and purified by standard methods to afford 6-(6-amino-3-fluoropyridin-2-yl)-$N^2$-(4,4-difluorocyclohexyl)-$N^4$-(3,5-difluorophenyl)-1,3,5-triazine-2,4-diamine.

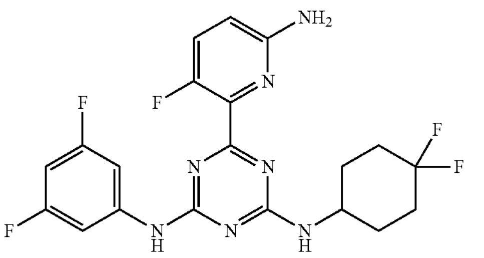

$^1H$ NMR (400 MHz, $CDCl_3$) δ 7.52-7.50 (m, 2H), 7.45-7.39 (m, 1H), 7.02-6.97 (m, 1H), 6.63-6.54 (m, 1H), 4.60 (s, 1H), 4.26-4.05 (m, 1H), 1.73-2.21 (m, 8H). LC-MS: m/z 452 $(M+H)^+$.

The procedure set forth in Example 34 was used to produce the following compounds using the appropriate starting materials.

Compound 6-(6-Amino-3-fluoropyridin-2-yl)-N2-(3,3-difluorocyclopentyl)-N4-(3,5-difluorophenyl)-1,3,5-triazine-2,4-diamine

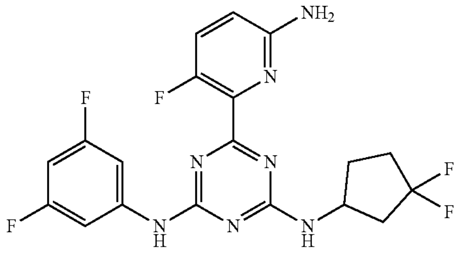 [SMILES: Nc1ccc(F)c(-c2nc(Nc3cc(F)cc(F)c3)nc(NC3CCC(F)(F)C3)n2)n1]

$^1H$ NMR (400 MHz, $CDCl_3$) δ 7.50-7.36 (m, 3H), 6.96-6.95 (m, 1H), 6.59-6.53 (m, 1H), 4.89-4.51 (m, 2H), 2.66-2.60 (m, 1H), 2.35-2.11 (m, 4H), 1.92-1.58 (m, 2H). LCMS: m/z 438 $(M+H)^+$.

Example 35: Preparation of $N^4$,$N^6$-bis(4,4-difluorocyclohexyl)-2-(6-(trifluoromethyl) pyrazin-2-yl) pyrimidine-4,6-diamine Scheme 35

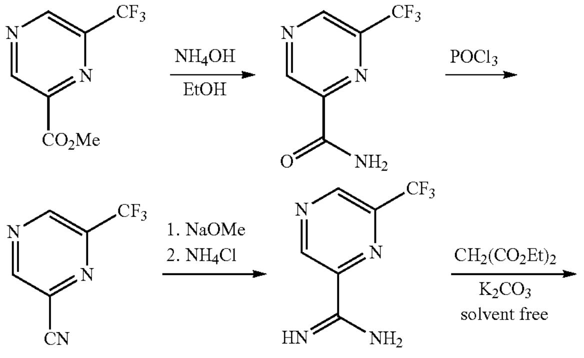

-continued

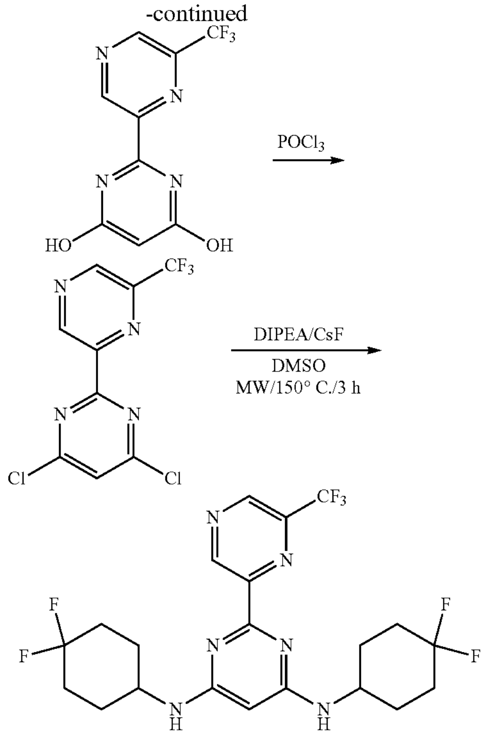

Step A: 6-(Trifluoromethyl)pyrazine-2-carboxamide. To a solution of methyl 6-(trifluoromethyl) pyrazine-2-carboxylate (15 g, 72.8 mmol) in EtOH (20 mL) was added $NH_4OH$ (6 mL, 156 mmol). The reaction mixture was stirred at r.t. for 4 hr then concentrated under reduced pressure. The residue was triturated with $H_2O$ (10 mL) and then filtered to afford 6-(trifluoromethyl)pyrazine-2-carboxamide. LC-MS: m/z 192 $(M+H)^+$.

Step B: 6-(Trifluoromethyl)pyrazine-2-carbonitrile. A mixture of 6-(trifluoromethyl) pyrazine-2-carboxamide (10 g, 52 mmol) in $POCl_3$ (80 mL) was stirred at 100° C. overnight. The reaction mixture was cooled to r.t. and concentrated under reduced pressure. The residue was partitioned between DCM and ice water. The organic layer was separated, washed with brine, dried over anhydrous $Na_2SO_4$, concentrated, and purified by standard methods to afford 6-(trifluoromethyl)pyrazine-2-carbonitrile. LC-MS: m/z 174 $(M+H)^+$.

Step C: 6-(Trifluoromethyl)pyrazine-2-carboximidamide hydrochloride. To a solution of 6-(trifluoromethyl) pyrazine-2-carbonitrile (3.4 g, 15 mmol) in MeOH (5 mL) was added a solution of sodium metal (35 mg, 1.5 mmol) in MeOH. The reaction mixture was stirred at r.t. for 12 hr, followed by addition of $NH_4Cl$ (1.5 g, 30 mmol). The mixture was stirred at 70° C. for 3 hr, then cooled to r.t. and concentrated under reduced pressure. The residue was diluted with EtOH (10 mL) and stirred at reflux for 0.5 hr. The resulting mixture was cooled to r.t. and filtered. The filtrate was concentrated under reduced pressure to afford 6-(trifluoromethyl) pyrazine-2-carboximidamide hydrochloride. LC-MS: m/z 191 $(M+H)^+$.

Step D: 2-(6-(trifluoromethyl)pyrazin-2-yl)pyrimidine-4,6(1H,5H)-dione. To a mixture of 6-(trifluoromethyl) pyrazine-2-carboximidamide hydrochloride (1.6 g, 7.0 mmol) in diethyl malonate (3.2 g, 21.2 mmol) was added potassium carbonate (3.0 g, 21.2 mmol). The reaction mixture was stirred at 120° C. for 8 hr. The resulting mixture was cooled to r.t. and triturated with petroleum ether. The solid was collected by filtration, washed with petroleum ether then treated with MeOH to form a suspension. The suspension was filtered and the filtrate was concentrated under reduced pressure to afford 2-(6-(trifluoromethyl)pyrazin-2-yl)pyrimidine-4,6-(1H,5H)-dione. LC-MS: m/z 259 $(M+H)^+$.

Step E: 4,6-Dichloro-2-(6-(trifluoromethyl) pyrazin-2-yl) pyrimidine. A mixture of 2-(6-(trifluoromethyl) pyrazin-2-yl) pyrimidine-4,6(1H, 5H)-dione (1.4 g, 5.4 mmol) in $POCl_3$ (10 mL) was stirred at 100° C. overnight then cooled to r.t. and concentrated under reduced pressure. The residue was purified by column chromatography (PE/EA=20/1 to 10/1) to afford 4,6-dichloro-2-(6-(trifluoromethyl) pyrazin-2-yl)pyrimidine. LC-MS: m/z 295 $(M+H)^+$.

Step F: $N^4$,$N^6$-bis (4,4-difluorocyclohexyl)-2-(6-(trifluoromethyl) pyrazin-2-yl) pyrimidine-4,6-diamine. To a mixture of 4,6-dichloro-2-(6-(trifluoromethyl) pyrazin-2-yl)pyrimidine (100 mg, 0.34 mmol), CsF (103 mg, 0.68 mmol) and 4,4-difluorocyclohexanamine hydrochloride (116 mg, 0.68 mmol) in DMSO (1 mL) was added DIPEA (220 mg, 0.17 mmol). The reaction mixture was stirred at 80° C. for 4 hr under nitrogen, and then stirred at 150° C. for 6 hr under microwave irradiation. The resulting mixture was cooled to r.t., quenched with water, and extracted with EtOAc. The combined organic layers were washed with brine, dried over anhydrous $Na_2SO_4$, and concentrated under reduced pressure. The residue was purified by standard methods to afford $N^4$,$N^6$-bis (4,4-difluorocyclohexyl)-2-(6-(trifluoromethyl) pyrazin-2-yl) pyrimidine-4,6-diamine.

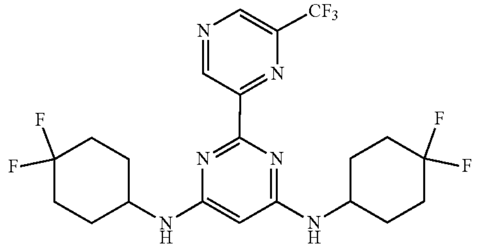 [SMILES: FC1(F)CCC(Nc2cc(NC3CCC(F)(F)CC3)nc(-c3cncc(C(F)(F)F)n3)n2)CC1]

$^1H$ NMR (400 MHz, $CDCl_3$) δ 9.73 (s, 1H), 9.00 (s, 1H), 5.31 (s, 1H), 4.95 (m, 2H), 3.76 (m, 2H), 2.20-2.09 (m, 8H), 1.98-1.85 (m, 4H), 1.72-1.63 (m, 4H). LC-MS: m/z 493 $(M+H)^+$.

Example 36. Preparation of Aromatic-aliphatic Triazine Compounds. The compounds of this Example are prepared by general Scheme 36, set forth below.

Scheme 36

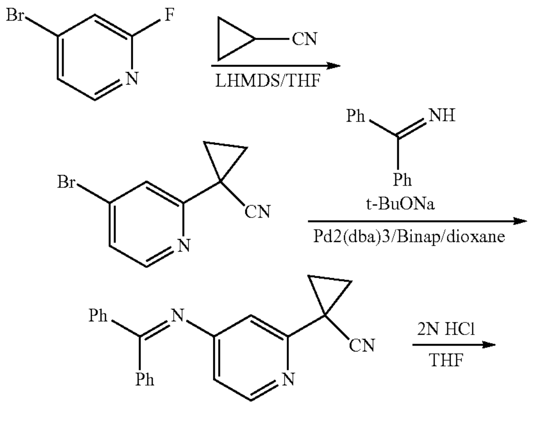

-continued

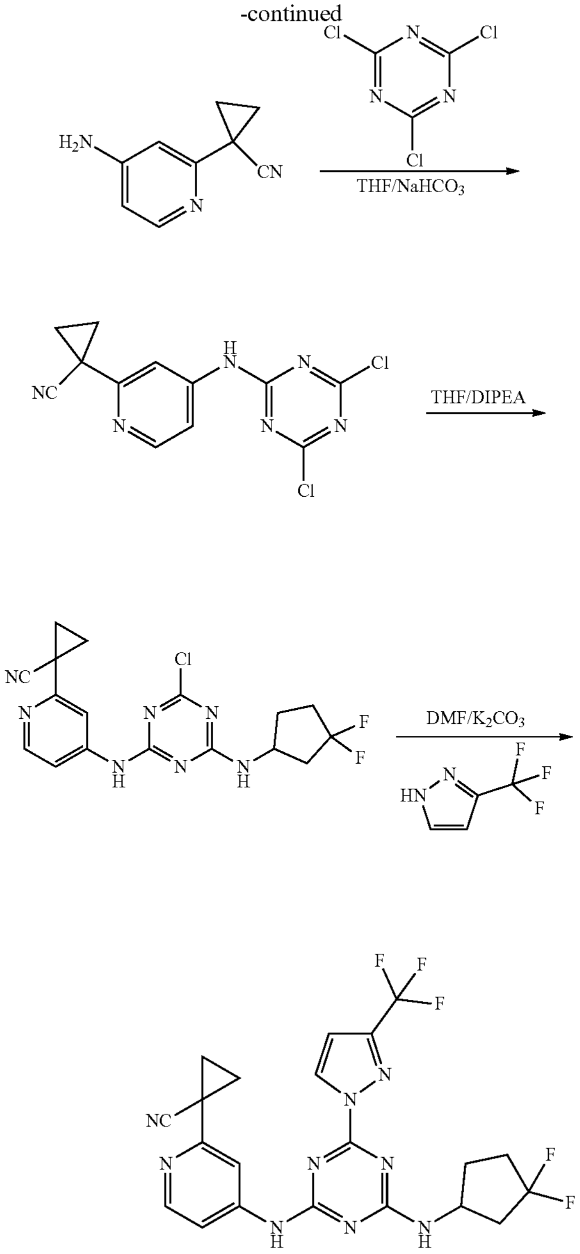

Step 1: Preparation of 1-(4-bromopyridin-2-yl)cyclopropanecarbonitrile. To a solution of 4-bromo-2-fluoropyridine (30 g, 170.47 mmol) and cyclopropane carbonitrile (22.9 g, 340.94 mmol) in THF (400 mL) below −10° C. was slowly added dropwise LiHMDS (1.2 mmol/L, 284 mL). The reaction mixture was then stirred at r.t. for 12 hr. The resulting mixture was cooled to 0° C., then quenched with brine (200 mL). The mixture was concentrated under reduced pressure. The residue was extracted with EtOAc (3×200 mL). The combined layers were dried over anhydrous $Na_2SO_4$ and concentrated and purified by standard methods to afford the desired product. LC-MS: m/z 223 $(M+H)^+$.

Step 2: Preparation of 1-(4-(diphenylmethyleneamino) pyridin-2-yl)cyclopro panecarbonitrile. To a solution of 1-(4-bromopyridin-2-yl)cyclopropanecarbonitrile (30 g, 134.48 mmol) and diphenyl methanimine (29.3 g, 161.38 mmol) in dioxane (150 mL) were added t-BuONa (19.4 g, 201.73 mmol), Binap (5.0 g, 8.1 mmol) and $Pd_2(dba)_3$ (2.5 g, 2.69 mmol). The mixture was heated to 100° C. for 1 hr under $N_2$ atmosphere, then cooled and filtered. The filtrate was concentrated to give the desired product. LC-MS: m/z 324 $(M+H)^+$.

Step 3: Preparation of 1-(4-aminopyridin-2-yl)cyclopropanecarbonitrile. A mixture of 1-(4-(diphenylmethyleneamino)pyridin-2-yl)cyclopropanecarbonitrile (42.1 g crude, 130 mmol) and THF/aq. HCl (2N) (200 mL, V:V=2:1) was stirred at r.t. for 1 hr and concentrated under reduced pressure. The aqueous layer was extracted with PE (3×100 mL), then adjusted to pH 8-9 with satd. aq. $Na_2CO_3$, and extracted with EtOAc (3×100 mL). The combined organic layers were dried over anhydrous $Na_2SO_4$, and concentrated concentrated and purified by standard methods to afford the desired product. $^1$HNMR ($CDCl_3$) δ 8.04-8.05 (d, J=4 Hz, 1H), 6.95-6.96 (d, J=4 Hz), 6.37-6.39 (m, 1H), 4.23 (br, 2H), 1.17-1.80 (m, 2H), 1.61-1.63 (m, 2H). LC-MS: m/z 160 $(M+H)^+$.

Step 4: Preparation of 1-(4-(4,6-dichloro-1,3,5-triazin-2-ylamino)pyridin-2-yl) cyclopropane carbonitrile. To a solution of 1-(4-aminopyridin-2-yl) cyclopropanecarbonitrile (2.5 g, 15.7 mmol), 2,4,6-trichloro-1,3,5-triazine (3.5 g, 18.8 mmol) in THF (40 mL) was added $NaHCO_3$(2.64 g, 31.4 mmol). The reaction mixture was stirred at r.t. overnight then filtered. The filtrate was concentrated and purified by standard methods to afford the desired product. LC-MS: m/z 307 $(M+H)^+$.

Step 5: Preparation of 1-(4-(4-chloro-6-(3,3-difluorocyclopentylamino)-1,3,5-triazin-2-yl amino) pyridin-2-yl)cyclopropanecarbonitrile. To a solution of 1-(4-(4,6-dichloro-1,3,5-triazin-2-ylamino)pyridin-2-yl) cyclopropanecarbonitrile (0.75 g, 2.44 mmol) and 3,3-difluorocyclopentanamine hydrochloride (0.39 g, 2.44 mmol) in THF (10 mL) at 0° C. was slowly added dropwise DIPEA (0.63 g, 4.88 mmol). The reaction mixture was stirred at r.t. for 8 hr, and then concentrated under reduced pressure. The residue was partitioned between EtOAc (20 mL) and HCl solution (10% wt, 3 mL). The aqueous layer was separated and extracted with EtOAc (2×5 mL). The combined organic layers were dried over anhydrous $Na_2SO_4$ and concentrated and purified by standard methods to afford the desired product. LC-MS: m/z 392 $(M+H)^+$.

Step 6: Preparation of 1-(4-(4-(3,3-difluorocyclopentylamino)-6-(3-(trifluoro methyl)-1H-pyrazol-1-yl)-1,3,5-triazin-2-ylamino)pyridin-2-yl)cyclopropanecarbonitrile. To a solution of 1-(4-(4-chloro-6-(3,3-difluorocyclopentylamino)-1,3,5-triazin-2-ylamino) pyridin-2-yl)cyclopropanecarbonitrile (0.6 g, 1.53 mmol) in DMF (600 mL) were added 3-(trifluoromethyl)-1H-pyrazole (0.2 g, 1.53 mmol) and $K_2CO_3$ (0.42 g, 3.06 mmol). The mixture was stirred at 35° C. overnight then concentrated under reduced pressure. The residue was dissolved in EtOAc (20 mL) then washed in sequence with aq. 10% LiCl solution (2×5 mL), 5% HCl solution (2×5 mL), and satd. aq. $NaHCO_3$(2×5 mL). The organic layer was separated, dried over anhydrous $Na_2SO_4$, and concentrated and purified by standard methods to afford the desired product. $^1$H NMR (400 MHz, $CDCl_3$) δ 8.81-8.21 (m, 3H), 7.75-7.43 (m, 1H), 7.17-6.88 (m, 1H), 6.74 (d, J=2.7 Hz, 1H), 6.05-5.76 (m, 1H), 5.12-4.41 (m, 1H), 2.86-2.61 (m, 1H), 2.57-2.00 (m, 4H), 1.97-1.78 (m, 3H), 1.76-1.68 (m, 2H). LC-MS: m/z 492 $(M+H)^+$.

The procedure set forth in Example 36 was used to produce the following compounds using the appropriate starting materials.

Compound (S)-1-(4-(4-(3,3-Difluorocyclopentylamino)-6-(3-(trifluoromethyl)-1H-pyrazol-1-yl)-1,3,5-triazin-2-ylamino)pyridin-2-yl)cyclopropanecarbonitrile

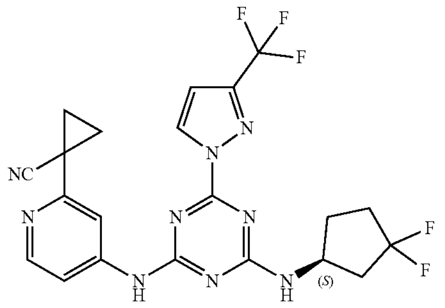

$^1$H NMR (400 MHz, $CDCl_3$) δ 8.51-8.64 (m, 2H), 8.30-8.32 (m, 1H), 7.70-7.87 (m, 1H), 7.96-7.14 (m, 1H), 6.66-6.75 (m, 1H), 5.86-6.07 (m, 1H), 4.64-4.93 (m, 1H), 2.44-2.76 (m, 1H), 2.04-2.30 (m, 4H), 1.72-1.94 (m, 5H). LC-MS: m/z 492 $(M+H)^+$.

Compound (R)-1-(4-(4-(3,3-Difluorocyclopentylamino)-6-(3-(trifluoromethyl)-1H-pyrazol-1-yl)-1,3,5-triazin-2-ylamino)pyridin-2-yl)cyclopropanecarbonitrile

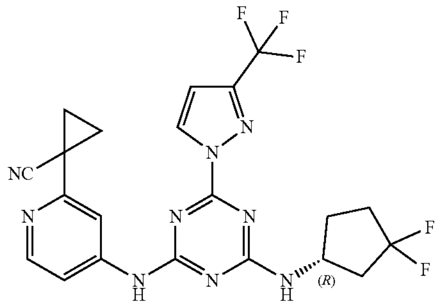

$^1$H NMR (400 MHz, $CDCl_3$) δ 8.59 (m, 2H), 8.32 (d, J=5.5 Hz, 1H), 7.52 (s, 1H), 6.95 (m, 1H), 6.74 (d, J=2.7 Hz, 1H), 5.91 (m, 1H), 4.83 (m, 1H), 2.69 (m, 1H), 2.31 (m, 4H), 1.76 (m, 5H).

LC-MS: m/z 492 $(M+H)^+$.

Compound 1-(4-((4-((4,4-Difluorocyclohexyl)amino)-6-(3-(trifluoromethyl)-1H-pyrazol-1-yl)-1,3,5-triazin-2-yl)amino)pyridin-2-yl)cyclopropanecarbonitrile

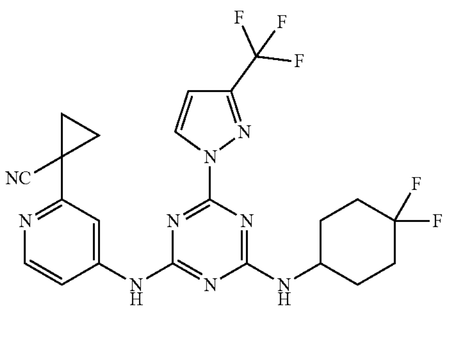 [SMILES: N#CC1(c2cc(Nc3nc(NC4CCC(F)(F)CC4)nc(-n4ccc(C(F)(F)F)n4)n3)ccn2)CC1]

$^1$H NMR (400 MHz, $CDCl_3$) δ 8.80-8.11 (m, 3H), 7.63 (m, 1H), 7.17-6.97 (m, 1H), 6.76 (t, J=3.4 Hz, 1H), 5.75 (m, 1H), 4.21 (m, 1H), 2.14 (m, 6H), 1.93-1.83 (m, 2H), 1.77-1.61 (m, 4H).

LCMS: m/z 506 $(M+H)^+$.

Compound 1-(4-((4-((3,3-Difluorocyclobutyl)amino)-6-(3-(trifluoromethyl)-1H-pyrazol-1-yl)-1,3,5-triazin-2-yl)amino)pyridin-2-yl)cyclopropanecarbonitrile

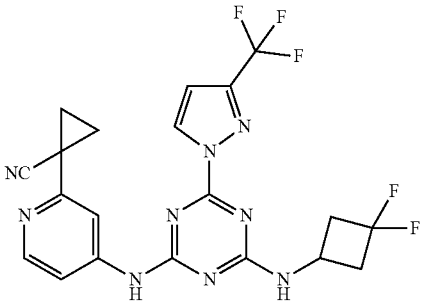 [SMILES: N#CC1(c2cc(Nc3nc(NC4CC(F)(F)C4)nc(-n4ccc(C(F)(F)F)n4)n3)ccn2)CC1]

$^1$H NMR (400 MHz, $CDCl_3$) δ: 8.78-8.50 (M, 2H), 8.32 (m, 1H), 7.86-7.56 (m, 1H), 7.13-6.98 (M, 1H), 6.74 (t, J=3.9 Hz, 1H), 6.18 (d, J=6.9 Hz, 1H), 4.85-4.42 (M, 1H), 3.28-3.05 (m, 2H), 2.83-2.47 (m, 2H), 1.91-1.85 (m, 2H), 1.76-1.69 (m, 2H). LCMS: m/z 478 $(M+H)^+$.

Compound 1-(4-((4-(3-(Trifluoromethyl)-1H-pyrazol-1-yl)-6-((1,1,1-trifluoropropan-2-yl)amino)-1,3,5-triazin-2-yl)amino)pyridin-2-yl)cyclopropanecarbonitrile

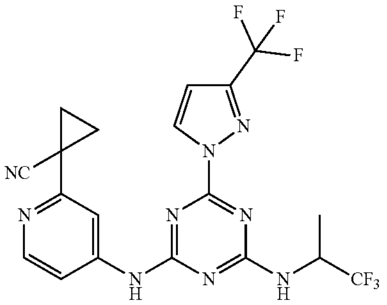 [SMILES: CC(Nc1nc(Nc2ccnc(C3(C#N)CC3)c2)nc(-n2ccc(C(F)(F)F)n2)n1)C(F)(F)F]

$^1$H NMR (400 MHz, $CDCl_3$) δ 8.84-8.27 (m, 3H), 7.71 (m, 1H), 7.11 (m, 1H), 6.76 (d, J=2.6 Hz, 1H), 5.91 (d, J=9.6 Hz, 1H), 5.03 (s, 1H), 1.87 (m, 2H), 1.76-1.72 (m, 2H), 1.49 (t, J=8.4 Hz, 3H). LCMS: m/z 484 $(M+H)^+$.

Compound (R)-1-(4-((4-(3-(trifluoromethyl)-1H-pyrazol-1-yl)-6-((1,1,1-trifluoropropan-2-yl)amino)-1,3,5-triazin-2-yl)amino)pyridin-2-yl)cyclopropanecarbonitrile

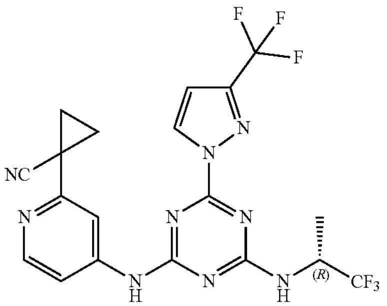

$^1$H NMR (400 MHz, $CDCl_3$) δ 8.65 (s, 1H), 8.48 (d, J=1.7 Hz, 1H), 8.35 (d, J=5.5 Hz, 1H), 7.59 (m, 1H), 7.14 (m, 1H), 6.76 (d, J=2.7 Hz, 1H), 5.75 (m, 1H), 5.02 (s, 1H), 1.93-1.76 (m, 2H), 1.69 (m, 2H), 1.49 (t, J=8.7 Hz, 3H). LCMS: m/z 484 $(M+H)^+$.

Compound (S)-1-(4-((4-(3-(trifluoromethyl)-1H-pyrazol-1-yl)-6-((1,1,1-trifluoropropan-2-yl)amino)-1,3,5-triazin-2-yl)amino)pyridin-2-yl)cyclopropanecarbonitrile

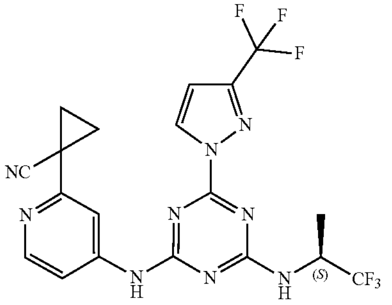

$^1$H NMR (400 MHz, $CDCl_3$) δ 8.67 (s, 1H), 8.50 (d, J=1.4 Hz, 1H), 8.38 (m, 1H), 7.64 (m, 1H), 7.07 (s, 1H), 6.77 (d, J=2.6 Hz, 1H), 5.82 (m, 1H), 5.34-4.85 (m, 1H), 1.97-1.85 (m, 2H), 1.77 (m, 2H), 1.57-1.44 (m, 3H). LCMS: m/z 484 $(M+H)^+$.

Compound $N^2$-(3,3-difluorocyclopentyl)-6-(3-(trifluoromethyl)-1H-pyrazol-1-yl)-$N^4$-(2-(trifluoromethyl)pyridin-4-yl)-1,3,5-triazine-2,4-diamine

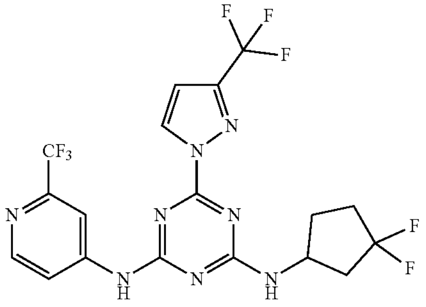 [SMILES: FC1(F)CCC(Nc2nc(Nc3ccnc(C(F)(F)F)c3)nc(-n3ccc(C(F)(F)F)n3)n2)C1]

$^1$H NMR (400 MHz, $CDCl_3$) δ 8.52 (m, 3H), 8.01-7.37 (m, 2H), 6.76 (t, J=3.7 Hz, 1H), 5.92 (m, 1H), 4.79-4.53 (m, 1H), 2.67 (m, 1H), 2.47-2.09 (m, 4H), 1.93-1.86 (m, 1H). LCMS: m/z 495 $(M+H)^+$.

Compound (S)—$N^2$-(3,3-difluorocyclopentyl)-6-(3-(trifluoromethyl)-1H-pyrazol-1-yl)-$N^4$-(2-(trifluoromethyl)pyridin-4-yl)-1,3,5-triazine-2,4-diamine

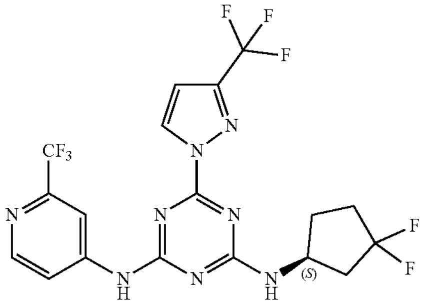

$^1$H NMR (400 MHz, $CDCl_3$) δ 8.64-8.55 (m, 2H), 8.48-8.11 (m, 1H), 7.75-7.41 (m, 2H), 6.77-6.75 (m, 1H), 5.97-5.73 (m, 1H), 4.71-4.61 (m, 1H), 2.74-2.61 (m, 1H), 2.42-2.36 (m, 2H), 2.30-2.16 (m, 2H), 1.93-1.86 (m, 1H). LCMS: m/z 495 $(M+H)^+$.

Compound $N^2$-(3,3-difluorocyclobutyl)-6-(3-(trifluoromethyl)-1H-pyrazol-1-yl)-$N^4$-(2-(trifluoromethyl)pyridin-4-yl)-1,3,5-triazine-2,4-diamine

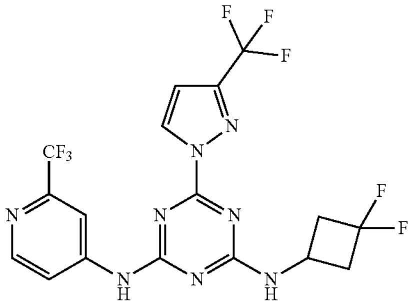

$^1$H NMR (400 MHz, $CD_3OD$) δ 8.69-8.62 (m, 1H), 8.51-7.67 (m, 3H), 6.84-6.834 (m, 1H), 4.51-4.29 (m, 1H), 3.09-3.02 (m, 2H), 2.68-2.64 (m, 2H). LCMS: m/z 481 $(M+H)^+$.

Compound $N^2$-(cyclopropylmethyl)-6-(3-(trifluoromethyl)-1H-pyrazol-1-yl)-$N^4$-(2-(trifluoromethyl) pyridin-4-yl)-1,3,5-triazine-2,4-diamine

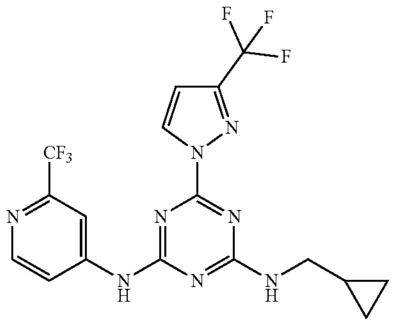 [SMILES: FC(F)(F)c1cc(Nc2nc(NCC3CC3)nc(-n3ccc(C(F)(F)F)n3)n2)ccn1]

$^1$H NMR (400 MHz, $CDCl_3$) δ 8.87-8.36 (m, 3H), 8.27-7.44 (m, 2H), 7.01-6.54 (m, 1H), 6.17-5.80 (m, 1H), 3.43 (m, 2H), 1.35-1.01 (m, 1H), 0.75-0.56 (m, 2H), 0.43-0.24 (m, 2H). LC-MS: m/z 445 $(M+H)^+$.

Compound 6-(3-(Trifluoromethyl)-1H-pyrazol-1-yl)-$N^2$-(2-(trifluoromethyl)pyridin-4-yl)-$N^4$-(1,1,1-trifluoropropan-2-yl)-1,3,5-triazine-2,4-diamine

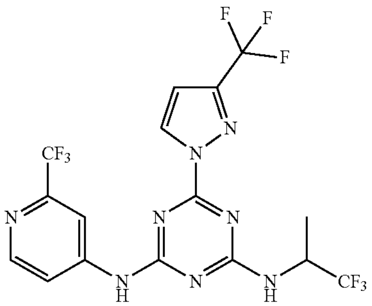 [SMILES: CC(Nc1nc(Nc2ccnc(C(F)(F)F)c2)nc(-n2ccc(C(F)(F)F)n2)n1)C(F)(F)F]

$^1$H NMR (400 MHz, $CDCl_3$) δ 8.69-8.08 (m, 3H), 7.68 (m, 2H), 6.77 (d, J=2.7 Hz, 1H), 5.86 (m, 1H), 4.93 (m, 1H), 1.52 (dd, J=7.1 Hz, 3H). LC-MS: m/z 487 $(M+H)^+$.

Compound (R)-6-(3-(trifluoromethyl)-1H-pyrazol-1-yl)-$N^2$-(2-(trifluoromethyl)pyridin-4-yl)-$N^4$-(1,1,1-trifluoropropan-2-yl)-1,3,5-triazine-2,4-diamine

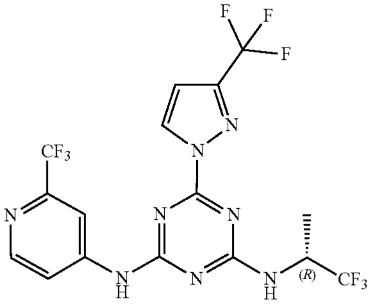

$^1$H NMR (400 MHz, $CDCl_3$) δ 8.74-8.48 (m, 2H), 8.46-7.74 (m, 2H), 7.72-7.34 (m, 1H), 6.77 (d, J=2.7 Hz, 1H), 6.08-5.53 (m, 1H), 5.11-4.77 (m, 1H), 1.52 (m, 3H). LC-MS: m/z 487 $(M+H)^+$.

Compound (S)-6-(3-(trifluoromethyl)-1H-pyrazol-1-yl)-$N^2$-(2-(trifluoromethyl)pyridin-4-yl)-$N^4$-(1,1,1-trifluoropropan-2-yl)-1,3,5-triazine-2,4-diamine

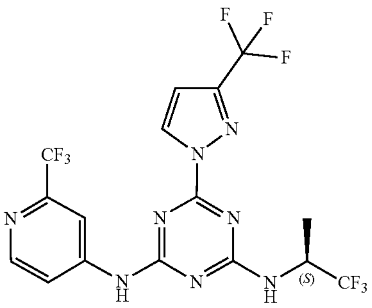

$^1$H NMR (400 MHz, $CDCl_3$) δ 8.65-8.61 (m, 1H), 8.56 (d, J=4 Hz, 1H), 8.37 (m, 1H), 8.08-7.81 (m, 1H), 7.70-7.44 (m, 1H), 6.76-6.68 (m, 1H), 5.97-5.78 (m, 1H), 5.05-4.82 (m, 1H), 1.53-1.49 (m, 3H). LCMS: m/z 487 $(M+H)^+$.

Compound 3-((4-((3,3-Difluorocyclobutyl)amino)-6-(3-(trifluoromethyl)-1H-pyrazol-1-yl)-1,3,5-triazin-2-yl)amino)-5-fluorobenzonitrile

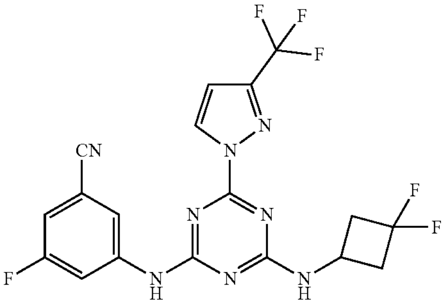 [SMILES: N#Cc1cc(F)cc(Nc2nc(NC3CC(F)(F)C3)nc(-n3ccc(C(F)(F)F)n3)n2)c1]

$^1$H NMR (400 MHz, $CDCl_3$) δ 8.61-8.54 (m, 1H), 7.86-7.78 (m, 1H), 7.69 (s, 1H) 7.60 (d, J=8 Hz, 1H), 7.13-7.08 (m, 1H), 6.76-6.74 (m, 1H), 6.01-5.94 (m, 1H), 4.58-4.42 (m, 1H), 3.20-3.10 (m, 2H), 2.80-2.54 (m, 2H). LCMS: m/z 455 $(M+H)^+$.

Compound 3-Fluoro-5-((4-(3-(trifluoromethyl)-1H-pyrazol-1-yl)-6-((1,1,1-trifluoropropan-2-yl)amino)-1,3,5-triazin-2-yl)amino)benzonitrile

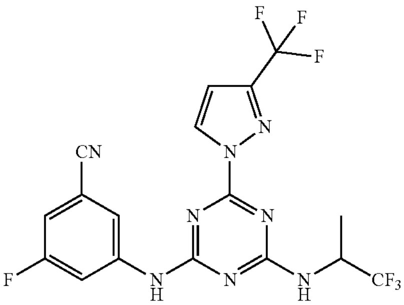 [SMILES: CC(Nc1nc(Nc2cc(F)cc(C#N)c2)nc(-n2ccc(C(F)(F)F)n2)n1)C(F)(F)F]

$^1$H NMR (400 MHz, $CDCl_3$) δ 8.60-8.53 (m, 1H), 7.99-7.62 (m, 3H), 7.14-7.09 (m, 1H), 6.76 (d, J=4 Hz, 1H), 5.90-5.82 (m, 1H), 5.04-4.98 (m, 1H), 4.87-4.81 (m, 3H). LCMS: m/z 461 $(M+H)^+$.

Compound 3-((4-((3,3-Difluorocyclopentyl)amino)-6-(3-(trifluoromethyl)-1H-pyrazol-1-yl)-1,3,5-triazin-2-yl)amino)-5-fluorobenzonitrile

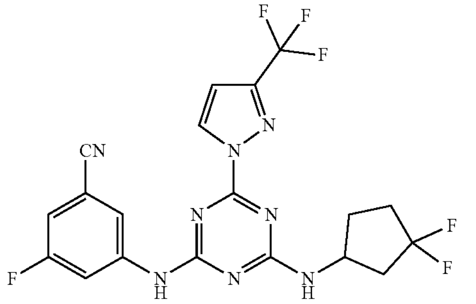 [SMILES: N#Cc1cc(F)cc(Nc2nc(NC3CCC(F)(F)C3)nc(-n3ccc(C(F)(F)F)n3)n2)c1]

$^1$H NMR (400 MHz, $CDCl_3$) δ 8.63-8.55 (m, 1H), 7.83-7.66 (m, 3H), 7.12-7.08 (m, 1H), 6.77-6.75 (m, 1H), 6.68 (d, J=4 Hz, 1H), 6.21-5.79 (m, 1H), 5.56-4.69 (m, 1H), 2.74-2.50 (m, 1H), 2.40-2.15 (m, 4H), 1.94-1.89 (m, 1H). LCMS: m/z 469 $(M+H)^+$.

Compound 4-((4-((3,3-Difluorocyclopentyl)amino)-6-(3-(trifluoromethyl)-1H-pyrazol-1-yl)-1,3,5-triazin-2-yl)amino)picolinonitrile

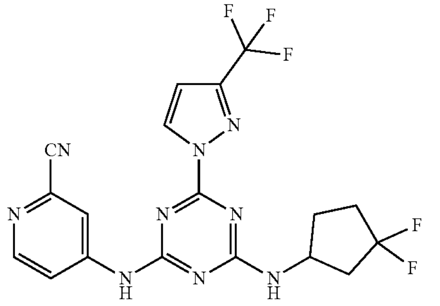 [SMILES: N#Cc1cc(Nc2nc(NC3CCC(F)(F)C3)nc(-n3ccc(C(F)(F)F)n3)n2)ccn1]

$^1$H NMR (400 MHz, $CDCl_3$) δ 8.74-8.31 (m, 4H), 7.83-7.51 (m, 1H), 6.76-6.67 (m, 1H), 6.24-6.19 (m, 1H), 4.70-4.55 (m, 1H), 2.78-2.62 (m, 1H), 2.45-2.13 (m, 4H), 1.98-1.91 (m, 1H).

LCMS: m/z 452 $(M+H)^+$.

Compound (S)-4-((4-((3,3-difluorocyclopentyl)amino)-6-(3-(trifluoromethyl)-1H-pyrazol-1-yl)-1,3,5-triazin-2-yl)amino)picolinonitrile

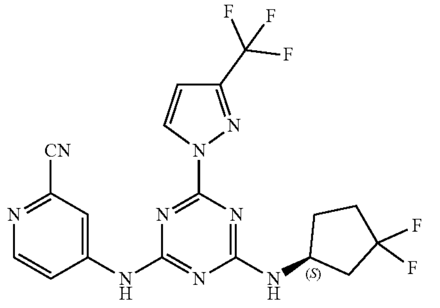

$^1$H NMR (400 MHz, DMSO-$d_6$) δ 10.89 (s, 1H), 8.90 (d, J=8 Hz, 1H), 8.70-8.66 (m, 1H), 8.58-8.42 (m, 2H), 8.00-7.95 (m, 1H), 7.09 (s, 1H), 4.65-4.43 (m, 1H), 2.69-2.57 (m, 1H), 2.36-2.08 (m, 4H), 1.91-1.80 (m, 1H). LCMS: m/z 452 $(M+H)^+$.

Compound 4-((4-((3,3-Difluorocyclobutyl)amino)-6-(3-(trifluoromethyl)-1H-pyrazol-1-yl)-1,3,5-triazin-2-yl)amino)picolinonitrile

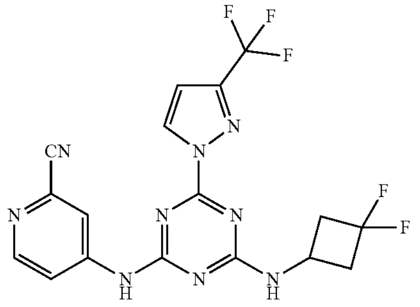 [SMILES: N#Cc1cc(Nc2nc(NC3CC(F)(F)C3)nc(-n3ccc(C(F)(F)F)n3)n2)ccn1]

$^1$H NMR (400 MHz, $CDCl_3$) δ 10.12 (s, 1H), 8.28-7.58 (m, 4H), 7.09-7.14 (m, 1H), 6.25 (s, 1H), 3.61-3.48 (m, 1H), 2.29-1.88 (m, 4H). LCMS: m/z 438 $(M+H)^+$.

Compound (R)-4-((4-(3-(trifluoromethyl)-1H-pyrazol-1-yl)-6-((1,1,1-trifluoropropan-2-yl)amino)-1,3,5-triazin-2-yl)amino)picolinonitrile

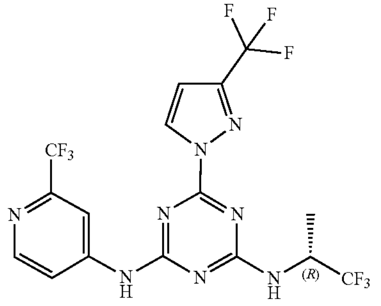

$^1$H NMR (400 MHz, $CDCl_3$) δ 8.64 (d, J=8 Hz, 1H), 8.61-8.57 (m, 1H), 8.45-8.32 (m, 1H), 8.14-7.84 (m, 1H), 7.78-7.48 (m, 1H), 6.78-6.68 (m, 1H), 6.05-5.96 (m, 1H), 5.26-4.70 (m, 1H), 1.57-1.51 (m, 3H). LCMS: m/z 444 $(M+H)^+$.

Compound $N^2$-(3,3-difluorocyclopentyl)-$N^4$-(3,5-difluorophenyl)-6-(3-(trifluoromethyl)-1H-pyrazol-1-yl)-1,3,5-triazine-2,4-diamine

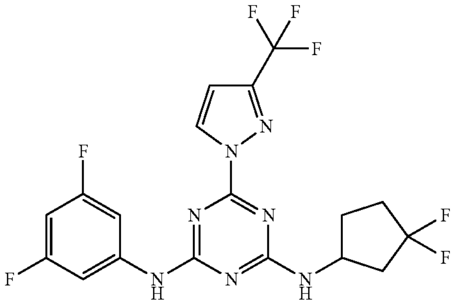 [SMILES: Fc1cc(F)cc(Nc2nc(NC3CCC(F)(F)C3)nc(-n3ccc(C(F)(F)F)n3)n2)c1]

$^1$H NMR (400 MHz, $CDCl_3$) δ 8.65-8.51 (m, 1H), 7.65-7.40 (m, 1H), 7.23 (m, 2H), 6.78-6.69 (m, 1H), 6.64-6.50 (m, 1H), 5.95-5.70 (m, 1H), 4.74-4.51 (m, 1H), 2.78-2.58 (m, 1H), 2.44-2.06 (m, 4H), 1.87 (d, J=3.8 Hz, 1H). LC-MS: m/z 462 $(M+H)^+$.

Compound $N^2$-(3,3-difluorocyclobutyl)-$N^4$-(3,5-difluorophenyl)-6-(3-(trifluoromethyl)-1H-pyrazol-1-yl)-1,3,5-triazine-2,4-diamine

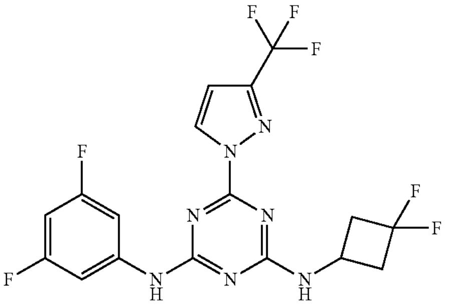 [SMILES: Fc1cc(F)cc(Nc2nc(NC3CC(F)(F)C3)nc(-n3ccc(C(F)(F)F)n3)n2)c1]

$^1$H NMR (400 MHz, $CDCl_3$) δ 8.73-8.40 (m, 1H), 7.61 (m, 1H), 7.22 (m, 2H), 6.73 (dd, J=6.7, 2.7 Hz, 1H), 6.61-6.43 (m, 1H), 6.00 (m, 1H), 4.44 (m, 1H), 3.29-3.02 (m, 2H), 2.85-2.38 (m, 2H). LC-MS: m/z 448 $(M+H)^+$.

Compound $N^2$-(3,5-difluorophenyl)-6-(3-(trifluoromethyl)-1H-pyrazol-1-yl)-$N^4$-(1,1,1-trifluoropropan-2-yl)-1,3,5-triazine-2,4-diamine

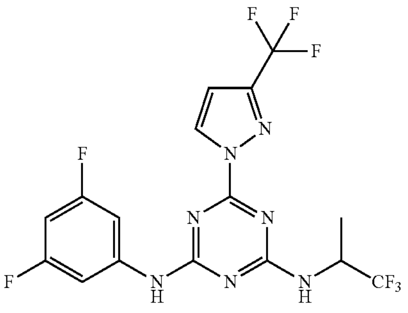 [SMILES: CC(Nc1nc(Nc2cc(F)cc(F)c2)nc(-n2ccc(C(F)(F)F)n2)n1)C(F)(F)F]

$^1$H NMR (400 MHz, $CDCl_3$) δ 8.62-8.51 (m, 1H), 7.78-7.35 (m, 1H), 7.25-7.12 (m, 2H), 6.74 (d, J=2.0 Hz, 1H), 6.65-6.52 (m, 1H), 5.85-5.62 (m, 1H), 5.06-4.80 (m, 1H), 1.48 (m, 3H).

LC-MS: m/z 454 $(M+H)^+$.

Compound 1-((4-((3,5-Difluorophenyl)amino)-6-(3-(trifluoromethyl)-1H-pyrazol-1-yl)-1,3,5-triazin-2-yl)amino)-2-methylpropan-2-ol

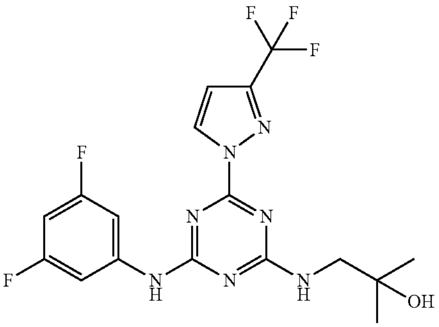 [SMILES: CC(C)(O)CNc1nc(Nc2cc(F)cc(F)c2)nc(-n2ccc(C(F)(F)F)n2)n1]

$^1$H NMR (400 MHz, $CDCl_3$) δ 8.53 (d, J=4 Hz, 1H), 7.70-7.53 (m, 1H), 7.23-7.19 (m, 2H), 6.71-6.67 (m, 1H), 6.57-6.51 (m, 1H), 6.28-6.08 (m, 1H), 3.73-3.56 (m, 2H), 2.46-1.49 (m, 6H), 1.24 (m, 1H). LCMS: m/z 430 $(M+H)^+$.

Example 37. Preparation of Aromatic-aliphatic Triazine Compounds of Formula Ic. The compounds of this Example are prepared by general Scheme 37, set forth below.

Scheme 37

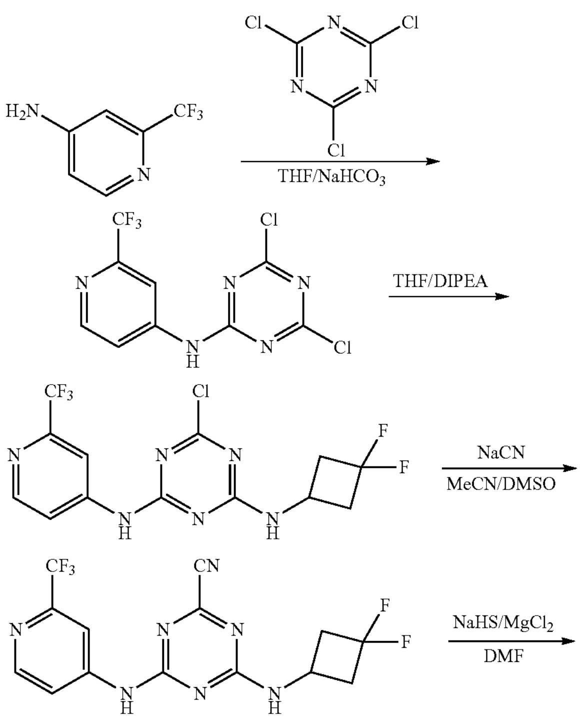

-continued

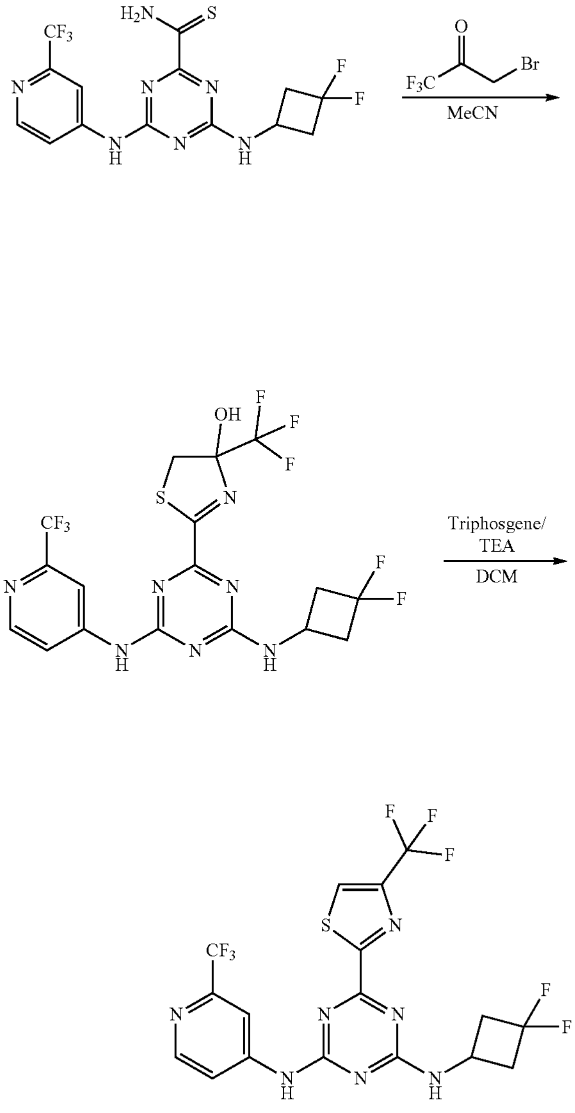

Step 1: Preparation of 4,6-dichloro-N-(2-(trifluoromethyl)pyridin-4-yl)-1,3,5-triazin-2-amine. To a solution of 2-(trifluoromethyl)pyridin-4-amine (3 g, 18.7 mmol) and 2,4,6-trichloro-1,3,5-triazine (3.6 g, 19.5 mmol) in THF (40 mL) was added $NaHCO_3$(3.1 g, 37.5 mmol). The reaction mixture was stirred at r.t. for 16 hr and filtered. The filtrate was concentrated concentrated and purified by standard methods to afford the desired product. LC-MS: m/z 310 $(M+H)^+$.

Step 2: Preparation of 6-chloro-$N^2$-(3,3-difluorocyclobutyl)-$N^4$-(2-(trifluoro methyl)pyridin-4-yl)-1,3,5-triazine-2,4-diamine. To a solution of 4,6-dichloro-N-(2-(trifluoromethyl)pyridin-4-yl)-1,3,5-triazin-2-amine (4 g, 12.9 mmol) and 3,3-difluorocyclobutanamine hydrochloride (1.9 g, 13.5 mmol) in THF (40 mL) was added DIPEA (4.8 g, 37.2 mmol). The reaction mixture was stirred at r.t. for 15 hr then concentrated under reduced pressure. The residue was partitioned between EtOAc (200 mL) and aq. HCl (10% wt, 50 mL). The aqueous layer was separated and extracted with EtOAc (2×100 mL). The combined organic layers were dried over anhydrous $Na_2SO_4$, concentrated and purified by standard methods to afford the desired product.

LC-MS: m/z 381 $(M+H)^+$.

Step 3: Preparation of 4-(3,3-difluorocyclobutylamino)-6-(2-(trifluoromethyl) pyridin-4-ylamino)-1,3,5-triazine-2-carbonitrile. To a solution of 6-chloro-$N^2$-(3,3-difluorocyclobutyl)-$N^4$-(2-(trifluoromethyl)pyridin-4-yl)-1,3,5-triazine-2,4-diamine (2.2 g, 5.77 mmol) in MeCN (30 mL) and DMSO (10 mL) at r.t. was added NaCN (2.9 g, 60 mmol). The reaction mixture was stirred at 60° C. overnight then partitioned between EtOAc (50 mL) and $H_2O$ (20 mL). The organic layer was separated, washed with brine, dried over anhydrous $Na_2SO_4$, concentrated and purified by standard methods to afford the desired product. LC-MS: m/z 372 $(M+H)^+$.

Step 4: Preparation of 4-(3,3-difluorocyclobutylamino)-6-(2-(trifluoromethyl) pyridin-4-ylamino)-1,3,5-triazine-2-carbothioamide. To a solution of 4-(3,3-difluorocyclobutylamino)-6-(2-(trifluoromethyl)pyridin-4-ylamino)-1,3,5-triazine-2-carbonitrile (0.7 g, 1.88 mmol) in DMF (15 mL) were added NaHS (0.5 g, 9.0 mmol) and $MgCl_2$ (0.85 g, 9.0 mmol). The reaction mixture was stirred at r.t. for 0.5 hr then partitioned between EtOAc (30 mL) and $H_2O$ (10 mL). The organic layer was separated, washed with brine, dried over anhydrous $Na_2SO_4$, and concentrated and purified by standard methods to afford the desired product. LC-MS: m/z 406 $(M+H)^+$.

Step 5: Preparation of 2-(4-(3,3-difluorocyclobutylamino)-6-(2-(trifluoromethyl) pyridin-4-ylamino)-1,3,5-triazin-2-yl)-4-(trifluoromethyl)-4,5-dihydrothiazol-4-ol. A mixture of 4-(3,3-difluorocyclobutylamino)-6-(2-(trifluoromethyl)pyridin-4-ylamino)-1,3,5-triazine-2-carbothioamide (350 mg, 0.86 mmol) and 3-bromo-1,1,1-trifluoropropan-2-one (180 mg, 0.95 mmol) in MeCN (10 mL) was stirred at 60° C. for 2 hr then partitioned between EtOAc (20 mL) and $H_2O$ (10 mL). The organic layer was separated, washed with brine, dried over anhydrous $Na_2SO_4$, and concentrated and purified by standard methods to afford the desired product.

$^1H$ NMR (400 MHz, DMSO-$d_6$) δ 10.94-10.86 (m, 1H), 9.08 (d, J=6.0 Hz, 1H), 8.69-8.48 (m, 2H), 7.86-7.78 (m, 2H), 4.30-4.21 (m, 1H), 3.76-3.71 (m, 1H), 3.53-3.41 (m, 1H), 3.11-2.93 (m, 2H), 2.87-2.66 (m, 2H). LC-MS: m/z 516 $(M+H)^+$.

Step 6: Preparation of $N^2$-(3,3-difluorocyclobutyl)-$N^4$-(2-(trifluoromethyl)pyridin-4-yl)-6-(4-(trifluoromethyl)thiazol-2-yl)-1,3,5-triazine-2,4-diamine. To a solution of 2-(4-(3,3-difluorocyclobutylamino)-6-(2-(trifluoromethyl) pyridin-4-ylamino)-1,3,5-triazin-2-yl)-4-(trifluoromethyl)-4,5-dihydrothiazol-4-ol (250 mg, 0.48 mmol) and TEA (0.4 mL, 2.4 mmol) in DCM (20 mL) at 0° C. was added dropwise a solution of triphosgene (290 mg, 0.96 mmol) in DCM (5 mL). The reaction mixture was stirred at 0° C. for 0.5 hr, and then partitioned between DCM (20 mL) and $H_2O$ (10 mL). The organic layer was separated, washed with brine, dried over anhydrous $Na_2SO_4$, and concentrated and purified by standard methods to afford the desired product. $^1H$ NMR (400 MHz, DMSO-$d_6$) δ 11.05-10.94 (m, 1H), 9.10 (d, J=6.1 Hz, 1H), 8.82 (s, 1H), 8.70 (s, 1H), 8.64 (t, J=5.4 Hz, 1H), 7.83 (d, J=5.4 Hz, 1H), 4.52-4.22 (m, 1H), 3.18-2.99 (m, 2H), 2.82 (dt, J=32.2, 14.2 Hz, 2H). LC-MS: m/z 498 $(M+H)^+$.

The procedure set forth above in Example 37 used to produce the following compounds using the appropriate starting materials.

Compound $N^2$-(cyclopropylmethyl)-$N^4$-(2-(trifluoromethyl)pyridin-4-yl)-6-(4-(trifluoromethyl)thiazol-2-yl)-1,3,5-triazine-2,4-diamine

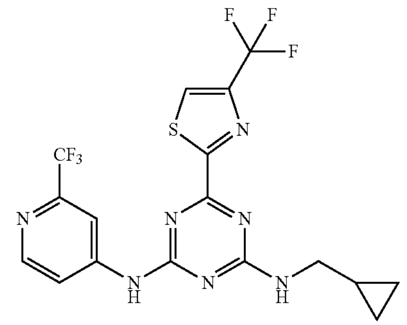 [SMILES: FC(F)(F)c1cc(Nc2nc(NCC3CC3)nc(-c3nc(C(F)(F)F)cs3)n2)ccn1]

$^1$H NMR (400 MHz, $CDCl_3$) δ 8.61 (t, J=5.7 Hz, 1H), 8.52-8.15 (m, 1H), 7.99 (s, 1H), 7.77-7.41 (m, 2H), 6.09-5.70 (m, 1H), 3.50-3.34 (m, 2H), 1.20-1.11 (m, 1H), 0.67-0.57 (m, 2H), 0.40-0.28 (m, 2H). LC-MS: m/z 462 $(M+H)^+$.

Compound $N^2$-(3,3-difluorocyclopentyl)-$N^4$-(2-(trifluoromethyl)pyridin-4-yl)-6-(4-(trifluoromethyl) thiazol-2-yl)-1,3,5-triazine-2,4-diamine

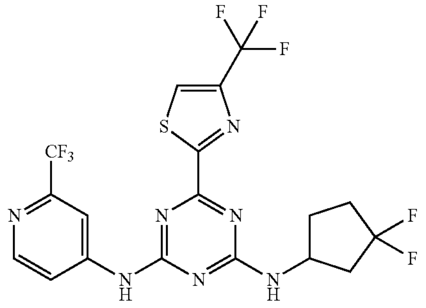 [SMILES: FC1(F)CCC(Nc2nc(Nc3ccnc(C(F)(F)F)c3)nc(-c3nc(C(F)(F)F)cs3)n2)C1]

$^1$H NMR (400 MHz, DMSO-$d_6$) δ 10.88 (s, 1H), 8.83 (d, J=6.9 Hz, 1H), 8.75 (s, 1H), 8.62 (s, 1H), 8.57 (d, J=5.5 Hz, 1H), 7.79 (d, J=5.5 Hz, 1H), 4.61-4.32 (m, 1H), 2.59-2.51 (m, 1H), 2.41-1.99 (m, 4H), 1.95-1.74 (m, 1H). LC-MS: m/z 512 $(M+H)^+$.

Compound $N^2$-(3,3-difluorocyclopentyl)-$N^4$-(3,5-difluorophenyl)-6-(4-(trifluoromethyl)thiazol-2-yl)-1,3,5-triazine-2,4-diamine

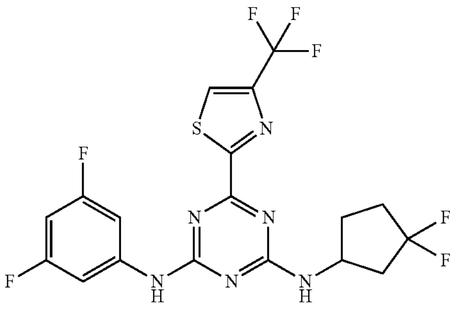 [SMILES: Fc1cc(F)cc(Nc2nc(NC3CCC(F)(F)C3)nc(-c3nc(C(F)(F)F)cs3)n2)c1]

$^1$H NMR (400 MHz, $CDCl_3$) δ 7.97 (s, 1H), 7.45-7.26 (m, 4H), 7.25-7.23 (m, 1H), 6.60-6.56 (m, 1H), 5.92-5.34 (m, 1H), 4.68-4.57 (m, 1H), 2.70-2.64 (m, 1H), 2.37-2.16 (m, 4H), 1.87 (s, 1H). LCMS: m/z 479 $(M+H)^+$.

Compound $N^2$-(3,3-difluorocyclobutyl)-$N^4$-(3,5-difluorophenyl)-6-(4-(trifluoromethyl)thiazol-2-yl)-1,3,5-triazine-2,4-diamine

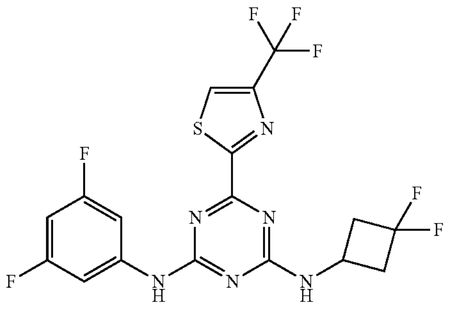 [SMILES: Fc1cc(F)cc(Nc2nc(NC3CC(F)(F)C3)nc(-c3nc(C(F)(F)F)cs3)n2)c1]

$^1$H NMR (400 MHz, $CDCl_3$) δ 7.97 (d, J=4 Hz, 1H), 7.60-7.47 (m, 1H), 7.26 (m, 1H), 7.26-7.22 (m, 1H), 6.61-6.53 (m, 1H), 6.00-5.74 (m, 1H), 4.52-4.41 (m, 1H), 3.15 (s, 2H), 2.70-2.57 (m, 2H). LCMS: m/z 465 $(M+H)^+$.

Compound 3-((4-((3,3-Difluorocyclobutyl)amino)-6-(4-(trifluoromethyl)thiazol-2-yl)-1,3,5-triazin-2-yl) amino)-5-fluorobenzonitrile

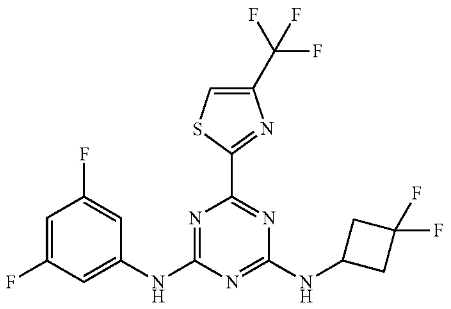 [SMILES: Fc1cc(F)cc(Nc2nc(NC3CC(F)(F)C3)nc(-c3nc(C(F)(F)F)cs3)n2)c1]

$^1$H NMR (400 MHz, $CDCl_3$) δ 8.01 (s, 1H), 7.87-7.797 (m, 2H), 7.66 (d, J=8 Hz, 1H), 7.14-7.10 (m, 1H), 5.99-5.75 (m, 1H), 4.72-4.58 (m, 1H), 2.79-2.65 (m, 1H), 2.40-2.18 (m, 3H).

LCMS: m/z 472 $(M+H)^+$.

Compound 3-((4-((3,3-Difluorocyclopentyl)amino)-6-(4-(trifluoromethyl)thiazol-2-yl)-1,3,5-triazin-2-yl)amino)-5-fluorobenzonitrile

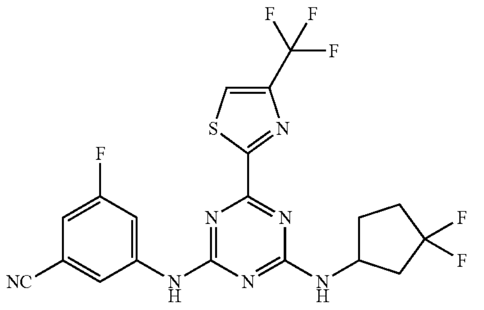 [SMILES: N#Cc1cc(F)cc(Nc2nc(NC3CCC(F)(F)C3)nc(-c3nc(C(F)(F)F)cs3)n2)c1]

$^1$H NMR (400 MHz, $CDCl_3$) δ 8.00 (s, 1H), 7.28-7.02 (m, 3H), 6.61 (s, 1H), 6.01-5.76 (m, 1H), 4.51-4.44 (m, 1H), 3.18 (s, 1H), 2.63 (m, 2H), 1.60-1.50 (m, 1H), 1.27-1.10 (m, 2H). LCMS: m/z 486 $(M+H)^+$.

Example 38. Preparation of Dialiphatic Pyrimidine Compounds of Formula S. The compounds of this Example are prepared by general Scheme 32, set forth below.

Scheme 32

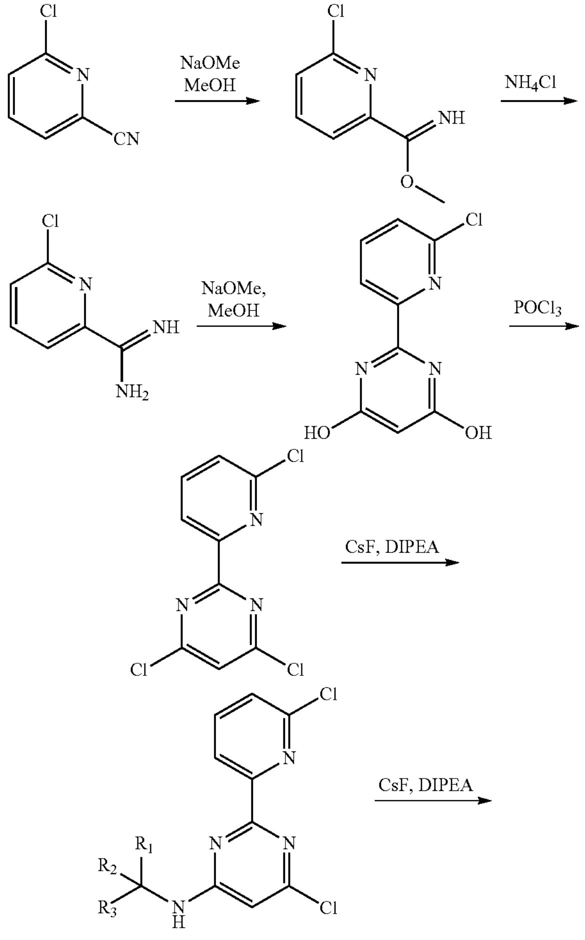

-continued

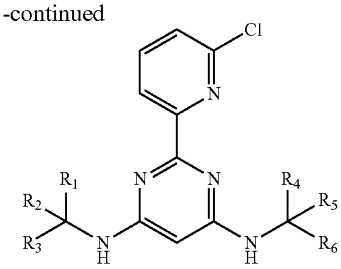

Formula S

Step 1: Preparation of methyl 6-chloropicolinimidate. To a solution of 6-chloropicolinonitrile (3 g, 22 mmol) in MeOH (25 mL) was added a freshly prepared solution of sodium metal (55 mg, 2.4 mol) in MeOH (5 mL). The reaction mixture was stirred at r.t. for 16 hr, and then concentrated under reduced pressure to afford the desired product. LC-MS: m/z 171 $(M+H)^+$.

Step 2: Preparation of 6-chloropicolinimidamide. A mixture of ammonium chloride (2.18 g, 40 mmol) and methyl 6-chloropicolinimidate (3.5 g, 20 mmol) in MeOH (30 mL) was a stirred at 70° C. for 3 hr, then cooled to r.t. and concentrated under reduced pressure. The residue was diluted with EtOH (40 mL) and stirred at reflux for 0.5 hr. The resulting mixture was cooled and filtered. The filtrate was concentrated under reduced pressure to give the desired product. LC-MS: m/z 156 $(M+H)^+$.

Step 3: Preparation of 2-(6-chloropyridin-2-yl)pyrimidine-4,6-diol. To a solution of sodium metal (0.9 g, 40 mmol) in MeOH (10 mL) was added 6-chloropicolinimidamide (2 g, 13 mmol) and dimethyl malonate (1.7 g, 13 mmol). The reaction mixture was stirred at 85° C. overnight, and then concentrated under reduced pressure. The residue was triturated with EtOAc (30 mL) and filtered. The solid was collected and dried under high vacuum to give the desired product. LC-MS: m/z 224 $(M+H)^+$.

Step 4: Preparation of 4,6-dichloro-2-(6-chloropyridin-2-yl)pyrimidine. A mixture of 2-(6-chloropyridin-2-yl)pyrimidine-4,6-diol (2 g, 9 mmol) in $POCl_3$ (20 mL) was stirred at 90° C. overnight then concentrated under reduced pressure. The residue was slowly poured into satd. aq. $NaHCO_3$ at 0° C. The resulting mixture was extracted with EtOAc (2×30 mL). Combined organic layers were washed with water (30 mL) and brine (30 mL), dried over anhydrous $Na_2SO_4$ and concentrated under reduced pressure. The residue was purified by standard methods to give the desired product. LC-MS: m/z 260 $(M+H)^+$.

Step 5: Preparation of (R)-6-chloro-2-(6-chloropyridin-2-yl)-N-(1,1,1-trifluoro propan-2-yl)pyrimidin-4-amine. A mixture of 4,6-dichloro-2-(6-chloropyridin-2-yl) pyrimidine (200 mg, 0.77 mmol), 1,1,1-trifluoropropan-2-amine hydrochloride (255 mg, 1.7 mmol), CsF (258 mg, 1.7 mmol), and DIPEA (497 mg, 3.85 mmol) in DMSO (3 mL) was stirred at 100° C. overnight. The resulting mixture was quenched with $H_2O$ (30 mL) and extracted with EtOAc (2×30 mL). The combined organic layers were washed with brine (30 mL), dried over anhydrous $Na_2SO_4$, and concentrated under reduced pressure. The residue was purified by standard methods to give the desired product. $^1$H NMR (400 MHz, DMSO-$d_6$) δ 8.37 (m, 2H), 8.04 (m, 1H), 7.68 (d, J=8 Hz, 1H), 6.89 (m, 1H), 5.02 (m, 1H), 1.38 (d, J=8 Hz, 3H). LC-MS: m/z 337 $(M+H)^+$.

Step 6: Preparation of (R)-2-(6-chloropyridin-2-yl)-$N^4$-(4,4-difluorocyclohexyl)-$N^6$-(1,1,1-trifluoropropan-2-yl)

pyrimidine-4,6-diamine. A mixture of (R)-6-chloro-2-(6-chloropyridin-2-yl)-N-(1,1,1-trifluoropropan-2-yl) pyrimidin-4-amine (100 mg, 0.3 mmol), 4,4-difluorocyclohexanamine hydrochloride (114 mg, 0.66 mmol), CsF (100 mg, 0.66 mmol), and DIPEA (194 mg, 1.5 mmol) in DMSO (3 mL) was stirred at 100° C. overnight. The resulting mixture was quenched with $H_2O$ (30 mL) and extracted with EtOAc (2×30 mL). The combined organic layers were washed with brine (30 mL), dried over anhydrous $Na_2SO_4$, concentrated, and purified by standard methods to give the desired product.

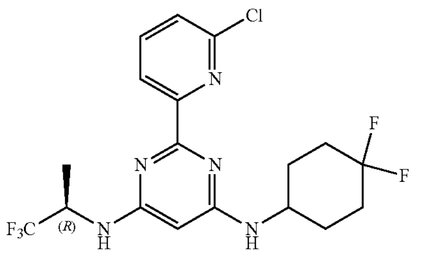

$^1$H NMR (400 MHz, DMSO-$d_6$) δ 8.25 (d, J=8 Hz, 1H), 8.15 (s, 1H), 7.96 (m, 1H), 7.56 (d, J=8 Hz, 1H), 7.31 (m, 1H), 7.06 (d, J=8 Hz, 1H), 5.62 (m, 1H), 5.30-4.84 (m, 1H), 2.33 (m, 1H), 2.14-1.90 (m, 5H), 1.65 (m, 2H), 1.32 (d, J=8 Hz, 3H). LCMS: m/z 436 $(M+H)^+$

Example 8. Enzymatic and Cell Assays

In Vitro Assays for IDH1m (R132H or R132C) Inhibitors

The following describes the experimental procedures that can be used to obtain data on columns 2 and 4 of Table 4 and column 2 of Table 5.

In the primary reaction, the reduction of α-KG acid to 2-HG is accompanied by a concomitant oxidation of NADPH to NADP. The amount of NADPH remaining at the end of the reaction time is measured in a secondary diaphorase/resazurin reaction in which the NADPH is consumed in a 1:1 molar ratio with the conversion of resazurin to the highly fluorescent resorufin. Uninhibited reactions exhibit a low fluorescence at the end of the assay, while reactions in which the consumption of NADPH by R132H IDH1 has been inhibited by a small molecule show a high fluorescence.

The primary reaction is performed in a volume of 50 μL 1× Buffer (150 mM NaCl, 20 mM Tris 7.5, 10 mM $MgCl_2$, 0.05% (w/v) bovine serum albumin), contained 0.25 ug/mL (2.7 nM) IDH1 wt/IDH1 R132H heterodimer, 0.3 mM alpha-ketoglutarate, 4 μM NADPH, and either 300 μM NADP (saturated) or 30 μM NADP (without saturation), and 1 uL of 50× compound in DMSO. The mixture of compound, enzyme, and cofactor is pre-incubated at room temperature for 1 hr prior to the addition of alpha-ketoglutarate. To perform the secondary reaction, 10 uL of 1× buffer containing 36 μg/ml diaphorase and 30 mM resazurin is added to the primary reaction and incubated for a further 5 minutes at 25° C. Florescence is read on a Spectramax platereader at Ex 544 Em 590. Compounds or compound dilutions are prepared in 100% DMSO concentration and diluted 1:50 into the final reaction. IDH1 wt/IDH1 R132C is assayed under similar conditions except that 1× Buffer is 50 mM $K_2HPO_4$, pH 6.5; 10 mM $MgCl_2$; 10% glycerol; 0.03% (w/v) bovine serum albumin and final concentrations are 0.4 ug/mL (4.3 nM) IDH1 wt/IDH1 R132C heterodimer, 0.02 mM alpha-ketoglutarate, 4 uM NADPH, and either 300 μM NADP (saturated) or 30 μM NADP (without saturation). IC50s are determined.

IDH1 or IDH2 wildtype (wt) and mutant heterodimers are expressed and purified by methods known in the art. For example, IDH1 wt/R132m heterodimer is expressed and purified as follows. Co-expression of IDH1 wt-his and IDH1R132C-flag is carried out in sf9 insect cells. Cells (25 g) are resuspended in 250 ml of 50 mM Tirs, 500 mM NaCl, pH7.4, at 4° C. with stirring. Cells are disrupted with 4 passes through an M-Y110 Micro fluidizer (Microfluidics) set to 500 psi, and then centrifuged at 22,000 rcf for 20 min at 4° C. The supernatant is harvested and loaded at 15 cm/h on a Histrap FF 5*1 ml column (GE) which is equilibrated with 50 mM Tirs, 500 mM NaCl, pH7.4. Host cell contaminants are removed by washing the column with equilibration buffer followed by equilibration buffer containing 20 mM imidazole and 60 mM imidazole to baseline. IDH1 wt-his homodimer and IDH1 wt-his/IDH1R132C-flag are eluted by equilibration buffer containing 250 mM imidazole. Fractions eluted by 250 mM imidazole are pooled together and loaded at 15 cm/h onto a column pre-packed with 10 ml ANTI-FLAG® M2 Affinity Gel (Sigma), the column is equilibrated with 50 mM Tris, 500 mM NaCl, pH7.4. After washing with equilibration buffer, IDH1 wt-his/IDH1R132C-flag heterodimer is eluted by equilibration buffer containing flag peptide (0.2 mg/ml). Aliquots of IDH1 wt-his/IDH1R132C-flag are flash frozen in liquid $N_2$ and stored at −80° C. Same conditions are used for the purification of IDH1 wt-his/IDH1R132H-flag.

In Vitro Assays for IDH1m (R132H or R132C) Inhibitors

The following describes the experimental procedures that can be used to obtain data on columns 3 and 6 of Table 4.

A test compound is prepared as 10 mM stock in DMSO and diluted to 50× final concentration in DMSO, for a 50 1 reaction mixture. IDH enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1-R132 homodimer enzyme is diluted to 0.125 μg/ml in 40 μl of Assay Buffer(150 mM NaCl, 20 mM Tris-Cl pH 7.5, 10 mM $MgCl_2$, 0.05% BSA, 2 mM b-mercaptoethanol); 1 μl of test compound dilution in DMSO is added and the mixture is incubated for 60 minutes at room temperature. The reaction is started with the addition of 10 μl of Substrate Mix (20 μl NADPH, 5 mM alpha-ketoglutarate, in Assay Buffer) and the mixture is incubated for 90 minutes at room temperature. The reaction is terminated with the addition of 25 μl of Detection Buffer (36 μg/ml diaphorase, 30 mM resazurin, in 1× Assay Buffer), and is incubated for 1 minute before reading on a SpectraMax platereader at Ex544/Em590.

Compounds are assayed for their activity against IDH1 R132C following the same assay as above with the following modifications: Assay Buffer is (50 mM potassium phosphate, pH 6.5; 40 mM sodium carbonate, 5 mM $MgCl_2$, 10% glycerol, 2 mM b-mercaptoethanol, and 0.03% BSA). The concentration of NADPH and alpha-ketoglutarate in the Substrate Buffer is 20 μM and 1 mM, respectively.

In Vitro Assays for IDH1m (R132H or R132C) Inhibitors

The following describes the experimental procedures that can be used to obtain data on columns 3 and 5 of Table 5.

A test compound is prepared as 10 mM stock in DMSO and diluted to 50× final concentration in DMSO, for a 50 μl reaction mixture. IDH enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1-R132H homodimer enzyme is diluted to 0.125 μg/ml in 40 μl of Assay Buffer(150 mM NaCl, 20 mM Tris-Cl pH 7.5, 10 mM $MgCl_2$, 0.05% BSA, 2 mM b-mercaptoethanol) containing 5 μM NADPH and 37.5 μM NADP; 1 μl of test compound dilution in DMSO is added and the mixture is incubated for 60 minutes at room temperature. The reaction is started with the addition of 10 μl of Substrate Mix (20 μl NADPH, 5 mM alpha-ketoglutarate, in Assay Buffer) and the mixture is incubated for 60 minutes at room temperature. The reaction is terminated with the addition of 25 μl of Detection Buffer (36 μg/ml diaphorase, 30 mM resazurin, in 1× Assay Buffer), and is incubated for 1 minute before reading on a SpectraMax platereader at Ex544/Em590.

Compounds are assayed for their activity against IDH1 R132C following the same assay as above with the following modifications: IDH1-R132C homodimer enzyme is diluted to 0.1875 μg/ml in 40 μl of Assay Buffer (50 mM potassium phosphate, pH 6.5; 40 mM sodium carbonate, 5 mM $MgCl_2$, 10% glycerol, 2 mM b-mercaptoethanol, and 0.03% BSA) containing 5 uM NADPH and 28.75 uM NADP. The concentration of alpha-ketoglutarate in the Substrate Buffer is 1 mM.

In Vitro Assays for IDH2m R140Q Inhibitors

The following describes the experimental procedures used to obtain data on column 7 of Table 4.

Compounds are assayed for IDH2 R140Q inhibitory activity through a cofactor depletion assay. Compounds are preincubated with enzyme, then the reaction is started by the addition of NADPH and α-KG, and allowed to proceed for 60 minutes under conditions previously demonstrated to be linear with respect for time for consumption of both cofactor and substrate. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 μl of 100× compound dilution series is placed, followed by the addition of 40 μl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 0.25 μg/ml IDH2 R140Q protein. The test compound is then incubated for one hour at room temperature with the enzyme; before starting the IDH2 reaction with the addition of 10 μl of substrate mix containing 4 μM NADPH and 1.6 mM α-KG in the buffer described above. After a further 16 hours of incubation at room temperature, the reaction is halted and the remaining NADPH measured through conversion of resazurin to resorufin by the addition of 25 μl Stop Mix (36 μg/ml diaphorase enzyme and 60 μM resazurin; in buffer). After one minute of incubation the plate is read on a plate reader at Ex544/Em590.

For determination of the inhibitory potency of compounds against IDH2 R140Q in an assay format similar to the above, a similar procedure is performed, except that the final testing concentration is 0.25 μg/ml IDH2 R140Q protein, 4 μM NADPH and 1.6 mM α-KG.

For determination of the inhibitory potency of compounds against IDH2 R140Q in a high throughput screening format, a similar procedure is performed, except that 0.25 μg/ml IDH2 R140Q protein is utilized in the preincubation step, and the reaction is started with the addition of 4 μM NADPH and 8 μM α-KG.

In Vitro Assays for IDH2m R140Q Inhibitors

The following describes the experimental procedures used to obtain data on column 6 of Table 5.

Compounds are assayed for IDH2 R140Q inhibitory activity through a cofactor depletion assay. Compounds are preincubated with enzyme and cofactor, then the reaction is started by the addition of α-KG, and allowed to proceed for 60 minutes under conditions previously demonstrated to be linear. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 μl of 50× compound dilution series is placed, followed by the addition of 40 μl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 0.39 μg/ml IDH2 R140Q protein, 5 uM NADPH and 750 uM NADP. The test compound is then incubated for 16 hrs at room temperature with the enzyme and cofactors before starting the IDH2 reaction with the addition of 10 μl of substrate mix containing 8 mM α-KG (final concentration 1.6 mM) in the buffer described above. After a further 1 hour of incubation at room temperature, the reaction is halted and the remaining NADPH measured through conversion of resazurin to resorufin by the addition of 25 μl Stop Mix (36 μg/ml diaphorase enzyme and 60 μM resazurin; in buffer). After one minute of incubation the plate is read on a plate reader at Ex544/Em590.

Cellular Assays for IDH1m (R132H or R132C) Inhibitors.

The following describes the experimental procedures that can be used to obtain data on column 5 of Table 4.

Cells (HT1080 or U87MG) are grown in T125 flasks in DMEM containing 10% FBS, lx penicillin/streptomycin and 500 ug/mL G418 (present in U87MG cells only). They are harvested by trypsin and seeded into 96 well white bottom plates at a density of 5000 cell/well in 100 ul/well in DMEM with 10% FBS. No cells are placed in columns 1 and 12. Cells are incubated overnight at 37° C. in 5% $CO_2$. The next day test compounds are made up at 2× the final concentration and 100 ul are added to each cell well. The final concentration of DMSO is 0.2% and the DMSO control wells are plated in row G. The plates are then placed in the incubator for 48 hours. At 48 hours, 100 ul of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of Promega Cell Titer Glo reagent is added to each well of media. The cell plate is then placed on an orbital shaker for 10 minutes and then allowed to sit at room temperature for 20 minutes. The plate is then read for luminescence with an integration time of 500 ms.

U87MG pLVX-IDH2 R140Q-Neo and HT1080 Cell Based Assays

The following describes the experimental procedures that are used to obtain data on column 8 of Table 4.

U87MG pLVX-IDH2 R140Q-neo cells are maintained in DMEM containing 10% FBS, 1× penicillin/streptomycin and 500 μg/uL G418. HT1080 cells are maintained in RPMI containing 10% FBS, 1× penicillin/streptomycin. Cells are seeded at a density of 5,000 (U87MG R140Q) or 2,500 (HT1080) cells/well into 96-well microtiter plates and incubated overnight at 37° C. and 5% $CO_2$. The next day compounds are prepared in 100% DMSO and then diluted in media for a final concentration of 0.2% DMSO. Media is removed from the cell plates and 200 μL of the compound dilutions are added to each well. After 48 hours of incubation with compound at 37° C., 100 μL of media are removed from each well and analyzed by LC-MS for 2-HG concentrations as described in Dang, L. et al. Nature, 2009, 462, 739-744. The cell plates are then allowed to incubate another 24 hours. At 72 hours post compound addition, Promega Cell Titer Glo reagent is added to each well and the plates are read for luminescence to determine any compound effects on growth inhibition ($GI_{50}$).

Cellular Assay for IDH1m R132H Inhibitors.

The following describes the experimental procedures that can be used to obtain data in column 4 of Table 5.

Neurosphere cells (TS603) are grown at 37C in 5% $CO_2$ in Stem Cell Technologies NeuroCult™ NS-A media supplemented with 1% Primocin, 1% Normocin, 0.0002% Heparin, 20 ng/mL EGF and 10 ng/mL bFGF. Cells are harvested, pelleted and resuspended in Accumax for cell dissociation and counting. Cells are counted and then resuspended in NeuroCult media with 2× heparin, EGF and bFGF at 4 million cells/10 mL media. 100 μl of cell solution are plated in each well of a 96 well with the exception of columns 1 and 12. Columns 1 and 12 contain 200 μL PBS. Compound dose responses are set up at a 2× concentration in Neurocult media without heparin, EGF and bFGF. The final concentration of DMSO is 0.25%. DMSO only control wells are plated in row H. The plates are then placed in the incubator for 48 hours. At 48 hours, 100 μl of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 μl of Promega Cell Titer Glo reagent is added to each well of media. The cell plate is then placed on an orbital shaker for 10 minutes and then allowed to sit at room temperature for 20 minutes. The plate is then read for luminescence with an integration time of 500 ms.

The data for various compounds of one aspect of the invention in the R132H enzymatic assay, R132C enzymatic assay, R140Q enzymatic assay, R132C cell-based assay, and R14Q cell-based assay as described above or similar thereto are presented below in Tables 2 and 3. For each assay, values indicated as "A" represent an IC50 of less than 50 nM; values indicated as "B" represent an IC50 of between 50 nM and 100 nM; values indicated as "C" represent an IC50 of greater than 100 nM and less than 1 μM; values indicated as "D" represent an IC50 of greater than or equal to 1 μM; values indicated as "no fit" are inactives and blank values represent that the compound was either inactive or not tested in that particular assay.

TABLE 4

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 1 | | D | | | D | A | A |
| 2 | | A | | A | A | A | A |
| 3 | | C | | | B | | |
| 4 | | B | | B | B | A | |
| 5 | | D | | | No Fit | | |
| 6 | | D | | | C | | |
| 7 | | C | | | D | A | |
| 8 | | No Fit | | | D | B | |
| 9 | | B | | | C | A | |
| 10 | | D | | | D | B | |
| 11 | | C | | B | B | A | |
| 12 | | D | | | D | B | |
| 13 | | A | | A | B | | |
| 14 | | D | | | D | D | |
| 15 | | D | | | D | | |
| 16 | | D | | | D | A | |
| 17 | | B | | A | B | | |
| 18 | | A | | B | B | | |
| 19 | | B | | B | B | | |
| 20 | A | B | | | B | A | |
| 21 | | D | | | D | A | |
| 22 | | B | | | C | A | |
| 23 | | B | | | B | | |
| 24 | | D | | | D | | |
| 25 | | D | | | D | | |
| 26 | | C | | | D | A | |
| 27 | | B | | | C | | |
| 28 | A | B | | B | B | | |
| 29 | | C | | | D | | |

TABLE 4-continued

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 30 | | B | | | C | B | |
| 31 | | A | | A | A | A | |
| 32 | | D | | | D | | |
| 33 | | A | | A | B | | |
| 34 | | A | | A | B | | |
| 35 | | D | | | D | | |
| 36 | A | A | | | B | | |
| 37 | | B | | | D | | |
| 38 | | B | | | C | | |
| 39 | | A | | B | B | | |
| 40 | | B | | | B | | |
| 41 | | B | | | D | | |
| 42 | | B | | | C | | |
| 43 | | C | | | D | | |
| 44 | | C | | | D | | |
| 45 | | A | | | B | | |
| 46 | | D | | | D | | |
| 47 | | D | | | No Fit | | |
| 48 | | D | | | No Fit | | |
| 49 | | D | | | D | | |
| 50 | A | A | | | B | | |
| 51 | | D | | | D | | |
| 52 | B | | A | | | | |
| 53 | C | | B | | | | |
| 54 | D | | D | | | | |
| 55 | C | | B | | | | |
| 56 | B | | A | | | | |
| 57 | D | | D | | | | |
| 58 | A | | A | | | | |
| 59 | A | | | | | | |
| 60 | A | | | | | | |
| 61 | D | | | | | | |
| 62 | B | | | | | | |
| 63 | B | | | | | | |
| 64 | B | | | | | | |
| 65 | No Fit | | | | | | |
| 66 | D | | | | | | |
| 67 | D | | | | | | |
| 69 | | | | | | | C |
| 70 | | | | | | | B |
| 71 | | | | | | | B |
| 72 | | | | | | D | B |
| 73 | | | | | | A | B |
| 74 | | | | | | A | B |
| 75 | | | | | | B | A |
| 76 | | B | | B | B | A | |
| 77 | | D | | | C | | |
| 78 | | No Fit | | | D | B | |
| 79 | | D | | | D | B | |
| 80 | | C | | B | B | A | |
| 81 | | D | | | D | B | |
| 82 | | D | | | D | A | |
| 83 | | D | | | D | | |
| 84 | | D | | | D | | |
| 85 | | B | | | C | B | |
| 86 | B | D | | | D | | |
| 87 | | B | | | D | | |
| 88 | | D | | | D | | |
| 89 | | D | | | D | | |
| 90 | C | | B | | | | |
| 91 | D | | D | | | | |
| 92 | D | | D | | | | |
| 93 | D | | | | | | |
| 94 | D | | | | | | |
| 95 | D | | | | | | |
| 96 | D | | | | | | |
| 100 | A | | | A | | A | |
| 101 | A | | A | A | | A | A |
| 102 | A | | | A | | A | A |
| 103 | A | | | A | | A | A |
| 104 | A | | | A | | A | A |
| 105 | A | | A | A | | A | A |

TABLE 4-continued

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 106 | A | | | C | | A | A |
| 107 | A | | | C | | A | A |
| 108 | A | | | B | | A | A |
| 109 | A | | | | | A | A |
| 110 | A | | A | B | | A | A |
| 111 | A | | | A | | A | A |
| 112 | A | | | C | | A | A |
| 113 | A | | A | A | | A | A |
| 114 | A | | | A | | A | A |
| 115 | A | | A | C | | A | A |
| 116 | A | | | C | | A | A |
| 117 | A | | A | D | | A | A |
| 118 | A | | | A | | A | A |
| 119 | A | | | B | | A | A |
| 120 | A | | | | | A | A |
| 121 | A | | A | A | | A | A |
| 122 | A | | | B | | A | A |
| 123 | A | | A | C | | A | A |
| 124 | A | | A | | | A | A |
| 125 | A | | A | | | A | A |
| 126 | A | | A | | | A | A |
| 127 | A | | A | B | | A | A |
| 128 | A | | A | A | | A | A |
| 129 | A | | | | | A | A |
| 130 | A | | A | A | | A | A |
| 131 | A | | A | | | A | A |
| 132 | A | | | C | | A | A |
| 133 | A | | | C | | A | A |
| 134 | A | | A | A | | A | A |
| 135 | A | | | | | | |
| 136 | A | | A | A | | A | A |
| 137 | A | | | B | | A | A |
| 138 | A | | | A | | A | A |
| 139 | A | | | | | A | A |
| 140 | A | | | C | | A | A |
| 141 | A | | | A | | A | A |
| 142 | A | | A | A | | A | A |
| 143 | A | | | B | | A | A |
| 144 | A | | | A | | A | A |
| 145 | A | | A | C | | A | A |
| 146 | A | | A | | | A | A |
| 147 | A | | A | C | | A | A |
| 148 | A | | | | | A | A |
| 149 | A | | A | B | | A | A |
| 150 | A | | | | | A | A |
| 151 | A | | A | B | | A | A |
| 152 | A | | A | | | A | A |
| 153 | A | | | B | | A | A |
| 154 | A | | | C | | A | A |
| 155 | A | | | B | | A | A |
| 156 | A | | | A | | A | A |
| 157 | A | | | A | | B | B |
| 158 | A | | | C | | A | A |
| 159 | A | | | C | | A | A |
| 160 | A | | | A | | A | A |
| 161 | A | | | A | | A | A |
| 162 | A | | A | | | A | A |
| 163 | A | | | C | | A | A |
| 164 | A | | A | | | A | A |
| 165 | A | | | C | | A | A |
| 166 | A | | | C | | | |
| 167 | A | | A | | | A | A |
| 168 | A | | | A | | A | A |
| 169 | A | | | A | | A | A |
| 170 | A | | A | | | A | A |
| 171 | A | | | C | | A | A |
| 172 | A | | | B | | A | A |
| 173 | A | | | B | | A | A |
| 174 | A | | | B | | A | A |
| 175 | A | | | C | | A | A |
| 176 | A | | A | C | | A | A |
| 177 | A | | | B | | A | A |

TABLE 4-continued

| Inhibitory Activities of Representative Compounds of formula I | | | | | | | |
|---|---|---|---|---|---|---|---|
| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
| 178 | A | | A | C | | A | A |
| 179 | A | | | C | | A | A |
| 180 | A | | | A | | B | C |
| 181 | A | | A | C | | A | A |
| 182 | A | | A | | | A | A |
| 183 | A | | | B | | A | A |
| 184 | A | | | | | A | A |
| 185 | A | | | B | | A | A |
| 186 | A | | | C | | A | A |
| 187 | A | | A | | | A | A |
| 188 | A | | | A | | | |
| 189 | A | | A | C | | A | A |
| 190 | A | | | C | | A | A |
| 191 | A | | A | C | | A | A |
| 192 | A | | A | C | | A | A |
| 193 | A | | A | | | A | A |
| 194 | A | | | B | | B | B |
| 195 | A | | | C | | A | A |
| 196 | A | | | B | | B | C |
| 197 | A | | | C | | A | A |
| 198 | A | | | | | A | A |
| 199 | A | | A | | | A | A |
| 200 | A | | | D | | A | A |
| 201 | A | | | B | | A | A |
| 202 | A | | | C | | A | A |
| 203 | A | | A | A | | A | A |
| 204 | A | | | | | A | A |
| 205 | A | | | B | | A | A |
| 206 | A | | | | | | |
| 207 | A | | | C | | A | A |
| 208 | A | | | | | | |
| 209 | A | | | C | | A | A |
| 210 | A | | | C | | A | A |
| 211 | A | | | C | | A | A |
| 212 | A | | | B | | A | A |
| 213 | A | | A | | | A | A |
| 214 | A | | A | | | A | A |
| 215 | A | | | C | | A | A |
| 216 | A | | | C | | A | A |
| 217 | A | | | C | | A | A |
| 218 | A | | | C | | A | A |
| 219 | A | | | | | | |
| 220 | A | | | C | | B | B |
| 221 | A | | | D | | A | A |
| 222 | A | | B | | | C | C |
| 223 | A | | B | | | A | A |
| 224 | A | | A | C | | A | A |
| 225 | A | | | | | | |
| 226 | A | | B | | | A | A |
| 227 | A | | B | | | C | C |
| 228 | A | | | | | A | A |
| 229 | A | | B | C | | A | A |
| 230 | A | | | | | A | A |
| 231 | A | | B | D | | A | A |
| 232 | A | | | D | | A | A |
| 233 | A | | | | | | |
| 234 | A | | | | | | |
| 235 | A | | | C | | A | A |
| 236 | A | | | D | | A | A |
| 237 | A | | A | C | | A | A |
| 238 | A | | | C | | | |
| 239 | A | | | C | | | |
| 240 | A | | | | | | |
| 241 | A | | C | | | | |
| 242 | B | | B | | | | |
| 243 | B | | | C | | | |
| 244 | B | | C | D | | A | A |
| 245 | B | | C | | | A | A |
| 246 | B | | B | | | B | B |
| 247 | B | | B | | | A | A |
| 248 | B | | C | | | C | A |
| 249 | B | | | C | | A | C |

TABLE 4-continued

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 250 | B | | C | | | C | A |
| 251 | B | | | C | | A | C |
| 252 | B | | C | | | A | A |
| 253 | B | | C | | | A | A |
| 254 | B | | | | | | |
| 255 | C | | C | C | | | |
| 256 | C | | B | | | A | A |
| 257 | C | | C | | | A | A |
| 258 | C | | | D | | | A |
| 259 | C | | | | | A | A |
| 260 | C | | B | D | | A | A |
| 261 | C | | B | | | A | A |
| 262 | C | | C | | | | |
| 263 | C | | C | C | | | |
| 264 | C | | | C | | | |
| 265 | C | | C | | | | |
| 266 | C | | C | D | | | |
| 267 | C | | C | | | A | A |
| 268 | C | | A | C | | B | B |
| 269 | C | | | | | | |
| 270 | C | | C | | | C | C |
| 271 | C | | C | | | | |
| 272 | C | | C | C | | C | C |
| 273 | C | | C | D | | | |
| 274 | C | | C | | | | |
| 275 | C | | | | | | |
| 276 | C | | C | | | | |
| 277 | C | | | | | B | B |
| 278 | C | | | | | D | D |
| 279 | C | | C | | | C | C |
| 280 | C | | D | D | | | |
| 281 | C | | | | | | |
| 282 | C | | | | | | |
| 283 | C | | | | | C | C |
| 284 | C | | | | | | |
| 285 | C | | | | | D | D |
| 286 | C | | | | | | |
| 287 | C | | | D | | C | C |
| 288 | C | | | | | C | C |
| 289 | C | | D | | | A | A |
| 290 | C | | | | | | |
| 291 | C | | | | | | |
| 292 | C | | | D | | | |
| 293 | C | | C | | | B | B |
| 294 | C | | | | | | |
| 295 | C | | | | | | |
| 296 | C | | D | | | | |
| 297 | C | | C | | | | |
| 298 | C | | D | | | A | A |
| 299 | C | | | | | | |
| 300 | C | | | | | | |
| 301 | C | | D | | | | |
| 302 | C | | C | | | C | C |
| 303 | D | | | | | | |
| 304 | D | | | | | | |
| 305 | D | | | | | | |
| 306 | D | | | | | | |
| 307 | D | | | | | | |
| 308 | D | | | | | C | C |
| 309 | D | | | | | | |
| 310 | D | | | | | | |
| 311 | D | | D | | | | |
| 312 | D | | | | | | |
| 313 | D | | | | | | |
| 314 | D | | | | | | |
| 315 | D | | | | | | |
| 316 | D | | | | | | |
| 317 | D | | | | | | |
| 318 | D | | | | | | |
| 319 | D | | | | | | |
| 320 | D | | | | | | |
| 321 | D | | D | | | | |

TABLE 4-continued

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 322 | D | | | | | | |
| 323 | D | | | | | | |
| 324 | D | | | | | | |
| 325 | D | | D | | | A | A |
| 326 | D | | | | | D | D |
| 327 | D | | | | | | |
| 328 | D | | | | | | |
| 329 | D | | | | | | |
| 330 | D | | | | | | |
| 331 | D | | | | | | |
| 332 | D | | | | | | |
| 333 | D | | | | | | |
| 334 | | | | | | | |
| 335 | | | | | | | |
| 336 | | | | | | | |
| 337 | | | | | | | |
| 338 | | | | | | | |
| 339 | | | | | | A | A |
| 340 | | | | | | A | A |
| 341 | | | | | | A | A |
| 342 | | | | | | A | A |
| 343 | | | | | | A | A |
| 344 | | | | | | B | B |
| 345 | | | | | | C | C |
| 346 | | | | | | A | A |
| 347 | | | | | | A | A |
| 348 | | | | | | A | A |
| 349 | | | | | | A | A |
| 350 | | | | B | | A | A |
| 351 | | | | | | A | A |
| 352 | | | | | | A | A |
| 353 | | | | | | A | A |
| 354 | | | | | | A | A |
| 355 | | | | | | A | A |
| 356 | | | | | | A | A |
| 357 | | | | | | A | A |
| 358 | | | | | | A | A |
| 359 | | | | | | A | A |
| 360 | | | | | | A | A |
| 361 | | | | | | A | A |
| 362 | | | | | | A | |
| 363 | | | | | | B | B |
| 364 | | | | | | A | A |
| 365 | | | | | | A | A |
| 366 | | | | | | A | A |
| 367 | | | | | | A | A |
| 368 | | | | | | A | A |
| 369 | | | | | | A | A |
| 370 | | | | | | A | A |
| 371 | | | | | | A | A |
| 372 | | | | | | A | A |
| 373 | | | | | | A | A |
| 374 | | | | | | A | A |
| 375 | | | | | | A | A |
| 376 | | | | | | A | A |
| 377 | | | | C | | A | A |
| 378 | | | | B | | A | A |
| 379 | | | | | | A | A |
| 380 | | | | | | A | A |
| 381 | | | | C | | A | A |
| 382 | | | | C | | A | A |
| 383 | | | | | | A | A |
| 384 | | | | C | | A | A |
| 385 | | | | C | | A | A |
| 386 | | | | A | | A | A |
| 387 | | | | | | A | A |
| 388 | | | | B | | A | A |
| 389 | | | | C | | A | A |
| 390 | | | | C | | A | A |
| 391 | | | | C | | A | A |
| 392 | | | | B | | A | A |
| 393 | | | | C | | A | A |

TABLE 4-continued

Inhibitory Activities of Representative Compounds of formula I

| Compound No. | IDH1 wt/R132H NADPH/NADP IC50 not saturated | IDH1 R132H IC50 | IDH1 wt/R132C NADPH/NADP IC50 | HT1080 IC50 | IDH1 R132C IC50 | IDH2 R140Q IC50 | U87MG IC50 |
|---|---|---|---|---|---|---|---|
| 394 | | | | C | | A | A |
| 395 | | | | | | A | A |
| 396 | | | | | | B | B |
| 397 | | | | | | A | A |
| 398 | | | | | | A | A |
| 399 | | | | A | | A | A |
| 400 | | | | | | A | A |
| 401 | | | | C | | A | A |
| 402 | | | | A | | A | A |
| 403 | | | | A | | A | A |
| 404 | | | | A | | A | A |
| 405 | | | | B | | A | A |
| 406 | | | | A | | A | A |
| 407 | | | | C | | A | A |
| 408 | | | | A | | A | A |
| 409 | | | | A | | A | A |
| 410 | | | | A | | A | A |
| 411 | | | | C | | B | B |
| 412 | | | | C | | | B |
| 413 | | | | C | | | A |
| 414 | A | C | | C | C | | |
| 415 | | C | | | C | | |
| 416 | A | C | | | D | | |
| 417 | | C | | | D | | |
| 418 | B | | | | | | |
| 419 | | D | | | | | C |
| 420 | | C | | C | | | B |
| 421 | C | | | | | | |

TABLE 5

Inhibitory Activities of Representative Compounds of formula I

| Compound No. | IDH1 wt/R132H NADPH/NADP IC50 saturated | IDH1 R132H NADPH/NADP IC50 | Neuro-sphere IC50 | IDH R132C NADPH/NADP IC50 | IDH2 R140Q 16 hr NADPH/NADP IC50 |
|---|---|---|---|---|---|
| 100 | | A | A | | |
| 101 | A | A | A | A | |
| 102 | | A | A | | |
| 103 | | A | A | | |
| 104 | | A | | | |
| 105 | | A | A | | |
| 106 | | A | A | A | |
| 107 | | A | A | | |
| 108 | | A | A | | |
| 109 | | | A | | |
| 110 | | B | A | | A |
| 111 | | A | A | | |
| 112 | | A | A | | |
| 113 | | A | A | | A |
| 114 | | | A | | |
| 115 | | A | A | | |
| 116 | A | A | A | | |
| 117 | | | | | A |
| 118 | | A | A | | |
| 119 | | A | A | | |
| 120 | | A | A | | |
| 121 | | B | A | | |
| 122 | | A | A | | |
| 123 | | A | A | | |
| 124 | | A | A | | |
| 125 | | | A | | |
| 126 | | B | A | | |
| 127 | | A | A | | A |
| 128 | | A | A | | |

TABLE 5-continued

Inhibitory Activities of Representative Compounds of formula I

| Compound No. | IDH1 wt/R132H NADPH/NADP IC50 saturated | IDH1 R132H NADPH/NADP IC50 | Neuro-sphere IC50 | IDH R132C NADPH/NADP IC50 | IDH2 R140Q 16 hr NADPH/NADP IC50 |
|---|---|---|---|---|---|
| 129 | | | A | | |
| 130 | | A | | | |
| 131 | | B | A | | |
| 132 | | A | A | | |
| 133 | | B | A | C | |
| 134 | | A | A | | |
| 135 | | | A | | |
| 136 | | A | A | | |
| 137 | | A | A | C | |
| 138 | | A | A | | |
| 139 | | | A | | |
| 140 | | A | A | | |
| 141 | | A | A | | |
| 142 | | A | A | | |
| 143 | | A | A | | |
| 144 | | A | A | | |
| 145 | | A | A | | |
| 146 | | A | A | | |
| 147 | | B | A | | |
| 148 | | | A | | |
| 149 | | A | A | | |
| 150 | | | A | | |
| 151 | | A | A | | |
| 152 | | A | A | | |
| 153 | | A | | | |
| 154 | | A | A | | |
| 155 | | A | A | | |
| 156 | | A | A | | |
| 157 | | A | A | | |

TABLE 5-continued

Inhibitory Activities of Representative Compounds of formula I

| Compound No. | IDH1 wt/R132H NADPH/NADP IC50 saturated | IDH1 R132H NADPH/NADP IC50 | Neurosphere IC50 | IDH R132C NADPH/NADP IC50 | IDH2 R140Q 16 hr NADPH/NADP IC50 |
|---|---|---|---|---|---|
| 158 | | B | A | C | |
| 159 | | A | A | | |
| 160 | | B | A | C | |
| 161 | | A | A | B | |
| 162 | | A | A | | |
| 163 | | B | A | | |
| 164 | | B | A | | |
| 165 | | B | A | | |
| 166 | | | A | | |
| 167 | | A | A | | A |
| 168 | | A | A | B | |
| 169 | | A | A | | |
| 170 | | C | A | | |
| 171 | | B | A | | |
| 172 | | A | A | | |
| 173 | | A | A | | |
| 174 | | A | A | B | |
| 175 | | B | A | | |
| 176 | | C | A | | |
| 177 | | B | A | | |
| 178 | | B | A | | A |
| 179 | | A | A | | |
| 180 | | A | A | | |
| 181 | | A | A | | |
| 182 | | C | A | | |
| 183 | | C | A | | |
| 184 | | | A | | |
| 185 | | A | A | | |
| 186 | | C | A | | |
| 187 | | C | A | | |
| 188 | | | A | | |
| 189 | | C | A | C | |
| 190 | | C | A | D | |
| 191 | | C | A | | |
| 192 | | C | A | | |
| 193 | | B | A | | A |
| 194 | | C | A | | |
| 195 | | B | A | | |
| 196 | | A | A | | |
| 197 | | C | A | | |
| 198 | | | A | | |
| 199 | | C | A | | |
| 200 | | B | A | | |
| 201 | | B | A | | |
| 202 | | C | A | | |
| 203 | | A | A | | A |
| 204 | | | A | | |
| 205 | | C | A | | |
| 206 | | | A | | |
| 207 | | B | A | | |
| 208 | | | A | | |
| 209 | | C | A | | |
| 210 | | B | A | | |
| 211 | | C | A | | |
| 212 | | C | A | | |
| 213 | | B | A | | |
| 214 | | C | A | | |
| 215 | | B | A | | |
| 216 | | C | A | | |
| 217 | | B | A | | |
| 218 | | | A | | |
| 219 | | | A | | |
| 220 | | B | A | | |
| 221 | | C | A | | |
| 222 | | C | A | | |
| 223 | | C | A | | |
| 224 | | C | A | | |
| 225 | | | A | | |
| 226 | | C | A | | |
| 227 | | C | A | | |
| 228 | | | A | | |

TABLE 5-continued

Inhibitory Activities of Representative Compounds of formula I

| Compound No. | IDH1 wt/R132H NADPH/NADP IC50 saturated | IDH1 R132H NADPH/NADP IC50 | Neurosphere IC50 | IDH R132C NADPH/NADP IC50 | IDH2 R140Q 16 hr NADPH/NADP IC50 |
|---|---|---|---|---|---|
| 229 | | C | A | | |
| 230 | | | A | | |
| 231 | | C | A | | |
| 232 | | C | A | | |
| 233 | | | | | |
| 234 | | C | | | C |
| 235 | | | A | | |
| 236 | | C | | | |
| 237 | | C | A | | |
| 238 | | C | A | | |
| 239 | | C | A | | |
| 240 | | | | | |
| 241 | | C | | | B |
| 242 | | C | | | |
| 243 | | D | A | | |
| 244 | | | A | | B |
| 245 | | | A | | A |
| 246 | | C | | | A |
| 247 | | C | A | | |
| 248 | | | | | A |
| 249 | | D | B | | |
| 250 | | C | A | | B |
| 251 | | C | A | | |
| 252 | | D | B | | |
| 253 | | C | A | | |
| 254 | | | B | | |
| 255 | | C | | | C |
| 256 | | D | A | | |
| 257 | | C | | | |
| 258 | | | | | |
| 259 | | | | | |
| 260 | | | | | |
| 261 | | D | B | | |
| 262 | | D | | | C |
| 263 | | C | | | C |
| 264 | | C | B | | |
| 265 | | D | | | C |
| 266 | | D | A | | C |
| 267 | | D | | | B |
| 268 | | D | A | | B |
| 269 | | | | | |
| 270 | | D | | | |
| 271 | | C | | | C |
| 272 | | D | | | |
| 273 | | D | | | D |
| 274 | | D | | | C |
| 275 | | D | | | |
| 276 | | D | | | |
| 277 | | | | | |
| 278 | | | | | |
| 279 | | D | | | |
| 280 | | D | | | C |
| 281 | | | | | |
| 282 | | | | | |
| 283 | | D | | | |
| 284 | | | | | |
| 285 | | | | | |
| 286 | | | | | |
| 287 | | D | | | |
| 288 | | | | | |
| 289 | | D | | | B |
| 290 | | | | | |
| 291 | | | | | |
| 292 | | | | | |
| 293 | | D | D | | |
| 294 | | | | | |
| 295 | | | | | |
| 296 | | D | | | |
| 297 | | D | | | |
| 298 | | D | | | B |
| 299 | | | | | |

TABLE 5-continued

Inhibitory Activities of Representative Compounds of formula I

| Compound No. | IDH1 wt/R132H NADPH/NADP IC50 saturated | IDH1 R132H NADPH/NADP IC50 | Neurosphere IC50 | IDH R132C NADPH/NADP IC50 | IDH2 R140Q 16 hr NADPH/NADP IC50 |
|---|---|---|---|---|---|
| 300 | | | | | |
| 301 | | D | | | |
| 302 | | D | | | |
| 303 | | | | | |
| 304 | | | | | |
| 305 | | | C | | |
| 306 | | | | | |
| 307 | | | | | |
| 308 | | D | C | | |
| 309 | | D | | | |
| 310 | | | | | |
| 311 | | D | | | |
| 312 | | | | | |
| 313 | | | | | |
| 314 | | | | | |
| 315 | | D | | | |
| 316 | | | | | |
| 317 | | D | | | |
| 318 | | | D | | |
| 319 | | D | | | |
| 320 | | | | | |
| 321 | | D | | | |
| 322 | | | | | |
| 323 | | | | | |
| 324 | | | | | |
| 325 | | | | | B |
| 326 | | | | | |
| 327 | | | | | |
| 328 | | D | | | |
| 329 | | | | | |
| 330 | | | | | |
| 331 | | | | | |
| 332 | | D | | | |
| 333 | | D | | | |
| 334 | | | | | |
| 335 | A | | A | | |
| 336 | A | | A | | |
| 337 | A | | A | | |
| 338 | B | | A | | |
| 339 | A | | A | | |
| 340 | C | | B | | |
| 341 | C | | A | | |
| 342 | C | | A | | |
| 343 | C | | | | |
| 344 | B | | A | | |
| 345 | A | | A | | |
| 346 | A | | A | | |
| 347 | A | | A | | |
| 348 | A | | A | | |
| 349 | A | | A | | |
| 350 | A | A | A | B | |
| 351 | A | | A | | |
| 352 | A | | A | | |
| 353 | A | | A | | |
| 354 | B | | A | | |
| 355 | A | | A | | |
| 356 | A | | A | | |
| 357 | B | | A | | |
| 358 | A | | A | | |
| 359 | A | | A | | |
| 360 | A | | A | | |
| 361 | B | | A | | |
| 362 | B | | | | |
| 363 | A | | A | | |
| 364 | B | | A | | |
| 365 | B | | A | | |
| 366 | A | | A | | |
| 367 | A | | A | | |
| 368 | A | A | A | | |
| 369 | A | | A | | |
| 370 | A | | A | | |
| 371 | A | | A | | |
| 372 | A | | A | | |
| 373 | A | | A | | |
| 374 | B | | A | | |
| 375 | C | | A | | |
| 376 | D | | | | |
| 377 | A | | A | | |
| 378 | A | | A | | |
| 379 | B | | A | | |
| 380 | C | | A | | |
| 381 | A | | A | | |
| 382 | B | C | A | | |
| 383 | C | | A | | |
| 384 | A | | A | | |
| 385 | B | | A | | |
| 386 | A | | A | | |
| 387 | C | | A | | |
| 388 | A | | A | | |
| 389 | A | B | A | C | |
| 390 | B | | A | | |
| 391 | A | B | A | C | |
| 392 | A | | A | | |
| 393 | A | B | A | C | |
| 394 | A | | A | | |
| 395 | A | | A | | |
| 396 | D | | | | |
| 397 | C | | | | |
| 398 | C | | | | |
| 399 | A | | A | | |
| 400 | A | C | A | C | |
| 401 | A | A | A | C | |
| 402 | B | | A | | |
| 403 | A | | A | | |
| 404 | A | | A | | |
| 405 | B | | A | | |
| 406 | A | | A | | |
| 407 | C | | A | | |
| 408 | A | | A | | |
| 409 | A | | A | | |
| 410 | A | A | A | A | |
| 411 | C | | A | | |
| 412 | C | | A | | |
| 413 | A | A | | | |
| 414 | | B | | C | A |
| 415 | | | | | |
| 416 | | | | | C |
| 417 | | C | | | |
| 418 | | | | | A |
| 419 | | C | | | |
| 421 | | C | | | |

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method for treating a cancer characterized by the presence of an isocitrate dehydrogenase 1 (IDH1) mutation comprising administering to a patient in need thereof a therapeutically effective amount of a compound having Formula (Ia) or a pharmaceutically acceptable salt or hydrate thereof, wherein:

(Ia)

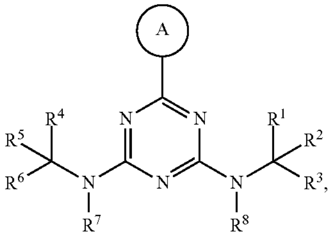

ring A is selected from phenyl, pyrazolyl, oxazolyl, isoxazolyl, pyridinyl, pyrimidinyl, pyrazinyl, and thiazolyl, and wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —$S(O)_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from —($C_1$-$C_6$ alkyl); —($C_2$-$C_6$ alkenyl) and —($C_2$-$C_6$ alkynyl), wherein any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$; and $R^7$ and $R^8$ are each independently selected from hydrogen and $C_1$-$C_6$ alkyl;

provided that (i) when A is an optionally substituted pyridyl, then (A) N($R^7$)C($R^4$)($R^5$)($R^6$) and N($R^8$)C($R^1$)($R^2$)($R^3$) are not both $NHCH_2CH_2OH$, and (B) when N($R^7$)C($R^4$)($R^5$)($R^6$) is NHC$(CH_3)_3$, then N($R^8$)C($R^1$)($R^2$)($R^3$) is not NH—$CH_2CH_3$;

(ii) when A is an optionally substituted heteroaryl selected from pyrazolyl, oxazolyl, isoxazolyl, pyridinyl, pyrimidinyl, pyrazinyl, and thiazolyl, then N($R^7$)C($R^4$)($R^5$)($R^6$) and N($R^8$)C($R^1$)($R^2$)($R^3$) are not both N$(CH_2CH_3)_2$, $NHCH_2CH_2$-i-propyl, or $NHCH_2CH$ $(CH_3)_2$;

(iii) when A is optionally substituted 1-pyrazolyl, then neither N($R^7$)C($R^4$)($R^5$)($R^6$) nor N($R^8$)C($R^1$)($R^2$)($R^3$) is NHisopropyl, $NHCH_2CH_3$, or N$(CH_2CH_3)_2$;

(iv) when A is an optionally substituted phenyl, then N($R^7$)C($R^4$)($R^5$)($R^6$) is not the same as N($R^8$)C($R^1$)($R^2$)($R^3$);

(v) when A is substituted 1-pyrazolyl, then (A) N($R^7$)C($R^4$)($R^5$)($R^6$); and N($R^8$)C($R^1$)($R^2$)($R^3$) are not both NHC$(CH_3)$ 3.

2. The method of claim 1, wherein ring A is a 6-member monocyclic heteroaryl selected from pyridinyl, pyrimidinyl and pyrazinyl and wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —$S(O)_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH.

3. The method of claim 1, wherein ring A is pyridinyl optionally substituted with up to two substituents independently selected from halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —$S(O)_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH.

4. The method of claim 1, wherein ring A is pyridinyl optionally substituted with halo or —$C_1$-$C_4$ haloalkyl.

5. The method of claim 1, wherein ring A is phenyl or a 6-member monocyclic heteroaryl selected from pyridinyl, pyrimidinyl and pyrazinyl wherein said phenyl or 6-member monocyclic heteroaryl is optionally substituted with up to two substituents independently selected from halo, —$C_1$-$C_4$ alkyl, —$C_1$-$C_4$ haloalkyl, —$C_1$-$C_4$ hydroxyalkyl, —NH—S$(O)_2$—($C_1$-$C_4$ alkyl), —$S(O)_2NH$($C_1$-$C_4$ alkyl), —$S(O)_2$—($C_1$-$C_4$ alkyl), $C_1$-$C_4$ alkoxy, —NH($C_1$-$C_4$ alkyl), —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH;

$R^1$ and $R^4$ are each independently selected from $C_1$-$C_4$ alkyl and $C_1$-$C_4$ haloalkyl;

$R^3$ and $R^6$ are both hydrogen;

$R^2$ and $R^5$ are each-($C_1$-$C_6$ alkyl);

wherein:

any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$; and $R^7$ and $R^8$ are each independently selected from hydrogen and $C_1$-$C_6$ alkyl.

6. The method of claim 1, wherein the compound has formula (B), wherein:

(B)

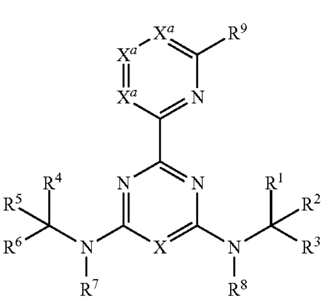

X is N;

each $X^a$ is independently N or C—$R^{9a}$, provided that when one $X^a$ is N, then the other two $X^a$ are both C—$R^{9a}$;

$R^9$ is selected from the group consisting of halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —$S(O)_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH;

each $R^{9a}$ is independently selected from the group consisting of hydrogen, halo, —$C_1$-$C_4$ alkyl, —$C_1$-$C_4$ haloalkyl, —$C_1$-$C_4$ hydroxyalkyl, —NH—$S(O)_2$—($C_1$-$C_4$ alkyl), —$S(O)_2NH$($C_1$-$C_4$ alkyl), —CN, —$S(O)_2$—($C_1$-$C_4$ alkyl), $C_1$-$C_4$ alkoxy, —NH($C_1$-$C_4$ alkyl), —N($C_1$-$C_4$ alkyl)$_2$, —OH, —$OCF_3$, —CN, —$NH_2$, —C(O)$NH_2$, —C(O)NH($C_1$-$C_4$ alkyl), —C(O)—N($C_1$-$C_4$ alkyl)$_2$, and cyclopropyl optionally substituted with OH;

$R^1$, $R^3$, $R^4$, and $R^6$ are each independently selected from hydrogen, $C_1$-$C_4$ alkyl, $C_1$-$C_4$ haloalkyl, —O—$C_1$-$C_4$ alkyl, and CN, wherein each said alkyl moiety of $R^1$, $R^3$, $R^4$, and $R^6$ are each independently optionally substituted with —OH, —$NH_2$, —CN, —O—$C_1$-$C_4$ alkyl, —NH($C_1$-$C_4$ alkyl), or —N($C_1$-$C_4$ alkyl)$_2$;

$R^2$ and $R^5$ are each independently selected from —($C_1$-$C_6$ alkyl); —($C_2$-$C_6$ alkenyl) and —($C_2$-$C_6$ alkynyl), wherein any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$; and $R^7$ and $R^8$ are each independently selected from hydrogen and $C_1$-$C_6$ alkyl.

7. The method of claim 6, wherein:

$R^1$ and $R^4$ are each independently selected from $C_1$-$C_4$ alkyl and $C_1$-$C_4$ haloalkyl;

$R^3$ and $R^6$ are both hydrogen; and $R^2$ and $R^5$ are each —($C_1$-$C_6$ alkyl);

wherein any alkyl or alkylene moiety present in $R^2$ and $R^5$ is optionally substituted with one or more —OH, —O($C_1$-$C_4$ alkyl), —$CO_2H$, or halo;

any terminal methyl moiety present in $R^2$ and $R^5$ is optionally replaced with —$CH_2OH$, $CF_3$, —$CH_2F$, —$CH_2Cl$, C(O)$CH_3$, C(O)$CF_3$, CN, or $CO_2H$; and $R^7$ and $R^8$ are each independently selected from hydrogen and $C_1$-$C_6$ alkyl.

8. The method of claim 6, wherein each $X^a$ is C—$R^{9a}$.

9. The method of claim 8, wherein each $R^{9a}$ is H.

10. The method of claim 6, wherein $R^9$ is selected from halo and —$C_1$-$C_4$ haloalkyl.

11. The method of claim 6, wherein $R^9$ is halo.

12. The method of claim 6, wherein $R^1$ and $R^4$ are each independently selected from the group consisting of $C_1$-$C_4$ alkyl and $C_1$-$C_4$ haloalkyl, and $R^2$ and $R^5$ are each —($C_1$-$C_6$ alkyl).

13. The method of claim 6, wherein $R^7$ and $R^8$ are both hydrogen.

14. The method of claim 1, wherein the compound is selected from:

3

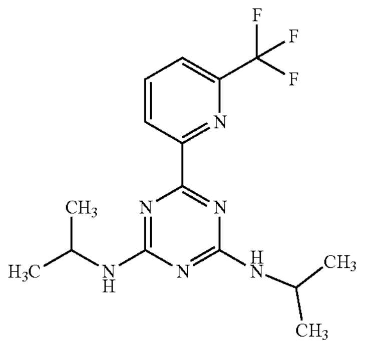

4

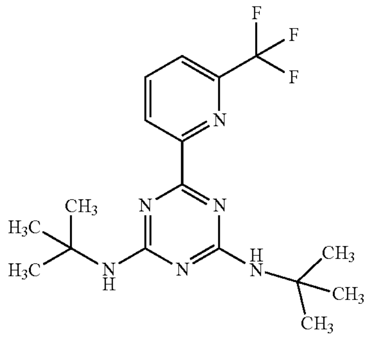

13

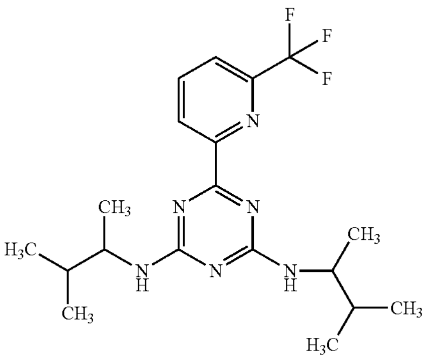

14

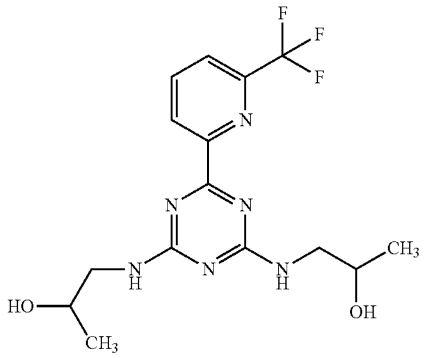

-continued
17
Chiral
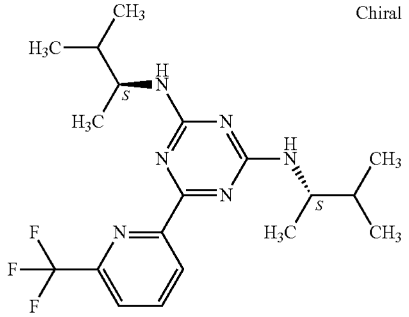
18
Chiral
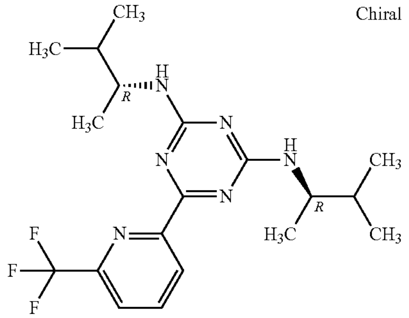
32
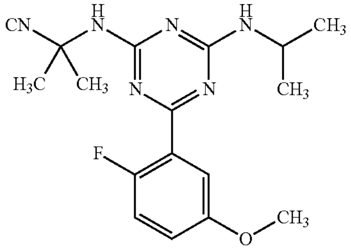
35
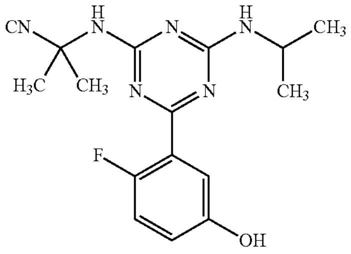
70
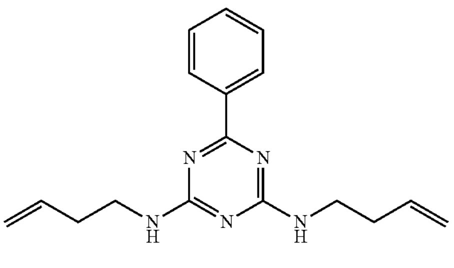
-continued
73
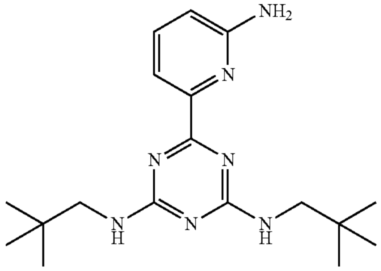
74
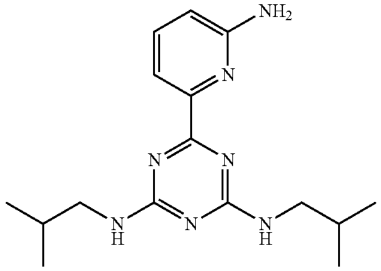
76
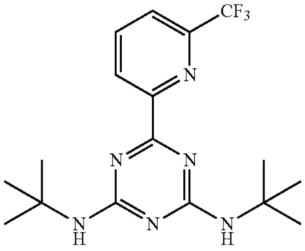
86
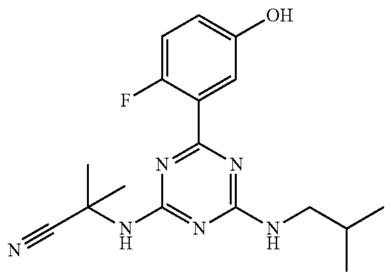
100
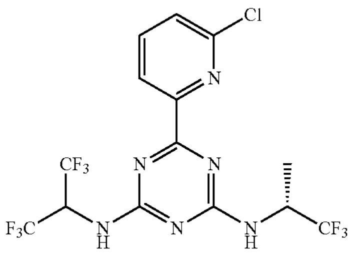
101
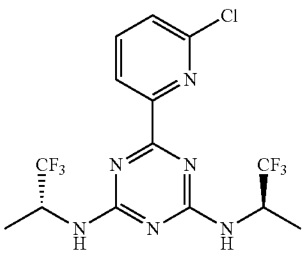

-continued
103
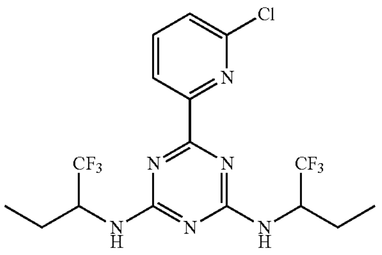
104
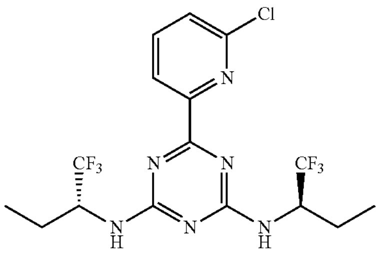
114
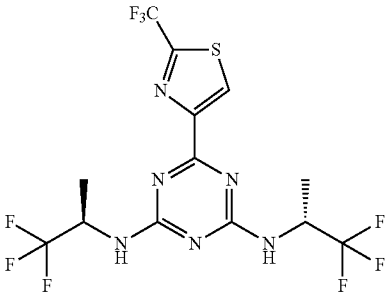
130
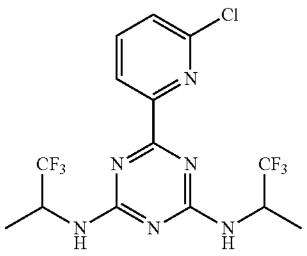
136
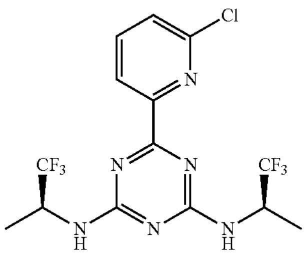
141
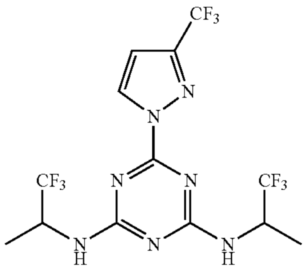
-continued
142
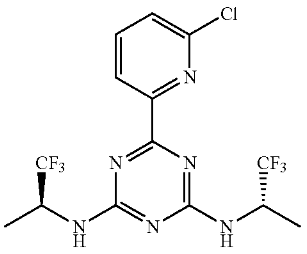
156
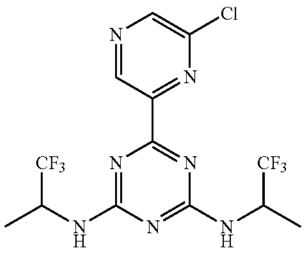
180
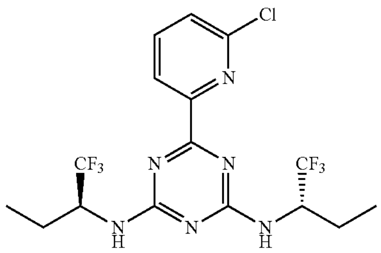
196
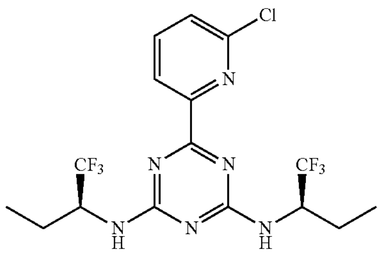
271
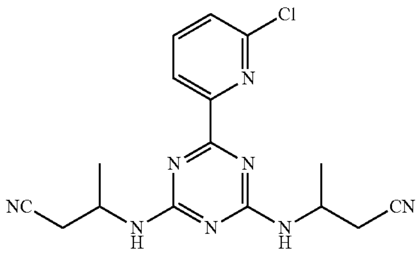
335
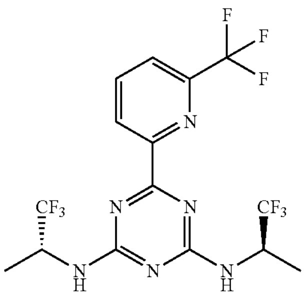

-continued

339

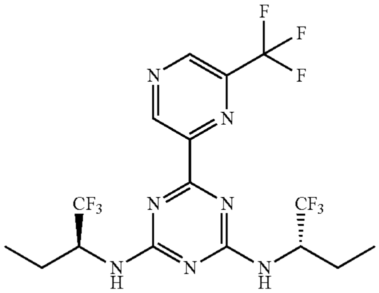

344

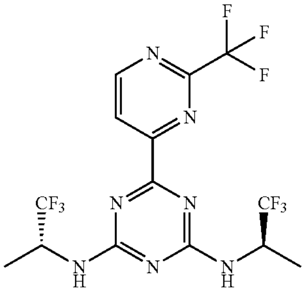

345

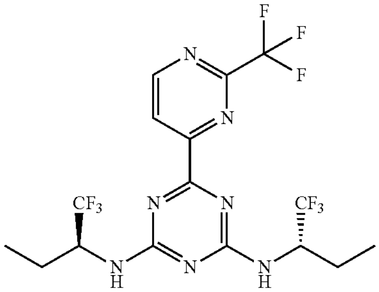

346

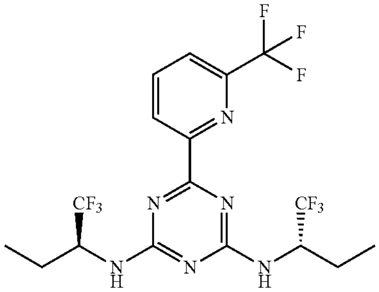

363

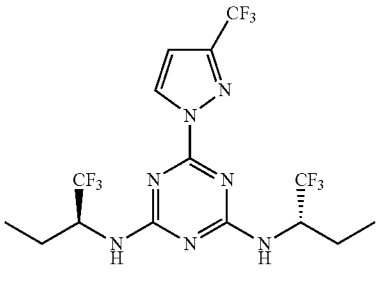

-continued

386

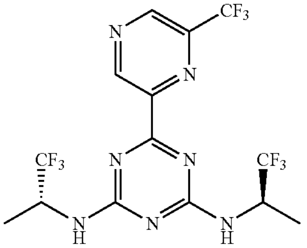

and

404

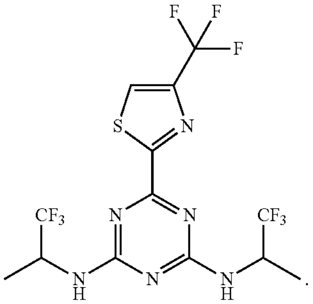

15. The method of claim 1, wherein the IDH1 mutation is an IDH1 R132H or R132C mutation.

16. A method for treating a cancer characterized by the presence of an isocitrate dehydrogenase 1 (IDH1) mutation comprising administering to a patient in need thereof a therapeutically effective amount of a compound having Formula:

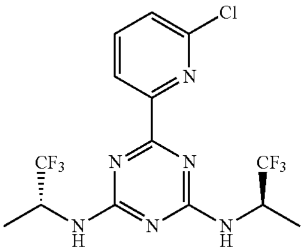

or a pharmaceutically acceptable salt or hydrate thereof.

17. The method of claim 16, wherein the IDH1 mutation is an IDH1 R132H or R132C mutation.

18. The method of claim 16, wherein the method further comprises administering a second therapeutic agent useful in the treatment of cancer.

19. A method for treating a cancer characterized by the presence of an isocitrate dehydrogenase 1 (IDH1) mutation comprising administering to a patient in need thereof a therapeutically effective amount of a pharmaceutical composition comprising

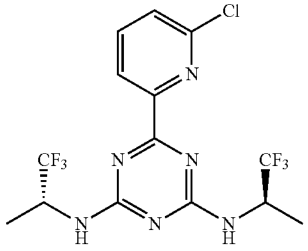
or a pharmaceutically acceptable salt or hydrate thereof and one or more pharmaceutically acceptable excipients.
20. The method of claim 19, wherein the IDH1 mutation is an IDH1 R132H or R132C mutation.
* * * * *